United States Patent
Ohata et al.

(10) Patent No.: US 8,802,713 B2
(45) Date of Patent: Aug. 12, 2014

(54) 3-ALKOXY-1-PHENYLPYRAZOLE DERIVATIVES AND PESTICIDES

(75) Inventors: Satoru Ohata, Iwata (JP); Katsuya Kato, Iwata (JP); Keiji Toriyabe, Iwata (JP); Yoshihiro Ito, Tokyo (JP); Ryuji Hamaguchi, Tokyo (JP); Yuki Nakano, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 467 days.

(21) Appl. No.: 12/682,059

(22) PCT Filed: Oct. 17, 2008

(86) PCT No.: PCT/JP2008/068902
§ 371 (c)(1),
(2), (4) Date: Apr. 8, 2010

(87) PCT Pub. No.: WO2009/051245
PCT Pub. Date: Apr. 23, 2009

(65) Prior Publication Data
US 2010/0210704 A1 Aug. 19, 2010

(30) Foreign Application Priority Data

Oct. 18, 2007 (JP) ................. 2007-271857
Oct. 18, 2007 (JP) ................. 2007-271858

(51) Int. Cl.
| | | |
|---|---|---|
| A61K 31/415 | (2006.01) | |
| C07D 231/10 | (2006.01) | |
| C07D 231/22 | (2006.01) | |
| A01N 43/56 | (2006.01) | |
| C07D 231/52 | (2006.01) | |

(52) U.S. Cl.
CPC .............. A01N 43/56 (2013.01); C07D 231/22 (2013.01); C07D 231/52 (2013.01)
USPC .............. 514/407; 548/367.1; 548/367.4; 548/369.4; 548/370.1; 548/368.4; 548/366.1

(58) Field of Classification Search
CPC ............................. A61K 31/415; C07D 231/10
USPC .............. 514/407; 548/366.1, 367.1, 367.4, 548/368.4, 369.4, 370.1
See application file for complete search history.

(56) References Cited

U.S. PATENT DOCUMENTS

2003/0069242 A1 4/2003 Toriyabe et al.
2005/0215797 A1 9/2005 Nakatani et al.

FOREIGN PATENT DOCUMENTS

| | | |
|---|---|---|
| JP | 48 2541 | 1/1973 |
| JP | 5 262741 | 10/1993 |
| JP | 2000 198768 | 7/2000 |
| JP | 2000 219679 | 8/2000 |
| JP | 2007-284356 | 11/2007 |
| JP | 2007-284386 | 11/2007 |
| JP | 2007-284387 | 11/2007 |
| WO | 2004 013106 | 2/2004 |
| WO | 2006 021462 | 3/2006 |
| WO | 2006 027198 | 3/2006 |
| WO | 2007 081019 | 7/2007 |

OTHER PUBLICATIONS

Mueller, Hans-Georg et al., Synthese Und Eigenschaften Von Thioncyanessigestern, Arch.Pharm., vol. 321, pp. 879-884 (1988).
Hartke, Klaus et al., "Zur Reaktion Von Dithionmalonsaeureestern Mit Nucleophilen Stickstorffbasen", Arch.Pharm., vol. 321, pp. 863-871 (1988).
Gotthardt, Hans et al., "Reaktionen Von 4,5-Diphenyl-1,3,4-Oxadiazolylium-2,Dicyan-methanid Mit Methanol und Singulett-Sauerstoe", Chem. Ber., vol. 118, pp. 403-408 (1985).
Extended European Search Report issued Dec. 23, 2011, in European Patent Application No. 08838803.8.

*Primary Examiner* — Samantha Shterengarts
(74) *Attorney, Agent, or Firm* — Oblon, Spivak, McClelland, Maier & Neustadt, L.L.P.

(57) ABSTRACT

To provide pesticides such as insecticides, miticides and nematicides, which are excellent in the safety, pesticidal effects, residual effectiveness, etc., which further have infiltration, and which can be applied by soil treatment.

A pesticide comprising a 3-alkoxy-1-phenyl-pyrazole derivative represented by the formula [I] or an agriculturally acceptable salt thereof as an active ingredient:

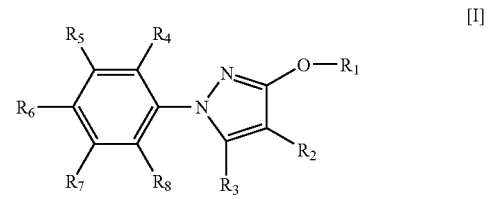

[I]

wherein, for example, $R_1$ is a $C_1$-$C_{10}$ alkyl group or the like, $R_2$ is a hydrogen atom or the like, $R_3$ is a hydrogen atom or the like, and each of $R_4$, $R_5$, $R_6$ and $R_8$ which are independent of one another, is a hydrogen atom or the like, and $R_7$ is a $C_2$-$C_4$ haloalkylthio group or the like.

23 Claims, No Drawings

3-ALKOXY-1-PHENYLPYRAZOLE DERIVATIVES AND PESTICIDES

TECHNICAL FIELD

The present invention relates to novel 3-alkoxy-1-phenyl-pyrazole derivatives and their salts, their production intermediates, and pesticides containing the derivatives or their salts as an active ingredient.

BACKGROUND ART

Heretofore, pyrazole derivatives analogous to those of the present invention, for example, Non-Patent Documents 1 to 3 and Patent Documents 1 to 6 are known. Among them, Non-Patent Documents 1 to 3 and Patent Documents 1, 3 and 4 disclose 3-alkoxy-1-phenyl-pyrazole derivatives but failed to disclose agricultural chemicals.

Patent Document 2 discloses 3-alkoxy-1-phenyl-pyrazole derivatives, but failed to disclose a 3-alkoxy-1-phenyl-pyrazole derivative wherein the 3-position of the phenyl group is substituted by a haloalkylthio group or a haloalkyl sulfinyl group, according to the present invention.

Further, Patent Document 5 discloses 4-alkoxypyrazole derivatives, but failed to disclose 3-alkoxy-1-phenyl-pyrazole derivatives according to the present invention.

Patent Document 6 discloses 3-, 4- or 5-phenylpyrazole derivatives wherein a carbon atom of pyrazole and a phenyl group are bonded, but failed to disclose 3-alkoxy-1-phenyl-pyrazole derivatives according to the present invention.

Non-Patent Document 1: Arch. Pharm., 321, 879 (1988)
Non-Patent Document 2: Arch. Pharm., 321, 863 (1988)
Non-Patent Document 3: Chem. Ber., 118, 403 (1985)
Patent Document 1: JP-B-48-2541
Patent Document 2: JP-A-5-262741
Patent Document 3: WO2006/027198
Patent Document 4: WO2006/021462
Patent Document 5: JP-A-2000-198768
Patent Document 6: WO2007/081019

DISCLOSURE OF THE INVENTION

Object to be Accomplished by the Invention

In recent years, in agricultural and horticultural fields, due to use of pesticides such as insecticides, miticides and nematicides for many years, pests have acquired resistance and are hardly controlled. Further, use of highly noxious pesticides has been a problem.

With respect to application of a pesticide, in a case where a pesticide is directly sprayed to a plant for example, no sufficient pesticidal effect is obtained in some cases due to non-uniform spraying, transpiration, decomposition by light, outflow of chemicals by rain, etc. On the other hand, when a pesticide is applied to the soil and is absorbed from e.g. the root of a plant, the chemical will spread all over the plant body, and a stable effect will be obtained. Further, pesticides applicable to soil treatment are advantageous to those who are engaged in agriculture from such a viewpoint that exposure to the chemical by spraying is small, and the method for applying the chemical is simple, thus leading to power saving.

However, at present, very few pesticides such as insecticides, miticides and nematicides, which can be utilized for soil treatment and which are practical, have been known.

It is an object of the present invention to solve the above problems of conventional pesticides such as insecticides, miticides and nematicides, and to provide pesticides such as insecticides, miticides and nematicides, which are excellent in the safety, pesticidal effects, residual effectiveness, etc., which have infiltration, and which can be applied by soil treatment.

Means to Accomplish the Object

To develop pesticides having the above-described preferred characteristics, the present inventors have prepared various 3-alkoxy-1-phenyl-pyrazole derivatives, and conducted extensive studies on their physiological activities. As a result, they have found that 3-alkoxy-1-phenyl-pyrazole derivatives (hereinafter sometimes referred to as the compounds of the present invention) represented by the following formula [I] have effects against various pests in agricultural and horticultural fields, and pests which have acquired resistance. They have found that the compounds exhibit very high effects especially against mites represented by two-spotted spider mite, Kanzawa spider mite and citrus red mite, pest hemipterans represented by brown rice planthopper, green rice leafhopper and cotton aphid, pest coleoptera represented by rice water weevil, rice leaf beetle and chafers, nematodes represented by southern root-knot nematode, and pest lepidopterans represented by diamondbackmoth, beat armyworm and cotton bollworm, have high activity even by soil treatment with which safe and labor-saving application becomes possible, and exhibit fungicidal effects against rice blast disease. The present invention has been accomplished on the basis of these discoveries.

The present invention provides the following (1) to (10).

(1) A 3-alkoxy-1-phenyl-pyrazole derivative represented by the formula [I] or an agriculturally acceptable salt thereof:

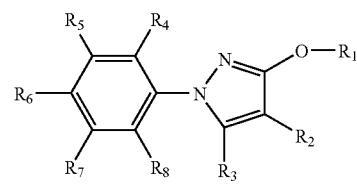

[I]

wherein $R_1$ is a $C_1$-$C_{10}$ alkyl group (which may be mono-substituted or poly-substituted preferably by a cyano group or a hydroxy group), a $C_1$-$C_{10}$ haloalkyl group, a $C_3$-$C_{10}$ cycloalkyl group (which may be mono-substituted or poly-substituted preferably by a halogen atom, a cyano group, a methyl group, a methoxy group or a trifluoromethyl group), a $C_3$-$C_8$ cycloalkyl $C_1$-$C_8$ alkyl group (which may be mono-substituted or poly-substituted preferably by a halogen atom, a cyano group, a methyl group, a methoxy group or a trifluoromethyl group), a $C_1$-$C_8$ alkoxy $C_1$-$C_8$ alkyl group (which may be mono-substituted or poly-substituted preferably by a halogen atom or a cyano group), a $C_1$-$C_8$ alkoxy $C_2$-$C_8$ alkenyl group (which may be mono-substituted or poly-substituted preferably by a halogen atom or a cyano group), a $C_1$-$C_8$ alkoxy $C_1$-$C_8$ alkoxy $C_1$-$C_8$ alkyl group (which may be mono-substituted or poly-substituted preferably by a halogen atom or a cyano group), a $C_2$-$C_{10}$ alkenyl group (which may be mono-substituted or poly-substituted preferably by a halogen atom or a cyano group), a $C_2$-$C_{10}$ alkynyl group (which may be mono-substituted or poly-substituted preferably by a halogen atom or a cyano group), a $C_2$-$C_{10}$ alkynyloxy $C_1$-$C_6$ alkyl group (which may be mono-substituted or poly-substituted preferably by a halogen atom or a cyano group), a $C_1$-$C_8$ alkylthio $C_1$-$C_8$ alkyl group (which may be mono-substituted or poly-substituted preferably by a halogen atom or a cyano group), a $C_1$-$C_8$ alkylsulfinyl $C_1$-$C_8$ alkyl group (which may be mono-substituted or poly-substituted preferably by a halogen atom or a cyano group), a $C_1$-$C_8$ alkylsulfonyl $C_1$-$C_8$ alkyl group (which may be mono-substituted or poly-substituted preferably by a halogen atom or a cyano group), a $C_1$-$C_{10}$ alkylsulfonyl group (which may be mono-substituted or poly-substituted preferably by a halogen atom or a cyano group), a benzenesulfonyl group (which may be mono-substituted or poly-substituted preferably by a halogen atom, a cyano group, a $C_1$-$C_8$ alkyl group, a $C_1$-$C_8$ alkoxy group, a trifluoromethyl group, a difluoromethoxy group, a trifluoromethoxy group or a trifluoromethylthio group), a $C_1$-$C_{10}$ thiocyanatoalkyl group (which may be mono-substituted or poly-substituted preferably by a halogen atom or a cyano group), an aryl-C(=X) group which may be mono-substituted or poly-substituted by a substituent group α, a $C_1$-$C_{10}$ alkyl-C(=X) group (which may be mono-substituted or poly-substituted preferably by a halogen atom, a cyano group, a $C_1$-$C_4$ alkoxy group or a $C_1$-$C_4$ alkylthio group), a $C_1$-$C_8$ alkyl C(=X)$C_1$-$C_4$ alkyl group (which may be mono-substituted or poly-substituted preferably by a halogen atom or a cyano group), a $C_1$-$C_8$ alkoxy C(=X)$C_1$-$C_8$ alkyl group (which may be mono-substituted or poly-substituted preferably by a halogen atom or a cyano group), a pentafluorothio $C_1$-$C_{10}$ alkyl group, a tri($C_1$-$C_3$)alkylsilyl $C_1$-$C_8$ alkyl group (which may be mono-substituted or poly-substituted preferably by a halogen atom or a cyano group), a $C_3$-$C_{10}$ trialkylsilyl group (which may be mono-substituted or poly-substituted preferably by a cyano group or a halogen atom), an aryl group which may be mono-substituted or poly-substituted by a substituent group α, an aryl $C_1$-$C_8$ alkyl group which may be mono-substituted or poly-substituted by a substituent group α, an aryloxy $C_1$-$C_8$ alkyl group which may be mono-substituted or poly-substituted by a substituent group α, an arylthio $C_1$-$C_8$ alkyl group which may be mono-substituted by a substituent group α, a heteroaryl group which may be mono-substituted or poly-substituted by a substituent group α, a heteroaryl $C_1$-$C_8$ alkyl group which may be mono-substituted or poly-substituted by a substituent group α, a heteroaryloxy $C_1$-$C_8$ alkyl group which may be mono-substituted or poly-substituted by a substituent group α, a heteroarylthio $C_1$-$C_8$ alkyl group which may be mono-substituted or poly-substituted by a substituent group α, a tetrahydrofurfuryl group, a tetrahydrofurfuryl $C_1$-$C_8$ alkyl group which may be mono-substituted or poly-substituted by a substituent group α, an $R_{1a}(R_{1b})$NC(=X) group or an $R_{1a}(R_{1b})$NC(=X)$C_1$-$C_4$ alkyl group;

$R_2$ is a hydrogen atom, a hydroxy group, a halogen atom, a cyano group, a $H_2$NC(=X) group, a carboxy group, a $C_1$-$C_4$ alkoxy C(=X) group, a HC(=X) group, a nitro group, an amino group, an azide group, a $C_1$-$C_4$ alkyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_1$-$C_4$ alkoxy $C_1$-$C_4$ alkyl group (which may be mono-substituted or poly-substituted preferably by a halogen atom or a cyano group), a $C_2$-$C_6$ alkenyl group (which may be mono-substituted or poly-substituted preferably by a halogen atom or a cyano group), a $C_2$-$C_6$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), or a $C_1$-$C_4$ alkyl C(=X) group (which may be mono-substituted or poly-substituted preferably by a halogen atom or a cyano group);

$R_3$ is a hydrogen atom, a hydroxy group, a halogen atom, a cyano group, a carboxy group, a HC(=X) group, an $R_{3a}(R_{3b})$N(C=X) group, an azide group, a nitro group, a $C_1$-$C_4$ alkyl group (which may be mono-substituted or poly-substituted preferably by a halogen atom, a cyano group, a hydroxy group, a $H_2$NC(=X) group, a carboxy group, a $C_1$-$C_4$ alkyl-(1H-1,2,4-triazol)-1-yl group, a $C_1$-$C_4$ alkoxy C(=X) group or 1,2,4-triazole), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_1$-$C_8$ cycloalkyl $C_1$-$C_4$ alkyl group (which may be mono-substituted or poly-substituted preferably by a halogen atom, a cyano group or a methyl group), a $C_1$-$C_6$ alkyl C(=X) group (which may be mono-substituted or poly-substituted preferably by a halogen atom or a cyano group), a $C_2$-$C_8$ alkenyl C(=X) group (which may be mono-substituted or poly-substituted preferably by a halogen atom or a cyano group), a $C_3$-$C_8$ cycloalkyl C(=X) group (which may be mono-substituted or poly-substituted preferably by a halogen atom, a cyano group or a $C_1$-$C_4$ alkyl group), a $C_1$-$C_6$ alkoxy group (which may be mono-substituted or poly-substituted preferably by a halogen atom or a cyano group), a $C_3$-$C_8$ cycloalkyloxy group (which may be mono-substituted or poly-substituted preferably by a halogen atom or a cyano group), a $C_1$-$C_6$ alkoxy $C_1$-$C_4$ alkyl group (which may be mono-substituted or poly-substituted preferably by a halogen atom or a cyano group), a $C_1$-$C_6$ alkoxy C(=X) group (which may be mono-substituted or poly-substituted preferably by a halogen atom or a cyano group), a mercapto group, a thiocyanato group, a $C_1$-$C_6$ alkylthio group (which may be mono-substituted or poly-substituted preferably by a halogen atom or a cyano group), a $C_1$-$C_6$ alkylsulfinyl group (which may be mono-substituted or poly-substituted preferably by a halogen atom or a cyano group), a $C_1$-$C_6$ alkylsulfonyl group (which may be mono-substituted or poly-substituted preferably by a halogen atom or a cyano group), a $C_3$-$C_8$ cycloalkylthio group (which may be mono-substituted or poly-substituted preferably by a halogen atom or a cyano group), a $C_3$-$C_8$ cycloalkylsulfinyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a $C_1$-$C_6$ alkylsulfonyloxy group (which may be mono-substituted or poly-substituted preferably by a halogen atom or a cyano group), an $R_{3a}(R_{3b})$N group, an $R_{3f}(R_{3g})$C=N group or an $R_{3h}$ON=C($R_3$) group;

each of $R_4$, $R_5$, $R_6$ and $R_8$ which are independent of one another, is a hydrogen atom, an amino group, an azide group, a nitro group, a hydroxy group, a halogen atom, a carbamoyl group, a cyano group, a carboxy group, a HC(=X) group, a $C_1$-$C_4$ alkyl group (which may be mono-substituted or poly-substituted preferably by a halogen atom), a $C_1$-$C_4$ alkoxy group (which may be mono-substituted or poly-substituted preferably by a halogen atom), a formylamino group, a $C_1$-$C_6$ alkyl C(=X) group, an amino group (which may be mono-substituted or poly-substituted preferably by a halogen atom or a cyano group), a $C_1$-$C_6$ alkylthiocarbonylamino group (which may be mono-substituted or poly-substituted preferably by a halogen atom or a cyano group), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), or a $C_3$-$C_6$ cycloalkyl group (which may be mono-substituted or poly-substituted preferably by a halogen atom, a cyano group or a methyl group);

$R_7$ is a $C_2$ haloalkylthio group, a $C_2$-$C_4$ haloalkylsulfinyl group, a $C_2$-$C_4$ haloalkenylthio group, a $C_2$-$C_4$ haloalkenylsulfinyl group, a cyclopropylmethylthio group (which may be mono-substituted or poly-substituted preferably by a halogen atom), or a cyclopropylmethylsulfinyl group (which may be mono-substituted or poly-substituted preferably by a halogen atom);

X is an oxygen atom or a sulfur atom;

each of $R_{1a}$ and $R_{1b}$ which are independent of each other, is a hydrogen atom, a $C_1$-$C_4$ alkyl group (which may be mono-substituted or poly-substituted preferably by a halogen atom or a cyano group), a $C_3$-$C_8$ cycloalkyl group (which may be mono-substituted or poly-substituted preferably by a halogen atom, a $C_1$-$C_4$ alkyl group, a $C_1$-$C_4$ alkoxy group or a cyano group), or a $C_1$-$C_4$ alkoxy group (which may be mono-substituted or poly-substituted preferably by a halogen atom or a cyano group), $R_{1a}$ and $R_{1b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{1a}$ and $R_{1b}$ are bonded;

each of $R_{3a}$ and $R_{3b}$ which are independent of each other, is a hydrogen atom, a cyano group, an amino group, a hydroxy group, a formyl group, a $C_1$-$C_6$ alkyl group (which may be mono-substituted or poly-substituted preferably by a halogen atom, a cyano group, a hydroxy group, a carboxy group, a $C_1$-$C_4$ alkoxy C(=X) group or a trimethylsilyl group), a $C_2$-$C_8$ alkenyl group (which may be mono-substituted or poly-substituted preferably by a halogen atom or a cyano group), a $C_2$-$C_8$ alkynyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_3$-$C_8$ cycloalkyl $C_1$-$C_4$ alkyl group (which may be mono-substituted or poly-substituted preferably by a halogen atom, a cyano group or a methyl group), a $C_1$-$C_8$ alkoxy $C_1$-$C_4$ alkyl group (which may be mono-substituted or poly-substituted preferably by a halogen atom, a cyano group or a trimethylsilyl group), a $C_1$-$C_8$ alkylthio $C_1$-$C_4$ alkyl group (which may be mono-substituted or poly-substituted preferably by a halogen atom or a cyano group), a $C_1$-$C_8$ alkylsulfinyl $C_1$-$C_4$ alkyl group (which may be mono-substituted or poly-substituted preferably by a halogen atom or a cyano group), a $C_1$-$C_8$ alkylsulfonyl $C_1$-$C_4$ alkyl group (which may be mono-substituted or poly-substituted preferably by a halogen atom or a cyano group), a $C_1$-$C_8$ alkylsulfonyl group (which may be mono-substituted or poly-substituted preferably by a halogen atom or a cyano group), a $C_1$-$C_8$ alkylsulfinyl group (which may be mono-substituted or poly-substituted preferably by a halogen atom or a cyano group), a $C_1$-$C_8$ alkylthio group (which may be mono-substituted or poly-substituted preferably by a halogen atom or a cyano group), a $C_2$-$C_8$ alkenylsulfonyl group (which may be mono-substituted or poly-substituted preferably by a halogen atom or a cyano group), a $C_1$-$C_8$ alkoxy $C_1$-$C_4$ alkylsulfonyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a di($C_1$-$C_6$alkyl)aminosulfonyl group (which may be mono-substituted or poly-substituted preferably by a halogen atom or a cyano group), a benzenesulfonyl group which may be mono-substituted or poly-substituted by a substituent group α, a $C_1$-$C_8$ alkyl C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxy C(=X) group or a dimethylamino group), a $C_1$-$C_8$ alkyl C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxycarbonyl group or a dimethylamino group), a $C_1$-$C_8$ alkoxy C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxy C(=X) group or a dimethylamino group), a $C_1$-$C_8$ alkoxy C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$alkylsulfinyl group, a $C_1$-$C_4$ alkylsulfonyl group, a $C_1$-$C_4$ alkoxycarbonyl group or a dimethylamino group), a $C_2$-$C_8$ alkenyl C(=X) group (which may be mono-substituted or poly-substituted preferably by a halogen atom, a cyano group or a hydroxy group), a $C_2$-$C_8$ alkynyl C(=X) group (which may be mono-substituted or poly-substituted preferably by a halogen atom, a cyano group or a hydroxy group), a $C_3$-$C_8$ cycloalkyl C(=X) group (which may be mono-substituted or poly-substituted preferably by a halogen atom, a cyano group or a hydroxy group), a $C_1$-$C_8$ alkyl C(=X)$C_1$-$C_4$ alkyl group (which may be mono-substituted or poly-substituted preferably by a halogen atom, a cyano group or a hydroxy group), an $R_{3c}(R_{3d})$N group, an $R_{3c}(R_{3d})$NC(=X) group, or a $C_1$-$C_8$ alkylthio C(=X) group (which may be mono-substituted or poly-substituted preferably by a halogen atom, a cyano group, a $C_1$-$C_4$ alkyl group, a $C_1$-$C_4$ alkoxy group, a trifluoromethyl group or a hydroxy group);

each of $R_{3c}$ and $R_{3d}$ which are independent of each other, is a hydrogen atom, a $C_1$-$C_4$ alkyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), or a $C_3$-$C_8$ cycloalkyl group (which may be mono-substituted or poly-substituted preferably by a halogen atom, a $C_1$-$C_4$ alkyl group, a $C_1$-$C_4$ alkoxy group or a cyano group);

$R_{3c}$ and $R_{3d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3c}$ and $R_{3d}$ are bonded;

each of $R_{3f}$ and $R_{3g}$ which are independent of each other, is a hydrogen atom, a halogen atom, a $C_1$-$C_8$ alkyl group (which may be mono-substituted or poly-substituted preferably by a halogen atom or a cyano group), a $C_1$-$C_8$ alkoxy group (which may be mono-substituted or poly-substituted preferably by a halogen atom or a cyano group), a $C_3$-$C_8$ cycloalkyl group (which may be mono-substituted or poly-substituted preferably by a halogen atom or a cyano group), an amino group, a dimethylamino group, a $C_1$-$C_4$ alkylthio group, an imidazolyl group, an aryl group which may be mono-substituted or poly-substituted by a substituent group α, or a heteroaryl group which may be mono-substituted or poly-substituted by a substituent group α;

$R_{3f}$ and $R_{3g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3f}$ and $R_{3g}$ are bonded; and each of $R_{3h}$ and $R_{3i}$ which are independent of each other, is hydrogen atom, a $C_1$-$C_4$ alkyl group (which may be mono-substituted or poly-substituted preferably by a halogen atom or a cyano group), a $C_2$-$C_8$ alkenyl group (which may be mono-substituted or poly-substituted preferably by a halogen atom or a cyano group), or a $C_2$-$C_8$ alkynyl group (which may be mono-substituted or poly-substituted preferably by a halogen atom or a cyano group); substituent group α:

a halogen atom, a cyano group, a hydroxy group, a nitro group, an amino group, a carboxy group, a formyl group, a $C_1$-$C_4$ alkyl group (which may be mono-substituted or poly-substituted preferably by a halogen atom, a cyano group or a methoxy group), a $C_1$-$C_4$ alkoxy group (which may be mono-substituted or poly-substituted preferably by a halogen atom or a cyano group), a $C_1$-$C_4$ alkoxycarbonyl group, a $C_3$-$C_8$ cycloalkyl group, a $C_1$-$C_4$ alkylthio group (which may be mono-substituted or poly-substituted preferably by a halogen atom, a cyano group or a methoxy group), a $C_1$-$C_4$ alkylsulfinyl group (which may be mono-substituted or poly-substituted preferably by a halogen atom, a cyano group or a methoxy group), a $C_1$-$C_4$ alkylsulfonyl group (which may be mono-substituted or poly-substituted preferably by a halogen atom, a cyano group or a methoxy group), or a $C_1$-$C_4$ alkylsulfonyloxy group (which may be mono-substituted or poly-substituted preferably by a halogen atom, a cyano group or a methoxy group).

(2) The 3-alkoxy-1-phenyl-pyrazole derivative or an agriculturally acceptable salt thereof according to the above (1), wherein in the above formula [I], $R_1$ is a $C_1$-$C_{10}$ alkyl group (which may be mono-substituted or poly-substituted preferably by a cyano group or a hydroxy group), a $C_1$-$C_{10}$ haloalkyl group, a $C_3$-$C_{10}$ cycloalkyl group (which may be mono-substituted or poly-substituted preferably by a halogen atom, a cyano group, a methyl group, a methoxy group or a trifluoromethyl group), a $C_3$-$C_8$ cycloalkyl $C_1$-$C_8$ alkyl group (which may be mono-substituted or poly-substituted preferably by a halogen atom, a cyano group, a methyl group, a methoxy group or a trifluoromethyl group), a $C_1$-$C_8$ alkoxy $C_1$-$C_8$ alkyl group (which may be mono-substituted or poly-substituted preferably by a halogen atom or a cyano group), a $C_1$-$C_8$ alkoxy $C_2$-$C_8$ alkenyl group (which may be mono-substituted or poly-substituted preferably by a halogen atom or a cyano group), a $C_1$-$C_8$ alkoxy $C_1$-$C_8$ alkoxy $C_1$-$C_8$ alkyl group (which may be mono-substituted or poly-substituted preferably by a halogen atom or a cyano group), a $C_2$-$C_{10}$ alkenyl group (which may be mono-substituted or poly-substituted preferably by a halogen atom or a cyano group), a $C_2$-$C_{10}$ alkynyl group (which may be mono-substituted or poly-substituted preferably by a halogen atom or a cyano group), a $C_2$-$C_{10}$ alkynyloxy $C_1$-$C_6$ alkyl group (which may be mono-substituted or poly-substituted preferably by a halogen atom or a cyano group), a $C_1$-$C_8$ alkylthio $C_1$-$C_8$ alkyl group (which may be mono-substituted or poly-substituted preferably by a halogen atom or a cyano group), a $C_1$-$C_8$ alkylsulfinyl $C_1$-$C_8$ alkyl group (which may be mono-substituted or poly-substituted preferably by a halogen atom or a cyano group), a $C_1$-$C_8$ alkylsulfonyl $C_1$-$C_8$ alkyl group (which may be mono-substituted preferably by a halogen atom or a cyano group), a $C_1$-$C_{10}$ alkylsulfonyl group (which may be mono-substituted or poly-substituted preferably by a halogen atom or a cyano group), a benzenesulfonyl group (which may be mono-substituted or poly-substituted preferably by a halogen atom, a cyano group, a $C_1$-$C_8$ alkyl group, a $C_1$-$C_8$ alkoxy group, a trifluoromethyl group, a difluoromethoxy group, a trifluoromethoxy group or a trifluoromethylthio group), a $C_1$-$C_{10}$ thiocyanatoalkyl group (which may be mono-substituted or poly-substituted preferably by a halogen atom or a cyano group), an aryl-C(=X) group which may be mono-substituted or poly-substituted by a substituent group α, a $C_1$-$C_{10}$ alkyl-C(=X) group (which may be mono-substituted or poly-substituted preferably by a halogen atom, a cyano group, a $C_1$-$C_4$ alkoxy group or a $C_1$-$C_4$ alkylthio group), a $C_1$-$C_8$ alkyl C(=X)$C_1$-$C_4$ alkyl group (which may be mono-substituted or poly-substituted preferably by a halogen atom or a cyano group), a $C_1$-$C_8$ alkoxy C(=X)$C_1$-$C_8$ alkyl group (which may be mono-substituted or poly-substituted preferably by a halogen atom or a cyano group), a pentafluorothio $C_1$-$C_{10}$ alkyl group, a tri($C_1$-$C_3$)alkylsilyl $C_1$-$C_8$ alkyl group (which may be mono-substituted or poly-substituted preferably by a halogen atom or a cyano group), a $C_3$-$C_{10}$ trialkylsilyl group (which may be mono-substituted or poly-substituted preferably by a cyano group or a halogen atom), an aryl group which may be mono-substituted or poly-substituted by a substituent group α, an aryl $C_1$-$C_8$ alkyl group which may be mono-substituted or poly-substituted by a substituent group α, an aryloxy $C_1$-$C_8$ alkyl group which may be mono-substituted or poly-substituted by a substituent group α, an arylthio $C_1$-$C_8$ alkyl group which may be mono-substituted or poly-substituted by a substituent group α, a heteroaryl group which may be mono-substituted or poly-substituted by a substituent group α, a heteroaryl $C_1$-$C_8$ alkyl group which may be mono-substituted or poly-substituted by a substituent group α, a heteroaryloxy $C_1$-$C_8$ alkyl group which may be mono-substituted or poly-substituted by a substituent group α, a heteroarylthio $C_1$-$C_8$ alkyl group which may be mono-substituted or poly-substituted by a substituent group α, a tetrahydrofurfuryl group, a tetrahydrofurfuryl $C_1$-$C_8$ alkyl group which may be mono-substituted or poly-substituted by a substituent group α, an $R_{1a}(R_{1b})$NC(=X) group or an $R_{1a}(R_{1b})$NC(=X)$C_1$-$C_4$ alkyl group;

$R_2$ is a hydrogen atom, a hydroxy group, a halogen atom, a cyano group, a $H_2$NC(=X) group, a carboxy group, a HC(=X) group, a nitro group, an amino group, an azide group, a $C_1$-$C_4$ alkyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_1$-$C_4$ alkoxy $C_1$-$C_4$ alkyl group (which may be mono-substituted or poly-substituted preferably by a halogen atom or a cyano group), a $C_2$-$C_6$ alkenyl group (which may be mono-substituted or poly-substituted preferably by a halogen atom or a cyano group), a $C_2$-$C_6$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), or a $C_1$-$C_4$ alkyl C(=X) group (which may be mono-substituted or poly-substituted preferably by a halogen atom or a cyano group);

$R_3$ is a hydrogen atom, a hydroxy group, a halogen atom, a cyano group, a carboxy group, a HC(=X) group, an $R_{3a}(R_{3b})$N(C=X) group, an azide group, a nitro group, a $C_1$-$C_4$ alkyl group (which may be mono-substituted or poly-substituted preferably by a halogen atom, a cyano group, a hydroxy group, a H₂NC(=X) group, a carboxy group, a $C_1$-$C_4$ alkoxy C(=X) group or 1,2,4-triazole), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_1$-$C_8$ cycloalkyl $C_1$-$C_4$ alkyl group (which may be mono-substituted or poly-substituted preferably by a halogen atom, a cyano group or a methyl group), a $C_1$-$C_6$ alkyl C(=X) group (which may be mono-substituted or poly-substituted preferably by a halogen atom or a cyano group), a $C_2$-$C_8$ alkenyl C(=X) group (which may be mono-substituted or poly-substituted preferably by a halogen atom or a cyano group), a $C_3$-$C_8$ cycloalkyl C(=X) group (which may be mono-substituted or poly-substituted preferably by a halogen atom, a cyano group or a $C_1$-$C_4$alkyl group), a $C_1$-$C_6$ alkoxy group (which may be mono-substituted or poly-substituted preferably by a halogen atom or a cyano group), a $C_3$-$C_8$ cycloalkyloxy group (which may be mono-substituted or poly-substituted preferably by a halogen atom or a cyano group), a $C_1$-$C_6$ alkoxy $C_1$-$C_4$ alkyl group (which may be mono-substituted or poly-substituted preferably by a halogen atom or a cyano group), a $C_1$-$C_6$ alkoxy C(=X) group (which may be mono-substituted or poly-substituted preferably by a halogen atom or a cyano group), a mercapto group, a thiocyanato group, a $C_1$-$C_6$alkylthio group (which may be mono-substituted or poly-substituted preferably by a halogen atom or a cyano group), a $C_1$-$C_6$ alkylsulfinyl group (which may be mono-substituted or poly-substituted preferably by a halogen atom or a cyano group), a $C_1$-$C_6$ alkylsulfonyl group (which may be mono-substituted or poly-substituted preferably by a halogen atom or a cyano group), a $C_3$-$C_8$ cycloalkylthio group (which may be mono-substituted or poly-substituted preferably by a halogen atom or a cyano group), a $C_3$-$C_8$ cycloalkylsulfinyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a $C_1$-$C_6$ alkylsulfonyloxy group (which may be mono-substituted or poly-substituted preferably by a halogen atom or a cyano group), an $R_{3a}(R_{3b})$N group, an $R_{3f}(R_{3g})$C=N group or an $R_{3h}$ON=C($R_{3i}$) group;

each of $R_4$, $R_5$, $R_6$ and $R_8$ which are independent of one another, is a hydrogen atom, an amino group, an azide group, a nitro group, a hydroxy group, a halogen atom, a carbamoyl group, a cyano group, a carboxy group, a HC(=X) group, a $C_1$-$C_4$ alkyl group (which may be mono-substituted or poly-substituted preferably by a halogen atom), a $C_1$-$C_4$ alkoxy group (which may be mono-substituted or poly-substituted preferably by a halogen atom), a formylamino group, a $C_1$-$C_6$alkylcarbonylamino group (which may be mono-substituted or poly-substituted preferably by a halogen atom or a cyano group), a $C_1$-$C_6$ alkylthiocarbonylamino group (which may be mono-substituted or poly-substituted preferably by a halogen atom or a cyano group), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), or a $C_3$-$C_6$ cycloalkyl group (which may be mono-substituted or poly-substituted preferably by a halogen atom, a cyano group or a methyl group);

$R_7$ is a $C_2$-$C_4$ haloalkylthio group, a $C_2$-$C_4$ haloalkylsulfinyl group, a $C_2$-$C_4$haloalkenylthio group, a $C_2$-$C_4$ haloalkenylsulfinyl group, a cyclopropylmethylthio group (which may be mono-substituted or poly-substituted preferably by a halogen atom), or a cyclopropylmethylsulfinyl group (which may be mono-substituted or poly-substituted preferably by a halogen atom);

X is an oxygen atom or a sulfur atom;

each of $R_{1a}$ and $R_{1b}$ which are independent of each other, is a hydrogen atom, a $C_1$-$C_4$ alkyl group (which may be mono-substituted or poly-substituted preferably by a halogen atom or a cyano group), a $C_3$-$C_8$ cycloalkyl group (which may be mono-substituted or poly-substituted preferably by a halogen atom, a $C_1$-$C_4$ alkyl group, a $C_1$-$C_4$ alkoxy group or a cyano group), or a $C_1$-$C_4$ alkoxy group (which may be mono-substituted or poly-substituted preferably by a halogen atom or a cyano group), $R_{1a}$ and $R_{1b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{1a}$ and $R_{1b}$ are bonded;

each of $R_{3a}$ and $R_{3b}$ which are independent of each other, is a hydrogen atom, a cyano group, an amino group, a hydroxy group, a $C_1$-$C_6$ alkyl group (which may be mono-substituted or poly-substituted preferably by a halogen atom, a cyano group, a hydroxy group, a carboxy group, a $C_1$-$C_4$ alkoxy C(=X) group or a trimethylsilyl group), a $C_2$-$C_8$ alkenyl group (which may be mono-substituted or poly-substituted preferably by a halogen atom or a cyano group), a $C_2$-$C_8$ alkynyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_3$-$C_8$ cycloalkyl $C_1$-$C_4$ alkyl group (which may be mono-substituted or poly-substituted preferably by a halogen atom, a cyano group or a methyl group), a $C_1$-$C_8$ alkoxy $C_1$-$C_4$ alkyl group (which may be mono-substituted or poly-substituted preferably by a halogen atom, a cyano group or a trimethylsilyl group), a $C_1$-$C_8$alkylthio $C_1$-$C_4$ alkyl group (which may be mono-substituted or poly-substituted preferably by a halogen atom or a cyano group), a $C_1$-$C_8$ alkylsulfinyl $C_1$-$C_4$ alkyl group (which may be mono-substituted or poly-substituted preferably by a halogen atom or a cyano group), a $C_1$-$C_8$ alkylsulfonyl $C_1$-$C_4$ alkyl group (which may be mono-substituted or poly-substituted preferably by a halogen atom or a cyano group), a $C_1$-$C_8$ alkylsulfonyl group (which may be mono-substituted or poly-substituted preferably by a halogen atom or a cyano group), a $C_1$-$C_8$ alkylsulfinyl group (which may be mono-substituted or poly-substituted preferably by a halogen atom or a cyano group), a $C_1$-$C_8$ alkylthio group (which may be mono-substituted or poly-substituted preferably by a halogen atom or a cyano group), a $C_2$-$C_8$ alkenylsulfonyl group (which may be mono-substituted or poly-substituted preferably by a halogen atom or a cyano group), a $C_1$-$C_8$ alkoxy $C_1$-$C_4$ alkylsulfonyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a di($C_1$-$C_6$ alkyl)aminosulfonyl group (which may be mono-substituted or poly-substituted preferably by a halogen atom or a cyano group), a benzenesulfonyl group which may be mono-substituted or poly-substituted by a substituent group α, a $C_1$-$C_8$ alkyl C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxy C(=X) group or a dimethylamino group), a $C_1$-$C_8$ alkyl C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxycarbonyl group or a dimethylamino group), a $C_1$-$C_8$alkoxy C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxy C(=X) group or a dimethylamino group), a $C_1$-$C_8$ alkoxy C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$ alkoxycarbonyl group or a dimethylamino group), a $C_2$-$C_8$ alkenyl C(=X) group (which may be mono-substituted or poly-substituted preferably by a halogen atom, a cyano group or a hydroxy group), a $C_2$-$C_8$ alkynyl C(=X) group (which may be mono-substituted or poly-substituted preferably by a halogen atom, a cyano group or a hydroxy group), a $C_3$-$C_8$ cycloalkyl C(=X) group (which may be mono-substituted or poly-substituted preferably by a halogen atom, a cyano group or a hydroxy group), a $C_1$-$C_8$ alkyl C(=X)$C_1$-$C_4$ alkyl group (which may be mono-substituted or poly-substituted preferably by a halogen atom, a cyano group or a hydroxy group), an $R_{3c}(R_{3d})$N group, an $R_{3c}(R_{3d})$NC(=X) group, or a $C_1$-$C_8$ alkylthio C(=X) group (which may be mono-substituted or poly-substituted preferably by a halogen atom, a cyano group, a $C_1$-$C_4$ alkyl group, a $C_1$-$C_4$ alkoxy group, a trifluoromethyl group or a hydroxy group);

each of $R_{3c}$ and $R_{3d}$ which are independent of each other, is a hydrogen atom, a $C_1$-$C_4$ alkyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), or a $C_3$-$C_8$ cycloalkyl group (which may be mono-substituted or poly-substituted preferably by a halogen atom, a $C_1$-$C_4$ alkyl group, a $C_1$-$C_4$ alkoxy group or a cyano group);

$R_{3c}$ and $R_{3d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3c}$ and $R_{3d}$ are bonded;

each of $R_{3f}$ and $R_{3g}$ which are independent of each other, is a hydrogen atom, a halogen atom, a $C_1$-$C_8$ alkyl group (which may be mono-substituted or poly-substituted preferably by a halogen atom or a cyano group), a $C_1$-$C_8$ alkoxy group (which may be mono-substituted or poly-substituted preferably by a halogen atom or a cyano group), a $C_3$-$C_8$ cycloalkyl group (which may be mono-substituted or poly-substituted preferably by a halogen atom or a cyano group), an amino group, a dimethylamino group, a $C_1$-$C_4$ alkylthio group, or an imidazolyl group;

$R_{3f}$ and $R_{3g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3f}$ and $R_{3g}$ are bonded; and each of $R_{3h}$ and $R_{3i}$ which are independent of each other, is hydrogen atom, a $C_1$-$C_4$ alkyl group (which may be mono-substituted or poly-substituted preferably by a halogen atom or a cyano group), a $C_2$-$C_8$ alkenyl group (which may be mono-substituted or poly-substituted preferably by a halogen atom or a cyano group), or a $C_2$-$C_8$ alkynyl group (which may be mono-substituted or poly-substituted preferably by a halogen atom or a cyano group); substituent group α:

a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a difluoromethoxy group, a trifluoromethoxy group, a $C_3$-$C_8$ cycloalkyl group, a trifluoromethyl group, a trifluoromethylthio group, a $C_1$-$C_4$ alkylthio group, a $C_1$-$C_4$ alkylsulfinyl group, a $C_1$-$C_4$ alkylsulfonyl group or a $C_1$-$C_4$ alkylsulfonyloxy group.

(3) A 3-alkoxy-1-phenyl-pyrazole derivative represented by the formula [I'] or an agriculturally acceptable salt thereof:

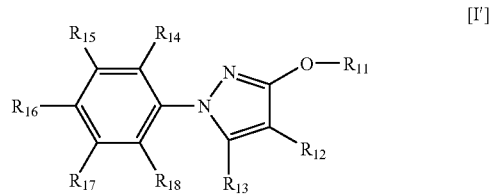

[I']

wherein $R_{11}$ is a $C_1$-$C_3$ alkyl group (which may be mono-substituted or poly-substituted preferably by a cyano group or a hydroxy group), or a $C_1$-$C_3$ haloalkyl group, $R_{12}$ is a hydrogen atom, a hydroxy group, a halogen atom, a cyano group, a nitro group, an amino group or a $C_1$-$C_3$ alkyl group (which may be mono-substituted or poly-substituted preferably by a halogen atom or a cyano group), $R_{13}$ is a hydrogen atom, a hydroxy group, a halogen atom, a cyano group, a carboxy group, a HC(=X) group, an $R_{13c}(R_{13d})$N(C=X) group, a $C_1$-$C_3$ alkyl group (which may be mono-substituted or poly-substituted preferably by a halogen atom, a cyano group, a hydroxy group, a $H_2$NC(=X) group, a carboxy group or a $C_1$-$C_3$ alkoxy C(=X) group), a $C_2$-$C_3$ alkenyl group (which may be mono-substituted or poly-substituted preferably by a halogen atom or a cyano group), a $C_2$-$C_3$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_1$-$C_3$alkyl C(=X) group (which may be mono-substituted or poly-substituted preferably by a halogen atom or a cyano group), a $C_2$-$C_3$ alkenyl C(=X) group (which may be mono-substituted or poly-substituted preferably by a halogen atom or a cyano group), a $C_3$-$C_8$ cycloalkyl C(=X) group (which may be mono-substituted or poly-substituted preferably by a halogen atom, a cyano group or a $C_1$-$C_3$ alkyl group), a $C_1$-$C_3$ alkoxy group (which may be mono-substituted or poly-substituted preferably by a halogen atom or a cyano group), a $C_3$-$C_6$ cycloalkyloxy group (which may be mono-substituted or poly-substituted preferably by a halogen atom or a cyano group), a $C_1$-$C_3$ alkoxy $C_1$-$C_3$ alkyl group (which may be mono-substituted or poly-substituted preferably by a halogen atom or a cyano group), a $C_1$-$C_3$ alkoxy C(=X) group (which may be mono-substituted or poly-substituted preferably by a halogen atom or a cyano group), an $R_{13a}(R_{13b})$N group or an $R_{13c}(R_{13d})$C=N group, each of $R_{14}$, $R_{15}$, $R_{16}$ and $R_{18}$ which are independent of one another, is a hydrogen atom, a hydroxy group, a halogen atom, a cyano group, a $C_1$-$C_3$ alkyl group (which may be mono-substituted or poly-substituted preferably by a halogen atom), or a $C_1$-$C_3$ alkoxy group (which may be mono-substituted or poly-substituted preferably by a halogen atom), $R_{17}$ is a $C_2$-$C_3$ haloalkylthio group or a $C_2$-$C_3$ haloalkylsulfinyl group, X is an oxygen atom or a sulfur atom, each of $R_{13a}$ and $R_{13b}$ which are independent of each other, is a hydrogen atom, a cyano group, a $C_1$-$C_3$ alkyl group (which may be mono-substituted or poly-substituted preferably by a halogen atom, a cyano group, a hydroxy group, a carboxy group, a $C_1$-$C_3$ alkoxy C(=X) group or a trimethylsilyl group), a $C_2$-$C_3$ alkenyl group (which may be mono-substituted or poly-substituted preferably by a halogen atom or a cyano group), a $C_2$-$C_3$ alkynyl group (which may be mono-substituted or poly-substituted preferably by a halogen atom or a cyano group), a $C_1$-$C_3$ alkoxy group (which may be mono-substituted or poly-substituted preferably by a halogen atom or a cyano group), a $C_1$-$C_3$ alkoxy $C_1$-$C_3$ alkyl group (which may be mono-substituted or poly-substituted preferably by a halogen atom, a cyano group or a trimethylsilyl group), a $C_1$-$C_3$ alkyl C(=X) group (which may be mono-substituted or poly-substituted preferably by a halogen atom, a cyano group, a hydroxy group, an acetyl group, a $C_1$-$C_3$ alkoxy group, a $C_1$-$C_3$ alkylthio group, a $C_1$-$C_3$ alkylsulfinyl group, a $C_1$-$C_3$alkylsulfonyl group, a $C_1$-$C_3$ alkoxy C(=X) group or a dimethylamino group), a $C_1$-$C_3$alkoxy C(=X) group (which may be mono-substituted or poly-substituted preferably by a halogen atom, a cyano group, a hydroxy group, an acetyl group, a $C_1$-$C_3$ alkoxy group, a $C_1$-$C_3$ alkylthio group, a $C_1$-$C_3$ alkylsulfinyl group, a $C_1$-$C_3$ alkylsulfonyl group or a $C_1$-$C_3$ alkoxy C(=X) group), a $C_2$-$C_3$ alkenyl C(=X) group (which may be mono-substituted or poly-substituted preferably by a halogen atom, a cyano group or a hydroxy group), a $C_3$-$C_6$ cycloalkyl C(=X) group (which may be mono-substituted or poly-substituted preferably by a halogen atom, a cyano group or a hydroxy group), or an $R_{13c}(R_{13d})$NC(=X) group, and each of $R_{13c}$ and $R_{13d}$ which are independent of each other, is a hydrogen atom, a $C_1$-$C_4$ alkyl group (which may be mono-substituted or poly-substituted preferably by a halogen atom or a cyano group), or a $C_1$-$C_4$ alkoxy group (which may be mono-substituted or poly-substituted preferably by halogen or a cyano group).

(4) A 3-alkoxy-1-phenyl-pyrazole derivative represented by the formula [I"] or an agriculturally acceptable salt thereof:

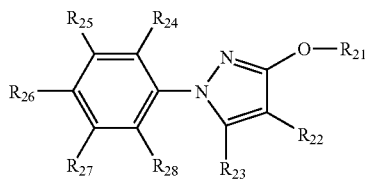

[I"]

wherein $R_{21}$ is a $C_3$-$C_{10}$ alkyl group (which may be mono-substituted or poly-substituted preferably by a cyano group or a hydroxy group), a $C_3$-$C_{10}$ haloalkyl group, a $C_3$-$C_{10}$ cycloalkyl group (which may be mono-substituted or poly-substituted preferably by a halogen atom, a cyano group, a methyl group, a methoxy group or a trifluoromethyl group), a $C_3$-$C_8$ cycloalkyl $C_1$-$C_8$ alkyl group (which may be mono-substituted or poly-substituted preferably by a halogen atom, a cyano group, a methyl group, a methoxy group or a trifluoromethyl group), a $C_1$-$C_8$ alkoxy $C_1$-$C_8$ alkyl group (which may be mono-substituted or poly-substituted preferably by a halogen atom or a cyano group), a $C_1$-$C_8$ alkoxy $C_2$-$C_8$ alkenyl group (which may be mono-substituted or poly-substituted preferably by a halogen atom or a cyano group), a $C_1$-$C_8$ alkoxy $C_1$-$C_8$ alkoxy $C_1$-$C_8$ alkyl group (which may be mono-substituted or poly-substituted preferably by a halogen atom or a cyano group), a $C_2$-$C_{10}$ alkenyl group (which may be mono-substituted or poly-substituted preferably by a halogen atom or a cyano group), a $C_2$-$C_{10}$ alkynyl group (which may be mono-substituted or poly-substituted preferably by a halogen atom or a cyano group), a $C_2$-$C_{10}$ alkynyloxy $C_1$-$C_6$ alkyl group (which may be mono-substituted or poly-substituted preferably by a halogen atom or a cyano group), a $C_1$-$C_8$ alkylthio $C_1$-$C_8$ alkyl group (which may be mono-substituted or poly-substituted preferably by a halogen atom or a cyano group), a $C_1$-$C_8$ alkylsulfinyl $C_1$-$C_8$ alkyl group (which may be mono-substituted or poly-substituted preferably by a halogen atom or a cyano group), a $C_1$-$C_8$ alkylsulfonyl $C_1$-$C_8$ alkyl group (which may be mono-substituted or poly-substituted preferably by a halogen atom or a cyano group), a $C_1$-$C_{10}$ alkylsulfonyl group (which may be mono-substituted or poly-substituted preferably by a halogen atom or a cyano group), a benzenesulfonyl group (which may be mono-substituted or poly-substituted preferably by a halogen atom, a cyano group, a $C_1$-$C_8$ alkyl group, a $C_1$-$C_8$ alkoxy group, a trifluoromethyl group, a difluoromethoxy group, a trifluoromethoxy group or a trifluoromethylthio group), a $C_1$-$C_{10}$ thiocyanatoalkyl group (which may be mono-substituted or poly-substituted preferably by a halogen atom or a cyano group), an aryl-C(=X) group which may be mono-substituted or poly-substituted by a substituent group α', a $C_1$-$C_{10}$ alkyl-C(=X) group (which may be mono-substituted or poly-substituted preferably by a halogen atom, a cyano group, a $C_1$-$C_4$ alkoxy group or a $C_1$-$C_4$ alkylthio group), a $C_1$-$C_8$ alkyl C(=X)$C_1$-$C_4$ alkyl group (which may be mono-substituted or poly-substituted preferably by a halogen atom or a cyano group), a $C_1$-$C_8$ alkoxy C(=X)$C_1$-$C_8$ alkyl group (which may be mono-substituted or poly-substituted preferably by a halogen atom or a cyano group), a pentafluorothio $C_1$-$C_{10}$ alkyl group, a tri($C_1$-$C_3$)alkylsilyl $C_1$-$C_8$ alkyl group (which may be mono-substituted or poly-substituted preferably by a halogen atom or a cyano group), a $C_3$-$C_{10}$ trialkylsilyl group (which may be mono-substituted or poly-substituted by a cyano group or a halogen atom), an aryl group which may be mono-substituted or poly-substituted by a substituent group α', an aryl $C_1$-$C_8$ alkyl group which may be mono-substituted or poly-substituted by a substituent group α', an aryloxy $C_1$-$C_8$ alkyl group which may be mono-substituted or poly-substituted by a substituent group α', an arylthio $C_1$-$C_8$ alkyl group which may be mono-substituted or poly-substituted by a substituent group α', a heteroaryl group which may be mono-substituted or poly-substituted by a substituent group α', a heteroaryl $C_1$-$C_8$ alkyl group which may be mono-substituted or poly-substituted by a substituent group α', a heteroaryloxy $C_1$-$C_8$ alkyl group which may be mono-substituted or poly-substituted by a substituent group α', a heteroarylthio $C_1$-$C_8$ alkyl group which may be mono-substituted or poly-substituted by a substituent group α', a tetrahydrofurfuryl group, a tetrahydrofurfuryl $C_1$-$C_8$ alkyl group which may be mono-substituted or poly-substituted by a substituent group α', an $R_{21a}(R_{21b})$NC(=X) group or an $R_{21a}(R_{21b})$NC(=X)$C_1$-$C_4$ alkyl group;

$R_{22}$ is a hydrogen atom, a hydroxy group, a halogen atom, a cyano group, a $H_2$NC(=X) group, a carboxy group, a HC(=X) group, a nitro group, an amino group, an azide group, a $C_1$-$C_4$ alkyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_1$-$C_4$ alkoxy $C_1$-$C_4$ alkyl group (which may be mono-substituted or poly-substituted preferably by a halogen atom or a cyano group), a $C_2$-$C_6$ alkenyl group (which may be mono-substituted or poly-substituted preferably by a halogen atom or a cyano group), a $C_2$-$C_6$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), or a $C_1$-$C_4$ alkyl C(=X) group (which may be mono-substituted or poly-substituted preferably by a halogen atom or a cyano group);

$R_{23}$ is a hydrogen atom, a hydroxy group, a halogen atom, a cyano group, a carboxy group, a HC(=X) group, an $R_{23a}(R_{23b})$N(C=X) group, an azide group, a nitro group, a $C_1$-$C_4$ alkyl group (which may be mono-substituted or poly-substituted preferably by a halogen atom, a cyano group, a hydroxy group, a $H_2$NC(=X) group, a carboxy group, a $C_1$-$C_4$ alkoxy C(=X) group or 1,2,4-triazole), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_1$-$C_8$ cycloalkyl $C_1$-$C_4$ alkyl group (which may be mono-substituted or poly-substituted preferably by a halogen atom, a cyano group or a methyl group), a $C_1$-$C_6$ alkyl C(=X) group (which may be mono-substituted or poly-substituted preferably by a halogen atom or a cyano group), a $C_2$-$C_8$ alkenyl C(=X) group (which may be mono-substituted or poly-substituted preferably by a halogen atom or a cyano group), a $C_3$-$C_8$ cycloalkyl C(=X) group (which may be mono-substituted or poly-substituted preferably by a halogen atom, a cyano group or a $C_1$-$C_4$alkyl group), a $C_1$-$C_6$ alkoxy group (which may be mono-substituted or poly-substituted preferably by a halogen atom or a cyano group), a $C_3$-$C_8$ cycloalkoxy group (which may be mono-substituted or poly-substituted preferably by a halogen atom or a cyano group), a $C_1$-$C_6$ alkoxy $C_1$-$C_4$ alkyl group (which may be mono-substituted or poly-substituted preferably by a halogen atom or a cyano group), a $C_1$-$C_6$ alkoxy C(=X) group (which may be mono-substituted or poly-substituted preferably by a halogen atom or a cyano group), a mercapto group, a thiocyanato group, a $C_1$-$C_6$alkylthio group (which may be mono-substituted or poly-substituted preferably by a halogen atom or a cyano group), a $C_1$-$C_6$ alkylsulfinyl group (which may be mono-substituted or poly-substituted preferably by a halogen atom or a cyano group), a $C_1$-$C_6$ alkylsulfonyl group (which may be mono-substituted or poly-substituted preferably by a halogen atom or a cyano group), a $C_3$-$C_8$ cycloalkylthio group (which may be mono-substituted or poly-substituted preferably by a halogen atom or a cyano group), a $C_3$-$C_8$ cycloalkylsulfinyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a $C_1$-$C_6$ alkylsulfonyloxy group (which may be mono-substituted or poly-substituted preferably by a halogen atom or a cyano group), an $R_{23a}(R_{23b})$N group, an $R_{23f}(R_{23g})$C=N group or an $R_{23h}$ON=C($R_{23i}$) group;

each of $R_{24}$, $R_{25}$, $R_{26}$ and $R_{28}$ which are independent of one another, is a hydrogen atom, an amino group, an azide group, a nitro group, a hydroxy group, a halogen atom, a carbamoyl group, a cyano group, a carboxy group, a HC(=X) group, a $C_1$-$C_4$ alkyl group (which may be mono-substituted or poly-substituted preferably by a halogen atom), a $C_1$-$C_4$ alkoxy group (which may be mono-substituted or poly-substituted preferably by a halogen atom), a formylamino group, a $C_1$-$C_6$alkylcarbonylamino group (which may be mono-substituted or poly-substituted preferably by a halogen atom or a cyano group), a $C_1$-$C_6$ alkylthiocarbonylamino group (which may be mono-substituted or poly-substituted preferably by a halogen atom or a cyano group), a $C_2$-$C_4$ alkenyl group (which may be mono-substituted or poly-substituted preferably by a halogen atom or a cyano group), a $C_2$-$C_4$ alkynyl group (which may be mono-substituted or poly-substituted preferably by a halogen atom or a cyano group), or a $C_3$-$C_6$ cycloalkyl group (which may be mono-substituted or poly-substituted preferably by a halogen atom, a cyano group or a methyl group);

$R_{27}$ is a $C_2$-$C_4$ haloalkylthio group, a $C_2$-$C_4$ haloalkylsulfinyl group, a $C_2$-$C_4$haloalkenylthio group, a $C_2$-$C_4$ haloalkenylsulfinyl group, a cyclopropylmethylthio group (which may be mono-substituted or poly-substituted preferably by a halogen atom), or a cyclopropylmethylsulfinyl group (which may be mono-substituted or poly-substituted preferably by a halogen atom);

X is an oxygen atom or a sulfur atom;

each of $R_{21a}$ and $R_{21b}$ which are independent of each other, is a hydrogen atom, a $C_1$-$C_4$ alkyl group (which may be mono-substituted or poly-substituted preferably by a halogen atom or a cyano group), a $C_3$-$C_8$ cycloalkyl group (which may be mono-substituted or poly-substituted preferably by a halogen atom, a $C_1$-$C_4$ alkyl group, a $C_1$-$C_4$ alkoxy group or a cyano group), or a $C_1$-$C_4$ alkoxy group (which may be mono-substituted or poly-substituted preferably by a halogen atom or a cyano group), $R_{21a}$ and $R_{21b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{21a}$ and $R_{21b}$ are bonded;

each of $R_{23a}$ and $R_{23b}$ which are independent of each other, is a hydrogen atom, a cyano group, an amino group, a hydroxy group, a $C_1$-$C_6$ alkyl group (which may be mono-substituted or poly-substituted preferably by a halogen atom, a cyano group, a hydroxy group, a carboxy group, a $C_2$-$C_4$ alkoxycarbonyl group or a trimethylsilyl group), a $C_2$-$C_8$ alkenyl group (which may be mono-substituted or poly-substituted preferably by a halogen atom or a cyano group), a $C_2$-$C_8$ alkynyl group (which may be mono-substituted or poly-substituted preferably by a halogen atom or a cyano group), a $C_1$-$C_4$ alkoxy group (which may be mono-substituted or poly-substituted preferably by a halogen atom or a cyano group), a $C_3$-$C_8$ cycloalkyl group (which may be mono-substituted or poly-substituted preferably by a halogen atom, a cyano group or a methyl group), a $C_3$-$C_8$ cycloalkyl $C_1$-$C_4$ alkyl group (which may be mono-substituted or poly-substituted preferably by a halogen atom, a cyano group or a methyl group), a $C_1$-$C_8$ alkoxy $C_1$-$C_4$ alkyl group (which may be mono-substituted or poly-substituted preferably by a halogen atom, a cyano group or a trimethylsilyl group), a $C_1$-$C_8$ alkylthio $C_1$-$C_4$ alkyl group (which may be mono-substituted or poly-substituted preferably by a halogen atom or a cyano group), a $C_1$-$C_8$ alkylsulfinyl $C_1$-$C_4$ alkyl group (which may be mono-substituted or poly-substituted preferably by a halogen atom or a cyano group), a $C_1$-$C_8$ alkylsulfonyl $C_1$-$C_4$ alkyl group (which may be mono-substituted or poly-substituted preferably by a halogen atom or a cyano group), a $C_1$-$C_8$ alkylsulfonyl group (which may be mono-substituted or poly-substituted preferably by a halogen atom or a cyano group), a $C_1$-$C_8$ alkylsulfinyl group (which may be mono-substituted or poly-substituted preferably by a halogen atom or a cyano group), a $C_1$-$C_8$ alkylthio group (which may be mono-substituted or poly-substituted preferably by a halogen atom or a cyano group), a $C_2$-$C_8$ alkenylsulfonyl group (which may be mono-substituted or poly-substituted preferably by a halogen atom or a cyano group), a $C_1$-$C_8$ alkoxy $C_1$-$C_4$ alkylsulfonyl group (which may be mono-substituted or poly-substituted preferably by a halogen atom or a cyano group), a $C_3$-$C_8$ cycloalkylsulfonyl group (which may be mono-substituted or poly-substituted preferably by a halogen atom or a cyano group), a di($C_1$-$C_6$alkyl)aminosulfonyl group (which may be mono-substituted or poly-substituted preferably by a halogen atom or a cyano group), a benzenesulfonyl group which may be mono-substituted or poly-substituted by a substituent group α', a $C_1$-$C_8$ alkyl C(=X) group (which may be mono-substituted or poly-substituted preferably by a halogen atom, a cyano group, a hydroxy group, an acetyl group, a $C_1$-$C_4$ alkoxy group, a $C_1$-$C_4$alkylthio group, a $C_1$-$C_4$ alkylsulfinyl group, a $C_1$-$C_4$ alkylsulfonyl group, a $C_1$-$C_4$alkoxycarbonyl group or a dimethylamino group), a $C_1$-$C_8$ alkyl C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$alkylthio group, a $C_1$-$C_4$ alkylsulfinyl group, a $C_1$-$C_4$ alkylsulfonyl group, a $C_1$-$C_4$alkoxycarbonyl group or a dimethylamino group), a $C_1$-$C_8$ alkoxy C(=X) group (which may be mono-substituted or poly-substituted preferably by a halogen atom, a cyano group, a hydroxy group, an acetyl group, a $C_1$-$C_4$ alkoxy group, a $C_1$-$C_4$ alkylthio group, a $C_1$-$C_4$ alkylsulfinyl group, a $C_1$-$C_4$ alkylsulfonyl group, a $C_1$-$C_4$alkoxycarbonyl group or a dimethylamino group), a $C_1$-$C_8$ alkoxy C(=X)C(=X) group (which may be mono-substituted or poly-substituted preferably by a halogen atom, a cyano group, a hydroxy group, an acetyl group, a $C_1$-$C_4$ alkoxy group, a $C_1$-$C_4$alkylthio group, a $C_1$-$C_4$ alkylsulfinyl group, a $C_1$-$C_4$ alkylsulfonyl group, a $C_1$-$C_4$alkoxycarbonyl group or a dimethylamino group), a $C_2$-$C_8$ alkenyl C(=X) group (which may be mono-substituted or poly-substituted preferably by a halogen atom, a cyano group or a hydroxy group), a $C_2$-$C_8$ alkynyl C(=X) group (which may be mono-substituted or poly-substituted preferably by a halogen atom, a cyano group or a hydroxy group), a $C_3$-$C_8$ cycloalkyl C(=X) group (which may be mono-substituted or poly-substituted preferably by a halogen atom, a cyano group or a hydroxy group), a $C_1$-$C_8$ alkyl C(=X)$C_1$-$C_4$ alkyl group (which may be mono-substituted or poly-substituted preferably by a halogen atom, a cyano group or a hydroxy group), an $R_{23c}(R_{23d})$N group, an $R_{23c}(R_{23d})$NC(=X) group, or a $C_1$-$C_8$ alkylthio C(=X) group (which may be mono-substituted or poly-substituted preferably by halogen, a cyano group, a $C_1$-$C_4$ alkyl group, a $C_1$-$C_4$ alkoxy group, a trifluoromethyl group or a hydroxy group);

each of $R_{23c}$ and $R_{23d}$ which are independent of each other, is a hydrogen atom, a $C_1$-$C_4$ alkyl group (which may be mono-substituted or poly-substituted preferably by halogen or a cyano group), a $C_1$-$C_4$ alkoxy group (which may be mono-substituted or poly-substituted preferably by halogen or a cyano group), or a $C_3$-$C_8$cycloalkyl group (which may be mono-substituted or poly-substituted preferably by a halogen atom, a $C_1$-$C_4$ alkyl group, a $C_1$-$C_4$ alkoxy group or a cyano group);

$R_{23c}$ and $R_{23d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{23c}$ and $R_{23d}$ are bonded;

each of $R_{23f}$ and $R_{23g}$ which are independent of each other, is a hydrogen atom, a halogen atom, a $C_1$-$C_8$ alkyl group (which may be mono-substituted or poly-substituted by halogen or a cyano group), a $C_1$-$C_8$ alkoxy group (which may be mono-substituted or poly-substituted preferably by halogen or a cyano group), a $C_3$-$C_8$cycloalkyl group (which may be mono-substituted or poly-substituted preferably by a halogen atom or a cyano group), an amino group, a dimethylamino group, a $C_1$-$C_4$alkylthio group, or an imidazolyl group;

$R_{23f}$ and $R_{23g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{23f}$ and $R_{23g}$ are bonded; and each of $R_{23h}$ and $R_{23i}$ which are independent of each other, is hydrogen atom, a $C_1$-$C_4$ alkyl group (which may be mono-substituted or poly-substituted preferably by a halogen atom or a cyano group), a $C_2$-$C_8$ alkenyl group (which may be mono-substituted or poly-substituted preferably by a halogen atom or a cyano group), or a $C_2$-$C_8$ alkynyl group (which may be mono-substituted or poly-substituted preferably by a halogen atom or a cyano group);

substituent group α':

a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a difluoromethoxy group, a trifluoromethoxy group, a $C_3$-$C_8$ cycloalkyl group, a trifluoromethyl group, a trifluoromethylthio group, a $C_1$-$C_4$alkylthio group, a $C_1$-$C_4$ alkylsulfinyl group, a $C_1$-$C_4$ alkylsulfonyl group, or a $C_1$-$C_4$alkylsulfonyloxy group.

(5) A pesticide comprising the 3-alkoxy-1-phenyl-pyrazole derivative or an agriculturally acceptable salt thereof as defined in the above (1), (2), (3) or (4) as an active ingredient.

(6) An agricultural or horticultural insecticide comprising the 3-alkoxy-1-phenylpyrazole derivative or an agriculturally acceptable salt thereof as defined in the above (1), (2), (3) or (4) as an active ingredient.

(7) A miticide comprising the 3-alkoxy-1-phenylpyrazole derivative or an agriculturally acceptable salt thereof as defined in the above (1), (2), (3) or (4) as an active ingredient.

(8) A nematicide comprising the 3-alkoxy-1-phenylpyrazole derivative or an agriculturally acceptable salt thereof as defined in the above (1), (2), (3) or (4) as an active ingredient.

(9) A method for controlling a pest, which comprises applying an effective amount of the 3-alkoxy-1-phenylpyrazole derivative or an agriculturally acceptable salt thereof as defined in the above (1), (2), (3) or (4).

(10) The 1-phenyl-pyrazole derivative or a salt thereof according to the above (1), wherein in the formula [I], $R_1$ is a hydrogen atom.

Effects of the Invention

The compounds of the present invention exhibit excellent pesticidal effects against a wide range of pests in agricultural and horticultural fields, and can control pests which have acquired resistance. Especially, they exhibit outstanding effects against mites represented by two-spotted spider mite, Kanzawa spider mite and citrus red mite, pest hemipterans represented by brown rice planthopper, green rice leafhopper and cotton aphid, pest coleoptera represented by rice water weevil, rice leaf beetle and chafers, nematodes represented by southern root-knot nematode, and pest lepidopterans represented by diamondbackmoth, rice stem borer and cotton bollworm. Further, since they are excellent in infiltration, safe and labor-saving application by soil treatment is possible.

BEST MODE FOR CARRYING OUT THE INVENTION

Symbols and terms used in this specification will be described below.

In the present invention, a pesticide means an insecticide, a miticide, a nematicide, etc. for agricultural and horticultural fields, for animals such as domestic animals and pets, for household use and for epidemic prevention.

The halogen atom represents a fluorine atom, a chlorine atom, a bromine atom or an iodine atom.

An expression by a symbol of element and a subscript such as $C_1$-$C_3$ means that the number of elements in the subsequent group is within the range of the number represented by the subscript. For example, in this case, the above expression means a number of carbon atoms of from 1 to 3, and an expression of $C_1$-$C_6$ means a number of carbon atoms of from 1 to 6, and an expression of $C_1$-$C_{12}$ means a number of carbon atoms of from 1 to 12.

The $C_1$-$C_4$ alkyl group means, unless otherwise specified, a linear or branched alkyl group having from 1 to 4 carbon atoms, such as a methyl group, an ethyl group, a n-propyl group, an isopropyl group, a n-butyl group, a s-butyl group, an isobutyl group or a tert-butyl group. The same applies hereinafter.

The $C_1$-$C_6$ alkyl group means, unless otherwise specified, a linear or branched alkyl group having from 1 to 6 carbon atoms, such as the above-exemplified group or a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a neopentyl group, a n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1,2,2-trimethylpropyl group or a 1-ethyl-1-methylpropyl group.

The $C_1$-$C_8$ alkyl group means, unless otherwise specified, a linear or branched alkyl group having from 1 to 8 carbon atoms, such as the above-exemplified group or a n-heptyl group, a 1-methylhexyl group, a 5-methylhexyl group, a 1,1-dimethylpentyl group, a 2,2-dimethylpentyl group, a 4,4-dimethylpentyl group, a 1-ethylpentyl group, a 2-ethylpentyl group, a 1,1,3-trimethylbutyl group, a 1,2,2-trimethylbutyl group, a 1,3,3-trimethylbutyl group, a 2,2,3-trimethylbutyl group, a 2,3,3-trimethylbutyl group, a 1-propylbutyl group, a 1,1,2,2-tetramethylpropyl group, an octyl group, a 1-methylheptyl group, a 3-methylheptyl group, a 6-methylheptyl group, a 2-ethylhexyl group, a 5,5-dimethylhexyl group, a 2,4,4-trimethylpentyl group or a 1-ethyl-1-methylpentyl group.

The $C_1$-$C_{10}$ alkyl group means, unless otherwise specified, a linear or branched alkyl group having from 1 to 10 carbon atoms, such as the above-exemplified group or a nonyl group, a 1-methyloctyl group, a 2-methyloctyl group, a 3-methyloctyl group, a 7-methyloctyl group, a 1-ethylheptyl group, a 6,6-dimethylheptyl group, a 3,5,5-trimethylhexyl group, a decyl group, a 1-methylnonyl group, a 2-methylnonyl group, a 6-methylnonyl group, a 7-methylnonyl group, a 8-methylnonyl group, a 1-ethyloctyl group or a 1-propylheptyl group.

The $C_3$-$C_{10}$ alkyl group means, unless otherwise specified, a linear or branched alkyl group having from 3 to 10 carbon atoms, such as a group having at least 3 carbon atoms exemplified for the above $C_1$-$C_{10}$ alkyl group.

The $C_1$-$C_4$ alkyl C(=X) group means a ($C_1$-$C_4$ alkyl)-C(=X) group wherein the alkyl moiety is as defined above, such as a methylcarbonyl group, a methylthiocarbonyl group, an ethylthiocarbonyl group, an ethylcarbonyl group, a propylcarbonyl group or a butylcarbonyl group.

The $C_1$-$C_6$ alkyl C(=X) group means a ($C_1$-$C_6$ alkyl)-C(=X) group wherein the alkyl moiety is as defined above, such as a methylcarbonyl group, a methylthiocarbonyl group, an ethylcarbonyl group, an ethylthiocarbonyl group, a propylcarbonyl group, a butylcarbonyl group, a pentylcarbonyl group or a hexylcarbonyl group.

The $C_1$-$C_8$ alkyl C(=X) group means a ($C_1$-$C_8$ alkyl)-C(=X) group wherein the alkyl moiety is as defined above, such as the above-exemplified group, or a heptylcarbonyl group or an octylcarbonyl group.

The $C_1$-$C_{10}$ alkyl C(=X) group means a ($C_1$-$C_{10}$ alkyl)-C(=X)— group wherein the alkyl moiety is as defined above, such as the above-exemplified group, or a nonylcarbonyl group or a decylcarbonyl group.

The $C_1$-$C_8$ alkyl C(=X)$C_1$-$C_4$ alkyl group means a ($C_1$-$C_8$ alkyl)-C(=X)—($C_1$-$C_4$alkyl) group wherein the alkyl moiety is as defined above, such as a methylcarbonylmethyl group, a methylthiocarbonylmethyl group, an ethylcarbonylmethyl group, a propylcarbonylmethyl group, a butylcarbonylmethyl group, a pentylcarbonylmethyl group, a hexylcarbonylmethyl group, a heptylcarbonylmethyl group or an octylcarbonylmethyl group.

The $C_1$-$C_8$ alkylcarbonylamino group means a ($C_1$-$C_8$ alkyl)carbonylamino group wherein the alkyl moiety is as defined above, such as a methylcarbonylamino group, an ethylcarbonylamino group, a propylcarbonylamino group, a hexylcarbonylamino group, a heptylcarbonylamino group or an octylcarbonylamino group.

The $C_1$-$C_8$ alkylthiocarbonylamino group means a ($C_1$-$C_8$ alkyl)-C(=S)NH group wherein the alkyl moiety is as defined above, such as a methylthiocarbonylamino group, an ethylthiocarbonylamino group, a propylthiocarbonylamino group, a hexylthiocarbonylamino group, a heptylthiocarbonylamino group or an octylthiocarbonylamino group.

The pentafluorothio $C_1$-$C_{10}$ alkyl group means a $F_5$S—($C_1$-$C_{10}$ alkyl) group wherein the alkyl moiety is as defined above, such as a pentafluorothiomethyl group, a pentafluorothioethyl group, a pentafluorothiopropyl group, a pentafluorothiobutyl group, a pentafluorothiopentyl group, a pentafluorothiohexyl group or a pentafluorothiodecyl group.

The $C_1$-$C_8$ haloalkyl group means, unless otherwise specified, a linear or branched alkyl group having from 1 to 8 carbon atoms substituted by from 1 to 17 identical or different halogen atoms, such as a fluoromethyl group, a chloromethyl group, a bromomethyl group, a difluoromethyl group, a dichloromethyl group, a trifluoromethyl group, a trichloromethyl group, a chlorodifluoromethyl group, a bromodifluoromethyl group, a 2-fluoroethyl group, a 1-chloroethyl group, a 2-chloroethyl group, a 1-bromoethyl group, a 2-bromoethyl group, a 2,2-difluoroethyl group, a 1,2-dichloroethyl group, a 2,2-dichloroethyl group, a 2,2,2-trifluoroethyl group, 2,2,2-trichloroethyl, 1,1,2,2-tetrafluoroethyl, a pentafluoroethyl group, a 2-bromo-2-chloroethyl group, a 2-chloro-1,1,2,2-tetrafluoroethyl group, a 1-chloro-1,2,2,2-tetrafluoroethyl group, a 1-chloropropyl group, a 2-chloropropyl group, a 3-chloropropyl group, a 2-bromopropyl group, a 3-bromopropyl group, a 2-bromo-1-methylethyl group, a 3-iodopropyl group, a 2,3-dichloropropyl group, a 2,3-dibromopropyl group, a 3,3,3-trifluoropropyl group, a 3,3,3-trifluoro-2-propyl group, a 3,3,3-trichloropropyl group, a 3-bromo-3,3-difluoropropyl group, a 2,2-difluoropropyl group, a 3,3-dichloro-3-fluoropropyl group, a 2,2,3,3-tetrafluoropropyl group, a 1-bromo-3,3,3-trifluoropropyl group, a 2,2,3,3,3-pentafluoropropyl group, a 2,2,2-trifluoro-1-trifluoromethylethyl group, a heptafluoropropyl group, a 1,2,2,2-tetrafluoro-1-trifluoromethylethyl group, a 1,1,2,3,3,3-hexafluoropropyl group, a 2-chlorobutyl group, a 3-chlorobutyl group, a 4-chlorobutyl group, a 2-chloro-1,1-dimethylethyl group, a 4-bromobutyl group, a 3-bromo-2-methylpropyl group, a 2-bromo-1,1-dimethylethyl group, a 2,2-dichloro-1,1-dimethylethyl group, a 2-chloro-1-chloromethyl-2-methylethyl group, a 4,4,4-trifluorobutyl group, a 3,3,3-trifluoro-1-methylpropyl group, a 3,3,3-trifluoro-2-methylpropyl group, a 2,3,4-trichlorobutyl group, a 2,2,2-trichloro-1,1-dimethylethyl group, a 4-chloro-4,4-difluorobutyl group, a 4,4-dichloro-4-fluorobutyl group, a 4-bromo-4,4-difluorobutyl group, a 2,4-dibromo-4,4-difluorobutyl group, a 3,4-dichloro-3,4,4-trifluorobutyl group, 3,3-dichloro-4,4,4-trifluorobutyl, a 4-bromo-3,3,4,4-tetrafluorobutyl group, a 4-bromo-3-chloro-3,4,4-trifluorobutyl group, a 2,2,3,3,4,4-hexafluorobutyl group, a 2,2,3,4,4,4-hexafluorobutyl group, a 2,2,2-trifluoro-1-methyl-1-trifluoromethylethyl group, a 3,3,3-trifluoro-2-trifluoromethylpropyl group, a 2,2,3,3,4,4,4-heptafluorobutyl group, a 3,3,4,4,4-pentafluoro-2-butyl group, a 2,3,3,3-tetrafluoro-2-trifluoromethylpropyl group, a 1,1,2,2,3,3,4,4-octafluorobutyl group, a nonafluorobutyl group, perfluoro-tert-butyl, a 4-chloro-1,1,2,2,3,3,4,4-octafluorobutyl group, a 5,5,5-trifluoropentyl group, a 4,4,5,5,5-pentafluoropentyl group, a 3,3,4,4,5,5,5-heptafluoropentyl group, a 3,3,4,4,5,5,5-heptafluoro-2-pentyl group, a 2,2,3,3,4,4,5,5,5-nonafluoropentyl group, a 2,2,3,3,4,4,5,5-octafluoropentyl group, a perfluoropentyl group, a 4,4,5,5,5-pentafluoro-2-butyl group, a 2,2-bis(trifluoromethyl)propyl group, a 2,2,3,3,4,4,5,5,6,6,6-undecafluorohexyl group, a 3,3,4,4,5,5,6,6,6-nonafluorohexyl group, a 4,4,5,5,6,6,6-heptafluorohexyl group, a 2,2,3,3,4,4,5,5,6,6-decafluorohexyl group, a 4,4,4-trifluoro-3,3-bis(trifluoromethyl)butyl group, a perfluorohexyl group, a 1H,1H-perfluoroheptyl group, a 1H,1H,2H,2H-perfluoroheptyl group, a 1H,1H,2H,2H,3H,3H-perfluoroheptyl group, a 1H,1H,7H-perfluoroheptyl group, a perfluoroheptyl group, a 2-(perfluoro-3-methylbutyl)ethyl group, a 1H,1H-perfluorooctyl group, a 1H,1H,2H,2H-perfluorooctyl group, a 1H,1H,2H,2H,3H,3H-perfluorooctyl group, a 6-(perfluorohexyl)ethyl group, a 1H,1H,8H-perfluorooctyl group or a perfluorooctyl group.

The $C_3$-$C_{10}$ haloalkyl group means, unless otherwise specified, a linear or branched alkyl group having from 3 to 10 carbon atoms substituted by from 1 to 21 identical or different halogen atoms, such as a group having at least 3 carbon atoms exemplified for the above $C_1$-$C_8$ haloalkyl group, or a 1H,1H-perfluorononyl group, a 1H,1H,2H,2H-perfluorononyl group, a 1H,1H,2H,2H,3H,3H-perfluorononyl group, a 6-(perfluoro-1-methylethyl)hexyl group, a 1H,1H,9H-perfluorononyl group, a perfluorononyl group, a 1H,1H-perfluorodecyl group, a 1H,1H,2H,2H-perfluorodecyl group, a 1H,1H,2H,2H,3H,3H-perfluorodecyl group, a 6-(perfluorobutyl)hexyl group, a 1H,1H,9H-perfluorodecyl group or a perfluorodecyl group.

The $C_3$-$C_6$ cycloalkyl group means, unless otherwise specified, a cycloalkyl group having from 3 to 6 carbon atoms, such as a cyclopropyl group, a cyclobutyl group, a cyclopentyl group or a cyclohexyl group.

The $C_3$-$C_8$ cycloalkyl group means, unless otherwise specified, a cycloalkyl group having from 3 to 8 carbon atoms, such as the above-exemplified group, or a cycloheptyl group or a cyclooctyl group.

The $C_3$-$C_{10}$ cycloalkyl group means, unless otherwise specified, a cycloalkyl group having from 3 to 10 carbon atoms, such as the above-exemplified group, or a cyclononyl group or a cyclodecyl group.

The $C_3$-$C_8$ cycloalkyl $C_1$-$C_4$ alkyl group means, unless otherwise specified, a ($C_3$-$C_8$ cycloalkyl)-($C_1$-$C_4$ alkyl) group wherein the cycloalkyl moiety and the alkyl moiety are as defined above, such as a cyclopropylmethyl group, a cyclobutylmethyl group, a cyclopentylmethyl group or a cyclohexylmethyl group.

The $C_3$-$C_8$ cycloalkyl $C_1$-$C_8$ alkyl group means, unless otherwise specified, a ($C_3$-$C_8$ cycloalkyl)-($C_1$-$C_8$ alkyl) group wherein the cycloalkyl moiety and the alkyl moiety are as defined above, such as the above-exemplified group, or a cyclopropylpentyl group, a cyclopropyloctyl group, a cyclobutylhexyl group, a cyclopentylheptyl group or a cyclohexyloctyl group.

The $C_3$-$C_8$ cycloalkyl C(=X) group means a ($C_3$-$C_8$ cycloalkyl)-C(=X)— group wherein the cycloalkyl moiety is as defined above, such as a cyclopropylcarbonyl group, a cyclopropylthiocarbonyl group, a cyclobutylcarbonyl group, a cyclopentylcarbonyl group or a cyclohexylcarbonyl group.

The $C_3$-$C_8$ cycloalkyloxy group means a ($C_3$-$C_8$ cycloalkyl)-O— group wherein the cycloalkyl moiety is as defined above, such as a cyclopropyloxy group, a cyclobutyloxy group, a cyclopentyloxy group, a cyclohexyloxy group, a cycloheptyloxy group or a cyclooctyloxy group.

The $C_3$-$C_8$ cyclo alkylthio group means a ($C_3$-$C_8$ cycloalkyl)-S— group wherein the cycloalkyl moiety is as defined above, such as a cyclopropylthio group, a cyclobutylthio group, a cyclopentylthio group, a cyclohexylthio group, a cycloheptylthio group or a cyclooctylthio group.

The $C_3$-$C_8$ cycloalkylsulfinyl group means a ($C_3$-$C_8$ cycloalkyl)-SO— group wherein the cycloalkyl moiety is as defined above, such as a cyclopropylsulfinyl group, a cyclobutylsulfinyl group, a cyclopentylsulfinyl group, a cyclohexylsulfinyl group, a cycloheptylsulfinyl group or a cyclooctylsulfinyl group.

The $C_3$-$C_8$ cycloalkylsulfonyl group means a ($C_3$-$C_8$ cycloalkyl)-$SO_2$— group wherein the cycloalkyl moiety is as defined above, such as a cyclopropylsulfonyl group, a cyclobutylsulfonyl group, a cyclopentylsulfonyl group, a cyclohexylsulfonyl group, a cycloheptylsulfonyl group or a cyclooctylsulfonyl group.

The $C_3$-$C_8$ cycloalkylsulfonyloxy group means a ($C_3$-$C_8$ cycloalkyl)-$SO_2$—O— group wherein the cycloalkyl moiety is as defined above, such as a cyclopropylsulfonyloxy group, a cyclobutylsulfonyloxy group, a cyclopentylsulfonyloxy group, a cyclohexylsulfonyloxy group, a cycloheptylsulfonyloxy group or a cyclooctylsulfonyloxy group.

The $C_2$-$C_4$ alkenyl group means, unless otherwise specified, a linear or branched alkenyl group having from 2 to 4 carbon atoms, such as a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group or a 1,3-butadienyl group.

The $C_2$-$C_8$ alkenyl group means, unless otherwise specified, a linear or branched alkenyl group having from 2 to 6 carbon atoms, such as the above-exemplified group, or 1-pentenyl, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, a 1-propyl-2-propenyl group, a 2-hexenyl group, a 1-methyl-1-pentenyl group, a 1-ethyl-2-butenyl group, a 3-hexenyl group, a 4-hexenyl group, a 5-hexenyl group, a 1-methyl-4-pentenyl group, a 1-ethyl-3-butenyl group, a 1-(isobutyl)vinyl group, a 1-ethyl-1-methyl-2-propenyl group, a 1-ethyl-2-methyl-2-propenyl group, a 1-(isopropyl)-2-propenyl group, a 2-methyl-2-pentenyl group, a 3-methyl-3-pentenyl group, a 4-methyl-3-pentenyl group, a 1,3-dimethyl-2-butenyl group, a 1,1-dimethyl-3-butenyl group, a 3-methyl-4-pentenyl group, a 4-methyl-4-pentenyl group, a 1,2-dimethyl-3-butenyl group, a 1,3-dimethyl-3-butenyl group, a 1,1,2-trimethyl-2-propenyl group, a 1,5-hexadienyl group, a 1-vinyl-3-butenyl group or a 2,4-hexadienyl group.

The $C_2$-$C_8$ alkenyl group means, unless otherwise specified, a linear or branched alkenyl group having from 2 to 8 carbon atoms, such as the above-exemplified group, or a 1-octenyl group or a 2-octenyl group.

The $C_2$-$C_{10}$ alkenyl group means, unless otherwise specified, a linear or branched alkenyl group having from 2 to 10 carbon atoms, such as the above-exemplified group, or a 1-nonenyl group, 1-decenyl group or a 2-decenyl group.

The $C_2$-$C_8$ alkenyl C(=X) group means a ($C_2$-$C_8$ alkenyl)-C(=X)— group wherein the alkenyl moiety is as defined above, such as an ethenylcarbonyl group, an ethenylthiocarbonyl group, a 2-propenylcarbonyl group, a 2-butenylcarbonyl group, a 3-pentenylcarbonyl group or a 3-hexenylcarbonyl group.

The $C_2$-$C_4$ alkynyl group means, unless otherwise specified, a linear or branched alkynyl group having from 2 to 4 carbon atoms, such as an ethinyl group, a 1-propynyl group, a 2-propynyl group, a 1-butynyl group, a 1-methyl-2-propynyl group, a 2-butynyl group or a 3-butynyl group.

The $C_2$-$C_6$ alkynyl group means, unless otherwise specified, a linear or branched alkynyl group having from 2 to 6 carbon atoms, such as the above-exemplified group, or a 1-pentynyl group, a 1-ethyl-2-propynyl group, a 2-pentynyl group, a 3-pentynyl group, a 1-methyl-2-butynyl group, a 4-pentynyl group, a 1-methyl-3-butynyl group, a 2-methyl-3-butynyl group, a 1-hexynyl group, a i-(n-propyl)-2-propynyl group, a 2-hexynyl group, a 1-ethyl-2-butynyl group, a 3-hexynyl group, a 1-methyl-2-pentynyl group, a 1-methyl-3-pentynyl group, a 4-methyl-1-pentynyl group, a 3-methyl-1-pentynyl group, a 5-hexynyl group, a 1-ethyl-3-butynyl group, a 1-ethyl-1-methyl-2-propynyl group, a 1-(isopropyl)-2-propynyl group, a 1,1-dimethyl-2-butynyl group or a 2,2-dimethyl-3-butynyl group.

The $C_2$-$C_8$ alkynyl group means, unless otherwise specified, a linear or branched alkynyl group having from 2 to 8 carbon atoms, such as the above-exemplified group, or a 2-octynyl group.

The $C_2$-$C_{10}$ alkynyl group means, unless otherwise specified, a linear or branched alkynyl group having from 2 to 10 carbon atoms, such as the above-exemplified group, or a 2-nonynyl group or a 2-decynyl group.

The $C_2$-$C_{10}$ alkynyloxy $C_1$-$C_6$ alkyl group means a ($C_2$-$C_{10}$ alkynyl)-O—($C_1$-$C_6$alkyl) group wherein the alkyl moiety and the alkynyl moiety are as defined above, such as an ethinyloxymethyl group, a 1-propynyloxyethyl group, a 1-butynyloxypropyl group, a 1-pentynyloxybutyl group, a 1-hexynyloxypentyl group or a 1-heptynyloxyhexyl group.

The $C_2$-$C_8$ alkynyl C(=X) group means a ($C_2$-$C_8$ alkynyl)-C(=X)— group wherein the alkynyl moiety is as defined above, such as an ethinylcarbonyl group, an ethinylthiocarbonyl group, a 1-propynylcarbonyl group, an 1-propynylthiocarbonyl group, a 2-propynylcarbonyl group, a 1-butynylcarbonyl group, a 1-methyl-2-propynylcarbonyl group, a 2-butynylcarbonyl group, a 3-butynylcarbonyl group, a 1-pentynylcarbonyl group, a 1-ethyl-2-propynylcarbonyl group, a 2-pentynylcarbonyl group, a 3-pentynylcarbonyl group, a 1-methyl-2-butynylcarbonyl group, a 4-pentynylcarbonyl group, a 1-methyl-3-butynylcarbonyl group, a 2-methyl-3-butynylcarbonyl group, a 1-hexynylcarbonyl group, a 1-(n-propyl)-2-propynylcarbonyl group, a 2-hexynylcarbonyl group, a 1-ethyl-2-butynylcarbonyl group, a 3-hexynylcarbonyl group, a 1-methyl-2-pentynylcarbonyl group, a 1-methyl-3-pentynylcarbonyl group, a 4-methyl-1-pentynylcarbonyl group, a 3-methyl-1-pentynylcarbonyl group, a 5-hexynylcarbonyl group, a 1-ethyl-3-butynylcarbonyl group, a 1-ethyl-1-methyl-2-propynylcarbonyl group, a 1-(isopropyl)-2-propynylcarbonyl group, a 1,1-dimethyl-2-butynylcarbonyl group, a 2,2-dimethyl-3-butynylcarbonyl group or a 2-octynylcarbonyl group.

The $C_1$-$C_4$ alkoxy group means a ($C_1$-$C_4$ alkyl)-O— group wherein the alkyl moiety is as defined above, such as a methoxy group, an ethoxy group, a n-propoxy group, an isopropoxy group, a n-butoxy group, an isobutoxy group or a tert-butoxy group.

The $C_1$-$C_6$ alkoxy group means an (alkyl)-O— group having from 1 to 6 carbon atoms wherein the alkyl moiety is as defined above, such as a methoxy group, an ethoxy group, a n-propoxy group, an isopropoxy group, a n-butoxy group, an isobutoxy group, a tert-butoxy group, a pentyloxy group, an isopentyloxy group, a hexyloxy group or an isohexyloxy group.

The $C_1$-$C_8$ alkoxy group means a ($C_1$-$C_8$ alkyl)-O— group wherein the alkyl moiety is as defined above, such as the above-exemplified group, or a heptyloxy group or an octyloxy group.

The $C_1$-$C_4$ alkoxy(C=X) group means a ($C_1$-$C_4$ alkoxy)C(=X)— group wherein the alkoxy moiety is as defined above, such as a group of e.g. methoxycarbonyl, methoxythiocarbonyl, ethoxycarbonyl, ethoxythiocarbonyl, n-propoxycarbonyl, isopropoxycarbonyl, n-butoxycarbonyl, isobutoxycarbonyl or tert-butoxycarbonyl.

The $C_1$-$C_4$ alkoxy $C_1$-$C_4$ alkyl group means a ($C_1$-$C_4$ alkoxy)-($C_1$-$C_4$ alkyl) group wherein the alkyl moiety and the alkoxy moiety are as defined above, such as a methoxymethyl group, a methoxypropyl group, a methoxybutyl group, an ethoxymethyl group, an ethoxypropyl group, an ethoxybutyl group, an isopropoxymethyl group, a n-butoxymethyl group, an isobutoxymethyl group, a 2-methoxyethyl group, a 2-ethoxyethyl group, a 2-propoxyethyl group, a 2-isopropoxyethyl group, a 2-(n-butoxy)ethyl group, a 2-isobutoxyethyl group, a 3-methoxypropyl group, a 3-ethoxypropyl group or a 4-methoxybutyl group.

The $C_1$-$C_8$ alkoxy $C_1$-$C_4$ alkyl group means a ($C_1$-$C_8$ alkoxy)-($C_1$-$C_4$ alkyl) group wherein the alkyl moiety and the alkoxy moiety are as defined above, such as the above-exemplified group, or a pentyloxymethyl group, a heptyloxymethyl group or an octyloxymethyl group.

The $C_1$-$C_8$ alkoxy $C_1$-$C_8$ alkyl group means a ($C_1$-$C_8$ alkoxy)-($C_1$-$C_8$ alkyl) group wherein the alkyl moiety and the alkoxy moiety are as defined above, such as a methoxymethyl group, an ethoxymethyl group, an isopropoxymethyl group, a n-butoxymethyl group, an isobutoxymethyl group, a pentyloxymethyl group, a 2-methoxyethyl group, a 2-ethoxyethyl group, a 2-propoxyethyl group, a 2-isopropoxyethyl group, a 2-(n-butoxy)ethyl group, a 2-isobutoxyethyl group, a 3-methoxypropyl group, a 3-ethoxypropyl group, a 4-methoxybutyl group, a 5-methoxypentyl group or a 6-methoxyhexyl group.

The $C_1$-$C_4$ alkoxy $C_1$-$C_4$ alkoxy $C_1$-$C_4$ alkyl group means a ($C_1$-$C_4$ alkoxy)-($C_1$-$C_4$ alkoxy)-($C_1$-$C_4$ alkyl) group wherein the alkyl moiety and the alkoxy moieties are as defined above, such as a 2-methoxyethoxymethyl group, a 2-(2-methoxyethoxy)ethyl group, a 2-{2-trifluoromethoxy-1,1,2,2-tetrafluoroethoxy)}-2,2-difluoroethyl group or a 2-{2-perfluoropropoxy(perfluoropropoxy)}-1,1,2-trifluoroethyl group.

The $C_1$-$C_8$ alkoxy $C_1$-$C_8$ alkoxy $C_1$-$C_8$ alkyl group (which may be mono-substituted or poly-substituted by a halogen atom or a cyano group) means a ($C_1$-$C_8$alkoxy)-($C_1$-$C_8$ alkoxy)-($C_1$-$C_8$ alkyl) group wherein the alkyl moiety and the alkoxy moieties are as defined above, and these moieties may be mono-substituted or poly-substituted by a halogen atom or a cyano group, such as a 2-methoxyethoxymethyl group, a 2-(2-methoxyethoxy)ethyl group, a 2-{2-trifluoromethoxy-1,1,2,2-tetrafluoroethoxy)}-2,2-difluoroethyl group or a 2-{2-perfluoropropoxy(perfluoropropoxy)}-1,1,2-trifluoroethyl group.

The $C_1$-$C_4$ alkoxy C(=X) group means a ($C_1$-$C_4$ alkyl)-O—C(=X)— group wherein the alkyl moiety is as defined above, such as a methoxycarbonyl group, a methoxythiocarbonyl group, an ethoxycarbonyl group, an ethoxythiocarbonyl group, a n-propoxycarbonyl group, an isopropoxycarbonyl group or a butoxycarbonyl group.

The $C_1$-$C_8$ alkoxy(C=X) group means a ($C_1$-$C_8$ alkyl)-O—C(=X)— group wherein the alkyl moiety is as defined above, such as the above-exemplified group, or a pentyloxycarbonyl group, a hexyloxycarbonyl group, a heptyloxycarbonyl group or an octyloxycarbonyl group.

The $C_1$-$C_8$ alkoxy C(=X)$C_1$-$C_8$ alkyl group means a ($C_1$-$C_8$ alkyl)-O—C(=X)—($C_1$-$C_8$ alkyl)- group wherein the alkyl moieties are as defined above, such as a methoxycarbonylmethyl group, an ethoxycarbonylmethyl group, a propoxycarbonylmethyl group, a butoxycarbonylmethyl group, a pentyloxycarbonylmethyl group, a hexyloxycarbonylmethyl group, a heptyloxycarbonylmethyl group or an octyloxycarbonylmethyl group.

The $C_1$-$C_8$ alkoxy $C_2$-$C_8$ alkenyl group means a ($C_1$-$C_8$ alkoxy)-($C_2$-$C_8$alkenyl) group wherein the alkyl moiety and the alkoxy moiety are as defined above, such as a methoxyethenyl group, a methoxypropenyl group, a methoxybutenyl group, a methoxymenthenyl group, a methoxyhexyl group, a methoxyheptenyl group or a methoxyoctenyl group.

The $C_1$-$C_8$ alkoxy $C_1$-$C_4$ alkylsulfonyl group means a ($C_1$-$C_8$ alkoxy)-($C_1$-$C_4$ alkyl)-$SO_2$— group wherein the alkyl moiety and the alkoxy moiety are as defined above, such as a methoxymethylsulfonyl group, an ethoxymethylsulfonyl group, a butoxymethylsulfonyl group or an octyloxymethylsulfonyl group.

The $C_1$-$C_4$ alkylthio group means a ($C_1$-$C_4$ alkyl)-S— group wherein the alkyl moiety is as defined above, such as a methylthio group, an ethylthio group, a n-propylthio group, an isopropylthio group, a butylthio group, an isobutylthio group or a tert-butylthio group.

The $C_1$-$C_8$ alkylthio group means a ($C_1$-$C_8$ alkyl)-S— group wherein the alkyl moiety is as defined above, such as the above-exemplified group, or a pentylthio group, a hexylthio group, a heptylthio group or an octylthio group.

The $C_1$-$C_8$ alkylthio $C_1$-$C_4$ alkyl group means a ($C_1$-$C_8$ alkyl)-S—($C_1$-$C_4$ alkyl)- group wherein the alkyl moiety is as defined above, such as a methylthiomethyl group, a methylthioethyl group, a methylthiopropyl group, a methylthiobutyl group, an ethylthiomethyl group, a propylthiomethyl group, a butylthiomethyl group, a pentylthiomethyl group, a hexylthiomethyl group or an octylthiomethyl group.

The $C_1$-$C_8$ alkylthio $C_1$-$C_8$ alkyl group means a ($C_1$-$C_8$ alkyl)-S—($C_1$-$C_8$ alkyl)- group wherein the alkyl moieties are as defined above, such as the above-exemplified group, or a propylthiopentyl group, a butylthiohexyl group, a pentylthiooctyl group or a hexylthiooctyl group.

The $C_1$-$C_4$ alkylsulfinyl group means a ($C_1$-$C_4$ alkyl)-SO— group wherein the alkyl moiety is as defined above, such as a methylsulfinyl group, an ethylsulfinyl group, a n-propylsulfinyl group, an isopropylsulfinyl group, a butylsulfinyl group, an isobutylsulfinyl group or a tert-butylsulfinyl group.

The $C_1$-$C_8$ alkylsulfinyl group means a ($C_1$-$C_8$ alkyl)-SO— group wherein the alkyl moiety is as defined above, such as the above-exemplified group, or an octylsulfinyl group.

The $C_1$-$C_8$ alkylsulfinyl $C_1$-$C_4$ alkyl group means a ($C_1$-$C_8$ alkyl)-SO—($C_1$-$C_4$alkyl) group wherein the alkyl moieties are as defined above, such as a methylsulfinylmethyl group, an ethylsulfinylmethyl group, a n-propylsulfinylmethyl group, an isopropylsulfinylmethyl group, a butylsulfinylmethyl group, an isobutylsulfinylmethyl group, a tert-butylsulfinylmethyl group, a pentylsulfinylmethyl group or a hexylsulfinylmethyl group.

The $C_1$-$C_8$ alkylsulfinyl $C_1$-$C_8$ alkyl group means a ($C_1$-$C_8$ alkyl)-SO—($C_1$-$C_8$alkyl) group wherein the alkyl moiety is as defined above, such as the above-exemplified group, or a pentylsulfinylpentyl group or a hexylsulfinyloctyl group.

The $C_1$-$C_4$ alkylsulfonyl group means a ($C_1$-$C_4$ alkyl)-$SO_2$— group wherein the alkyl moiety is as defined above, such as a methylsulfonyl group, an ethylsulfonyl group, a n-propylsulfonyl group or an isopropylsulfonyl group.

The $C_1$-$C_8$ alkylsulfonyl group means a ($C_1$-$C_8$ alkyl)-$SO_2$— group wherein the alkyl moiety is as defined above, such as the above-exemplified group, or a pentylsulfonyl group, a hexylsulfonyl group, a heptylsulfonyl group or an octylsulfonyl group.

The $C_1$-$C_{10}$ alkylsulfonyl group means a ($C_1$-$C_{10}$ alkyl)-$SO_2$— group wherein the alkyl moiety is as defined above, such as the above-exemplified group, or a nonylsulfonyl group or a decylsulfonyl group.

The $C_1$-$C_8$ alkylsulfonyl $C_1$-$C_4$ alkyl group means a ($C_1$-$C_8$ alkyl)-$SO_2$—($C_1$-$C_4$alkyl) group wherein the alkyl moieties are as defined above, such as a methylsulfonylmethyl group, an ethylsulfonylethyl group, a n-propylsulfonylpropyl group or an isopropylsulfonylpropyl group.

The $C_1$-$C_8$ alkylsulfonyl $C_1$-$C_8$ alkyl group means a ($C_1$-$C_8$ alkyl)-$SO_2$—($C_1$-$C_8$alkyl) group wherein the alkyl moieties are as defined above, such as the above-exemplified group, or a methylsulfonylpentyl group, an ethylsulfonylhexyl group, a n-propylsulfonylhexyl group or an isopropylsulfonyloctyl group.

The $C_1$-$C_4$ alkylsulfonyloxy group means a ($C_1$-$C_4$ alkyl)-$SO_2$—O— group wherein the alkyl moiety is as defined above, such as a methylsulfonyloxy group, an ethylsulfonyloxy group, a n-propylsulfonyloxy group or an isopropylsulfonyloxy group.

The $C_2$-$C_8$ alkenylsulfonyl group means a ($C_2$-$C_8$ alkenyl)-$SO_2$— group wherein the alkenyl group is as defined above, such as a vinylsulfonyl group, a 1-propenylsulfonyl group, an isopropenylsulfonyl group, a 2-propenylsulfonyl group, a 1-butenylsulfonyl group, a 1-methyl-1-propenylsulfonyl group, a 2-butenylsulfonyl group, a 1-methyl-2-propenylsulfonyl group, a 3-butenylsulfonyl group, a 2-methyl-1-propenylsulfonyl group, a 2-methyl-2-propenylsulfonyl group or a 1,3-butadienylsulfonyl group.

The $C_2$-$C_8$ thiocyanatoalkyl group means a NCS—($C_2$-$C_8$ alkyl) group wherein the alkyl moiety is as defined above, such as a thiocyanatoethyl group, a thiocyanatopropyl group, a thiocyanatobutyl group, a thiocyanatopentyl group or a thiocyanatohexyl group.

The $C_1$-$C_{10}$ thiocyanatoalkyl group means a NCS—($C_1$-$C_{10}$ alkyl) group wherein the alkyl moiety is as defined above, such as a thiocyanatomethyl group, a thiocyanatoethyl group, a thiocyanatopropyl group, a thiocyanatobutyl group, a thiocyanatopentyl group, a thiocyanatohexyl group or a thiocyanatodecyl group.

The $C_1$-$C_8$ haloalkylcarbonyl group means a ($C_1$-$C_8$ haloalkyl)-C(=O)— group wherein the haloalkyl moiety is as defined above, such as a chloroacetyl group, a chlorodifluoroacetyl group, a difluoroacetyl group, a trifluoroacetyl group, a dichloroacetyl group, a trichloroacetyl group or a pentafluoropropionyl group.

The $C_1$-$C_8$ alkyl C(=X)C(=X) group means a ($C_1$-$C_4$ alkyl)-C(=X)—C(=X) group wherein the alkyl moiety is as defined above, such as a methylcarbonylcarbonyl group, a methylthiocarbonylcarbonyl group, an ethylcarbonylthiocarbonyl group, an ethylthiocarbonylcarbonyl group, a propylcarbonylcarbonyl group, a butylthiocarbonylcarbonyl group, a pentylcarbonylthiocarbonyl group or a hexylcarbonylcarbonyl group.

The $C_1$-$C_8$ alkoxy C(=X)C(=X) group means a ($C_1$-$C_8$ alkyl)-O—C(=X)—C(=X) group wherein the alkyl moiety is as defined above, such as an ethoxycarbonylcarbonyl group, a methoxythiocarbonylcarbonyl group, an ethoxycarbonylcarbonyl group, an ethoxycarbonylthiocarbonyl group, a n-propoxycarbonylcarbonyl group, an isopropoxycarbonylcarbonyl group, a butoxythiocarbonylcarbonyl group, a pentyloxythiocarbonylcarbonyl group, a hexyloxycarbonylthiocarbonyl group, a heptyloxycarbonylthiocarbonyl group or an octyloxythiocarbonylcarbonyl group.

The aryl group means an aromatic hydrocarbon group, such as phenyl or naphthyl.

The aryl ($C_1$-$C_4$) alkyl group means an (aryl)-($C_1$-$C_4$ alkyl) group wherein the aryl and the alkyl moiety are as defined above, such as a benzyl group, a phenethyl group, a 3-phenylpropyl group or a naphthylmethyl group.

The aryl $C_1$-$C_8$ alkyl group means an (aryl)-($C_1$-$C_8$ alkyl) group wherein the aryl and the alkyl moiety are as defined above, such as the above-exemplified group, or a 5-phenylpentyl group, a 6-phenylhexyl group or a 7-phenylheptyl group.

The aryloxy $C_1$-$C_8$ alkyl group means an (aryl)-O—($C_1$-$C_8$ alkyl) group wherein the aryl and the alkyl moiety are as defined above, such as a phenoxymethyl group, a 2-phenoxyethyl group, a 3-phenoxypropyl group, a 1-naphthyloxymethyl group, a 2-naphthyloxymethyl group or a 2-(1-naphthyloxy)ethyl group.

The arylthio $C_1$-$C_8$ alkyl group means an (aryl)-S—($C_1$-$C_8$ alkyl) group wherein the aryl and the alkyl moiety are as defined above, such as a phenylthiomethyl group, a phenylthiomethyl group, a naphthylthiomethyl group or a naphthylthioethyl group.

The aryl C(=X) group may, for example, be a phenylcarbonyl group, a phenylthiocarbonyl group or a naphthylcarbonylethyl group.

The aryl C(=X)$C_1$-$C_4$ alkyl group may, for example, be a phenylcarbonylmethyl group or a phenylcarbonylethyl group.

The aryloxy $C_1$-$C_8$ alkyl group may, for example, be a phenoxymethyl group or a phenoxyethyl group.

The arylthio $C_1$-$C_8$ alkyl group may, for example, be a phenylthiomethyl group or a phenylthioethyl group.

The heteroaryl group means an aromatic heterocyclic group or a condensed heterocyclic group, such as a pyrrolyl group, a furanyl group, a thienyl group, an oxazolyl group, an isoxazolyl group, an imidazolyl group, a 1,2,4-oxadiazolyl group, a 1,2,3-oxadiazolyl group, a 1,3,4-oxadiazolyl group, a 1,2,4-triazolyl group, a 1,2,3-triazolyl group, a thiazolyl group, an isothiazolyl group, a 1,2,4-thiadiazolyl group, a 1,2,3-thiadiazolyl group, a 1,3,4-thiadiazolyl group, a pyridyl group, a pyrimidinyl group, a pyrazinyl group, a pyridazinyl group, a 1,3,5-triazinyl group, a 1,2,4-triazinyl group, a benzoxazolyl group, a benzimidazolyl group, a benzotriazolyl group, a benzothiazolyl group, a quinolinyl group, a quinazolinyl group, a quinoxalinyl group, a phthalazinyl group or a naphthylidinyl group.

The heteroaryl $C_1$-$C_4$ alkyl group means a (heteroaryl)-($C_1$-$C_4$ alkyl) group wherein the heteroaryl and the alkyl moiety are as defined above, such as a thienylmethyl group or a pyridylmethyl group.

The heteroaryl $C_1$-$C_8$ alkyl group means a (heteroaryl)-($C_1$-$C_8$ alkyl) group wherein the heteroaryl and the alkyl moiety are as defined above, such as a 2-thienylmethyl group, a 3-thienylmethyl group, a 2-pyridylmethyl group or a 3-pyridylmethyl group.

The heteroaryl $C_1$-$C_4$ alkyl C(=X) group means a (heteroaryl)-($C_1$-$C_4$ alkyl)-C(=X)— group wherein the heteroaryl and the alkyl moiety are as defined above, such as a 2-thienylmethylcarbonyl group, a 3-thienylmethylcarbonyl group, a 2-pyridylmethylcarbonyl group or a 3-pyridylmethylcarbonyl group.

The heteroaryloxy $C_1$-$C_8$ alkyl group means a (heteroaryl)-O—($C_1$-$C_8$ alkyl) group wherein the heteroaryl and the alkyl moiety are as defined above, such as a 2-pyridyloxymethyl group or a 3-pyridyloxyethyl group.

The heteroarylthio $C_1$-$C_8$ alkyl group means a (heteroaryl)-S—($C_1$-$C_8$ alkyl) group wherein the heteroaryl and the alkyl moiety are as defined above, such as a 2-pyridylthiomethyl group or a 3-pyridylthioethyl group.

The tetrahydrofurfuryl $C_1$-$C_8$ alkyl group means a (tetrahydrofurfuryl)-($C_1$-$C_8$alkyl) group wherein the alkyl moiety is as defined above, such as a 2-tetrahydrofurfurylmethyl group, a 3-tetrahydrofurfurylmethyl group, a 2-(2-tetrahydrofurfuryl)ethyl group or a 2-(3-tetrahydrofurfuryl)ethyl group.

The tri($C_1$-$C_3$)alkylsilyl $C_1$-$C_8$ alkyl group may, for example, be a trimethylsilylmethyl group, a 2-trimethylsilylethyl group, a 3-trimethylsilylpropyl group or a 4-trimethylsilylbutyl group.

The $C_3$-$C_{10}$ trialkylsilyl group may, for example, be a trimethylsilyl group, a triethylsilyl group or a tripropylsilyl group.

The $C_2$-$C_4$ haloalkylthio group may, for example, be a 1-chloroethylthio group, a 2-fluoroethylthio group, a 2,2-difluoroethylthio group, a 2,2,2-trifluoroethylthio group, a 1,2,2,2-tetrafluoroethylthio group, a 1,1,2,2,2-pentafluoroethylthio group, a 2-chloro-2,2-difluoroethylthio group, a 1-chloro-2,2-difluoroethylthio group, 1-chloropropylthio, a 2-chloropropylthio group, a 3-chloropropylthio group, a 2,2,3,3-tetrafluoropropylthio group, a 3,3,3-trifluoropropylthio group, a 2,2,3,3,3-pentafluoropropylthio group or a 2,2,3,3,4,4,4-octafluorobutylthio group.

The $C_2$-$C_4$ haloalkylsulfinyl group may, for example, be a 1-chloroethylsulfinyl group, a 2-fluoroethylsulfinyl group, 2,2-difluoroethylsulfinyl, a 2,2,2-trifluoroethylsulfinyl group, a 1,2,2,2-tetrafluoroethylsulfinyl group, a 1,1,2,2,2-pentafluoroethylsulfinyl group, a 1-chloro-2,2-difluoroethylsulfinyl group, a 1-chloropropylsulfinyl group, 2-chloropropylsulfinyl, a 3-chloropropylsulfinyl group, a 2,2,3,3-tetrafluoropropylsulfinyl group, a 3,3,3- trifluoropropylsulfinyl group, a 2,2,3,3,3-pentafluoropropylsulfinyl group or a 2,2,3,3,3,4,4,4-octafluorobutylsulfinyl group.

The $C_2$-$C_4$ haloalkenylthio group may, for example, be a 2,2-difluoroethenylthio group, a 2-fluoro-2-propenylthio group, a 3,3-difluoro-2-propenylthio group or a 3,3-dichloro-2-propenylthio group.

The $C_2$-$C_4$ haloalkynylsulfinyl group may, for example, be a 4,4,4-trifluoro-2-butynylsulfinyl group.

The cyclopropylmethylthio group may, for example, be cyclopropylmethylthio or a 2,2-difluorocyclopropylmethylthio group.

The cyclopropylmethylsulfinyl group may, for example, be cyclopropylmethylsulfinyl or a 2,2-difluorocyclopropylmethylsulfinyl group.

Now, specific examples of the compounds of the present invention represented by the formula [I] will be given in Tables 1 to 38. However, the compounds of the present invention are not limited to such compounds. Further, these compounds include optical isomers, and E- and Z-isomers. The compound numbers will be referred to in the following description.

The symbols in the Tables denote the following respective corresponding groups.

Pr-n: Propyl group,
Pr-c: Cyclopropyl group,
Bu-c: Cyclobutyl group,
Pen-c: Cyclopentyl group,
Hex-c: Cyclohexyl group,
$CH_2Ph(4\text{-}CF_3)$: 4-Trifluoromethylbenzyl group,
$SO_2Ph(4\text{-}CH_3)$: 4-Methylphenylsulfonyl group.

TABLE 1

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-1 | $SO_2CH_3$ | H | H | F | H | $CH_3$ | $SCH_2CF_3$ | H |
| 1-2 | $SO_2CH_3$ | H | H | F | H | $CH_3$ | $S(O)CH_2CF_3$ | H |
| 1-3 | $SO_2CF_3$ | H | $NHC(O)CH_3$ | F | H | $CH_3$ | $SCH_2CF_3$ | H |
| 1-4 | $SO_2CF_3$ | H | $NHC(O)CH_3$ | F | H | $CH_3$ | $S(O)CH_2CF_3$ | H |
| 1-5 | $CH_2SCF_3$ | H | $NHC(O)CH_3$ | F | H | $CH_3$ | $SCH_2CF_3$ | H |
| 1-6 | $CH_2SCF_3$ | H | $NHC(O)CH_3$ | F | H | $CH_3$ | $S(O)CH_2CF_3$ | H |
| 1-7 | $CH_2C_2F_5$ | H | H | F | H | $CH_3$ | $SCH_2CF_3$ | H |
| 1-8 | $CH_2C_2F_5$ | H | H | F | H | $CH_3$ | $S(O)CH_2CF_3$ | H |
| 1-9 | $CF_2CHFCF_3$ | H | $NH_2$ | F | H | $CH_3$ | $SCH_2CF_3$ | H |
| 1-10 | $CF_2CHFCF_3$ | H | $NH_2$ | F | H | $CH_3$ | $S(O)CH_2CF_3$ | H |
| 1-11 | $CH_2C_2F_5$ | H | $NH_2$ | F | H | $CH_3$ | $SCH_2CF_3$ | H |
| 1-12 | $CH_2C_2F_5$ | H | $NH_2$ | F | H | $CH_3$ | $S(O)CH_2CF_3$ | H |
| 1-13 | $CF_2CHFCF_3$ | H | $NHC(O)CH_3$ | F | H | $CH_3$ | $SCH_2CF_3$ | H |
| 1-14 | $CF_2CHFCF_3$ | H | $NHC(O)CH_3$ | F | H | $CH_3$ | $S(O)CH_2CF_3$ | H |
| 1-15 | $CF_2CHFOCF_3$ | H | $NHC(O)CH_3$ | F | H | $CH_3$ | $SCH_2CF_3$ | H |
| 1-16 | $CF_2CHFOCF_3$ | H | $NHC(O)CH_3$ | F | H | $CH_3$ | $S(O)CH_2CF_3$ | H |
| 1-17 | $CH_2C_2F_5$ | H | $NHC(O)CH_3$ | F | H | $CH_3$ | $SCH_2CF_3$ | H |
| 1-18 | $CH_2C_2F_5$ | H | $NHC(O)CH_3$ | F | H | $CH_3$ | $S(O)CH_2CF_3$ | H |
| 1-19 | $CH_2C{\equiv}CH$ | H | $NHC(O)CH_3$ | F | H | $CH_3$ | $SCH_2CF_3$ | H |
| 1-20 | $CH_2C{\equiv}CH$ | H | $NHC(O)CH_3$ | F | H | $CH_3$ | $S(O)CH_2CF_3$ | H |
| 1-21 | $CH_2CH{=}CHCl$ | H | $NHC(O)CH_3$ | F | H | $CH_3$ | $SCH_2CF_3$ | H |
| 1-22 | $CH_2CH{=}CHCl$ | H | $NHC(O)CH_3$ | F | H | $CH_3$ | $S(O)CH_2CF_3$ | H |
| 1-23 | $CH_2CH_2CH_3$ | H | $NHC(O)CH_3$ | F | H | $CH_3$ | $SCH_2CF_3$ | H |
| 1-24 | $CH_2CH_2CH_3$ | H | $NHC(O)CH_3$ | F | H | $CH_3$ | $S(O)CH_2CF_3$ | H |
| 1-25 | $CH(CH_3)_2$ | H | $NHC(O)CH_3$ | F | H | $CH_3$ | $SCH_2CF_3$ | H |
| 1-26 | $CH(CH_3)_2$ | H | $NHC(O)CH_3$ | F | H | $CH_3$ | $S(O)CH_2CF_3$ | H |
| 1-27 | $CH_2C_2F_5$ | H | $NHCH_3$ | F | H | $CH_3$ | $SCH_2CF_3$ | H |
| 1-28 | $CH_2C_2F_5$ | H | $NHCH_3$ | F | H | $CH_3$ | $S(O)CH_2CF_3$ | H |
| 1-29 | $CH_2C_2F_5$ | H | $NHC(O)CF_3$ | F | H | $CH_3$ | $SCH_2CF_3$ | H |
| 1-30 | $CH_2C_2F_5$ | H | $NHC(O)CF_3$ | F | H | $CH_3$ | $S(O)CH_2CF_3$ | H |
| 1-31 | $CH_2C_2F_5$ | H | $NHC(O)OCH_3$ | F | H | $CH_3$ | $SCH_2CF_3$ | H |
| 1-32 | $CH_2C_2F_5$ | H | $NHC(O)OCH_3$ | F | H | $CH_3$ | $S(O)CH_2CF_3$ | H |
| 1-33 | $CH_2C_2F_5$ | H | $N\{C(O)CH_3\}CH_3$ | F | H | $CH_3$ | $SCH_2CF_3$ | H |
| 1-34 | $CH_2C_2F_5$ | H | $N\{C(O)CH_3\}CH_3$ | F | H | $CH_3$ | $S(O)CH_2CF_3$ | H |
| 1-35 | $CH_2C_2F_5$ | H | $N\{C(O)CH_3\}CH_2CN$ | F | H | $CH_3$ | $SCH_2CF_3$ | H |
| 1-36 | $CH_2C_2F_5$ | H | $N\{C(O)CH_3\}CH_2CN$ | F | H | $CH_3$ | $S(O)CH_2CF_3$ | H |
| 1-37 | $CH_2C_2F_5$ | H | $N\{C(O)CH_3\}C(O)OCH_3$ | F | H | $CH_3$ | $SCH_2CF_3$ | H |
| 1-38 | $CH_2C_2F_5$ | H | $N\{C(O)CH_3\}C(O)OCH_3$ | F | H | $CH_3$ | $S(O)CH_2CF_3$ | H |
| 1-39 | $CH_2C_2F_5$ | Cl | H | F | H | $CH_3$ | $SCH_2CF_3$ | H |
| 1-40 | $CH_2C_2F_5$ | Cl | H | F | H | $CH_3$ | $S(O)CH_2CF_3$ | H |
| 1-41 | $CH_2C_2F_5$ | F | $NH_2$ | F | H | $CH_3$ | $SCH_2CF_3$ | H |
| 1-42 | $CH_2C_2F_5$ | F | $NH_2$ | F | H | $CH_3$ | $S(O)CH_2CF_3$ | H |
| 1-43 | $CH_2C_2F_5$ | Cl | $NH_2$ | F | H | $CH_3$ | $SCH_2CF_3$ | H |
| 1-44 | $CH_2C_2F_5$ | Cl | $NH_2$ | F | H | $CH_3$ | $S(O)CH_2CF_3$ | H |
| 1-45 | $CH_2C_2F_5$ | Br | $NH_2$ | F | H | $CH_3$ | $SCH_2CF_3$ | H |
| 1-46 | $CH_2C_2F_5$ | Br | $NH_2$ | F | H | $CH_3$ | $S(O)CH_2CF_3$ | H |
| 1-47 | $CH_2C_2F_5$ | F | $NHC(O)CH_3$ | F | H | $CH_3$ | $SCH_2CF_3$ | H |
| 1-48 | $CH_2C_2F_5$ | F | $NHC(O)CH_3$ | F | H | $CH_3$ | $S(O)CH_2CF_3$ | H |

TABLE 1-continued

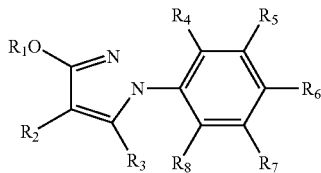

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-49 | $CH_2C_2F_5$ | Br | $NHC(O)CF_3$ | F | H | $CH_3$ | $SCH_2CF_3$ | H |
| 1-50 | $CH_2C_2F_5$ | Br | $NHC(O)CF_3$ | F | H | $CH_3$ | $S(O)CH_2CF_3$ | H |
| 1-51 | $CH_2C_3F_7$ | H | H | F | H | $CH_3$ | $SCH_2CF_3$ | H |

TABLE 2

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-52 | $CH_2C_3F_7$ | H | H | F | H | $CH_3$ | $S(O)CH_2CF_3$ | H |
| 1-53 | $CH_2C_3F_7$ | H | $NH_2$ | F | H | $CH_3$ | $SCH_2CF_3$ | H |
| 1-54 | $CH_2C_3F_7$ | H | $NH_2$ | F | H | $CH_3$ | $S(O)CH_2CF_3$ | H |
| 1-55 | $CH_2CH_2OCH_2CF_3$ | H | $NH_2$ | F | H | $CH_3$ | $SCH_2CF_3$ | H |
| 1-56 | $CH_2CH_2OCH_2CF_3$ | H | $NH_2$ | F | H | $CH_3$ | $S(O)CH_2CF_3$ | H |
| 1-57 | $CH_2C_3F_7$ | H | $NHC(O)CH_3$ | F | H | $CH_3$ | $SCH_2CF_3$ | H |
| 1-58 | $CH_2C_3F_7$ | H | $NHC(O)CH_3$ | F | H | $CH_3$ | $S(O)CH_2CF_3$ | H |
| 1-59 | cyclopropyl-CF$_2$-CH$_2$- (gem-difluoro) | H | $NHC(O)CH_3$ | F | H | $CH_3$ | $SCH_2CF_3$ | H |
| 1-60 | cyclopropyl-CF$_2$-CH$_2$- (gem-difluoro) | H | $NHC(O)CH_3$ | F | H | $CH_3$ | $S(O)CH_2CF_3$ | H |
| 1-61 | $CH_2CH_2CH_2CF_3$ | H | $NHC(O)CH_3$ | F | H | $CH_3$ | $SCH_2CF_3$ | H |
| 1-62 | $CH_2CH_2CH_2CF_3$ | H | $NHC(O)CH_3$ | F | H | $CH_3$ | $S(O)CH_2CF_3$ | H |
| 1-63 | $CH_2CH_2OCH_2CF_3$ | H | $NHC(O)CH_3$ | F | H | $CH_3$ | $SCH_2CF_3$ | H |
| 1-64 | $CH_2CH_2OCH_2CF_3$ | H | $NHC(O)CH_3$ | F | H | $CH_3$ | $S(O)CH_2CF_3$ | H |
| 1-65 | $CH(CH_3)CH_2CH_3$ | H | $NHC(O)CH_3$ | F | H | $CH_3$ | $SCH_2CF_3$ | H |
| 1-66 | $CH(CH_3)CH_2CH_3$ | H | $NHC(O)CH_3$ | F | H | $CH_3$ | $S(O)CH_2CF_3$ | H |
| 1-67 | $CH_2Si(CH_3)_3$ | H | $NHC(O)CH_3$ | F | H | $CH_3$ | $SCH_2CF_3$ | H |
| 1-68 | $CH_2Si(CH_3)_3$ | H | $NHC(O)CH_3$ | F | H | $CH_3$ | $S(O)CH_2CF_3$ | H |
| 1-69 | $CH_2C_3F_7$ | Cl | H | F | H | $CH_3$ | $SCH_2CF_3$ | H |
| 1-70 | $CH_2C_3F_7$ | Cl | H | F | H | $CH_3$ | $S(O)CH_2CF_3$ | H |
| 1-71 | $CH_2CH_2OCH_2CF_3$ | H | $N(CH_3)C(O)CH_3$ | F | H | $CH_3$ | $SCH_2CF_3$ | H |
| 1-72 | $CH_2CH_2OCH_2CF_3$ | H | $N(CH_3)C(O)CH_3$ | F | H | $CH_3$ | $S(O)CH_2CF_3$ | H |
| 1-73 | $CH_2C_4F_9$ | H | H | F | H | $CH_3$ | $SCH_2CF_3$ | H |
| 1-74 | $CH_2C_4F_9$ | H | H | F | H | $CH_3$ | $S(O)CH_2CF_3$ | H |
| 1-75 | $CH_2C_4F_9$ | H | $NH_2$ | F | H | $CH_3$ | $SCH_2CF_3$ | H |
| 1-76 | $CH_2C_4F_9$ | H | $NH_2$ | F | H | $CH_3$ | $S(O)CH_2CF_3$ | H |
| 1-77 | $CH_2C_4F_9$ | H | $NHC(O)CH_3$ | F | H | $CH_3$ | $SCH_2CF_3$ | H |
| 1-78 | $CH_2C_4F_9$ | H | $NHC(O)CH_3$ | F | H | $CH_3$ | $S(O)CH_2CF_3$ | H |
| 1-79 | Pen-c | H | $NHC(O)CH_3$ | F | H | $CH_3$ | $SCH_2CF_3$ | H |
| 1-80 | Pen-c | H | $NHC(O)CH_3$ | F | H | $CH_3$ | $S(O)CH_2CF_3$ | H |
| 1-81 | $CH_2C_5F_{11}$ | H | H | F | H | $CH_3$ | $SCH_2CF_3$ | H |
| 1-82 | $CH_2C_5F_{11}$ | H | H | F | H | $CH_3$ | $S(O)CH_2CF_3$ | H |
| 1-83 | $CH_2C_5F_{11}$ | H | $NH_2$ | F | H | $CH_3$ | $SCH_2CF_3$ | H |
| 1-84 | $CH_2C_5F_{11}$ | H | $NH_2$ | F | H | $CH_3$ | $S(O)CH_2CF_3$ | H |
| 1-85 | $CH_2C_5F_{11}$ | H | $NHC(O)CH_3$ | F | H | $CH_3$ | $SCH_2CF_3$ | H |
| 1-86 | $CH_2C_5F_{11}$ | H | $NHC(O)CH_3$ | F | H | $CH_3$ | $S(O)CH_2CF_3$ | H |
| 1-87 | $C(O)CH_3$ | H | $N\{C(O)CH_3\}_2$ | F | H | $CH_3$ | $SCH_2CF_3$ | H |
| 1-88 | $C(O)CH_3$ | H | $N\{C(O)CH_3\}_2$ | F | H | $CH_3$ | $S(O)CH_2CF_3$ | H |
| 1-89 | $CF_2CHFCF_3$ | H | $CH_3$ | F | H | $CH_3$ | $SCH_2CF_3$ | H |
| 1-90 | $CF_2CHFCF_3$ | H | $CH_3$ | F | H | $CH_3$ | $S(O)CH_2CF_3$ | H |
| 1-91 | $CH_2C_2F_5$ | H | $CH_3$ | F | H | $CH_3$ | $SCH_2CF_3$ | H |
| 1-92 | $CH_2C_2F_5$ | H | $CH_3$ | F | H | $CH_3$ | $S(O)CH_2CF_3$ | H |
| 1-93 | $CH_2C_2F_5$ | Cl | $CH_3$ | F | H | $CH_3$ | $SCH_2CF_3$ | H |
| 1-94 | $CH_2C_2F_5$ | Cl | $CH_3$ | F | H | $CH_3$ | $S(O)CH_2CF_3$ | H |
| 1-95 | $CH_2CH_2CH_3$ | H | $CH_3$ | F | H | $CH_3$ | $SCH_2CF_3$ | H |
| 1-96 | $CH_2CH_2CH_3$ | H | $CH_3$ | F | H | $CH_3$ | $S(O)CH_2CF_3$ | H |
| 1-97 | $CH(CH_3)CH_2CH_3$ | H | $CH_3$ | F | H | $CH_3$ | $SCH_2CF_3$ | H |
| 1-98 | $CH(CH_3)CH_2CH_3$ | H | $CH_3$ | F | H | $CH_3$ | $S(O)CH_2CF_3$ | H |
| 1-99 | $CH_2C_3F_7$ | H | $CH_3$ | F | H | $CH_3$ | $SCH_2CF_3$ | H |
| 1-100 | $CH_2C_3F_7$ | H | $CH_3$ | F | H | $CH_3$ | $S(O)CH_2CF_3$ | H |
| 1-101 | $CH_2C_4F_9$ | H | $CH_3$ | F | H | $CH_3$ | $SCH_2CF_3$ | H |

TABLE 2-continued

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-102 | $CH_2C_4F_9$ | H | $CH_3$ | F | H | $CH_3$ | $S(O)CH_2CF_3$ | H |
| 1-103 | $(CH_2)_3CF_3$ | H | $CH_3$ | F | H | $CH_3$ | $SCH_2CF_3$ | H |
| 1-104 | $(CH_2)_3CF_3$ | H | $CH_3$ | F | H | $CH_3$ | $S(O)CH_2CF_3$ | H |
| 1-105 | $CF_2CHFOCF_3$ | H | $CH_3$ | F | H | $CH_3$ | $SCH_2CF_3$ | H |
| 1-106 | $CF_2CHFOCF_3$ | H | $CH_3$ | F | H | $CH_3$ | $S(O)CH_2CF_3$ | H |

TABLE 3

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-107 | $CH_2C_5F_{11}$ | H | $CH_3$ | F | H | $CH_3$ | $SCH_2CF_3$ | H |
| 1-108 | $CH_2C_5F_{11}$ | H | $CH_3$ | F | H | $CH_3$ | $S(O)CH_2CF_3$ | H |
| 1-109 | $CH_2Ph(4-CF_3)$ | H | $CH_3$ | F | H | $CH_3$ | $SCH_2CF_3$ | H |
| 1-110 | $CH_2Ph(4-CF_3)$ | H | $CH_3$ | F | H | $CH_3$ | $S(O)CH_2CF_3$ | H |
| 1-111 | $CH_2C_2F_5$ | Cl | Cl | F | H | $CH_3$ | $SCH_2CF_3$ | H |
| 1-112 | $CH_2C_2F_5$ | Cl | Cl | F | H | $CH_3$ | $S(O)CH_2CF_3$ | H |
| 1-113 | $CH_2C_2F_5$ | Br | Br | F | H | $CH_3$ | $SCH_2CF_3$ | H |
| 1-114 | $CH_2C_2F_5$ | Br | Br | F | H | $CH_3$ | $S(O)CH_2CF_3$ | H |
| 1-115 | $CH_2C_2F_5$ | H | $NHC(O)CH_2CH_3$ | F | H | $CH_3$ | $SCH_2CF_3$ | H |
| 1-116 | $CH_2C_2F_5$ | H | $NHC(O)CH_2CH_3$ | F | H | $CH_3$ | $S(O)CH_2CF_3$ | H |
| 1-117 | $CH_2C_2F_5$ | H | $NHC(O)CH_2OCH_3$ | F | H | $CH_3$ | $SCH_2CF_3$ | H |
| 1-118 | $CH_2C_2F_5$ | H | $NHC(O)CH_2OCH_3$ | F | H | $CH_3$ | $S(O)CH_2CF_3$ | H |
| 1-119 | $CH_2C_2F_5$ | H | $NHC(O)Pr\text{-}c$ | F | H | $CH_3$ | $SCH_2CF_3$ | H |
| 1-120 | $CH_2C_2F_5$ | H | $NHC(O)Pr\text{-}c$ | F | H | $CH_3$ | $S(O)CH_2CF_3$ | H |
| 1-121 | $CH_2C_2F_5$ | H | $NHC(O)CH=CH_2$ | F | H | $CH_3$ | $SCH_2CF_3$ | H |
| 1-122 | $CH_2C_2F_5$ | H | $NHC(O)CH=CH_2$ | F | H | $CH_3$ | $S(O)CH_2CF_3$ | H |
| 1-123 | $CH_2C_2F_5$ | H | $NHC(O)CHF_2$ | F | H | $CH_3$ | $SCH_2CF_3$ | H |
| 1-124 | $CH_2C_2F_5$ | H | $NHC(O)CHF_2$ | F | H | $CH_3$ | $S(O)CH_2CF_3$ | H |
| 1-125 | $CH_2C_2F_5$ | H | $N=C(CH_3)OCH_2CF_3$ | F | H | $CH_3$ | $SCH_2CF_3$ | H |
| 1-126 | $CH_2C_2F_5$ | H | $N=C(CH_3)OCH_2CF_3$ | F | H | $CH_3$ | $S(O)CH_2CF_3$ | H |
| 1-127 | $CH_2C_2F_5$ | H | $N\{C(O)CH_3\}CH_2CH=CH_2$ | F | H | $CH_3$ | $SCH_2CF_3$ | H |
| 1-128 | $CH_2C_2F_5$ | H | $N\{C(O)CH_3\}CH_2CH=CH_2$ | F | H | $CH_3$ | $S(O)CH_2CF_3$ | H |
| 1-129 | $CH_2C_2F_5$ | H | $N\{C(O)CH_3\}CH_2C\equiv CH$ | F | H | $CH_3$ | $SCH_2CF_3$ | H |
| 1-130 | $CH_2C_2F_5$ | H | $N\{C(O)CH_3\}CH_2C\equiv CH$ | F | H | $CH_3$ | $S(O)CH_2CF_3$ | H |
| 1-131 | $CH_2C\equiv CCH_3$ | H | $CH_3$ | F | H | $CH_3$ | $SCH_2CF_3$ | H |
| 1-132 | $CH_2C\equiv CCH_3$ | H | $CH_3$ | F | H | $CH_3$ | $S(O)CH_2CF_3$ | H |
| 1-133 | $CH_2C_2F_5$ | H | CN | F | H | $CH_3$ | $SCH_2CF_3$ | H |
| 1-134 | $CH_2C_2F_5$ | H | CN | F | H | $CH_3$ | $S(O)CH_2CF_3$ | H |
| 1-135 | $CH_2C_2F_5$ | H | $NHCH_2C(O)OCH_2CH_3$ | F | H | $CH_3$ | $SCH_2CF_3$ | H |
| 1-136 | $CH_2C_2F_5$ | H | $NHCH_2C(O)OCH_2CH_3$ | F | H | $CH_3$ | $S(O)CH_2CF_3$ | H |
| 1-137 | $CH_2C_2F_5$ | H | $NHCH_2C(O)OH$ | F | H | $CH_3$ | $SCH_2CF_3$ | H |
| 1-138 | $CH_2C_2F_5$ | H | $NHCH_2C(O)OH$ | F | H | $CH_3$ | $S(O)CH_2CF_3$ | H |
| 1-139 | $CH_2C_2F_5$ | H | $C(O)NH_2$ | F | H | $CH_3$ | $SCH_2CF_3$ | H |
| 1-140 | $CH_2C_2F_5$ | H | $C(O)NH_2$ | F | H | $CH_3$ | $S(O)CH_2CF_3$ | H |
| 1-141 | $CH_2C_2F_5$ | H | $C(O)NHCH_3$ | F | H | $CH_3$ | $SCH_2CF_3$ | H |
| 1-142 | $CH_2C_2F_5$ | H | $C(O)NHCH_3$ | F | H | $CH_3$ | $S(O)CH_2CF_3$ | H |
| 1-143 | $CH_2C_2F_5$ | H | $C(O)OCH_2CH_3$ | F | H | $CH_3$ | $SCH_2CF_3$ | H |
| 1-144 | $CH_2C_2F_5$ | H | $C(O)OCH_2CH_3$ | F | H | $CH_3$ | $S(O)CH_2CF_3$ | H |
| 1-145 | $CH_2C_2F_5$ | H | $C(O)OH$ | F | H | $CH_3$ | $SCH_2CF_3$ | H |
| 1-146 | $CH_2C_2F_5$ | H | $NHC(O)N(CH_3)_2$ | F | H | $CH_3$ | $SCH_2CF_3$ | H |
| 1-147 | $CH_2C_2F_5$ | H | $NHC(O)N(CH_3)_2$ | F | H | $CH_3$ | $S(O)CH_2CF_3$ | H |
| 1-148 | $CH_2C_3F_7$ | H | $C(O)NH_2$ | F | H | $CH_3$ | $SCH_2CF_3$ | H |
| 1-149 | $CH_2C_3F_7$ | H | $C(O)NH_2$ | F | H | $CH_3$ | $S(O)CH_2CF_3$ | H |
| 1-150 | $CF_2CHFCF_3$ | H | $C(O)NH_2$ | F | H | $CH_3$ | $SCH_2CF_3$ | H |
| 1-151 | $CF_2CHFCF_3$ | H | $C(O)NH_2$ | F | H | $CH_3$ | $S(O)CH_2CF_3$ | H |
| 1-152 | $CH_2C_3F_7$ | H | $C(O)OCH_2CH_3$ | F | H | $CH_3$ | $SCH_2CF_3$ | H |
| 1-153 | $CH_2C_3F_7$ | H | $C(O)OCH_2CH_3$ | F | H | $CH_3$ | $S(O)CH_2CF_3$ | H |
| 1-154 | $CH_2C_3F_7$ | H | $C(O)OH$ | F | H | $CH_3$ | $SCH_2CF_3$ | H |
| 1-155 | $CF_2CHFCF_3$ | H | CN | F | H | $CH_3$ | $SCH_2CF_3$ | H |
| 1-156 | $CF_2CHFCF_3$ | H | CN | F | H | $CH_3$ | $S(O)CH_2CF_3$ | H |
| 1-157 | $CH_2C_3F_7$ | H | CN | F | H | $CH_3$ | $SCH_2CF_3$ | H |
| 1-158 | $CH_2C_3F_7$ | H | CN | F | H | $CH_3$ | $S(O)CH_2CF_3$ | H |
| 1-159 | $CH_2C_2F_5$ | H | $NHCH_2CH=CH_2$ | F | H | $CH_3$ | $SCH_2CF_3$ | H |
| 1-160 | $CH_2C_2F_5$ | H | $NHCH_2CH=CH_2$ | F | H | $CH_3$ | $S(O)CH_2CF_3$ | H |
| 1-161 | $CH_2C_2F_5$ | H | $NHCH_2C\equiv CH$ | F | H | $CH_3$ | $SCH_2CF_3$ | H |
| 1-162 | $CH_2C_2F_5$ | H | $NHCH_2C\equiv CH$ | F | H | $CH_3$ | $S(O)CH_2CF_3$ | H |

TABLE 4

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-163 | $CH_2C_2F_5$ | H | $NHCH_2C\equiv CH$ | F | H | $CH_3$ | $SCH_2CF_2Cl$ | H |
| 1-164 | $CH_2C_2F_5$ | H | $NHCH_2C\equiv CH$ | F | H | $CH_3$ | $S(O)CH_2CF_2Cl$ | H |

TABLE 4-continued

| Comp. No. | R₁ | R₂ | R₃ | R₄ | R₅ | R₆ | R₇ | R₈ |
|---|---|---|---|---|---|---|---|---|
| 1-165 | CH$_2$C$_2$F$_5$ | H | N{C(O)CH$_3$}CH$_2$C≡CH | F | H | CH$_3$ | SCH$_2$CF$_2$Cl | H |
| 1-166 | CH$_2$C$_2$F$_5$ | H | N{C(O)CH$_3$}CH$_2$C≡CH | F | H | CH$_3$ | S(O)CH$_2$CF$_2$Cl | H |
| 1-167 | CH$_2$C$_2$F$_5$ | H | NHC(O)CF$_2$Cl | F | H | CH$_3$ | SCH$_2$CF$_3$ | H |
| 1-168 | CH$_2$C$_2$F$_5$ | H | NHC(O)CF$_2$Cl | F | H | CH$_3$ | S(O)CH$_2$CF$_3$ | H |
| 1-169 | CH$_2$C$_2$F$_5$ | H | NHCH$_2$CN | F | H | CH$_3$ | SCH$_2$CF$_3$ | H |
| 1-170 | CH$_2$C$_2$F$_5$ | H | NHCH$_2$CN | F | H | CH$_3$ | S(O)CH$_2$CF$_3$ | H |
| 1-171 | CH$_2$C$_2$F$_5$ | H | N{C(O)CH$_3$}CH$_2$CF=CH$_2$ | F | H | CH$_3$ | SCH$_2$CF$_3$ | H |
| 1-172 | CH$_2$C$_2$F$_5$ | H | N{C(O)CH$_3$}CH$_2$CF=CH$_2$ | F | H | CH$_3$ | SCH$_2$CF$_2$Cl | H |
| 1-173 | CH$_2$C$_2$F$_5$ | H | NHCH$_2$CF=CH$_2$ | F | H | CH$_3$ | SCH$_2$CF$_3$ | H |
| 1-174 | CH$_2$C$_2$F$_5$ | H | NHCH$_2$CF=CH$_2$ | F | H | CH$_3$ | S(O)CH$_2$CF$_3$ | H |
| 1-175 | CH$_2$C$_2$F$_5$ | H | NHCH$_2$CF=CH$_2$ | F | H | CH$_3$ | SCH$_2$CF$_2$Cl | H |
| 1-176 | CH$_2$C$_2$F$_5$ | H | NHCH$_2$CF=CH$_2$ | F | H | CH$_3$ | S(O)CH$_2$CF$_2$Cl | H |
| 1-177 | CH$_2$C$_2$F$_5$ | H | NHC(O)CH$_3$ | F | H | CH$_3$ | SCH$_2$CF$_2$Cl | H |
| 1-178 | CH$_2$C$_2$F$_5$ | H | NHC(O)CH$_3$ | F | H | CH$_3$ | S(O)CH$_2$CF$_2$Cl | H |
| 1-179 | CH$_2$C$_2$F$_5$ | H | NHC(O)CH$_3$ | F | H | CH$_3$ | SCH$_2$CH$_2$CF$_3$ | H |
| 1-180 | CH$_2$C$_2$F$_5$ | H | NHC(O)CH$_3$ | F | H | CH$_3$ | S(O)CH$_2$CH$_2$CF$_3$ | H |
| 1-181 | CH$_2$C$_2$F$_5$ | H | NHC(O)CH$_3$ | F | H | CH$_3$ | SCH$_2$CF$_2$CF$_3$ | H |
| 1-182 | CH$_2$C$_2$F$_5$ | H | NHC(O)CH$_3$ | F | H | CH$_3$ | SCH$_2$Pr-c | H |
| 1-183 | CH$_2$C$_2$F$_5$ | H | NHC(O)CH$_3$ | F | H | CH$_3$ | S(O)CH$_2$Pr-c | H |
| 1-184 | CH$_2$C$_2$F$_5$ | H | NHC(O)CH$_3$ | F | H | CH$_3$ | SCH$_2$CF=CH$_3$ | H |
| 1-185 | CH$_2$C$_2$F$_5$ | H | NHC(O)CH$_3$ | F | H | CH$_3$ | S(O)CH$_2$CF=CH$_2$ | H |
| 1-186 | CF$_2$CHFCF$_3$ | H | NHCH$_3$ | F | H | CH$_3$ | SCH$_2$CF$_3$ | H |
| 1-187 | CF$_2$CHFCF$_3$ | H | NHCH$_3$ | F | H | CH$_3$ | S(O)CH$_2$CF$_3$ | H |
| 1-188 | CF$_2$CHFCF$_3$ | H | N(CH$_3$)C(O)CH$_3$ | F | H | CH$_3$ | SCH$_2$CF$_3$ | H |
| 1-189 | CH$_2$C$_3$F$_7$ | H | NHC(O)CH$_3$ | F | H | CH$_3$ | SCH$_2$CF$_2$Cl | H |
| 1-190 | CH$_2$C$_3$F$_7$ | H | NHC(O)CH$_3$ | F | H | CH$_3$ | S(O)CH$_2$CF$_2$Cl | H |
| 1-191 | CH$_2$CF=CHCF$_3$ | H | NHC(O)CH$_3$ | F | H | CH$_3$ | SCH$_2$CF$_3$ | H |
| 1-192 | CH$_2$CF=CHCF$_3$ | H | NHC(O)CH$_3$ | F | H | CH$_3$ | S(O)CH$_2$CF$_3$ | H |
| 1-193 | CH$_2$C$_2$F$_5$ | H | OCH$_3$ | F | H | CH$_3$ | SCH$_2$CF$_3$ | H |
| 1-194 | CH$_2$C$_2$F$_5$ | H | OCH$_3$ | F | H | CH$_3$ | S(O)CH$_2$CF$_3$ | H |
| 1-195 | CF$_2$CHFCF$_3$ | H | OCH$_3$ | F | H | CH$_3$ | SCH$_2$CF$_3$ | H |
| 1-196 | CF$_2$CHFCF$_3$ | H | OCH$_3$ | F | H | CH$_3$ | S(O)CH$_2$CF$_3$ | H |
| 1-197 | CH$_2$C$_3$F$_7$ | H | OCH$_3$ | F | H | CH$_3$ | SCH$_2$CF$_3$ | H |
| 1-198 | CH$_2$C$_3$F$_7$ | H | OCH$_3$ | F | H | CH$_3$ | S(O)CH$_2$CF$_3$ | H |
| 1-199 | CH$_2$C$_2$F$_5$ | H | C(O)H | F | H | CH$_3$ | SCH$_2$CF$_3$ | H |
| 1-200 | CH$_2$C$_2$F$_5$ | H | C(O)H | F | H | CH$_3$ | S(O)CH$_2$CF$_3$ | H |
| 1-201 | CH$_2$C$_2$F$_5$ | H | CH$_2$OH | F | H | CH$_3$ | SCH$_2$CF$_3$ | H |
| 1-202 | CH$_2$C$_2$F$_5$ | H | CH$_2$OH | F | H | CH$_3$ | S(O)CH$_2$CF$_3$ | H |
| 1-203 | CH$_2$C$_2$F$_5$ | H | 1-ethyl-1,2,4-triazol-5-yl | F | H | CH$_3$ | SCH$_2$CF$_3$ | H |
| 1-204 | CH$_2$C$_2$F$_5$ | H | 1-ethyl-1,2,4-triazol-5-yl | F | H | CH$_3$ | S(O)CH$_2$CF$_3$ | H |
| 1-205 | CH$_2$C$_2$F$_5$ | H | CH=N—OH | F | H | CH$_3$ | SCH$_2$CF$_3$ | H |
| 1-206 | CH$_2$C$_2$F$_5$ | H | CH=N—OH | F | H | CH$_3$ | S(O)CH$_2$CF$_3$ | H |
| 1-207 | CH$_2$C$_2$F$_5$ | H | CH=N—OCH$_3$ | F | H | CH$_3$ | SCH$_2$CF$_3$ | H |
| 1-208 | CH$_2$C$_2$F$_5$ | H | CH=N—OCH$_3$ | F | H | CH$_3$ | S(O)CH$_2$CF$_3$ | H |
| 1-209 | CH$_2$C$_2$F$_5$ | Cl | NHC(O)CH$_3$ | F | H | CH$_3$ | SCH$_2$CF$_3$ | H |
| 1-210 | CH$_2$C$_2$F$_5$ | Cl | NHC(O)CH$_3$ | F | H | CH$_3$ | S(O)CH$_2$CF$_3$ | H |
| 1-211 | CH$_2$C$_2$F$_5$ | Cl | N(CH$_3$)C(O)CH$_3$ | F | H | CH$_3$ | SCH$_2$CF$_3$ | H |
| 1-212 | CH$_2$C$_2$F$_5$ | Cl | N(CH$_3$)C(O)CH$_3$ | F | H | CH$_3$ | S(O)CH$_2$CF$_3$ | H |
| 1-213 | CH$_2$C$_2$F$_5$ | Cl | N{C(O)CH$_3$}$_2$ | F | H | CH$_3$ | SCH$_2$CF$_3$ | H |
| 1-214 | CH$_2$C$_2$F$_5$ | Cl | NHCH$_3$ | F | H | CH$_3$ | SCH$_2$CF$_3$ | H |
| 1-215 | CH$_2$C$_2$F$_5$ | Cl | NHCH$_3$ | F | H | CH$_3$ | S(O)CH$_2$CF$_3$ | H |
| 1-216 | CH$_2$C$_2$F$_5$ | NH$_2$ | NH$_2$ | F | H | CH$_3$ | SCH$_2$CF$_3$ | H |

TABLE 5

| Comp. No. | R₁ | R₂ | R₃ | R₄ | R₅ | R₆ | R₇ | R₈ |
|---|---|---|---|---|---|---|---|---|
| 1-217 | CH$_2$=CCH$_3$ | H | NHC(O)CH$_3$ | F | H | CH$_3$ | SCH$_2$CF$_3$ | H |
| 1-218 | CH$_2$=CCH$_3$ | H | NHC(O)CH$_3$ | F | H | CH$_3$ | S(O)CH$_2$CF$_3$ | H |
| 1-219 | CH(CH$_3$)CH$_2$CH$_2$CH$_3$ | H | CH$_3$ | F | H | CH$_3$ | SCH$_2$CF$_3$ | H |
| 1-220 | CH(CH$_3$)CH$_2$CH$_2$CH$_3$ | H | CH$_3$ | F | H | CH$_3$ | S(O)CH$_2$CF$_3$ | H |
| 1-221 | CH$_2$CH(CH$_3$)CH$_2$CH$_3$ | H | CH$_3$ | F | H | CH$_3$ | SCH$_2$CF$_3$ | H |
| 1-222 | CH$_2$CH(CH$_3$)CH$_2$CH$_3$ | H | CH$_3$ | F | H | CH$_3$ | S(O)CH$_2$CF$_3$ | H |
| 1-223 | CH$_2$CH$_2$C(CH$_3$)$_3$ | H | CH$_3$ | F | H | CH$_3$ | SCH$_2$CF$_3$ | H |
| 1-224 | CH$_2$CH$_2$C(CH$_3$)$_3$ | H | CH$_3$ | F | H | CH$_3$ | S(O)CH$_2$CF$_3$ | H |
| 1-225 | CH$_2$Pr-c | H | CH$_3$ | F | H | CH$_3$ | SCH$_2$CF$_3$ | H |

TABLE 5-continued

| Comp. No. | R₁ | R₂ | R₃ | R₄ | R₅ | R₆ | R₇ | R₈ |
|---|---|---|---|---|---|---|---|---|
| 1-226 | CH₂Pr-c | H | CH₃ | F | H | CH₃ | S(O)CH₂CF₃ | H |
| 1-227 | CH₂Bu-c | H | CH₃ | F | H | CH₃ | SCH₂CF₃ | H |
| 1-228 | CH₂Bu-c | H | CH₃ | F | H | CH₃ | S(O)CH₂CF₃ | H |
| 1-229 | CH₂Pen-c | H | CH₃ | F | H | CH₃ | SCH₂CF₃ | H |
| 1-230 | CH₂Pen-c | H | CH₃ | F | H | CH₃ | S(O)CH₂CF₃ | H |
| 1-231 | 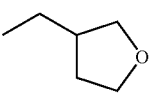 | H | CH₃ | F | H | CH₃ | SCH₂CF₃ | H |
| 1-232 | 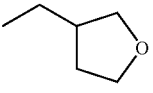 | H | CH₃ | F | H | CH₃ | S(O)CH₂CF₃ | H |
| 1-233 | 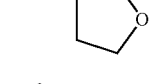 | H | CH₃ | F | H | CH₃ | SCH₂CF₃ | H |
| 1-234 | 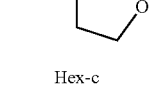 | H | CH₃ | F | H | CH₃ | S(O)CH₂CF₃ | H |
| 1-235 | Hex-c | H | CH₃ | F | H | CH₃ | SCH₂CF₃ | H |
| 1-236 | Hex-c | H | CH₃ | F | H | CH₃ | S(O)CH₂CF₃ | H |
| 1-237 | CH(CH₂CH₃)₂ | H | CH₃ | F | H | CH₃ | SCH₂CF₃ | H |
| 1-238 | CH(CH₂CH₃)₂ | H | CH₃ | F | H | CH₃ | S(O)CH₂CF₃ | H |
| 1-239 | CH₂CH₂OCH₃ | H | CH₃ | F | H | CH₃ | SCH₂CF₃ | H |
| 1-240 | CH₂CH₂OCH₃ | H | CH₃ | F | H | CH₃ | S(O)CH₂CF₃ | H |
| 1-241 | CH₂CH₂SCH₃ | H | CH₃ | F | H | CH₃ | SCH₂CF₃ | H |
| 1-242 | CH₂CH₂SCH₃ | H | CH₃ | F | H | CH₃ | S(O)CH₂CF₃ | H |
| 1-243 | CH₂CH₂SOCH₃ | H | CH₃ | F | H | CH₃ | SCH₂CF₃ | H |
| 1-244 | CH₂CH₂SOCH₃ | H | CH₃ | F | H | CH₃ | S(O)CH₂CF₃ | H |
| 1-245 | CH(CH₃)CN | H | NHC(O)CH₃ | F | H | CH₃ | SCH₂CF₃ | H |
| 1-246 | CH(CH₃)CN | H | NHC(O)CH₃ | F | H | CH₃ | S(O)CH₂CF₃ | H |
| 1-247 | CH₂CF₂CHF₂ | H | NHC(O)CH₃ | F | H | CH₃ | SCH₂CF₃ | H |
| 1-248 | CH₂CF₂CHF₂ | H | NHC(O)CH₃ | F | H | CH₃ | S(O)CH₂CF₃ | H |
| 1-249 | CH₂CH₂CF₃ | H | CH₃ | F | H | CH₃ | SCH₂CF₃ | H |
| 1-250 | CH₂CH₂CF₃ | H | CH₃ | F | H | CH₃ | S(O)CH₂CF₃ | H |
| 1-251 | CH₂CHFCF₃ | H | H | F | H | CH₃ | SCH₂CF₃ | H |
| 1-252 | CH₂CHFCF₃ | H | H | F | H | CH₃ | S(O)CH₂CF₃ | H |
| 1-253 | CH₂CHFCF₃ | H | Cl | F | H | CH₃ | SCH₂CF₃ | H |
| 1-254 | CH₂CHFCF₃ | H | Cl | F | H | CH₃ | S(O)CH₂CF₃ | H |
| 1-255 | CH₂CHFCF₃ | Br | Br | F | H | CH₃ | SCH₂CF₃ | H |
| 1-256 | CH₂CHFCF₃ | Br | Br | F | H | CH₃ | S(O)CH₂CF₃ | H |
| 1-257 | CH₂CHFCF₃ | Cl | H | F | H | CH₃ | SCH₂CF₃ | H |
| 1-258 | CH₂CHFCF₃ | Cl | H | F | H | CH₃ | S(O)CH₂CF₃ | H |
| 1-259 | CH₂CHFCF₃ | Br | H | F | H | CH₃ | SCH₂CF₃ | H |
| 1-260 | CH₂CHFCF₃ | Br | H | F | H | CH₃ | S(O)CH₂CF₃ | H |
| 1-261 | CH₂CHFCF₃ | Cl | NHCH₃ | F | H | CH₃ | SCH₂CF₃ | H |
| 1-262 | CH₂CHFCF₃ | Cl | NHCH₃ | F | H | CH₃ | S(O)CH₂CF₃ | H |
| 1-263 | CH₂CHFCF₃ | Cl | NH₂ | F | H | CH₃ | SCH₂CF₃ | H |
| 1-264 | CH₂CHFCF₃ | Cl | NH₂ | F | H | CH₃ | S(O)CH₂CF₃ | H |
| 1-265 | CH₂CHFCF₃ | Cl | Cl | F | H | CH₃ | SCH₂CF₃ | H |
| 1-266 | CH₂CHFCF₃ | Cl | Cl | F | H | CH₃ | S(O)CH₂CF₃ | H |
| 1-267 | CF₂CF₂CF₃ | H | NHC(O)CH₃ | F | H | CH₃ | SCH₂CF₃ | H |
| 1-268 | CF₂CF₂CF₃ | H | NHC(O)CH₃ | F | H | CH₃ | S(O)CH₂CF₃ | H |
| 1-269 | CF₂CF₂CF₃ | H | CH₃ | F | H | CH₃ | SCH₂CF₃ | H |
| 1-270 | CF₂CF₂CF₃ | H | CH₃ | F | H | CH₃ | S(O)CH₂CF₃ | H |

TABLE 6

| Comp. No. | R₁ | R₂ | R₃ | R₄ | R₅ | R₆ | R₇ | R₈ |
|---|---|---|---|---|---|---|---|---|
| 1-271 | C(CF₃)=CFCF₃ | H | NHC(O)CH₃ | F | H | CH₃ | SCH₂CF₃ | H |
| 1-272 | C(CF₃)=CFCF₃ | H | NHC(O)CH₃ | F | H | CH₃ | S(O)CH₂CF₃ | H |
| 1-273 | CH(CH₃)CF₃ | H | CH₃ | F | H | CH₃ | SCH₂CF₃ | H |
| 1-274 | CH(CH₃)CF₃ | H | CH₃ | F | H | CH₃ | S(O)CH₂CF₃ | H |
| 1-275 | CH(CH₃)CF₃ | H | NHC(O)CH₃ | F | H | CH₃ | SCH₂CF₃ | H |
| 1-276 | CH(CH₃)CF₃ | H | NHC(O)CH₃ | F | H | CH₃ | S(O)CH₂CF₃ | H |
| 1-277 | CH(CH₃)CF₂CF₃ | H | CH₃ | F | H | CH₃ | SCH₂CF₃ | H |
| 1-278 | CH(CH₃)CF₂CF₃ | H | CH₃ | F | H | CH₃ | S(O)CH₂CF₃ | H |

TABLE 6-continued

| Comp. No. | R₁ | R₂ | R₃ | R₄ | R₅ | R₆ | R₇ | R₈ |
|---|---|---|---|---|---|---|---|---|
| 1-279 | CH(CH₃)CF₂CF₃ | H | NHC(O)CH₃ | F | H | CH₃ | SCH₂CF₃ | H |
| 1-280 | CH(CH₃)CF₂CF₃ | H | NHC(O)CH₃ | F | H | CH₃ | S(O)CH₂CF₃ | H |
| 1-281 | CH(CH₃)CF₂CF₂CF₃ | H | CH₃ | F | H | CH₃ | SCH₂CF₃ | H |
| 1-282 | CH(CH₃)CF₂CF₂CF₃ | H | CH₃ | F | H | CH₃ | S(O)CH₂CF₃ | H |
| 1-283 | CH(CH₃)CF₂CF₂CF₃ | H | NHC(O)CH₃ | F | H | CH₃ | SCH₂CF₃ | H |
| 1-284 | CH(CH₃)CF₂CF₂CF₃ | H | NHC(O)CH₃ | F | H | CH₃ | S(O)CH₂CF₃ | H |
| 1-285 | CH₂CH₂Si(CH₃)₃ | H | CH₃ | F | H | CH₃ | SCH₂CF₃ | H |
| 1-286 | CH₂CH₂Si(CH₃)₃ | H | CH₃ | F | H | CH₃ | S(O)CH₂CF₃ | H |
| 1-287 | CF₂CHFOCF₃ | H | NHCH₃ | F | H | CH₃ | SCH₂CF₃ | H |
| 1-288 | CF₂CHFOCF₃ | H | NHCH₃ | F | H | CH₃ | S(O)CH₂CF₃ | H |
| 1-289 | CF₂CHFOCF₃ | Cl | H | F | H | CH₃ | SCH₂CF₃ | H |
| 1-290 | CF₂CHFOCF₃ | Cl | H | F | H | CH₃ | S(O)CH₂CF₃ | H |
| 1-291 | CF₂CHFOCF₃ | Cl | Cl | F | H | CH₃ | SCH₂CF₃ | H |
| 1-292 | CF₂CHFOCF₃ | Cl | Cl | F | H | CH₃ | S(O)CH₂CF₃ | H |
| 1-293 | CH₂CH₂CH₂CH(CH₃)₂ | H | CH₃ | F | H | CH₃ | SCH₂CF₃ | H |
| 1-294 | CH₂CH₂CH₂CH(CH₃)₂ | H | CH₃ | F | H | CH₃ | S(O)CH₂CF₃ | H |
| 1-295 | CH₂CH₂OCH₂CH₂OCH₃ | H | CH₃ | F | H | CH₃ | SCH₂CF₃ | H |
| 1-296 | CH₂CH₂OCH₂CH₂OCH₃ | H | CH₃ | F | H | CH₃ | S(O)CH₂CF₃ | H |
| 1-297 | CH₂CH₂CH₂OCH₃ | H | CH₃ | F | H | CH₃ | SCH₂CF₃ | H |
| 1-298 | CH₂CH₂CH₂OCH₃ | H | CH₃ | F | H | CH₃ | S(O)CH₂CF₃ | H |
| 1-299 | CH₂CH₂CH₂Si(CH₃)₃ | H | CH₃ | F | H | CH₃ | SCH₂CF₃ | H |
| 1-300 | CH₂CH₂CH₂Si(CH₃)₃ | H | CH₃ | F | H | CH₃ | S(O)CH₂CF₃ | H |
| 1-301 | CH₂CH₂CH₂CF(CF₃)₂ | H | CH₃ | F | H | CH₃ | SCH₂CF₃ | H |
| 1-302 | CH₂CH₂CH₂CF(CF₃)₂ | H | CH₃ | F | H | CH₃ | S(O)CH₂CF₃ | H |
| 1-303 | CH₂CH₂CH₂C₂F₅ | H | CH₃ | F | H | CH₃ | SCH₂CF₃ | H |
| 1-304 | CH₂CH₂CH₂C₂F₅ | H | CH₃ | F | H | CH₃ | S(O)CH₂CF₃ | H |
| 1-305 | CH₂CH₂CH₂C₃F₇ | H | CH₃ | F | H | CH₃ | SCH₂CF₃ | H |
| 1-306 | CH₂CH₂CH₂C₃F₇ | H | CH₃ | F | H | CH₃ | S(O)CH₂CF₃ | H |
| 1-307 | CH₂CH₂CH₂C₄F₉ | H | CH₃ | F | H | CH₃ | SCH₂CF₃ | H |
| 1-308 | CH₂CH₂CH₂C₄F₉ | H | CH₃ | F | H | CH₃ | S(O)CH₂CF₃ | H |
| 1-309 | CH₂CH₂CH₂C₆F₁₃ | H | CH₃ | F | H | CH₃ | SCH₂CF₃ | H |
| 1-310 | CH₂CH₂CH₂C₆F₁₃ | H | CH₃ | F | H | CH₃ | S(O)CH₂CF₃ | H |
| 1-311 | CH₂CH₂C₄F₉ | H | CH₃ | F | H | CH₃ | SCH₂CF₃ | H |
| 1-312 | CH₂CH₂C₄F₉ | H | CH₃ | F | H | CH₃ | S(O)CH₂CF₃ | H |
| 1-313 | CH₂CH₂C₆F₁₃ | H | CH₃ | F | H | CH₃ | SCH₂CF₃ | H |
| 1-314 | CH₂CH₂C₆F₁₃ | H | CH₃ | F | H | CH₃ | S(O)CH₂CF₃ | H |
| 1-315 | CH₂CH₂C₈F₁₇ | H | CH₃ | F | H | CH₃ | SCH₂CF₃ | H |
| 1-316 | CH₂CH₂C₈F₁₇ | H | CH₃ | F | H | CH₃ | S(O)CH₂CF₃ | H |
| 1-317 | CF₂CHFOC₂F₅ | H | CH₃ | F | H | CH₃ | SCH₂CF₃ | H |
| 1-318 | CF₂CHFOC₂F₅ | H | CH₃ | F | H | CH₃ | S(O)CH₂CF₃ | H |
| 1-319 | CH₂CH₂OC(CF₃)₃ | H | CH₃ | F | H | CH₃ | SCH₂CF₃ | H |
| 1-320 | CH₂CH₂OC(CF₃)₃ | H | CH₃ | F | H | CH₃ | S(O)CH₂CF₃ | H |
| 1-321 | CH₂CF₂CF₂CF₂CHF₂ | H | CH₃ | F | H | CH₃ | SCH₂CF₃ | H |
| 1-322 | CH₂CF₂CF₂CF₂CHF₂ | H | CH₃ | F | H | CH₃ | S(O)CH₂CF₃ | H |
| 1-323 | CH₂CF₂OCF₂CF₂OCF₃ | H | CH₃ | F | H | CH₃ | SCH₂CF₃ | H |
| 1-324 | CH₂CF₂OCF₂CF₂OCF₃ | H | CH₃ | F | H | CH₃ | S(O)CH₂CF₃ | H |
| 1-325 | CF₂CHFOC₃F₇ | H | CH₃ | F | H | CH₃ | SCH₂CF₃ | H |
| 1-326 | CF₂CHFOC₃F₇ | H | CH₃ | F | H | CH₃ | S(O)CH₂CF₃ | H |

TABLE 7

| Comp. No. | R₁ | R₂ | R₃ | R₄ | R₅ | R₆ | R₇ | R₈ |
|---|---|---|---|---|---|---|---|---|
| 1-327 | pentafluorophenyl | H | CH₃ | F | H | CH₃ | SCH₂CF₃ | H |
| 1-328 | pentafluorophenyl | H | CH₃ | F | H | CH₃ | S(O)CH₂CF₃ | H |

TABLE 7-continued

| Comp. No. | R₁ | R₂ | R₃ | R₄ | R₅ | R₆ | R₇ | R₈ |
|---|---|---|---|---|---|---|---|---|
| 1-329 | 2-Br-3,4,5,6-tetrafluorophenyl | H | $CH_3$ | F | H | $CH_3$ | $SCH_2CF_3$ | H |
| 1-330 | 2-Br-3,4,5,6-tetrafluorophenyl | H | $CH_3$ | F | H | $CH_3$ | $S(O)CH_2CF_3$ | H |
| 1-331 | $CH_2C_4F_9$ | H | $CH{=}NOCH_3$ | F | H | $CH_3$ | $SCH_2CF_3$ | H |
| 1-332 | $CH_2C_4F_9$ | H | $CH{=}NOCH_3$ | F | H | $CH_3$ | $S(O)CH_2CF_3$ | H |
| 1-333 | $CH_2C_4F_9$ | H | $CH{=}NOCH_2CH_3$ | F | H | $CH_3$ | $SCH_2CF_3$ | H |
| 1-334 | $CH_2C_4F_9$ | H | $CH{=}NOCH_2CH_3$ | F | H | $CH_3$ | $S(O)CH_2CF_3$ | H |
| 1-335 | $CH_2C_4F_9$ | H | $CH{=}NOCH(CH_3)_2$ | F | H | $CH_3$ | $SCH_2CF_3$ | H |
| 1-336 | $CH_2C_4F_9$ | H | $CH{=}NOCH(CH_3)_2$ | F | H | $CH_3$ | $S(O)CH_2CF_3$ | H |
| 1-337 | $CH_2C_4F_9$ | H | $CH{=}NOCH_2CH{=}CH_2$ | F | H | $CH_3$ | $SCH_2CF_3$ | H |
| 1-338 | $CH_2C_4F_9$ | H | $CH{=}NOCH_2CH{=}CH_2$ | F | H | $CH_3$ | $S(O)CH_2CF_3$ | H |
| 1-339 | $CH_2C_4F_9$ | H | CN | F | H | $CH_3$ | $SCH_2CF_3$ | H |
| 1-340 | $CH_2C_4F_9$ | H | CN | F | H | $CH_3$ | $S(O)CH_2CF_3$ | H |
| 1-341 | $CH_2C_4F_9$ | H | C(O)H | F | H | $CH_3$ | $SCH_2CF_3$ | H |
| 1-342 | $CH_2C_4F_9$ | H | $C(O)NH_2$ | F | H | $CH_3$ | $SCH_2CF_3$ | H |
| 1-343 | $CH_2C_4F_9$ | H | $C(O)OCH_2CH_3$ | F | H | $CH_3$ | $SCH_2CF_3$ | H |
| 1-344 | $CH_2C_4F_9$ | H | $NHCH_3$ | F | H | $CH_3$ | $SCH_2CF_3$ | H |
| 1-345 | $CF_2CHFOC_2F_5$ | H | $NHCH_3$ | F | H | $CH_3$ | $SCH_2CF_3$ | H |
| 1-346 | $CF_2CHFOC_2F_5$ | H | $NHCH_3$ | F | H | $CH_3$ | $S(O)CH_2CF_3$ | H |
| 1-347 | $CF_2CHFOC_3F_7$ | H | $NHCH_3$ | F | H | $CH_3$ | $SCH_2CF_3$ | H |
| 1-348 | $CF_2CHFOC_3F_7$ | H | $NHCH_3$ | F | H | $CH_3$ | $S(O)CH_2CF_3$ | H |
| 1-349 | $CH_2C_4F_9$ | H | $NHCH_2CH{=}CH_2$ | F | H | $CH_3$ | $SCH_2CF_3$ | H |
| 1-350 | $CH_2C_4F_9$ | H | $NHCH_2CH{=}CH_2$ | F | H | $CH_3$ | $S(O)CH_2CF_3$ | H |
| 1-351 | $CH_2C_4F_9$ | H | $NHCH_2C{\equiv}CH$ | F | H | $CH_3$ | $SCH_2CF_3$ | H |
| 1-352 | $CH_2C_4F_9$ | H | $NHCH_2C{\equiv}CH$ | F | H | $CH_3$ | $S(O)CH_2CF_3$ | H |
| 1-353 | $CF_2CHFOC_2F_5$ | H | $NHCH_2C{\equiv}CH$ | F | H | $CH_3$ | $SCH_2CF_3$ | H |
| 1-354 | $CF_2CHFOC_2F_5$ | H | $NHCH_2C{\equiv}CH$ | F | H | $CH_3$ | $S(O)CH_2CF_3$ | H |
| 1-355 | $CH_2C_5F_{11}$ | H | $NHCH_2C{\equiv}CH$ | F | H | $CH_3$ | $SCH_2CF_3$ | H |
| 1-356 | $CH_2C_5F_{11}$ | H | $NHCH_2C{\equiv}CH$ | F | H | $CH_3$ | $S(O)CH_2CF_3$ | H |
| 1-357 | $CF_2CHFOC_3F_7$ | H | $NHCH_2C{\equiv}CH$ | F | H | $CH_3$ | $SCH_2CF_3$ | H |
| 1-358 | $CF_2CHFOC_3F_7$ | H | $NHCH_2C{\equiv}CH$ | F | H | $CH_3$ | $S(O)CH_2CF_3$ | H |
| 1-359 | $CH_2C_4F_9$ | H | $NHCH_2CF{=}CH_2$ | F | H | $CH_3$ | $SCH_2CF_3$ | H |
| 1-360 | $CH_2C_4F_9$ | H | $NHCH_2CF{=}CH_2$ | F | H | $CH_3$ | $S(O)CH_2CF_3$ | H |
| 1-361 | $CH_2C_4F_9$ | H | $N\{C(O)CH_3\}CH_2CH{=}CH_2$ | F | H | $CH_3$ | $SCH_2CF_3$ | H |
| 1-362 | $CH_2C_4F_9$ | H | $N\{C(O)CH_3\}CH_2C{\equiv}CH$ | F | H | $CH_3$ | $SCH_2CF_3$ | H |
| 1-363 | $CH_2C_4F_9$ | H | $N\{C(O)CH_3\}CH_2CF{=}CH_2$ | F | H | $CH_3$ | $SCH_2CF_3$ | H |
| 1-364 | $CH_2C_4F_9$ | H | $OCH_3$ | F | H | $CH_3$ | $SCH_2CF_3$ | H |
| 1-365 | $CH_2C_4F_9$ | H | $OCH_3$ | F | H | $CH_3$ | $S(O)CH_2CF_3$ | H |
| 1-366 | $CF{=}CFC_4F_9$ | H | $NHC(O)CH_3$ | F | H | $CH_3$ | $SCH_2CF_3$ | H |
| 1-367 | $CF{=}CFC_4F_9$ | H | $NHC(O)CH_3$ | F | H | $CH_3$ | $S(O)CH_2CF_3$ | H |
| 1-368 | $CF_2CHFOC_2F_5$ | H | $NHC(O)CH_3$ | F | H | $CH_3$ | $SCH_2CF_3$ | H |
| 1-369 | $CF_2CHFOC_2F_5$ | H | $NHC(O)CH_3$ | F | H | $CH_3$ | $S(O)CH_2CF_3$ | H |
| 1-370 | $CF_2CHFOC_3F_7$ | H | $NHC(O)CH_3$ | F | H | $CH_3$ | $SCH_2CF_3$ | H |
| 1-371 | $CF_2CHFOC_3F_7$ | H | $NHC(O)CH_3$ | F | H | $CH_3$ | $S(O)CH_2CF_3$ | H |
| 1-372 | $CH_2CH_2CH_2CF(CF_3)_2$ | H | $NHC(O)CH_3$ | F | H | $CH_3$ | $SCH_2CF_3$ | H |
| 1-373 | $CH_2CH_2CH_2CF(CF_3)_2$ | H | $NHC(O)CH_3$ | F | H | $CH_3$ | $S(O)CH_2CF_3$ | H |
| 1-374 | $CH_2CF_2OCF_2CF_2OCF_3$ | H | $NHC(O)CH_3$ | F | H | $CH_3$ | $SCH_2CF_3$ | H |
| 1-375 | $CH_2CF_2OCF_2CF_2OCF_3$ | H | $NHC(O)CH_3$ | F | H | $CH_3$ | $S(O)CH_2CF_3$ | H |
| 1-376 | $CH_2CF_2CF_2CF_2CHF_2$ | H | $NHC(O)CH_3$ | F | H | $CH_3$ | $SCH_2CF_3$ | H |
| 1-377 | $CH_2CF_2CF_2CF_2CHF_2$ | H | $NHC(O)CH_3$ | F | H | $CH_3$ | $S(O)CH_2CF_3$ | H |

TABLE 8

| Comp. No. | R₁ | R₂ | R₃ | R₄ | R₅ | R₆ | R₇ | R₈ |
|---|---|---|---|---|---|---|---|---|
| 1-378 | $SO_2Ph(4\text{-}CH_3)$ | H | $NH_2$ | F | H | $CH_3$ | $SCH_2CF_3$ | H |
| 1-379 | $SO_2Ph(4\text{-}CH_3)$ | H | $NH_2$ | F | H | $CH_3$ | $S(O)CH_2CF_3$ | H |
| 1-380 | $SO_2Ph(4\text{-}CH_3)$ | H | $NHC(O)CH_3$ | F | H | $CH_3$ | $SCH_2CF_3$ | H |
| 1-381 | $SO_2Ph(4\text{-}CH_3)$ | H | $NHC(O)CH_3$ | F | H | $CH_3$ | $S(O)CH_2CF_3$ | H |
| 1-382 | $CF_2CHFOC_2F_5$ | Cl | H | F | H | $CH_3$ | $SCH_2CF_3$ | H |

TABLE 8-continued

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-383 | $CF_2CHFOC_2F_5$ | Cl | H | F | H | $CH_3$ | $S(O)CH_2CF_3$ | H |
| 1-384 | $CF_2CHFOC_2F_5$ | Cl | Cl | F | H | $CH_3$ | $SCH_2CF_3$ | H |
| 1-385 | $CF_2CHFOC_2F_5$ | Cl | Cl | F | H | $CH_3$ | $S(O)CH_2CF_3$ | H |
| 1-386 | $CH_2CH_2OCH(CF_3)_2$ | H | $CH_3$ | F | H | $CH_3$ | $SCH_2CF_3$ | H |
| 1-387 | $CH_2CH_2OCH(CF_3)_2$ | H | $CH_3$ | F | H | $CH_3$ | $S(O)CH_2CF_3$ | H |
| 1-388 | $CH_2CH_2CH_2OC(CF_3)_3$ | H | $CH_3$ | F | H | $CH_3$ | $SCH_2CF_3$ | H |
| 1-389 | $CH_2CH_2CH_2OC(CF_3)_3$ | H | $CH_3$ | F | H | $CH_3$ | $S(O)CH_2CF_3$ | H |
| 1-390 | $CH_2CH_2CH_2OCH(CF_3)_2$ | H | $CH_3$ | F | H | $CH_3$ | $SCH_2CF_3$ | H |
| 1-391 | $CH_2CH_2CH_2OCH(CF_3)_2$ | H | $CH_3$ | F | H | $CH_3$ | $S(O)CH_2CF_3$ | H |
| 1-392 | $CF(CF_3)_2$ | H | H | F | H | $CH_3$ | $SCH_2CF_3$ | H |
| 1-393 | $CF(CF_3)_2$ | H | H | F | H | $CH_3$ | $S(O)CH_2CF_3$ | H |
| 1-394 | $CF_2CF_2CF_3$ | H | H | F | H | $CH_3$ | $SCH_2CF_3$ | H |
| 1-395 | $CF_2CF_2CF_3$ | H | H | F | H | $CH_3$ | $S(O)CH_2CF_3$ | H |
| 1-396 | $CF_2(CF_2)_2CF_3$ | H | H | F | H | $CH_3$ | $SCH_2CF_3$ | H |
| 1-397 | $CF_2(CF_2)_2CF_3$ | H | H | F | H | $CH_3$ | $S(O)CH_2CF_3$ | H |
| 1-398 | $CF_2(CF_2)_3CF_3$ | H | H | F | H | $CH_3$ | $SCH_2CF_3$ | H |
| 1-399 | $CF_2(CF_2)_3CF_3$ | H | H | F | H | $CH_3$ | $S(O)CH_2CF_3$ | H |
| 1-400 | $CF_2(CF_2)_4CF_3$ | H | H | F | H | $CH_3$ | $SCH_2CF_3$ | H |
| 1-401 | $CF_2(CF_2)_4CF_3$ | H | H | F | H | $CH_3$ | $S(O)CH_2CF_3$ | H |
| 1-402 | $CF_2(CF_2)_5CF_3$ | H | H | F | H | $CH_3$ | $SCH_2CF_3$ | H |
| 1-403 | $CF_2(CF_2)_5CF_3$ | H | H | F | H | $CH_3$ | $S(O)CH_2CF_3$ | H |
| 1-404 | $CF_2(CF_2)_6CF_3$ | H | H | F | H | $CH_3$ | $SCH_2CF_3$ | H |
| 1-405 | $CF_2(CF_2)_6CF_3$ | H | H | F | H | $CH_3$ | $S(O)CH_2CF_3$ | H |
| 1-406 | $CF_2(CF_2)_7CF_3$ | H | H | F | H | $CH_3$ | $SCH_2CF_3$ | H |
| 1-407 | $CF_2(CF_2)_7CF_3$ | H | H | F | H | $CH_3$ | $S(O)CH_2CF_3$ | H |
| 1-408 | $CF_2(CF_2)_8CF_3$ | H | H | F | H | $CH_3$ | $SCH_2CF_3$ | H |
| 1-409 | $CF_2(CF_2)_8CF_3$ | H | H | F | H | $CH_3$ | $S(O)CH_2CF_3$ | H |
| 1-410 | $CF_2CHFOCF_3$ | H | H | F | H | $CH_3$ | $SCH_2CF_3$ | H |
| 1-411 | $CF_2CHFOCF_3$ | H | H | F | H | $CH_3$ | $S(O)CH_2CF_3$ | H |
| 1-412 | $CF_2CHFOC_2F_5$ | H | H | F | H | $CH_3$ | $SCH_2CF_3$ | H |
| 1-413 | $CF_2CHFOC_2F_5$ | H | H | F | H | $CH_3$ | $S(O)CH_2CF_3$ | H |
| 1-414 | $CF_2CHFOC_3F_7$ | H | H | F | H | $CH_3$ | $SCH_2CF_3$ | H |
| 1-415 | $CF_2CHFOC_3F_7$ | H | H | F | H | $CH_3$ | $S(O)CH_2CF_3$ | H |
| 1-416 | $CF_2CHFOC_4F_9$ | H | H | F | H | $CH_3$ | $SCH_2CF_3$ | H |
| 1-417 | $CF_2CHFOC_4F_9$ | H | H | F | H | $CH_3$ | $S(O)CH_2CF_3$ | H |
| 1-418 | $CF_2CHFOC_5F_{11}$ | H | H | F | H | $CH_3$ | $SCH_2CF_3$ | H |
| 1-419 | $CF_2CHFOC_5F_{11}$ | H | H | F | H | $CH_3$ | $S(O)CH_2CF_3$ | H |
| 1-420 | $CF_2CHFOCF(CF_3)_2$ | H | H | F | H | $CH_3$ | $SCH_2CF_3$ | H |
| 1-421 | $CF_2CHFOCF(CF_3)_2$ | H | H | F | H | $CH_3$ | $S(O)CH_2CF_3$ | H |
| 1-422 | $CF_2CHFCF_2OCF_3$ | H | H | F | H | $CH_3$ | $SCH_2CF_3$ | H |
| 1-423 | $CF_2CHFCF_2OCF_3$ | H | H | F | H | $CH_3$ | $S(O)CH_2CF_3$ | H |
| 1-424 | $CH_2CF(CF_3)OC_3F_7$ | H | H | F | H | $CH_3$ | $SCH_2CF_3$ | H |
| 1-425 | $CH_2CF(CF_3)OC_3F_7$ | H | H | F | H | $CH_3$ | $S(O)CH_2CF_3$ | H |
| 1-426 | $CH_2CF_2O(CF_2)_2OCF_3$ | H | H | F | H | $CH_3$ | $SCH_2CF_3$ | H |
| 1-427 | $CH_2CF_2O(CF_2)_2OCF_3$ | H | H | F | H | $CH_3$ | $S(O)CH_2CF_3$ | H |
| 1-428 | $CH_2CF_2O(CF_2)_2OCF_2CF_3$ | H | H | F | H | $CH_3$ | $SCH_2CF_3$ | H |
| 1-429 | $CH_2CF_2O(CF_2)_2OCF_2CF_3$ | H | H | F | H | $CH_3$ | $S(O)CH_2CF_3$ | H |
| 1-430 | $CH_2(CF_2)_3CHF_2$ | H | H | F | H | $CH_3$ | $SCH_2CF_3$ | H |
| 1-431 | $CH_2(CF_2)_3CHF_2$ | H | H | F | H | $CH_3$ | $S(O)CH_2CF_3$ | H |
| 1-432 | $CH_2(CF_2)_4CHF_2$ | H | H | F | H | $CH_3$ | $SCH_2CF_3$ | H |
| 1-433 | $CH_2(CF_2)_4CHF_2$ | H | H | F | H | $CH_3$ | $S(O)CH_2CF_3$ | H |

TABLE 9

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-434 | $CH_2CH_2CH_2(CF_2)_4CF_3$ | H | H | F | H | $CH_3$ | $SCH_2CF_3$ | H |
| 1-435 | $CH_2CH_2CH_2(CF_2)_4CF_3$ | H | H | F | H | $CH_3$ | $S(O)CH_2CF_3$ | H |
| 1-436 | $CH_2CH_2CH_2(CF_2)_5CF_3$ | H | H | F | H | $CH_3$ | $SCH_2CF_3$ | H |
| 1-437 | $CH_2CH_2CH_2(CF_2)_5CF_3$ | H | H | F | H | $CH_3$ | $S(O)CH_2CF_3$ | H |
| 1-438 | $CF(CF_3)_2$ | H | $NH_2$ | F | H | $CH_3$ | $SCH_2CF_3$ | H |
| 1-439 | $CF(CF_3)_2$ | H | $NH_2$ | F | H | $CH_3$ | $S(O)CH_2CF_3$ | H |
| 1-440 | $CF_2CF_2CF_3$ | H | $NH_2$ | F | H | $CH_3$ | $SCH_2CF_3$ | H |
| 1-441 | $CF_2CF_2CF_3$ | H | $NH_2$ | F | H | $CH_3$ | $S(O)CH_2CF_3$ | H |
| 1-442 | $CF_2(CF_2)_2CF_3$ | H | $NH_2$ | F | H | $CH_3$ | $SCH_2CF_3$ | H |
| 1-443 | $CF_2(CF_2)_2CF_3$ | H | $NH_2$ | F | H | $CH_3$ | $S(O)CH_2CF_3$ | H |
| 1-444 | $CF_2(CF_2)_3CF_3$ | H | $NH_2$ | F | H | $CH_3$ | $SCH_2CF_3$ | H |
| 1-445 | $CF_2(CF_2)_3CF_3$ | H | $NH_2$ | F | H | $CH_3$ | $S(O)CH_2CF_3$ | H |
| 1-446 | $CF_2(CF_2)_4CF_3$ | H | $NH_2$ | F | H | $CH_3$ | $SCH_2CF_3$ | H |
| 1-447 | $CF_2(CF_2)_4CF_3$ | H | $NH_2$ | F | H | $CH_3$ | $S(O)CH_2CF_3$ | H |
| 1-448 | $CF_2(CF_2)_5CF_3$ | H | $NH_2$ | F | H | $CH_3$ | $SCH_2CF_3$ | H |
| 1-449 | $CF_2(CF_2)_5CF_3$ | H | $NH_2$ | F | H | $CH_3$ | $S(O)CH_2CF_3$ | H |
| 1-450 | $CF_2(CF_2)_6CF_3$ | H | $NH_2$ | F | H | $CH_3$ | $SCH_2CF_3$ | H |
| 1-451 | $CF_2(CF_2)_6CF_3$ | H | $NH_2$ | F | H | $CH_3$ | $S(O)CH_2CF_3$ | H |
| 1-452 | $CF_2(CF_2)_7CF_3$ | H | $NH_2$ | F | H | $CH_3$ | $SCH_2CF_3$ | H |

TABLE 9-continued

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-453 | CF$_2$(CF$_2$)$_7$CF$_3$ | H | NH$_2$ | F | H | CH$_3$ | S(O)CH$_2$CF$_3$ | H |
| 1-454 | CF$_2$(CF$_2$)$_8$CF$_3$ | H | NH$_2$ | F | H | CH$_3$ | SCH$_2$CF$_3$ | H |
| 1-455 | CF$_2$(CF$_2$)$_8$CF$_3$ | H | NH$_2$ | F | H | CH$_3$ | S(O)CH$_2$CF$_3$ | H |
| 1-456 | CF$_2$CHFOCF$_3$ | H | NH$_2$ | F | H | CH$_3$ | SCH$_2$CF$_3$ | H |
| 1-457 | CF$_2$CHFOCF$_3$ | H | NH$_2$ | F | H | CH$_3$ | S(O)CH$_2$CF$_3$ | H |
| 1-458 | CF$_2$CHFOC$_2$F$_5$ | H | NH$_2$ | F | H | CH$_3$ | SCH$_2$CF$_3$ | H |
| 1-459 | CF$_2$CHFOC$_2$F$_5$ | H | NH$_2$ | F | H | CH$_3$ | S(O)CH$_2$CF$_3$ | H |
| 1-460 | CF$_2$CHFOC$_3$F$_7$ | H | NH$_2$ | F | H | CH$_3$ | SCH$_2$CF$_3$ | H |
| 1-461 | CF$_2$CHFOC$_3$F$_7$ | H | NH$_2$ | F | H | CH$_3$ | S(O)CH$_2$CF$_3$ | H |
| 1-462 | CF$_2$CHFOC$_4$F$_9$ | H | NH$_2$ | F | H | CH$_3$ | SCH$_2$CF$_3$ | H |
| 1-463 | CF$_2$CHFOC$_4$F$_9$ | H | NH$_2$ | F | H | CH$_3$ | S(O)CH$_2$CF$_3$ | H |
| 1-464 | CF$_2$CHFOC$_5$F$_{11}$ | H | NH$_2$ | F | H | CH$_3$ | SCH$_2$CF$_3$ | H |
| 1-465 | CF$_2$CHFOC$_5$F$_{11}$ | H | NH$_2$ | F | H | CH$_3$ | S(O)CH$_2$CF$_3$ | H |
| 1-466 | CF$_2$CHFOCF(CF$_3$)$_2$ | H | NH$_2$ | F | H | CH$_3$ | SCH$_2$CF$_3$ | H |
| 1-467 | CF$_2$CHFOCF(CF$_3$)$_2$ | H | NH$_2$ | F | H | CH$_3$ | S(O)CH$_2$CF$_3$ | H |
| 1-468 | CF$_2$CHFCF$_2$OCF$_3$ | H | NH$_2$ | F | H | CH$_3$ | SCH$_2$CF$_3$ | H |
| 1-469 | CF$_2$CHFCF$_2$OCF$_3$ | H | NH$_2$ | F | H | CH$_3$ | S(O)CH$_2$CF$_3$ | H |
| 1-470 | CH$_2$CF(CF$_3$)OC$_3$F$_7$ | H | NH$_2$ | F | H | CH$_3$ | SCH$_2$CF$_3$ | H |
| 1-471 | CH$_2$CF(CF$_3$)OC$_3$F$_7$ | H | NH$_2$ | F | H | CH$_3$ | S(O)CH$_2$CF$_3$ | H |
| 1-472 | CH$_2$CF$_2$O(CF$_2$)$_2$OCF$_3$ | H | NH$_2$ | F | H | CH$_3$ | SCH$_2$CF$_3$ | H |
| 1-473 | CH$_2$CF$_2$O(CF$_2$)$_2$OCF$_3$ | H | NH$_2$ | F | H | CH$_3$ | S(O)CH$_2$CF$_3$ | H |
| 1-474 | CH$_2$CF$_2$O(CF$_2$)$_2$OCF$_2$CF$_3$ | H | NH$_2$ | F | H | CH$_3$ | SCH$_2$CF$_3$ | H |
| 1-475 | CH$_2$CF$_2$O(CF$_2$)$_2$OCF$_2$CF$_3$ | H | NH$_2$ | F | H | CH$_3$ | S(O)CH$_2$CF$_3$ | H |
| 1-476 | CH$_2$(CF$_2$)$_3$CHF$_2$ | H | NH$_2$ | F | H | CH$_3$ | SCH$_2$CF$_3$ | H |
| 1-477 | CH$_2$(CF$_2$)$_3$CHF$_2$ | H | NH$_2$ | F | H | CH$_3$ | S(O)CH$_2$CF$_3$ | H |
| 1-478 | CH$_2$(CF$_2$)$_4$CHF$_2$ | H | NH$_2$ | F | H | CH$_3$ | SCH$_2$CF$_3$ | H |
| 1-479 | CH$_2$(CF$_2$)$_4$CHF$_2$ | H | NH$_2$ | F | H | CH$_3$ | S(O)CH$_2$CF$_3$ | H |
| 1-480 | CH$_2$CH$_2$CH$_2$(CF$_2$)$_4$CF$_3$ | H | NH$_2$ | F | H | CH$_3$ | SCH$_2$CF$_3$ | H |
| 1-481 | CH$_2$CH$_2$CH$_2$(CF$_2$)$_4$CF$_3$ | H | NH$_2$ | F | H | CH$_3$ | S(O)CH$_2$CF$_3$ | H |
| 1-482 | CH$_2$CH$_2$CH$_2$(CF$_2$)$_5$CF$_3$ | H | NH$_2$ | F | H | CH$_3$ | SCH$_2$CF$_3$ | H |
| 1-483 | CH$_2$CH$_2$CH$_2$(CF$_2$)$_5$CF$_3$ | H | NH$_2$ | F | H | CH$_3$ | S(O)CH$_2$CF$_3$ | H |
| 1-484 | CF(CF$_3$)$_2$ | H | NHC(O)CH$_3$ | F | H | CH$_3$ | SCH$_2$CF$_3$ | H |
| 1-485 | CF(CF$_3$)$_2$ | H | NHC(O)CH$_3$ | F | H | CH$_3$ | S(O)CH$_2$CF$_3$ | H |
| 1-486 | CF$_2$(CF$_2$)$_2$CF$_3$ | H | NHC(O)CH$_3$ | F | H | CH$_3$ | SCH$_2$CF$_3$ | H |
| 1-487 | CF$_2$(CF$_2$)$_2$CF$_3$ | H | NHC(O)CH$_3$ | F | H | CH$_3$ | S(O)CH$_2$CF$_3$ | H |
| 1-488 | CF$_2$(CF$_2$)$_3$CF$_3$ | H | NHC(O)CH$_3$ | F | H | CH$_3$ | SCH$_2$CF$_3$ | H |
| 1-489 | CF$_2$(CF$_2$)$_3$CF$_3$ | H | NHC(O)CH$_3$ | F | H | CH$_3$ | S(O)CH$_2$CF$_3$ | H |

TABLE 10

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-490 | CF$_2$(CF$_2$)$_4$CF$_3$ | H | NHC(O)CH$_3$ | F | H | CH$_3$ | SCH$_2$CF$_3$ | H |
| 1-491 | CF$_2$(CF$_2$)$_4$CF$_3$ | H | NHC(O)CH$_3$ | F | H | CH$_3$ | S(O)CH$_2$CF$_3$ | H |
| 1-492 | CF$_2$(CF$_2$)$_5$CF$_3$ | H | NHC(O)CH$_3$ | F | H | CH$_3$ | SCH$_2$CF$_3$ | H |
| 1-493 | CF$_2$(CF$_2$)$_5$CF$_3$ | H | NHC(O)CH$_3$ | F | H | CH$_3$ | S(O)CH$_2$CF$_3$ | H |
| 1-494 | CF$_2$(CF$_2$)$_6$CF$_3$ | H | NHC(O)CH$_3$ | F | H | CH$_3$ | SCH$_2$CF$_3$ | H |
| 1-495 | CF$_2$(CF$_2$)$_6$CF$_3$ | H | NHC(O)CH$_3$ | F | H | CH$_3$ | S(O)CH$_2$CF$_3$ | H |
| 1-496 | CF$_2$(CF$_2$)$_7$CF$_3$ | H | NHC(O)CH$_3$ | F | H | CH$_3$ | SCH$_2$CF$_3$ | H |
| 1-497 | CF$_2$(CF$_2$)$_7$CF$_3$ | H | NHC(O)CH$_3$ | F | H | CH$_3$ | S(O)CH$_2$CF$_3$ | H |
| 1-498 | CF$_2$(CF$_2$)$_8$CF$_3$ | H | NHC(O)CH$_3$ | F | H | CH$_3$ | SCH$_2$CF$_3$ | H |
| 1-499 | CF$_2$(CF$_2$)$_8$CF$_3$ | H | NHC(O)CH$_3$ | F | H | CH$_3$ | S(O)CH$_2$CF$_3$ | H |
| 1-500 | CF$_2$CHFOC$_4$F$_9$ | H | NHC(O)CH$_3$ | F | H | CH$_3$ | SCH$_2$CF$_3$ | H |
| 1-501 | CF$_2$CHFOC$_4$F$_9$ | H | NHC(O)CH$_3$ | F | H | CH$_3$ | S(O)CH$_2$CF$_3$ | H |
| 1-502 | CF$_2$CHFOC$_5$F$_{11}$ | H | NHC(O)CH$_3$ | F | H | CH$_3$ | SCH$_2$CF$_3$ | H |
| 1-503 | CF$_2$CHFOC$_5$F$_{11}$ | H | NHC(O)CH$_3$ | F | H | CH$_3$ | S(O)CH$_2$CF$_3$ | H |
| 1-504 | CF$_2$CHFOCF(CF$_3$)$_2$ | H | NHC(O)CH$_3$ | F | H | CH$_3$ | SCH$_2$CF$_3$ | H |
| 1-505 | CF$_2$CHFOCF(CF$_3$)$_2$ | H | NHC(O)CH$_3$ | F | H | CH$_3$ | S(O)CH$_2$CF$_3$ | H |
| 1-506 | CF$_2$CHFCF$_2$OCF$_3$ | H | NHC(O)CH$_3$ | F | H | CH$_3$ | SCH$_2$CF$_3$ | H |
| 1-507 | CF$_2$CHFCF$_2$OCF$_3$ | H | NHC(O)CH$_3$ | F | H | CH$_3$ | S(O)CH$_2$CF$_3$ | H |
| 1-508 | CH$_2$CF(CF$_3$)OC$_3$F$_7$ | H | NHC(O)CH$_3$ | F | H | CH$_3$ | SCH$_2$CF$_3$ | H |
| 1-509 | CH$_2$CF(CF$_3$)OC$_3$F$_7$ | H | NHC(O)CH$_3$ | F | H | CH$_3$ | S(O)CH$_2$CF$_3$ | H |
| 1-510 | CH$_2$CF$_2$O(CF$_2$)$_2$OCF$_2$CF$_3$ | H | NHC(O)CH$_3$ | F | H | CH$_3$ | SCH$_2$CF$_3$ | H |
| 1-511 | CH$_2$CF$_2$O(CF$_2$)$_2$OCF$_2$CF$_3$ | H | NHC(O)CH$_3$ | F | H | CH$_3$ | S(O)CH$_2$CF$_3$ | H |
| 1-512 | CH$_2$(CF$_2$)$_4$CHF$_2$ | H | NHC(O)CH$_3$ | F | H | CH$_3$ | SCH$_2$CF$_3$ | H |
| 1-513 | CH$_2$(CF$_2$)$_4$CHF$_2$ | H | NHC(O)CH$_3$ | F | H | CH$_3$ | S(O)CH$_2$CF$_3$ | H |
| 1-514 | CH$_2$CH$_2$CH$_2$(CF$_2$)$_4$CF$_3$ | H | NHC(O)CH$_3$ | F | H | CH$_3$ | SCH$_2$CF$_3$ | H |
| 1-515 | CH$_2$CH$_2$CH$_2$(CF$_2$)$_4$CF$_3$ | H | NHC(O)CH$_3$ | F | H | CH$_3$ | S(O)CH$_2$CF$_3$ | H |
| 1-516 | CH$_2$CH$_2$CH$_2$(CF$_2$)$_5$CF$_3$ | H | NHC(O)CH$_3$ | F | H | CH$_3$ | SCH$_2$CF$_3$ | H |
| 1-517 | CH$_2$CH$_2$CH$_2$(CF$_2$)$_5$CF$_3$ | H | NHC(O)CH$_3$ | F | H | CH$_3$ | S(O)CH$_2$CF$_3$ | H |
| 1-518 | CF(CF$_3$)$_2$ | H | NHCH$_3$ | F | H | CH$_3$ | SCH$_2$CF$_3$ | H |
| 1-519 | CF(CF$_3$)$_2$ | H | NHCH$_3$ | F | H | CH$_3$ | S(O)CH$_2$CF$_3$ | H |
| 1-520 | CF$_2$CF$_2$CF$_3$ | H | NHCH$_3$ | F | H | CH$_3$ | SCH$_2$CF$_3$ | H |
| 1-521 | CF$_2$CF$_2$CF$_3$ | H | NHCH$_3$ | F | H | CH$_3$ | S(O)CH$_2$CF$_3$ | H |
| 1-522 | CF$_2$(CF$_2$)$_2$CF$_3$ | H | NHCH$_3$ | F | H | CH$_3$ | SCH$_2$CF$_3$ | H |

TABLE 10-continued

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-523 | $CF_2(CF_2)_2CF_3$ | H | $NHCH_3$ | F | H | $CH_3$ | $S(O)CH_2CF_3$ | H |
| 1-524 | $CF_2(CF_2)_3CF_3$ | H | $NHCH_3$ | F | H | $CH_3$ | $SCH_2CF_3$ | H |
| 1-525 | $CF_2(CF_2)_3CF_3$ | H | $NHCH_3$ | F | H | $CH_3$ | $S(O)CH_2CF_3$ | H |
| 1-526 | $CF_2(CF_2)_4CF_3$ | H | $NHCH_3$ | F | H | $CH_3$ | $SCH_2CF_3$ | H |
| 1-527 | $CF_2(CF_2)_4CF_3$ | H | $NHCH_3$ | F | H | $CH_3$ | $S(O)CH_2CF_3$ | H |
| 1-528 | $CF_2(CF_2)_5CF_3$ | H | $NHCH_3$ | F | H | $CH_3$ | $SCH_2CF_3$ | H |
| 1-529 | $CF_2(CF_2)_5CF_3$ | H | $NHCH_3$ | F | H | $CH_3$ | $S(O)CH_2CF_3$ | H |
| 1-530 | $CF_2(CF_2)_6CF_3$ | H | $NHCH_3$ | F | H | $CH_3$ | $SCH_2CF_3$ | H |
| 1-531 | $CF_2(CF_2)_6CF_3$ | H | $NHCH_3$ | F | H | $CH_3$ | $S(O)CH_2CF_3$ | H |
| 1-532 | $CF_2(CF_2)_7CF_3$ | H | $NHCH_3$ | F | H | $CH_3$ | $SCH_2CF_3$ | H |
| 1-533 | $CF_2(CF_2)_7CF_3$ | H | $NHCH_3$ | F | H | $CH_3$ | $S(O)CH_2CF_3$ | H |
| 1-534 | $CF_2(CF_2)_8CF_3$ | H | $NHCH_3$ | F | H | $CH_3$ | $SCH_2CF_3$ | H |
| 1-535 | $CF_2(CF_2)_8CF_3$ | H | $NHCH_3$ | F | H | $CH_3$ | $S(O)CH_2CF_3$ | H |
| 1-536 | $CF_2CHFOC_4F_9$ | H | $NHCH_3$ | F | H | $CH_3$ | $SCH_2CF_3$ | H |
| 1-537 | $CF_2CHFOC_4F_9$ | H | $NHCH_3$ | F | H | $CH_3$ | $S(O)CH_2CF_3$ | H |
| 1-538 | $CF_2CHFOC_5F_{11}$ | H | $NHCH_3$ | F | H | $CH_3$ | $SCH_2CF_3$ | H |
| 1-539 | $CF_2CHFOC_5F_{11}$ | H | $NHCH_3$ | F | H | $CH_3$ | $S(O)CH_2CF_3$ | H |
| 1-540 | $CF_2CHFOCF(CF_3)_2$ | H | $NHCH_3$ | F | H | $CH_3$ | $SCH_2CF_3$ | H |
| 1-541 | $CF_2CHFOCF(CF_3)_2$ | H | $NHCH_3$ | F | H | $CH_3$ | $S(O)CH_2CF_3$ | H |
| 1-542 | $CF_2CHFCF_2OCF_3$ | H | $NHCH_3$ | F | H | $CH_3$ | $SCH_2CF_3$ | H |
| 1-543 | $CF_2CHFCF_2OCF_3$ | H | $NHCH_3$ | F | H | $CH_3$ | $S(O)CH_2CF_3$ | H |
| 1-544 | $CH_2CF(CF_3)OC_3F_7$ | H | $NHCH_3$ | F | H | $CH_3$ | $SCH_2CF_3$ | H |
| 1-545 | $CH_2CF(CF_3)OC_3F_7$ | H | $NHCH_3$ | F | H | $CH_3$ | $S(O)CH_2CF_3$ | H |

TABLE 11

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-546 | $CH_2CF_2O(CF_2)_2OCF_3$ | H | $NHCH_3$ | F | H | $CH_3$ | $SCH_2CF_3$ | H |
| 1-547 | $CH_2CF_2O(CF_2)_2OCF_3$ | H | $NHCH_3$ | F | H | $CH_3$ | $S(O)CH_2CF_3$ | H |
| 1-548 | $CH_2CF_2O(CF_2)_2OCF_2CF_3$ | H | $NHCH_3$ | F | H | $CH_3$ | $SCH_2CF_3$ | H |
| 1-549 | $CH_2CF_2O(CF_2)_2OCF_2CF_3$ | H | $NHCH_3$ | F | H | $CH_3$ | $S(O)CH_2CF_3$ | H |
| 1-550 | $CH_2(CF_2)_3CHF_2$ | H | $NHCH_3$ | F | H | $CH_3$ | $SCH_2CF_3$ | H |
| 1-551 | $CH_2(CF_2)_3CHF_2$ | H | $NHCH_3$ | F | H | $CH_3$ | $S(O)CH_2CF_3$ | H |
| 1-552 | $CH_2(CF_2)_4CHF_2$ | H | $NHCH_3$ | F | H | $CH_3$ | $SCH_2CF_3$ | H |
| 1-553 | $CH_2(CF_2)_4CHF_2$ | H | $NHCH_3$ | F | H | $CH_3$ | $S(O)CH_2CF_3$ | H |
| 1-554 | $CH_2CH_2CH_2(CF_2)_4CF_3$ | H | $NHCH_3$ | F | H | $CH_3$ | $SCH_2CF_3$ | H |
| 1-555 | $CH_2CH_2CH_2(CF_2)_4CF_3$ | H | $NHCH_3$ | F | H | $CH_3$ | $S(O)CH_2CF_3$ | H |
| 1-556 | $CH_2CH_2CH_2(CF_2)_5CF_3$ | H | $NHCH_3$ | F | H | $CH_3$ | $SCH_2CF_3$ | H |
| 1-557 | $CH_2CH_2CH_2(CF_2)_5CF_3$ | H | $NHCH_3$ | F | H | $CH_3$ | $S(O)CH_2CF_3$ | H |
| 1-558 | $CF_2CHFCF_3$ | H | $NHCH_2C{\equiv}CH$ | F | H | $CH_3$ | $SCH_2CF_3$ | H |
| 1-559 | $CF_2CHFCF_3$ | H | $NHCH_2C{\equiv}CH$ | F | H | $CH_3$ | $S(O)CH_2CF_3$ | H |
| 1-560 | $CF(CF_3)_2$ | H | $NHCH_2C{\equiv}CH$ | F | H | $CH_3$ | $SCH_2CF_3$ | H |
| 1-561 | $CF(CF_3)_2$ | H | $NHCH_2C{\equiv}CH$ | F | H | $CH_3$ | $S(O)CH_2CF_3$ | H |
| 1-562 | $CF_2CF_2CF_3$ | H | $NHCH_2C{\equiv}CH$ | F | H | $CH_3$ | $SCH_2CF_3$ | H |
| 1-563 | $CF_2CF_2CF_3$ | H | $NHCH_2C{\equiv}CH$ | F | H | $CH_3$ | $S(O)CH_2CF_3$ | H |
| 1-564 | $CF_2(CF_2)_2CF_3$ | H | $NHCH_2C{\equiv}CH$ | F | H | $CH_3$ | $SCH_2CF_3$ | H |
| 1-565 | $CF_2(CF_2)_2CF_3$ | H | $NHCH_2C{\equiv}CH$ | F | H | $CH_3$ | $S(O)CH_2CF_3$ | H |
| 1-566 | $CF_2(CF_2)_3CF_3$ | H | $NHCH_2C{\equiv}CH$ | F | H | $CH_3$ | $SCH_2CF_3$ | H |
| 1-567 | $CF_2(CF_2)_3CF_3$ | H | $NHCH_2C{\equiv}CH$ | F | H | $CH_3$ | $S(O)CH_2CF_3$ | H |
| 1-568 | $CF_2(CF_2)_4CF_3$ | H | $NHCH_2C{\equiv}CH$ | F | H | $CH_3$ | $SCH_2CF_3$ | H |
| 1-569 | $CF_2(CF_2)_4CF_3$ | H | $NHCH_2C{\equiv}CH$ | F | H | $CH_3$ | $S(O)CH_2CF_3$ | H |
| 1-570 | $CF_2(CF_2)_5CF_3$ | H | $NHCH_2C{\equiv}CH$ | F | H | $CH_3$ | $SCH_2CF_3$ | H |
| 1-571 | $CF_2(CF_2)_5CF_3$ | H | $NHCH_2C{\equiv}CH$ | F | H | $CH_3$ | $S(O)CH_2CF_3$ | H |
| 1-572 | $CF_2(CF_2)_6CF_3$ | H | $NHCH_2C{\equiv}CH$ | F | H | $CH_3$ | $SCH_2CF_3$ | H |
| 1-573 | $CF_2(CF_2)_6CF_3$ | H | $NHCH_2C{\equiv}CH$ | F | H | $CH_3$ | $S(O)CH_2CF_3$ | H |
| 1-574 | $CF_2(CF_2)_7CF_3$ | H | $NHCH_2C{\equiv}CH$ | F | H | $CH_3$ | $SCH_2CF_3$ | H |
| 1-575 | $CF_2(CF_2)_7CF_3$ | H | $NHCH_2C{\equiv}CH$ | F | H | $CH_3$ | $S(O)CH_2CF_3$ | H |
| 1-576 | $CF_2(CF_2)_8CF_3$ | H | $NHCH_2C{\equiv}CH$ | F | H | $CH_3$ | $SCH_2CF_3$ | H |
| 1-577 | $CF_2(CF_2)_8CF_3$ | H | $NHCH_2C{\equiv}CH$ | F | H | $CH_3$ | $S(O)CH_2CF_3$ | H |
| 1-578 | $CF_2CHFOCF_3$ | H | $NHCH_2C{\equiv}CH$ | F | H | $CH_3$ | $SCH_2CF_3$ | H |
| 1-579 | $CF_2CHFOCF_3$ | H | $NHCH_2C{\equiv}CH$ | F | H | $CH_3$ | $S(O)CH_2CF_3$ | H |
| 1-580 | $CF_2CHFOC_4F_9$ | H | $NHCH_2C{\equiv}CH$ | F | H | $CH_3$ | $SCH_2CF_3$ | H |
| 1-581 | $CF_2CHFOC_4F_9$ | H | $NHCH_2C{\equiv}CH$ | F | H | $CH_3$ | $S(O)CH_2CF_3$ | H |
| 1-582 | $CF_2CHFOC_5F_{11}$ | H | $NHCH_2C{\equiv}CH$ | F | H | $CH_3$ | $SCH_2CF_3$ | H |
| 1-583 | $CF_2CHFOC_5F_{11}$ | H | $NHCH_2C{\equiv}CH$ | F | H | $CH_3$ | $S(O)CH_2CF_3$ | H |
| 1-584 | $CF_2CHFOCF(CF_3)_2$ | H | $NHCH_2C{\equiv}CH$ | F | H | $CH_3$ | $SCH_2CF_3$ | H |
| 1-585 | $CF_2CHFOCF(CF_3)_2$ | H | $NHCH_2C{\equiv}CH$ | F | H | $CH_3$ | $S(O)CH_2CF_3$ | H |
| 1-586 | $CF_2CHFCF_2OCF_3$ | H | $NHCH_2C{\equiv}CH$ | F | H | $CH_3$ | $SCH_2CF_3$ | H |
| 1-587 | $CF_2CHFCF_2OCF_3$ | H | $NHCH_2C{\equiv}CH$ | F | H | $CH_3$ | $S(O)CH_2CF_3$ | H |
| 1-588 | $CH_2CF(CF_3)OC_3F_7$ | H | $NHCH_2C{\equiv}CH$ | F | H | $CH_3$ | $SCH_2CF_3$ | H |
| 1-589 | $CH_2CF(CF_3)OC_3F_7$ | H | $NHCH_2C{\equiv}CH$ | F | H | $CH_3$ | $S(O)CH_2CF_3$ | H |
| 1-590 | $CH_2CF_2O(CF_2)_2OCF_3$ | H | $NHCH_2C{\equiv}CH$ | F | H | $CH_3$ | $SCH_2CF_3$ | H |
| 1-591 | $CH_2CF_2O(CF_2)_2OCF_3$ | H | $NHCH_2C{\equiv}CH$ | F | H | $CH_3$ | $S(O)CH_2CF_3$ | H |
| 1-592 | $CH_2CF_2O(CF_2)_2OCF_2CF_3$ | H | $NHCH_2C{\equiv}CH$ | F | H | $CH_3$ | $SCH_2CF_3$ | H |

TABLE 11-continued

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-593 | CH$_2$CF$_2$O(CF$_2$)$_2$OCF$_2$CF$_3$ | H | NHCH$_2$C≡CH | F | H | CH$_3$ | S(O)CH$_2$CF$_3$ | H |
| 1-594 | CH$_2$(CF$_2$)$_3$CHF$_2$ | H | NHCH$_2$C≡CH | F | H | CH$_3$ | SCH$_2$CF$_3$ | H |
| 1-595 | CH$_2$(CF$_2$)$_3$CHF$_2$ | H | NHCH$_2$C≡CH | F | H | CH$_3$ | S(O)CH$_2$CF$_3$ | H |
| 1-596 | CH$_2$(CF$_2$)$_4$CHF$_2$ | H | NHCH$_2$C≡CH | F | H | CH$_3$ | SCH$_2$CF$_3$ | H |
| 1-597 | CH$_2$(CF$_2$)$_4$CHF$_2$ | H | NHCH$_2$C≡CH | F | H | CH$_3$ | S(O)CH$_2$CF$_3$ | H |
| 1-598 | CH$_2$CH$_2$CH$_2$(CF$_2$)$_4$CF$_3$ | H | NHCH$_2$C≡CH | F | H | CH$_3$ | SCH$_2$CF$_3$ | H |
| 1-599 | CH$_2$CH$_2$CH$_2$(CF$_2$)$_4$CF$_3$ | H | NHCH$_2$C≡CH | F | H | CH$_3$ | S(O)CH$_2$CF$_3$ | H |
| 1-600 | CH$_2$CH$_2$CH$_2$(CF$_2$)$_5$CF$_3$ | H | NHCH$_2$C≡CH | F | H | CH$_3$ | SCH$_2$CF$_3$ | H |
| 1-601 | CH$_2$CH$_2$CH$_2$(CF$_2$)$_5$CF$_3$ | H | NHCH$_2$C≡CH | F | H | CH$_3$ | S(O)CH$_2$CF$_3$ | H |

TABLE 12

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-602 | CF$_2$CHFCF$_3$ | H | NHCH$_2$CH=CH$_2$ | F | H | CH$_3$ | SCH$_2$CF$_3$ | H |
| 1-603 | CF$_2$CHFCF$_3$ | H | NHCH$_2$CH=CH$_2$ | F | H | CH$_3$ | S(O)CH$_2$CF$_3$ | H |
| 1-604 | CF(CF$_3$)$_2$ | H | NHCH$_2$CH=CH$_2$ | F | H | CH$_3$ | SCH$_2$CF$_3$ | H |
| 1-605 | CF(CF$_3$)$_2$ | H | NHCH$_2$CH=CH$_2$ | F | H | CH$_3$ | S(O)CH$_2$CF$_3$ | H |
| 1-606 | CF$_2$CF$_2$CF$_3$ | H | NHCH$_2$CH=CH$_2$ | F | H | CH$_3$ | SCH$_2$CF$_3$ | H |
| 1-607 | CF$_2$CF$_2$CF$_3$ | H | NHCH$_2$CH=CH$_2$ | F | H | CH$_3$ | S(O)CH$_2$CF$_3$ | H |
| 1-608 | CF$_2$(CF$_2$)$_2$CF$_3$ | H | NHCH$_2$CH=CH$_2$ | F | H | CH$_3$ | SCH$_2$CF$_3$ | H |
| 1-609 | CF$_2$(CF$_2$)$_2$CF$_3$ | H | NHCH$_2$CH=CH$_2$ | F | H | CH$_3$ | S(O)CH$_2$CF$_3$ | H |
| 1-610 | CF$_2$(CF$_2$)$_3$CF$_3$ | H | NHCH$_2$CH=CH$_2$ | F | H | CH$_3$ | SCH$_2$CF$_3$ | H |
| 1-611 | CF$_2$(CF$_2$)$_3$CF$_3$ | H | NHCH$_2$CH=CH$_2$ | F | H | CH$_3$ | S(O)CH$_2$CF$_3$ | H |
| 1-612 | CF$_2$(CF$_2$)$_4$CF$_3$ | H | NHCH$_2$CH=CH$_2$ | F | H | CH$_3$ | SCH$_2$CF$_3$ | H |
| 1-613 | CF$_2$(CF$_2$)$_4$CF$_3$ | H | NHCH$_2$CH=CH$_2$ | F | H | CH$_3$ | S(O)CH$_2$CF$_3$ | H |
| 1-614 | CF$_2$(CF$_2$)$_5$CF$_3$ | H | NHCH$_2$CH=CH$_2$ | F | H | CH$_3$ | SCH$_2$CF$_3$ | H |
| 1-615 | CF$_2$(CF$_2$)$_5$CF$_3$ | H | NHCH$_2$CH=CH$_2$ | F | H | CH$_3$ | S(O)CH$_2$CF$_3$ | H |
| 1-616 | CF$_2$(CF$_2$)$_6$CF$_3$ | H | NHCH$_2$CH=CH$_2$ | F | H | CH$_3$ | SCH$_2$CF$_3$ | H |
| 1-617 | CF$_2$(CF$_2$)$_6$CF$_3$ | H | NHCH$_2$CH=CH$_2$ | F | H | CH$_3$ | S(O)CH$_2$CF$_3$ | H |
| 1-618 | CF$_2$(CF$_2$)$_7$CF$_3$ | H | NHCH$_2$CH=CH$_2$ | F | H | CH$_3$ | SCH$_2$CF$_3$ | H |
| 1-619 | CF$_2$(CF$_2$)$_7$CF$_3$ | H | NHCH$_2$CH=CH$_2$ | F | H | CH$_3$ | S(O)CH$_2$CF$_3$ | H |
| 1-620 | CF$_2$(CF$_2$)$_8$CF$_3$ | H | NHCH$_2$CH=CH$_2$ | F | H | CH$_3$ | SCH$_2$CF$_3$ | H |
| 1-621 | CF$_2$(CF$_2$)$_8$CF$_3$ | H | NHCH$_2$CH=CH$_2$ | F | H | CH$_3$ | S(O)CH$_2$CF$_3$ | H |
| 1-622 | CF$_2$CHFOCF$_3$ | H | NHCH$_2$CH=CH$_2$ | F | H | CH$_3$ | SCH$_2$CF$_3$ | H |
| 1-623 | CF$_2$CHFOCF$_3$ | H | NHCH$_2$CH=CH$_2$ | F | H | CH$_3$ | S(O)CH$_2$CF$_3$ | H |
| 1-624 | CF$_2$CHFOC$_2$F$_5$ | H | NHCH$_2$CH=CH$_2$ | F | H | CH$_3$ | SCH$_2$CF$_3$ | H |
| 1-625 | CF$_2$CHFOC$_2$F$_5$ | H | NHCH$_2$CH=CH$_2$ | F | H | CH$_3$ | S(O)CH$_2$CF$_3$ | H |
| 1-626 | CF$_2$CHFOC$_3$F$_7$ | H | NHCH$_2$CH=CH$_2$ | F | H | CH$_3$ | SCH$_2$CF$_3$ | H |
| 1-627 | CF$_2$CHFOC$_3$F$_7$ | H | NHCH$_2$CH=CH$_2$ | F | H | CH$_3$ | S(O)CH$_2$CF$_3$ | H |
| 1-628 | CF$_2$CHFOC$_4$F$_9$ | H | NHCH$_2$CH=CH$_2$ | F | H | CH$_3$ | SCH$_2$CF$_3$ | H |
| 1-629 | CF$_2$CHFOC$_4$F$_9$ | H | NHCH$_2$CH=CH$_2$ | F | H | CH$_3$ | S(O)CH$_2$CF$_3$ | H |
| 1-630 | CF$_2$CHFOC$_5$F$_{11}$ | H | NHCH$_2$CH=CH$_2$ | F | H | CH$_3$ | SCH$_2$CF$_3$ | H |
| 1-631 | CF$_2$CHFOC$_5$F$_{11}$ | H | NHCH$_2$CH=CH$_2$ | F | H | CH$_3$ | S(O)CH$_2$CF$_3$ | H |
| 1-632 | CF$_2$CHFOCF(CF$_3$)$_2$ | H | NHCH$_2$CH=CH$_2$ | F | H | CH$_3$ | SCH$_2$CF$_3$ | H |
| 1-633 | CF$_2$CHFOCF(CF$_3$)$_2$ | H | NHCH$_2$CH=CH$_2$ | F | H | CH$_3$ | S(O)CH$_2$CF$_3$ | H |
| 1-634 | CF$_2$CHFCF$_2$OCF$_3$ | H | NHCH$_2$CH=CH$_2$ | F | H | CH$_3$ | SCH$_2$CF$_3$ | H |
| 1-635 | CF$_2$CHFCF$_2$OCF$_3$ | H | NHCH$_2$CH=CH$_2$ | F | H | CH$_3$ | S(O)CH$_2$CF$_3$ | H |
| 1-636 | CH$_2$CF(CF$_3$)OC$_3$F$_7$ | H | NHCH$_2$CH=CH$_2$ | F | H | CH$_3$ | SCH$_2$CF$_3$ | H |
| 1-637 | CH$_2$CF(CF$_3$)OC$_3$F$_7$ | H | NHCH$_2$CH=CH$_2$ | F | H | CH$_3$ | S(O)CH$_2$CF$_3$ | H |
| 1-638 | CH$_2$CF$_2$O(CF$_2$)$_2$OCF$_3$ | H | NHCH$_2$CH=CH$_2$ | F | H | CH$_3$ | SCH$_2$CF$_3$ | H |
| 1-639 | CH$_2$CF$_2$O(CF$_2$)$_2$OCF$_3$ | H | NHCH$_2$CH=CH$_2$ | F | H | CH$_3$ | S(O)CH$_2$CF$_3$ | H |
| 1-640 | CH$_2$CF$_2$O(CF$_2$)$_2$OCF$_2$CF$_3$ | H | NHCH$_2$CH=CH$_2$ | F | H | CH$_3$ | SCH$_2$CF$_3$ | H |
| 1-641 | CH$_2$CF$_2$O(CF$_2$)$_2$OCF$_2$CF$_3$ | H | NHCH$_2$CH=CH$_2$ | F | H | CH$_3$ | S(O)CH$_2$CF$_3$ | H |
| 1-642 | CH$_2$(CF$_2$)$_3$CHF$_2$ | H | NHCH$_2$CH=CH$_2$ | F | H | CH$_3$ | SCH$_2$CF$_3$ | H |
| 1-643 | CH$_2$(CF$_2$)$_3$CHF$_2$ | H | NHCH$_2$CH=CH$_2$ | F | H | CH$_3$ | S(O)CH$_2$CF$_3$ | H |
| 1-644 | CH$_2$(CF$_2$)$_4$CHF$_2$ | H | NHCH$_2$CH=CH$_2$ | F | H | CH$_3$ | SCH$_2$CF$_3$ | H |
| 1-645 | CH$_2$(CF$_2$)$_4$CHF$_2$ | H | NHCH$_2$CH=CH$_2$ | F | H | CH$_3$ | S(O)CH$_2$CF$_3$ | H |
| 1-646 | CH$_2$CH$_2$CH$_2$(CF$_2$)$_4$CF$_3$ | H | NHCH$_2$CH=CH$_2$ | F | H | CH$_3$ | SCH$_2$CF$_3$ | H |
| 1-647 | CH$_2$CH$_2$CH$_2$(CF$_2$)$_4$CF$_3$ | H | NHCH$_2$CH=CH$_2$ | F | H | CH$_3$ | S(O)CH$_2$CF$_3$ | H |
| 1-648 | CH$_2$CH$_2$CH$_2$(CF$_2$)$_5$CF$_3$ | H | NHCH$_2$CH=CH$_2$ | F | H | CH$_3$ | SCH$_2$CF$_3$ | H |
| 1-649 | CH$_2$CH$_2$CH$_2$(CF$_2$)$_5$CF$_3$ | H | NHCH$_2$CH=CH$_2$ | F | H | CH$_3$ | S(O)CH$_2$CF$_3$ | H |
| 1-650 | CF(CF$_3$)$_2$ | H | CN | F | H | CH$_3$ | SCH$_2$CF$_3$ | H |
| 1-651 | CF(CF$_3$)$_2$ | H | CN | F | H | CH$_3$ | S(O)CH$_2$CF$_3$ | H |
| 1-652 | CF$_2$CF$_2$CF$_3$ | H | CN | F | H | CH$_3$ | SCH$_2$CF$_3$ | H |
| 1-653 | CF$_2$CF$_2$CF$_3$ | H | CN | F | H | CH$_3$ | S(O)CH$_2$CF$_3$ | H |
| 1-654 | CF$_2$(CF$_2$)$_2$CF$_3$ | H | CN | F | H | CH$_3$ | SCH$_2$CF$_3$ | H |
| 1-655 | CF$_2$(CF$_2$)$_2$CF$_3$ | H | CN | F | H | CH$_3$ | S(O)CH$_2$CF$_3$ | H |
| 1-656 | CF$_2$(CF$_2$)$_3$CF$_3$ | H | CN | F | H | CH$_3$ | SCH$_2$CF$_3$ | H |
| 1-657 | CF$_2$(CF$_2$)$_3$CF$_3$ | H | CN | F | H | CH$_3$ | S(O)CH$_2$CF$_3$ | H |

TABLE 13

| Comp. No. | R₁ | R₂ | R₃ | R₄ | R₅ | R₆ | R₇ | R₈ |
|---|---|---|---|---|---|---|---|---|
| 1-658 | CF$_2$(CF$_2$)$_4$CF$_3$ | H | CN | F | H | CH$_3$ | SCH$_2$CF$_3$ | H |
| 1-659 | CF$_2$(CF$_2$)$_4$CF$_3$ | H | CN | F | H | CH$_3$ | S(O)CH$_2$CF$_3$ | H |
| 1-660 | CF$_2$(CF$_2$)$_5$CF$_3$ | H | CN | F | H | CH$_3$ | SCH$_2$CF$_3$ | H |
| 1-661 | CF$_2$(CF$_2$)$_5$CF$_3$ | H | CN | F | H | CH$_3$ | S(O)CH$_2$CF$_3$ | H |
| 1-662 | CF$_2$(CF$_2$)$_6$CF$_3$ | H | CN | F | H | CH$_3$ | SCH$_2$CF$_3$ | H |
| 1-663 | CF$_2$(CF$_2$)$_6$CF$_3$ | H | CN | F | H | CH$_3$ | S(O)CH$_2$CF$_3$ | H |
| 1-664 | CF$_2$(CF$_2$)$_7$CF$_3$ | H | CN | F | H | CH$_3$ | SCH$_2$CF$_3$ | H |
| 1-665 | CF$_2$(CF$_2$)$_7$CF$_3$ | H | CN | F | H | CH$_3$ | S(O)CH$_2$CF$_3$ | H |
| 1-666 | CF$_2$(CF$_2$)$_8$CF$_3$ | H | CN | F | H | CH$_3$ | SCH$_2$CF$_3$ | H |
| 1-667 | CF$_2$(CF$_2$)$_8$CF$_3$ | H | CN | F | H | CH$_3$ | S(O)CH$_2$CF$_3$ | H |
| 1-668 | CF$_2$CHFOCF$_3$ | H | CN | F | H | CH$_3$ | SCH$_2$CF$_3$ | H |
| 1-669 | CF$_2$CHFOCF$_3$ | H | CN | F | H | CH$_3$ | S(O)CH$_2$CF$_3$ | H |
| 1-670 | CF$_2$CHFOC$_2$F$_5$ | H | CN | F | H | CH$_3$ | SCH$_2$CF$_3$ | H |
| 1-671 | CF$_2$CHFOC$_2$F$_5$ | H | CN | F | H | CH$_3$ | S(O)CH$_2$CF$_3$ | H |
| 1-672 | CF$_2$CHFOC$_3$F$_7$ | H | CN | F | H | CH$_3$ | SCH$_2$CF$_3$ | H |
| 1-673 | CF$_2$CHFOC$_3$F$_7$ | H | CN | F | H | CH$_3$ | S(O)CH$_2$CF$_3$ | H |
| 1-674 | CF$_2$CHFOC$_4$F$_9$ | H | CN | F | H | CH$_3$ | SCH$_2$CF$_3$ | H |
| 1-675 | CF$_2$CHFOC$_4$F$_9$ | H | CN | F | H | CH$_3$ | S(O)CH$_2$CF$_3$ | H |
| 1-676 | CF$_2$CHFOC$_5$F$_{11}$ | H | CN | F | H | CH$_3$ | SCH$_2$CF$_3$ | H |
| 1-677 | CF$_2$CHFOC$_5$F$_{11}$ | H | CN | F | H | CH$_3$ | S(O)CH$_2$CF$_3$ | H |
| 1-678 | CF$_2$CHFOCF(CF$_3$)$_2$ | H | CN | F | H | CH$_3$ | SCH$_2$CF$_3$ | H |
| 1-679 | CF$_2$CHFOCF(CF$_3$)$_2$ | H | CN | F | H | CH$_3$ | S(O)CH$_2$CF$_3$ | H |
| 1-680 | CF$_2$CHFCF$_2$OCF$_3$ | H | CN | F | H | CH$_3$ | SCH$_2$CF$_3$ | H |
| 1-681 | CF$_2$CHFCF$_2$OCF$_3$ | H | CN | F | H | CH$_3$ | S(O)CH$_2$CF$_3$ | H |
| 1-682 | CH$_2$CF(CF$_3$)OC$_3$F$_7$ | H | CN | F | H | CH$_3$ | SCH$_2$CF$_3$ | H |
| 1-683 | CH$_2$CF(CF$_3$)OC$_3$F$_7$ | H | CN | F | H | CH$_3$ | S(O)CH$_2$CF$_3$ | H |
| 1-684 | CH$_2$CF$_2$O(CF$_2$)$_2$OCF$_3$ | H | CN | F | H | CH$_3$ | SCH$_2$CF$_3$ | H |
| 1-685 | CH$_2$CF$_2$O(CF$_2$)$_2$OCF$_3$ | H | CN | F | H | CH$_3$ | S(O)CH$_2$CF$_3$ | H |
| 1-686 | CH$_2$CF$_2$O(CF$_2$)$_2$OCF$_2$CF$_3$ | H | CN | F | H | CH$_3$ | SCH$_2$CF$_3$ | H |
| 1-687 | CH$_2$CF$_2$O(CF$_2$)$_2$OCF$_2$CF$_3$ | H | CN | F | H | CH$_3$ | S(O)CH$_2$CF$_3$ | H |
| 1-688 | CH$_2$(CF$_2$)$_3$CHF$_2$ | H | CN | F | H | CH$_3$ | SCH$_2$CF$_3$ | H |
| 1-689 | CH$_2$(CF$_2$)$_3$CHF$_2$ | H | CN | F | H | CH$_3$ | S(O)CH$_2$CF$_3$ | H |
| 1-690 | CH$_2$(CF$_2$)$_4$CHF$_2$ | H | CN | F | H | CH$_3$ | SCH$_2$CF$_3$ | H |
| 1-691 | CH$_2$(CF$_2$)$_4$CHF$_2$ | H | CN | F | H | CH$_3$ | S(O)CH$_2$CF$_3$ | H |
| 1-692 | CH$_2$CH$_2$CH$_2$(CF$_2$)$_4$CF$_3$ | H | CN | F | H | CH$_3$ | SCH$_2$CF$_3$ | H |
| 1-693 | CH$_2$CH$_2$CH$_2$(CF$_2$)$_4$CF$_3$ | H | CN | F | H | CH$_3$ | S(O)CH$_2$CF$_3$ | H |
| 1-694 | CH$_2$CH$_2$CH$_2$(CF$_2$)$_5$CF$_3$ | H | CN | F | H | CH$_3$ | SCH$_2$CF$_3$ | H |
| 1-695 | CH$_2$CH$_2$CH$_2$(CF$_2$)$_5$CF$_3$ | H | CN | F | H | CH$_3$ | S(O)CH$_2$CF$_3$ | H |
| 1-696 | CF(CF$_3$)$_2$ | H | CH$_3$ | F | H | CH$_3$ | SCH$_2$CF$_3$ | H |
| 1-697 | CF(CF$_3$)$_2$ | H | CH$_3$ | F | H | CH$_3$ | S(O)CH$_2$CF$_3$ | H |
| 1-698 | CF$_2$(CF$_2$)$_2$CF$_3$ | H | CH$_3$ | F | H | CH$_3$ | SCH$_2$CF$_3$ | H |
| 1-699 | CF$_2$(CF$_2$)$_2$CF$_3$ | H | CH$_3$ | F | H | CH$_3$ | S(O)CH$_2$CF$_3$ | H |
| 1-700 | CF$_2$(CF$_2$)$_3$CF$_3$ | H | CH$_3$ | F | H | CH$_3$ | SCH$_2$CF$_3$ | H |
| 1-701 | CF$_2$(CF$_2$)$_3$CF$_3$ | H | CH$_3$ | F | H | CH$_3$ | S(O)CH$_2$CF$_3$ | H |
| 1-702 | CF$_2$(CF$_2$)$_4$CF$_3$ | H | CH$_3$ | F | H | CH$_3$ | SCH$_2$CF$_3$ | H |
| 1-703 | CF$_2$(CF$_2$)$_4$CF$_3$ | H | CH$_3$ | F | H | CH$_3$ | S(O)CH$_2$CF$_3$ | H |
| 1-704 | CF$_2$(CF$_2$)$_5$CF$_3$ | H | CH$_3$ | F | H | CH$_3$ | SCH$_2$CF$_3$ | H |
| 1-705 | CF$_2$(CF$_2$)$_5$CF$_3$ | H | CH$_3$ | F | H | CH$_3$ | S(O)CH$_2$CF$_3$ | H |
| 1-706 | CF$_2$(CF$_2$)$_6$CF$_3$ | H | CH$_3$ | F | H | CH$_3$ | SCH$_2$CF$_3$ | H |
| 1-707 | CF$_2$(CF$_2$)$_6$CF$_3$ | H | CH$_3$ | F | H | CH$_3$ | S(O)CH$_2$CF$_3$ | H |
| 1-708 | CF$_2$(CF$_2$)$_7$CF$_3$ | H | CH$_3$ | F | H | CH$_3$ | SCH$_2$CF$_3$ | H |
| 1-709 | CF$_2$(CF$_2$)$_7$CF$_3$ | H | CH$_3$ | F | H | CH$_3$ | S(O)CH$_2$CF$_3$ | H |
| 1-710 | CF$_2$(CF$_2$)$_8$CF$_3$ | H | CH$_3$ | F | H | CH$_3$ | SCH$_2$CF$_3$ | H |
| 1-711 | CF$_2$(CF$_2$)$_8$CF$_3$ | H | CH$_3$ | F | H | CH$_3$ | S(O)CH$_2$CF$_3$ | H |
| 1-712 | CF$_2$CHFOC$_4$F$_9$ | H | CH$_3$ | F | H | CH$_3$ | SCH$_2$CF$_3$ | H |
| 1-713 | CF$_2$CHFOC$_4$F$_9$ | H | CH$_3$ | F | H | CH$_3$ | S(O)CH$_2$CF$_3$ | H |

TABLE 14

| Comp. No. | R₁ | R₂ | R₃ | R₄ | R₅ | R₆ | R₇ | R₈ |
|---|---|---|---|---|---|---|---|---|
| 1-714 | CF$_2$CHFOC$_5$F$_{11}$ | H | CH$_3$ | F | H | CH$_3$ | SCH$_2$CF$_3$ | H |
| 1-715 | CF$_2$CHFOC$_5$F$_{11}$ | H | CH$_3$ | F | H | CH$_3$ | S(O)CH$_2$CF$_3$ | H |
| 1-716 | CF$_2$CHFOCF(CF$_3$)$_2$ | H | CH$_3$ | F | H | CH$_3$ | SCH$_2$CF$_3$ | H |
| 1-717 | CF$_2$CHFOCF(CF$_3$)$_2$ | H | CH$_3$ | F | H | CH$_3$ | S(O)CH$_2$CF$_3$ | H |
| 1-718 | CF$_2$CHFCF$_2$OCF$_3$ | H | CH$_3$ | F | H | CH$_3$ | SCH$_2$CF$_3$ | H |
| 1-719 | CF$_2$CHFCF$_2$OCF$_3$ | H | CH$_3$ | F | H | CH$_3$ | S(O)CH$_2$CF$_3$ | H |
| 1-720 | CH$_2$CF(CF$_3$)OC$_3$F$_7$ | H | CH$_3$ | F | H | CH$_3$ | SCH$_2$CF$_3$ | H |
| 1-721 | CH$_2$CF(CF$_3$)OC$_3$F$_7$ | H | CH$_3$ | F | H | CH$_3$ | S(O)CH$_2$CF$_3$ | H |
| 1-722 | CH$_2$CF$_2$O(CF$_2$)$_2$OCF$_2$CF$_3$ | H | CH$_3$ | F | H | CH$_3$ | SCH$_2$CF$_3$ | H |
| 1-723 | CH$_2$CF$_2$O(CF$_2$)$_2$OCF$_2$CF$_3$ | H | CH$_3$ | F | H | CH$_3$ | S(O)CH$_2$CF$_3$ | H |
| 1-724 | CH$_2$(CF$_2$)$_4$CHF$_2$ | H | CH$_3$ | F | H | CH$_3$ | SCH$_2$CF$_3$ | H |
| 1-725 | CH$_2$(CF$_2$)$_4$CHF$_2$ | H | CH$_3$ | F | H | CH$_3$ | S(O)CH$_2$CF$_3$ | H |
| 1-726 | CH$_2$CH$_2$CH$_2$(CF$_2$)$_4$CF$_3$ | H | CH$_3$ | F | H | CH$_3$ | SCH$_2$CF$_3$ | H |
| 1-727 | CH$_2$CH$_2$CH$_2$(CF$_2$)$_4$CF$_3$ | H | CH$_3$ | F | H | CH$_3$ | S(O)CH$_2$CF$_3$ | H |

TABLE 14-continued

| Comp. No. | R₁ | R₂ | R₃ | R₄ | R₅ | R₆ | R₇ | R₈ |
|---|---|---|---|---|---|---|---|---|
| 1-728 | CF₂CHFCF₃ | H | CF₃ | F | H | CH₃ | SCH₂CF₃ | H |
| 1-729 | CF₂CHFCF₃ | H | CF₃ | F | H | CH₃ | S(O)CH₂CF₃ | H |
| 1-730 | CF(CF₃)₂ | H | CF₃ | F | H | CH₃ | SCH₂CF₃ | H |
| 1-731 | CF(CF₃)₂ | H | CF₃ | F | H | CH₃ | S(O)CH₂CF₃ | H |
| 1-732 | CF₂CF₂CF₃ | H | CF₃ | F | H | CH₃ | SCH₂CF₃ | H |
| 1-733 | CF₂CF₂CF₃ | H | CF₃ | F | H | CH₃ | S(O)CH₂CF₃ | H |
| 1-734 | CF₂(CF₂)₂CF₃ | H | CF₃ | F | H | CH₃ | SCH₂CF₃ | H |
| 1-735 | CF₂(CF₂)₂CF₃ | H | CF₃ | F | H | CH₃ | S(O)CH₂CF₃ | H |
| 1-736 | CF₂(CF₂)₃CF₃ | H | CF₃ | F | H | CH₃ | SCH₂CF₃ | H |
| 1-737 | CF₂(CF₂)₃CF₃ | H | CF₃ | F | H | CH₃ | S(O)CH₂CF₃ | H |
| 1-738 | CF₂(CF₂)₄CF₃ | H | CF₃ | F | H | CH₃ | SCH₂CF₃ | H |
| 1-739 | CF₂(CF₂)₄CF₃ | H | CF₃ | F | H | CH₃ | S(O)CH₂CF₃ | H |
| 1-740 | CF₂(CF₂)₅CF₃ | H | CF₃ | F | H | CH₃ | SCH₂CF₃ | H |
| 1-741 | CF₂(CF₂)₅CF₃ | H | CF₃ | F | H | CH₃ | S(O)CH₂CF₃ | H |
| 1-742 | CF₂(CF₂)₆CF₃ | H | CF₃ | F | H | CH₃ | SCH₂CF₃ | H |
| 1-743 | CF₂(CF₂)₆CF₃ | H | CF₃ | F | H | CH₃ | S(O)CH₂CF₃ | H |
| 1-744 | CF₂(CF₂)₇CF₃ | H | CF₃ | F | H | CH₃ | SCH₂CF₃ | H |
| 1-745 | CF₂(CF₂)₇CF₃ | H | CF₃ | F | H | CH₃ | S(O)CH₂CF₃ | H |
| 1-746 | CF₂(CF₂)₈CF₃ | H | CF₃ | F | H | CH₃ | SCH₂CF₃ | H |
| 1-747 | CF₂(CF₂)₈CF₃ | H | CF₃ | F | H | CH₃ | S(O)CH₂CF₃ | H |
| 1-748 | CF₂CHFOCF₃ | H | CF₃ | F | H | CH₃ | SCH₂CF₃ | H |
| 1-749 | CF₂CHFOCF₃ | H | CF₃ | F | H | CH₃ | S(O)CH₂CF₃ | H |
| 1-750 | CF₂CHFOC₂F₅ | H | CF₃ | F | H | CH₃ | SCH₂CF₃ | H |
| 1-751 | CF₂CHFOC₂F₅ | H | CF₃ | F | H | CH₃ | S(O)CH₂CF₃ | H |
| 1-752 | CF₂CHFOC₃F₇ | H | CF₃ | F | H | CH₃ | SCH₂CF₃ | H |
| 1-753 | CF₂CHFOC₃F₇ | H | CF₃ | F | H | CH₃ | S(O)CH₂CF₃ | H |
| 1-754 | CF₂CHFOC₄F₉ | H | CF₃ | F | H | CH₃ | SCH₂CF₃ | H |
| 1-755 | CF₂CHFOC₄F₉ | H | CF₃ | F | H | CH₃ | S(O)CH₂CF₃ | H |
| 1-756 | CF₂CHFOC₅F₁₁ | H | CF₃ | F | H | CH₃ | SCH₂CF₃ | H |
| 1-757 | CF₂CHFOC₅F₁₁ | H | CF₃ | F | H | CH₃ | S(O)CH₂CF₃ | H |
| 1-758 | CF₂CHFOCF(CF₃)₂ | H | CF₃ | F | H | CH₃ | SCH₂CF₃ | H |
| 1-759 | CF₂CHFOCF(CF₃)₂ | H | CF₃ | F | H | CH₃ | S(O)CH₂CF₃ | H |
| 1-760 | CF₂CHFCF₂OCF₃ | H | CF₃ | F | H | CH₃ | SCH₂CF₃ | H |
| 1-761 | CF₂CHFCF₂OCF₃ | H | CF₃ | F | H | CH₃ | S(O)CH₂CF₃ | H |
| 1-762 | CH₂CF(CF₃)OC₃F₇ | H | CF₃ | F | H | CH₃ | SCH₂CF₃ | H |
| 1-763 | CH₂CF(CF₃)OC₃F₇ | H | CF₃ | F | H | CH₃ | S(O)CH₂CF₃ | H |
| 1-764 | CH₂CF₂O(CF₂)₂OCF₃ | H | CF₃ | F | H | CH₃ | SCH₂CF₃ | H |
| 1-765 | CH₂CF₂O(CF₂)₂OCF₃ | H | CF₃ | F | H | CH₃ | S(O)CH₂CF₃ | H |
| 1-766 | CH₂CF₂O(CF₂)₂OCF₂CF₃ | H | CF₃ | F | H | CH₃ | SCH₂CF₃ | H |
| 1-767 | CH₂CF₂O(CF₂)₂OCF₂CF₃ | H | CF₃ | F | H | CH₃ | S(O)CH₂CF₃ | H |
| 1-768 | CH₂(CF₂)₃CHF₂ | H | CF₃ | F | H | CH₃ | SCH₂CF₃ | H |
| 1-769 | CH₂(CF₂)₃CHF₂ | H | CF₃ | F | H | CH₃ | S(O)CH₂CF₃ | H |

TABLE 15

| Comp. No. | R₁ | R₂ | R₃ | R₄ | R₅ | R₆ | R₇ | R₈ |
|---|---|---|---|---|---|---|---|---|
| 1-770 | CH₂(CF₂)₄CHF₂ | H | CF₃ | F | H | CH₃ | SCH₂CF₃ | H |
| 1-771 | CH₂(CF₂)₄CHF₂ | H | CF₃ | F | H | CH₃ | S(O)CH₂CF₃ | H |
| 1-772 | CH₂CH₂CH₂(CF₂)₄CF₃ | H | CF₃ | F | H | CH₃ | SCH₂CF₃ | H |
| 1-773 | CH₂CH₂CH₂(CF₂)₄CF₃ | H | CF₃ | F | H | CH₃ | S(O)CH₂CF₃ | H |
| 1-774 | CH₂CH₂CH₂(CF₂)₅CF₃ | H | CF₃ | F | H | CH₃ | SCH₂CF₃ | H |
| 1-775 | CH₂CH₂CH₂(CF₂)₅CF₃ | H | CF₃ | F | H | CH₃ | S(O)CH₂CF₃ | H |
| 1-776 | CF(CF₃)₂ | H | OCH₃ | F | H | CH₃ | SCH₂CF₃ | H |
| 1-777 | CF(CF₃)₂ | H | OCH₃ | F | H | CH₃ | S(O)CH₂CF₃ | H |
| 1-778 | CF₂CF₂CF₃ | H | OCH₃ | F | H | CH₃ | SCH₂CF₃ | H |
| 1-779 | CF₂CF₂CF₃ | H | OCH₃ | F | H | CH₃ | S(O)CH₂CF₃ | H |
| 1-780 | CF₂(CF₂)₂CF₃ | H | OCH₃ | F | H | CH₃ | SCH₂CF₃ | H |
| 1-781 | CF₂(CF₂)₂CF₃ | H | OCH₃ | F | H | CH₃ | S(O)CH₂CF₃ | H |
| 1-782 | CF₂(CF₂)₃CF₃ | H | OCH₃ | F | H | CH₃ | SCH₂CF₃ | H |
| 1-783 | CF₂(CF₂)₃CF₃ | H | OCH₃ | F | H | CH₃ | S(O)CH₂CF₃ | H |
| 1-784 | CF₂(CF₂)₄CF₃ | H | OCH₃ | F | H | CH₃ | SCH₂CF₃ | H |
| 1-785 | CF₂(CF₂)₄CF₃ | H | OCH₃ | F | H | CH₃ | S(O)CH₂CF₃ | H |
| 1-786 | CF₂(CF₂)₅CF₃ | H | OCH₃ | F | H | CH₃ | SCH₂CF₃ | H |
| 1-787 | CF₂(CF₂)₅CF₃ | H | OCH₃ | F | H | CH₃ | S(O)CH₂CF₃ | H |
| 1-788 | CF₂(CF₂)₆CF₃ | H | OCH₃ | F | H | CH₃ | SCH₂CF₃ | H |
| 1-789 | CF₂(CF₂)₆CF₃ | H | OCH₃ | F | H | CH₃ | S(O)CH₂CF₃ | H |
| 1-790 | CF₂(CF₂)₇CF₃ | H | OCH₃ | F | H | CH₃ | SCH₂CF₃ | H |
| 1-791 | CF₂(CF₂)₇CF₃ | H | OCH₃ | F | H | CH₃ | S(O)CH₂CF₃ | H |
| 1-792 | CF₂(CF₂)₈CF₃ | H | OCH₃ | F | H | CH₃ | SCH₂CF₃ | H |
| 1-793 | CF₂(CF₂)₈CF₃ | H | OCH₃ | F | H | CH₃ | S(O)CH₂CF₃ | H |
| 1-794 | CF₂CHFOCF₃ | H | OCH₃ | F | H | CH₃ | SCH₂CF₃ | H |
| 1-795 | CF₂CHFOCF₃ | H | OCH₃ | F | H | CH₃ | S(O)CH₂CF₃ | H |
| 1-796 | CF₂CHFOC₂F₅ | H | OCH₃ | F | H | CH₃ | SCH₂CF₃ | H |
| 1-797 | CF₂CHFOC₂F₅ | H | OCH₃ | F | H | CH₃ | S(O)CH₂CF₃ | H |

TABLE 15-continued

| Comp. No. | R₁ | R₂ | R₃ | R₄ | R₅ | R₆ | R₇ | R₈ |
|---|---|---|---|---|---|---|---|---|
| 1-798 | CF₂CHFOC₃F₇ | H | OCH₃ | F | H | CH₃ | SCH₂CF₃ | H |
| 1-799 | CF₂CHFOC₃F₇ | H | OCH₃ | F | H | CH₃ | S(O)CH₂CF₃ | H |
| 1-800 | CF₂CHFOC₄F₉ | H | OCH₃ | F | H | CH₃ | SCH₂CF₃ | H |
| 1-801 | CF₂CHFOC₄F₉ | H | OCH₃ | F | H | CH₃ | S(O)CH₂CF₃ | H |
| 1-802 | CF₂CHFOC₅F₁₁ | H | OCH₃ | F | H | CH₃ | SCH₂CF₃ | H |
| 1-803 | CF₂CHFOC₅F₁₁ | H | OCH₃ | F | H | CH₃ | S(O)CH₂CF₃ | H |
| 1-804 | CF₂CHFOCF(CF₃)₂ | H | OCH₃ | F | H | CH₃ | SCH₂CF₃ | H |
| 1-805 | CF₂CHFOCF(CF₃)₂ | H | OCH₃ | F | H | CH₃ | S(O)CH₂CF₃ | H |
| 1-806 | CF₂CHFCF₂OCF₃ | H | OCH₃ | F | H | CH₃ | SCH₂CF₃ | H |
| 1-807 | CF₂CHFCF₂OCF₃ | H | OCH₃ | F | H | CH₃ | S(O)CH₂CF₃ | H |
| 1-808 | CH₂CF(CF₃)OC₃F₇ | H | OCH₃ | F | H | CH₃ | SCH₂CF₃ | H |
| 1-809 | CH₂CF(CF₃)OC₃F₇ | H | OCH₃ | F | H | CH₃ | S(O)CH₂CF₃ | H |
| 1-810 | CH₂CF₂O(CF₂)₂OCF₃ | H | OCH₃ | F | H | CH₃ | SCH₂CF₃ | H |
| 1-811 | CH₂CF₂O(CF₂)₂OCF₃ | H | OCH₃ | F | H | CH₃ | S(O)CH₂CF₃ | H |
| 1-812 | CH₂CF₂O(CF₂)₂OCF₂CF₃ | H | OCH₃ | F | H | CH₃ | SCH₂CF₃ | H |
| 1-813 | CH₂CF₂O(CF₂)₂OCF₂CF₃ | H | OCH₃ | F | H | CH₃ | S(O)CH₂CF₃ | H |
| 1-814 | CH₂(CF₂)₃CHF₂ | H | OCH₃ | F | H | CH₃ | SCH₂CF₃ | H |
| 1-815 | CH₂(CF₂)₃CHF₂ | H | OCH₃ | F | H | CH₃ | S(O)CH₂CF₃ | H |
| 1-816 | CH₂(CF₂)₄CHF₂ | H | OCH₃ | F | H | CH₃ | SCH₂CF₃ | H |
| 1-817 | CH₂(CF₂)₄CHF₂ | H | OCH₃ | F | H | CH₃ | S(O)CH₂CF₃ | H |
| 1-818 | CH₂CH₂CH₂(CF₂)₄CF₃ | H | OCH₃ | F | H | CH₃ | SCH₂CF₃ | H |
| 1-819 | CH₂CH₂CH₂(CF₂)₄CF₃ | H | OCH₃ | F | H | CH₃ | S(O)CH₂CF₃ | H |
| 1-820 | CH₂CH₂CH₂(CF₂)₅CF₃ | H | OCH₃ | F | H | CH₃ | SCH₂CF₃ | H |
| 1-821 | CH₂CH₂CH₂(CF₂)₅CF₃ | H | OCH₃ | F | H | CH₃ | S(O)CH₂CF₃ | H |
| 1-822 | CF₂CHFCF₃ | H | OCHF₂ | F | H | CH₃ | SCH₂CF₃ | H |
| 1-823 | CF₂CHFCF₃ | H | OCHF₂ | F | H | CH₃ | S(O)CH₂CF₃ | H |
| 1-824 | CF(CF₃)₂ | H | OCHF₂ | F | H | CH₃ | SCH₂CF₃ | H |
| 1-825 | CF(CF₃)₂ | H | OCHF₂ | F | H | CH₃ | S(O)CH₂CF₃ | H |

TABLE 16

| Comp. No. | R₁ | R₂ | R₃ | R₄ | R₅ | R₆ | R₇ | R₈ |
|---|---|---|---|---|---|---|---|---|
| 1-826 | CF₂CF₂CF₃ | H | OCHF₂ | F | H | CH₃ | SCH₂CF₃ | H |
| 1-827 | CF₂CF₂CF₃ | H | OCHF₂ | F | H | CH₃ | S(O)CH₂CF₃ | H |
| 1-828 | CF₂(CF₂)₂CF₃ | H | OCHF₂ | F | H | CH₃ | SCH₂CF₃ | H |
| 1-829 | CF₂(CF₂)₂CF₃ | H | OCHF₂ | F | H | CH₃ | S(O)CH₂CF₃ | H |
| 1-830 | CF₂(CF₂)₃CF₃ | H | OCHF₂ | F | H | CH₃ | SCH₂CF₃ | H |
| 1-831 | CF₂(CF₂)₃CF₃ | H | OCHF₂ | F | H | CH₃ | S(O)CH₂CF₃ | H |
| 1-832 | CF₂(CF₂)₄CF₃ | H | OCHF₂ | F | H | CH₃ | SCH₂CF₃ | H |
| 1-833 | CF₂(CF₂)₄CF₃ | H | OCHF₂ | F | H | CH₃ | S(O)CH₂CF₃ | H |
| 1-834 | CF₂(CF₂)₅CF₃ | H | OCHF₂ | F | H | CH₃ | SCH₂CF₃ | H |
| 1-835 | CF₂(CF₂)₅CF₃ | H | OCHF₂ | F | H | CH₃ | S(O)CH₂CF₃ | H |
| 1-836 | CF₂(CF₂)₆CF₃ | H | OCHF₂ | F | H | CH₃ | SCH₂CF₃ | H |
| 1-837 | CF₂(CF₂)₆CF₃ | H | OCHF₂ | F | H | CH₃ | S(O)CH₂CF₃ | H |
| 1-838 | CF₂(CF₂)₇CF₃ | H | OCHF₂ | F | H | CH₃ | SCH₂CF₃ | H |
| 1-839 | CF₂(CF₂)₇CF₃ | H | OCHF₂ | F | H | CH₃ | S(O)CH₂CF₃ | H |
| 1-840 | CF₂(CF₂)₈CF₃ | H | OCHF₂ | F | H | CH₃ | SCH₂CF₃ | H |
| 1-841 | CF₂(CF₂)₈CF₃ | H | OCHF₂ | F | H | CH₃ | S(O)CH₂CF₃ | H |
| 1-842 | CF₂CHFOCF₃ | H | OCHF₂ | F | H | CH₃ | SCH₂CF₃ | H |
| 1-843 | CF₂CHFOCF₃ | H | OCHF₂ | F | H | CH₃ | S(O)CH₂CF₃ | H |
| 1-844 | CF₂CHFOC₂F₅ | H | OCHF₂ | F | H | CH₃ | SCH₂CF₃ | H |
| 1-845 | CF₂CHFOC₂F₅ | H | OCHF₂ | F | H | CH₃ | S(O)CH₂CF₃ | H |
| 1-846 | CF₂CHFOC₃F₇ | H | OCHF₂ | F | H | CH₃ | SCH₂CF₃ | H |
| 1-847 | CF₂CHFOC₃F₇ | H | OCHF₂ | F | H | CH₃ | S(O)CH₂CF₃ | H |
| 1-848 | CF₂CHFOC₄F₉ | H | OCHF₂ | F | H | CH₃ | SCH₂CF₃ | H |
| 1-849 | CF₂CHFOC₄F₉ | H | OCHF₂ | F | H | CH₃ | S(O)CH₂CF₃ | H |
| 1-850 | CF₂CHFOC₅F₁₁ | H | OCHF₂ | F | H | CH₃ | SCH₂CF₃ | H |
| 1-851 | CF₂CHFOC₅F₁₁ | H | OCHF₂ | F | H | CH₃ | S(O)CH₂CF₃ | H |
| 1-852 | CF₂CHFOCF(CF₃)₂ | H | OCHF₂ | F | H | CH₃ | SCH₂CF₃ | H |
| 1-853 | CF₂CHFOCF(CF₃)₂ | H | OCHF₂ | F | H | CH₃ | S(O)CH₂CF₃ | H |
| 1-854 | CF₂CHFCF₂OCF₃ | H | OCHF₂ | F | H | CH₃ | SCH₂CF₃ | H |
| 1-855 | CF₂CHFCF₂OCF₃ | H | OCHF₂ | F | H | CH₃ | S(O)CH₂CF₃ | H |
| 1-856 | CH₂CF(CF₃)OC₃F₇ | H | OCHF₂ | F | H | CH₃ | SCH₂CF₃ | H |
| 1-857 | CH₂CF(CF₃)OC₃F₇ | H | OCHF₂ | F | H | CH₃ | S(O)CH₂CF₃ | H |
| 1-858 | CH₂CF₂O(CF₂)₂OCF₃ | H | OCHF₂ | F | H | CH₃ | SCH₂CF₃ | H |
| 1-859 | CH₂CF₂O(CF₂)₂OCF₃ | H | OCHF₂ | F | H | CH₃ | S(O)CH₂CF₃ | H |
| 1-860 | CH₂CF₂O(CF₂)₂OCF₂CF₃ | H | OCHF₂ | F | H | CH₃ | SCH₂CF₃ | H |
| 1-861 | CH₂CF₂O(CF₂)₂OCF₂CF₃ | H | OCHF₂ | F | H | CH₃ | S(O)CH₂CF₃ | H |
| 1-862 | CH₂(CF₂)₃CHF₂ | H | OCHF₂ | F | H | CH₃ | SCH₂CF₃ | H |
| 1-863 | CH₂(CF₂)₃CHF₂ | H | OCHF₂ | F | H | CH₃ | S(O)CH₂CF₃ | H |
| 1-864 | CH₂(CF₂)₄CHF₂ | H | OCHF₂ | F | H | CH₃ | SCH₂CF₃ | H |
| 1-865 | CH₂(CF₂)₄CHF₂ | H | OCHF₂ | F | H | CH₃ | S(O)CH₂CF₃ | H |
| 1-866 | CH₂CH₂CH₂(CF₂)₄CF₃ | H | OCHF₂ | F | H | CH₃ | SCH₂CF₃ | H |
| 1-867 | CH₂CH₂CH₂(CF₂)₄CF₃ | H | OCHF₂ | F | H | CH₃ | S(O)CH₂CF₃ | H |
| 1-868 | CH₂CH₂CH₂(CF₂)₅CF₃ | H | OCHF₂ | F | H | CH₃ | SCH₂CF₃ | H |
| 1-869 | CH₂CH₂CH₂(CF₂)₅CF₃ | H | OCHF₂ | F | H | CH₃ | S(O)CH₂CF₃ | H |
| 1-870 | CF(CF₃)₂ | H | Cl | F | H | CH₃ | SCH₂CF₃ | H |

TABLE 16-continued

| Comp. No. | R₁ | R₂ | R₃ | R₄ | R₅ | R₆ | R₇ | R₈ |
|---|---|---|---|---|---|---|---|---|
| 1-871 | CF(CF₃)₂ | H | Cl | F | H | CH₃ | S(O)CH₂CF₃ | H |
| 1-872 | CF₂CF₂CF₃ | H | Cl | F | H | CH₃ | SCH₂CF₃ | H |
| 1-873 | CF₂CF₂CF₃ | H | Cl | F | H | CH₃ | S(O)CH₂CF₃ | H |
| 1-874 | CF₂(CF₂)₂CF₃ | H | Cl | F | H | CH₃ | SCH₂CF₃ | H |
| 1-875 | CF₂(CF₂)₂CF₃ | H | Cl | F | H | CH₃ | S(O)CH₂CF₃ | H |
| 1-876 | CF₂(CF₂)₃CF₃ | H | Cl | F | H | CH₃ | SCH₂CF₃ | H |
| 1-877 | CF₂(CF₂)₃CF₃ | H | Cl | F | H | CH₃ | S(O)CH₂CF₃ | H |
| 1-878 | CF₂(CF₂)₄CF₃ | H | Cl | F | H | CH₃ | SCH₂CF₃ | H |
| 1-879 | CF₂(CF₂)₄CF₃ | H | Cl | F | H | CH₃ | S(O)CH₂CF₃ | H |
| 1-880 | CF₂(CF₂)₅CF₃ | H | Cl | F | H | CH₃ | SCH₂CF₃ | H |
| 1-881 | CF₂(CF₂)₅CF₃ | H | Cl | F | H | CH₃ | S(O)CH₂CF₃ | H |

TABLE 17

| Comp. No. | R₁ | R₂ | R₃ | R₄ | R₅ | R₆ | R₇ | R₈ |
|---|---|---|---|---|---|---|---|---|
| 1-882 | CF₂(CF₂)₆CF₃ | H | Cl | F | H | CH₃ | SCH₂CF₃ | H |
| 1-883 | CF₂(CF₂)₆CF₃ | H | Cl | F | H | CH₃ | S(O)CH₂CF₃ | H |
| 1-884 | CF₂(CF₂)₇CF₃ | H | Cl | F | H | CH₃ | SCH₂CF₃ | H |
| 1-885 | CF₂(CF₂)₇CF₃ | H | Cl | F | H | CH₃ | S(O)CH₂CF₃ | H |
| 1-886 | CF₂(CF₂)₈CF₃ | H | Cl | F | H | CH₃ | SCH₂CF₃ | H |
| 1-887 | CF₂(CF₂)₈CF₃ | H | Cl | F | H | CH₃ | S(O)CH₂CF₃ | H |
| 1-888 | CF₂CHFOCF₃ | H | Cl | F | H | CH₃ | SCH₂CF₃ | H |
| 1-889 | CF₂CHFOCF₃ | H | Cl | F | H | CH₃ | S(O)CH₂CF₃ | H |
| 1-890 | CF₂CHFOC₂F₅ | H | Cl | F | H | CH₃ | SCH₂CF₃ | H |
| 1-891 | CF₂CHFOC₂F₅ | H | Cl | F | H | CH₃ | S(O)CH₂CF₃ | H |
| 1-892 | CF₂CHFOC₃F₇ | H | Cl | F | H | CH₃ | SCH₂CF₃ | H |
| 1-893 | CF₂CHFOC₃F₇ | H | Cl | F | H | CH₃ | S(O)CH₂CF₃ | H |
| 1-894 | CF₂CHFOC₄F₉ | H | Cl | F | H | CH₃ | SCH₂CF₃ | H |
| 1-895 | CF₂CHFOC₄F₉ | H | Cl | F | H | CH₃ | S(O)CH₂CF₃ | H |
| 1-896 | CF₂CHFOC₅F₁₁ | H | Cl | F | H | CH₃ | SCH₂CF₃ | H |
| 1-897 | CF₂CHFOC₅F₁₁ | H | Cl | F | H | CH₃ | S(O)CH₂CF₃ | H |
| 1-898 | CF₂CHFOCF(CF₃)₂ | H | Cl | F | H | CH₃ | SCH₂CF₃ | H |
| 1-899 | CF₂CHFOCF(CF₃)₂ | H | Cl | F | H | CH₃ | S(O)CH₂CF₃ | H |
| 1-900 | CF₂CHFCF₂OCF₃ | H | Cl | F | H | CH₃ | SCH₂CF₃ | H |
| 1-901 | CF₂CHFCF₂OCF₃ | H | Cl | F | H | CH₃ | S(O)CH₂CF₃ | H |
| 1-902 | CH₂CF(CF₃)OC₃F₇ | H | Cl | F | H | CH₃ | SCH₂CF₃ | H |
| 1-903 | CH₂CF(CF₃)OC₃F₇ | H | Cl | F | H | CH₃ | S(O)CH₂CF₃ | H |
| 1-904 | CH₂CF₂O(CF₂)₂OCF₃ | H | Cl | F | H | CH₃ | SCH₂CF₃ | H |
| 1-905 | CH₂CF₂O(CF₂)₂OCF₃ | H | Cl | F | H | CH₃ | S(O)CH₂CF₃ | H |
| 1-906 | CH₂CF₂O(CF₂)₂OCF₂CF₃ | H | Cl | F | H | CH₃ | SCH₂CF₃ | H |
| 1-907 | CH₂CF₂O(CF₂)₂OCF₂CF₃ | H | Cl | F | H | CH₃ | S(O)CH₂CF₃ | H |
| 1-908 | CH₂(CF₂)₃CHF₂ | H | Cl | F | H | CH₃ | SCH₂CF₃ | H |
| 1-909 | CH₂(CF₂)₃CHF₂ | H | Cl | F | H | CH₃ | S(O)CH₂CF₃ | H |
| 1-910 | CH₂(CF₂)₄CHF₂ | H | Cl | F | H | CH₃ | SCH₂CF₃ | H |
| 1-911 | CH₂(CF₂)₄CHF₂ | H | Cl | F | H | CH₃ | S(O)CH₂CF₃ | H |
| 1-912 | CH₂CH₂CH₂(CF₂)₄CF₃ | H | Cl | F | H | CH₃ | SCH₂CF₃ | H |
| 1-913 | CH₂CH₂CH₂(CF₂)₄CF₃ | H | Cl | F | H | CH₃ | S(O)CH₂CF₃ | H |
| 1-914 | CH₂CH₂CH₂(CF₂)₅CF₃ | H | Cl | F | H | CH₃ | SCH₂CF₃ | H |
| 1-915 | CH₂CH₂CH₂(CF₂)₅CF₃ | H | Cl | F | H | CH₃ | S(O)CH₂CF₃ | H |
| 1-916 | CF₂CHFCF₃ | H | Br | F | H | CH₃ | SCH₂CF₃ | H |
| 1-917 | CF₂CHFCF₃ | H | Br | F | H | CH₃ | S(O)CH₂CF₃ | H |
| 1-918 | CF₂(CF₃)₂ | H | Br | F | H | CH₃ | SCH₂CF₃ | H |
| 1-919 | CF₂(CF₃)₂ | H | Br | F | H | CH₃ | S(O)CH₂CF₃ | H |
| 1-920 | CF₂CF₂CF₃ | H | Br | F | H | CH₃ | SCH₂CF₃ | H |
| 1-921 | CF₂CF₂CF₃ | H | Br | F | H | CH₃ | S(O)CH₂CF₃ | H |
| 1-922 | CF₂(CF₂)₂CF₃ | H | Br | F | H | CH₃ | SCH₂CF₃ | H |
| 1-923 | CF₂(CF₂)₂CF₃ | H | Br | F | H | CH₃ | S(O)CH₂CF₃ | H |
| 1-924 | CF₂(CF₂)₃CF₃ | H | Br | F | H | CH₃ | SCH₂CF₃ | H |
| 1-925 | CF₂(CF₂)₃CF₃ | H | Br | F | H | CH₃ | S(O)CH₂CF₃ | H |
| 1-926 | CF₂(CF₂)₄CF₃ | H | Br | F | H | CH₃ | SCH₂CF₃ | H |
| 1-927 | CF₂(CF₂)₄CF₃ | H | Br | F | H | CH₃ | S(O)CH₂CF₃ | H |
| 1-928 | CF₂(CF₂)₅CF₃ | H | Br | F | H | CH₃ | SCH₂CF₃ | H |
| 1-929 | CF₂(CF₂)₅CF₃ | H | Br | F | H | CH₃ | S(O)CH₂CF₃ | H |
| 1-930 | CF₂(CF₂)₆CF₃ | H | Br | F | H | CH₃ | SCH₂CF₃ | H |
| 1-931 | CF₂(CF₂)₆CF₃ | H | Br | F | H | CH₃ | S(O)CH₂CF₃ | H |
| 1-932 | CF₂(CF₂)₇CF₃ | H | Br | F | H | CH₃ | SCH₂CF₃ | H |
| 1-933 | CF₂(CF₂)₇CF₃ | H | Br | F | H | CH₃ | S(O)CH₂CF₃ | H |
| 1-934 | CF₂(CF₂)₈CF₃ | H | Br | F | H | CH₃ | SCH₂CF₃ | H |
| 1-935 | CF₂(CF₂)₈CF₃ | H | Br | F | H | CH₃ | S(O)CH₂CF₃ | H |
| 1-936 | CF₂CHFOCF₃ | H | Br | F | H | CH₃ | SCH₂CF₃ | H |
| 1-937 | CF₂CHFOCF₃ | H | Br | F | H | CH₃ | S(O)CH₂CF₃ | H |

TABLE 18

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-938 | CF$_2$CHFOC$_2$F$_5$ | H | Br | F | H | CH$_3$ | SCH$_2$CF$_3$ | H |
| 1-939 | CF$_2$CHFOC$_2$F$_5$ | H | Br | F | H | CH$_3$ | S(O)CH$_2$CF$_3$ | H |
| 1-940 | CF$_2$CHFOC$_3$F$_7$ | H | Br | F | H | CH$_3$ | SCH$_2$CF$_3$ | H |
| 1-941 | CF$_2$CHFOC$_3$F$_7$ | H | Br | F | H | CH$_3$ | S(O)CH$_2$CF$_3$ | H |
| 1-942 | CF$_2$CHFOC$_4$F$_9$ | H | Br | F | H | CH$_3$ | SCH$_2$CF$_3$ | H |
| 1-943 | CF$_2$CHFOC$_4$F$_9$ | H | Br | F | H | CH$_3$ | S(O)CH$_2$CF$_3$ | H |
| 1-944 | CF$_2$CHFOC$_5$F$_{11}$ | H | Br | F | H | CH$_3$ | SCH$_2$CF$_3$ | H |
| 1-945 | CF$_2$CHFOC$_5$F$_{11}$ | H | Br | F | H | CH$_3$ | S(O)CH$_2$CF$_3$ | H |
| 1-946 | CF$_2$CHFOCF(CF$_3$)$_2$ | H | Br | F | H | CH$_3$ | SCH$_2$CF$_3$ | H |
| 1-947 | CF$_2$CHFOCF(CF$_3$)$_2$ | H | Br | F | H | CH$_3$ | S(O)CH$_2$CF$_3$ | H |
| 1-948 | CF$_2$CHFCF$_3$ | H | Br | F | H | CH$_3$ | SCH$_2$CF$_3$ | H |
| 1-949 | CF$_2$CHFCF$_2$OCF$_3$ | H | Br | F | H | CH$_3$ | S(O)CH$_2$CF$_3$ | H |
| 1-950 | CH$_2$CF(CF$_3$)OC$_3$F$_7$ | H | Br | F | H | CH$_3$ | SCH$_2$CF$_3$ | H |
| 1-951 | CH$_2$CF(CF$_3$)OC$_3$F$_7$ | H | Br | F | H | CH$_3$ | S(O)CH$_2$CF$_3$ | H |
| 1-952 | CH$_2$CF$_2$O(CF$_2$)$_2$OCF$_3$ | H | Br | F | H | CH$_3$ | SCH$_2$CF$_3$ | H |
| 1-953 | CH$_2$CF$_2$O(CF$_2$)$_2$OCF$_3$ | H | Br | F | H | CH$_3$ | S(O)CH$_2$CF$_3$ | H |
| 1-954 | CH$_2$CF$_2$O(CF$_2$)$_2$OCF$_2$CF$_3$ | H | Br | F | H | CH$_3$ | SCH$_2$CF$_3$ | H |
| 1-955 | CH$_2$CF$_2$O(CF$_2$)$_2$OCF$_2$CF$_3$ | H | Br | F | H | CH$_3$ | S(O)CH$_2$CF$_3$ | H |
| 1-956 | CH$_2$(CF$_2$)$_3$CHF$_2$ | H | Br | F | H | CH$_3$ | SCH$_2$CF$_3$ | H |
| 1-957 | CH$_2$(CF$_2$)$_3$CHF$_2$ | H | Br | F | H | CH$_3$ | S(O)CH$_2$CF$_3$ | H |
| 1-958 | CH$_2$(CF$_2$)$_4$CHF$_2$ | H | Br | F | H | CH$_3$ | SCH$_2$CF$_3$ | H |
| 1-959 | CH$_2$(CF$_2$)$_4$CHF$_2$ | H | Br | F | H | CH$_3$ | S(O)CH$_2$CF$_3$ | H |
| 1-960 | CH$_2$CH$_2$CH$_2$(CF$_2$)$_4$CF$_3$ | H | Br | F | H | CH$_3$ | SCH$_2$CF$_3$ | H |
| 1-961 | CH$_2$CH$_2$CH$_2$(CF$_2$)$_4$CF$_3$ | H | Br | F | H | CH$_3$ | S(O)CH$_2$CF$_3$ | H |
| 1-962 | CH$_2$CH$_2$CH$_2$(CF$_2$)$_5$CF$_3$ | H | Br | F | H | CH$_3$ | SCH$_2$CF$_3$ | H |
| 1-963 | CH$_2$CH$_2$CH$_2$(CF$_2$)$_5$CF$_3$ | H | Br | F | H | CH$_3$ | S(O)CH$_2$CF$_3$ | H |
| 1-964 | CF(CF$_3$)$_2$ | Cl | NH$_2$ | F | H | CH$_3$ | SCH$_2$CF$_3$ | H |
| 1-965 | CF(CF$_3$)$_2$ | Cl | NH$_2$ | F | H | CH$_3$ | S(O)CH$_2$CF$_3$ | H |
| 1-966 | CF$_2$CF$_2$CF$_3$ | Cl | NH$_2$ | F | H | CH$_3$ | SCH$_2$CF$_3$ | H |
| 1-967 | CF$_2$CF$_2$CF$_3$ | Cl | NH$_2$ | F | H | CH$_3$ | S(O)CH$_2$CF$_3$ | H |
| 1-968 | CF$_2$(CF$_2$)$_2$CF$_3$ | Cl | NH$_2$ | F | H | CH$_3$ | SCH$_2$CF$_3$ | H |
| 1-969 | CF$_2$(CF$_2$)$_2$CF$_3$ | Cl | NH$_2$ | F | H | CH$_3$ | S(O)CH$_2$CF$_3$ | H |
| 1-970 | CF$_2$(CF$_2$)$_3$CF$_3$ | Cl | NH$_2$ | F | H | CH$_3$ | SCH$_2$CF$_3$ | H |
| 1-971 | CF$_2$(CF$_2$)$_3$CF$_3$ | Cl | NH$_2$ | F | H | CH$_3$ | S(O)CH$_2$CF$_3$ | H |
| 1-972 | CF$_2$(CF$_2$)$_4$CF$_3$ | Cl | NH$_2$ | F | H | CH$_3$ | SCH$_2$CF$_3$ | H |
| 1-973 | CF$_2$(CF$_2$)$_4$CF$_3$ | Cl | NH$_2$ | F | H | CH$_3$ | S(O)CH$_2$CF$_3$ | H |
| 1-974 | CF$_2$(CF$_2$)$_5$CF$_3$ | Cl | NH$_2$ | F | H | CH$_3$ | SCH$_2$CF$_3$ | H |
| 1-975 | CF$_2$(CF$_2$)$_5$CF$_3$ | Cl | NH$_2$ | F | H | CH$_3$ | S(O)CH$_2$CF$_3$ | H |
| 1-976 | CF$_2$(CF$_2$)$_6$CF$_3$ | Cl | NH$_2$ | F | H | CH$_3$ | SCH$_2$CF$_3$ | H |
| 1-977 | CF$_2$(CF$_2$)$_6$CF$_3$ | Cl | NH$_2$ | F | H | CH$_3$ | S(O)CH$_2$CF$_3$ | H |
| 1-978 | CF$_2$(CF$_2$)$_7$CF$_3$ | Cl | NH$_2$ | F | H | CH$_3$ | SCH$_2$CF$_3$ | H |
| 1-979 | CF$_2$(CF$_2$)$_7$CF$_3$ | Cl | NH$_2$ | F | H | CH$_3$ | S(O)CH$_2$CF$_3$ | H |
| 1-980 | CF$_2$(CF$_2$)$_8$CF$_3$ | Cl | NH$_2$ | F | H | CH$_3$ | SCH$_2$CF$_3$ | H |
| 1-981 | CF$_2$(CF$_2$)$_8$CF$_3$ | Cl | NH$_2$ | F | H | CH$_3$ | S(O)CH$_2$CF$_3$ | H |
| 1-982 | CF$_2$CHFOC$_4$F$_9$ | Cl | NH$_2$ | F | H | CH$_3$ | SCH$_2$CF$_3$ | H |
| 1-983 | CF$_2$CHFOC$_4$F$_9$ | Cl | NH$_2$ | F | H | CH$_3$ | S(O)CH$_2$CF$_3$ | H |
| 1-984 | CF$_2$CHFOC$_5$F$_{11}$ | Cl | NH$_2$ | F | H | CH$_3$ | SCH$_2$CF$_3$ | H |
| 1-985 | CF$_2$CHFOC$_5$F$_{11}$ | Cl | NH$_2$ | F | H | CH$_3$ | S(O)CH$_2$CF$_3$ | H |
| 1-986 | CF$_2$CHFOCF(CF$_3$)$_2$ | Cl | NH$_2$ | F | H | CH$_3$ | SCH$_2$CF$_3$ | H |
| 1-987 | CF$_2$CHFOCF(CF$_3$)$_2$ | Cl | NH$_2$ | F | H | CH$_3$ | S(O)CH$_2$CF$_3$ | H |
| 1-988 | CF$_2$CHFCF$_2$OCF$_3$ | Cl | NH$_2$ | F | H | CH$_3$ | SCH$_2$CF$_3$ | H |
| 1-989 | CF$_2$CHFCF$_2$OCF$_3$ | Cl | NH$_2$ | F | H | CH$_3$ | S(O)CH$_2$CF$_3$ | H |
| 1-990 | CH$_2$CF(CF$_3$)OC$_3$F$_7$ | Cl | NH$_2$ | F | H | CH$_3$ | SCH$_2$CF$_3$ | H |
| 1-991 | CH$_2$CF(CF$_3$)OC$_3$F$_7$ | Cl | NH$_2$ | F | H | CH$_3$ | S(O)CH$_2$CF$_3$ | H |
| 1-992 | CH$_2$CF$_2$O(CF$_2$)$_2$OCF$_3$ | Cl | NH$_2$ | F | H | CH$_3$ | SCH$_2$CF$_3$ | H |
| 1-993 | CH$_2$CF$_2$O(CF$_2$)$_2$OCF$_3$ | Cl | NH$_2$ | F | H | CH$_3$ | S(O)CH$_2$CF$_3$ | H |

TABLE 19

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-994 | CH$_2$CF$_2$O(CF$_2$)$_2$OCF$_2$CF$_3$ | Cl | NH$_2$ | F | H | CH$_3$ | SCH$_2$CF$_3$ | H |
| 1-995 | CH$_2$CF$_2$O(CF$_2$)$_2$OCF$_2$CF$_3$ | Cl | NH$_2$ | F | H | CH$_3$ | S(O)CH$_2$CF$_3$ | H |
| 1-996 | CH$_2$(CF$_2$)$_3$CHF$_2$ | Cl | NH$_2$ | F | H | CH$_3$ | SCH$_2$CF$_3$ | H |
| 1-997 | CH$_2$(CF$_2$)$_3$CHF$_2$ | Cl | NH$_2$ | F | H | CH$_3$ | S(O)CH$_2$CF$_3$ | H |
| 1-998 | CH$_2$(CF$_2$)$_4$CHF$_2$ | Cl | NH$_2$ | F | H | CH$_3$ | SCH$_2$CF$_3$ | H |
| 1-999 | CH$_2$(CF$_2$)$_4$CHF$_2$ | Cl | NH$_2$ | F | H | CH$_3$ | S(O)CH$_2$CF$_3$ | H |
| 1-1000 | CH$_2$CH$_2$CH$_2$(CF$_2$)$_4$CF$_3$ | Cl | NH$_2$ | F | H | CH$_3$ | SCH$_2$CF$_3$ | H |
| 1-1001 | CH$_2$CH$_2$CH$_2$(CF$_2$)$_4$CF$_3$ | Cl | NH$_2$ | F | H | CH$_3$ | S(O)CH$_2$CF$_3$ | H |
| 1-1002 | CH$_2$CH$_2$CH$_2$(CF$_2$)$_5$CF$_3$ | Cl | NH$_2$ | F | H | CH$_3$ | SCH$_2$CF$_3$ | H |
| 1-1003 | CH$_2$CH$_2$CH$_2$(CF$_2$)$_5$CF$_3$ | Cl | NH$_2$ | F | H | CH$_3$ | S(O)CH$_2$CF$_3$ | H |
| 1-1004 | CF(CF$_3$)$_2$ | Cl | NHCH$_3$ | F | H | CH$_3$ | SCH$_2$CF$_3$ | H |
| 1-1005 | CF(CF$_3$)$_2$ | Cl | NHCH$_3$ | F | H | CH$_3$ | S(O)CH$_2$CF$_3$ | H |
| 1-1006 | CF$_2$CF$_2$CF$_3$ | Cl | NHCH$_3$ | F | H | CH$_3$ | SCH$_2$CF$_3$ | H |
| 1-1007 | CF$_2$CF$_2$CF$_3$ | Cl | NHCH$_3$ | F | H | CH$_3$ | S(O)CH$_2$CF$_3$ | H |

TABLE 19-continued

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-1008 | $CF_2(CF_2)_2CF_3$ | Cl | $NHCH_3$ | F | H | $CH_3$ | $SCH_2CF_3$ | H |
| 1-1009 | $CF_2(CF_2)_2CF_3$ | Cl | $NHCH_3$ | F | H | $CH_3$ | $S(O)CH_2CF_3$ | H |
| 1-1010 | $CF_2(CF_2)_3CF_3$ | Cl | $NHCH_3$ | F | H | $CH_3$ | $SCH_2CF_3$ | H |
| 1-1011 | $CF_2(CF_2)_3CF_3$ | Cl | $NHCH_3$ | F | H | $CH_3$ | $S(O)CH_2CF_3$ | H |
| 1-1012 | $CF_2(CF_2)_4CF_3$ | Cl | $NHCH_3$ | F | H | $CH_3$ | $SCH_2CF_3$ | H |
| 1-1013 | $CF_2(CF_2)_4CF_3$ | Cl | $NHCH_3$ | F | H | $CH_3$ | $S(O)CH_2CF_3$ | H |
| 1-1014 | $CF_2(CF_2)_5CF_3$ | Cl | $NHCH_3$ | F | H | $CH_3$ | $SCH_2CF_3$ | H |
| 1-1015 | $CF_2(CF_2)_5CF_3$ | Cl | $NHCH_3$ | F | H | $CH_3$ | $S(O)CH_2CF_3$ | H |
| 1-1016 | $CF_2(CF_2)_6CF_3$ | Cl | $NHCH_3$ | F | H | $CH_3$ | $SCH_2CF_3$ | H |
| 1-1017 | $CF_2(CF_2)_6CF_3$ | Cl | $NHCH_3$ | F | H | $CH_3$ | $S(O)CH_2CF_3$ | H |
| 1-1018 | $CF_2(CF_2)_7CF_3$ | Cl | $NHCH_3$ | F | H | $CH_3$ | $SCH_2CF_3$ | H |
| 1-1019 | $CF_2(CF_2)_7CF_3$ | Cl | $NHCH_3$ | F | H | $CH_3$ | $S(O)CH_2CF_3$ | H |
| 1-1020 | $CF_2(CF_2)_8CF_3$ | Cl | $NHCH_3$ | F | H | $CH_3$ | $SCH_2CF_3$ | H |
| 1-1021 | $CF_2(CF_2)_8CF_3$ | Cl | $NHCH_3$ | F | H | $CH_3$ | $S(O)CH_2CF_3$ | H |
| 1-1022 | $CF_2CHFOC_4F_9$ | Cl | $NHCH_3$ | F | H | $CH_3$ | $SCH_2CF_3$ | H |
| 1-1023 | $CF_2CHFOC_4F_9$ | Cl | $NHCH_3$ | F | H | $CH_3$ | $S(O)CH_2CF_3$ | H |
| 1-1024 | $CF_2CHFOC_5F_{11}$ | Cl | $NHCH_3$ | F | H | $CH_3$ | $SCH_2CF_3$ | H |
| 1-1025 | $CF_2CHFOC_5F_{11}$ | Cl | $NHCH_3$ | F | H | $CH_3$ | $S(O)CH_2CF_3$ | H |
| 1-1026 | $CF_2CHFOCF(CF_3)_2$ | Cl | $NHCH_3$ | F | H | $CH_3$ | $SCH_2CF_3$ | H |
| 1-1027 | $CF_2CHFOCF(CF_3)_2$ | Cl | $NHCH_3$ | F | H | $CH_3$ | $S(O)CH_2CF_3$ | H |
| 1-1028 | $CF_2CHFCF_2OCF_3$ | Cl | $NHCH_3$ | F | H | $CH_3$ | $SCH_2CF_3$ | H |
| 1-1029 | $CF_2CHFCF_2OCF_3$ | Cl | $NHCH_3$ | F | H | $CH_3$ | $S(O)CH_2CF_3$ | H |
| 1-1030 | $CH_2CF(CF_3)OC_3F_7$ | Cl | $NHCH_3$ | F | H | $CH_3$ | $SCH_2CF_3$ | H |
| 1-1031 | $CH_2CF(CF_3)OC_3F_7$ | Cl | $NHCH_3$ | F | H | $CH_3$ | $S(O)CH_2CF_3$ | H |
| 1-1032 | $CH_2CF_2O(CF_2)_2OCF_3$ | Cl | $NHCH_3$ | F | H | $CH_3$ | $SCH_2CF_3$ | H |
| 1-1033 | $CH_2CF_2O(CF_2)_2OCF_3$ | Cl | $NHCH_3$ | F | H | $CH_3$ | $S(O)CH_2CF_3$ | H |
| 1-1034 | $CH_2CF_2O(CF_2)_2OCF_2CF_3$ | Cl | $NHCH_3$ | F | H | $CH_3$ | $SCH_2CF_3$ | H |
| 1-1035 | $CH_2CF_2O(CF_2)_2OCF_2CF_3$ | Cl | $NHCH_3$ | F | H | $CH_3$ | $S(O)CH_2CF_3$ | H |
| 1-1036 | $CH_2(CF_2)_3CHF_2$ | Cl | $NHCH_3$ | F | H | $CH_3$ | $SCH_2CF_3$ | H |
| 1-1037 | $CH_2(CF_2)_3CHF_2$ | Cl | $NHCH_3$ | F | H | $CH_3$ | $S(O)CH_2CF_3$ | H |
| 1-1038 | $CH_2(CF_2)_4CHF_2$ | Cl | $NHCH_3$ | F | H | $CH_3$ | $SCH_2CF_3$ | H |
| 1-1039 | $CH_2(CF_2)_4CHF_2$ | Cl | $NHCH_3$ | F | H | $CH_3$ | $S(O)CH_2CF_3$ | H |
| 1-1040 | $CH_2CH_2CH_2(CF_2)_4CF_3$ | Cl | $NHCH_3$ | F | H | $CH_3$ | $SCH_2CF_3$ | H |
| 1-1041 | $CH_2CH_2CH_2(CF_2)_4CF_3$ | Cl | $NHCH_3$ | F | H | $CH_3$ | $S(O)CH_2CF_3$ | H |
| 1-1042 | $CH_2CH_2CH_2(CF_2)_5CF_3$ | Cl | $NHCH_3$ | F | H | $CH_3$ | $SCH_2CF_3$ | H |
| 1-1043 | $CH_2CH_2CH_2(CF_2)_5CF_3$ | Cl | $NHCH_3$ | F | H | $CH_3$ | $S(O)CH_2CF_3$ | H |
| 1-1044 | $CF(CF_3)_2$ | Cl | Cl | F | H | $CH_3$ | $SCH_2CF_3$ | H |
| 1-1045 | $CF(CF_3)_2$ | Cl | Cl | F | H | $CH_3$ | $S(O)CH_2CF_3$ | H |
| 1-1046 | $CF_2CF_2CF_3$ | Cl | Cl | F | H | $CH_3$ | $SCH_2CF_3$ | H |
| 1-1047 | $CF_2CF_2CF_3$ | Cl | Cl | F | H | $CH_3$ | $S(O)CH_2CF_3$ | H |
| 1-1048 | $CF_2(CF_2)_2CF_3$ | Cl | Cl | F | H | $CH_3$ | $SCH_2CF_3$ | H |
| 1-1049 | $CF_2(CF_2)_2CF_3$ | Cl | Cl | F | H | $CH_3$ | $S(O)CH_2CF_3$ | H |

TABLE 20

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-1050 | $CF_2(CF_2)_3CF_3$ | Cl | Cl | F | H | $CH_3$ | $SCH_2CF_3$ | H |
| 1-1051 | $CF_2(CF_2)_3CF_3$ | Cl | Cl | F | H | $CH_3$ | $S(O)CH_2CF_3$ | H |
| 1-1052 | $CF_2(CF_2)_4CF_3$ | Cl | Cl | F | H | $CH_3$ | $SCH_2CF_3$ | H |
| 1-1053 | $CF_2(CF_2)_4CF_3$ | Cl | Cl | F | H | $CH_3$ | $S(O)CH_2CF_3$ | H |
| 1-1054 | $CF_2(CF_2)_5CF_3$ | Cl | Cl | F | H | $CH_3$ | $SCH_2CF_3$ | H |
| 1-1055 | $CF_2(CF_2)_5CF_3$ | Cl | Cl | F | H | $CH_3$ | $S(O)CH_2CF_3$ | H |
| 1-1056 | $CF_2(CF_2)_6CF_3$ | Cl | Cl | F | H | $CH_3$ | $SCH_2CF_3$ | H |
| 1-1057 | $CF_2(CF_2)_6CF_3$ | Cl | Cl | F | H | $CH_3$ | $S(O)CH_2CF_3$ | H |
| 1-1058 | $CF_2(CF_2)_7CF_3$ | Cl | Cl | F | H | $CH_3$ | $SCH_2CF_3$ | H |
| 1-1059 | $CF_2(CF_2)_7CF_3$ | Cl | Cl | F | H | $CH_3$ | $S(O)CH_2CF_3$ | H |
| 1-1060 | $CF_2(CF_2)_8CF_3$ | Cl | Cl | F | H | $CH_3$ | $SCH_2CF_3$ | H |
| 1-1061 | $CF_2(CF_2)_8CF_3$ | Cl | Cl | F | H | $CH_3$ | $S(O)CH_2CF_3$ | H |
| 1-1062 | $CF_2CHFOC_3F_7$ | Cl | Cl | F | H | $CH_3$ | $SCH_2CF_3$ | H |
| 1-1063 | $CF_2CHFOC_3F_7$ | Cl | Cl | F | H | $CH_3$ | $S(O)CH_2CF_3$ | H |
| 1-1064 | $CF_2CHFOC_4F_9$ | Cl | Cl | F | H | $CH_3$ | $SCH_2CF_3$ | H |
| 1-1065 | $CF_2CHFOC_4F_9$ | Cl | Cl | F | H | $CH_3$ | $S(O)CH_2CF_3$ | H |
| 1-1066 | $CF_2CHFOC_5F_{11}$ | Cl | Cl | F | H | $CH_3$ | $SCH_2CF_3$ | H |
| 1-1067 | $CF_2CHFOC_5F_{11}$ | Cl | Cl | F | H | $CH_3$ | $S(O)CH_2CF_3$ | H |
| 1-1068 | $CF_2CHFOCF(CF_3)_2$ | Cl | Cl | F | H | $CH_3$ | $SCH_2CF_3$ | H |
| 1-1069 | $CF_2CHFOCF(CF_3)_2$ | Cl | Cl | F | H | $CH_3$ | $S(O)CH_2CF_3$ | H |
| 1-1070 | $CF_2CHFCF_2OCF_3$ | Cl | Cl | F | H | $CH_3$ | $SCH_2CF_3$ | H |
| 1-1071 | $CF_2CHFCF_2OCF_3$ | Cl | Cl | F | H | $CH_3$ | $S(O)CH_2CF_3$ | H |
| 1-1072 | $CH_2CF(CF_3)OC_3F_7$ | Cl | Cl | F | H | $CH_3$ | $SCH_2CF_3$ | H |
| 1-1073 | $CH_2CF(CF_3)OC_3F_7$ | Cl | Cl | F | H | $CH_3$ | $S(O)CH_2CF_3$ | H |
| 1-1074 | $CH_2CF_2O(CF_2)_2OCF_3$ | Cl | Cl | F | H | $CH_3$ | $SCH_2CF_3$ | H |
| 1-1075 | $CH_2CF_2O(CF_2)_2OCF_3$ | Cl | Cl | F | H | $CH_3$ | $S(O)CH_2CF_3$ | H |
| 1-1076 | $CH_2CF_2O(CF_2)_2OCF_2CF_3$ | Cl | Cl | F | H | $CH_3$ | $SCH_2CF_3$ | H |
| 1-1077 | $CH_2CF_2O(CF_2)_2OCF_2CF_3$ | Cl | Cl | F | H | $CH_3$ | $S(O)CH_2CF_3$ | H |

TABLE 20-continued

| Comp. No. | R₁ | R₂ | R₃ | R₄ | R₅ | R₆ | R₇ | R₈ |
|---|---|---|---|---|---|---|---|---|
| 1-1078 | CH₂(CF₂)₃CHF₂ | Cl | Cl | F | H | CH₃ | SCH₂CF₃ | H |
| 1-1079 | CH₂(CF₂)₃CHF₂ | Cl | Cl | F | H | CH₃ | S(O)CH₂CF₃ | H |
| 1-1080 | CH₂(CF₂)₄CHF₂ | Cl | Cl | F | H | CH₃ | SCH₂CF₃ | H |
| 1-1081 | CH₂(CF₂)₄CHF₂ | Cl | Cl | F | H | CH₃ | S(O)CH₂CF₃ | H |
| 1-1082 | CH₂CH₂CH₂(CF₂)₄CF₃ | Cl | Cl | F | H | CH₃ | SCH₂CF₃ | H |
| 1-1083 | CH₂CH₂CH₂(CF₂)₄CF₃ | Cl | Cl | F | H | CH₃ | S(O)CH₂CF₃ | H |
| 1-1084 | CH₂CH₂CH₂(CF₂)₅CF₃ | Cl | Cl | F | H | CH₃ | SCH₂CF₃ | H |
| 1-1085 | CH₂CH₂CH₂(CF₂)₅CF₃ | Cl | Cl | F | H | CH₃ | S(O)CH₂CF₃ | H |
| 1-1086 | CF(CF₃)₂ | Br | Br | F | H | CH₃ | SCH₂CF₃ | H |
| 1-1087 | CF(CF₃)₂ | Br | Br | F | H | CH₃ | S(O)CH₂CF₃ | H |
| 1-1088 | CF₂CF₂CF₃ | Br | Br | F | H | CH₃ | SCH₂CF₃ | H |
| 1-1089 | CF₂CF₂CF₃ | Br | Br | F | H | CH₃ | S(O)CH₂CF₃ | H |
| 1-1090 | CF₂(CF₂)₂CF₃ | Br | Br | F | H | CH₃ | SCH₂CF₃ | H |
| 1-1091 | CF₂(CF₂)₂CF₃ | Br | Br | F | H | CH₃ | S(O)CH₂CF₃ | H |
| 1-1092 | CF₂(CF₂)₃CF₃ | Br | Br | F | H | CH₃ | SCH₂CF₃ | H |
| 1-1093 | CF₂(CF₂)₃CF₃ | Br | Br | F | H | CH₃ | S(O)CH₂CF₃ | H |
| 1-1094 | CF₂(CF₂)₄CF₃ | Br | Br | F | H | CH₃ | SCH₂CF₃ | H |
| 1-1095 | CF₂(CF₂)₄CF₃ | Br | Br | F | H | CH₃ | S(O)CH₂CF₃ | H |
| 1-1096 | CF₂(CF₂)₅CF₃ | Br | Br | F | H | CH₃ | SCH₂CF₃ | H |
| 1-1097 | CF₂(CF₂)₅CF₃ | Br | Br | F | H | CH₃ | S(O)CH₂CF₃ | H |
| 1-1098 | CF₂(CF₂)₆CF₃ | Br | Br | F | H | CH₃ | SCH₂CF₃ | H |
| 1-1099 | CF₂(CF₂)₆CF₃ | Br | Br | F | H | CH₃ | S(O)CH₂CF₃ | H |
| 1-1100 | CF₂(CF₂)₇CF₃ | Br | Br | F | H | CH₃ | SCH₂CF₃ | H |
| 1-1101 | CF₂(CF₂)₇CF₃ | Br | Br | F | H | CH₃ | S(O)CH₂CF₃ | H |
| 1-1102 | CF₂(CF₂)₈CF₃ | Br | Br | F | H | CH₃ | SCH₂CF₃ | H |
| 1-1103 | CF₂(CF₂)₈CF₃ | Br | Br | F | H | CH₃ | S(O)CH₂CF₃ | H |
| 1-1104 | CF₂CHFOCF₃ | Br | Br | F | H | CH₃ | SCH₂CF₃ | H |
| 1-1105 | CF₂CHFOCF₃ | Br | Br | F | H | CH₃ | S(O)CH₂CF₃ | H |

TABLE 21

| Comp. No. | R₁ | R₂ | R₃ | R₄ | R₅ | R₆ | R₇ | R₈ |
|---|---|---|---|---|---|---|---|---|
| 1-1106 | CF₂CHFOC₂F₅ | Br | Br | F | H | CH₃ | SCH₂CF₃ | H |
| 1-1107 | CF₂CHFOC₂F₅ | Br | Br | F | H | CH₃ | S(O)CH₂CF₃ | H |
| 1-1108 | CF₂CHFOC₃F₇ | Br | Br | F | H | CH₃ | SCH₂CF₃ | H |
| 1-1109 | CF₂CHFOC₃F₇ | Br | Br | F | H | CH₃ | S(O)CH₂CF₃ | H |
| 1-1110 | CF₂CHFOC₄F₉ | Br | Br | F | H | CH₃ | SCH₂CF₃ | H |
| 1-1111 | CF₂CHFOC₄F₉ | Br | Br | F | H | CH₃ | S(O)CH₂CF₃ | H |
| 1-1112 | CF₂CHFOC₅F₁₁ | Br | Br | F | H | CH₃ | SCH₂CF₃ | H |
| 1-1113 | CF₂CHFOC₅F₁₁ | Br | Br | F | H | CH₃ | S(O)CH₂CF₃ | H |
| 1-1114 | CF₂CHFOCF(CF₃)₂ | Br | Br | F | H | CH₃ | SCH₂CF₃ | H |
| 1-1115 | CF₂CHFOCF(CF₃)₂ | Br | Br | F | H | CH₃ | S(O)CH₂CF₃ | H |
| 1-1116 | CF₂CHFCF₂OCF₃ | Br | Br | F | H | CH₃ | SCH₂CF₃ | H |
| 1-1117 | CF₂CHFCF₂OCF₃ | Br | Br | F | H | CH₃ | S(O)CH₂CF₃ | H |
| 1-1118 | CH₂CF(CF₃)OC₃F₇ | Br | Br | F | H | CH₃ | SCH₂CF₃ | H |
| 1-1119 | CH₂CF(CF₃)OC₃F₇ | Br | Br | F | H | CH₃ | S(O)CH₂CF₃ | H |
| 1-1120 | CH₂CF₂O(CF₂)₂OCF₃ | Br | Br | F | H | CH₃ | SCH₂CF₃ | H |
| 1-1121 | CH₂CF₂O(CF₂)₂OCF₃ | Br | Br | F | H | CH₃ | S(O)CH₂CF₃ | H |
| 1-1122 | CH₂CF₂O(CF₂)₂OCF₂CF₃ | Br | Br | F | H | CH₃ | SCH₂CF₃ | H |
| 1-1123 | CH₂CF₂O(CF₂)₂OCF₂CF₃ | Br | Br | F | H | CH₃ | S(O)CH₂CF₃ | H |
| 1-1124 | CH₂(CF₂)₃CHF₂ | Br | Br | F | H | CH₃ | SCH₂CF₃ | H |
| 1-1125 | CH₂(CF₂)₃CHF₂ | Br | Br | F | H | CH₃ | S(O)CH₂CF₃ | H |
| 1-1126 | CH₂(CF₂)₄CHF₂ | Br | Br | F | H | CH₃ | SCH₂CF₃ | H |
| 1-1127 | CH₂(CF₂)₄CHF₂ | Br | Br | F | H | CH₃ | S(O)CH₂CF₃ | H |
| 1-1128 | CH₂CH₂CH₂(CF₂)₄CF₃ | Br | Br | F | H | CH₃ | SCH₂CF₃ | H |
| 1-1129 | CH₂CH₂CH₂(CF₂)₄CF₃ | Br | Br | F | H | CH₃ | S(O)CH₂CF₃ | H |
| 1-1130 | CH₂CH₂CH₂(CF₂)₅CF₃ | Br | Br | F | H | CH₃ | SCH₂CF₃ | H |
| 1-1131 | CH₂CH₂CH₂(CF₂)₅CF₃ | Br | Br | F | H | CH₃ | S(O)CH₂CF₃ | H |
| 1-1132 | CF(CF₃)₂ | Cl | H | F | H | CH₃ | SCH₂CF₃ | H |
| 1-1133 | CF(CF₃)₂ | Cl | H | F | H | CH₃ | S(O)CH₂CF₃ | H |
| 1-1134 | CF₂CF₂CF₃ | Cl | H | F | H | CH₃ | SCH₂CF₃ | H |
| 1-1135 | CF₂CF₂CF₃ | Cl | H | F | H | CH₃ | S(O)CH₂CF₃ | H |
| 1-1136 | CF₂(CF₂)₂CF₃ | Cl | H | F | H | CH₃ | SCH₂CF₃ | H |
| 1-1137 | CF₂(CF₂)₂CF₃ | Cl | H | F | H | CH₃ | S(O)CH₂CF₃ | H |
| 1-1138 | CF₂(CF₂)₃CF₃ | Cl | H | F | H | CH₃ | SCH₂CF₃ | H |
| 1-1139 | CF₂(CF₂)₃CF₃ | Cl | H | F | H | CH₃ | S(O)CH₂CF₃ | H |
| 1-1140 | CF₂(CF₂)₄CF₃ | Cl | H | F | H | CH₃ | SCH₂CF₃ | H |
| 1-1141 | CF₂(CF₂)₄CF₃ | Cl | H | F | H | CH₃ | S(O)CH₂CF₃ | H |
| 1-1142 | CF₂(CF₂)₅CF₃ | Cl | H | F | H | CH₃ | SCH₂CF₃ | H |
| 1-1143 | CF₂(CF₂)₅CF₃ | Cl | H | F | H | CH₃ | S(O)CH₂CF₃ | H |
| 1-1144 | CF₂(CF₂)₆CF₃ | Cl | H | F | H | CH₃ | SCH₂CF₃ | H |
| 1-1145 | CF₂(CF₂)₆CF₃ | Cl | H | F | H | CH₃ | S(O)CH₂CF₃ | H |
| 1-1146 | CF₂(CF₂)₇CF₃ | Cl | H | F | H | CH₃ | SCH₂CF₃ | H |
| 1-1147 | CF₂(CF₂)₇CF₃ | Cl | H | F | H | CH₃ | S(O)CH₂CF₃ | H |

TABLE 21-continued

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-1148 | $CF_2(CF_2)_8CF_3$ | Cl | H | F | H | $CH_3$ | $SCH_2CF_3$ | H |
| 1-1149 | $CF_2(CF_2)_8CF_3$ | Cl | H | F | H | $CH_3$ | $S(O)CH_2CF_3$ | H |
| 1-1150 | $CF_2CHFOC_3F_7$ | Cl | H | F | H | $CH_3$ | $SCH_2CF_3$ | H |
| 1-1151 | $CF_2CHFOC_3F_7$ | Cl | H | F | H | $CH_3$ | $S(O)CH_2CF_3$ | H |
| 1-1152 | $CF_2CHFOC_4F_9$ | Cl | H | F | H | $CH_3$ | $SCH_2CF_3$ | H |
| 1-1153 | $CF_2CHFOC_4F_9$ | Cl | H | F | H | $CH_3$ | $S(O)CH_2CF_3$ | H |
| 1-1154 | $CF_2CHFOC_5F_{11}$ | Cl | H | F | H | $CH_3$ | $SCH_2CF_3$ | H |
| 1-1155 | $CF_2CHFOC_5F_{11}$ | Cl | H | F | H | $CH_3$ | $S(O)CH_2CF_3$ | H |
| 1-1156 | $CF_2CHFOCF(CF_3)_2$ | Cl | H | F | H | $CH_3$ | $SCH_2CF_3$ | H |
| 1-1157 | $CF_2CHFOCF(CF_3)_2$ | Cl | H | F | H | $CH_3$ | $S(O)CH_2CF_3$ | H |
| 1-1158 | $CF_2CHFCF_2OCF_3$ | Cl | H | F | H | $CH_3$ | $SCH_2CF_3$ | H |
| 1-1159 | $CF_2CHFCF_2OCF_3$ | Cl | H | F | H | $CH_3$ | $S(O)CH_2CF_3$ | H |
| 1-1160 | $CH_2CF(CF_3)OC_3F_7$ | Cl | H | F | H | $CH_3$ | $SCH_2CF_3$ | H |
| 1-1161 | $CH_2CF(CF_3)OC_3F_7$ | Cl | H | F | H | $CH_3$ | $S(O)CH_2CF_3$ | H |

TABLE 22

| Comp. No. | $R_1$ | $R_2$ | $R_3$ | $R_4$ | $R_5$ | $R_6$ | $R_7$ | $R_8$ |
|---|---|---|---|---|---|---|---|---|
| 1-1162 | $CH_2CF_2O(CF_2)_2OCF_3$ | Cl | H | F | H | $CH_3$ | $SCH_2CF_3$ | H |
| 1-1163 | $CH_2CF_2O(CF_2)_2OCF_3$ | Cl | H | F | H | $CH_3$ | $S(O)CH_2CF_3$ | H |
| 1-1164 | $CH_2CF_2O(CF_2)_2OCF_2CF_3$ | Cl | H | F | H | $CH_3$ | $SCH_2CF_3$ | H |
| 1-1165 | $CH_2CF_2O(CF_2)_2OCF_2CF_3$ | Cl | H | F | H | $CH_3$ | $S(O)CH_2CF_3$ | H |
| 1-1166 | $CH_2(CF_2)_3CHF_2$ | Cl | H | F | H | $CH_3$ | $SCH_2CF_3$ | H |
| 1-1167 | $CH_2(CF_2)_3CHF_2$ | Cl | H | F | H | $CH_3$ | $S(O)CH_2CF_3$ | H |
| 1-1168 | $CH_2(CF_2)_4CHF_2$ | Cl | H | F | H | $CH_3$ | $SCH_2CF_3$ | H |
| 1-1169 | $CH_2(CF_2)_4CHF_2$ | Cl | H | F | H | $CH_3$ | $S(O)CH_2CF_3$ | H |
| 1-1170 | $CH_2CH_2CH_2(CF_2)_4CF_3$ | Cl | H | F | H | $CH_3$ | $SCH_2CF_3$ | H |
| 1-1171 | $CH_2CH_2CH_2(CF_2)_4CF_3$ | Cl | H | F | H | $CH_3$ | $S(O)CH_2CF_3$ | H |
| 1-1172 | $CH_2CH_2CH_2(CF_2)_5CF_3$ | Cl | H | F | H | $CH_3$ | $SCH_2CF_3$ | H |
| 1-1173 | $CH_2CH_2CH_2(CF_2)_5CF_3$ | Cl | H | F | H | $CH_3$ | $S(O)CH_2CF_3$ | H |
| 1-1174 | $CF(CF_3)_2$ | Br | H | F | H | $CH_3$ | $SCH_2CF_3$ | H |
| 1-1175 | $CF(CF_3)_2$ | Br | H | F | H | $CH_3$ | $S(O)CH_2CF_3$ | H |
| 1-1176 | $CF_2CF_2CF_3$ | Br | H | F | H | $CH_3$ | $SCH_2CF_3$ | H |
| 1-1177 | $CF_2CF_2CF_3$ | Br | H | F | H | $CH_3$ | $S(O)CH_2CF_3$ | H |
| 1-1178 | $CF_2(CF_2)_2CF_3$ | Br | H | F | H | $CH_3$ | $SCH_2CF_3$ | H |
| 1-1179 | $CF_2(CF_2)_2CF_3$ | Br | H | F | H | $CH_3$ | $S(O)CH_2CF_3$ | H |
| 1-1180 | $CF_2(CF_2)_3CF_3$ | Br | H | F | H | $CH_3$ | $SCH_2CF_3$ | H |
| 1-1181 | $CF_2(CF_2)_3CF_3$ | Br | H | F | H | $CH_3$ | $S(O)CH_2CF_3$ | H |
| 1-1182 | $CF_2(CF_2)_4CF_3$ | Br | H | F | H | $CH_3$ | $SCH_2CF_3$ | H |
| 1-1183 | $CF_2(CF_2)_4CF_3$ | Br | H | F | H | $CH_3$ | $S(O)CH_2CF_3$ | H |
| 1-1184 | $CF_2(CF_2)_5CF_3$ | Br | H | F | H | $CH_3$ | $SCH_2CF_3$ | H |
| 1-1185 | $CF_2(CF_2)_5CF_3$ | Br | H | F | H | $CH_3$ | $S(O)CH_2CF_3$ | H |
| 1-1186 | $CF_2(CF_2)_6CF_3$ | Br | H | F | H | $CH_3$ | $SCH_2CF_3$ | H |
| 1-1187 | $CF_2(CF_2)_6CF_3$ | Br | H | F | H | $CH_3$ | $S(O)CH_2CF_3$ | H |
| 1-1188 | $CF_2(CF_2)_7CF_3$ | Br | H | F | H | $CH_3$ | $SCH_2CF_3$ | H |
| 1-1189 | $CF_2(CF_2)_7CF_3$ | Br | H | F | H | $CH_3$ | $S(O)CH_2CF_3$ | H |
| 1-1190 | $CF_2(CF_2)_8CF_3$ | Br | H | F | H | $CH_3$ | $SCH_2CF_3$ | H |
| 1-1191 | $CF_2(CF_2)_8CF_3$ | Br | H | F | H | $CH_3$ | $S(O)CH_2CF_3$ | H |
| 1-1192 | $CF_2CHFOCF_3$ | Br | H | F | H | $CH_3$ | $SCH_2CF_3$ | H |
| 1-1193 | $CF_2CHFOCF_3$ | Br | H | F | H | $CH_3$ | $S(O)CH_2CF_3$ | H |
| 1-1194 | $CF_2CHFOC_2F_5$ | Br | H | F | H | $CH_3$ | $SCH_2CF_3$ | H |
| 1-1195 | $CF_2CHFOC_2F_5$ | Br | H | F | H | $CH_3$ | $S(O)CH_2CF_3$ | H |
| 1-1196 | $CF_2CHFOC_3F_7$ | Br | H | F | H | $CH_3$ | $SCH_2CF_3$ | H |
| 1-1197 | $CF_2CHFOC_3F_7$ | Br | H | F | H | $CH_3$ | $S(O)CH_2CF_3$ | H |
| 1-1198 | $CF_2CHFOC_4F_9$ | Br | H | F | H | $CH_3$ | $SCH_2CF_3$ | H |
| 1-1199 | $CF_2CHFOC_4F_9$ | Br | H | F | H | $CH_3$ | $S(O)CH_2CF_3$ | H |
| 1-1200 | $CF_2CHFOC_5F_{11}$ | Br | H | F | H | $CH_3$ | $SCH_2CF_3$ | H |
| 1-1201 | $CF_2CHFOC_5F_{11}$ | Br | H | F | H | $CH_3$ | $S(O)CH_2CF_3$ | H |
| 1-1202 | $CF_2CHFOCF(CF_3)_2$ | Br | H | F | H | $CH_3$ | $SCH_2CF_3$ | H |
| 1-1203 | $CF_2CHFOCF(CF_3)_2$ | Br | H | F | H | $CH_3$ | $S(O)CH_2CF_3$ | H |
| 1-1204 | $CF_2CHFCF_2OCF_3$ | Br | H | F | H | $CH_3$ | $SCH_2CF_3$ | H |
| 1-1205 | $CF_2CHFCF_2OCF_3$ | Br | H | F | H | $CH_3$ | $S(O)CH_2CF_3$ | H |
| 1-1206 | $CH_2CF(CF_3)OC_3F_7$ | Br | H | F | H | $CH_3$ | $SCH_2CF_3$ | H |
| 1-1207 | $CH_2CF(CF_3)OC_3F_7$ | Br | H | F | H | $CH_3$ | $S(O)CH_2CF_3$ | H |
| 1-1208 | $CH_2CF_2O(CF_2)_2OCF_3$ | Br | H | F | H | $CH_3$ | $SCH_2CF_3$ | H |
| 1-1209 | $CH_2CF_2O(CF_2)_2OCF_3$ | Br | H | F | H | $CH_3$ | $S(O)CH_2CF_3$ | H |
| 1-1210 | $CH_2CF_2O(CF_2)_2OCF_2CF_3$ | Br | H | F | H | $CH_3$ | $SCH_2CF_3$ | H |
| 1-1211 | $CH_2CF_2O(CF_2)_2OCF_2CF_3$ | Br | H | F | H | $CH_3$ | $S(O)CH_2CF_3$ | H |
| 1-1212 | $CH_2(CF_2)_3CHF_2$ | Br | H | F | H | $CH_3$ | $SCH_2CF_3$ | H |
| 1-1213 | $CH_2(CF_2)_3CHF_2$ | Br | H | F | H | $CH_3$ | $S(O)CH_2CF_3$ | H |
| 1-1214 | $CH_2(CF_2)_4CHF_2$ | Br | H | F | H | $CH_3$ | $SCH_2CF_3$ | H |
| 1-1215 | $CH_2(CF_2)_4CHF_2$ | Br | H | F | H | $CH_3$ | $S(O)CH_2CF_3$ | H |
| 1-1216 | $CH_2CH_2CH_2(CF_2)_4CF_3$ | Br | H | F | H | $CH_3$ | $SCH_2CF_3$ | H |
| 1-1217 | $CH_2CH_2CH_2(CF_2)_4CF_3$ | Br | H | F | H | $CH_3$ | $S(O)CH_2CF_3$ | H |

TABLE 23

| Comp. No. | R₁ | R₂ | R₃ | R₄ | R₅ | R₆ | R₇ | R₈ |
|---|---|---|---|---|---|---|---|---|
| 1-1218 | CH₂CH₂CH₂(CF₂)₅CF₃ | Br | H | F | H | CH₃ | SCH₂CF₃ | H |
| 1-1219 | CH₂CH₂CH₂(CF₂)₅CF₃ | Br | H | F | H | CH₃ | S(O)CH₂CF₃ | H |
| 1-1220 | CH₂CF₂CF₃ | H | NHC(O)CH₃ | H | H | CH₃ | SCH₂CF₃ | H |
| 1-1221 | CH₂CF₂CF₃ | H | NHC(O)CH₃ | H | H | CH₃ | S(O)CH₂CF₃ | H |
| 1-1222 | CH₂CF₂CF₃ | H | CH₃ | H | H | CH₃ | SCH₂CF₃ | H |
| 1-1223 | CH₂CF₂CF₃ | H | CH₃ | H | H | CH₃ | S(O)CH₂CF₃ | H |
| 1-1224 | CH₂CF₂CF₃ | H | NHC(O)CH₃ | Cl | H | CH₃ | SCH₂CF₃ | H |
| 1-1225 | CH₂CF₂CF₃ | H | NHC(O)CH₃ | Cl | H | CH₃ | S(O)CH₂CF₃ | H |
| 1-1226 | CH₂CF₂CF₃ | H | CH₃ | Cl | H | CH₃ | SCH₂CF₃ | H |
| 1-1227 | CH₂CF₂CF₃ | H | CH₃ | Cl | H | CH₃ | S(O)CH₂CF₃ | H |
| 1-1228 | CH₂CF₂CF₃ | H | NHC(O)CH₃ | CH₃ | H | CH₃ | SCH₂CF₃ | H |
| 1-1229 | CH₂CF₂CF₃ | H | NHC(O)CH₃ | CH₃ | H | CH₃ | S(O)CH₂CF₃ | H |
| 1-1230 | CH₂CF₂CF₃ | H | CH₃ | CH₃ | H | CH₃ | SCH₂CF₃ | H |
| 1-1231 | CH₂CF₂CF₃ | H | CH₃ | CH₃ | H | CH₃ | S(O)CH₂CF₃ | H |
| 1-1232 | CH₂CF₂CF₃ | H | NHC(O)CH₃ | H | H | Cl | SCH₂CF₃ | H |
| 1-1233 | CH₂CF₂CF₃ | H | NHC(O)CH₃ | H | H | Cl | S(O)CH₂CF₃ | H |
| 1-1234 | CH₂CF₂CF₃ | H | CH₃ | H | H | Cl | SCH₂CF₃ | H |
| 1-1235 | CH₂CF₂CF₃ | H | CH₃ | H | H | Cl | S(O)CH₂CF₃ | H |
| 1-1236 | CH₂CF₂CF₃ | H | NHC(O)CH₃ | F | H | CN | SCH₂CF₃ | H |
| 1-1237 | CH₂CF₂CF₃ | H | NHC(O)CH₃ | F | H | CN | S(O)CH₂CF₃ | H |
| 1-1238 | CH₂CF₂CF₃ | H | CH₃ | F | H | CN | SCH₂CF₃ | H |
| 1-1239 | CH₂CF₂CF₃ | H | CH₃ | F | H | CN | S(O)CH₂CF₃ | H |
| 1-1240 | CH₂CF₂CF₃ | H | NHC(O)CH₃ | H | H | CN | SCH₂CF₃ | H |
| 1-1241 | CH₂CF₂CF₃ | H | NHC(O)CH₃ | H | H | CN | S(O)CH₂CF₃ | H |
| 1-1242 | CH₂CF₂CF₃ | H | CH₃ | H | H | CN | SCH₂CF₃ | H |
| 1-1243 | CH₂CF₂CF₃ | H | CH₃ | H | H | CN | S(O)CH₂CF₃ | H |
| 1-1244 | CH₂CF₂CF₃ | H | NHC(O)CH₃ | H | H | OCH₃ | SCH₂CF₃ | H |
| 1-1245 | CH₂CF₂CF₃ | H | NHC(O)CH₃ | H | H | OCH₃ | S(O)CH₂CF₃ | H |
| 1-1246 | CH₂CF₂CF₃ | H | CH₃ | H | H | OCH₃ | SCH₂CF₃ | H |
| 1-1247 | CH₂CF₂CF₃ | H | CH₃ | H | H | OCH₃ | S(O)CH₂CF₃ | H |
| 1-1248 | CH₂CF₂CF₃ | H | CH₃ | F | H | CH₃ | SCH₂CH₂CF₃ | H |
| 1-1249 | CH₂CF₂CF₃ | H | CH₃ | F | H | CH₃ | S(O)CH₂CH₂CF₃ | H |
| 1-1250 | CH₂CH₂OCH(CF₃)₂ | H | CH₃ | F | H | CH₃ | SCH₂CF₃ | H |
| 1-1251 | CH₂CH₂OCH(CF₃)₂ | H | CH₃ | F | H | CH₃ | S(O)CH₂CF₃ | H |
| 1-1252 | CH₂CH₂CH₂OC(CF₃)₃ | H | CH₃ | F | H | CH₃ | SCH₂CF₃ | H |
| 1-1253 | CH₂CH₂CH₂OC(CF₃)₃ | H | CH₃ | F | H | CH₃ | S(O)CH₂CF₃ | H |
| 1-1254 | CH₂CH₂CH₂OCH(CF₃)₂ | H | CH₃ | F | H | CH₃ | SCH₂CF₃ | H |
| 1-1255 | CH₂CH₂CH₂OCH(CF₃)₂ | H | CH₃ | F | H | CH₃ | S(O)CH₂CF₃ | H |
| 1-1256 | CH₂CF₂CF₂CF₂CF₃ | H | NHCH₃ | F | H | CH₃ | SCH₂CF₃ | H |
| 1-1257 | CF₂CHFOCF₂CF₃ | Br | NH₂ | F | H | CH₃ | SCH₂CF₃ | H |
| 1-1258 | CH₂CF₂CF₂CH₂OCH₂CF₃ | H | NHC(O)CH₃ | F | H | CH₃ | SCH₂CF₃ | H |
| 1-1259 | CH₂CF₂CF₂CH₂OCH₂CF₃ | H | NHC(O)CH₃ | F | H | CH₃ | S(O)CH₂CF₃ | H |
| 1-1260 | CF₂CHFCF₃ | Br | NH₂ | F | H | CH₃ | SCH₂CF₃ | H |
| 1-1261 | CF₂CHFCF₃ | Br | NH₂ | F | H | CH₃ | S(O)CH₂CF₃ | H |
| 1-1262 | CF(CF₃)₂ | Br | NH₂ | F | H | CH₃ | SCH₂CF₃ | H |
| 1-1263 | CF(CF₃)₂ | Br | NH₂ | F | H | CH₃ | S(O)CH₂CF₃ | H |
| 1-1264 | CF₂CF₂CF₃ | Br | NH₂ | F | H | CH₃ | SCH₂CF₃ | H |
| 1-1265 | CF₂CF₂CF₃ | Br | NH₂ | F | H | CH₃ | S(O)CH₂CF₃ | H |
| 1-1266 | CF₂(CF₂)₂CF₃ | Br | NH₂ | F | H | CH₃ | SCH₂CF₃ | H |
| 1-1267 | CF₂(CF₂)₂CF₃ | Br | NH₂ | F | H | CH₃ | S(O)CH₂CF₃ | H |
| 1-1268 | CF₂(CF₂)₃CF₃ | Br | NH₂ | F | H | CH₃ | SCH₂CF₃ | H |
| 1-1269 | CF₂(CF₂)₃CF₃ | Br | NH₂ | F | H | CH₃ | S(O)CH₂CF₃ | H |
| 1-1270 | CF₂(CF₂)₄CF₃ | Br | NH₂ | F | H | CH₃ | SCH₂CF₃ | H |
| 1-1271 | CF₂(CF₂)₄CF₃ | Br | NH₂ | F | H | CH₃ | S(O)CH₂CF₃ | H |
| 1-1272 | CF₂(CF₂)₅CF₃ | Br | NH₂ | F | H | CH₃ | SCH₂CF₃ | H |
| 1-1273 | CF₂(CF₂)₅CF₃ | Br | NH₂ | F | H | CH₃ | S(O)CH₂CF₃ | H |
| 1-1274 | CF₂(CF₂)₆CF₃ | Br | NH₂ | F | H | CH₃ | SCH₂CF₃ | H |
| 1-1275 | CF₂(CF₂)₆CF₃ | Br | NH₂ | F | H | CH₃ | S(O)CH₂CF₃ | H |

TABLE 24

| Comp. No. | R₁ | R₂ | R₃ | R₄ | R₅ | R₆ | R₇ | R₈ |
|---|---|---|---|---|---|---|---|---|
| 1-1276 | CF₂(CF₂)₇CF₃ | Br | NH₂ | F | H | CH₃ | SCH₂CF₃ | H |
| 1-1277 | CF₂(CF₂)₇CF₃ | Br | NH₂ | F | H | CH₃ | S(O)CH₂CF₃ | H |
| 1-1278 | CF₂(CF₂)₈CF₃ | Br | NH₂ | F | H | CH₃ | SCH₂CF₃ | H |
| 1-1279 | CF₂(CF₂)₈CF₃ | Br | NH₂ | F | H | CH₃ | S(O)CH₂CF₃ | H |
| 1-1280 | CF₂CHFOCF₃ | Br | NH₂ | F | H | CH₃ | SCH₂CF₃ | H |
| 1-1281 | CF₂CHFOCF₃ | Br | NH₂ | F | H | CH₃ | S(O)CH₂CF₃ | H |
| 1-1282 | CF₂CHFOC₂F₅ | Br | NH₂ | F | H | CH₃ | SCH₂CF₃ | H |
| 1-1283 | CF₂CHFOC₂F₅ | Br | NH₂ | F | H | CH₃ | S(O)CH₂CF₃ | H |
| 1-1284 | CF₂CHFOC₃F₇ | Br | NH₂ | F | H | CH₃ | S(O)CH₂CF₃ | H |
| 1-1285 | CF₂CHFOC₄F₉ | Br | NH₂ | F | H | CH₃ | SCH₂CF₃ | H |
| 1-1286 | CF₂CHFOC₄F₉ | Br | NH₂ | F | H | CH₃ | S(O)CH₂CF₃ | H |
| 1-1287 | CF₂CHFOC₅F₁₁ | Br | NH₂ | F | H | CH₃ | SCH₂CF₃ | H |

TABLE 24-continued

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1288 | CF$_2$CHFOC$_5$F$_{11}$ | Br | NH$_2$ | F | H | CH$_3$ | S(O)CH$_2$CF$_3$ | H |
| 1-1289 | CF$_2$CHFOCF(CF$_3$)$_2$ | Br | NH$_2$ | F | H | CH$_3$ | SCH$_2$CF$_3$ | H |
| 1-1290 | CF$_2$CHFOCF(CF$_3$)$_2$ | Br | NH$_2$ | F | H | CH$_3$ | S(O)CH$_2$CF$_3$ | H |
| 1-1291 | CF$_2$CHFCF$_2$OCF$_3$ | Br | NH$_2$ | F | H | CH$_3$ | SCH$_2$CF$_3$ | H |
| 1-1292 | CF$_2$CHFCF$_2$OCF$_3$ | Br | NH$_2$ | F | H | CH$_3$ | S(O)CH$_2$CF$_3$ | H |
| 1-1293 | CH$_2$CF(CF$_3$)OC$_3$F$_7$ | Br | NH$_2$ | F | H | CH$_3$ | SCH$_2$CF$_3$ | H |
| 1-1294 | CH$_2$CF(CF$_3$)OC$_3$F$_7$ | Br | NH$_2$ | F | H | CH$_3$ | S(O)CH$_2$CF$_3$ | H |
| 1-1295 | CH$_2$CF$_2$O(CF$_2$)$_2$OCF$_3$ | Br | NH$_2$ | F | H | CH$_3$ | SCH$_2$CF$_3$ | H |
| 1-1296 | CH$_2$CF$_2$O(CF$_2$)$_2$OCF$_3$ | Br | NH$_2$ | F | H | CH$_3$ | S(O)CH$_2$CF$_3$ | H |
| 1-1297 | CH$_2$CF$_2$O(CF$_2$)$_2$OCF$_2$CF$_3$ | Br | NH$_2$ | F | H | CH$_3$ | SCH$_2$CF$_3$ | H |
| 1-1298 | CH$_2$CF$_2$O(CF$_2$)$_2$OCF$_2$CF$_3$ | Br | NH$_2$ | F | H | CH$_3$ | S(O)CH$_2$CF$_3$ | H |
| 1-1299 | CH$_2$(CF$_2$)$_3$CHF$_2$ | Br | NH$_2$ | F | H | CH$_3$ | SCH$_2$CF$_3$ | H |
| 1-1300 | CH$_2$(CF$_2$)$_3$CHF$_2$ | Br | NH$_2$ | F | H | CH$_3$ | S(O)CH$_2$CF$_3$ | H |
| 1-1301 | CH$_2$(CF$_2$)$_4$CHF$_2$ | Br | NH$_2$ | F | H | CH$_3$ | SCH$_2$CF$_3$ | H |
| 1-1302 | CH$_2$(CF$_2$)$_4$CHF$_2$ | Br | NH$_2$ | F | H | CH$_3$ | S(O)CH$_2$CF$_3$ | H |
| 1-1303 | CH$_2$CH$_2$CH$_2$(CF$_2$)$_4$CF$_3$ | Br | NH$_2$ | F | H | CH$_3$ | SCH$_2$CF$_3$ | H |
| 1-1304 | CH$_2$CH$_2$CH$_2$(CF$_2$)$_4$CF$_3$ | Br | NH$_2$ | F | H | CH$_3$ | S(O)CH$_2$CF$_3$ | H |
| 1-1305 | CH$_2$CH$_2$CH$_2$(CF$_2$)$_5$CF$_3$ | Br | NH$_2$ | F | H | CH$_3$ | SCH$_2$CF$_3$ | H |
| 1-1306 | CH$_2$CH$_2$CH$_2$(CF$_2$)$_5$CF$_3$ | Br | NH$_2$ | F | H | CH$_3$ | S(O)CH$_2$CF$_3$ | H |
| 1-1307 | CF$_2$CHFCF$_3$ | Br | NHCH$_3$ | F | H | CH$_3$ | SCH$_2$CF$_3$ | H |
| 1-1308 | CF$_2$CHFCF$_3$ | Br | NHCH$_3$ | F | H | CH$_3$ | S(O)CH$_2$CF$_3$ | H |
| 1-1309 | CF(CF$_3$)$_2$ | Br | NHCH$_3$ | F | H | CH$_3$ | SCH$_2$CF$_3$ | H |
| 1-1310 | CF(CF$_3$)$_2$ | Br | NHCH$_3$ | F | H | CH$_3$ | S(O)CH$_2$CF$_3$ | H |
| 1-1311 | CF$_2$CF$_2$CF$_3$ | Br | NHCH$_3$ | F | H | CH$_3$ | SCH$_2$CF$_3$ | H |
| 1-1312 | CF$_2$CF$_2$CF$_3$ | Br | NHCH$_3$ | F | H | CH$_3$ | S(O)CH$_2$CF$_3$ | H |
| 1-1313 | CF$_2$(CF$_2$)$_2$CF$_3$ | Br | NHCH$_3$ | F | H | CH$_3$ | SCH$_2$CF$_3$ | H |
| 1-1314 | CF$_2$(CF$_2$)$_2$CF$_3$ | Br | NHCH$_3$ | F | H | CH$_3$ | S(O)CH$_2$CF$_3$ | H |
| 1-1315 | CF$_2$(CF$_2$)$_3$CF$_3$ | Br | NHCH$_3$ | F | H | CH$_3$ | SCH$_2$CF$_3$ | H |
| 1-1316 | CF$_2$(CF$_2$)$_3$CF$_3$ | Br | NHCH$_3$ | F | H | CH$_3$ | S(O)CH$_2$CF$_3$ | H |
| 1-1317 | CF$_2$(CF$_2$)$_4$CF$_3$ | Br | NHCH$_3$ | F | H | CH$_3$ | SCH$_2$CF$_3$ | H |
| 1-1318 | CF$_2$(CF$_2$)$_4$CF$_3$ | Br | NHCH$_3$ | F | H | CH$_3$ | S(O)CH$_2$CF$_3$ | H |
| 1-1319 | CF$_2$(CF$_2$)$_5$CF$_3$ | Br | NHCH$_3$ | F | H | CH$_3$ | SCH$_2$CF$_3$ | H |
| 1-1320 | CF$_2$(CF$_2$)$_5$CF$_3$ | Br | NHCH$_3$ | F | H | CH$_3$ | S(O)CH$_2$CF$_3$ | H |
| 1-1321 | CF$_2$(CF$_2$)$_6$CF$_3$ | Br | NHCH$_3$ | F | H | CH$_3$ | SCH$_2$CF$_3$ | H |
| 1-1322 | CF$_2$(CF$_2$)$_6$CF$_3$ | Br | NHCH$_3$ | F | H | CH$_3$ | S(O)CH$_2$CF$_3$ | H |
| 1-1323 | CF$_2$(CF$_2$)$_7$CF$_3$ | Br | NHCH$_3$ | F | H | CH$_3$ | SCH$_2$CF$_3$ | H |
| 1-1324 | CF$_2$(CF$_2$)$_7$CF$_3$ | Br | NHCH$_3$ | F | H | CH$_3$ | S(O)CH$_2$CF$_3$ | H |
| 1-1325 | CF$_2$(CF$_2$)$_8$CF$_3$ | Br | NHCH$_3$ | F | H | CH$_3$ | SCH$_2$CF$_3$ | H |
| 1-1326 | CF$_2$(CF$_2$)$_8$CF$_3$ | Br | NHCH$_3$ | F | H | CH$_3$ | S(O)CH$_2$CF$_3$ | H |
| 1-1327 | CF$_2$CHFOCF$_3$ | Br | NHCH$_3$ | F | H | CH$_3$ | SCH$_2$CF$_3$ | H |
| 1-1328 | CF$_2$CHFOCF$_3$ | Br | NHCH$_3$ | F | H | CH$_3$ | S(O)CH$_2$CF$_3$ | H |
| 1-1329 | CF$_2$CHFOC$_2$F$_5$ | Br | NHCH$_3$ | F | H | CH$_3$ | SCH$_2$CF$_3$ | H |
| 1-1330 | CF$_2$CHFOC$_2$F$_5$ | Br | NHCH$_3$ | F | H | CH$_3$ | S(O)CH$_2$CF$_3$ | H |
| 1-1331 | CF$_2$CHFOC$_3$F$_7$ | Br | NHCH$_3$ | F | H | CH$_3$ | SCH$_2$CF$_3$ | H |

TABLE 25

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1332 | CF$_2$CHFOC$_3$F$_7$ | Br | NHCH$_3$ | F | H | CH$_3$ | S(O)CH$_2$CF$_3$ | H |
| 1-1333 | CF$_2$CHFOC$_4$F$_8$ | Br | NHCH$_3$ | F | H | CH$_3$ | SCH$_2$CF$_3$ | H |
| 1-1334 | CF$_2$CHFOC$_4$F$_9$ | Br | NHCH$_3$ | F | H | CH$_3$ | S(O)CH$_2$CF$_3$ | H |
| 1-1335 | CF$_2$CHFOC$_5$F$_{11}$ | Br | NHCH$_3$ | F | H | CH$_3$ | SCH$_2$CF$_3$ | H |
| 1-1336 | CF$_2$CHFOC$_5$F$_{11}$ | Br | NHCH$_3$ | F | H | CH$_3$ | S(O)CH$_2$CF$_3$ | H |
| 1-1337 | CF$_2$CHFOCF(CF$_3$)$_2$ | Br | NHCH$_3$ | F | H | CH$_3$ | SCH$_2$CF$_3$ | H |
| 1-1338 | CF$_2$CHFOCF(CF$_3$)$_2$ | Br | NHCH$_3$ | F | H | CH$_3$ | S(O)CH$_2$CF$_3$ | H |
| 1-1339 | CF$_2$CHFCF$_2$OCF$_3$ | Br | NHCH$_3$ | F | H | CH$_3$ | SCH$_2$CF$_3$ | H |
| 1-1340 | CF$_2$CHFCF$_2$OCF$_3$ | Br | NHCH$_3$ | F | H | CH$_3$ | S(O)CH$_2$CF$_3$ | H |
| 1-1341 | CH$_2$CF(CF$_3$)OC$_3$F$_7$ | Br | NHCH$_3$ | F | H | CH$_3$ | SCH$_2$CF$_3$ | H |
| 1-1342 | CH$_2$CF(CF$_3$)OC$_3$F$_7$ | Br | NHCH$_3$ | F | H | CH$_3$ | S(O)CH$_2$CF$_3$ | H |
| 1-1343 | CH$_2$CF$_2$O(CF$_2$)$_2$OCF$_3$ | Br | NHCH$_3$ | F | H | CH$_3$ | SCH$_2$CF$_3$ | H |
| 1-1344 | CH$_2$CF$_2$O(CF$_2$)$_2$OCF$_3$ | Br | NHCH$_3$ | F | H | CH$_3$ | S(O)CH$_2$CF$_3$ | H |
| 1-1345 | CH$_2$CF$_2$O(CF$_2$)$_2$OCF$_2$CF$_3$ | Br | NHCH$_3$ | F | H | CH$_3$ | SCH$_2$CF$_3$ | H |
| 1-1346 | CH$_2$CF$_2$O(CF$_2$)$_2$OCF$_2$CF$_3$ | Br | NHCH$_3$ | F | H | CH$_3$ | S(O)CH$_2$CF$_3$ | H |
| 1-1347 | CH$_2$(CF$_2$)$_3$CHF$_2$ | Br | NHCH$_3$ | F | H | CH$_3$ | SCH$_2$CF$_3$ | H |
| 1-1348 | CH$_2$(CF$_2$)$_3$CHF$_2$ | Br | NHCH$_3$ | F | H | CH$_3$ | S(O)CH$_2$CF$_3$ | H |
| 1-1349 | CH$_2$(CF$_2$)$_4$CHF$_2$ | Br | NHCH$_3$ | F | H | CH$_3$ | SCH$_2$CF$_3$ | H |
| 1-1350 | CH$_2$(CF$_2$)$_4$CHF$_2$ | Br | NHCH$_3$ | F | H | CH$_3$ | S(O)CH$_2$CF$_3$ | H |
| 1-1351 | CH$_2$CH$_2$CH$_2$(CF$_2$)$_4$CF$_3$ | Br | NHCH$_3$ | F | H | CH$_3$ | SCH$_2$CF$_3$ | H |
| 1-1352 | CH$_2$CH$_2$CH$_2$(CF$_2$)$_4$CF$_3$ | Br | NHCH$_3$ | F | H | CH$_3$ | S(O)CH$_2$CF$_3$ | H |
| 1-1353 | CH$_2$CH$_2$CH$_2$(CF$_2$)$_5$CF$_3$ | Br | NHCH$_3$ | F | H | CH$_3$ | SCH$_2$CF$_3$ | H |
| 1-1354 | CH$_2$CH$_2$CH$_2$(CF$_2$)$_5$CF$_3$ | Br | NHCH$_3$ | F | H | CH$_3$ | S(O)CH$_2$CF$_3$ | H |
| 1-1355 | CHF$_2$ | H | H | F | H | CH$_3$ | SCH$_2$CF$_3$ | H |
| 1-1356 | CHF$_2$ | H | H | F | H | CH$_3$ | S(O)CH$_2$CF$_3$ | H |
| 1-1357 | CH$_3$ | H | H | F | H | CH$_3$ | SCH$_2$CF$_3$ | H |

TABLE 25-continued

| Comp. No. | R₁ | R₂ | R₃ | R₄ | R₅ | R₆ | R₇ | R₈ |
|---|---|---|---|---|---|---|---|---|
| 1-1358 | CH₃ | H | H | F | H | CH₃ | S(O)CH₂CF₃ | H |
| 1-1359 | CHF₂ | H | NHC(O)CH₃ | F | H | CH₃ | SCH₂CF₃ | H |
| 1-1360 | CHF₂ | H | NHC(O)CH₃ | F | H | CH₃ | S(O)CH₂CF₃ | H |
| 1-1361 | CH(CH₃)CN | H | NHC(O)CH₃ | F | H | CH₃ | SCH₂CF₃ | H |
| 1-1362 | CH(CH₃)CN | H | NHC(O)CH₃ | F | H | CH₃ | S(O)CH₂CF₃ | H |
| 1-1363 | CH₂CF₃ | H | H | F | H | CH₃ | SCH₂CF₃ | H |
| 1-1364 | CH₂CF₃ | H | H | F | H | CH₃ | S(O)CH₂CF₃ | H |
| 1-1365 | CH₂CF₃ | H | NH₂ | F | H | CH₃ | SCH₂CF₃ | H |
| 1-1366 | CH₂CF₃ | H | NH₂ | F | H | CH₃ | S(O)CH₂CF₃ | H |
| 1-1367 | CF₂CHF₂ | H | NHC(O)CH₃ | F | H | CH₃ | SCH₂CF₃ | H |
| 1-1368 | CF₂CHF₂ | H | NHC(O)CH₃ | F | H | CH₃ | S(O)CH₂CF₃ | H |
| 1-1369 | CH₂CF₃ | H | NHC(O)CH₃ | F | H | CH₃ | SCH₂CF₃ | H |
| 1-1370 | CH₂CF₃ | H | NHC(O)CH₃ | F | H | CH₃ | S(O)CH₂CF₃ | H |
| 1-1371 | CH₂CF₂Cl | H | NHC(O)CH₃ | F | H | CH₃ | SCH₂CF₃ | H |
| 1-1372 | CH₂CF₂Cl | H | NHC(O)CH₃ | F | H | CH₃ | S(O)CH₂CF₃ | H |
| 1-1373 | CH₂C₂F₅ | H | CH₂OH | F | H | CH₃ | SCH₂CF₃ | H |
| 1-1374 | CH₂C₂F₅ | H | CH₂OH | F | H | CH₃ | S(O)CH₂CF₃ | H |
| 1-1375 | CH₂CN | H | NHC(O)CH₃ | F | H | CH₃ | SCH₂CF₃ | H |
| 1-1376 | CH₂CN | H | NHC(O)CH₃ | F | H | CH₃ | S(O)CH₂CF₃ | H |
| 1-1377 | CH₂CH₂F | H | NHC(O)CH₃ | F | H | CH₃ | SCH₂CF₃ | H |
| 1-1378 | CH₂CH₂F | H | NHC(O)CH₃ | F | H | CH₃ | S(O)CH₂CF₃ | H |
| 1-1379 | CH₂CF₃ | Cl | H | F | H | CH₃ | SCH₂CF₃ | H |
| 1-1380 | CH₂CF₃ | Cl | H | F | H | CH₃ | S(O)CH₂CF₃ | H |
| 1-1381 | CH₂CF₃ | F | NH₂ | F | H | CH₃ | SCH₂CF₃ | H |
| 1-1382 | CH₂CF₃ | F | NH₂ | F | H | CH₃ | S(O)CH₂CF₃ | H |
| 1-1383 | CH₂CF₃ | Cl | NH₂ | F | H | CH₃ | SCH₂CF₃ | H |
| 1-1384 | CH₂CF₃ | Cl | NH₂ | F | H | CH₃ | S(O)CH₂CF₃ | H |
| 1-1385 | CH₂C₂F₅ | H | H | F | H | CH₃ | SCH₂CF₃ | H |
| 1-1386 | CH₂C₂F₅ | H | H | F | H | CH₃ | S(O)CH₂CF₃ | H |
| 1-1387 | CF₂CHF₂ | H | NHC(O)CH₃ | F | H | CH₃ | SCH₂CF₂Cl | H |

TABLE 26

| Comp. No. | R₁ | R₂ | R₃ | R₄ | R₅ | R₆ | R₇ | R₈ |
|---|---|---|---|---|---|---|---|---|
| 1-1388 | CF₂CHF₂ | H | NHC(O)CH₃ | F | H | CH₃ | S(O)CH₂CF₂Cl | H |
| 1-1389 | CH₂CF₂Cl | H | NHC(O)CH₃ | F | H | CH₃ | SCH₂CF₂Cl | H |
| 1-1390 | CH₂CF₂Cl | H | NHC(O)CH₃ | F | H | CH₃ | S(O)CH₂CF₂Cl | H |
| 1-1391 | CH₂C₂F₅ | H | NHC(O)CH₃ | F | H | CH₃ | S(O)CH₂CF₂CF₃ | H |
| 1-1392 | CF₂CHF₂ | H | N(CH₃)C(O)CH₃ | F | H | CH₃ | SCH₂CF₃ | H |
| 1-1393 | CF₂CHF₂ | H | N(CH₃)C(O)CH₃ | F | H | CH₃ | S(O)CH₂CF₃ | H |
| 1-1394 | CF₂CHF₂ | H | N(CH₃)C(O)CH₃ | F | H | CH₃ | SCH₂CF₂Cl | H |
| 1-1395 | CF₂CHF₂ | H | N(CH₃)C(O)CH₃ | F | H | CH₃ | S(O)CH₂CF₂Cl | H |
| 1-1396 | CF₂CHFCF₃ | H | N(CH₃)C(O)CH₃ | F | H | CH₃ | S(O)CH₂CF₃ | H |
| 1-1397 | CH₂C₂F₅ | Cl | N{C(O)CH₃}₂ | F | H | CH₃ | S(O)CH₂CF₃ | H |
| 1-1398 | CH₂C₂F₅ | H | N{C(O)CH₃}CH₂CF=CH₂ | F | H | CH₃ | S(O)CH₂CF₃ | H |
| 1-1399 | CH₂C₂F₅ | H | N{C(O)CH₃}CH₂CF=CH₂ | F | H | CH₃ | S(O)CH₂CF₂Cl | H |
| 1-1400 | CF₂CHF₂ | H | N{C(O)CH₃}CH₂C≡CH | F | H | CH₃ | SCH₂CF₃ | H |
| 1-1401 | CF₂CHF₂ | H | N{C(O)CH₃}CH₂C≡CH | F | H | CH₃ | S(O)CH₂CF₃ | H |
| 1-1402 | CF₂CHF₂ | H | NHCH₃ | F | H | CH₃ | SCH₂CF₃ | H |
| 1-1403 | CF₂CHF₂ | H | NHCH₃ | F | H | CH₃ | S(O)CH₂CF₃ | H |
| 1-1404 | CF₂CHF₂ | H | NHCH₃ | F | H | CH₃ | SCH₂CF₂Cl | H |
| 1-1405 | CF₂CHF₂ | H | NHCH₃ | F | H | CH₃ | S(O)CH₂CF₂Cl | H |
| 1-1406 | CF₂CHF₂ | Br | H | F | H | CH₃ | SCH₂CF₃ | H |
| 1-1407 | CF₂CHF₂ | Br | H | F | H | CH₃ | S(O)CH₂CF₃ | H |
| 1-1408 | CF₂CHF₂ | Br | Br | F | H | CH₃ | SCH₂CF₃ | H |
| 1-1409 | CF₂CHF₂ | Br | Br | F | H | CH₃ | S(O)CH₂CF₃ | H |
| 1-1410 | CHF₂ | H | C(=O)OH | F | H | CH₃ | SCH₂CF₃ | H |
| 1-1411 | CHF₂ | H | CH₃ | F | H | CH₃ | SCH₂CF₃ | H |
| 1-1412 | CHF₂ | H | CH₃ | F | H | CH₃ | S(O)CH₂CF₃ | H |
| 1-1413 | CH₃ | H | CH₃ | F | H | CH₃ | SCH₂CF₃ | H |
| 1-1414 | CH₃ | H | CH₃ | F | H | CH₃ | S(O)CH₂CF₃ | H |
| 1-1415 | CH₂CF₃ | H | CH₃ | F | H | CH₃ | SCH₂CF₃ | H |
| 1-1416 | CH₂CF₃ | H | CH₃ | F | H | CH₃ | S(O)CH₂CF₃ | H |
| 1-1417 | CF₂CHF₂ | H | CH₃ | F | H | CH₃ | SCH₂CF₃ | H |
| 1-1418 | CF₂CHF₂ | H | CH₃ | F | H | CH₃ | S(O)CH₂CF₃ | H |
| 1-1419 | CH₂CF₂Cl | H | CH₃ | F | H | CH₃ | SCH₂CF₃ | H |
| 1-1420 | CH₂CF₂Cl | H | CH₃ | F | H | CH₃ | S(O)CH₂CF₃ | H |
| 1-1421 | CF₂CHF₂ | H | NHCH₂C≡CH | F | H | CH₃ | SCH₂CF₃ | H |
| 1-1422 | CF₂CHF₂ | H | NHCH₂C≡CH | F | H | CH₃ | S(O)CH₂CF₃ | H |
| 1-1423 | CF₂CHF₂ | H | Cl | F | H | CH₃ | SCH₂CF₃ | H |
| 1-1424 | CF₂CHF₂ | H | Cl | F | H | CH₃ | S(O)CH₂CF₃ | H |
| 1-1425 | CF₂CHFCl | H | CH₃ | F | H | CH₃ | SCH₂CF₃ | H |
| 1-1426 | CF₂CHFCl | H | CH₃ | F | H | CH₃ | S(O)CH₂CF₃ | H |
| 1-1427 | CF₂CHFCl | H | NHC(O)CH₃ | F | H | CH₃ | SCH₂CF₃ | H |

TABLE 26-continued

| Comp. No. | R₁ | R₂ | R₃ | R₄ | R₅ | R₆ | R₇ | R₈ |
|---|---|---|---|---|---|---|---|---|
| 1-1428 | CF₂CHFCl | H | NHC(O)CH₃ | F | H | CH₃ | S(O)CH₂CF₃ | H |
| 1-1429 | CH₂CF₃ | H | NHC(O)CH₂CH₃ | F | H | CH₃ | SCH₂CF₃ | H |
| 1-1430 | CH₂CF₃ | H | NHC(O)CH₂CH₃ | F | H | CH₃ | S(O)CH₂CF₃ | H |
| 1-1431 | CH₂CF₃ | H | NHC(O)CH₂OCH₃ | F | H | CH₃ | SCH₂CF₃ | H |
| 1-1432 | CH₂CF₃ | H | NHC(O)CH₂OCH₃ | F | H | CH₃ | S(O)CH₂CF₃ | H |
| 1-1433 | CH₂CF₃ | H | NHC(O)Pr-c | F | H | CH₃ | SCH₂CF₃ | H |
| 1-1434 | CH₂CF₃ | H | NHC(O)Pr-c | F | H | CH₃ | S(O)CH₂CF₃ | H |
| 1-1435 | CF₂CHF₂ | H | C(O)OH | F | H | CH₃ | SCH₂CF₃ | H |
| 1-1436 | CH₂CN | H | CH₃ | F | H | CH₃ | SCH₂CF₃ | H |
| 1-1437 | CH₂CN | H | CH₃ | F | H | CH₃ | S(O)CH₂CF₃ | H |
| 1-1438 | CF₂CHFCF₃ | H | C(O)OH | F | H | CH₃ | SCH₂CF₃ | H |
| 1-1439 | CH₂CF₃ | H | CN | F | H | CH₃ | SCH₂CF₃ | H |
| 1-1440 | CH₂CF₃ | H | CN | F | H | CH₃ | S(O)CH₂CF₃ | H |
| 1-1441 | CH₂CF₃ | H | C(O)NH₂ | F | H | CH₃ | SCH₂CF₃ | H |
| 1-1442 | CH₂CF₃ | H | C(O)NH₂ | F | H | CH₃ | S(O)CH₂CF₃ | H |
| 1-1443 | CH₂CF₃ | H | C(O)NHCH₃ | F | H | CH₃ | SCH₂CF₃ | H |

TABLE 27

| Comp. No. | R₁ | R₂ | R₃ | R₄ | R₅ | R₆ | R₇ | R₈ |
|---|---|---|---|---|---|---|---|---|
| 1-1444 | CH₂CF₃ | H | C(O)NHCH₃ | F | H | CH₃ | S(O)CH₂CF₃ | H |
| 1-1445 | CH₂CF₃ | H | C(O)OCH₂CH₃ | F | H | CH₃ | SCH₂CF₃ | H |
| 1-1446 | CH₂CF₃ | H | C(O)OCH₂CH₃ | F | H | CH₃ | S(O)CH₂CF₃ | H |
| 1-1447 | CH₂CF₃ | H | C(O)OH | F | H | CH₃ | SCH₂CF₃ | H |
| 1-1448 | CF₂CHFCl | H | C(O)OH | F | H | CH₃ | SCH₂CF₃ | H |
| 1-1449 | CH₂C₂F₅ | H | NHC(O)CH₂Cl | F | H | CH₃ | SCH₂CF₃ | H |
| 1-1450 | CH₂C₂F₅ | H | NHC(O)CH₂Cl | F | H | CH₃ | S(O)CH₂CF₃ | H |
| 1-1451 | CF₂CHF₂ | Cl | H | F | H | CH₃ | SCH₂CF₃ | H |
| 1-1452 | CF₂CHF₂ | Cl | H | F | H | CH₃ | S(O)CH₂CF₃ | H |
| 1-1453 | CH₂CF₃ | H | NHC(O)CH₂Cl | F | H | CH₃ | SCH₂CF₃ | H |
| 1-1454 | CH₂CF₃ | H | NHC(O)CH₂Cl | F | H | CH₃ | S(O)CH₂CF₃ | H |
| 1-1455 | CH₂CF₃ | H | NHC(O)CH=CH₂ | F | H | CH₃ | SCH₂CF₃ | H |
| 1-1456 | CH₂CF₃ | H | NHC(O)CH=CH₂ | F | H | CH₃ | S(O)CH₂CF₃ | H |
| 1-1457 | CF₂CHFCl | H | C(O)NH₂ | F | H | CH₃ | SCH₂CF₃ | H |
| 1-1458 | CF₂CHFCl | H | C(O)NH₂ | F | H | CH₃ | S(O)CH₂CF₃ | H |
| 1-1459 | CF₂CHFCl | H | CN | F | H | CH₃ | SCH₂CF₃ | H |
| 1-1460 | CF₂CHFCl | H | CN | F | H | CH₃ | S(O)CH₂CF₃ | H |
| 1-1461 | CH₃ | H | OCH₃ | F | H | CH₃ | SCH₂CF₃ | H |
| 1-1462 | CH₃ | H | OCH₃ | F | H | CH₃ | S(O)CH₂CF₃ | H |
| 1-1463 | CHF₂ | H | OCH₃ | F | H | CH₃ | SCH₂CF₃ | H |
| 1-1464 | CHF₂ | H | OCH₃ | F | H | CH₃ | S(O)CH₂CF₃ | H |
| 1-1465 | CF₂CHFCl | H | OCH₃ | F | H | CH₃ | SCH₂CF₃ | H |
| 1-1466 | CF₂CHFCl | H | OCH₃ | F | H | CH₃ | S(O)CH₂CF₃ | H |
| 1-1467 | CH₂CF₃ | H | OCH₃ | F | H | CH₃ | SCH₂CF₃ | H |
| 1-1468 | CH₂CF₃ | H | OCH₃ | F | H | CH₃ | S(O)CH₂CF₃ | H |
| 1-1469 | CH₃ | H | OCH₂C₂F₅ | F | H | CH₃ | SCH₂CF₃ | H |
| 1-1470 | CH₃ | H | OCH₂C₂F₅ | F | H | CH₃ | S(O)CH₂CF₃ | H |
| 1-1471 | CH₃ | H | OCH₂CH₃ | F | H | CH₃ | SCH₂CF₃ | H |
| 1-1472 | CH₃ | H | OCH₂CH₃ | F | H | CH₃ | S(O)CH₂CF₃ | H |
| 1-1473 | CF₃ | H | H | F | H | CH₃ | SCH₂CF₃ | H |
| 1-1474 | CF₃ | H | H | F | H | CH₃ | S(O)CH₂CF₃ | H |
| 1-1475 | CF₂CF₃ | H | H | F | H | CH₃ | SCH₂CF₃ | H |
| 1-1476 | CF₂CF₃ | H | H | F | H | CH₃ | S(O)CH₂CF₃ | H |
| 1-1477 | CF₃ | H | NH₂ | F | H | CH₃ | SCH₂CF₃ | H |
| 1-1478 | CF₃ | H | NH₂ | F | H | CH₃ | S(O)CH₂CF₃ | H |
| 1-1479 | CF₂CF₃ | H | NH₂ | F | H | CH₃ | SCH₂CF₃ | H |
| 1-1480 | CF₂CF₃ | H | NH₂ | F | H | CH₃ | S(O)CH₂CF₃ | H |
| 1-1481 | CF₃ | H | NHC(O)CH₃ | F | H | CH₃ | SCH₂CF₃ | H |
| 1-1482 | CF₃ | H | NHC(O)CH₃ | F | H | CH₃ | S(O)CH₂CF₃ | H |
| 1-1483 | CF₂CF₃ | H | NHC(O)CH₃ | F | H | CH₃ | SCH₂CF₃ | H |
| 1-1484 | CF₂CF₃ | H | NHC(O)CH₃ | F | H | CH₃ | S(O)CH₂CF₃ | H |
| 1-1485 | CF₃ | H | NHCH₃ | F | H | CH₃ | SCH₂CF₃ | H |
| 1-1486 | CF₃ | H | NHCH₃ | F | H | CH₃ | S(O)CH₂CF₃ | H |
| 1-1487 | CF₂CF₃ | H | NHCH₃ | F | H | CH₃ | SCH₂CF₃ | H |
| 1-1488 | CF₂CF₃ | H | NHCH₃ | F | H | CH₃ | S(O)CH₂CF₃ | H |
| 1-1489 | CF₃ | H | CN | F | H | CH₃ | SCH₂CF₃ | H |
| 1-1490 | CF₃ | H | CN | F | H | CH₃ | S(O)CH₂CF₃ | H |
| 1-1491 | CF₂CF₃ | H | CN | F | H | CH₃ | SCH₂CF₃ | H |
| 1-1492 | CF₂CF₃ | H | CN | F | H | CH₃ | S(O)CH₂CF₃ | H |
| 1-1493 | CF₃ | H | CH₃ | F | H | CH₃ | SCH₂CF₃ | H |
| 1-1494 | CF₃ | H | CH₃ | F | H | CH₃ | S(O)CH₂CF₃ | H |
| 1-1495 | CF₂CF₃ | H | CH₃ | F | H | CH₃ | SCH₂CF₃ | H |
| 1-1496 | CF₂CF₃ | H | CH₃ | F | H | CH₃ | S(O)CH₂CF₃ | H |
| 1-1497 | CF₃ | Cl | NH₂ | F | H | CH₃ | SCH₂CF₃ | H |

TABLE 27-continued

| Comp. No. | R₁ | R₂ | R₃ | R₄ | R₅ | R₆ | R₇ | R₈ |
|---|---|---|---|---|---|---|---|---|
| 1-1498 | CF₃ | Cl | NH₂ | F | H | CH₃ | S(O)CH₂CF₃ | H |
| 1-1499 | CF₂CF₃ | Cl | NH₂ | F | H | CH₃ | SCH₂CF₃ | H |

TABLE 28

| Comp. No. | R₁ | R₂ | R₃ | R₄ | R₅ | R₆ | R₇ | R₈ |
|---|---|---|---|---|---|---|---|---|
| 1-1500 | CF₂CF₃ | Cl | NH₂ | F | H | CH₃ | S(O)CH₂CF₃ | H |
| 1-1501 | CF₃ | Cl | NHCH₃ | F | H | CH₃ | SCH₂CF₃ | H |
| 1-1502 | CF₃ | Cl | NHCH₃ | F | H | CH₃ | S(O)CH₂CF₃ | H |
| 1-1503 | CF₂CF₃ | Cl | NHCH₃ | F | H | CH₃ | SCH₂CF₃ | H |
| 1-1504 | CF₂CF₃ | Cl | NHCH₃ | F | H | CH₃ | S(O)CH₂CF₃ | H |
| 1-1505 | CH₂C₄F₉ | Cl | H | F | H | CH₃ | SCH₂CF₃ | H |
| 1-1506 | CH₂C₄F₉ | Cl | H | F | H | CH₃ | S(O)CH₂CF₃ | H |
| 1-1507 | CH₂C₄F₉ | Br | NH₂ | F | H | CH₃ | SCH₂CF₃ | H |
| 1-1508 | CH₂C₄F₉ | Br | NH₂ | F | H | CH₃ | S(O)CH₂CF₃ | H |
| 1-1509 | CH₂C₄F₉ | Br | H | F | H | CH₃ | SCH₂CF₃ | H |
| 1-1510 | CH₂C₄F₉ | Br | H | F | H | CH₃ | S(O)CH₂CF₃ | H |
| 1-1511 | CH₂C₄F₉ | Cl | Cl | F | H | CH₃ | SCH₂CF₃ | H |
| 1-1512 | CH₂C₄F₉ | Cl | Cl | F | H | CH₃ | S(O)CH₂CF₃ | H |
| 1-1513 | CF₂CHFOC₂F₅ | H | NHC₂H₅ | F | H | CH₃ | SCH₂CF₃ | H |
| 1-1514 | CF₂CHFOC₂F₅ | H | NHC₂H₅ | F | H | CH₃ | S(O)CH₂CF₃ | H |
| 1-1515 | CF₂CHFOC₂F₅ | Cl | NH₂ | F | H | CH₃ | SCH₂CF₃ | H |
| 1-1516 | CF₂CHFOC₂F₅ | Cl | NH₂ | F | H | CH₃ | S(O)CH₂CF₃ | H |
| 1-1517 | CH₂CH₂CH₂SC≡N | H | H | F | H | CH₃ | SCH₂CF₃ | H |
| 1-1518 | CH₂CH₂CH₂SC≡N | H | H | F | H | CH₃ | S(O)CH₂CF₃ | H |
| 1-1519 | CH(CH₃)CF₃ | H | H | F | H | CH₃ | SCH₂CF₃ | H |
| 1-1520 | CH(CH₃)CF₃ | H | H | F | H | CH₃ | S(O)CH₂CF₃ | H |
| 1-1521 | CH₂C₆F₁₃ | H | NHC(O)CH₃ | F | H | CH₃ | SCH₂CF₃ | H |
| 1-1522 | CH₂C₆F₁₃ | H | NHC(O)CH₃ | F | H | CH₃ | S(O)CH₂CF₃ | H |
| 1-1523 | CH₂C₆F₁₃ | H | NHCH₃ | F | H | CH₃ | SCH₂CF₃ | H |
| 1-1524 | CH₂C₆F₁₃ | H | NHCH₃ | F | H | CH₃ | S(O)CH₂CF₃ | H |
| 1-1525 | CH₂C₆F₁₃ | H | NHCH₂C≡CH | F | H | CH₃ | SCH₂CF₃ | H |
| 1-1526 | CH₂C₆F₁₃ | H | NHCH₂C≡CH | F | H | CH₃ | S(O)CH₂CF₃ | H |
| 1-1527 | CH₂CH₂CF(CF₃)₂ | H | NHC(O)CH₃ | F | H | CH₃ | SCH₂CF₃ | H |
| 1-1528 | CH₂CH₂CF(CF₃)₂ | H | NHC(O)CH₃ | F | H | CH₃ | S(O)CH₂CF₃ | H |
| 1-1529 | CF₂CHFCF₃ | H | CHF₂ | F | H | CH₃ | SCH₂CF₃ | H |
| 1-1530 | CF₂CHFCF₃ | H | CHF₂ | F | H | CH₃ | S(O)CH₂CF₃ | H |
| 1-1531 | CF₂CHFOCF₃ | H | CHF₂ | F | H | CH₃ | SCH₂CF₃ | H |
| 1-1532 | CF₂CHFOCF₃ | H | CHF₂ | F | H | CH₃ | S(O)CH₂CF₃ | H |
| 1-1533 | CF₂CHFOC₂F₅ | H | CHF₂ | F | H | CH₃ | SCH₂CF₃ | H |
| 1-1534 | CF₂CHFOC₂F₅ | H | CHF₂ | F | H | CH₃ | S(O)CH₂CF₃ | H |
| 1-1535 | C₂H₅ | H | H | F | H | CH₃ | SCH₂CF₃ | H |
| 1-1536 | C₂H₅ | H | H | F | H | CH₃ | S(O)CH₂CF₃ | H |
| 1-1537 | C₃H₇ | H | H | F | H | CH₃ | SCH₂CF₃ | H |
| 1-1538 | C₃H₇ | H | H | F | H | CH₃ | S(O)CH₂CF₃ | H |
| 1-1539 | CH(CH₃)₂ | H | H | F | H | CH₃ | SCH₂CF₃ | H |
| 1-1540 | CH(CH₃)₂ | H | H | F | H | CH₃ | S(O)CH₂CF₃ | H |
| 1-1541 | CH₂C₂F₅ | H | CHF₂ | F | H | CH₃ | SCH₂CF₃ | H |
| 1-1542 | CH₂C₂F₅ | H | CHF₂ | F | H | CH₃ | S(O)CH₂CF₃ | H |
| 1-1543 | CH₂C₄F₉ | H | CHF₂ | F | H | CH₃ | SCH₂CF₃ | H |
| 1-1544 | CH₂C₄F₉ | H | CHF₂ | F | H | CH₃ | S(O)CH₂CF₃ | H |
| 1-1545 | CF₂CHFCF₃ | I | H | F | H | CH₃ | SCH₂CF₃ | H |
| 1-1546 | CF₂CHFCF₃ | I | H | F | H | CH₃ | S(O)CH₂CF₃ | H |
| 1-1547 | CF₂CHFCF₃ | I | NH₂ | F | H | CH₃ | SCH₂CF₃ | H |
| 1-1548 | CF₂CHFCF₃ | I | NH₂ | F | H | CH₃ | S(O)CH₂CF₃ | H |
| 1-1549 | CF₂CHFOC₂F₅ | Cl | N=CHPh | F | H | CH₃ | SCH₂CF₃ | H |
| 1-1550 | CF₂CHFOC₂F₅ | Cl | N=CHPh | F | H | CH₃ | S(O)CH₂CF₃ | H |
| 1-1551 | CH₂C₂F₅ | H | NHC(O)H | F | H | CH₃ | SCH₂CF₃ | H |
| 1-1552 | CH₂C₂F₅ | H | NHC(O)H | F | H | CH₃ | S(O)CH₂CF₃ | H |
| 1-1553 | CF₂CHFCl | H | H | F | H | CH₃ | SCH₂CF₃ | H |
| 1-1554 | CF₂CHFCl | H | H | F | H | CH₃ | S(O)CH₂CF₃ | H |
| 1-1555 | CH₂Ph(4-OCF₃) | H | H | F | H | CH₃ | SCH₂CF₃ | H |

TABLE 29

| Comp. No. | R₁ | R₂ | R₃ | R₄ | R₅ | R₆ | R₇ | R₈ |
|---|---|---|---|---|---|---|---|---|
| 1-1556 | $CH_2Ph(4-OCF_3)$ | H | H | F | H | $CH_3$ | $SCH_2CF_3$ | H |
| 1-1557 | 3-Cl-5-CF₃-pyridin-2-yl | H | H | F | H | $CH_3$ | $SCH_2CF_3$ | H |
| 1-1558 | 3-Cl-5-CF₃-pyridin-2-yl | H | H | F | H | $CH_3$ | $S(O)CH_2CF_3$ | H |
| 1-1559 | $CH_2Ph(4-SCF_3)$ | H | H | F | H | $CH_3$ | $SCH_2CF_3$ | H |
| 1-1560 | $CH_2Ph(4-SCF_3)$ | H | H | F | H | $CH_3$ | $S(O)CH_2CF_3$ | H |
| 1-1561 | $CH_2Ph(4-SCF_3)$ | Cl | H | F | H | $CH_3$ | $SCH_2CF_3$ | H |
| 1-1562 | $CH_2Ph(4-SCF_3)$ | Cl | H | F | H | $CH_3$ | $S(O)CH_2CF_3$ | H |
| 1-1563 | $CH_2Ph(4-OCF_3)$ | Cl | H | F | H | $CH_3$ | $SCH_2CF_3$ | H |
| 1-1664 | $CH_2Ph(4-OCF_3)$ | Cl | H | F | H | $CH_3$ | $S(O)CH_2CF_3$ | H |
| 1-1565 | $CH_2Ph(4-CF_3)$ | H | H | F | H | $CH_3$ | $SCH_2CF_3$ | H |
| 1-1566 | $CH_2Ph(4-CF_3)$ | H | H | F | H | $CH_3$ | $S(O)CH_2CF_3$ | H |
| 1-1567 | $CH_2Ph(4-F,3-CF_3)$ | H | H | F | H | $CH_3$ | $SCH_2CF_3$ | H |
| 1-1568 | $CH_2Ph(4-F,3-CF_3)$ | H | H | F | H | $CH_3$ | $S(O)CH_2CF_3$ | H |
| 1-1569 | 5-CF₃-pyridin-2-yl | H | H | F | H | $CH_3$ | $SCH_2CF_3$ | H |
| 1-1570 | 5-CF₃-pyridin-2-yl | H | H | F | H | $CH_3$ | $S(O)CH_2CF_3$ | H |
| 1-1571 | $CH_2Ph(4-F,3-CF_3)$ | Cl | H | F | H | $CH_3$ | $SCH_2CF_3$ | H |
| 1-1572 | $CH_2Ph(4-F,3-CF_3)$ | Cl | H | F | H | $CH_3$ | $S(O)CH_2CF_3$ | H |
| 1-1573 | 3-Cl-5-CF₃-pyridin-2-yl | Cl | H | F | H | $CH_3$ | $SCH_2CF_3$ | H |
| 1-1574 | 3-Cl-5-CF₃-pyridin-2-yl | Cl | H | F | H | $CH_3$ | $S(O)CH_2CF_3$ | H |
| 1-1675 | 5-CF₃-pyridin-2-yl | Cl | H | F | H | $CH_3$ | $SCH_2CF_3$ | H |
| 1-1576 | 5-CF₃-pyridin-2-yl | Cl | H | F | H | $CH_3$ | $S(O)CH_2CF_3$ | H |
| 1-1577 | $CF_2CHFCF_3$ | H | $CH_2F$ | F | H | $CH_3$ | $SCH_2CF_3$ | H |
| 1-1578 | $CF_2CHFCF_3$ | H | $CH_2F$ | F | H | $CH_3$ | $S(O)CH_2CF_3$ | H |
| 1-1579 | $CF_2CHFOCF_3$ | H | $CH_2F$ | F | H | $CH_3$ | $SCH_2CF_3$ | H |
| 1-1580 | $CF_2CHFOCF_3$ | H | $CH_2F$ | F | H | $CH_3$ | $S(O)CH_2CF_3$ | H |
| 1-1581 | $CH_2C_4F_9$ | H | $CH_2F$ | F | H | $CH_3$ | $SCH_2CF_3$ | H |
| 1-1582 | $CH_2C_4F_9$ | H | $CH_2F$ | F | H | $CH_3$ | $S(O)CH_2CF_3$ | H |
| 1-1583 | $CH_2Ph(4-SCF_3)$ | H | $CH_3$ | F | H | $CH_3$ | $SCH_2CF_3$ | H |
| 1-1584 | $CH_2Ph(4-SCF_3)$ | H | $CH_3$ | F | H | $CH_3$ | $S(O)CH_2CF_3$ | H |
| 1-1585 | $Ph(4-CF_3)$ | H | H | F | H | $CH_3$ | $SCH_2CF_3$ | H |
| 1-1586 | $Ph(4-CF_3)$ | H | H | F | H | $CH_3$ | $S(O)CH_2CF_3$ | H |
| 1-1587 | $CF_2CHFOCF_3$ | CN | H | F | H | $CH_3$ | $SCH_2CF_3$ | H |
| 1-1588 | $CF_2CHFOCF_3$ | CN | H | F | H | $CH_3$ | $S(O)CH_2CF_3$ | H |

TABLE 29-continued

| Comp. No. | R₁ | R₂ | R₃ | R₄ | R₅ | R₆ | R₇ | R₈ |
|---|---|---|---|---|---|---|---|---|
| 1-1589 | C₂H₅ | C(O)OC₂H₅ | H | F | H | CH₃ | SCH₂CF₃ | H |
| 1-1590 | C₂H₅ | C(O)OC₂H₅ | H | F | H | CH₃ | S(O)CH₂CF₃ | H |
| 1-1591 | CF₂CHFOCF₃ | C(O)OC₂H₅ | H | F | H | CH₃ | SCH=CF₂ | H |
| 1-1592 | CF₂CHFOCF₃ | C(O)OC₂H₅ | H | F | H | CH₃ | S(O)CH=CF₂ | H |
| 1-1593 | CH₂C₃F₇ | H | NHC(O)H | F | H | CH₃ | SCH₂CF₃ | H |
| 1-1594 | CH₂C₃F₇ | H | NHC(O)H | F | H | CH₃ | S(O)CH₂CF₃ | H |
| 1-1595 | CH₂Ph(4-F,2-CF₃) | H | H | F | H | CH₃ | SCH₂CF₃ | H |
| 1-1596 | CH₂Ph(4-F,2-CF₃) | H | H | F | H | CH₃ | S(O)CH₂CF₃ | H |
| 1-1597 | CF₂C(CF₃)=CH₂ | H | H | F | H | CH₃ | SCH₂CF₃ | H |
| 1-1598 | CF₂C(CF₃)=CH₂ | H | H | F | H | CH₃ | S(O)CH₂CF₃ | H |
| 1-1599 | CH₂Ph(4-OCF₃) | H | CH₃ | F | H | CH₃ | SCH₂CF₃ | H |
| 1-1600 | CH₂Ph(4-OCF₃) | H | CH₃ | F | H | CH₃ | S(O)CH₂CF₃ | H |
| 1-1601 | CH₂Ph(2-F,4-CF₃) | H | H | F | H | CH₃ | SCH₂CF₃ | H |
| 1-1602 | CH₂Ph(2-F,4-CF₃) | H | H | F | H | CH₃ | S(O)CH₂CF₃ | H |

TABLE 30

| Comp. No. | R₁ | R₂ | R₃ | R₄ | R₅ | R₆ | R₇ | R₈ |
|---|---|---|---|---|---|---|---|---|
| 1-1603 | CH₂Ph(4-OCH₃) | H | H | F | H | CH₃ | SCH₂CF₃ | H |
| 1-1604 | CH₂Ph(4-OCH₃) | H | H | F | H | CH₃ | S(O)CH₂CF₃ | H |
| 1-1605 | 5-ethyl-2-chloropyridin-yl | H | H | F | H | CH₃ | SCH₂CF₃ | H |
| 1-1606 | 5-ethyl-2-chloropyridin-yl | H | H | F | H | CH₃ | S(O)CH₂CF₃ | H |
| 1-1607 | CF₂CHFOC₂F₅ | H | NHC(O)H | F | H | CH₃ | SCH₂CF₃ | H |
| 1-1608 | CF₂CHFOC₂F₅ | H | NHC(O)H | F | H | CH₃ | S(O)CH₂CF₃ | H |
| 1-1609 | 3-ethylpyridin-yl | H | H | F | H | CH₃ | SCH₂CF₃ | H |
| 1-1610 | 3-ethylpyridin-yl | H | H | F | H | CH₃ | S(O)CH₂CF₃ | H |
| 1-1611 | CH₂Ph(4-OCF₃) | H | NHC(O)Pr-c | F | H | CH₃ | SCH₂CF₃ | H |
| 1-1612 | CH₂Ph(4-OCF₃) | H | NHC(O)Pr-C | F | H | CH₃ | S(O)CH₂CF₃ | H |
| 1-1613 | CH₂Ph(4-CH₃) | H | H | F | H | CH₃ | SCH₂CF₃ | H |
| 1-1614 | CH₂Ph(4-CH₃) | H | H | F | H | CH₃ | S(O)CH₂CF₃ | H |
| 1-1615 | CH₃ | H | OH | F | H | CH₃ | SCH₂CF₃ | H |
| 1-1616 | CH₃ | H | OH | F | H | CH₃ | S(O)CH₂CF₃ | H |
| 1-1617 | CH₂Ph(4-OCHF₂) | H | H | F | H | CH₃ | SCH₂CF₃ | H |
| 1-1618 | CH₂Ph(4-OCHF₂) | H | H | F | H | CH₃ | S(O)CH₂CF₃ | H |
| 1-1619 | CH₂Ph(4-OCHF₂) | H | NH₂ | F | H | CH₃ | SCH₂CF₃ | H |
| 1-1620 | CH₂Ph(4-OCHF₂) | H | NH₂ | F | H | CH₃ | S(O)CH₂CF₃ | H |
| 1-1621 | CH₂Ph(4-OCHF₂) | H | NHC(O)CH₃ | F | H | CH₃ | SCH₂CF₃ | H |
| 1-1622 | CH₂Ph(4-OCHF₂) | H | NHC(O)CH₃ | F | H | CH₃ | S(O)CH₂CF₃ | H |
| 1-1623 | CH₂Ph(4-OCHF₂) | H | NHCH₃ | F | H | CH₃ | SCH₂CF₃ | H |
| 1-1624 | CH₂Ph(4-OCHF₂) | H | NHCH₃ | F | H | CH₃ | S(O)CH₂CF₃ | H |
| 1-1625 | CH₂Ph(4-OCHF₂) | H | NHCH₂C≡CH | F | H | CH₃ | SCH₂CF₃ | H |
| 1-1626 | CH₂Ph(4-OCHF₂) | H | NHCH₂C≡CH | F | H | CH₃ | S(O)CH₂CF₃ | H |
| 1-1627 | CH₂Ph(4-OCHF₂) | H | NHCH₂CH=CH₂ | F | H | CH₃ | SCH₂CF₃ | H |
| 1-1628 | CH₂Ph(4-OCHF₂) | H | NHCH₂CH=CH₂ | F | H | CH₃ | S(O)CH₂CF₃ | H |
| 1-1629 | CH₂Ph(4-OCHF₂) | H | CN | F | H | CH₃ | SCH₂CF₃ | H |
| 1-1630 | CH₂Ph(4-OCHF₂) | H | CN | F | H | CH₃ | S(O)CH₂CF₃ | H |
| 1-1631 | CH₂Ph(4-OCHF₂) | H | CH₃ | F | H | CH₃ | SCH₂CF₃ | H |
| 1-1632 | CH₂Ph(4-OCHF₂) | H | CH₃ | F | H | CH₃ | S(O)CH₂CF₃ | H |
| 1-1633 | CH₂Ph(4-OCHF₂) | H | CH₂F | F | H | CH₃ | SCH₂CF₃ | H |
| 1-1634 | CH₂Ph(4-OCHF₂) | H | CH₂F | F | H | CH₃ | S(O)CH₂CF₃ | H |
| 1-1635 | CH₂Ph(4-OCHF₂) | H | CHF₂ | F | H | CH₃ | SCH₂CF₃ | H |
| 1-1636 | CH₂Ph(4-OCHF₂) | H | CHF₂ | F | H | CH₃ | S(O)CH₂CF₃ | H |
| 1-1637 | CH₂Ph(4-OCHF₂) | H | CF₃ | F | H | CH₃ | SCH₂CF₃ | H |
| 1-1638 | CH₂Ph(4-OCHF₂) | H | CF₃ | F | H | CH₃ | S(O)CH₂CF₃ | H |
| 1-1639 | CH₂Ph(4-OCHF₂) | H | OCH₃ | F | H | CH₃ | SCH₂CF₃ | H |
| 1-1640 | CH₂Ph(4-OCHF₂) | H | OCH₃ | F | H | CH₃ | S(O)CH₂CF₃ | H |

TABLE 30-continued

| Comp. No. | R₁ | R₂ | R₃ | R₄ | R₅ | R₆ | R₇ | R₈ |
|---|---|---|---|---|---|---|---|---|
| 1-1641 | CH₂Ph(4-OCHF₂) | H | OCHF₂ | F | H | CH₃ | SCH₂CF₃ | H |
| 1-1642 | CH₂Ph(4-OCHF₂) | H | OCHF₂ | F | H | CH₃ | S(O)CH₂CF₃ | H |
| 1-1643 | CH₂Ph(4-OCHF₂) | H | Cl | F | H | CH₃ | SCH₂CF₃ | H |
| 1-1644 | CH₂Ph(4-OCHF₂) | H | Cl | F | H | CH₃ | S(O)CH₂CF₃ | H |
| 1-1645 | CH₂Ph(4-OCHF₂) | H | Br | F | H | CH₃ | SCH₂CF₃ | H |
| 1-1646 | CH₂Ph(4-OCHF₂) | H | Br | F | H | CH₃ | S(O)CH₂CF₃ | H |
| 1-1647 | CH₂Ph(4-OCHF₂) | Cl | NH₂ | F | H | CH₃ | SCH₂CF₃ | H |
| 1-1648 | CH₂Ph(4-OCHF₂) | Cl | NH₂ | F | H | CH₃ | S(O)CH₂CF₃ | H |
| 1-1649 | CH₂Ph(4-OCHF₂) | Cl | NHCH₃ | F | H | CH₃ | SCH₂CF₃ | H |
| 1-1650 | CH₂Ph(4-OCHF₂) | Cl | NHCH₃ | F | H | CH₃ | S(O)CH₂CF₃ | H |
| 1-1651 | CH₂Ph(4-OCHF₂) | Cl | Cl | F | H | CH₃ | SCH₂CF₃ | H |
| 1-1652 | CH₂Ph(4-OCHF₂) | Cl | Cl | F | H | CH₃ | S(O)CH₂CF₃ | H |
| 1-1653 | CH₂Ph(4-OCHF₂) | Br | Br | F | H | CH₃ | SCH₂CF₃ | H |
| 1-1654 | CH₂Ph(4-OCHF₂) | Br | Br | F | H | CH₃ | S(O)CH₂CF₃ | H |

TABLE 31

| Comp. No. | R₁ | R₂ | R₃ | R₄ | R₅ | R₆ | R₇ | R₈ |
|---|---|---|---|---|---|---|---|---|
| 1-1655 | CH₂Ph(4-OCHF₂) | Cl | H | F | H | CH₃ | SCH₂CF₃ | H |
| 1-1656 | CH₂Ph(4-OCHF₂) | Cl | H | F | H | CH₃ | S(O)CH₂CF₃ | H |
| 1-1657 | CH₂Ph(4-OCHF₂) | Br | H | F | H | CH₃ | SCH₂CF₃ | H |
| 1-1658 | CH₂Ph(4-OCHF₂) | Br | H | F | H | CH₃ | S(O)CH₂CF₃ | H |
| 1-1659 | CH₂Ph(4-OCF₃) | H | NH₂ | F | H | CH₃ | SCH₂CF₃ | H |
| 1-1660 | CH₂Ph(4-OCF₃) | H | NH₂ | F | H | CH₃ | S(O)CH₂CF₃ | H |
| 1-1661 | CH₂Ph(4-OCF₃) | H | NHC(O)CH₃ | F | H | CH₃ | SCH₂CF₃ | H |
| 1-1662 | CH₂Ph(4-OCF₃) | H | NHC(O)CH₃ | F | H | CH₃ | S(O)CH₂CF₃ | H |
| 1-1663 | CH₂Ph(4-OCF₃) | H | NHCH₃ | F | H | CH₃ | SCH₂CF₃ | H |
| 1-1664 | CH₂Ph(4-OCF₃) | H | NHCH₃ | F | H | CH₃ | S(O)CH₂CF₃ | H |
| 1-1665 | CH₂Ph(4-OCF₃) | H | NHCH₂C≡CH | F | H | CH₃ | SCH₂CF₃ | H |
| 1-1666 | CH₂Ph(4-OCF₃) | H | NHCH₂C≡CH | F | H | CH₃ | S(O)CH₂CF₃ | H |
| 1-1667 | CH₂Ph(4-OCF₃) | H | NHCH₂CH=CH₂ | F | H | CH₃ | SCH₂CF₃ | H |
| 1-1668 | CH₂Ph(4-OCF₃) | H | NHCH₂CH=CH₂ | F | H | CH₃ | S(O)CH₂CF₃ | H |
| 1-1669 | CH₂Ph(4-OCF₃) | H | CN | F | H | CH₃ | SCH₂CF₃ | H |
| 1-1670 | CH₂Ph(4-OCF₃) | H | CN | F | H | CH₃ | S(O)CH₂CF₃ | H |
| 1-1671 | CH₂Ph(4-OCF₃) | H | CH₂F | F | H | CH₃ | SCH₂CF₃ | H |
| 1-1672 | CH₂Ph(4-OCF₃) | H | CH₂F | F | H | CH₃ | S(O)CH₂CF₃ | H |
| 1-1673 | CH₂Ph(4-OCF₃) | H | CHF₂ | F | H | CH₃ | SCH₂CF₃ | H |
| 1-1674 | CH₂Ph(4-OCF₃) | H | CHF₂ | F | H | CH₃ | S(O)CH₂CF₃ | H |
| 1-1675 | CH₂Ph(4-OCF₃) | H | CF₃ | F | H | CH₃ | SCH₂CF₃ | H |
| 1-1676 | CH₂Ph(4-OCF₃) | H | CF₃ | F | H | CH₃ | S(O)CH₂CF₃ | H |
| 1-1677 | CH₂Ph(4-OCF₃) | H | OCH₃ | F | H | CH₃ | SCH₂CF₃ | H |
| 1-1678 | CH₂Ph(4-OCF₃) | H | OCH₃ | F | H | CH₃ | S(O)CH₂CF₃ | H |
| 1-1679 | CH₂Ph(4-OCF₃) | H | OCHF₂ | F | H | CH₃ | SCH₂CF₃ | H |
| 1-1680 | CH₂Ph(4-OCF₃) | H | OCHF₂ | F | H | CH₃ | S(O)CH₂CF₃ | H |
| 1-1681 | CH₂Ph(4-OCF₃) | H | Cl | F | H | CH₃ | SCH₂CF₃ | H |
| 1-1682 | CH₂Ph(4-OCF₃) | H | Cl | F | H | CH₃ | S(O)CH₂CF₃ | H |
| 1-1683 | CH₂Ph(4-OCF₃) | H | Br | F | H | CH₃ | SCH₂CF₃ | H |
| 1-1684 | CH₂Ph(4-OCF₃) | H | Br | F | H | CH₃ | S(O)CH₂CF₃ | H |
| 1-1685 | CH₂Ph(4-OCF₃) | Cl | NH₂ | F | H | CH₃ | SCH₂CF₃ | H |
| 1-1686 | CH₂Ph(4-OCF₃) | Cl | NH₂ | F | H | CH₃ | S(O)CH₂CF₃ | H |
| 1-1687 | CH₂Ph(4-OCF₃) | Cl | NHCH₃ | F | H | CH₃ | SCH₂CF₃ | H |
| 1-1688 | CH₂Ph(4-OCF₃) | Cl | NHCH₃ | F | H | CH₃ | S(O)CH₂CF₃ | H |
| 1-1689 | CH₂Ph(4-OCF₃) | Cl | Cl | F | H | CH₃ | SCH₂CF₃ | H |
| 1-1690 | CH₂Ph(4-OCF₃) | Cl | Cl | F | H | CH₃ | S(O)CH₂CF₃ | H |
| 1-1691 | CH₂Ph(4-OCF₃) | Br | Br | F | H | CH₃ | SCH₂CF₃ | H |
| 1-1692 | CH₂Ph(4-OCF₃) | Br | Br | F | H | CH₃ | S(O)CH₂CF₃ | H |
| 1-1693 | CH₂Ph(4-OCF₃) | Br | H | F | H | CH₃ | SCH₂CF₃ | H |
| 1-1694 | CH₂Ph(4-OCF₃) | Br | H | F | H | CH₃ | S(O)CH₂CF₃ | H |
| 1-1695 | Ph | H | H | F | H | CH₃ | SCH₂CF₃ | H |
| 1-1696 | Ph | H | H | F | H | CH₃ | S(O)CH₂CF₃ | H |
| 1-1697 | Ph | H | NH₂ | F | H | CH₃ | SCH₂CF₃ | H |
| 1-1698 | Ph | H | NH₂ | F | H | CH₃ | S(O)CH₂CF₃ | H |
| 1-1699 | Ph | H | NHC(O)CH₃ | F | H | CH₃ | SCH₂CF₃ | H |
| 1-1700 | Ph | H | NHC(O)CH₃ | F | H | CH₃ | S(O)CH₂CF₃ | H |
| 1-1701 | Ph | H | NHCH₃ | F | H | CH₃ | SCH₂CF₃ | H |
| 1-1702 | Ph | H | NHCH₃ | F | H | CH₃ | S(O)CH₂CF₃ | H |
| 1-1703 | Ph | H | NHCH₂C≡CH | F | H | CH₃ | SCH₂CF₃ | H |
| 1-1704 | Ph | H | NHCH₂C≡CH | F | H | CH₃ | S(O)CH₂CF₃ | H |
| 1-1705 | Ph | H | NHCH₂CH=CH₂ | F | H | CH₃ | SCH₂CF₃ | H |
| 1-1706 | Ph | H | NHCH₂CH=CH₂ | F | H | CH₃ | S(O)CH₂CF₃ | H |
| 1-1707 | Ph | H | CN | F | H | CH₃ | SCH₂CF₃ | H |
| 1-1708 | Ph | H | CN | F | H | CH₃ | S(O)CH₂CF₃ | H |
| 1-1709 | Ph | H | CH₃ | F | H | CH₃ | SCH₂CF₃ | H |
| 1-1710 | Ph | H | CH₃ | F | H | CH₃ | S(O)CH₂CF₃ | H |

TABLE 32

| Comp. No. | R₁ | R₂ | R₃ | R₄ | R₅ | R₆ | R₇ | R₈ |
|---|---|---|---|---|---|---|---|---|
| 1-1711 | Ph | H | CH₂F | F | H | CH₃ | SCH₂CF₃ | H |
| 1-1712 | Ph | H | CH₂F | F | H | CH₃ | S(O)CH₂CF₃ | H |
| 1-1713 | Ph | H | CHF₂ | F | H | CH₃ | SCH₂CF₃ | H |
| 1-1714 | Ph | H | CHF₂ | F | H | CH₃ | S(O)CH₂CF₃ | H |
| 1-1715 | Ph | H | CF₃ | F | H | CH₃ | SCH₂CF₃ | H |
| 1-1716 | Ph | H | CF₃ | F | H | CH₃ | S(O)CH₂CF₃ | H |
| 1-1717 | Ph | H | OCH₃ | F | H | CH₃ | SCH₂CF₃ | H |
| 1-1718 | Ph | H | OCH₃ | F | H | CH₃ | S(O)CH₂CF₃ | H |
| 1-1719 | Ph | H | OCHF₂ | F | H | CH₃ | SCH₂CF₃ | H |
| 1-1720 | Ph | H | OCHF₂ | F | H | CH₃ | S(O)CH₂CF₃ | H |
| 1-1721 | Ph | H | Cl | F | H | CH₃ | SCH₂CF₃ | H |
| 1-1722 | Ph | H | Cl | F | H | CH₃ | S(O)CH₂CF₃ | H |
| 1-1723 | Ph | H | Br | F | H | CH₃ | SCH₂CF₃ | H |
| 1-1724 | Ph | H | Br | F | H | CH₃ | S(O)CH₂CF₃ | H |
| 1-1725 | Ph | Cl | NH₂ | F | H | CH₃ | SCH₂CF₃ | H |
| 1-1726 | Ph | Cl | NH₂ | F | H | CH₃ | S(O)CH₂CF₃ | H |
| 1-1727 | Ph | Cl | NHCH₃ | F | H | CH₃ | SCH₂CF₃ | H |
| 1-1728 | Ph | Cl | NHCH₃ | F | H | CH₃ | S(O)CH₂CF₃ | H |
| 1-1729 | Ph | Cl | Cl | F | H | CH₃ | SCH₂CF₃ | H |
| 1-1730 | Ph | Cl | Cl | F | H | CH₃ | S(O)CH₂CF₃ | H |
| 1-1731 | Ph | Br | Br | F | H | CH₃ | SCH₂CF₃ | H |
| 1-1732 | Ph | Br | Br | F | H | CH₃ | S(O)CH₂CF₃ | H |
| 1-1733 | Ph | Cl | H | F | H | CH₃ | SCH₂CF₃ | H |
| 1-1734 | Ph | Cl | H | F | H | CH₃ | S(O)CH₂CF₃ | H |
| 1-1735 | Ph | Br | H | F | H | CH₃ | SCH₂CF₃ | H |
| 1-1736 | Ph | Br | H | F | H | CH₃ | S(O)CH₂CF₃ | H |
| 1-1737 | Ph(4-CF₃) | H | NH₂ | F | H | CH₃ | SCH₂CF₃ | H |
| 1-1738 | Ph(4-CF₃) | H | NH₂ | F | H | CH₃ | S(O)CH₂CF₃ | H |
| 1-1739 | Ph(4-CF₃) | H | NHC(O)CH₃ | F | H | CH₃ | SCH₂CF₃ | H |
| 1-1740 | Ph(4-CF₃) | H | NHC(O)CH₃ | F | H | CH₃ | S(O)CH₂CF₃ | H |
| 1-1741 | Ph(4-CF₃) | H | NHCH₃ | F | H | CH₃ | SCH₂CF₃ | H |
| 1-1742 | Ph(4-CF₃) | H | NHCH₃ | F | H | CH₃ | S(O)CH₂CF₃ | H |
| 1-1743 | Ph(4-CF₃) | H | NHCH₂C≡CH | F | H | CH₃ | SCH₂CF₃ | H |
| 1-1744 | Ph(4-CF₃) | H | NHCH₂C≡CH | F | H | CH₃ | S(O)CH₂CF₃ | H |
| 1-1745 | Ph(4-CF₃) | H | NHCH₂CH=CH₂ | F | H | CH₃ | SCH₂CF₃ | H |
| 1-1746 | Ph(4-CF₃) | H | NHCH₂CH=CH₂ | F | H | CH₃ | S(O)CH₂CF₃ | H |
| 1-1747 | Ph(4-CF₃) | H | CN | F | H | CH₃ | SCH₂CF₃ | H |
| 1-1748 | Ph(4-CF₃) | H | CN | F | H | CH₃ | S(O)CH₂CF₃ | H |
| 1-1749 | Ph(4-CF₃) | H | CH₃ | F | H | CH₃ | SCH₂CF₃ | H |
| 1-1750 | Ph(4-CF₃) | H | CH₃ | F | H | CH₃ | S(O)CH₂CF₃ | H |
| 1-1751 | Ph(4-CF₃) | H | CH₂F | F | H | CH₃ | SCH₂CF₃ | H |
| 1-1752 | Ph(4-CF₃) | H | CH₂F | F | H | CH₃ | S(O)CH₂CF₃ | H |
| 1-1753 | Ph(4-CF₃) | H | CHF₂ | F | H | CH₃ | SCH₂CF₃ | H |
| 1-1754 | Ph(4-CF₃) | H | CHF₂ | F | H | CH₃ | S(O)CH₂CF₃ | H |
| 1-1755 | Ph(4-CF₃) | H | CF₃ | F | H | CH₃ | SCH₂CF₃ | H |
| 1-1756 | Ph(4-CF₃) | H | CF₃ | F | H | CH₃ | S(O)CH₂CF₃ | H |
| 1-1757 | Ph(4-CF₃) | H | OCH₃ | F | H | CH₃ | SCH₂CF₃ | H |
| 1-1758 | Ph(4-CF₃) | H | OCH₃ | F | H | CH₃ | S(O)CH₂CF₃ | H |
| 1-1759 | Ph(4-CF₃) | H | OCHF₂ | F | H | CH₃ | SCH₂CF₃ | H |
| 1-1760 | Ph(4-CF₃) | H | OCHF₂ | F | H | CH₃ | S(O)CH₂CF₃ | H |
| 1-1761 | Ph(4-CF₃) | H | Cl | F | H | CH₃ | SCH₂CF₃ | H |
| 1-1762 | Ph(4-CF₃) | H | Cl | F | H | CH₃ | S(O)CH₂CF₃ | H |
| 1-1763 | Ph(4-CF₃) | H | Br | F | H | CH₃ | SCH₂CF₃ | H |
| 1-1764 | Ph(4-CF₃) | H | Br | F | H | CH₃ | S(O)CH₂CF₃ | H |
| 1-1765 | Ph(4-CF₃) | Cl | NH₂ | F | H | CH₃ | SCH₂CF₃ | H |
| 1-1766 | Ph(4-CF₃) | Cl | NH₂ | F | H | CH₃ | S(O)CH₂CF₃ | H |

TABLE 33

| Comp. No. | R₁ | R₂ | R₃ | R₄ | R₅ | R₆ | R₇ | R₈ |
|---|---|---|---|---|---|---|---|---|
| 1-1767 | Ph(4-CF₃) | Cl | NHCH₃ | F | H | CH₃ | SCH₂CF₃ | H |
| 1-1768 | Ph(4-CF₃) | Cl | NHCH₃ | F | H | CH₃ | S(O)CH₂CF₃ | H |
| 1-1769 | Ph(4-CF₃) | Cl | Cl | F | H | CH₃ | SCH₂CF₃ | H |
| 1-1770 | Ph(4-CF₃) | Cl | Cl | F | H | CH₃ | S(O)CH₂CF₃ | H |
| 1-1771 | Ph(4-CF₃) | Br | Br | F | H | CH₃ | SCH₂CF₃ | H |
| 1-1772 | Ph(4-CF₃) | Br | Br | F | H | CH₃ | S(O)CH₂CF₃ | H |
| 1-1773 | Ph(4-CF₃) | Cl | H | F | H | CH₃ | SCH₂CF₃ | H |
| 1-1774 | Ph(4-CF₃) | Cl | H | F | H | CH₃ | S(O)CH₂CF₃ | H |
| 1-1775 | Ph(4-CF₃) | Br | H | F | H | CH₃ | SCH₂CF₃ | H |
| 1-1776 | Ph(4-CF₃) | Br | H | F | H | CH₃ | S(O)CH₂CF₃ | H |
| 1-1777 | Ph(4-CN) | H | H | F | H | CH₃ | SCH₂CF₃ | H |
| 1-1778 | Ph(4-CN) | H | H | F | H | CH₃ | S(O)CH₂CF₃ | H |
| 1-1779 | Ph(4-CN) | H | NH₂ | F | H | CH₃ | SCH₂CF₃ | H |
| 1-1780 | Ph(4-CN) | H | NH₂ | F | H | CH₃ | S(O)CH₂CF₃ | H |

TABLE 33-continued

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1781 | Ph(4-CN) | H | NHC(O)CH$_3$ | F | H | CH$_3$ | SCH$_2$CF$_3$ | H |
| 1-1782 | Ph(4-CN) | H | NHC(O)CH$_3$ | F | H | CH$_3$ | S(O)CH$_2$CF$_3$ | H |
| 1-1783 | Ph(4-CN) | H | NHCH$_3$ | F | H | CH$_3$ | SCH$_2$CF$_3$ | H |
| 1-1784 | Ph(4-CN) | H | NHCH$_3$ | F | H | CH$_3$ | S(O)CH$_2$CF$_3$ | H |
| 1-1785 | Ph(4-CN) | H | NHCH$_2$C≡CH | F | H | CH$_3$ | SCH$_2$CF$_3$ | H |
| 1-1786 | Ph(4-CN) | H | NHCH$_2$C≡CH | F | H | CH$_3$ | S(O)CH$_2$CF$_3$ | H |
| 1-1787 | Ph(4-CN) | H | NHCH$_2$CH═CH$_2$ | F | H | CH$_3$ | SCH$_2$CF$_3$ | H |
| 1-1788 | Ph(4-CN) | H | NHCH$_2$CH═CH$_2$ | F | H | CH$_3$ | S(O)CH$_2$CF$_3$ | H |
| 1-1789 | Ph(4-CN) | H | CN | F | H | CH$_3$ | SCH$_2$CF$_3$ | H |
| 1-1790 | Ph(4-CN) | H | CN | F | H | CH$_3$ | S(O)CH$_2$CF$_3$ | H |
| 1-1791 | Ph(4-CN) | H | CH$_3$ | F | H | CH$_3$ | SCH$_2$CF$_3$ | H |
| 1-1792 | Ph(4-CN) | H | CH$_3$ | F | H | CH$_3$ | S(O)CH$_2$CF$_3$ | H |
| 1-1793 | Ph(4-CN) | H | CH$_2$F | F | H | CH$_3$ | SCH$_2$CF$_3$ | H |
| 1-1794 | Ph(4-CN) | H | CH$_2$F | F | H | CH$_3$ | S(O)CH$_2$CF$_3$ | H |
| 1-1795 | Ph(4-CN) | H | CHF$_2$ | F | H | CH$_3$ | SCH$_2$CF$_3$ | H |
| 1-1796 | Ph(4-CN) | H | CHF$_2$ | F | H | CH$_3$ | S(O)CH$_2$CF$_3$ | H |
| 1-1797 | Ph(4-CN) | H | CF$_3$ | F | H | CH$_3$ | SCH$_2$CF$_3$ | H |
| 1-1798 | Ph(4-CN) | H | CF$_3$ | F | H | CH$_3$ | S(O)CH$_2$CF$_3$ | H |
| 1-1799 | Ph(4-CN) | H | OCH$_3$ | F | H | CH$_3$ | SCH$_2$CF$_3$ | H |
| 1-1800 | Ph(4-CN) | H | OCH$_3$ | F | H | CH$_3$ | S(O)CH$_2$CF$_3$ | H |
| 1-1801 | Ph(4-CN) | H | OCHF$_2$ | F | H | CH$_3$ | SCH$_2$CF$_3$ | H |
| 1-1802 | Ph(4-CN) | H | OCHF$_2$ | F | H | CH$_3$ | S(O)CH$_2$CF$_3$ | H |
| 1-1803 | Ph(4-CN) | H | Cl | F | H | CH$_3$ | SCH$_2$CF$_3$ | H |
| 1-1804 | Ph(4-CN) | H | Cl | F | H | CH$_3$ | S(O)CH$_2$CF$_3$ | H |
| 1-1805 | Ph(4-CN) | H | Br | F | H | CH$_3$ | SCH$_2$CF$_3$ | H |
| 1-1806 | Ph(4-CN) | H | Br | F | H | CH$_3$ | S(O)CH$_2$CF$_3$ | H |
| 1-1807 | Ph(4-CN) | Cl | NH$_2$ | F | H | CH$_3$ | SCH$_2$CF$_3$ | H |
| 1-1808 | Ph(4-CN) | Cl | NH$_2$ | F | H | CH$_3$ | S(O)CH$_2$CF$_3$ | H |
| 1-1809 | Ph(4-CN) | Cl | NHCH$_3$ | F | H | CH$_3$ | SCH$_2$CF$_3$ | H |
| 1-1810 | Ph(4-CN) | Cl | NHCH$_3$ | F | H | CH$_3$ | S(O)CH$_2$CF$_3$ | H |
| 1-1811 | Ph(4-CN) | Cl | Cl | F | H | CH$_3$ | SCH$_2$CF$_3$ | H |
| 1-1812 | Ph(4-CN) | Cl | Cl | F | H | CH$_3$ | S(O)CH$_2$CF$_3$ | H |
| 1-1813 | Ph(4-CN) | Br | Br | F | H | CH$_3$ | SCH$_2$CF$_3$ | H |
| 1-1814 | Ph(4-CN) | Br | Br | F | H | CH$_3$ | S(O)CH$_2$CF$_3$ | H |
| 1-1815 | Ph(4-CN) | Cl | H | F | H | CH$_3$ | SCH$_2$CF$_3$ | H |
| 1-1816 | Ph(4-CN) | Cl | H | F | H | CH$_3$ | S(O)CH$_2$CF$_3$ | H |
| 1-1817 | Ph(4-CN) | Br | H | F | H | CH$_3$ | SCH$_2$CF$_3$ | H |
| 1-1818 | Ph(4-CN) | Br | H | F | H | CH$_3$ | S(O)CH$_2$CF$_3$ | H |
| 1-1819 | Ph(4-CH$_3$) | H | H | F | H | CH$_3$ | SCH$_2$CF$_3$ | H |
| 1-1820 | Ph(4-CH$_3$) | H | H | F | H | CH$_3$ | S(O)CH$_2$CF$_3$ | H |
| 1-1821 | Ph(4-CH$_3$) | H | NH$_2$ | F | H | CH$_3$ | SCH$_2$CF$_3$ | H |
| 1-1822 | Ph(4-CH$_3$) | H | NH$_2$ | F | H | CH$_3$ | S(O)CH$_2$CF$_3$ | H |

TABLE 34

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1823 | Ph(4-CH$_3$) | H | NHC(O)CH$_3$ | F | H | CH$_3$ | SCH$_2$CF$_3$ | H |
| 1-1824 | Ph(4-CH$_3$) | H | NHC(O)CH$_3$ | F | H | CH$_3$ | S(O)CH$_2$CF$_3$ | H |
| 1-1825 | Ph(4-CH$_3$) | H | NHCH$_3$ | F | H | CH$_3$ | SCH$_2$CF$_3$ | H |
| 1-1826 | Ph(4-CH$_3$) | H | NHCH$_3$ | F | H | CH$_3$ | S(O)CH$_2$CF$_3$ | H |
| 1-1827 | Ph(4-CH$_3$) | H | NHCH$_2$C≡CH | F | H | CH$_3$ | SCH$_2$CF$_3$ | H |
| 1-1828 | Ph(4-CH$_3$) | H | NHCH$_2$C≡CH | F | H | CH$_3$ | S(O)CH$_2$CF$_3$ | H |
| 1-1829 | Ph(4-CH$_3$) | H | NHCH$_2$CH═CH$_2$ | F | H | CH$_3$ | SCH$_2$CF$_3$ | H |
| 1-1830 | Ph(4-CH$_3$) | H | NHCH$_2$CH═CH$_2$ | F | H | CH$_3$ | S(O)CH$_2$CF$_3$ | H |
| 1-1831 | Ph(4-CH$_3$) | H | CN | F | H | CH$_3$ | SCH$_2$CF$_3$ | H |
| 1-1832 | Ph(4-CH$_3$) | H | CN | F | H | CH$_3$ | S(O)CH$_2$CF$_3$ | H |
| 1-1833 | Ph(4-CH$_3$) | H | CH$_3$ | F | H | CH$_3$ | SCH$_2$CF$_3$ | H |
| 1-1834 | Ph(4-CH$_3$) | H | CH$_3$ | F | H | CH$_3$ | S(O)CH$_2$CF$_3$ | H |
| 1-1835 | Ph(4-CH$_3$) | H | CH$_2$F | F | H | CH$_3$ | SCH$_2$CF$_3$ | H |
| 1-1836 | Ph(4-CH$_3$) | H | CH$_2$F | F | H | CH$_3$ | S(O)CH$_2$CF$_3$ | H |
| 1-1837 | Ph(4-CH$_3$) | H | CHF$_2$ | F | H | CH$_3$ | SCH$_2$CF$_3$ | H |
| 1-1838 | Ph(4-CH$_3$) | H | CHF$_2$ | F | H | CH$_3$ | S(O)CH$_2$CF$_3$ | H |
| 1-1839 | Ph(4-CH$_3$) | H | CF$_3$ | F | H | CH$_3$ | SCH$_2$CF$_3$ | H |
| 1-1840 | Ph(4-CH$_3$) | H | CF$_3$ | F | H | CH$_3$ | S(O)CH$_2$CF$_3$ | H |
| 1-1841 | Ph(4-CH$_3$) | H | OCH$_3$ | F | H | CH$_3$ | SCH$_2$CF$_3$ | H |
| 1-1842 | Ph(4-CH$_3$) | H | OCH$_3$ | F | H | CH$_3$ | S(O)CH$_2$CF$_3$ | H |
| 1-1843 | Ph(4-CH$_3$) | H | OCHF$_2$ | F | H | CH$_3$ | SCH$_2$CF$_3$ | H |
| 1-1844 | Ph(4-CH$_3$) | H | OCHF$_2$ | F | H | CH$_3$ | S(O)CH$_2$CF$_3$ | H |
| 1-1845 | Ph(4-CH$_3$) | H | Cl | F | H | CH$_3$ | SCH$_2$CF$_3$ | H |
| 1-1846 | Ph(4-CH$_3$) | H | Cl | F | H | CH$_3$ | S(O)CH$_2$CF$_3$ | H |
| 1-1847 | Ph(4-CH$_3$) | H | Br | F | H | CH$_3$ | SCH$_2$CF$_3$ | H |
| 1-1848 | Ph(4-CH$_3$) | H | Br | F | H | CH$_3$ | S(O)CH$_2$CF$_3$ | H |
| 1-1849 | Ph(4-CH$_3$) | Cl | NH$_2$ | F | H | CH$_3$ | SCH$_2$CF$_3$ | H |
| 1-1850 | Ph(4-CH$_3$) | Cl | NH$_2$ | F | H | CH$_3$ | S(O)CH$_2$CF$_3$ | H |

TABLE 34-continued

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1851 | Ph(4-CH$_3$) | Cl | NHCH$_3$ | F | H | CH$_3$ | SCH$_2$CF$_3$ | H |
| 1-1852 | Ph(4-CH$_3$) | Cl | NHCH$_3$ | F | H | CH$_3$ | S(O)CH$_2$CF$_3$ | H |
| 1-1853 | Ph(4-CH$_3$) | Cl | Cl | F | H | CH$_3$ | SCH$_2$CF$_3$ | H |
| 1-1854 | Ph(4-CH$_3$) | Cl | Cl | F | H | CH$_3$ | S(O)CH$_2$CF$_3$ | H |
| 1-1855 | Ph(4-CH$_3$) | Br | Br | F | H | CH$_3$ | SCH$_2$CF$_3$ | H |
| 1-1856 | Ph(4-CH$_3$) | Br | Br | F | H | CH$_3$ | S(O)CH$_2$CF$_3$ | H |
| 1-1857 | Ph(4-CH$_3$) | Cl | H | F | H | CH$_3$ | SCH$_2$CF$_3$ | H |
| 1-1858 | Ph(4-CH$_3$) | Cl | H | F | H | CH$_3$ | S(O)CH$_2$CF$_3$ | H |
| 1-1859 | Ph(4-CH$_3$) | Br | H | F | H | CH$_3$ | SCH$_2$CF$_3$ | H |
| 1-1860 | Ph(4-CH$_3$) | Br | H | F | H | CH$_3$ | S(O)CH$_2$CF$_3$ | H |
| 1-1861 | Ph(4-OCF$_3$) | H | H | F | H | CH$_3$ | SCH$_2$CF$_3$ | H |
| 1-1862 | Ph(4-OCF$_3$) | H | H | F | H | CH$_3$ | S(O)CH$_2$CF$_3$ | H |
| 1-1863 | Ph(4-OCF$_3$) | H | NH$_2$ | F | H | CH$_3$ | SCH$_2$CF$_3$ | H |
| 1-1864 | Ph(4-OCF$_3$) | H | NH$_2$ | F | H | CH$_3$ | S(O)CH$_2$CF$_3$ | H |
| 1-1865 | Ph(4-OCF$_3$) | H | NHC(O)CH$_3$ | F | H | CH$_3$ | SCH$_2$CF$_3$ | H |
| 1-1866 | Ph(4-OCF$_3$) | H | NHC(O)CH$_3$ | F | H | CH$_3$ | S(O)CH$_2$CF$_3$ | H |
| 1-1867 | Ph(4-OCF$_3$) | H | NHCH$_3$ | F | H | CH$_3$ | SCH$_2$CF$_3$ | H |
| 1-1868 | Ph(4-OCF$_3$) | H | NHCH$_3$ | F | H | CH$_3$ | S(O)CH$_2$CF$_3$ | H |
| 1-1869 | Ph(4-OCF$_3$) | H | NHCH$_2$C≡CH | F | H | CH$_3$ | SCH$_2$CF$_3$ | H |
| 1-1870 | Ph(4-OCF$_3$) | H | NHCH$_2$C≡CH | F | H | CH$_3$ | S(O)CH$_2$CF$_3$ | H |
| 1-1871 | Ph(4-OCF$_3$) | H | NHCH$_2$CH=CH$_2$ | F | H | CH$_3$ | SCH$_2$CF$_3$ | H |
| 1-1872 | Ph(4-OCF$_3$) | H | NHCH$_2$CH=CH$_2$ | F | H | CH$_3$ | S(O)CH$_2$CF$_3$ | H |
| 1-1873 | Ph(4-OCF$_3$) | H | CN | F | H | CH$_3$ | SCH$_2$CF$_3$ | H |
| 1-1874 | Ph(4-OCF$_3$) | H | CN | F | H | CH$_3$ | S(O)CH$_2$CF$_3$ | H |
| 1-1875 | Ph(4-OCF$_3$) | H | CH$_3$ | F | H | CH$_3$ | SCH$_2$CF$_3$ | H |
| 1-1876 | Ph(4-OCF$_3$) | H | CH$_3$ | F | H | CH$_3$ | S(O)CH$_2$CF$_3$ | H |
| 1-1877 | Ph(4-OCF$_3$) | H | CH$_2$F | F | H | CH$_3$ | SCH$_2$CF$_3$ | H |
| 1-1878 | Ph(4-OCF$_3$) | H | CH$_2$F | F | H | CH$_3$ | S(O)CH$_2$CF$_3$ | H |

TABLE 35

| Comp. No. | R$_1$ | R$_2$ | R$_3$ | R$_4$ | R$_5$ | R$_6$ | R$_7$ | R$_8$ |
|---|---|---|---|---|---|---|---|---|
| 1-1879 | Ph(4-OCF$_3$) | H | CHF$_2$ | F | H | CH$_3$ | SCH$_2$CF$_3$ | H |
| 1-1880 | Ph(4-OCF$_3$) | H | CHF$_2$ | F | H | CH$_3$ | S(O)CH$_2$CF$_3$ | H |
| 1-1881 | Ph(4-OCF$_3$) | H | CF$_3$ | F | H | CH$_3$ | SCH$_2$CF$_3$ | H |
| 1-1882 | Ph(4-OCF$_3$) | H | CF$_3$ | F | H | CH$_3$ | S(O)CH$_2$CF$_3$ | H |
| 1-1883 | Ph(4-OCF$_3$) | H | OCH$_3$ | F | H | CH$_3$ | SCH$_2$CF$_3$ | H |
| 1-1884 | Ph(4-OCF$_3$) | H | OCH$_3$ | F | H | CH$_3$ | S(O)CH$_2$CF$_3$ | H |
| 1-1885 | Ph(4-OCF$_3$) | H | OCHF$_2$ | F | H | CH$_3$ | SCH$_2$CF$_3$ | H |
| 1-1886 | Ph(4-OCF$_3$) | H | OCHF$_2$ | F | H | CH$_3$ | S(O)CH$_2$CF$_3$ | H |
| 1-1887 | Ph(4-OCF$_3$) | H | Cl | F | H | CH$_3$ | SCH$_2$CF$_3$ | H |
| 1-1888 | Ph(4-OCF$_3$) | H | Cl | F | H | CH$_3$ | S(O)CH$_2$CF$_3$ | H |
| 1-1889 | Ph(4-OCF$_3$) | H | Br | F | H | CH$_3$ | SCH$_2$CF$_3$ | H |
| 1-1890 | Ph(4-OCF$_3$) | H | Br | F | H | CH$_3$ | S(O)CH$_2$CF$_3$ | H |
| 1-1891 | Ph(4-OCF$_3$) | Cl | NH$_2$ | F | H | CH$_3$ | SCH$_2$CF$_3$ | H |
| 1-1892 | Ph(4-OCF$_3$) | Cl | NH$_2$ | F | H | CH$_3$ | S(O)CH$_2$CF$_3$ | H |
| 1-1893 | Ph(4-OCF$_3$) | Cl | NHCH$_3$ | F | H | CH$_3$ | SCH$_2$CF$_3$ | H |
| 1-1894 | Ph(4-OCF$_3$) | Cl | NHCH$_3$ | F | H | CH$_3$ | S(O)CH$_2$CF$_3$ | H |
| 1-1895 | Ph(4-OCF$_3$) | Cl | Cl | F | H | CH$_3$ | SCH$_2$CF$_3$ | H |
| 1-1896 | Ph(4-OCF$_3$) | Cl | Cl | F | H | CH$_3$ | S(O)CH$_2$CF$_3$ | H |
| 1-1897 | Ph(4-OCF$_3$) | Br | Br | F | H | CH$_3$ | SCH$_2$CF$_3$ | H |
| 1-1898 | Ph(4-OCF$_3$) | Br | Br | F | H | CH$_3$ | S(O)CH$_2$CF$_3$ | H |
| 1-1899 | Ph(4-OCF$_3$) | Cl | H | F | H | CH$_3$ | SCH$_2$CF$_3$ | H |
| 1-1900 | Ph(4-OCF$_3$) | Cl | H | F | H | CH$_3$ | S(O)CH$_2$CF$_3$ | H |
| 1-1901 | Ph(4-OCF$_3$) | Br | H | F | H | CH$_3$ | SCH$_2$CF$_3$ | H |
| 1-1902 | Ph(4-OCF$_3$) | Br | H | F | H | CH$_3$ | S(O)CH$_2$CF$_3$ | H |
| 1-1903 | Ph(4-OCF$_3$) | H | H | F | H | CH$_3$ | SCH$_2$CF$_3$ | H |
| 1-1904 | Ph(4-OCF$_3$) | H | H | F | H | CH$_3$ | S(O)CH$_2$CF$_3$ | H |
| 1-1905 | Ph(4-OCF$_3$) | H | NH$_2$ | F | H | CH$_3$ | SCH$_2$CF$_3$ | H |
| 1-1906 | Ph(4-OCF$_3$) | H | NH$_2$ | F | H | CH$_3$ | S(O)CH$_2$CF$_3$ | H |
| 1-1907 | Ph(4-OCF$_3$) | H | NHC(O)CH$_3$ | F | H | CH$_3$ | SCH$_2$CF$_3$ | H |
| 1-1908 | Ph(4-OCF$_3$) | H | NHC(O)CH$_3$ | F | H | CH$_3$ | S(O)CH$_2$CF$_3$ | H |
| 1-1909 | Ph(4-OCF$_3$) | H | NHCH$_3$ | F | H | CH$_3$ | SCH$_2$CF$_3$ | H |
| 1-1910 | Ph(4-OCF$_3$) | H | NHCH$_3$ | F | H | CH$_3$ | S(O)CH$_2$CF$_3$ | H |
| 1-1911 | Ph(4-OCF$_3$) | H | NHCH$_2$C≡CH | F | H | CH$_3$ | SCH$_2$CF$_3$ | H |
| 1-1912 | Ph(4-OCF$_3$) | H | NHCH$_2$C≡CH | F | H | CH$_3$ | S(O)CH$_2$CF$_3$ | H |
| 1-1913 | Ph(4-OCF$_3$) | H | NHCH$_2$CH=CH$_2$ | F | H | CH$_3$ | SCH$_2$CF$_3$ | H |
| 1-1914 | Ph(4-OCF$_3$) | H | NHCH$_2$CH=CH$_2$ | F | H | CH$_3$ | S(O)CH$_2$CF$_3$ | H |
| 1-1915 | Ph(4-OCF$_3$) | H | CN | F | H | CH$_3$ | SCH$_2$CF$_3$ | H |
| 1-1916 | Ph(4-OCF$_3$) | H | CN | F | H | CH$_3$ | S(O)CH$_2$CF$_3$ | H |
| 1-1917 | Ph(4-OCF$_3$) | H | CH$_3$ | F | H | CH$_3$ | SCH$_2$CF$_3$ | H |
| 1-1918 | Ph(4-OCF$_3$) | H | CH$_3$ | F | H | CH$_3$ | S(O)CH$_2$CF$_3$ | H |
| 1-1919 | Ph(4-OCF$_3$) | H | CH$_2$F | F | H | CH$_3$ | SCH$_2$CF$_3$ | H |
| 1-1920 | Ph(4-OCF$_3$) | H | CH$_2$F | F | H | CH$_3$ | S(O)CH$_2$CF$_3$ | H |

TABLE 35-continued

| Comp. No. | R₁ | R₂ | R₃ | R₄ | R₅ | R₆ | R₇ | R₈ |
|---|---|---|---|---|---|---|---|---|
| 1-1921 | Ph(4-OCF₃) | H | CHF₂ | F | H | CH₃ | SCH₂CF₃ | H |
| 1-1922 | Ph(4-OCF₃) | H | CHF₂ | F | H | CH₃ | S(O)CH₂CF₃ | H |
| 1-1923 | Ph(4-OCF₃) | H | CF₃ | F | H | CH₃ | SCH₂CF₃ | H |
| 1-1924 | Ph(4-OCF₃) | H | CF₃ | F | H | CH₃ | S(O)CH₂CF₃ | H |
| 1-1925 | Ph(4-OCF₃) | H | OCH₃ | F | H | CH₃ | SCH₂CF₃ | H |
| 1-1926 | Ph(4-OCF₃) | H | OCH₃ | F | H | CH₃ | S(O)CH₂CF₃ | H |
| 1-1927 | Ph(4-OCF₃) | H | OCHF₂ | F | H | CH₃ | SCH₂CF₃ | H |
| 1-1928 | Ph(4-OCF₃) | H | OCHF₂ | F | H | CH₃ | S(O)CH₂CF₃ | H |
| 1-1929 | Ph(4-OCF₃) | H | Cl | F | H | CH₃ | SCH₂CF₃ | H |
| 1-1930 | Ph(4-OCF₃) | H | Cl | F | H | CH₃ | S(O)CH₂CF₃ | H |
| 1-1931 | Ph(4-OCF₃) | H | Br | F | H | CH₃ | SCH₂CF₃ | H |
| 1-1932 | Ph(4-OCF₃) | H | Br | F | H | CH₃ | S(O)CH₂CF₃ | H |
| 1-1933 | Ph(4-OCF₃) | Cl | NH₂ | F | H | CH₃ | SCH₂CF₃ | H |
| 1-1934 | Ph(4-OCF₃) | Cl | NH₂ | F | H | CH₃ | S(O)CH₂CF₃ | H |

TABLE 36

| Comp. No. | R₁ | R₂ | R₃ | R₄ | R₅ | R₆ | R₇ | R₈ |
|---|---|---|---|---|---|---|---|---|
| 1-1935 | Ph(4-OCF₃) | Cl | NHCH₃ | F | H | CH₃ | SCH₂CF₃ | H |
| 1-1936 | Ph(4-OCF₃) | Cl | NHCH₃ | F | H | CH₃ | S(O)CH₂CF₃ | H |
| 1-1937 | Ph(4-OCF₃) | Cl | Cl | F | H | CH₃ | SCH₂CF₃ | H |
| 1-1938 | Ph(4-OCF₃) | Cl | Cl | F | H | CH₃ | S(O)CH₂CF₃ | H |
| 1-1939 | Ph(4-OCF₃) | Br | Br | F | H | CH₃ | SCH₂CF₃ | H |
| 1-1940 | Ph(4-OCF₃) | Br | Br | F | H | CH₃ | S(O)CH₂CF₃ | H |
| 1-1941 | Ph(4-OCF₃) | Cl | H | F | H | CH₃ | SCH₂CF₃ | H |
| 1-1942 | Ph(4-OCF₃) | Cl | H | F | H | CH₃ | S(O)CH₂CF₃ | H |
| 1-1943 | Ph(4-OCF₃) | Br | H | F | H | CH₃ | SCH₂CF₃ | H |
| 1-1944 | Ph(4-OCF₃) | Br | H | F | H | CH₃ | S(O)CH₂CF₃ | H |
| 1-1945 | Ph(4-Cl) | H | H | F | H | CH₃ | SCH₂CF₃ | H |
| 1-1946 | Ph(4-Cl) | H | H | F | H | CH₃ | S(O)CH₂CF₃ | H |
| 1-1947 | Ph(4-Cl) | H | NH₂ | F | H | CH₃ | SCH₂CF₃ | H |
| 1-1948 | Ph(4-Cl) | H | NH₂ | F | H | CH₃ | S(O)CH₂CF₃ | H |
| 1-1949 | Ph(4-Cl) | H | NHC(O)CH₃ | F | H | CH₃ | SCH₂CF₃ | H |
| 1-1950 | Ph(4-Cl) | H | NHC(O)CH₃ | F | H | CH₃ | S(O)CH₂CF₃ | H |
| 1-1951 | Ph(4-Cl) | H | NHCH₃ | F | H | CH₃ | SCH₂CF₃ | H |
| 1-1952 | Ph(4-Cl) | H | NHCH₃ | F | H | CH₃ | S(O)CH₂CF₃ | H |
| 1-1953 | Ph(4-Cl) | H | NHCH₂C≡CH | F | H | CH₃ | SCH₂CF₃ | H |
| 1-1954 | Ph(4-Cl) | H | NHCH₂C≡CH | F | H | CH₃ | S(O)CH₂CF₃ | H |
| 1-1955 | Ph(4-Cl) | H | NHCH₂CH=CH₂ | F | H | CH₃ | SCH₂CF₃ | H |
| 1-1956 | Ph(4-Cl) | H | NHCH₂CH=CH₂ | F | H | CH₃ | S(O)CH₂CF₃ | H |
| 1-1957 | Ph(4-Cl) | H | CN | F | H | CH₃ | SCH₂CF₃ | H |
| 1-1958 | Ph(4-Cl) | H | CN | F | H | CH₃ | S(O)CH₂CF₃ | H |
| 1-1959 | Ph(4-Cl) | H | CH₃ | F | H | CH₃ | SCH₂CF₃ | H |
| 1-1960 | Ph(4-Cl) | H | CH₃ | F | H | CH₃ | S(O)CH₂CF₃ | H |
| 1-1961 | Ph(4-Cl) | H | CH₂F | F | H | CH₃ | SCH₂CF₃ | H |
| 1-1962 | Ph(4-Cl) | H | CH₂F | F | H | CH₃ | S(O)CH₂CF₃ | H |
| 1-1963 | Ph(4-Cl) | H | CHF₂ | F | H | CH₃ | SCH₂CF₃ | H |
| 1-1964 | Ph(4-Cl) | H | CHF₂ | F | H | CH₃ | S(O)CH₂CF₃ | H |
| 1-1965 | Ph(4-Cl) | H | CF₃ | F | H | CH₃ | SCH₂CF₃ | H |
| 1-1966 | Ph(4-Cl) | H | CF₃ | F | H | CH₃ | S(O)CH₂CF₃ | H |
| 1-1967 | Ph(4-Cl) | H | OCH₃ | F | H | CH₃ | SCH₂CF₃ | H |
| 1-1968 | Ph(4-Cl) | H | OCH₃ | F | H | CH₃ | S(O)CH₂CF₃ | H |
| 1-1969 | Ph(4-Cl) | H | OCHF₂ | F | H | CH₃ | SCH₂CF₃ | H |
| 1-1970 | Ph(4-Cl) | H | OCHF₂ | F | H | CH₃ | S(O)CH₂CF₃ | H |
| 1-1971 | Ph(4-Cl) | H | Cl | F | H | CH₃ | SCH₂CF₃ | H |
| 1-1972 | Ph(4-Cl) | H | Cl | F | H | CH₃ | S(O)CH₂CF₃ | H |
| 1-1973 | Ph(4-Cl) | H | Br | F | H | CH₃ | SCH₂CF₃ | H |
| 1-1974 | Ph(4-Cl) | H | Br | F | H | CH₃ | S(O)CH₂CF₃ | H |
| 1-1975 | Ph(4-Cl) | Cl | NH₂ | F | H | CH₃ | SCH₂CF₃ | H |
| 1-1976 | Ph(4-Cl) | Cl | NH₂ | F | H | CH₃ | S(O)CH₂CF₃ | H |
| 1-1977 | Ph(4-Cl) | Cl | NHCH₃ | F | H | CH₃ | SCH₂CF₃ | H |
| 1-1978 | Ph(4-Cl) | Cl | NHCH₃ | F | H | CH₃ | S(O)CH₂CF₃ | H |
| 1-1979 | Ph(4-Cl) | Cl | Cl | F | H | CH₃ | SCH₂CF₃ | H |
| 1-1980 | Ph(4-Cl) | Cl | Cl | F | H | CH₃ | S(O)CH₂CF₃ | H |
| 1-1981 | Ph(4-Cl) | Br | Br | F | H | CH₃ | SCH₂CF₃ | H |
| 1-1982 | Ph(4-Cl) | Br | Br | F | H | CH₃ | S(O)CH₂CF₃ | H |
| 1-1983 | Ph(4-Cl) | Cl | H | F | H | CH₃ | SCH₂CF₃ | H |
| 1-1984 | Ph(4-Cl) | Cl | H | F | H | CH₃ | S(O)CH₂CF₃ | H |
| 1-1985 | Ph(4-Cl) | Br | H | F | H | CH₃ | SCH₂CF₃ | H |
| 1-1986 | Ph(4-Cl) | Br | H | F | H | CH₃ | S(O)CH₂CF₃ | H |
| 1-1987 | Ph(4-Cl) | H | H | F | H | CH₃ | SCH₂CF₃ | H |
| 1-1988 | Ph(4-Cl) | H | H | F | H | CH₃ | S(O)CH₂CF₃ | H |
| 1-1989 | Ph(4-Cl) | H | NH₂ | F | H | CH₃ | SCH₂CF₃ | H |
| 1-1990 | Ph(4-Cl) | H | NH₂ | F | H | CH₃ | S(O)CH₂CF₃ | H |

TABLE 37

| Comp. No. | R₁ | R₂ | R₃ | R₄ | R₅ | R₆ | R₇ | R₈ |
|---|---|---|---|---|---|---|---|---|
| 1-1991 | Ph(4-Cl) | H | NHC(O)CH₃ | F | H | CH₃ | SCH₂CF₃ | H |
| 1-1992 | Ph(4-Cl) | H | NHC(O)CH₃ | F | H | CH₃ | S(O)CH₂CF₃ | H |
| 1-1993 | Ph(4-Cl) | H | NHCH₃ | F | H | CH₃ | SCH₂CF₃ | H |
| 1-1994 | Ph(4-Cl) | H | NHCH₃ | F | H | CH₃ | S(O)CH₂CF₃ | H |
| 1-1995 | Ph(4-Cl) | H | NHCH₂C≡CH | F | H | CH₃ | SCH₂CF₃ | H |
| 1-1996 | Ph(4-Cl) | H | NHCH₂C≡CH | F | H | CH₃ | S(O)CH₂CF₃ | H |
| 1-1997 | Ph(4-Cl) | H | NHCH₂CH=CH₂ | F | H | CH₃ | SCH₂CF₃ | H |
| 1-1998 | Ph(4-Cl) | H | NHCH₂CH=CH₂ | F | H | CH₃ | S(O)CH₂CF₃ | H |
| 1-1999 | Ph(4-Cl) | H | CN | F | H | CH₃ | SCH₂CF₃ | H |
| 1-2000 | Ph(4-Cl) | H | CN | F | H | CH₃ | S(O)CH₂CF₃ | H |
| 1-2001 | Ph(4-Cl) | H | CH₃ | F | H | CH₃ | SCH₂CF₃ | H |
| 1-2002 | Ph(4-Cl) | H | CH₃ | F | H | CH₃ | S(O)CH₂CF₃ | H |
| 1-2003 | Ph(4-Cl) | H | CH₂F | F | H | CH₃ | SCH₂CF₃ | H |
| 1-2004 | Ph(4-Cl) | H | CH₂F | F | H | CH₃ | S(O)CH₂CF₃ | H |
| 1-2005 | Ph(4-Cl) | H | CHF₂ | F | H | CH₃ | SCH₂CF₃ | H |
| 1-2006 | Ph(4-Cl) | H | CHF₂ | F | H | CH₃ | S(O)CH₂CF₃ | H |
| 1-2007 | Ph(4-Cl) | H | CF₃ | F | H | CH₃ | SCH₂CF₃ | H |
| 1-2008 | Ph(4-Cl) | H | CF₃ | F | H | CH₃ | S(O)CH₂CF₃ | H |
| 1-2009 | Ph(4-Cl) | H | OCH₃ | F | H | CH₃ | SCH₂CF₃ | H |
| 1-2010 | Ph(4-Cl) | H | OCH₃ | F | H | CH₃ | S(O)CH₂CF₃ | H |
| 1-2011 | Ph(4-Cl) | H | OCHF₂ | F | H | CH₃ | SCH₂CF₃ | H |
| 1-2012 | Ph(4-Cl) | H | OCHF₂ | F | H | CH₃ | S(O)CH₂CF₃ | H |
| 1-2013 | Ph(4-Cl) | H | Cl | F | H | CH₃ | SCH₂CF₃ | H |
| 1-2014 | Ph(4-Cl) | H | Cl | F | H | CH₃ | S(O)CH₂CF₃ | H |
| 1-2015 | Ph(4-Cl) | H | Br | F | H | CH₃ | SCH₂CF₃ | H |
| 1-2016 | Ph(4-Cl) | H | Br | F | H | CH₃ | S(O)CH₂CF₃ | H |
| 1-2017 | Ph(4-Cl) | Cl | NH₂ | F | H | CH₃ | SCH₂CF₃ | H |
| 1-2018 | Ph(4-Cl) | Cl | NH₂ | F | H | CH₃ | S(O)CH₂CF₃ | H |
| 1-2019 | Ph(4-Cl) | Cl | NHCH₃ | F | H | CH₃ | SCH₂CF₃ | H |
| 1-2020 | Ph(4-Cl) | Cl | NHCH₃ | F | H | CH₃ | S(O)CH₂CF₃ | H |
| 1-2021 | Ph(4-Cl) | Cl | Cl | F | H | CH₃ | SCH₂CF₃ | H |
| 1-2022 | Ph(4-Cl) | Cl | Cl | F | H | CH₃ | S(O)CH₂CF₃ | H |
| 1-2023 | Ph(4-Cl) | Br | Br | F | H | CH₃ | SCH₂CF₃ | H |
| 1-2024 | Ph(4-Cl) | Br | Br | F | H | CH₃ | S(O)CH₂CF₃ | H |
| 1-2025 | Ph(4-Cl) | Cl | H | F | H | CH₃ | SCH₂CF₃ | H |
| 1-2026 | Ph(4-Cl) | Cl | H | F | H | CH₃ | S(O)CH₂CF₃ | H |
| 1-2027 | Ph(4-Cl) | Br | H | F | H | CH₃ | SCH₂CF₃ | H |
| 1-2028 | Ph(4-Cl) | Br | H | F | H | CH₃ | S(O)CH₂CF₃ | H |
| 1-2029 | CH₂CH₂OCH₂C≡CH | H | H | F | H | CH₃ | SCH₂CF₃ | H |
| 1-2130 | CH₂CH₂OCH₂C≡CH | H | H | F | H | CH₃ | S(O)CH₂CF₃ | H |
| 1-2131 | CH₂CH₂C(O)CH₃ | H | H | F | H | CH₃ | SCH₂CF₃ | H |
| 1-2132 | CH₂CH₂C(O)CH₃ | H | H | F | H | CH₃ | S(O)CH₂CF₃ | H |
| 1-2133 | CH₂CH₂C(O)OCH₃ | H | H | F | H | CH₃ | SCH₂CF₃ | H |
| 1-2134 | CH₂CH₂C(O)OCH₃ | H | H | F | H | CH₃ | S(O)CH₂CF₃ | H |
| 1-2135 | CH₂CH₂SF₅ | H | H | F | H | CH₃ | SCH₂CF₃ | H |
| 1-2136 | CH₂CH₂SF₅ | H | H | F | H | CH₃ | S(O)CH₂CF₃ | H |
| 1-2137 | Si(CH₃)₃ | H | H | F | H | CH₃ | SCH₂CF₃ | H |
| 1-2138 | Si(CH₃)₃ | H | H | F | H | CH₃ | S(O)CH₂CF₃ | H |
| 1-2139 | CH₂CH₂OPh | H | H | F | H | CH₃ | SCH₂CF₃ | H |
| 1-2040 | CH₂CH₂OPh | H | H | F | H | CH₃ | S(O)CH₂CF₃ | H |
| 1-2041 | CH₂CH₂SPh | H | H | F | H | CH₃ | SCH₂CF₃ | H |
| 1-2042 | CH₂CH₂SPh | H | H | F | H | CH₃ | S(O)CH₂CF₃ | H |
| 1-2043 | 2-(propyloxy)pyridine | H | H | F | H | CH₃ | SCH₂CF₃ | H |
| 1-2044 | 2-(propyloxy)pyridine | H | H | F | H | CH₃ | S(O)CH₂CF₃ | H |

TABLE 38

| Comp. No. | R₁ | R₂ | R₃ | R₄ | R₅ | R₆ | R₇ | R₈ |
|---|---|---|---|---|---|---|---|---|
| 1-2045 | (propyl-S-pyridin-2-yl) | H | H | F | H | CH₃ | SCH₂CF₃ | H |
| 1-2046 | (propyl-S-pyridin-2-yl) | H | H | F | H | CH₃ | S(O)CH₂CF₃ | H |
| 1-2047 | CH₂C₂F₅ | OH | H | F | H | CH₃ | SCH₂CF₃ | H |
| 1-2048 | CH₂C₂F₅ | OH | H | F | H | CH₃ | S(O)CH₂CF₃ | H |
| 1-2049 | CH₂C₂F₅ | C(O)OH | H | F | H | CH₃ | SCH₂CF₃ | H |
| 1-2050 | CH₂C₂F₅ | C(O)OH | H | F | H | CH₃ | S(O)CH₂CF₃ | H |
| 1-2051 | CH₂C₂F₅ | C(O)H | H | F | H | CH₃ | SCH₂CF₃ | H |
| 1-2052 | CH₂C₂F₅ | C(O)H | H | F | H | CH₃ | S(O)CH₂CF₃ | H |
| 1-2053 | CH₂C₂F₅ | NO₂ | H | F | H | CH₃ | SCH₂CF₃ | H |
| 1-2054 | CH₂C₂F₅ | NO₂ | H | F | H | CH₃ | S(O)CH₂CF₃ | H |
| 1-2055 | CH₂C₂F₅ | CH₃ | H | F | H | CH₃ | SCH₂CF₃ | H |
| 1-2056 | CH₂C₂F₅ | CH₃ | H | F | H | CH₃ | S(O)CH₂CF₃ | H |
| 1-2057 | CH₂C₂F₅ | OCH₃ | H | F | H | CH₃ | SCH₂CF₃ | H |
| 1-2058 | CH₂C₂F₅ | OCH₃ | H | F | H | CH₃ | S(O)CH₂CF₃ | H |
| 1-2059 | CH₂C₂F₅ | CH₂OCH₃ | H | F | H | CH₃ | SCH₂CF₃ | H |
| 1-2060 | CH₂C₂F₅ | CH₂OCH₃ | H | F | H | CH₃ | S(O)CH₂CF₃ | H |
| 1-2061 | CH₂C₂F₅ | CH=CH₂ | H | F | H | CH₃ | SCH₂CF₃ | H |
| 1-2062 | CH₂C₂F₅ | CH=CH₂ | H | F | H | CH₃ | S(O)CH₂CF₃ | H |
| 1-2063 | CH₂C₂F₅ | C≡CCH₃ | H | F | H | CH₃ | SCH₂CF₃ | H |
| 1-2064 | CH₂C₂F₅ | C≡CCH₃ | H | F | H | CH₃ | S(O)CH₂CF₃ | H |
| 1-2065 | CH₂C₂F₅ | C(O)CH₃ | H | F | H | CH₃ | SCH₂CF₃ | H |
| 1-2066 | CH₂C₂F₅ | C(O)CH₃ | H | F | H | CH₃ | S(O)CH₂CF₃ | H |
| 1-2067 | CH₂C₂F₅ | H | OH | F | H | CH₃ | SCH₂CF₃ | H |
| 1-2068 | CH₂C₂F₅ | H | OH | F | H | CH₃ | S(O)CH₂CF₃ | H |
| 1-2069 | CH₂C₂F₅ | H | CH=CH₂ | F | H | CH₃ | SCH₂CF₃ | H |
| 1-2070 | CH₂C₂F₅ | H | CH=CH₂ | F | H | CH₃ | S(O)CH₂CF₃ | H |
| 1-2071 | CH₂C₂F₅ | H | C≡CCH₃ | F | H | CH₃ | SCH₂CF₃ | H |
| 1-2072 | CH₂C₂F₅ | H | C≡CCH₃ | F | H | CH₃ | S(O)CH₂CF₃ | H |
| 1-2073 | CH₂C₂F₅ | H | CH₂Pr-C | F | H | CH₃ | SCH₂CF₃ | H |
| 1-2074 | CH₂C₂F₅ | H | CH₂Pr-C | F | H | CH₃ | S(O)CH₂CF₃ | H |
| 1-2075 | CH₂C₂F₅ | H | C(O)CH₃ | F | H | CH₃ | SCH₂CF₃ | H |
| 1-2076 | CH₂C₂F₅ | H | C(O)CH₃ | F | H | CH₃ | S(O)CH₂CF₃ | H |
| 1-2077 | CH₂C₂F₅ | H | CH₂OCH₃ | F | H | CH₃ | SCH₂CF₃ | H |
| 1-2078 | CH₂C₂F₅ | H | CH₂OCH₃ | F | H | CH₃ | S(O)CH₂CF₃ | H |
| 1-2079 | CH₂C₂F₅ | H | NHCN | F | H | CH₃ | SCH₂CF₃ | H |
| 1-2080 | CH₂C₂F₅ | H | NHCN | F | H | CH₃ | S(O)CH₂CF₃ | H |
| 1-2081 | CH₂C₂F₅ | H | NHCH₂Pr-c | F | H | CH₃ | SCH₂CF₃ | H |
| 1-2082 | CH₂C₂F₅ | H | NHCH₂Pr-c | F | H | CH₃ | S(O)CH₂CF₃ | H |
| 1-2083 | CH₂C₂F₅ | H | NHC₂H₄OCH₃ | F | H | CH₃ | SCH₂CF₃ | H |
| 1-2084 | CH₂C₂F₅ | H | NHC₂H₄OCH₃ | F | H | CH₃ | S(O)CH₂CF₃ | H |
| 1-2085 | CH₂C₂F₅ | H | NHC(O)C(O)CH₃ | F | H | CH₃ | SCH₂CF₃ | H |
| 1-2086 | CH₂C₂F₅ | H | NHC(O)C(O)CH₃ | F | H | CH₃ | S(O)CH₂CF₃ | H |
| 1-2087 | CH₂C₂F₅ | H | NHC(O)C(O)OCH₃ | F | H | CH₃ | SCH₂CF₃ | H |
| 1-2088 | CH₂C₂F₅ | H | NHC(O)C(O)OCH₃ | F | H | CH₃ | S(O)CH₂CF₃ | H |
| 1-2089 | CH₂C₂F₅ | H | NCH(O)CH₂C≡CH | F | H | CH₃ | SCH₂CF₃ | H |
| 1-2090 | CH₂C₂F₅ | H | NCH(O)CH₂C≡CH | F | H | CH₃ | S(O)CH₂CF₃ | H |
| 1-2091 | CH₂C₂F₅ | H | NHC(O)NH₂ | F | H | CH₃ | SCH₂CF₃ | H |
| 1-2092 | CH₂C₂F₅ | H | NHC(O)NH₂ | F | H | CH₃ | S(O)CH₂CF₃ | H |
| 1-2093 | CH₂Ph{4-S(O)₂CF₃} | H | CH₃ | F | H | CH₃ | SCH₂CF₃ | H |
| 1-2094 | CH₂Ph{4-S(O)₂CF₃} | H | CH₃ | F | H | CH₃ | S(O)CH₂CF₃ | H |
| 1-2095 | CH₂Ph{4-OS(O)₂CF₃} | H | CH₃ | F | H | CH₃ | SCH₂CF₃ | H |
| 1-2096 | CH₂Ph{4-OS(O)₂CF₃} | H | CH₃ | F | H | CH₃ | S(O)CH₂CF₃ | H |

The compounds of the present invention represented by the following formula [I] can be produced in accordance with the following production processes. However, their production is not limited to these processes.

Hereinafter, for example, a compound represented by the formula [I-I] and "a compound [I-I]" are the same.

<Production Process 1>

A compound of the present invention of the formula [I] can be produced by a process exemplified by the following scheme:

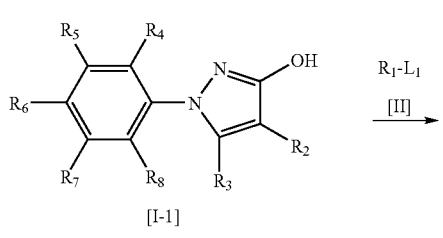

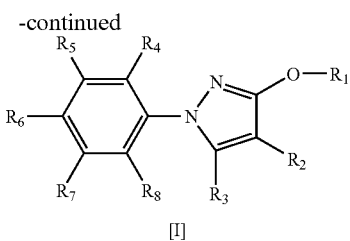

[I]

wherein $R_1$, $R_2$, $R_3$, $R_4$, $R_5$, $R_6$, $R_7$ and $R_8$ are as defined above, and $L_1$ is a halogen atom, a $C_1$-$C_8$ alkylsulfonyloxy group (which may be mono-substituted or poly-substituted by halogen atom), a benzenesulfonyloxy group (which may be mono-substituted or poly-substituted by a halogen atom, a lower alkyl group or a nitro group), a hydroxy group or a dihydroxyboryl group ($B(OH)_2$). As the compound [II], for example, an iodonium compound, a perfluoro $C_2$-$C_{10}$ alkylolefin, a perfluoro $C_1$-$C_8$ alkoxytrifluoroethylene, diazomethane or trimethylsilyldiazomethane may also be used.

The compound of the present invention represented by the formula [I] can be produced by reacting the compound [I-1] with the compound [II] in a solvent in the presence or absence of a base. Further, in a case where $L_1$ is a dihydroxyboryl group ($B(OH)_2$), it can be produced by reaction in the presence of a catalyst.

Further, in a case where $R_2$ and $R_3$ are a hydroxy group, production is possible in the same manner as above.

The amount of use of the compound [II] may be properly selected from a range of from 1 to 100 mols per 1 mol of the compound [I-1], and is preferably from 1.1 to 3.3mols.

The solvent to be used in this reaction may, for example, be an ether such as diethyl ether, tetrahydrofuran or dioxane; an aromatic hydrocarbon such as benzene, toluene, xylene or chlorobenzene; a halogenated hydrocarbon such as dichloromethane, chloroform or dichloroethane; an aprotic polar solvent such as N,N-dimethylformamide, N,N-dimethylacetamide, N-methyl-2-pyrrolidone, dimethylsulfoxide or sulfolane; an alcohol such as methanol, ethanol or isopropyl alcohol; a nitrile such as acetonitrile or propionitrile; an ester such as ethyl acetate, ethyl propionate; an aliphatic hydrocarbon such as pentane, hexane, cyclohexane or heptane; a pyridine such as pyridine or picoline; or water; or a solvent mixture thereof.

The amount of the above solvent is from 0.5 to 100 L per 1 mol of the compound [I-1], preferably from 1.0 to 10 L.

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or an alkali metal bicarbonate such as sodium hydrogen carbonate or potassium hydrogen carbonate; a metal hydride such as sodium hydride or potassium hydride; a metal salt of an alcohol such as sodium methoxide, sodium ethoxide or potassium tert-butoxide; or an organic base such as triethylamine, N,N-dimethylaniline, pyridine, 4-N,N-dimethylaminopyridine or 1,8-diazabicyclo[5.4.0]-7-undecene.

The amount of use of the base may be properly selected from a range of from 0 to 5 mols per 1 mol of the compound [I-1], and is preferably from 0 to 1.2 mols.

The reaction temperature may be optionally selected from a range of from −30° C. to the reflux temperature of the reaction system, and it is preferably within a range of from 0° C. to 150° C.

The reaction time varies depending upon the reaction temperature, the reaction substrate, the reaction amount, etc., and it is usually from 10 minutes to 20 hours.

In a case where a compound [II] wherein $L_1$ is a hydroxy group is used, the compound [I] can be produced also by using an azodicarboxylic acid ester in a solvent in the presence of triphenylphosphine.

The azodicarboxylic acid ester may, for example, be diethyl azodicarboxylate or dibenzyl azodicarboxylate.

The amount of use of triphenylphosphine is from 1 to 3 mols, preferably 1.1mols per 1 mol of the compound [I-1].

The amount of use of azodicarboxylic acid ester is from 1 to 3 mols, preferably 1.1 mols per 1 mol of the compound [I-1].

The solvent to be preferably used may, for example, be an ether such as diethyl ether, tetrahydrofuran or dioxane.

Further, in a case where a perfluoro $C_2$-$C_{10}$ alkylolefin or a perfluoro $C_1$-$C_8$ alkoxytrifluoroethylene or the like is used as the compound [II], the solvent may, for example, be preferably an ether such as diethyl ether, tetrahydrofuran or dioxane; an aromatic hydrocarbon such as benzene, toluene, xylene or chlorobenzene; or an aprotic polar solvent such as acetonitrile, N,N-dimethylformamide, N,N-dimethylacetamide, N-methyl-2-pyrrolidone, dimethylsulfoxide or sulfolane.

The base to be used in this reaction may, for example, be preferably an organic base such as triethylamine, N,N-dimethylaniline, pyridine, 4-N,N-dimethylaminopyridine or 1,8-diazabicyclo[5.4.0]-7-undecene, and two types of bases may be used simultaneously.

The amount of use of the base is from 0.01 to 1,000 mols, preferably from 0.1to 50 mols per 1 mol of the compound [II], and this amount of use is the same as the amount of use of the catalyst and the amount of use of a solvent.

The reaction temperature may be optionally selected from a range of from −30° C. to the reflux temperature of the reaction system, and it is preferably within a range of from 0° C. to 50° C. The reaction time varies depending upon the reaction temperature, the reaction substrate, the reaction amount, etc., and it is usually from 1 to 20 hours.

The perfluoro $C_2$-$C_{10}$ alkylolefin may, for example, be hexafluoropropene, and the perfluoro $C_1$-$C_8$ alkoxytrifluoroethylene may, for example, be trifluoromethoxytrifluoroethylene, pentafluoroethoxytrifluoroethylene or heptafluoropropoxytrifluoroethylene.

Further, in a case where an iodonium compound is used as the compound [II], the amount of use is from 1 to 10 mols, preferably from 1 to 3 mols per 1 mol of the compound [II].

The solvent to be used may, for example, be preferably a halogenated hydrocarbon such as dichloromethane or dichloroethane, and the base to be used may, for example, be preferably a pyridine such as pyridine.

The reaction temperature may be optionally selected from a range of from −30° C. to the reflux temperature of the reaction system, and it is preferably within a range of from 0° C. to 50° C. The reaction time varies depending upon the reaction temperature, the reaction substrate, the reaction amount, etc., and it is usually from 5 minutes to 20 hours.

The iodonium compound may, for example, be perfluoropropyl phenyliodonium trifluoromethanesulfonate, perfluoroisopropyl phenyliodonium trifluoromethanesulfonate, perfluorobutyl phenyliodonium trifluoromethanesulfonate, perfluoropentyl phenyliodonium trifluoromethanesulfonate, perfluorohexyl phenyliodonium trifluoromethanesulfonate or perfluorooctyl phenyliodonium trifluoromethanesulfonate.

In a case where $L_1$ is a dihydroxyboryl group ($B(OH)_2$), the solvent to be used in this reaction may, for example, be preferably a halogenated hydrocarbon such as dichloromethane or dichloroethane, and the base to be used may, for example, be preferably an organic base such as triethylamine, N,N-dimethylaniline, pyridine, 4-N,N-dimethylaminopyridine or 1,8-diazabicyclo[5.4.0]-7-undecene, and two types of bases may be used simultaneously.

The amount of use of a compound wherein $L_1$ is a dihydroxyboryl group ($B(OH)_2$) is from 1 to 10 mols, preferably from 1 to 3 mols per 1 mol of the compound [II].

In this reaction, as the catalyst, copper acetate may be used, and its amount of use is from 0.1 to 10 mols, preferably from 1 to 3 mols per 1 mol of the compound [II]. Further, in such a case, powdery molecular sieves 4 A may be used as an additive, and the amount of use is from 1 to 100 g, preferably from 10 to 20 g per 1 g of the compound [II].

The reaction temperature may be optionally selected from a range of from −30° C. to the reflux temperature of the reaction system, and it is preferably within a range of room temperature.

The reaction time varies depending upon the reaction temperature, the reaction substrate, the reaction amount, etc., and it is usually from 1 to 48 hours.

<Production Process 2>

A compound of the present invention represented by the formula [I-a] can be produced also by a process exemplified by the following scheme:

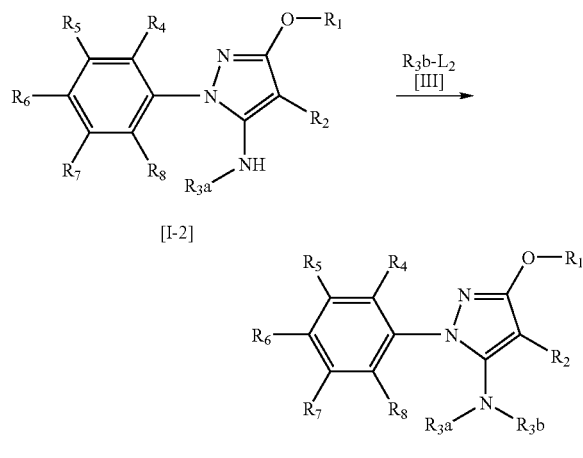

wherein $R_1$, $R_2$, $R_4$, $R_5$, $R_6$, $R_7$, $R_8$, $R_{3a}$ and $R_{3b}$ are as defined above, and $L_2$ is a halogen atom, a $C_1$-$C_8$ alkylsulfonyloxy group (which may be mono-substituted or poly-substituted by a halogen atom), a benzenesulfonyloxy group (which may be mono-substituted or poly-substituted by a halogen atom, a lower alkyl group or a nitro group), a $C_1$-$C_8$ alkylcarbonyloxy group (which may be mono-substituted or poly-substituted by a halogen atom), or a hydroxy group.

That is, the compound of the present invention of the formula [I] can be produced by reacting the compound [I-2] with the compound [III] in a solvent in the presence or absence of a base.

The amount of use of the compound [III] may be properly selected from a range of from 1 to 100 mols per 1 mol of the compound [I-2], and is preferably from 1.1 to 2.2mols.

The solvent to be used in this reaction may, for example, be an ether such as diethyl ether, tetrahydrofuran or dioxane; an aromatic hydrocarbon such as benzene, toluene, xylene or chlorobenzene; a halogenated hydrocarbon such as dichloromethane, chloroform or dichloroethane; an aprotic polar solvent such as N,N-dimethylformamide, N,N-dimethylacetamide, N-methyl-2-pyrrolidone, dimethylsulfoxide or sulfolane; an alcohol such as methanol, ethanol or isopropyl alcohol; a nitrile such as acetonitrile or propionitrile; an ester such as ethyl acetate or ethyl propionate; an aliphatic hydrocarbon such as pentane, hexane, cyclohexane or heptane; a pyridine such as pyridine or picoline; or water; or a solvent mixture thereof.

The amount of the solvent is from 0.5 to 100 L, preferably from 1 to 10 L per 1mol of the compound [I-2].

The base to be used in this reaction may, for example, be an inorganic base such as a hydroxide of an alkali metal such as sodium hydroxide or potassium hydroxide, a hydroxide of an alkaline earth metal such as calcium hydroxide or magnesium hydroxide, a carbonate of an alkali metal such as sodium carbonate or potassium carbonate, or an alkali metal bicarbonate such as sodium hydrogen carbonate or potassium hydrogen carbonate; a metal hydride such as sodium hydride or potassium hydride; a metal salt of an alcohol such as sodium methoxide, sodium ethoxide or potassium tert-butoxide; or an organic base such as triethylamine, N,N-dimethylaniline, pyridine, 4-N,N-dimethylaminopyridine or 1,8-diazabicyclo[5.4.0]-7-undecene; or ammonia.

The amount of use of the base may be properly selected from a range of from 0 to 5 mols per 1 mol of the compound [I-2], and is preferably from 0 to 2.2 mols.

The reaction temperature may be optionally selected from a range of from −30° C. to the reflux temperature of the reaction system, and it is preferably within a range of from 0° C. to 150° C.

The reaction time varies depending upon the reaction temperature, the reaction substrate, the reaction amount, etc., and it is usually from 10 minutes to 20 hours.

<Production Process 3>

A compound of the present invention represented by the formula [I-b] can be produced by a process exemplified by the following scheme:

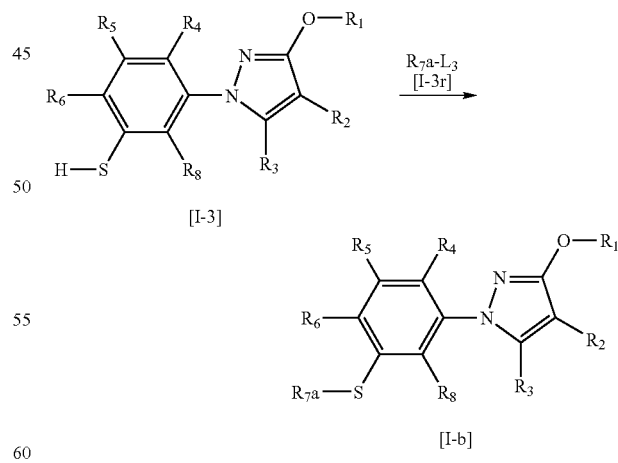

wherein $R_1$, $R_2$, $R_3$, $R_4$, $R_5$, $R_6$ and $R_8$, are as defined above, $R_{7a}$ is a $C_2$-$C_4$ haloalkyl group, a $C_2$-$C_4$ haloalkenyl group or a cyclopropylmethyl group (which may be mono-substituted or poly-substituted by a halogen atom), and $L_3$ is a halogen atom, a $C_1$-$C_8$ alkylsulfonyloxy group (which may be mono-substituted or poly-substituted by a halogen atom), or a benzenesulfonyloxy group (which may be mono-substituted or poly-substituted by a halogen atom, a lower alkyl group or a nitro group).

That is, the compound of the present invention of the formula [I-b] can be produced by reacting the compound [I-3] with the compound [I-3r] in a solvent in the presence or absence of a base or a radical initiator. Further, a disulfide compound which is an oxidative dimer of the compound [I-3] may be used instead of the compound [I-3].

The amount of use of the compound [I-3r] may be properly selected from a range of from 1 to 5 mols per 1 mol of the compound [I-3], and is preferably from 1 to 1.5 mols.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as N,N-dimethylformamide, N,N-dimethylacetamide, N-methyl-2-pyrrolidone, dimethylsulfoxide or sulfolane; an alcohol such as methanol, ethanol or methyl cellosolve; an aliphatic hydrocarbon such as pentane, hexane, cyclohexane or heptane; a pyridine such as pyridine or picoline; or water; or a solvent mixture thereof.

The amount of the solvent is from 0.5 to 100 L, preferably from 1 to 10 L per 1mol of the compound [I-3].

The base to be used in this reaction may be the same one as defined for the above Production Process 2.

The amount of the base may be properly selected from a range of from 0 to 5mols per 1 mol of the compound [I-3], and is preferably from 0 to 1.5 mols.

The radical initiator to be used in this reaction may, for example be sulfurous acid, a sulfite salt or a sulfite adduct such as Rongalit (sodium formaldehyde sulfoxylate).

In a case where the radical initiator is used, its amount of use may be properly selected from a range of from 0.01 to 5 mols per 1 mol of the compound [I-3], and is preferably from 0.05 to 1.2 mols.

The reaction temperature may be optionally selected from a range of from 0° C. to the reflux temperature of the reaction system, and it is preferably within a range of from 20° C. to 60° C.

The reaction time varies depending upon the reaction temperature, the reaction substrate, the reaction amount, etc., and it is usually from 30 minutes to 20 hours.

<Production Process 4>

A compound of the present invention represented by the formula [I-2] can be produced by a process exemplified by the following scheme:

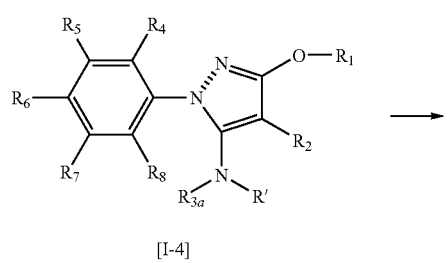

[I-4]

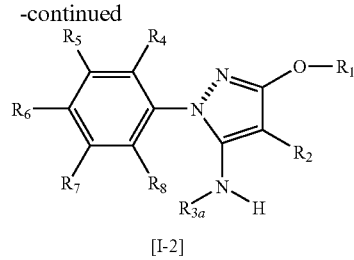

[I-2]

wherein $R_1$, $R_2$, $R_4$, $R_5$, $R_6$, $R_7$, $R_8$ and $R_{3a}$ are as defined above, and R' is an acetyl group.

That is, the compound of the present invention represented by the formula [I-2] can be produced by reacting the compound [I-4] in a solvent in the presence or absence of a base or an acid.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as N,N-dimethylformamide, N,N-dimethylacetamide, N-methyl-l-2-pyrrolidone, dimethylsulfoxide or sulfolane; an alcohol such as methanol, ethanol or methyl cellosolve; an aliphatic hydrocarbon such as pentane, hexane, cyclohexane or heptane; a pyridine such as pyridine or picoline; water, a carboxylic acid such as acetic acid; or a solvent mixture thereof.

The amount of use of the solvent is from 0.5 to 100 L, preferably from 1 to 10 L per 1 mol of the compound [I-4].

The base to be used in this reaction may be the same one as defined for the above Production Process 2. The amount of use of the base may be properly selected from a range of from 0 to 10 mols per 1 mol of the compound [I-4], and is preferably from 0 to 2 mols.

The acid to be used in this reaction may, for example, be a sulfonic acid such as methanesulfonic acid or p-toluenesulfonic acid; an inorganic acid such as hydrochloric acid, hydrobromic acid or sulfuric acid, or a carboxylic acid such as acetic acid or trifluoroacetic acid.

The amount of use of the acid may be properly selected from a range of from 0to 100 mols per 1 mol of the compound [I-4], and is preferably from 0 to 10 mols.

The reaction temperature may be optionally selected from a range of from 0° C. to the reflux temperature of the reaction system, and it is preferably within a range of from 20° C. to 120° C.

The reaction time varies depending upon the reaction temperature, the reaction substrate, the reaction amount, etc., and it is usually from 0.5 to 48 hours.

<Production Process 5>

A compound of the present invention represented by the formula [I] can be produced also by a process exemplified by the following scheme:

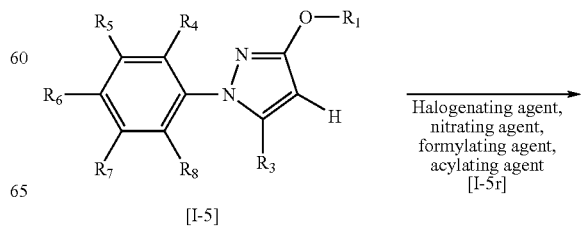

[I-5]

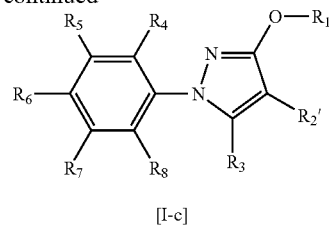

[I-c]

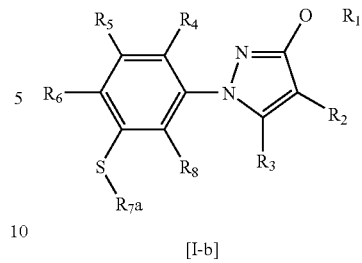

[I-b]

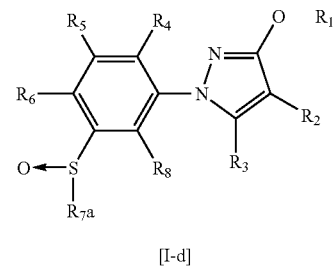

[I-d]

wherein $R_1$, $R_3$, $R_4$, $R_5$, $R_6$, $R_7$ and $R_8$ are as defined above, and R2' is a halogen atom, a nitro group, a formyl group or a trifluoroacetyl group.

That is, the compound of the present invention represented by the formula [I-c] can be produced by reacting the compound [I-5] with a halogenating agent, a nitrating agent, a formylating agent or an acylating agent in a solvent.

The halogenating agent may, for example, be fluorine, chlorine, bromine, iodine, N-chlorosuccinimide, N-bromosuccinimide, N-iodosuccinimide, sulfuryl chloride, iodine monochloride, tert-butyl hypochlorite, N-fluoro-N'-(chloromethyl)-triethylenediaminebis(tetrafluoroborate) or 1-fluoro-2,6-dichloropyridinium tetrafluoroborate.

The nitrating agent may, for example, be nitric acid, potassium nitrate, fuming nitric acid or nitronium tetrafluoroborate.

The formylating agent may, for example, be a Vilsmeier reagent.

The acylating agent may, for example, be trifluoroacetic anhydride.

As a Lewis acid catalyst, aluminum chloride, titanium tetrachloride, iron or ferric chloride may, for example, be used. The amount of use of the Lewis acid catalyst may be properly selected from a range of from 1 to 5 mols per 1 mol of the compound [I-5], and is preferably from 1 to 2 mols.

The amount of use of the halogenating agent, the nitrating agent, the formylating agent or the acylating agent may be properly selected from a range of from 1 to 5 mols per 1 mol of the compound [I-5], and is preferably from 1 to 2 mols.

The solvent to be used in this reaction may, for example, be sulfuric acid; an ether such as diethyl ether, tetrahydrofuran or dioxane; an aromatic hydrocarbon such as benzene, toluene, xylene or chlorobenzene; a halogenated hydrocarbon such as dichloromethane, chloroform or dichloroethane; an aprotic polar solvent such as N,N-dimethylformamide, N,N-dimethylacetamide, N-methyl-2-pyrrolidone, dimethylsulfoxide or sulfolane; an alcohol such as methanol, ethanol or isopropyl alcohol; a nitrile such as acetonitrile or propionitrile; water; a carboxylic acid such as acetic acid; an acid anhydride such as acetic anhydride; pyridine; carbon disulfide; or a solvent mixture thereof.

The amount of use of the solvent is from 0.5 to 100 L, preferably from 1 to 10 L per 1 mol of the compound [I-5].

The reaction temperature may be optionally selected from a range of from −60° C. to the reflux temperature of the reaction system, and it is preferably within a range of from −20° C. to 100° C.

The reaction time varies depending upon the reaction temperature, the reaction substrate, the reaction amount, etc., and it is usually from 10 minutes to 20 hours.

<Production Process 6>

A compound of the present invention represented by the formula [I-d] can be produced also by a process exemplified by the following scheme:

wherein $R_1$, $R_2$, $R_3$, $R_4$, $R_5$, $R_6$, $R_8$ and $R_{7a}$ are as defined above.

The compound [I-d] of the present invention can be produced by reacting the compound [I-b] with an oxidizing agent in a solvent in the presence or absence of a catalyst.

The oxidizing agent to be used in this reaction may, for example, be hydrogen peroxide, m-chloroperbenzoic acid, perbenzoic acid, sodium periodate, OXONE (tradename, manufactured by E.I. DuPont, containing potassium hydrogenperoxosulfate), N-chlorosuccinimide, N-bromosuccinimide, tert-butyl hypochlorite or sodium hypochlorite.

The amount of use of the oxidizing agent may be properly selected from a range of from 1 to 6 mols per 1 mol of the compound [I-b], and is preferably from 1 to 1.2 mols.

The catalyst to be used in this reaction may, for example, be sodium tungstate.

The amount of use of the catalyst may be properly selected from a range of from 0 to 1 mol per 1 mol of the compound [I-b], and is preferably from 0.001 to 0.1mol.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as acetonitrile, N,N-dimethylformamide, N,N-dimethylacetamide, N-methyl-2-pyrrolidone, dimethylsulfoxide or sulfolane; an alcohol such as methanol, ethanol or isopropyl alcohol; a halogenated hydrocarbon such as dichloromethane, chloroform or dichloroethane; an aliphatic hydrocarbon such as pentane, hexane, cyclohexane or heptane; a ketone such as acetone, methyl ethyl ketone or cyclohexanone; a carboxylic acid such as acetic acid; water; or a solvent mixture thereof.

The amount of use of the solvent is from 0.5 to 100 L, preferably from 1 to 10 L per 1 mol of the compound [I-b].

The reaction temperature may be optionally selected from a range of from −60° C. to the reflux temperature of the reaction system, and it is preferably within a range of from 0° C. to 50° C.

The reaction time varies depending upon the reaction temperature, the reaction substrate, the reaction amount, etc., and it is usually from 10 minutes to 20 hours.

<Production Process 7>

An intermediate compound [I-1a] for production of the compound [I] as a starting material in the production process 1, which is a compound of the present invention, can be produced by a process exemplified by the following scheme:

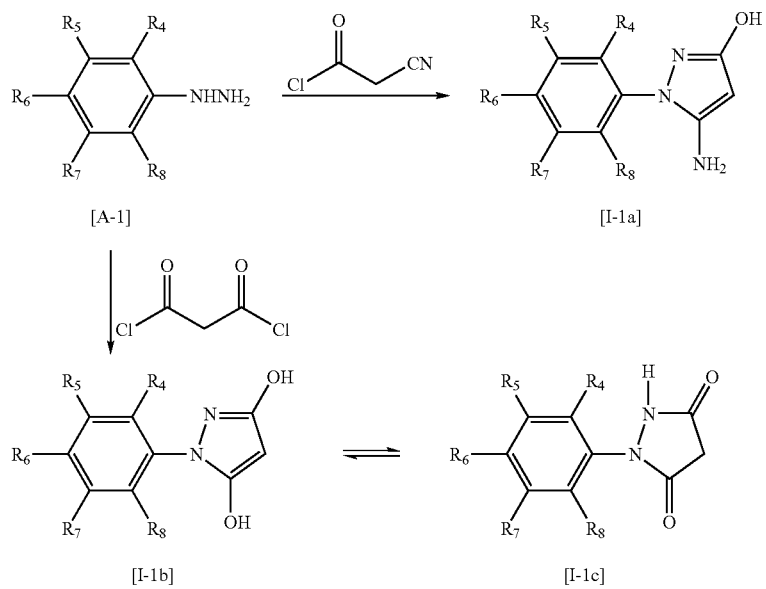

wherein R$_4$, R$_5$, R$_6$, R$_7$ and R$_8$ are as defined above.

The compound [I-1a] can be produced by reacting the compound [A-1] with cyanoacetyl chloride in the presence or absence of an acid or a base.

The compound [I-1b] can be produced by reacting the compound [A-1] with malonyl chloride in the presence or absence of an acid or a base (J. Am. Chem. Soc., Vol. 65, No. 53 (1943)). The compounds [I-1b] and [I-1c] are in a chemical equilibrium state.

The acid to be used for production of the compound [I-1a] and the compound [I-1b] may, for example, be a sulfonic acid such as methanesulfonic acid or p-toluenesulfonic acid; an inorganic acid such as hydrochloric acid, hydrobromic acid or sulfuric acid; or a carboxylic acid such as acetic acid or trifluoroacetic acid.

The amount of use of cyanoacetyl chloride may be properly selected from a range of from 1 to 3 mols per 1 mol of the compound [A-1], and is preferably from 1 to 1.5 mols.

The base to be used in this reaction may be the same one as defined for the above Production Process 2.

The amount of use of the acid or the base may be properly selected from a range of from 0 to 10 mols per 1 mol of the compound [A-1], and is preferably from 0.001 to 1 mol.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as acetonitrile, N,N-dimethylformamide, N,N-dimethylacetamide, N-methyl-2-pyrrolidone, dimethylsulfoxide or sulfolane; an alcohol such as methanol, ethanol, propanol or isopropyl alcohol; a halogenated hydrocarbon such as dichloromethane, chloroform or dichloroethane; an aliphatic hydrocarbon such as pentane, hexane, cyclohexane or heptane; a ketone such as acetone, methyl ethyl ketone or cyclohexanone; a carboxylic acid such as acetic acid; water; or a solvent mixture thereof.

The amount of use of the solvent is from 0.5 to 100 L, preferably from 1 to 10 L per 1 mol of the compound [A-1].

The reaction temperature may be optionally selected from a range of from 0° C. to the reflux temperature of the reaction system, and it is preferably within a range of from 0° C. to 70° C.

The reaction time varies depending upon the reaction temperature, the reaction substrate, the reaction amount, etc., and it is usually from 10 minutes to 20 hours.

<Production Process 8>

A compound [I-1] which is a compound of the present invention and which is a starting material in Production Process 1 can be produced by a process exemplified by the following scheme:

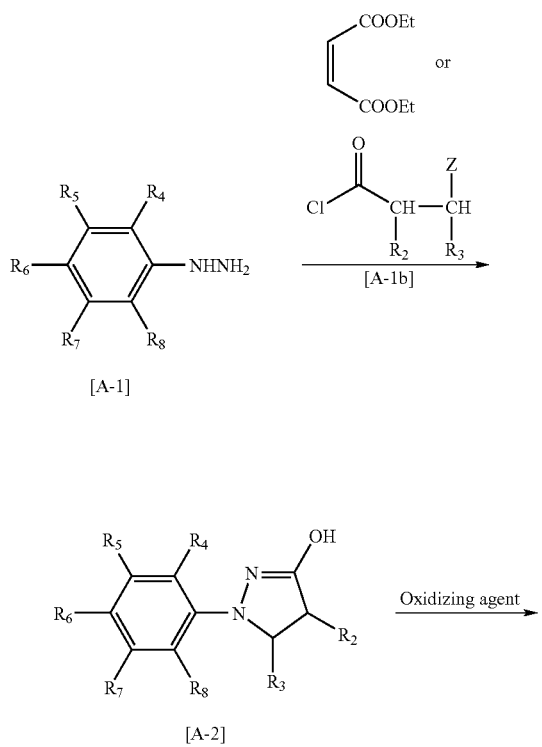

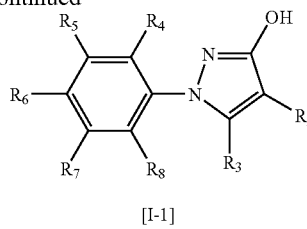

[I-1]

wherein Z is a halogen atom, and $R_2$, $R_3$, $R_4$, $R_5$, $R_6$, $R_7$ and $R_8$ are as defined above.

The compound [A-1] and the compound [A-1b] are reacted in a solvent in the presence of a base to produce the compound [A-2], which is then reacted with an oxidizing agent to produce the compound [I-1].

The amount of use of the compound [A-1] may be properly selected from a range of from 1 to 2 mols per 1 mol of the compound [A-1b], and is preferably 1 mol.

The base to be used in this reaction may be the same base as defined for the above Production Process 2.

The amount of use of the base may be properly selected from a range of from 1 to 5 mols per 1 mol of the compound [A-1b], and is preferably from 1 to 2 mol.

The oxidizing agent to be used in this reaction may, for example, be hydrogen peroxide, m-chloroperbenzoic acid, perbenzoic acid, sodium periodate, OXONE (tradename, manufactured by E.I. DuPont, containing potassium hydrogenperoxosulfate), N-chlorosuccinimide, N-bromosuccinimide, tert-butyl hypochlorite, sodium hypochlorite, potassium permanganate or manganese dioxide. Further, such an oxidizing agent may be used in combination with a base, and further, by adding an ammonium salt such as tetra-n-butylammonium bromide, the reaction will be accelerated.

The amount of use of the oxidizing agent may be properly selected from a range of from 0.5 to 5 mols per 1 mol of the compound [A-2], and is preferably from 0.5 to 2 mols.

The solvent to be used in this reaction may be the same solvent as defined for the above Production Process 7.

The amount of use of the solvent is from 0.5 to 100 L, preferably from 1 to 10 L per 1 mol of the compound [A-1] or the compound [A-2].

In both the reactions, the reaction temperature may be optionally selected from a range of from 0° C. to the reflux temperature of the reaction system, and it is preferably within a range of from 0° C. to 50° C. The reaction time varies depending upon the reaction temperature, the reaction substrate, the reaction amount, etc., and it is usually from 10 minutes to 10 hours.

<Production Process 9>

The compound [I-1] which is a compound of the present invention and which is a starting material in Production Process 1 can be produced also by a process exemplified by the following scheme:

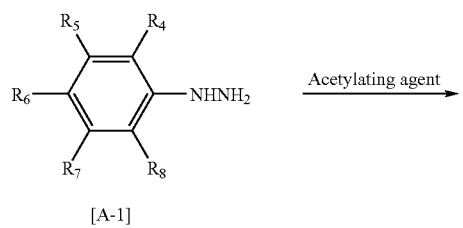

[A-1]

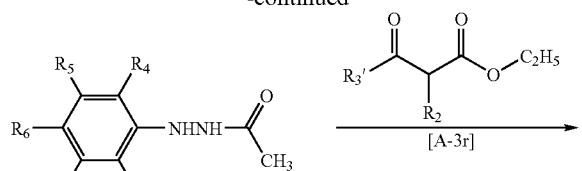

[A-3]

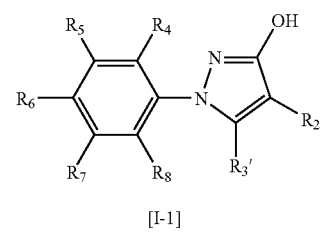

[I-1]

wherein R3' is a methyl group or an ethoxycarbonyl group, and $R_2$, $R_4$, $R_5$, $R_6$, $R_7$ and $R_8$ are as defined above.

The compound [A-1] is acetylated in accordance with a conventional method to produce the compound [A-3], which is reacted with the compound [A-3r] to produce the compound [I-1] (a method disclosed in WO2006/021462).

The acetylating agent to be used may, for example, be acetyl chloride or acetic anhydride.

The amount of use of the acetylating agent may be properly selected from a range of from 1 to 3 mols per 1 mol of the compound [A-1], and is preferably from 1 to 1.2 mols.

The amount of use of the compound [A-3r] may be properly selected from a range of from 1 to 5 mols per 1 mol of the compound [A-3], and is preferably from 1 to 2 mols.

The reaction temperature may be optionally selected from a range of from 0° C. to the reflux temperature of the reaction system, and it is preferably within a range of from 0° C. to 100° C.

The reaction time varies depending upon the reaction temperature, the reaction substrate, the reaction amount, etc., and it is usually from 10 minutes to 10 hours.

<Production Process 10>

The compound [I-3] which is a starting material in Production Process 3, can be produced by a process exemplified by the following scheme:

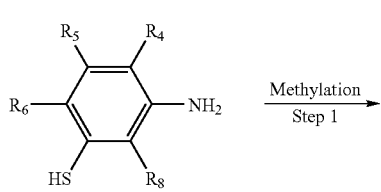

[I-3a]

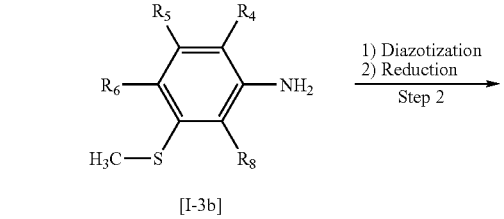

[I-3b]

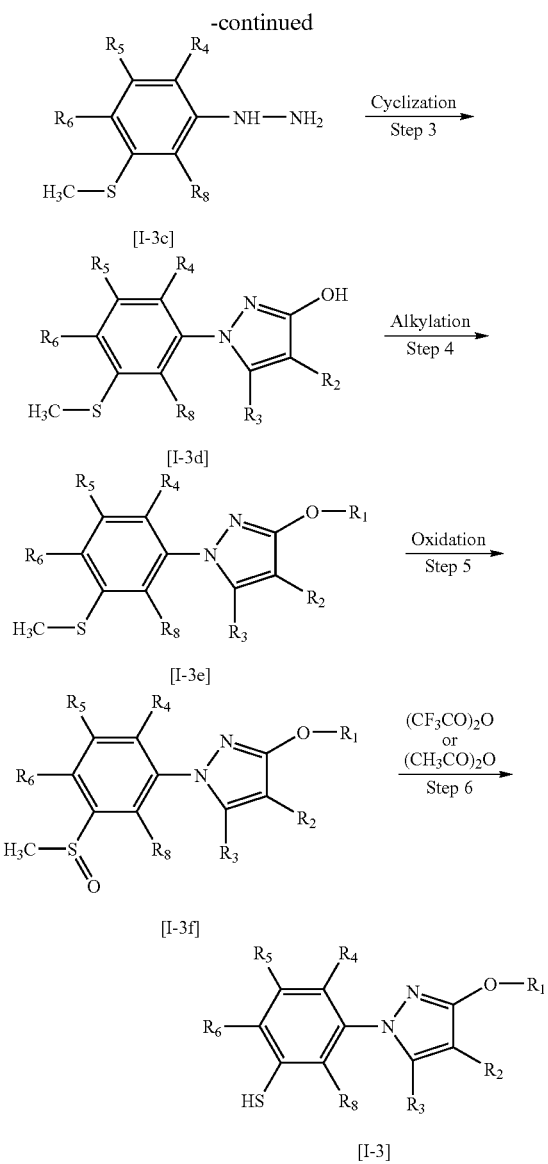

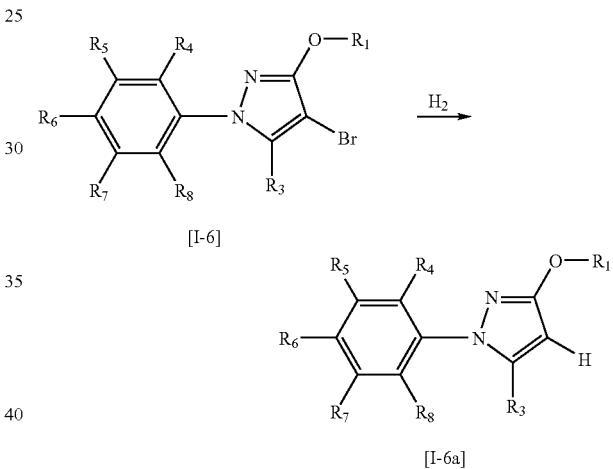

wherein $R_1$, $R_2$, $R_3$, $R_4$, $R_5$, $R_6$ and $R_8$ are as defined above.

The compound [I-3a] is methylated to obtain the compound [I-3b] (step 1), which is diazotized and reduced to produce the compound [I-3c] (step 2). This production process is disclosed in WO2006/043635.

The compound [I-3d] can be produced in the same manner as in the above Production Process 7 or 8 (step 3).

Further, the compound [I-3e] can be produced in the same manner as in the above Production Process 1 (step 4), and the compound [I-3f] can be produced in the same manner as in the above production process 6 (step 5).

The compound [I-3] can be produced by reacting the compound [I-3f] with trifluoroacetic anhydride or acetic anhydride in the presence of a base in or without a solvent (step 6).

The amount of use of trifluoroacetic anhydride may be properly selected from a range of from 1 to 100 mols per 1 mol of the compound [I-3f], and is preferably from 1.1 to 1.2 mol. In a case where acetic anhydride is used, its amount may be properly selected from a range of from 1 to 100 mols per 1 mol of the compound [I-3f], and is preferably the same amount as the reaction solvent.

The solvent to be used in this step 6 may, for example, be an aromatic hydrocarbon such as benzene, toluene, xylene or chlorobenzene; a halogenated hydrocarbon such as dichloromethane; or a solvent mixture thereof.

The amount of use of the solvent is from 0.5 to 100 L, preferably from 0 to 10 L per 1 mol of the compound [I-3f].

The base to be used in this step 6 may be the same base as defined for the production process 2. The amount of use of the base may be properly selected from a range of from 3 to 10 mols per 1 mol of the compound [I-3f], and is preferably from 3 to 5 mols.

The reaction temperature may be optionally selected from a range of from −30° C. to the reflux temperature of the reaction system, and it is preferably within a range of from 0° C. to 150° C.

The reaction time varies depending upon the reaction temperature, the reaction substrate, the reaction amount, etc., and it is usually from 10 minutes to 20 hours.

<Production Process 11>

The compound of the present invention represented by the formula [I-6a] can be produced also by a process exemplified by the following scheme:

wherein $R_1$, $R_3$, $R_4$, $R_5$, $R_6$, $R_7$ and $R_8$ are as defined above.

That is, the compound of the present invention represented by the formula [I-6a] can be produced by reacting the compound [I-6] with hydrogen in the presence of a metal catalyst in the presence or absence of a base in a solvent.

The amount of use of hydrogen may be properly selected from a range of from 1 to 1.3 mols per 1 mol of the compound [I-6], and is preferably from 1 to 1.1 mols.

As the metal catalyst, for example, a palladium catalyst such as palladium-carbon may be used, and the amount of use of the catalyst may be properly selected from a range of from 0.1 to 1 part by mass per 1 part by mass of the compound of the formula [I-6], and is preferably from 0.2 to 0.5 part by mass.

The base to be used in this step may be the same base as defined for the above Production Process 2.

The amount of use of the base may be properly selected from a range of from 0 to 5 mols per 1 mol of the compound [I-6], and is preferably from 0 to 1.1 mols.

The solvent to be used in this reaction may, for example, be an alcohol such as methanol, ethanol or isopropyl alcohol; a carboxylic acid such as acetic acid; water; or a solvent mixture thereof.

The amount of use of the solvent is from 0.5 to 100 L, preferably from 1 to 10 L per 1 mol of the compound [I-6].

The reaction temperature may be optionally selected from a range of from −60° C. to the reflux temperature of the reaction system, and it is preferably within a range of from −20° C. to 100° C.

The reaction time varies depending upon the reaction temperature, the reaction substrate, the reaction amount, etc., and it is usually from 0.5 to 240 hours.

<Production Process 12>

The compound of the present invention represented by the formula [I-7a] can be produced also by a process exemplified by the following scheme:

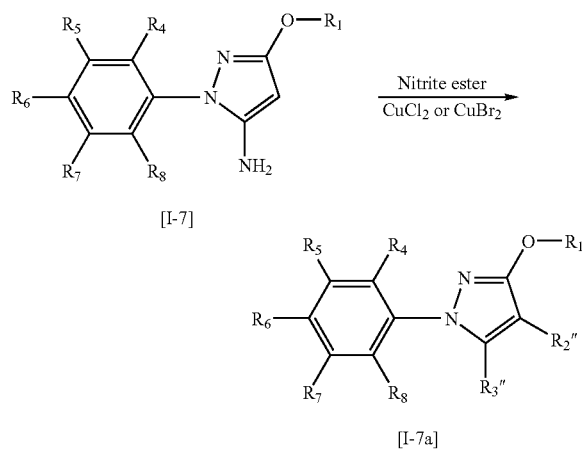

[I-7]

[I-7a]

wherein $R_1$, $R_4$, $R_5$, $R_6$, $R_7$ and $R_8$ are as defined above, and each of $R_2''$ and $R_3''$ which are independent of each other, is a hydrogen atom, a chlorine atom or a bromine atom.

That is, the compound of the present invention represented by the formula [I-7a] can be produced by reacting the compound [I-7] with a nitrite ester in the presence or absence of copper(II) chloride or copper(II) bromide in a solvent.

The amount of use of copper(II) chloride or copper(II) bromide may be properly selected from a range of from 0 to 20 mols per 1 mol of the compound [I-7], and is preferably from 0.0 to 5 mols.

The nitrite ester may, for example, be tert-butyl nitrite or amyl nitrite. The amount of use of the nitrite ester may be properly selected from a range of from 1 to 5mols per 1 mol of the compound [I-7], and is preferably from 1 to 2 mols.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as acetonitrile, N,N-dimethylformamide, N,N-dimethylacetamide, N-methyl-2-pyrrolidone, dimethylsulfoxide or sulfolane; a halogenated hydrocarbon such as dichloromethane, chloroform or dichloroethane; an aliphatic hydrocarbon such as pentane, hexane, cyclohexane or heptane; a ketone such as acetone, methyl ethyl ketone or cyclohexanone; a carboxylic acid such as acetic acid; or a solvent mixture thereof.

The amount of use of the solvent is from 0.5 to 100 L, preferably from 1 to 10 L per 1 mol of the compound [I-7] in both the cases.

In both the reactions, the reaction temperature may be optionally selected from a range of from −20° C. to the reflux temperature of the reaction system, and it is preferably within a range of from 0° C. to 100° C. The reaction time varies depending upon the reaction temperature, the reaction substrate, the reaction amount, etc., and it is usually from 10 minutes to 24 hours.

<Production Process 13>

A compound represented by the formula [I-8a] to a compound of the present invention represented by the formula [I-8h] can be produced also by a common process exemplified by the following scheme. The compound [I-8] can be produced by a process disclosed in <Production Process 9> or <Production Process 1>.

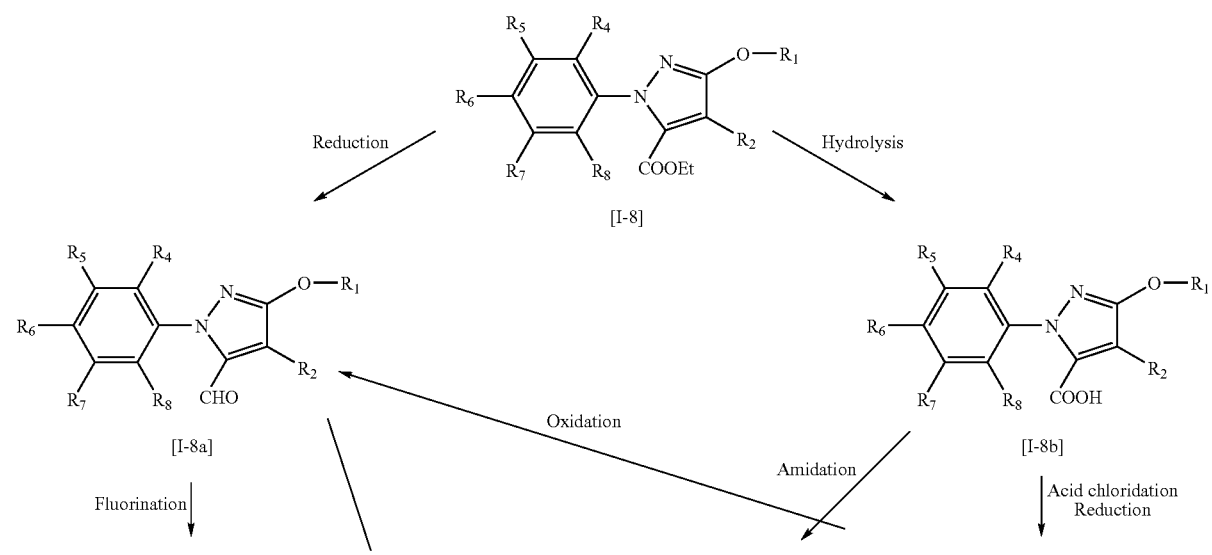

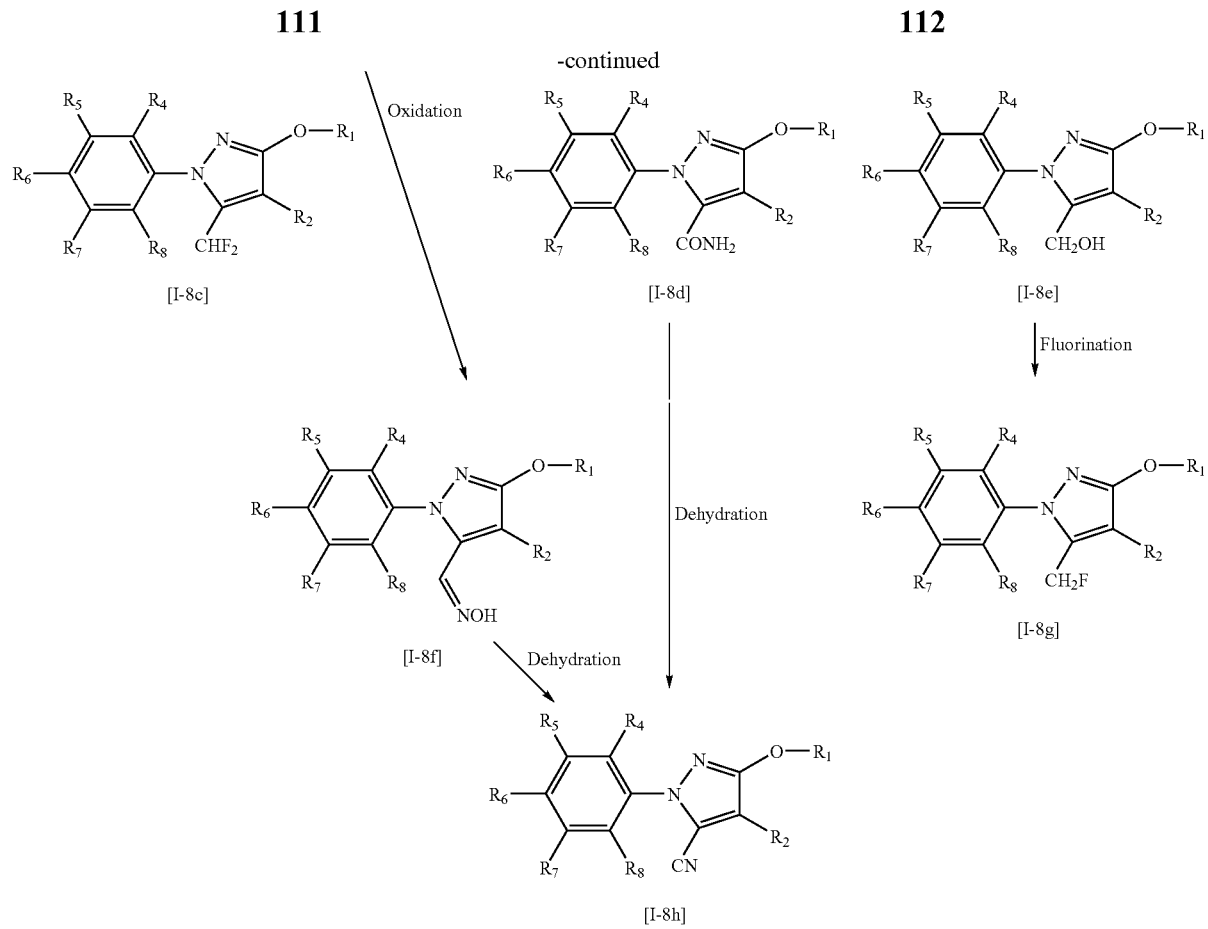

wherein $R_1$, $R_2$, $R_4$, $R_5$, $R_6$, $R_7$ and $R_8$ are as defined above.

That is, the compound [I-8a] can be produced by reacting the compound [I-8] with a reducing agent in the presence of a solvent at low temperature.

The reducing agent to be used in this reaction may be an organic aluminum compound such as diisobutylaluminum hydride.

The amount of use of the reducing agent is within a range of from 1 to 2 mols, preferably from 1 to 1.3 mols per 1 mol of the compound [I-8].

The compound [I-8b] can be produced by hydrolyzing the compound [I-8] by using a base or an acid.

The base to be used in this reaction may, for example, be a hydroxide of an alkali metal such as sodium hydroxide or potassium hydroxide.

The amount of use of the base is within a range of from 1 to 5 mols, preferably from 1 to 2 mols per 1 mol of the compound [I-8].

The acid to be used in this reaction may, for example, be hydrochloric acid, hydrobromic acid or sulfuric acid.

The amount of use of the acid is within a range of from 1 mol to the amount of the solvent, preferably from 1 to 100 mols per 1 mol of the compound [I-8].

The compound [I-8c] can be produced by reacting the compound [I-8a] with a fluorinating agent such as diethylamino sulfur trifluoride. The compound [I-8g] can also be produced by reacting the compound [I-8e] with a fluorinating agent such as diethylamino sulfate trifluoride.

The amount of use of the fluorinating agent is within a range of from 1 to 2 mols, preferably from 1 to 1.2 mols per 1 mol of the compound [I-8a] or the compound [I-8g].

The solvent to be used in this reaction may, for example, be dichloromethane, dichloroethane or chlorobenzene.

The compound [I-8d] can be produced by reacting the compound [I-8b] with e.g. oxalyl dichloride, thionyl chloride or N,N'-carbonyldiimidazole, followed by reaction with ammonia.

The compound [I-8e] can be produced by reacting the compound [I-8b] with e.g. oxalyl dichloride or thionyl chloride to obtain an acid chloride, which is then reduced by a reducing agent such as sodium borohydride.

The compound [I-8f] can be produced by reacting the compound [I-8a] with hydroxyammonium chloride.

The amount of use of hydroxyammonium chloride is within a range of from 1 to 5 mols, preferably from 1 to 2 mols per 1 mol of the compound [I-8a].

The compound [I-8h] can be produced by reacting the compound [I-8d] or [1-8f] with e.g. oxalyl dichloride, thionyl chloride, acetic anhydride or trifluoroacetic anhydride. In a case where $R_2$ is an ethoxycarbonyl group, in the same manner as above, $R_2$ can be cyanated.

The compound [I-8a] can be produced also by reacting the compound [I-8e] with an oxidizing agent such as manganese dioxide in a solvent. The amount of use of the oxidizing agent is within a range of from 2 to 500 mols, preferably from 8 mols to 50 mols per 1 mol of the compound [I-8a].

The solvent to be used in this reaction may, for example, be a halogenated hydrocarbon such as dichloromethane, chloroform or dichloroethane; an aliphatic hydrocarbon such as pentane, hexane, cyclohexane or heptane; an alcohol such as methanol or ethanol; or a solvent mixture thereof.

Further, the Production Process 13 is a process of converting the substituent at the 5-position of the pyrazole ring, and with respect to the 4-position of the pyrazole ring also, production is possible in the same manner as in this Production Process.

<Production Process 14>

A compound of the present invention represented by the formula [I-9] can be produced by a process exemplified by the following scheme from a compound represented by the formula [A-1]:

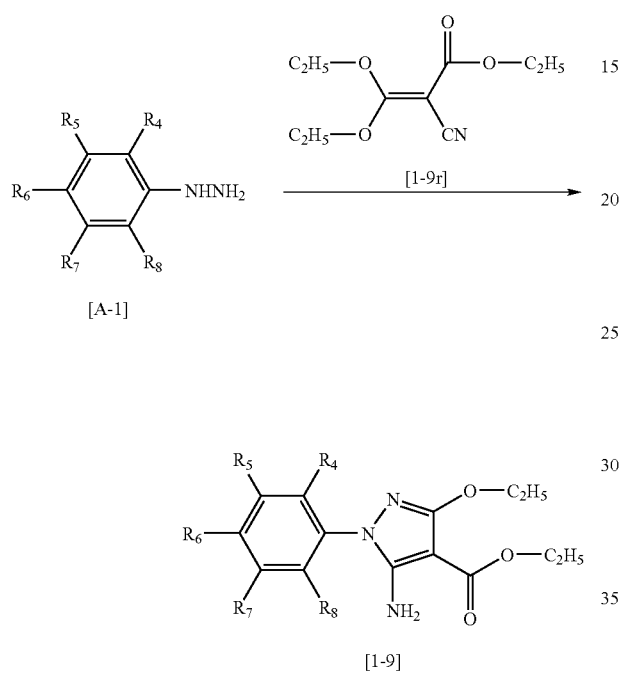

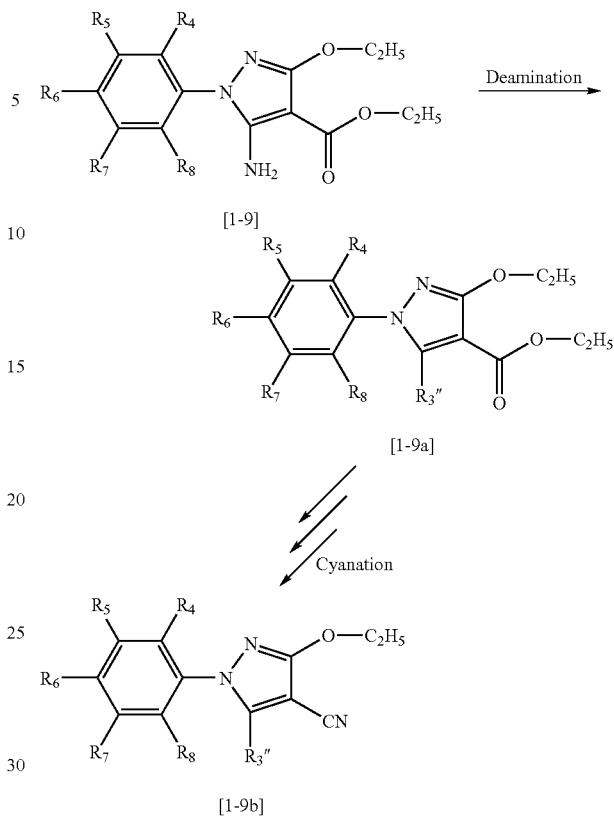

wherein $R_4$, $R_5$, $R_6$, $R_7$ and $R_8$ are as defined above.

It can be produced by reacting the compound represented by the formula [A-1] with the compound represented by the formula [I-9r] in the presence of a solvent.

The amount of use of the compound [I-9r] is within a range of from 1 to 2 mols, preferably from 1 to 1.2 mols per 1 mol of the compound [A-1].

The solvent to be used in the present reaction may, for example, be an alcohol such as methanol, ethanol or isopropyl alcohol; water; a carboxylic acid such as acetic acid; or a solvent mixture thereof.

The reaction temperature may be optionally selected from a range of from −20° C. to the reflux temperature of the reaction system, and it is preferably within a range of from 0° C. to 100° C.

The reaction time varies depending upon the reaction temperature, the reaction substrate, the reaction amount, etc., and it is usually from 0.5 to 24 hours.

Further, by a production process exemplified by the following scheme, production of the compound [I-9a] by deamination of the pyrazole 5-position, can be carried out in the same manner as in the above Production Process 12, and production of the compound [I-9b] which is a cyanated product of the ethoxycarbonyl group at the pyrazole 4-position, can be carried out in the same manner as in the above Production Process 13.

wherein R3", $R_4$, $R_5$, $R_8$, $R_7$ and $R_8$ are as defined above.

<Production Process 15>

The compound of the present invention represented by the formula [I-1] can be produced also by a process exemplified by the following scheme from a compound represented by the formula [I-d]:

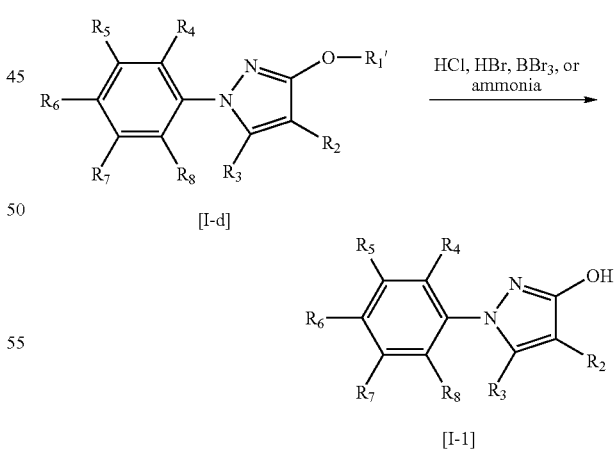

wherein R1' is a methyl group, an acetyl group or a benzyl group, and $R_2$, $R_3$, $R_4$, $R_5$, $R_6$, $R_7$ and $R_8$ are as defined above.

The formula [I-1] can be produced by reacting the formula [I-d] with hydrogen chloride (hydrochloric acid), a hydrogen bromide solution, boron tribromide or ammonia in the presence of a solvent.

The amount of use of hydrogen chloride, the hydrogen bromide solution or boron tribromide is within a range of from 1 to 1,000 mols, preferably from 1.0 to 100mols per 1 mol of the compound [I-d].

The solvent to be used in this reaction may, for example, be an alcohol such as methanol, ethanol or isopropyl alcohol; water; a carboxylic acid such as acetic acid; or a solvent mixture thereof; or dichloromethane, dichloroethane, chlorobenzene, etc.

The reaction temperature may be optionally selected from a range of from −68° C. to the reflux temperature of the reaction system, and it is preferably within a range of from 0° C. to 100° C.

The reaction time varies depending upon the reaction temperature, the reaction substrate, the reaction amount, etc., and it is usually from 0.5 to 24 hours.

<Production Process 16>

The compound represented by the formula [I-10] can be produced from a compound represented by the formula [A-3] by means of the compounds represented by the formulae [I-10a] and [I-10b].

carbonate of an alkali metal such as sodium carbonate or potassium carbonate; or a bicarbonate of an alkali metal such as sodium hydrogen carbonate or potassium hydrogen carbonate; a metal hydride such as sodium hydride or potassium hydride; or an organic base such as triethylamine, N,N-dimethylaniline, pyridine, 4-N,N-dimethylaminopyridine or 1,8-diazabicyclo[5.4.0]-7-undecene.

The amount of use of the base may be properly selected from a range of from 0 to 5 mols per 1 mol of the compound [A-3], and is preferably from 0 to 1.2 mols.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as acetonitrile, N,N-dimethylformamide, N,N-dimethylacetamide, N-methyl-2-pyrrolidone, dimethylsulfoxide or sulfolane; a halogenated hydrocarbon such as dichloromethane, chloroform or dichloroethane, an aliphatic hydrocarbon such as pentane, hexane, cyclohexane or heptane; a ketone such as acetone, methyl ethyl ketone or cyclohexanone; a carboxylic acid such as acetic acid; or a solvent mixture thereof.

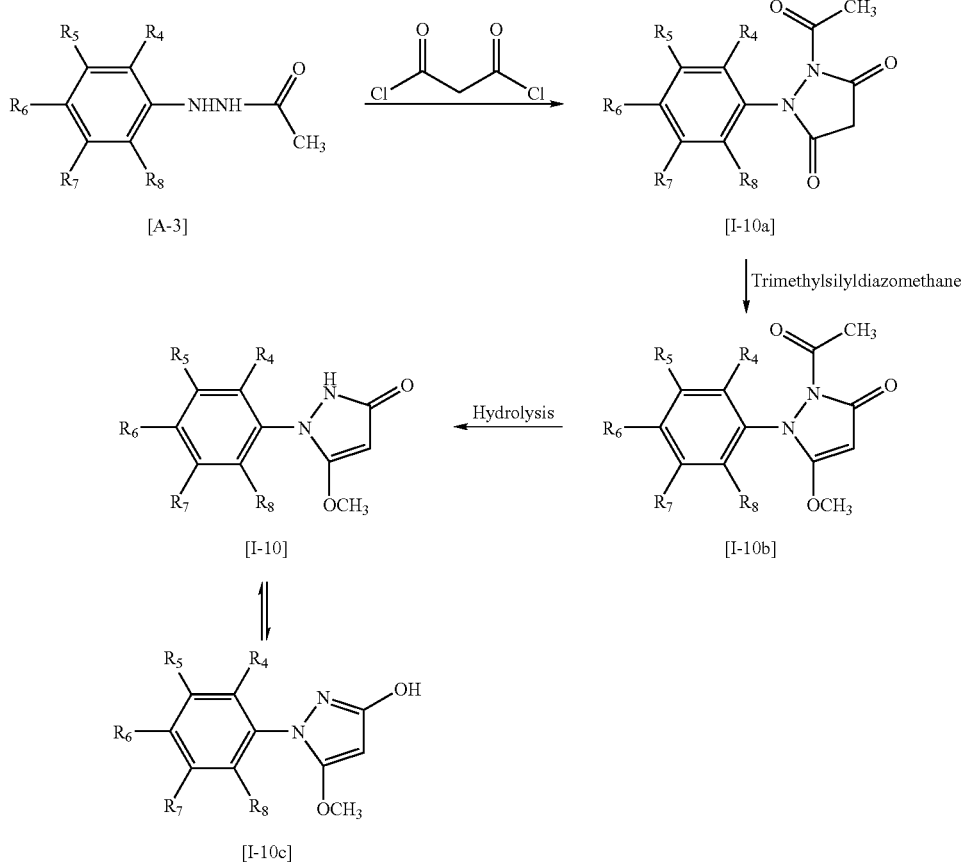

The compound [I-10a] can be produced by reacting the compound [A-3] with malonyl chloride in the presence or absence of a base in a solvent.

The amount of use of malonyl chloride is from 1 to 3 mols, preferably 1.0 mol per 1 mol of [A-3].

The base to be used may, for example, be an inorganic base such as a hydroxide of an alkali metal such as sodium hydroxide or potassium hydroxide; a hydroxide of an alkaline earth metal such as calcium hydroxide or magnesium hydroxide; a The amount of the above solvent is from 0.5 to 100 L, preferably from 1.0 to 10L per 1 mol of the compound [A-3].

The reaction temperature may be optionally selected from a range of from −68° C. to the reflux temperature of the reaction system, and it is preferably within a range of from 0° C. to 100° C. The reaction time varies depending upon the reaction temperature, the reaction substrate, the reaction amount, etc., and it is usually from 0.5 to 24 hours.

The compound [I-10b] can be produced by reacting the compound [I-10a] with trimethylsilyldiazomethane in the presence or absence of a base in a solvent.

The amount of use of trimethylsilyldiazomethane is from 1 to 3 mols, preferably 1.0 mol per 1 mol of [1-10a].

The base to be used may, for example, be an inorganic base such as a hydroxide of an alkali metal such as sodium hydroxide or potassium hydroxide; a hydroxide of an alkaline earth metal such as calcium hydroxide or magnesium hydroxide; a carbonate of an alkali metal such as sodium carbonate or potassium carbonate; or a bicarbonate of an alkali metal such as sodium hydrogen carbonate or potassium hydrogen carbonate; a metal hydride such as sodium hydride or potassium hydride; or an organic base such as triethylamine, N,N-dimethylaniline, pyridine, 4-N,N-dimethylaminopyridine or 1,8-diazabicyclo[5.4.0]-7-undecene.

The amount of use of the base may be properly selected from a range of from 0 to 5 mols per 1 mol of the compound [I-10a], preferably from 0 to 1.2 mols.

The solvent to be used in this reaction may, for example, be an ether such as diethyl ether, tetrahydrofuran or dioxane; an aromatic hydrocarbon such as benzene, toluene, xylene or chlorobenzene; an aprotic polar solvent such as acetonitrile, N,N-dimethylformamide, N,N-dimethylacetamide, N-methyl-2-pyrrolidone, dimethylsulfoxide or sulfolane; a halogenated hydrocarbon such as dichloromethane, chloroform or dichloroethane; an aliphatic hydrocarbon such as pentane, hexane, cyclohexane or heptane; a ketone such as acetone, methyl ethyl ketone or cyclohexanone; a carboxylic acid such as acetic acid; an alcoholic solvent such as methanol or ethanol; or a solvent mixture thereof.

The amount of the above solvent is from 0.5 to 100 L, preferably from 1.0 to 10L per 1 mol of the compound [I-10a].

The reaction temperature may be optionally selected from a range of from −68° C. to the reflux temperature of the reaction system, and it is preferably within a range of from 0° C. to 100° C. The reaction time varies depending upon the reaction temperature, the reaction substrate, the reaction amount, etc., and it is usually from 0.5to 24 hours.

The compound [I-10] can be produced in the same manner as in the process of hydrolysis disclosed in Production Process 13 from the compound [I-10b]. The compound [I-10] and the compound [I-10c] are in a chemical equilibrium state.

When a compound of the present invention is used as the active ingredient of a pesticide, it may be used by itself. However, it can be formulated into various formulations such as an emulsifiable concentrate, a suspension, a dust, a granule, a tablet, a wettable powder, a water-soluble concentrate, a liquid formulation, a flowable, a water dispersible granule, an aerosol, a paste, an oil miscible solution, an emulsion and a smoking agent in combination with various carriers, surfactants and other adjuvants which are commonly used for formulation as agricultural adjuvants. They are blended usually in such proportions that the active ingredient is from 0.1 to 90mass %, preferably from 1 to 70 mass % and the agricultural adjuvants are from 10 to 99.9 mass %, preferably from 20 to 90 mass % based on the entire amount (100mass %) of the pesticide.

The carriers to be used for such formulation may be classified into solid carriers and liquid carriers. The solid carriers include, for example, animal and plant powders such as starch, activated carbon, soybean powder, wheat flour, wood flour, fish flour and powdered milk, and mineral powders such as talc, kaolin, bentonite, calcium carbonate, zeolite, diatomaceous earth, white carbon, clay, alumina, ammonium sulfate and urea. The liquid carriers include, for example, water; alcohols such as isopropyl alcohol and ethylene glycol; ketones such as cyclohexanone, methyl ethyl ketone and isophorone; ethers such as dioxane and tetrahydrofuran; aliphatic hydrocarbons such as kerosene and light oil; aromatic hydrocarbons such as xylene, trimethylbenzene, tetramethylbenzen, methylnaphthalene and solvent naphtha; halogenated hydrocarbons such as chlorobenzene; acid amides such as dimethylacetamide; esters such as glycerin esters of fatty acids; nitriles such as acetonitrile; and sulfur-containing compounds such as dimethyl sulfoxide.

The surfactants include, for example, metal salts of alkylbenzenesulfonic acids, metal salts of dinaphthylmethanedisulfonic acids, salts of alcohol sulfates, alkylarylsulfonates, lignin sulfonates, polyoxyethylene glycol ethers, polyoxyethylene alkyl aryl ethers, polyoxyethylene sorbitan monoalkylates and salts of a formalin condensate of naphthalenesulfonate.

The other adjuvants include, for example, adhesive agents and thickeners such as carboxymethylcellulose, gum arabic, sodium arginate, guar gum, tragacanth gum, and polyvinyl alcohol; antifoaming agents such as metal soap; physical property improvers such as fatty acids, alkyl phosphate salts, silicone and paraffin; and coloring agents.

When these formulations are practically used, they may be used directly or after diluted with a diluent such as water to a predetermined concentration.

Various formulations containing the compounds of the present invention, whether diluted or not, may be applied by conventional methods, i.e., application methods (such as spraying, misting, atomizing, dusting, granule application, paddy water application and seeding box application), soil treatment (such as mixing or drenching), surface application (such as painting, dressing and covering), dipping, poison bait or smoking.

Further, the above active ingredients may be incorporated into livestock feeds so as to prevent infestation or growth of pest, especially pest insects after they are voided in excrement.

Otherwise, they can also be applied by a so-called ultra-low volume, high concentration application method. The proportion of the active ingredient in a pesticide in the case of the ultra-low volume, high concentration application method, is suitably selected as required, and it is from 0.1 to 20 mass %, preferably from 0.5 to 10mass % in the case of a dust or a granule, and from 1 to 80% mass %, preferably from 10 to 50 mass % in the case of an emulsifiable concentrate or a wettable powder.

The pesticides of the present invention are applied, when they are diluted with a diluent, usually at an active ingredient concentration of from 0.1 to 5,000 ppm. When they are used directly, the dose per unit area is from 0.1 to 5,000 g, preferably from 5 to 2,000 g per 1 ha in terms of the compound that serves as the active ingredient. However, the dose is not limited to such specific range.

The compounds of the present invention are sufficiently effective when used alone. However, they may be used, if necessary, in combination or in admixture with fertilizers or other agrochemicals such as insecticides, miticides, nematicides, fungicides, antivirus agents, attractants, herbicides and plant growth modulating agents, and such combined or admixed use can sometimes produce improved effects.

Examples of other insecticidal compounds which may be used in combination or in admixture, will be given below.

Acetamiprid, clothianidin, dinotefuran, imidacloprid, nitenpyram, thiacloprid, thiamethoxam, ethiprole, fipronil, acetoprol, chromafenozide, halofenozide, methoxyfenozide, tebufenozide, acrinathrin, allethrin, alpha-cypermethrin, beta-cyfluthrin, beta-cypermethrin, bifenthrin, bioallethrin, bioresmethrin, cycloprothrin, cyfluthrin, cyhalothrin, cypermethrin, cyphenothrin, deltamethrin, empenthrin, esfenvalerate, fenpropathrin, fenvalerate, flucythrinate, flumethrin, gamma-cyhalothrin, imiprothrin, lambda-cyhalothrin, methothrin, permethrin, phenothrin, prallethrin, resmethrin, Kadethrin, tau-fluvalinate, tefluthrin, tetramethrin, zeta-cypermethrin, tralomethrin, transfluthrin, etofenprox, halfenprox, silafluofen, bensultap, cartap, thiocyclam, thiosultap-sodium, acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos, dicrotophos, dimethoate, dimethylvinphos, disulfoton, EPN, ethion, ethoprophos, famphur, fenamiphos, fenitrothion, fenthion, fosthiazate, heptenophos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion, imicyafos, flupyrazofos, aldicarb, bendiocarb, benfuracarb, carbaryl, carbofuran, carbosulfan, ethiofencarb, fenobucarb, formetanate, furathiocarb, isoprocarb, methiocarb, methomyl, metolcarb, oxamyl, pirimicarb, propoxur, trimethacarb, XMC, xylylcarb, alanycarb, butocarboxim, butoxycarboxim, thiodicarb, thiofanox, bistrifluoron, chlorfluazuron, diflubenzuron, flucycloxuron, flufenoxuron, hexaflumuron, lufenuron, novaluron, noviflumuron, teflubenzuron, triflumuron, abamectin, emamectin, chlorfenapyr, fenoxycarb, hydroprene, kinoprene, methoprene, pyriproxyfen, dienochlor, cyenopyrafen, cyflumetofen, spiromesifen, spirodiclofen, spirotetramat, Flubendiamide, flurimfen, flonicamid, metaflumizon, rynaxypyr, lepmectin, pyridalyl, fluacrypyrim, indoxacarb, bromopropylate, triazamate, fenazaquin, fenpyroximate, pyridaben, tebufenpyrad, clofentezine, etoxazole, hexythiazox, pymetrozine, buprofezin, 1,3-dichloropropene (1,3-D), isocarbophos, ammonium N-methyldithiocarbamate (NCS), azocyclotin, endosulfan, chlordane, chloropicrin, cyhexatin, spinosad, sodium dimethyldithiocarbamate, fenbutatin oxide, flusulfamide, methyl isothiocyanate (MITC), rotenone, CL900167, sodium aluminium fluoride, pyrifluquinazon, RU-15525, XDE-175 and ZXI-8901.

Examples of other fungicidal compounds which may be used in combination or in admixture, will be given below.

Amisulbrom, benomyl, benthiavalicarb-isopropyl, benthiopyrade, ethaboxam, bitertanol, blasticidin-S, boscalid, captan, carbendazol, carpropamid, chlorothalonil, cyazofamid, cyflufenamid, cymoxanil, diclomezine, dimoxystrobin, dithianon, edifenphos, fenamidone, fenarimol, fenbuconazole, fluazinam, fluopicolide, fluoxastrobin, flutolanil, folpet, fosetyl, fthalide, guazatine, hexaconazole, hydroxyisoxazole, hymexazol, iprobenfos, iprodione, iprovalicarb, isoprothiolane, isotianil, kasugamycin, mandipropamid, maneb, mepanipyrim, mepronil, metalaxyl, metrafenone, myclobutanyl, orysastrobin, oxadixyl, oxolinic acid, pefurazoate, pencycuron, phenazine oxide, picoxystrobin, polycarbamate, polyoxin, probenazole, prochloraz, procymidone, propamocarb-hydrochloride, propiconazole, propineb, proquinazid, pyraclostrobin, pyribencarb, pyroquilon, simeconazole, Streptomycin, tecloftalam, thiabendazole, thiophanate-methyl, thiuram, tiadinil, tolnifanide, triadimefon, tricyclazole, trifloxystrobin, triflumizole, triforine, validamycin, vinchlozoline, zineb and ziram.

Examples of other herbicidal compounds and plant growth modulating compounds which may be used in combination or in admixture, will be given below.

Diphenamid, naproanilide, napropamide, pentanochlor, propanil, flamprop-M, MCPA-thioethyl, clodinafop-propargyl, cyhalofop-butyl, diclofop-methyl, fenoxaprop-P-ethyl, fenoxaprop-ethyl, fluazifop-butyl, fluazifop-P-butyl, haloxyfop, haloxyfop-P, haloxyfop-P-methyl, metamifop, propaquizafop, quizalofop-ethyl, quizalofop-P, quizalofop-P-ethyl, quizalofop-P-tefuryl, isoxaben, propyzamide, chlorthal-dimethyl, benfuresate, ethofumesate, 2,3,6-TBA, dicamba, dichlobenil, bentazone, benazolin, diquat dibromide, paraquat dichloride, asulam, carbetamide, chlorpropham, propham, acetochlor, alachlor, butachlor, dimethachlor, dimethenamid, metazachlor, metolachlor, pethoxamid, pretilachlor, propachlor, propisochlor, S-metolachlor, thenylchlor, alloxydim, butroxydim, clethodim, cycloxydim, profoxydim, sethoxydim, tepraloxydim, tralkoxydim, benfluralin, butralin, dinitramine, ethalfluralin, oryzalin, pendimethalin, trifluralin, dinoterb, DNOC, acifluorfen, bifenox, fluoroglycofen-ethyl, fomesafen, HC-252, lactofen, oxyfluorfen, aclonifen, glyphosate, glyphosate-trimesium (sulfosate), bromoxynil, ioxynil, imazamethabenzmethyl, imazamox, imazamethapyr(imazapic), imazapyr, imazaquin, imazethapyr, isoxaflutole, clomazone, cinidonethyl, flumiclorac-pentyl, flumioxazin, oxadiargyi, oxadiazon, pentoxazone, flufenacet, mefenacet, 2,4-D, 2,4-DB, clomeprop, dichlorprop, dichlorprop-P, MCPA, MCPB, mecoprop, mecoprop-P potassium, desmedipham, phenmedipham, pyraflufen-ethyl, pyridate, forchlorfenuron, thidiazuron, bilanafos, glufosinate-ammonium, glufosinate-sodium, butamifos, bensulide, naptalam, benzofenap, pyrazolynate, pyrazoxyfen, pyrasulfotole, maleic hydrazide, norflurazon, chloridazon, dithiopyr, thiazopyr, diflufenican, picolinafen, clopyralid, fluoroxypyr, picloram, triclopyr, diflumetorim, butafenacil, fenclorim, ancymidol, flurprimidol, bispyribac-sodium, pyribenzoxim, pyriftalid, pyriminobac-methyl, pyrithiobac-sodium, chlormequat chloride, mepiquat chloride, quinoxyfen, quinclorac, quinmerac, diflufenzopyr, flucarbazone-sodium, propoxycarbazone-sodium, propoxycarbazone, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazosulfuron, iodosulfulon-methyl-sodium, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, tritosulfuron, flucetosulfuron, fentrazamide, fluthiacet-methyl, butylate, cycloate, dimepiperate, EPTC, esprocarb, molinate, orbencarb, pebulate, prosulfocarb, thiobencarb, tiocarbazil, tri-allate, pyributicarb, ametryn, atrazine, cyanazine, dimethametryn, prometon, prometryn, propazine, simazine, simetryn, terbumeton, terbuthylazine, terbutryn, trietazine, hexazinone, metamitron, metribuzin, amitrole, flupoxame, amicarbazone, carfentrazone-ethyl, sulfentrazone, cloransulam-methyl, diclosulam, florasulam, flumetsulam, metosulam, penoxsulam, mesotrione, sulcotrione, tefuryltrion, bromacil, lenacil, terbacil, chlorotoluron, dimefuron, diuron, fluometuron, isoproturon, isouron, karbutilate, linuron, methabenzthiazuron, metobenzuron, metoxuron, monolinuron, neburon, siduron, tebuthiuron, oxaziclomefone, anilofos, benzobicyclon, prodiamine, cinmethylin, pyraclonil, pyroxysulam, triaziflam, etobenzanid, bromobutide, daimuron, cafenstrole, benzfendizone, pinoxaden, aminopyralid, topramezone, tembotrione, indanofan, pyrimisulfan, thiencarbazone, bencarbazone and pyroxasulfone.

The above agricultural formulations are disclosed in The Pesticidal Manual, 13th edition (published by British Crop Protection Council, 2004), SHIBUYA INDEX 10th edition, 11th edition and 12th edition, published by Shibuya Index Research Association), or Monthly Fine Chemical 2006, vol. 35, No. 7 (published by CMC Publishing Co., Ltd., 2006) or known.

The compounds of the present invention exhibit excellent pesticidal effects against pests such as pest orthoptera, pest thysanoptera, pest hemipterans, pest coleoptera, pest diptera, pest lepidopterans, pest hymenoptera, pest collembola, pest thysanura, pest blattaria, pest isoptera, pest psocoptera, pest mallophaga, pest anoplura, plant-parasitic mites, plant-parasitic nematodes, plant-parasitic molluscs, other pests, unfavorable animals, insanitary insects, and parasites. As examples of the above pests, the following species may be mentioned.

Pest orthoptera, for example, family Tettigoniidae, *Ruspolia lineosa*, etc., family Gryllidae, Emma field cricket (*Teleogryllus emma*), etc., family Gryllotalpidae, mole cricket (*Gryllotalpa orientalis*), family Acrididae, rice grasshopper (*Oxya hyla intricate*), migratory locust (*Locusta migratoria*), migratory glasshopper (*Melanoplus sanquinipes*), etc., family Pyrgomorphoidae, smaller longheaded locust (*Atractomorpha lata*), family Eneopterinae, *Euscyrtus japonicus*, family Tridactylidae, *Xya iaponicus*, etc.

Pest thysanoptera, for example, family Thripidae, flower thrips (*Frankliniella intonsa*), western flower thrips (*Frankliniella occidentalis*), yellow tea thrips (*Scirtothrips dorsalis*), melon thrips (*Thrips palmi*), onion thrips (*Thrips tabaci*), etc., family Phlaeothripidae, *Ponticulothrips diospyrosi*, rice aculeated thrips (*Haplothrips aculeatus*), etc.

Pest hemipterans, for example, family Cicadidae, *Mogannia minuta*, etc., family Aphrophoridae, *Aphrophora intermedia*, etc., family Membracidae, *Machaerotypus sibiricus*, etc., family Cicadellidae, grape leafhopper (*Arboridia apicalis*), tea green leafhopper (*Empoasca onukii*), green rice leafhopper (*Nephotettix cincticeps*), zig-zag rice leafhopper (*Recilia dorsalis*), etc., family Cixiidae, *Pentastiridius apicalis*, etc., family Delphacidae, small brown planthopper (*Laodelphax striatellus*), brown rice planthopper (*Nilaparvata lugens*), white-backed planthopper (*Sogatella furcifera*), etc., family Meenoplidae, *Nisia nervosa*, etc., family Derbidae, *Kamendaka saccharivora*, etc., family Achilidae, red fungus bug (*Achilus flammeus*), etc., family Ricaniidae, *Orosanga japonicus*, etc., family Flatidae, *Mimophantia maritima*, etc., family Psyllidae, *Cacopsylla pyrisuga*, etc., family Calophyidae, *Calophya mangiferae*, etc., family Phylloxeridae, grape phylloxera (*Daktulosphaira vitifoliae*), etc., family Adelgidae, larch wooly adelgid (*Adelges laricis*), hemlock wooly adelgid (*Adelges tsugae*), etc., family Aphdidae, pea aphid (*Acyrthosiphon pisum*), cotton aphid (*Aphis gossypii*), spiraea aphid (*Aphis spiraecola*), turrip aphid (*Lipaphis erysimi*), green peach aphid (*Myzus persicae*), green bug (*Schizaphis graminum*), bird cherry-oat aphid (*Rhopalosiphum padi*), etc., family Aleyrodidae, orange spiny whitefly (*Aleurocanthus spiniferus*), sweetpotato whitefly (*Bemisia tabaci*), silverleaf whitefly (*Bemisia argentifolii*), greenhouse whitefly (*Trialeurodes vaporariorum*), etc., family Margarodidae, giant margarodid scale (*Drosicha corpulenta*), *Icerva purchasi*, etc., family Pseudococcidae, pineapple mealybug (*Dysmicoccus brevipes*), citrus mealybug (*Planococcus citri*), Comstock mealybug (*Pseudococcus comstocki*), etc., family Coccidae, soft scale (*Ceroplastes ceriferus*), etc., family Aclerdidae, *Aclerda takahashii*, etc., family Diaspididae, California red scale (*Aonidiella aurantii*), San Jose scale (*Cosmockaspis perniciosus*), arrowhead scale (*Unaspis yanonensis*), etc., family Miridae, western tarnished plant bug (*Lygus hesperus*), rice leaf bug (*Triqonotylus caelestialium*), etc., family Tingitidae, Azalea lace bug (*Stephanitis pyrioides*), pear lace bug (*Stephanitis nashi*), etc., family Pentatomidae, whitespotted spined bug (*Eysarcoris aeneus*), rice stink bug (*Lagynotomus elongatus*), southern green stink bug (*Nezara viridula*), brownwinged green bug (*Plautia crossota*), etc., family Thyreocoridae, bean plataspid (*Megacopta cribraria*), etc., family Lygaeidae, oriental chinch bug (*Cavelerius saccharivorus*), etc., family Malcidae, *Malcus japonicus*, etc., family Pyrrhocoridae, red cotton stainer (*Dysdercus cingulatus*), etc., family Alylidae, paddy bug (*Leptocorisa acuta*), rice bug (*Leptocorisa chinensis*), etc., family Coreidae, coreid bug (*Anacanthocoris striicornis*), etc., family Rhopalidae, *Rhopalus maculatus*, etc., family Cimicidae, bed bug (*Cimex lectularis*), etc.

Pest Coleoptera, for example, family Scarabalidae, cupreous chafer (*Anomala cuprea*), soybeam beetle (*Anomala rufocuprea*), Japanese beetle (*Popillia japonica*), coconut rhinoceros beetle (*Oryctes rhinoceros*), etc., family Elateridae, barley wireworm (*Agriotes oqurae*), sugarcane click beetle (*Melanotus okinawensis*), sweetpotato wireworm (*Melanotus fortnumi fortnumi*), etc., family Dermestidae, varied carpet beetle (*Anthrenus verbasci*), etc., family Bostrichidae, *Heterobostrychus hamatipennis*, etc., family Anobiidae, drugstore beetle (*Stegobium paniceum*), etc., family Ptinidae, brown spider beetle (*Pinus clavipes*), etc., family Trogossitidae, cadelle beetle (*Tenebroides manritanicus*), etc., family Cleridae, red-legged ham beetle (*Necrobia rufipes*), family Nitidulidae, dried fruit beetle (*Carpophilus hemipterus*), etc., family Silvanidae, foreign grain beetle (*Ahasverus advena*), etc., family Laemophloeidae, rusty grain beetle (*Cryptolestes ferrugineus*), etc., family Coccinellidae, Mexican bean beetle (*Epilachna varivestis*), twenty-eight-spotted ladybird (*Henosepilachna vigintioctopunctata*), etc., family Tenebrioridae, mealworn beetle (*Tenebrio molitor*), red flour beetle (*Tribolium castaneum*), etc., family Meloidae, bean blister beetle (*Epicauta qorhami*), etc., family Cerambycidae, Asian longhorn beetle (*Anoplophora glabripennis*), grape borer (*Xylotrechus pvrrhoderus*), Japanese pine sawyer (*Monochamus alternatus*), etc., family Bruchidae, adzuki bean weevil (*Callosobruchus chinensis*), etc., family Chrysomelidae, Colorado potato beetle (*Leptinotarsa decemlineata*), western corn rootworm (*Diabrotica virgifera*), brassica leaf beetle (*Phaedon brassicae*), flea beetle (*Phyllotreta striolata*), etc., family Brentidae, sweetpotato weevil (*Cylas formicarius*), etc., family Curculionidae, alfalfa weevil (*Hypera postica*), vegetable weevil (*Listroderes costirostris*), west Indian sweetpotato weevil (*Euscepes postfasciatus*), etc., family Erirhinidae, rice plant weevil (*Echinocnemus bipunctatus*), rice water weevil (*Lissorhoptrus oryzophilus*), etc., family Curculioridae, maize weevil (*Sitophilus zeamais*), hunting billbug (*Sphenophrus venatus*), etc., family Scolytidae, common pine shoot beetle (*Tomicus piniperda*), etc., family Platypodidae, ambrosia beetle (*Crossotarsus niponicus*), etc., family Bostrichidae, *Lyctus brunneus*, etc.

Pest diptera, for example, family Tipulidae, rice crane fly (*Tipula aino*), etc., family Bibionidae, lovebug (*Plecia nearctica*), etc., family Mycetoplilidae, *Exechia shiitakevora*, etc., family Sciaridae, potato scab-gnat (*Pnyxia scabiei*), etc., family Cecidomyiidae, soybean pod gall midge (*Asphondylia yushimai*), hessian fly (*Mayetiola destructor*), etc., family Culicidae, yellow fever mosquito (*Aedes aegypti*), common house mosquito (*Culex pipiens pallens*), etc., family Simuliidae, *Simulium takahashii*, etc., family Chironomidae, rice midge (*Chironomus oryzae*), etc., family Tabanidae, deerfly (*Chrysops suavis*), *Tabanus trigonus*, etc., family Syrphidae, onion bulb fly (*Eumerus strigatus*), etc., family Tephritidae, oriental fruit fly (*Bactrocera dorsalis*), Japanese cherry fruit fly (*Euphranta japonica*), Mediterranean fruit fly (*Ceratitis capitata*), etc., family Agromyzidae, American serpentine leafminer (*Liriomyza trifolii*), garden pea leafminer (*Chromatomyia horticola*), etc., family Chloropidae, wheat stem maggot (*Meromyza nigriventris*), etc., family Drosophilidae, cherry drosophila (*Drosophila suzukii*), common fruit fly (*Drosophila melanogaster*), etc., family Ephydridae, rice leafminer (*Hydrellia griseola*), etc., family Hippoboscidae, forest fly (*Hippobosca equina*), etc., family Scathophagidae, *Parallelomma sasakawae*, etc., family Anthomyiidae, onion fly (*Delia antiqua*), seed-corn fly (*Delia platura*), etc., family Fanniidae, little house fly (*Fannia canicularis*), etc., family Muscidae, housefly (*Musca domestica*), stable fly (*Stomoxys calcitrans*), etc., family Sarcophagidae, flesh fly (*Sarcophaga pereqrina*), etc., family Gastrophilidae, horse bot fly (*Gasterophilus intestinalis*), etc., family Hypodermatidae, common cattle grab (*Hypoderma lineatum*), etc., family Oestridae, ship nasal botfly (*Oestrus ovis*), etc.

Pest lepidopterans, for example, family Hepialidae, swift moth (*Endoclita excrescens*), etc., family Heliozelidae, *Antispila ampelopsia*, etc., family Cossidae, *Zeuzera leuconotum*, etc., family Tortricidae, apple tortrix (*Archips fuscocupreanus*), summer fruit tortrix moth (*Adoxophyes orana fasciata*), oriental fruit moth (*Grapholita molesta*), oriental tea tortrix (*Homona magnanima*), soybean pod borer (*Leguminivora glycinivorella*), codling moth (*Cydia pomonella*), etc., family Tortricidae, vine moth (*Eupoecilia ambiguella*), etc., family Psychidae, *Bambalina* sp., tea bagworm (*Eumeta minuscula*), etc., family Tineidae, European grain moth (*Nemapoqon granella*), casemaking clothes moth (*Tinea translucens*), etc., family Bucculatricidae, pear leaf miner (*Bucculatrix pyrivorella*), etc., family Lyonetiidae, peach leaf miner (*Lyonetia clerkella*), etc., family Gracillariidae, tea leafroller (*Caloptilia theivora*), apple leafminer (*Phyllonorycter ringoniella*), etc., family Phyllocnistidae, citrus leafminer (*Phyllocnistis citrella*), etc., family Acrolepiidae, allium leafminer (*Acrolepiopsis sapporensis*), etc., family Yponomeutidae, diamondback moth (*Plutella xylostella*), *Yponomeuta orientalis*, etc., family Argyresthiidae, apple fruit moth (*Argyresthia conjugella*), etc., family Sesiidae, *Nokona regalis*, etc., family Gelechiidae, potato tuberworm (*Phthorimaea operculella*), Angoumois grain moth (*Sitotroga cerealella*), pink bollworm (*Pectinophora gossvpiella*), etc., family Carposinidae, peach fruit moth (*Carposina sasakii*), etc., family Zygaenidae, *Illiberis pruni*, etc., family Limacodidae, oriental moth (*Monema flavescens*), etc., family Crambidae, *Ancylolomia japonica*, rice stem borer (*Chilo suppressalis*), rice leafroller (*Cnaphalocrocis medinalis*, oriental corn borer (*Ostrinia furnacalis*), European corn borer (*Ostrinia nubilalis*), etc., family Pyralidae, tropical warehouse moth (*Cadra cautella*), greater wax moth (*Galleria mellonella*), etc., family Pterophoridae, *Nippoptilia vitis*, etc., family Papilionidae, Asian swallowtail (*Papilio xuthus*), etc., family Pieridae, common cabbage worm (*Pieris rapae*), etc., family Hesperiidae, migrant skipper (*Parnara guttata guttata*), etc., family Geometridae, giant looper (*Ascotis selenaria*), etc., family Lasiocampidae, pine moth (*Dendrolimus spectabilis*), tent caterpillar (*Malacosoma neustrium testaceum*), etc., family Sphingidae, convolvulus hawk-moth (*Agrius convolvuli*), etc., family Lymantriidae, tea tussock moth (*Arna pseudoconspersa*), gypsy moth (*Lymantria dispar*), etc., family Arctiidae, fall webworm (*Hyphantria cunea*), etc., family Noctuidae, black cutworm moth (*Agrotis ipsilon*), *Autographa nigrisigna*, cotton bollworm (*Helicoverpa armigera*), corn earworm (*Helicoverpa zea*), tabaco budworm (*Heliothis virescens*), beet armyworm (*Spodoptera exigua*), common cutworm (*Spodoptera litura*), etc.

Pest hymenoptera, for example, family Argidae, rose argid sawfly (*Arge pagana*), etc., family Tenthredinidae, chestnut sawfly (*Apethymus kuri*), turnip sawfly (*Athalia rosae ruficornis*), etc., family Cynipidae, chestnut gall wasp (*Dryocosmus kuriphilus*), etc., family Vespidae, hornet (*Vespa simillima xanthoptera*), etc., family Formicidae, red imported fire ant (*Solenopsis invicta*), etc., family Megachilidae, *Megachile nipponica*, etc.

Pest collembola, for example, family Sminthuridae, garden springtail (*Bourletiella hortensis*), etc.

Pest thysanura, for example, family Lepismatidae, silverfish (*Lepisma saccharina*), *Ctenolepisma villosa*, etc.

Pest blattaria, for example, family Blattidae, American cockroach (*Periplaneta americana*), family Biattellidae, German cockroach (*Blattella germanica*), etc.

Pest isoptera, for example, family Kalotermitidae, western drywood termite (*Incisitermes minor*), etc., family Rhinotermitidae, Formosan subterranean termite (*Coptotermes formosanus*), etc., family Termitidae, black-winged subterranean termite (*Odontotermes formosanus*), etc.

Pest psocoptera, for example, family Trogiidae, booklouse (*Trogium pulsatorium*), etc., family Liposcelididae, *Liposcelis corrodens*, etc.

Pest mallophaga, for example, family Philopteridae, poultry wing louse (*Lipeurus caponis*), etc., family Trichodectidae, cattlebiting louse (*Damalinia bovis*), etc.

Pest anoplura, for example, family Haematopinidae, pig louse (*Haematopinus suis*), etc., family Pediculidae, body louse (*Pediculus humanus*), etc., family Linognathidae, dogsucking louse (*Linognathus setosus*), etc., family Pediculidae, crab louse (*Pthirus pubis*), etc.

Plant-parasitic mites, for example, family Eupodidae, blue oat mite (*Penthaleus major*), etc., family Tarsonemidae, cyclamen mite (*Phytonemus pallidus*), broad mite (*Polyphagotarsonemus latus*), etc., family Pyemotidae, one of pyemotesmite (*Siteroptes* sp.), etc., family Tenuipalpidae, citrus flat mite (*Brevipalpus lewisi*), etc., family Tuckerellidae, tuckerellid mite (*Tuckerella pavoniformis*), etc., family Tetranychidae, apricot spider mite (*Eotetranychus boreus*), citrus red mite (*Panonychus citri*), European red mite (*Panonychus ulmi*), two-spotted spider mite (*Tetranvchus urticae*), Kanzawa spider mite (*Tetranychus kanzawai*), etc., family Phytoptidae, *Trisetacus pini*, etc., family Eriophyidae, pink citrus rust mite (*Aculops pelekassi*), pear rust mite (*Epitrimerus pyri*), citrus rust mite (*Phyllocoptruta oleivora*), etc., family Diptilomiopidae, *Diptacus crenatae*, etc., family Acaridae, brown legged grain mite (*Aleuroglyphus ovatus*), mould mite (*Tyrophagus putrescentiae*), bulb mite (*Rhizoglyphus robini*), etc.

Plant-parasitic nematodes, for example, family Longidoridae, California dagger nematode (*Xiphinema index*), etc., family Trichodoridae, Christie's stubby root nematode (*Paratrichodorus minor*), etc., family Rhabditidae, *Rhabditella* sp., etc., family Tylenchidae *Aglenchus* sp., etc., family Tylodoridae *Cephalenchus* sp., etc., family Anguinidae, strawberry bud nematode (*Nothotylenchus acris*), potato rot nematode (*Ditylenchus destructor*), etc., family Hoplolaimidae, reniform nematode (*Rotylenchulus reniformis*), Steiner's spiral nematode (*Helicotylenchus dihystera*), etc., family Paratylenchidae, *Paratylenchus curvitatus*, etc., family Meloidogynidae, southern root-knot nematode (*Meloidogyne incognita*), northern root-knot nematode (*Meloidogyne* hapla), etc., family Heteroderidae, potato cyst nematode (*Globodera rostochiensis*), soybean cyst nematode (*Heterodera glycines*), etc., family Telotylenchi, tobacco stunt nematode (*Tylenchorhynchus claytoni*), etc., family Tylenchidae, *Psilenchus* sp., etc., family Criconematidae, one of ring nematode (*Criconemoides* sp.), etc., family Tylenchulidae, citrus root nematode (*Tylenchulus semipenetrans*), etc., family Sphaeronematidae, *Sphaeronema camelliae*, etc., family Pratylenchidae, citrus burrowing nematode (*Radopholus citrophilus*), banana root nematode (*Radopholus similis*), false root-knot nematode (*Nacobbus aberrans*), northern root lesion nematode (*Pratylenchus penetrans*), root lesion nematode (*Pratylenchus coffeae*), etc., family Iotonchiidae, *Iotonchium ungulatum*, etc., family Aphlenchidae, mycophagous nematode worm (*Aphelenchus avenae*), etc., family Aphelenchoididae, rice white tip nematode (*Aphelenchoides besseyi*), strawberry foliar nematode (*Aphelenchoides fragariae*), etc., family Parasitaphelenchidae, pine wood nematode (*Bursaphelenchus xylophilus*), etc.

Plant-parasitic molluscs, for example, family Ampullarridae, channeled applesnail (*Pomacea canaliculata*), etc., family Veronicellidae, garden slug (*Leavicaulis alte*), etc., family Achatinidae, giant African snail (*Achatina fulica*), etc., family Philomycidae, *Meghimatium bilineatum*, etc., family Succineidae, refined amber snail (*Succinea lauta*), etc., family Discidae, poor disk snail (*Discus pauper*), etc., family Zonitidae, glass snail (*Zonitoides yessoensis*), etc., family Limacidae, yellow slug (*Limax flavus*), grey field slug (*Deroceras reticulatum*), etc., family Helicarionidae, *Parakaliella harimensis*, etc., family Bradybaenidae, Korean round snail (*Acusta despecta sieboldiana*), Asian trampsnail (*Bradybaena similaris*), etc.

Other pests, unfavorable animals, insanitary insects, insects on domestic animals, and parasites, for example, order Acarina, family Macronyssidae, temperate poultry mite (*Ornithonyssus sylviarum*), etc., family Parasitidae, varroa mite (*Varroa jacobsoni*), etc., family Dermanyssidae, red mite (*Dermanyssus gallinae*), etc., family Macronyssidae, temperate poultry mite (*Ornithonyssus sylviarlum*), etc., family Ixodidae, cattle tick (*Boophilus microplus*), brown dog tick (*Rhipicephalus sanquineus*), bush tick (*Haemaphysalis longicornis*), etc., family Sarcoptidae, scabies mite (*Sarcoptes scabiei*), etc., order Isopoda, family Armadillidiidae, common woodlouse (*Armadillidium vulgare*), etc., order Decapoda, family Cambaridae, red swamp crawfish (*Procambarus clarkii*), etc., order Isopoda, family Oniscidae, common pillbug (*Armadillidium vulgare*), etc., class Chilopoda, for example, order Scutigeromorpha, family Scutigeridae, house centipede (*Thereuonema tuberculate*), family Scolopendridae, Vietnamese centipede (*Scolopendra subspinipes*), etc., class Diplopoda, for example, order Polydesmida, family Paradoxosomatidae, greenhouse millipede (*Oxidus gracilis*), etc., order Araneae, family Theridiidae, redback spider (*Latrodectus hasseltii*), etc., order Araneae, family Clubionidae, *Chiracanthium japonicum*, etc., order Scorpiones, Arabian fat-tailed scorpion (*Androctonus crassicauda*), etc., nemathelminthe endoparasite, roundworm (*Ascaris lumbricoides*), etc., pinworm (*Syphacia* sp.), etc., filaria (*Wuchereria bancrofti*), etc., flatworm endoparasite, Chinese liver fluke (*Distomum* sp.), lung fluke (*Paragonimus westermanii*), *Metagonimus yokokawai*, *Schistosoma japonicum*, pork tapeworm (*Taenia solium*), *Taeniarhynchus saginatus*, *Echinococcus* sp., tapeworm (*Diphyllobothrium latum*), etc.

The compounds of the present invention exhibit pesticidal effects also against the above-described pests which have acquired resistance to existing pesticides, etc.

The compounds of the present invention can be used for plants which have acquired characteristics such as resistance to pests, resistance to diseases or resistance to herbicides, by gene recombination, artificial hybridization, etc. Further, they have controlling effects also against pests which show resistance to organophosphorus compounds, carbamate compounds, synthetic pyrethroid compounds, acylurea compounds or conventional insecticides.

Now, production processes, formulation methods and application of the compounds of the present invention will be described in detail with reference to Examples, but they are by no means restricted to such specific Examples.

EXAMPLES

In the following Examples, the support for column chromatography is a silica gel, and the compositional ratio (e.g. 1:4) of the developing solvent (e.g. ethyl acetate:hexane) is based on the volume in all cases.

Further, the concentration of an aqueous solution of e.g. sodium thiosulfate, sodium hydrogen carbonate or potassium carbonate used in Examples is from a 1mass % aqueous solution to a saturated aqueous solution in all cases.

Example 1

Preparation of 5-acetylamino-1-{2-fluoro-4-methyl-5-(2,2,2-trifluoroethylthio)phenyl}-3-(2,2,3,3,3-pentafluoropropoxy)pyrazole (compound No. 1-17 of the present invention)

5.0 g of 5-acetylamino-1-{2-fluoro-4-methyl-5-(2,2,2-trifluoroethylthio)phenyl}-3-hydroxypyrazole was dissolved in 100 mL of dimethylsulfoxide, and 2.3 g of potassium carbonate was added, followed by stirring at room temperature for 5 minutes. To this solution, 6.4 g of 2,2,3,3,3-pentafluoropropyl nonafluorobutanesulfonate was added, followed by stirring at room temperature for 12 hours. Extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 5.3 g of 5-acetylamino-1-{2-fluoro-4-methyl-5-(2,2,2-trifluoroethylthio)phenyl}-3-(2,2,3,3,3-pentafluoropropoxy)pyrazole.

$^1$H-NMR (CDCL$_3$/TMS δ (ppm) value) δ: 2.08 (3H, s), 2.53 (3H, s), 3.40 (2H, q), 4.66 (3H, t), 6.22 (1H, s), 7.03 (1H, brs), 7.16 (1H, d), 7.60 (1H, d)

Example 2

Preparation of 5-acetylamino-1-{2-fluoro-4-methyl-5-(2,2,2-trifluoroethylsulfinyl)phenyl}-3-(2,2,3,3,3-pentafluoropropoxy)pyrazole (compound No. 1-18 of the present invention)

0.2 g of 5-acetylamino-1-{2-fluoro-4-methyl-5-(2,2,2-trifluoroethylthio)phenyl}-3-(2,2,3,3,3-pentafluoropropoxy) pyrazole was dissolved in 10 mL of chloroform, and 0.1g of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:

hexane=1:2) to obtain 0.2 g of 5-acetylamino-1-{2-fluoro-4-methyl-5-(2,2,2-trifluoroethylsulfinyl)phenyl}-3-(2,2,3,3,3-pentafluoropropoxy)pyrazole.

$^1$H-NMR (CDCL$_3$/TMS δ (ppm) value) δ: 2.08 (3H, s), 2.46 (3H, s), 3.43-3.53 (2H, m), 4.67 (2H, t), 6.19 (1H, s), 7.20 (1H, d), 7.22 (1H, brs), 8.08 (1H, d)

Example 3

Preparation of 5-amino-1-{2-fluoro-4-methyl-5-(2,2,2-trifluoroethylthio)phenyl}-3-(1,1,2,3,3,3-hexafluoropropoxy)pyrazole (compound No. 1-9 of the present invention)

1.2 g of 5-acetylamino-1-{2-fluoro-4-methyl-5-(2,2,2-trifluoroethylthio)phenyl}-3-(1,1,2,3,3,3-hexafluoropropoxy)pyrazole was dissolved in 50 mL of ethanol, and an aqueous solution comprising 0.5 g of concentrated sulfuric acid in 2.0 mL of water was added, followed by reflux with heating for 6 hours. After cooling to room temperature, the solvent was distilled off under reduced pressure, and extraction with ethyl acetate was carried out. The organic layer was dried over anhydrous magnesium sulfate, the solvent was distilled off under reduced pressure, and the obtained residue was purified by column chromatography (developing solvent ethyl acetate:hexane=1:4) to obtain 0.9 g of 5-amino-1-{2-fluoro-4-methyl-5-(2,2,2-trifluoroethylthio)phenyl}-3-(1,1,2,3,3,3-hexafluoropropoxy)pyrazole.

$^1$H-NMR (CDCL$_3$/TMS δ (ppm) value) δ: 2.52 (3H, s), 3.39 (2H, q), 3.83 (2H, s), 5.03-5.20 (1H, m), 5.47 (1H, s), 7.14 (1H, d), 7.64 (1H, d)

Example 4

Preparation of 5-amino-1-{2-fluoro-4-methyl-5-(2,2,2-trifluoroethylthio)phenyl}-4-fluoro-3-(2,2,3,3,3-pentafluoropropoxy)pyrazole (compound No. 1-41 of the present invention)

1.0 g of 5-amino-1-{2-fluoro-4-methyl-5-(2,2,2-trifluoroethylthio)phenyl}-3-(2,2,3,3,3-pentafluoropropoxy)pyrazole was dissolved in 30 mL of acetonitrile, and 0.8g of N-fluoro-N'-(chloromethyl)-triethylenediaminebis(tetrafluoroborate) was added, followed by stirring at room temperature for 24 hours. Then, the solvent was distilled off under reduced pressure, and the obtained residue was purified by column chromatography (developing solvent ethyl acetate:hexane=1:4) to obtain 0.3 g of 5-amino-1-{2-fluoro-4-methyl-5-(2,2,2-trifluoroethylthio)phenyl}-4-fluoro-3-(2,2,3,3,3-pentafluoropropoxy)pyrazole.

$^1$H-NMR (CDCL$_3$/TMS δ (ppm) value) δ: 2.51 (3H, s), 3.38 (2H, q), 3.62 (2H, s), 4.70 (2H, t), 7.12 (1H, d), 7.59 (1H, d)

Example 5

Preparation of 5-amino-4-chloro-1-{2-fluoro-4-methyl-5-(2,2,2-trifluoroethylthio)phenyl}-3-(2,2,3,3,3-pentafluoropropoxy)pyrazole (compound No. 1-43 of the present invention)

0.9 g of 5-amino-1-{2-fluoro-4-methyl-5-(2,2,2-trifluoroethylthio)phenyl}-3-(2,2,3,3,3-pentafluoropropoxy)pyrazole was dissolved in 10 mL of acetonitrile, and 0.3g of N-chlorosuccinimide was added under cooling with ice. After stirring for 10minutes under cooling with ice, the solvent was distilled off under reduced pressure, extraction with ethyl acetate was carried out, and the organic layer was dried over anhydrous magnesium sulfate. Then, the solvent was distilled off under reduced pressure, and the obtained residue was purified by column chromatography (developing solvent ethyl acetate:hexane=1:4) to obtain 0.9 g of 5-amino-4-chloro-1-{2-fluoro-4-methyl-5-(2,2,2-trifluoroethylthio)phenyl}-3-(2,2,3,3,3-pentafluoropropoxy)pyrazole.

$^1$H-NMR (CDCL$_3$/TMS δ (ppm) value) δ: 2.52 (3H, s), 3.38 (2H, q), 3.88 (2H, s), 4.70 (2H, t), 7.14 (1H, d), 7.60 (1H, d)

Example 6

Preparation of 5-amino-4-bromo-1-{2-fluoro-4-methyl-5-(2,2,2-trifluoroethylthio)phenyl}-3-(2,2,3,3,3-pentafluoropropoxy)pyrazole (compound No. 1-45 of the present invention)

2.0 g of 5-amino-1-{2-fluoro-4-methyl-5-(2,2,2-trifluoroethylthio)phenyl}-3-(2,2,3,3,3-pentafluoropropoxy)pyrazole was dissolved in 50 mL of acetonitrile, and 0.8g of N-bromosuccinimide was added under cooling with ice. After stirring for 10minutes under cooling with ice, the solvent was distilled off under reduced pressure, extraction with ethyl acetate was carried out, and the organic layer was dried over anhydrous magnesium sulfate. Then, the solvent was distilled off under reduced pressure, and the obtained residue was purified by column chromatography (developing solvent ethyl acetate:hexane=1:4) to obtain 2.0 g of 5-amino-4-bromo-1-{2-fluoro-4-methyl-5-(2,2,2-trifluoroethylthio)phenyl}-3-(2,2,3,3,3-pentafluoropropoxy)pyrazole.

$^1$H-NMR (CDCL$_3$/TMS δ (ppm) value) δ: 2.52 (3H, s), 3.38 (2H, q), 3.92 (2H, s), 4.70 (2H, t), 7.14 (1H, d), 7.60 (1H, d)

Example 7

Preparation of 1-{2-fluoro-4-methyl-5-(2,2,2-trifluoroethylthio)phenyl}-3-(2,2,3,3,3-pentafluoropropoxy)-5-trifluoroacetylaminopyrazole (compound No. 1-29 of the present invention)

1.2 g of 4-bromo-1-{2-fluoro-4-methyl-5-(2,2,2-trifluoroethylthio)phenyl}-3-(2,2,3,3,3-pentafluoropropoxy)-5-trifluoroacetylaminopyrazole was dissolved in 200 mL of ethanol, and 1.2 g of 10% palladium carbon was added. 430 mL of hydrogen was blown over a period of 10 days at room temperature under reduced pressure, the solvent was distilled off under reduced pressure, and the obtained residue was purified by column chromatography (developing solvent ethyl acetate:hexane:acetic acid=10:40:1) to obtain 1.0 g of 1-{2-fluoro-4-methyl-5-(2,2,2-trifluoroethylthio)phenyl}-3-(2,2,3,3,3-pentafluoropropoxy)-5-trifluoroacetylaminopyrazole.

$^1$H-NMR (CDCL$_3$/TMS δ (ppm) value) δ: 2.54 (3H, s), 3.40 (2H, q), 4.70 (2H, t), 6.30 (1H, s), 7.19 (1H, d), 7.63 (1H, d)

Example 8

Preparation of 1-{2-fluoro-4-methyl-5-(2,2,2-trifluoroethylthio)phenyl}-5-methyl-3-(2,2,3,3,3-pentafluoropropoxy)pyrazole (compound No. 1-91 of the present invention)

0.7 g of 3-hydroxy-1-{2-fluoro-4-methyl-5-(2,2,2-trifluoroethylthio)phenyl}-5-methylpyrazole was dissolved in 15 mL of dimethylsulfoxide, and 0.36 g of potassium carbonate and 0.94 g of 2,2,3,3,3-pentafluoropropyl nonafluorobutyl sulfonate were added, followed by stirring at room temperature for 5 hours. After completion of the reaction, the reaction solution was poured into water, extraction with ethyl acetate was carried out, washing with a saturated salt solution was carried out, the organic layer was dried over anhydrous magnesium sulfate, the solvent was distilled off under reduced pressure, and the obtained residue was purified by column chromatography (ethyl acetate:hexane=1:10) to obtain 0.90 g of 1-{2-fluoro-4-methyl-5-(2,2,2-trifluoroethylthio)phenyl}-5-methyl-3-(2,2,3,3,3-pentafluoropropoxy)pyrazole.

$^1$H-NMR (CDCL$_3$/TMS δ (ppm) value) δ: 2.13 (3H, s), 2.52 (3H, s), 3.37 (2H, q), 4.65(2H, t), 5.74 (1H, s), 7.12 (1H, d), 7.56 (1H, d)

Example 9

Preparation of 1-{2-fluoro-4-methyl-5-(2,2,2-trifluoroethylsulfinyl)phenyl}-5-methyl-3-(2,2,3,3,3-pentafluoropropoxy)pyrazole (compound No. 1-92 of the present invention)

0.3 g of 1-{2-fluoro-4-methyl-5-(2,2,2-trifluoroethylthio)phenyl}-5-methyl-3-(2,2,3,3,3-pentafluoropropoxy)pyrazole was dissolved in 10 mL of chloroform, and 0.16g of m-chloroperbenzoic acid (purity: 75%) was slowly added under cooling with ice. After stirring for 30 minutes under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (ethyl acetate:hexane=1:2) to obtain 0.30 g of 1-{2-fluoro-4-methyl-5-(2,2,2-trifluoroethylsulfinyl)phenyl}-5-methyl-3-(2,2,3,3,3-pentafluoropropoxy)pyrazole.

$^1$H-NMR (CDCL$_3$/TMS δ (ppm) value) δ: 2.15 (3H, s), 2.46 (3H, s), 3.40-3.59 (2H, q), 4.65 (2H, t), 5.77 (1H, s), 7.17 (1H, d), 8.06 (1H, d)

Example 10

Preparation of 1-{2-fluoro-4-methyl-5-(2,2,2-trifluoroethylthio)phenyl}-4,5-dichloro-3-(2,2,3,3,3-pentafluoropropoxy)pyrazole (compound No. 1-111 of the present invention)

0.7 g of 1-{2-fluoro-4-methyl-5-(2,2,2-trifluoroethylthio)phenyl}-5-amino-3-(2,2,3,3,3-pentafluoropropoxy)pyrazole was dissolved in 15 mL of acetonitrile, 1.04 g of copper(II) chloride was added, and tert-butyl nitrite (0.24 g) was dropwise added under cooling with ice. After stirring at room temperature for 12 hours, the solvent was distilled off under reduced pressure, extraction with ethyl acetate was carried out, and the organic layer was dried over anhydrous magnesium sulfate. Then, the solvent was distilled off under reduced pressure, and the obtained residue was purified by column chromatography (ethyl acetate:hexane=1:10) to obtain 0.3 g of 1-{2-fluoro-4-methyl-5-(2,2,2-trifluoroethylthio)phenyl}-4,5-dichloro-3-(2,2,3,3,3-pentafluoropropoxy)pyrazole.

$^1$H-NMR (CDCL$_3$/TMS δ (ppm) value) δ: 2.55 (3H, s), 3.37 (2H, q), 4.71 (2H, t), 7.15(1H, d), 7.55 (1H, d)

Example 11

Preparation of 5-acetylamino-1-{2-fluoro-4-methyl-5-(2,2,2-trifluoroethylthio)phenyl}-3-(1,1,2,2,3,3,3-heptafluoropropoxy)pyrazole (compound No. 1-267 of the present invention)

2.1 g of 5-acetylamino-1-{2-fluoro-4-methyl-5-(2,2,2-trifluoroethylthio)phenyl}-3-hydroxypyrazole was dissolved in 60 mL of dichloromethane, and 0.51 g of pyridine was added. To the obtained solution, 3.0 g of (perfluoro-n-propyl)phenyliodonium trifluoromethanesulfonate was slowly added, followed by stirring at room temperature for 1 hour. The solvent was distilled off under reduced pressure, a saturated salt solution was added, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:4) to obtain 0.10 g of 5-acetylamino-1-{2-fluoro-4-methyl-5-(2,2,2-trifluoroethylthio)phenyl}-3-(1,1,2,2,3,3,3-heptafluoropropoxy)pyrazole.

$^1$H-NMR (CDCL$_3$/TMS δ (ppm) value) δ: 2.11 (3H, s), 2.55 (3H, s), 3.41 (2H, q), 6.53 (1H, s), 7.10 (1H, brs), 7.19 (1H, d), 7.63 (1H, d)

Example 12

Preparation of 5-acetylamino-1-{2-fluoro-4-methyl-5-(2,2,2-trifluoroethylsulfinyl)phenyl}-3-(1,1,2,2,3,3,3-heptafluoropropoxy)pyrazole (compound No. 1-268 of the present invention)

60 mg of 5-acetylamino-1-{2-fluoro-4-methyl-5-(2,2,2-trifluoroethylthio)phenyl}-3-(1,1,2,2,3,3,3-heptafluoropropoxy)pyrazole was dissolved in 10 mL of chloroform, and 30 mg of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. The solvent was distilled off under reduced pressure, and the obtained residue was purified by column chromatography (developing solvent ethyl acetate:hexane=1:2) to obtain 53mg of 5-acetylamino-1-{2-fluoro-4-methyl-5-(2,2,2-trifluoroethylsulfinyl)phenyl}-3-(1,1,2,2,3,3,3-heptafluoropropoxy)pyrazole.

$^1$H-NMR (CDCL$_3$/TMS δ (ppm) value) δ: 2.10 (3H, s), 2.48 (3H, s), 3.41-3.62 (2H, m), 6.50 (1H, s), 7.22 (1H, d), 7.49 (1H, brs), 8.09 (1H, d)

Example 13

Preparation of 5-acetylamino-1-{2-fluoro-4-methyl-5-(2,2,2-trifluoroethylthio)phenyl}-3-{1,1,2-trifluoro-2-(trifluoromethoxy)ethoxy}pyrazole (compound No. 1-15 of the present invention)

3.0 g of 5-acetylamino-1-{2-fluoro-4-methyl-5-(2,2,2-trifluoroethylthio)phenyl}-3-hydroxypyrazole was dissolved in 40 mL of dimethylformamide, 25 g of triethylamine was added, and stirring was carried out at 50° C. for 3 hours while trifluoromethyl trifluorovinyl ether was blown. To this solution, ethyl acetate was added, the solution was washed with a saturated aqueous solution of citric acid, the organic layer was dried over anhydrous magnesium sulfate, the solvent was distilled off under reduced pressure, and the obtained residue was purified by column chromatography (developing solvent ethyl acetate:hexane=1:4) to obtain 1.71 g of 5-acetylamino-1-{2-fluoro-4-methyl-5-(2,2,2-trifluoroethylthio)phenyl}-3-{1,1,2-trifluoro-2-(trifluoromethoxy)ethoxy}pyrazole.
$^1$H-NMR (CDCL$_3$/TMS δ (ppm) value) δ: 2.45 (3H, s), 3.37-3.57 (2H, m), 3.76 (2H, s), 4.65 (2H, t), 5.25 (1H, s), 7.17 (1H, d), 8.12 (1H, d)

Example 14

Preparation of 5-acetylamino-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-16 of the present invention)

0.5 g of 5-acetylamino-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 0.22 g of m-chloroperbenzoic acid (purity: 75%) was added under cooling with ice. After stirring for 30 minutes under cooling with ice, the solution was washed with an aqueous sodium thiosulfate solution and then washed with an aqueous sodium hydrogen carbonate solution, and dried over anhydrous sodium sulfate. Then, the solvent was distilled off under reduced pressure, and the obtained residue was purified by column chromatography (developing solvent ethyl acetate:hexane=1:1) to obtain 0.46 g of 5-acetylamino-1-{2-fluoro-4-methyl-5-(2,2,2-trifluoroethylsulfinyl)phenyl}-3-{1,1,2-trifluoro-2-(trifluoromethoxy)ethoxy}pyrazole.
$^1$H-NMR (CDCL$_3$/TMS δ (ppm) value) δ: 2.07 (3H, s), 2.45 (3H, s), 3.38-3.56 (2H, m), 6.03 (1H, d), 6.44 (1H, s), 7.20 (1H, d), 7.77 (1H, brs), 8.01 (1H, d)

Example 15

Preparation of 4-chloro-1-{2-fluoro-4-methyl-5-(2,2,2-trifluoroethylthio)phenyl}-3-{1,1,2-trifluoro-2-(trifluoromethoxy)ethoxy}pyrazole (compound No. 1-289 of the present invention)

0.9 g of 5-amino-1-{2-fluoro-4-methyl-5-(2,2,2-trifluoroethylthio)phenyl}-3-{1,1,2-trifluoro-2-(trifluoromethoxy)ethoxy}pyrazole was dissolved in 30 mL of acetonitrile, and 0.27 g of N-chlorosuccinimide was added under cooling with ice. After stirring for 10 minutes under cooling with ice, the solvent was distilled off under reduced pressure, extraction with ethyl acetate was carried out, and the organic layer was dried over anhydrous magnesium sulfate. The solvent was distilled off under reduced pressure, and the obtained residue was purified by column chromatography (developing solvent ethyl acetate:hexane=1:4) to obtain 5-amino-4-chloro-1-{2-fluoro-4-methyl-5-(2,2,2-trifluoroethylthio)phenyl}-3-{1,1,2-trifluoro-2-(trifluoromethoxy)ethoxy}pyrazole. Then, the obtained pyrazole derivative was dissolved in 30 mL of tetrahydrofuran, and 0.3 mL of t-butyl nitrite was added under cooling with ice. After stirring at room temperature for 12 hours, the solvent was distilled off under reduced pressure, and the obtained residue was purified by column chromatography (ethyl acetate:hexane=1:10) to obtain 0.75 of 4-chloro-1-{2-fluoro-4-methyl-5-(2,2,2-trifluoroethylthio)phenyl}-3-{1,1,2-trifluoro-2-(trifluoromethoxy)ethoxy}pyrazole.
$^1$H-NMR (CDCL$_3$/TMS δ (ppm) value) δ: 2.50 (3H, s), 3.40 (2H, q), 6.15 (1H, dt), 7.13 (1H, d), 7.93 (1H, s), 7.94 (1H, d)

Example 16

Preparation of 4-chloro-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-290 of the present invention)

0.24 g of 4-chloro-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 0.11 g of m-chloroperbenzoic acid (purity: 75%) was added under cooling with ice. After stirring for 30 minutes under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure, and the obtained residue was purified by column chromatography (developing solvent ethyl acetate:hexane=1:2) to obtain 0.21 g of 4-chloro-1-{2-fluoro-4-methyl-5-(2,2,2-trifluoroethylsulfinyl)phenyl}-3-{1,1,2-trifluoro-2-(trifluoromethoxy)ethoxy}pyrazole.
$^1$H-NMR (CDCL$_3$/TMS δ (ppm) value) δ: 2.45 (3H, s), 3.39-3.62 (2H, m), 6.13 (1H, dt), 7.19 (1H, d), 7.97 (1H, s), 8.41 (1H, s)

Example 17

Preparation of 4,5-dichloro-1-{2-fluoro-4-methyl-5-(2,2,2-trifluoroethylthio)phenyl}-3-{1,1,2-trifluoro-2-(trifluoromethoxy)ethoxy}pyrazole (compound No. 1-291 of the present invention)

0.7 g of 5-amino-1-{2-fluoro-4-methyl-5-(2,2,2-trifluoroethylthio)phenyl}-3-{1,1,2-trifluoro-2-(trifluoromethoxy)ethoxy}pyrazole was dissolved in 30 mL of acetonitrile, 2.9 g of copper(II) chloride was added, and 0.36 g of tert-butyl nitrite was added under reflux with heating. After reflux with heating for 2 hours, the solvent was distilled off under reduced pressure, a saturated salt solution was added, and extraction with ethyl acetate was carried out. The organic layer was dried over anhydrous sodium sulfate, the solvent was distilled off under reduced pressure, and the obtained residue was purified by column chromatography (developing solvent ethyl acetate:hexane=1:8) to obtain 0.59 g of 4,5-dichloro-1-{2-fluoro-4-methyl-5-(2,2,2-trifluoroethylthio)phenyl}-3-{1,1,2-trifluoro-2-(trifluoromethoxy)ethoxy}pyrazole.
$^1$H-NMR (CDCL$_3$/TMS δ (ppm) value) δ: 2.56 (3H, s), 3.38 (2H, q), 6.11 (1H, dt), 7.17 (1H, d), 7.59 (1H, d)

Example 18

Preparation of 4,5-dichloro-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-292 of the present invention)

0.35 g of 4,5-dichloro-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 0.15 g of m-chloroperbenzoic acid (purity: 75%) was added under cooling with ice. After stirring for 30 minutes under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure, and the obtained residue was purified by column chromatography (developing solvent ethyl acetate:hexane=1:2) to obtain 0.35 g of 4,5-dichloro-1-{2-fluoro-4-methyl-5-(2,2,2-trifluoroethylsulfinyl)phenyl}-3-{1,1,2-trifluoro-2-(trifluoromethoxy)ethoxy}pyrazole.

$^1$H-NMR (CDCL$_3$/TMS δ (ppm) value) δ: 2.49 (3H, s), 3.41-3.59 (2H, m), 6.09 (1H, dt), 7.23 (1H, d), 8.10 (1H, d)

Example 19

Preparation of 1-{2-fluoro-4-methyl-5-(2,2,2-trifluoroethylthio)phenyl}-5-methyl-3-(3,3,3-trifluoropropoxy)pyrazole (compound No. 1-249 of the present invention)

0.6 g of 1-{2-fluoro-4-methyl-5-(2,2,2-trifluoroethylthio)phenyl}-3-hydroxy-5-methylpyrazole was dissolved in 4 mL of tetrahydrofuran, and 0.23 g of 3,3,3-trifluoropropanol, 0.75 g of triphenylphosphine and 0.71 g of 1,1'-(azodicarbonyl)dipiperidine were added, followed by stirring at room temperature for 12hours. After completion of the reaction, the reaction solution was distilled off under reduced pressure, and the obtained residue was purified by column chromatography (ethyl acetate:hexane=1:4) to obtain 0.61 g of 1-{2-fluoro-4-methyl-5-(2,2,2-trifluoroethylthio)phenyl}-5-methyl-3-(3,3,3-trifluoropropoxy)pyrazole.

$^1$H-NMR (CDCL$_3$/TMS δ (ppm) value) δ: 2.13 (3H, s), 2.52 (3H, s), 2.53-2.70 (2H, m), 3.37 (2H, q), 4.41 (2H, t), 5.67 (1H, s), 7.10 (1H, d), 7.57 (1H, d)

Example 20

Preparation of 1-{2-fluoro-4-methyl-5-(2,2,2-trifluoroethylsulfinyl)phenyl}-5-methyl-3-(3,3,3-trifluoropropoxy)pyrazole (compound No. 1-250 of the present invention)

0.29 g of 1-{2-fluoro-4-methyl-5-(2,2,2-trifluoroethylthio)phenyl}-5-methyl-3-(3,3,3-trifluoropropoxy)pyrazole was dissolved in 10 mL of chloroform, and 0.17 g of m-chloroperbenzoic acid (purity: 75%) was slowly added under cooling with ice. After stirring for 30 minutes under cooling with ice, the solution was washed with an aqueous sodium thiosulfate solution and then washed with an aqueous sodium hydrogen carbonate solution, and then dried over anhydrous magnesium sulfate. The solvent was distilled off under reduced pressure, and the obtained residue was purified by column chromatography (ethyl acetate:hexane=1:2) to obtain 0.30 g of 1-{2-fluoro-4-methyl-5-(2,2,2-trifluoroethylsulfinyl)phenyl}-5-methyl-3-(3,3,3-trifluoropropoxy)pyrazole.

$^1$H-NMR (CDCL$_3$/TMS δ (ppm) value) δ: 2.15 (3H, s), 2.45 (3H, s), 2.53-2.70 (2H, m), 3.39-3.59 (2H, m), 4.41 (2H, t), 5.70 (1H, s), 7.15 (1H, d), 8.06 (1H, d)

Example 21

Preparation of 1-{2-fluoro-4-methyl-5-(2,2,2-trifluoroethylthio)phenyl}-3-(1,1,2,3,3,3-hexafluoropropoxy)-5-methylaminopyrazole (compound No. 1-186 of the present invention)

0.5 g of 5-acetylamino-1-{2-fluoro-4-methyl-5-2,2,2-trifluoroethylthio)phenyl}-3-{1,1,2-trifluoro-2-(heptafluoropropoxy)ethoxy}pyrazole was dissolved in 5 mL of dimethylformamide, and the solution was dropwise added to a suspension having 55mg of sodium hydride suspended in 10 mL of dimethylformamide under cooling with ice, and after completion of the dropwise addition, stirring was carried out at room temperature for 30 minutes. The reaction solution was cooled with ice again, and 0.21 g of methyl iodide was added, followed by stirring at room temperature for 1 hour. Then, water was injected, extraction with ethyl acetate was carried out, and after washing with water, the organic layer was dried over anhydrous magnesium sulfate. The solvent was distilled off under reduced pressure, the obtained residue was dissolved in 10 mL of ethanol, and 10 mL of a 35 mass % hydrochloric acid aqueous solution was added, followed by stirring under reflux with heating for 1 hour. The reaction mixture was poured into water, extraction with ethyl acetate was carried out, and after washing with water, the organic layer was dried over anhydrous magnesium sulfate. The solvent was distilled off under reduced pressure, and the obtained residue was purified by column chromatography (developing solvent ethyl acetate:hexane=1:4) to obtain 0.44 g of 1-{2-fluoro-4-methyl-5-(2,2,2-trifluoroethylthio)phenyl}-3-(1,1,2,3,3,3-hexafluoropropoxy)-5-methylaminopyrazole.

$^1$H-NMR (CDCL$_3$/TMS δ (ppm) value) δ: 2.50 (3H, s), 2.84 (3H, d), 3.38 (2H, q), 3.64 (1H, brd), 5.01-5.25 (1H, m), 5.34 (1H, s), 7.12 (1H, d), 7.60 (1H, d)

Example 22

Preparation of 1-{2-fluoro-4-methyl-5-(2,2,2-trifluoroethylsulfinyl)phenyl}-3-(1,1,2,3,3,3-hexafluoropropoxy)-5-methylaminopyrazole (compound No. 1-187 of the present invention)

0.4 g of 5-methylamino-1-{2-fluoro-4-methyl-5-(2,2,2-trifluoroethylthio)phenyl}-3-(1,1,2,3,3,3-hexafluoropropoxy)pyrazole was dissolved in 10 mL of chloroform, and 190 mg of m-chloroperbenzoic acid (purity: 75%) was added under cooling with ice. After stirring for 1 hour under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure, and the obtained residue was purified by column chromatography (developing solvent ethyl acetate:hexane=1:2) to obtain 0.4 g of 1-{2-fluoro-4-methyl-5-(2,2,2-trifluoroethylsulfinyl)phenyl}-3-(1,1,2,3,3,3-hexafluoropropoxy)-5-methylaminopyrazole.

$^1$H-NMR (CDCL$_3$/TMS δ (ppm) value) δ: 2.45 (3H, s), 2.84 (3H, d), 3.35-3.58 (2H, m), 3.64 (1H, brd), 5.01-5.22 (1H, m), 5.36 (1H, s), 7.17 (1H, d), 8.10 (1H, d)

Example 23

Preparation of 1-{2-fluoro-4-methyl-5-(2,2,2-trifluoroethylthio)phenyl}-5-methylamino-3-{1,1,2-trifluoro-2-(heptafluoropropoxy)ethoxy}pyrazole (compound No. 1-347 of the present invention)

0.5 g of 5-acetylamino-1-{2-fluoro-4-methyl-5-(2,2,2-trifluoroethylthio)phenyl}-3-{1,1,2-trifluoro-2-(heptafluoropropoxy)ethoxy}pyrazole was dissolved in 5 mL of dimethylformamide, and under cooling with ice, the solution was dropwise added to a suspension having 40 mg of sodium hydride suspended in 10 mL of dimethylformamide, and after completion of the dropwise addition, stirring was carried out at room temperature for 30 minutes. The reaction solution was cooled with ice again, and 0.13 g of methyl iodide was added, followed by stirring at room temperature for 1 hour. Then, the reaction mixture was poured into water, extraction with ethyl acetate was carried out, and after washing with water, the organic layer was dried over anhydrous magnesium sulfate. The solvent was distilled off under reduced pressure, the obtained residue was dissolved in 10 mL of ethanol, and 10 mL of a 35 mass % hydrochloric acid aqueous solution was added, followed by stirring under reflux with heating for one hour. The reaction mixture was poured into water, extraction with ethyl acetate was carried out, and after washing with water, the organic layer was dried over anhydrous magnesium sulfate. The solvent was distilled off under reduced pressure, and the obtained residue was purified by column chromatography (developing solvent ethyl acetate:hexane=1:4) to obtain 0.31 g of 1-{2-fluoro-4-methyl-5-(2,2,2-trifluoroethylthio)phenyl}-5-methylamino-3-{1,1,2-trifluoro-2-(heptafluoropropoxy)ethoxy}pyrazole.

$^1$H-NMR (CDCL$_3$/TMS δ (ppm) value) δ: 2.51 (3H, s), 2.84 (3H, d), 3.37 (2H, q), 3.63 (1H, s), 5.32 (1H, s), 6.15-6.30 (1H, m), 7.12 (1H, d), 7.60 (1H, d)

Example 24

Preparation of 1-{2-fluoro-4-methyl-5-(2,2,2-trifluoroethylsulfinyl)phenyl}-5-methylamino-3-{1,1,2-trifluoro-2-(heptafluoropropoxy)ethoxy}pyrazole (compound No. 1-348 of the present invention)

0.15 g of 1-{2-fluoro-4-methyl-5-(2,2,2-trifluoroethylthio)phenyl}-5-methylamino-3-{1,1,2-trifluoro-2-(heptafluoropropoxy)ethoxy}pyrazole was dissolved in 10 mL of chloroform, and 73 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure, and the obtained residue was purified by column chromatography (developing solvent ethyl acetate:hexane=1:2) to obtain 0.12 g of 1-{2-fluoro-4-methyl-5-(2,2,2-trifluoroethylsulfinyl)phenyl}-5-methylamino-3-{1,1,2-trifluoro-2-(heptafluoropropoxy)ethoxy}pyrazole.

$^1$H-NMR (CDCL$_3$/TMS δ (ppm) value) δ: 2.45 (3H, s), 2.84 (3H, d), 3.37-3.56 (2H, m), 3.62 (1H, s), 5.34 (1H, s), 6.14-6.27 (1H, m), 7.17 (1H, d), 8.10 (1H, d)

Example 25

Preparation of 1-{2-fluoro-4-methyl-5-(2,2,2-trifluoroethylthio)phenyl}-3-(2,2,3,3,3-pentafluoropropoxy)-5-(2-propynylamino)pyrazole (compound No. 1-161 of the present invention)

2.0 g of 5-acetylamino-1-{2-fluoro-4-methyl-5-(2,2,2-trifluoroethylthio)phenyl}-3-(2,2,3,3,3-pentafluoropropoxy)pyrazole was dissolved in 15 mL of dimethylformamide, and under cooling with ice, the solution was dropwise added to a suspension having 0.23 g of sodium hydride suspended in 10 mL of dimethylformamide, and after completion of the dropwise addition, stirring was carried out at room temperature for 30minutes. The reaction solution was cooled with ice again, and 0.72 g of 1-bromo-2-propyne was added, followed by stirring at room temperature for 1 hour. Then, the reaction mixture was poured into water, extraction with ethyl acetate was carried out, and after washing with water, the organic layer was dried over anhydrous magnesium sulfate. The solvent was distilled off under reduced pressure, the obtained residue was dissolved in 20 mL of ethanol, and 20 mL of a 35 mass % hydrochloric acid aqueous solution was added, followed by stirring under reflux with heating for 2 hours. The reaction mixture was poured into water, extraction with ethyl acetate was carried out, and after washing with water, the organic layer was dried over anhydrous magnesium sulfate. The solvent was distilled off under reduced pressure, and the obtained residue was purified by column chromatography (developing solvent ethyl acetate:hexane=1:4) to obtain 1.4 g of 1-{2-fluoro-4-methyl-5-(2,2,2-trifluoroethylthio)phenyl}-3-(2,2,3,3,3-pentafluoropropoxy)-5-(2-propynylamino)pyrazole.

$^1$H-NMR (CDCL$_3$/TMS δ (ppm) value) δ: 2.28 (1H, t), 2.51 (3H, s), 3.38 (2H, q), 3.84 (3H, brs) 4.65 (2H, t), 5.30 (1H, s), 7.12 (1H, d), 7.60 (1H, d)

Example 26

Preparation of 1-{2-fluoro-4-methyl-5-(2,2,2-trifluoroethylsulfinyl)phenyl}-3-(2,2,3,3,3-pentafluoropropoxy)-5-(2-propynylamino)pyrazole (compound No. 1-162 of the present invention)

0.51 g of 1-{2-fluoro-4-methyl-5-(2,2,2-trifluoroethylthio)phenyl}-3-(2,2,3,3,3-pentafluoropropoxy)-5-(2-propynylamino)pyrazole was dissolved in 10 mL of chloroform, and 240 mg of m-chloroperbenzoic acid (purity: 75%) was added under cooling with ice. After stirring for 1 hour under cooling with ice, the solution was washed with an aqueous sodium thiosulfate solution and then washed with an aqueous sodium hydrogen carbonate solution and then dried over anhydrous sodium sulfate. The solvent was distilled off under reduced pressure, and the obtained residue was purified by column chromatography (developing solvent ethyl acetate:hexane=1:2) to obtain 0.39 g of 1-{2-fluoro-4-methyl-5-(2,2,2-trifluoroethylsulfinyl)phenyl}-3-(2,2,3,3,3-pentafluoropropoxy)-5-(2-propynylamino)pyrazole.

$^1$H-NMR (CDCL$_3$/TMS δ (ppm) value) δ: 2.29 (1H, t), 2.44 (3H, s), 3.38-3.57 (2H, m), 3.84 (3H, brs) 4.65 (2H, t), 5.33 (1H, s), 7.17 (1H, d), 8.09 (1H, d)

Example 27

Preparation of 1-{2-fluoro-4-methyl-5-(2,2,2-trifluoroethylthio)phenyl}-5-(2-propynylamino)-3-{1,1,2-trifluoro-2-(heptafluoropropoxy)ethoxy}pyrazole (compound No. 1-357 of the present invention)

0.7 g of 5-acetylamino-1-{2-fluoro-4-methyl-5-(2,2,2-trifluoroethylthio)phenyl}-3-{1,1,2-trifluoro-2-(heptafluoropropoxy)ethoxy}pyrazole was dissolved in 5 mL of dimethylformamide, and under cooling with ice, the solution was dropwise added to a suspension having 50 mg of sodium hydride suspended in 10 mL of dimethylformamide, and after completion of the dropwise addition, stirring was carried out at room temperature for 30 minutes. The reaction solution was cooled with ice again, and 0.15 g of 1-bromo-2-propyne was added, followed by stirring at room temperature for 1 hour. Then, the reaction mixture was poured into water, extraction with ethyl acetate was carried out, and after washing with water, the organic layer was dried over anhydrous magnesium sulfate. The solvent was distilled off under reduced pressure, the obtained residue was dissolved in 20 mL of ethanol, and 20 mL of a 35mass % hydrochloric acid aqueous solution was added, followed by stirring under reflux with heating for 2 hours. The reaction mixture was poured into water, extraction with ethyl acetate was carried out, and after washing with water, the organic layer was dried over anhydrous magnesium sulfate. The solvent was distilled off under reduced pressure, and the obtained residue was purified by column chromatography (developing solvent ethyl acetate:hexane=1:4) to obtain 0.3 g of 1-{2-fluoro-4-methyl-5-(2,2,2-trifluoroethylthio)phenyl}-5-(2-propynylamino)-3-{1,1,2-trifluoro-2-(heptafluoropropoxy)ethoxy}pyrazole.
$^1$H-NMR (CDCL$_3$/TMS δ (ppm) value) δ: 2.30 (1H, t), 2.51 (3H, s), 3.68 (2H, q), 3.87 (2H, s), 3.87 (1H, s), 5.52 (1H, s), 6.13-6.33 (1H, m), 7.14 (1H, d), 7.61 (1H, d)

Example 28

Preparation of 1-{2-fluoro-4-methyl-5-(2,2,2-trifluoroethylsulfinyl)phenyl}-5-(2-propynylamino)-3-{1,1,2-trifluoro-2-(heptafluoropropoxy)ethoxy}pyrazole (compound No. 1-358 of the present invention)

0.17 g of 1-{2-fluoro-4-methyl-5-(2,2,2-trifluoroethylthio)phenyl}-5-(2-propynylamino)-3-{1,1,2-trifluoro-2-(heptafluoropropoxy)ethoxy}pyrazole was dissolved in 10 mL of chloroform, and 80 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure, and the obtained residue was purified by column chromatography (developing solvent ethyl acetate:hexane=1:2) to obtain 0.13 g of 1-{2-fluoro-4-methyl-5-(2,2,2-trifluoroethylsulfinyl)phenyl}-5-(2-propynylamino)-3-{1,1,2-trifluoro-2-(heptafluoropropoxy)ethoxy}pyrazole.
$^1$H-NMR (CDCL$_3$/TMS δ (ppm) value) δ: 2.30 (1H, s), 2.45 (3H, s), 3.38-3.59 (2H, m), 3.87 (2H, s), 3.87 (1H, s), 6.13-6.27 (1H, m), 7.18 (1H, d), 8.11 (1H, d)

Example 29

Preparation of 5-chloro-1-{2-fluoro-4-methyl-5-(2,2,2-trifluoroethylthio)phenyl}-3-(1,1,2,3,3,3-hexafluoropropoxy)pyrazole (compound No. 1-253 of the present invention)

1.09 g of 5-amino-1-{2-fluoro-4-methyl-5-(2,2,2-trifluoroethylthio)phenyl}-3-(1,1,2,3,3,3-hexafluoropropoxy)pyrazole was dissolved in 30 mL of acetonitrile, 0.31 g of copper(II) chloride was added, and 0.4 g of tert-butyl nitrite was dropwise added at −20° C., followed by stirring at −20° C. for 2 hours. The reaction mixture was poured into water, extraction with ethyl acetate was carried out, and after washing with water, the organic layer was dried over anhydrous magnesium sulfate. Then, the solvent was distilled off under reduced pressure, and the obtained residue was purified by column chromatography (developing solvent ethyl acetate:hexane=1:40) to obtain 0.23 g of 5-chloro-1-{2-fluoro-4-methyl-5-(2,2,2-trifluoroethylthio)phenyl}-3-(1,1,2,3,3,3-hexafluoropropoxy)pyrazole.
$^1$H-NMR (CDCL$_3$/TMS δ (ppm) value) δ: 2.54 (3H, s), 3.37 (2H, q), 5.02-5.18 (1H, m), 6.24 (1H, s), 7.15 (1H, d), 7.60 (1H, d)

Example 30

Preparation of 5-chloro 1-{2-fluoro-4-methyl-5-(2,2,2-trifluoroethylsulfinyl)phenyl}-3-(1,1,2,3,3,3-hexafluoropropoxy)pyrazole (compound No. 1-254 of the present invention)

0.15 g of 5-chloro 1-{2-fluoro-4-methyl-5-(2,2,2-trifluoroethylthio)phenyl}-3-(1,1,2,3,3,3-hexafluoropropoxy)pyrazole was dissolved in 10 mL of chloroform, and 90mg of m-chloroperbenzoic acid (purity: 75%) was added under cooling with ice. After stirring for 1 hour under cooling with ice, the solution was washed with an aqueous sodium thiosulfate solution and then washed with an aqueous sodium hydrogen carbonate solution, and then dried over anhydrous sodium sulfate. The solvent was distilled off under reduced pressure to obtain 0.16 g of 5-chloro 1-{2-fluoro-4-methyl-5-(2,2,2-trifluoroethylsulfinyl)phenyl}-3-(1,1,2,3,3,3-hexafluoropropoxy)pyrazole.
$^1$H-NMR (CDCL$_3$/TMS δ (ppm) value) δ: 2.47 (3H, s), 3.31-3.59 (2H, m), 5.01-5.19 (1H, m), 6.27 (1H, s), 7.21 (1H, d), 8.10 (1H, d)

Example 31

Preparation of 5-acetylamino-1-{2-fluoro-4-methyl-5-(2,2,2-trifluoroethylthio)phenyl}-3-{1,1,2-trifluoro-2-(heptafluoropropoxy)ethoxy}pyrazole (compound No. 1-370 of the present invention) 5.0 g of 5-acetylamino-1-{2-fluoro-4-methyl-5-(2,2,2-trifluoroethylthio)phenyl}-3-hydroxypyrazole was dissolved in 40 mL of dimethylformamide, 27.8 g of triethylamine was added, and stirring was carried out at 60° C. for 4 hours while heptafluoropropyl trifluorovinyl ether was blown. The reaction mixture was poured into water, extraction with ethyl acetate was carried out, and after washing with water, the organic layer was dried over anhydrous magnesium sulfate. Then, the solvent was distilled off under reduced pressure, and the obtained residue was purified by column chromatography (developing solvent ethyl acetate:hexane=1:2) to obtain 1.56 g of 5-acetylamino-1-{2-fluoro-4-methyl-5-(2,2,2-trifluoroethylthio)phenyl}-3-{1,1,2-trifluoro-2-(heptafluoropropoxy)ethoxy}pyrazole.

$^1$H-NMR (CDCL$_3$/TMS δ (ppm) value) δ: 2.10 (3H, s), 2.54 (3H, s), 3.40 (2H, q), 6.21 (1H, dt), 6.49 (1H, s), 7.14 (1H, brs), 7.18 (1H, d), 7.61 (1H, d)

Example 32

Preparation of 5-acetylamino-1-{2-fluoro-4-methyl-5-(2,2,2-trifluoroethylsulfinyl)phenyl}-3-{1,1,2-trifluoro-2-(heptafluoropropoxy)ethoxy}pyrazole (compound No. 1-371 of the present invention)

0.45 g of 5-acetylamino-1-{2-fluoro-4-methyl-5-(2,2,2-trifluoroethylthio)phenyl}-3-{1,1,2-trifluoro-2-(heptafluoropropoxy)ethoxy}pyrazole was dissolved in 10 mL of chloroform, and 1.6 g of m-chloroperbenzoic acid (purity: 75%) was added under cooling with ice. After stirring for 30 minutes under cooling with ice, the solution was washed with an aqueous sodium thiosulfate solution and then washed with an aqueous sodium hydrogen carbonate solution, and then dried over anhydrous sodium sulfate. Then, the solvent was distilled off under reduced pressure, and the obtained residue was purified by column chromatography (developing solvent ethyl acetate:hexane=1:1) to obtain 0.41 g of 5-acetylamino-1-{2-fluoro-4-methyl-5-(2,2,2-trifluoroethylsulfinyl)phenyl}-3-{1,1,2-trifluoro-2-(heptafluoropropoxy)ethoxy}pyrazole.
$^1$H-NMR (CDCL$_3$/TMS δ (ppm) value) δ: 2.09 (3H, s), 2.47 (3H, s), 3.40-3.61 (2H, m), 6.19 (1H, dt), 6.45 (1H, s), 7.21 (1H, d), 7.55 (1H, brs), 8.07 (1H, d)

Example 33

Preparation of 5-acetylamino-3-[2,2-difluoro-2-{2-trifluoromethoxy-(1,1,2,2-tetrafluoroethoxy)}ethoxy]-1-{2-fluoro-4-methyl-5-(2,2,2-trifluoroethylthio)phenyl}pyrazole (compound No. 1-374 of the present invention)

0.5 g of 5-acetylamino-1-{2-fluoro-4-methyl-5-(2,2,2-trifluoroethylthio)phenyl}-3-hydroxypyrazole was dissolved in 10 mL of dimethylsulfoxide, and 0.28 g of potassium carbonate and 1.0 g of 2,2-difluoro-2-{2-trifluoromethoxy-(1,1,2,2-tetrafluoroethoxy)}ethyl nonafluorobutylsulfonate were added, followed by stirring at room temperature for 12 hours. After completion of the reaction, the reaction solution was poured into water, extraction with ethyl acetate was carried out, and after washing with a saturated salt solution, the organic layer was dried over anhydrous magnesium sulfate, the solvent was distilled off under reduced pressure, and the obtained residue was purified by column chromatography (ethyl acetate:hexane=1:4) to obtain 0.67 g of 5-acetylamino-3-[2,2-difluoro-2-{2-trifluoromethoxy-(1,1,2,2-tetrafluoroethoxy)}ethoxy]-1-{2-fluoro-4-methyl-5-(2,2,2-trifluoroethylthio)phenyl}pyrazole.

$^1$H-NMR (CDCL$_3$/TMS δ (ppm) value) δ: 2.08 (3H, s), 2.53 (3H, s), 3.39 (2H, q), 4.60 (2H, t), 6.22 (1H, s), 7.05 (1H, brs), 7.16 (1H, d), 7.59 (1H, d)

Example 34

Preparation of 5-acetylamino-3-[2,2-difluoro-2-{2-trifluoromethoxy-(1,1,2,2-tetrafluoroethoxy)}ethoxy]-1-{2-fluoro-4-methyl-5-(2,2,2-trifluoroethylsulfinyl)phenyl}pyrazole (compound No. 1-375)

0.42 g of 5-acetylamino-3-[2,2-difluoro-2-{2-trifluoromethoxy-(1,1,2,2-tetrafluoroethoxy)}]-1-{2-fluoro-4-methyl-5-(2,2,2-trifluoroethylthio)phenyl}pyrazole was dissolved in 10 mL of chloroform, and 0.15 g of m-chloroperbenzoic acid (purity: 75%) was added under cooling with ice. After stirring for 30 minutes under cooling with ice, the solution was washed with an aqueous sodium thiosulfate solution and then washed with an aqueous sodium hydrogen carbonate solution, and then dried over anhydrous sodium sulfate. Then, the solvent was distilled off under reduced pressure, and the obtained residue was purified by column chromatography (developing solvent ethyl acetate:hexane=1:1) to obtain 0.43 g of 5-acetylamino-3-[2,2-difluoro-2-{2-trifluoromethoxy-(1,1,2,2-tetrafluoroethoxy)}ethoxy]-1-{2-fluoro-4-methyl-5-(2,2,2-trifluoroethylsulfinyl)phenyl}pyrazole.

$^1$H-NMR (CDCL$_3$/TMS δ (ppm) value) δ: 2.08 (3H, s), 2.46 (3H, s), 3.41-3.60 (2H, m), 4.61 (2H, t), 6.19 (1H, s), 7.20 (1H, d), 7.30 (1H, brs), 8.07 (1H, d)

Example 35

Preparation of 5-acetylamino-1-{2-fluoro-4-methyl-5-(2-chloro-2,2-difluoroethylthio)phenyl}-3-(2,2,3,3,3-pentafluoropropoxy)pyrazole (compound No. 1-177 of the present invention)

9.2 g of 2-fluoro-4-methyl-5-mercaptoaniline disclosed in WO2006/043635 was dissolved in 70 mL of water, and 9.7 g of potassium carbonate and 8.3 g of iodomethane were added under cooling with ice, followed by stirring at room temperature for 2 hours. The formed crystals were collected by filtration and washed with water to obtain 10.0 g of 2-fluoro-4-methyl-5-methylthioaniline.

Then, a solution of 9.2 g of the obtained 2-fluoro-4-methyl-5-methylthioaniline in 10 mL of acetic acid was dropwise added to a mixed solution comprising 32 g of concentrated sulfuric acid, 4.1 g of sodium nitrite and 15 mL of acetic acid at 5° C. or below over a period of 15 minutes, followed by stirring at 5° C. or below for 3 hours. This reaction mixture was dropwise added to a mixed solution comprising 20.2 g of tin(II) chloride dihydrate and 100 mL of a 6N hydrochloric acid aqueous solution at 5° C. or below, followed by stirring for 30 minutes. To this reaction mixture, 20 mL of toluene was added, followed by neutralized with a 10% sodium hydroxide aqueous solution. Insoluble matters were separated by filtration, and the organic layer was dried over anhydrous magnesium sulfate and concentrated under reduced pressure to obtain 6.2 g of 2-fluoro-4-methyl-5-methylthiophenylhydrazine.

Then, the obtained hydrazine derivative was dissolved in 50 mL of tetrahydrofuran, and to this solution, 5.1 g of cyanoacetyl chloride was added, followed by stirring at room temperature for 2 hours. Then, the solvent was distilled off under reduced pressure, the residue was dissolved in 50 mL of 1-propanol, and 3.1 g of methanesulfonic acid was added, followed by reflux with heating for 3 hours. After cooling to room temperature, the solvent was distilled off under reduced pressure, followed by neutralization with sodium hydrogen carbonate to a pH of 7, and extraction with ethyl acetate was carried out. The organic layer was dried over anhydrous magnesium sulfate, and the solvent was distilled off under reduced pressure to obtain 5.5 g of 5-amino-1-(2-fluoro-4-methyl-5-methylthiophenyl)-3-hydroxypyrazole in the form of yellow crystals (melting point: 230-232° C.).

Then, the obtained pyrazole derivative was dissolved in 50 mL of toluene, and to this solution, 6.0 g of acetyl chloride was added, followed by reflux with heating for 12 hours. After cooling to room temperature, the solvent was distilled off under reduced pressure, the residue was dissolved in 30 mL of ethanol, and 20 mL of a 25mass % ammonia water was added, followed by stirring at room temperature for 30minutes. The solvent was distilled off under reduced pressure, and the obtained solid was washed with diisopropyl ether to obtain 5.2 g of 5-acetylamino-1-(2-fluoro-4-methyl-5-methylthiophenyl)-3-hydroxypyrazole in the form of pale yellow crystals (melting point: 204-205° C.).

Then, 5.0 g of 5-acetylamino-1-(2-fluoro-4-methyl-5-methylthiophenyl)-3-hydroxypyrazole was dissolved in 100 mL of dimethylsulfoxide, and 2.1 g of potassium carbonate was added, followed by stirring at room temperature for 5 minutes. To this solution, 6.2 g of 2,2,3,3,3-pentafluoropropyl nonafluorobutanesulfonate was added, followed by stirring at room temperature for 12 hours. Then, extraction with ethyl acetate was carried out, the organic layer was dried over anhydrous magnesium sulfate, the solvent was distilled off under reduced pressure, and the obtained residue was purified by silica gel column chromatography (developing solvent ethyl acetate:hexane=1:4) to obtain 5.1 g of 5-acetylamino-1-(2-fluoro-4-methyl-5-methylthiophenyl)-3-(2,2,3,3,3-pentafluoropropoxy)pyrazole ($^1$H-NMR (CDCL$_3$/TMS δ (ppm) value) δ: 2.13 (3H, s), 2.37 (3H, s), 2.47 (3H, s), 4.67 (2H, t), 6.22 (1H, s), 7.07 (1H, d), 7.14 (1H, brs), 7.17 (1H, d)).

Then, 5.0 g of 5-acetylamino-1-(2-fluoro-4-methyl-5-methylthiophenyl)-3-(2,2,3,3,3-pentafluoropropoxy)pyrazole was dissolved in 150 mL of chloroform, and 3.4 g of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by silica gel column chromatography (developing solvent ethyl acetate:hexane=1:2) to obtain 4.7 g of 5-acetylamino-1-(2-fluoro-4-methyl-5-methylsulfinylphenyl)-3-(2,2,3,3,3-pentafluoropropoxy)pyrazole ($^1$H-NMR (CDCL$_3$/TMS δ (ppm) value) δ: 2.09 (3H, s), 2.43 (3H, s), 2.74 (3H, s), 4.66 (2H, t), 6.21 (1H, s), 7.15 (1H, d), 7.45 (1H, brs), 8.02 (1H, d)).

Then, 4.5 g of 5-acetylamino-1-(2-fluoro-4-methyl-5-methylsulfinylphenyl)-3-(2,2,3,3,3-pentafluoropropoxy)pyrazole was dissolved in 200 mL of acetic anhydride, followed by stirring at 120° C. for 6 hours. Acetic anhydride was distilled off under reduced pressure, the obtained residue was dissolved in 150 mL of ethanol, and 4.0 g of potassium carbonate was added, followed by stirring at room temperature for 12hours. Neutralization with a 6N hydrochloric acid aqueous solution was carried out, and extraction with ethyl acetate was carried out. The organic layer was dried over anhydrous magnesium sulfate, the solvent was distilled off under reduced pressure, and the obtained residue was purified by silica gel column chromatography (developing solvent ethyl acetate:hexane=1:4) to obtain 3.8 g of 5-acetylamino-1-(2-fluoro-4-methyl-5-mercaptophenyl)-3-(2,2,3,3,3-pentafluoropropoxy)pyrazole ($^1$H-NMR (CDCL$_3$/TMS δ (ppm) value) δ: 2.09 (3H, s), 2.38 (3H, s), 3.39 (1H, s), 4.66 (2H, t), 6.20 (1H, s), 7.09 (1H, d), 7.14 (1H, brs), 7.39 (1H, d)).

Then, 1.5 g of 5-acetylamino-1-(2-fluoro-4-methyl-5-mercaptophenyl)-3-(2,2,3,3,3-pentafluoropropoxy)pyrazole was dissolved in 20 mL of dimethylformamide, and 0.32 g of sodium carbonate and 1.5 g of 2-chloro-2,2-difluoroethyl nonafluorobutanesulfonate were added, followed by stirring at room temperature for 12hours. Then, extraction with ethyl acetate was carried out, the organic layer was dried over anhydrous magnesium sulfate, the solvent was distilled off under reduced pressure, the obtained residue was purified by silica gel column chromatography (developing solvent ethyl acetate:hexane=1:4) to obtain 1.3 g of 5-acetylamino-1-{2-fluoro-4-methyl-5-(2-chloro-2,2-difluoroethylthio)phenyl}-3-(2,2,3,3,3-pentafluoropropoxy)pyrazole.

$^1$H-NMR (CDCL$_3$/TMS δ (ppm) value) δ: 2.08 (3H, s), 2.53 (3H, s), 3.62 (2H, t), 4.66 (2H, t), 6.21 (1H, s), 7.07 (1H, brs), 7.15 (1H, d), 7.60 (1H, d)

Example 36

Preparation of 5-acetylamino-1-{2-fluoro-4-methyl-5-(2-chloro-2,2-difluoroethylsulfinyl)phenyl}-3-(2,2,3,3,3-pentafluoropropoxy)pyrazole (compound No. 1-178 of the present invention)

0.6 g of 5-acetylamino-1-{2-fluoro-4-methyl-5-(2-chloro-2,2-difluoroethylthio)phenyl}-3-(2,2,3,3,3-pentafluoropropoxy)pyrazole was dissolved in 20mL of chloroform, and 0.3 g of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and dried over anhydrous magnesium sulfate. Then, the solvent was distilled off under reduced pressure, the obtained residue was purified by silica gel column chromatography (developing solvent ethyl acetate:hexane=1:2) to obtain 0.6 g of the title compound.

$^1$H-NMR (CDCL$_3$/TMS δ (ppm) value) δ: 2.05 (3H, d), 2.43 (3H, s), 3.41-3.51 (2H, m), 4.65 (2H, t), 6.14 (1H, s), 7.18 (1H, d), 7.68 (1H, brs), 8.01 (1H, d)

Example 37

Preparation of 5-acetylamino-1-{2-fluoro-4-methyl-5-(2,2,2-trifluoroethylthio)phenyl}-3-(1,1,2,2-tetrafluoroethoxy)pyrazole (compound No. 1-1367 of the present invention)

1.0 g of 5-acetylamino-1-{2-fluoro-4-methyl-5-(2,2,2-trifluoroethylthio)phenyl}-3-hydroxypyrazole was dissolved in 50 mL of dimethylformamide, and 0.04 g of potassium carbonate was added, followed by stirring at 90° C. Further, 1.5 g of a cadmium powder was added to 50 mL of acetonitrile, 4.9 g of tetrafluoro-1,2-diiodoethane was dropwise added under reflux with heating to form tetrafluoroethylene, which was blown at 90° C. for one hour. Then, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 0.4 g of 5-acetylamino-1-{2-fluoro-4-methyl-5-(2,2,2-trifluoroethylthio)phenyl}-3-(1,1,2,2-tetrafluoroethoxy)pyrazole.

$^1$H-NMR (CDCL$_3$/TMS δ (ppm) value) δ: 2.06 (3H, s), 2.52 (1H, s), 3.40 (2H, q), 5.85-6.12 (1H, m), 6.45 (1H, s), 7.15 (1H, d), 7.45 (1H, s), 7.60 (1H, d)

Example 38

Preparation of 5-acetylamino-1-{2-fluoro-4-methyl-5-(2,2,2-trifluoroethylsulfinyl)phenyl}-3-(1,1,2,2-tetrafluoroethoxy)pyrazole (compound No. 1-1368 of the present invention)

0.4 g of 5-acetylamino-1-{2-fluoro-4-methyl-5-(2,2,2-trifluoroethylthio)phenyl}-3-(1,1,2,2-tetrafluoroethoxy)pyrazole was dissolved in 10 mL of chloroform, and 0.2 g of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.3 g of 5-acetylamino-1-{2-fluoro-4-methyl-5-(2,2,2-trifluoroethylsulfinyl)phenyl}-3-(1,1,2,2-tetrafluoroethoxy)pyrazole.

$^1$H-NMR (CDCL$_3$/TMS δ (ppm) value) δ: 2.07 (3H, s), 2.45 (3H, s), 3.37-3.59 (2H, m), 5.99 (1H, t), 6.44 (1H, s), 7.20 (1H, d), 7.76 (1H, brs), 8.04 (1H, d)

Example 39

Preparation of 5-amino-4-chloro-1-{2-fluoro-4-methyl-5-(2,2,2-trifluoroethylthio)phenyl}-3-(1,1,2,3,3,3-hexafluoropropoxy)pyrazole (compound No. 1-263 of the present invention)

2.9 g of 5-amino-1-{2-fluoro-4-methyl-5-(2,2,2-trifluoroethylthio)phenyl}-3-(1,1,2,3,3,3-hexafluoropropoxy)pyrazole was dissolved in 30 mL of acetonitrile, and 0.9g of N-chlorosuccinimide was added under cooling with ice. After stirring for 30minutes under cooling with ice, the solvent was distilled off under reduced pressure, extraction with ethyl acetate was carried out, and the organic layer was dried over anhydrous magnesium sulfate. Then, the solvent was distilled off under reduced pressure, and the obtained residue was purified by column chromatography (developing solvent ethyl acetate:hexane=1:4) to obtain 3.12 g of 5-amino-4-chloro-1-{2-fluoro-4-methyl-5-(2,2,2-trifluoroethylthio)phenyl}-3-(1,1,2,3,3,3-hexafluoropropoxy)pyrazole.

$^1$H-NMR (CDCL$_3$/TMS δ (ppm) value) δ: 2.53 (3H, s), 3.39 (2H, q), 3.95 (2H, brs), 5.22 (1H, dq), 7.15 (1H, d), 7.62 (1H, d)

Example 40

Preparation of 5-amino-4-chloro 1-{2-fluoro-4-methyl-5-(2,2,2-trifluoroethylsulfinyl)phenyl}-3-(1,1,2,3,3,3-hexafluoropropoxy)pyrazole (compound No. 1-264 of the present invention)

0.3 g of 4-chloro-1-{2-fluoro-4-methyl-5-(2,2,2-trifluoroethylthio)phenyl}-3-(1,1,2,3,3,3-hexafluoropropoxy)-5-aminopyrazole was dissolved in 10 mL of chloroform, and 140 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous sodium sulfate. Then, the solvent was distilled off under reduced pressure, and the obtained residue was purified by column chromatography (developing solvent ethyl acetate:hexane=1:2) to obtain 0.24 g of 5-amino-4-chloro 1-{2-fluoro-4-methyl-5-(2,2,2-trifluoroethylsulfinyl)phenyl}-3-(1,1,2,3,3,3-hexafluoropropoxy)pyrazole.

$^1$H-NMR (CDCL$_3$/TMS δ (ppm) value) δ: 2.47 (3H, s), 3.39-3.61 (2H, m), 3.96 (2H, brs), 5.20 (1H, dq), 7.21 (1H, d), 8.13 (1H, d)

Example 41

Preparation of 4-chloro-1-{2-fluoro-4-methyl-5-(2,2,2-trifluoroethylthio)phenyl}-3-(1,1,2,3,3,3-hexafluoropropoxy)-5-methylaminopyrazole (compound No. 1-261 of the present invention)

0.8 g of 5-amino-4-chloro-1-{2-fluoro-4-methyl-5-(2,2,2-trifluoroethylthio)phenyl}-3-(1,1,2,3,3,3-hexafluoropropoxy)pyrazole was dissolved in 20 mL of acetic anhydride. After stirring for 3 hours under reflux with heating, acetic anhydride was distilled off under reduced pressure, the obtained residue was dissolved in 20 mL of tetrahydrofuran, and 20 mL of a 25 mass % ammonia water was added under cooling with ice. After stirring for one hour under cooling with ice, the solvent was distilled off under reduced pressure, extraction with ethyl acetate was carried out, and the organic layer was dried over anhydrous magnesium sulfate. Then, the solvent was distilled off under reduced pressure, the obtained residue was dissolved in 5 mL of dimethylformamide, and the solution was dropwise added to a suspension having 50 mg of sodium hydride suspended in 10 mL of dimethylformamide under cooling with ice. After completion of the dropwise addition, stirring was carried out at room temperature for 30 minutes. The reaction solution was cooled with ice again, and 0.18 g of methyl iodide was added, followed by stirring at room temperature for one hour. Water was injected, extraction with ethyl acetate was carried out, and after washing with water, the organic layer was dried over anhydrous magnesium sulfate. Then, the solvent was distilled off under reduced pressure, the obtained residue was dissolved in 10 mL of ethanol, and 10 mL of a 35 mass % hydrochloric acid aqueous solution was added, followed by stirring under reflux with heating for one hour. The reaction mixture was poured into water, extraction with ethyl acetate was carried out, and after washing with water, the organic layer was dried over anhydrous magnesium sulfate. Then, the solvent was distilled off under reduced pressure, and the obtained residue was purified by column chromatography (developing solvent ethyl acetate:hexane=1:4) to obtain 0.34 g of 4-chloro-1-{2-fluoro-4-methyl-5-(2,2,2-trifluoroethylthio)phenyl}-3-(1,1,2,3,3,3-hexafluoropropoxy)-5-methylaminopyrazole.

$^1$H-NMR (CDCL$_3$/TMS δ (ppm) value) δ: 2.53 (3H, s), 2.91 (3H, d), 3.38 (2H, q), 3.51 (1H, brs), 5.22 (1H, dq), 7.14 (1H, d), 7.59 (1H, d)

Example 42

Preparation of 4-chloro-1-{2-fluoro-4-methyl-5-(2,2,2-trifluoroethylsulfinyl)phenyl}-3-(1,1,2,3,3,3-hexafluoropropoxy)-5-methylaminopyrazole (compound No. 1-262 of the present invention)

0.24 g of 4-chloro-1-{2-fluoro-4-methyl-5-(2,2,2-trifluoroethylthio)phenyl}-3-(1,1,2,3,3,3-hexafluoropropoxy)-5-methylaminopyrazole was dissolved in 10 mL of chloroform, and 120 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous sodium sulfate. Then, the solvent was distilled off under reduced pressure, and the obtained residue was purified by column chromatography (developing solvent ethyl acetate:hexane=1:2) to obtain 0.24 g of 4-chloro-1-{2-fluoro-4-methyl-5-(2,2,2-trifluoroethylsulfinyl)phenyl}-3-(1,1,2,3,3,3-hexafluoropropoxy)-5-methylaminopyrazole.

$^1$H-NMR (CDCL$_3$/TMS δ (ppm) value) δ: 2.46 (3H, s), 2.90 (3H, s), 3.39-3.60 (2H, m), 5.20 (1H, dq), 7.19 (1H, d), 8.10 (1H, d)

Example 43

Preparation of 5-acetylamino-1-{2-fluoro-4-methyl-5-(2,2,2-trifluoroethylthio)phenyl}-3-(2,2,3,3,4,4,5,5,5-nonafluoropentyloxy)pyrazole (compound No. 1-77 of the present invention)

0.5 g of 5-acetylamino-1-{2-fluoro-4-methyl-5-(2,2,2-trifluoroethylthio)phenyl}-3-hydroxypyrazole was dissolved in 10 mL of dimethylsulfoxide, and 0.23 g of potassium carbonate was added, followed by stirring at room temperature for 5 minutes. To this solution, 0.79 g of 2,2,3,3,3-pentafluoropropyl nonafluorobutanesulfonate was added, followed by stirring at room temperature for 12 hours. Then, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 0.55 g of 5-acetylamino-1-{2-fluoro-4-methyl-5-(2,2,2-trifluoroethylthio)phenyl}-3-(2,2,3,3,4,4,5,5,5-nonafluoropentyloxy)pyrazole.

$^1$H-NMR (CDCL$_3$/TMS δ (ppm) value) δ: 2.09 (3H, s), 2.53 (3H, s), 3.40 (2H, q), 4.72 (2H, t), 6.22 (1H, s), 7.03 (1H, brs), 7.16 (1H, d), 7.60 (1H, d)

Example 44

Preparation of 5-acetylamino-1-{2-fluoro-4-methyl-5-(2,2,2-trifluoroethylsulfinyl)phenyl}-3-(2,2,3,3,4,4,5,5,5-nonafluoropentyloxy)pyrazole (compound No. 1-78 of the present invention)

0.2 g of 5-acetylamino-1-{2-fluoro-4-methyl-5-(2,2,2-trifluoroethylthio)phenyl}-3-(2,2,3,3,4,4,5,5,5-nonafluoropentyloxy)pyrazole was dissolved in 10 mL of chloroform, and 77 mg of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.19 g of 5-acetylamino-1-{2-fluoro-4-methyl-5-(2,2,2-trifluoroethylsulfinyl)phenyl}-3-(2,2,3,3,4,4,5,5,5-nonafluoropentyloxy)pyrazole.

$^1$H-NMR (CDCL$_3$/TMS δ (ppm) value) δ: 2.08 (3H, s), 2.46 (3H, s), 3.41-3.54 (2H, m), 4.72 (2H, t), 6.19 (1H, s), 7.20 (1H, d), 7.24 (1H, brs), 8.08 (1H, d)

Example 45

Preparation of ethyl 1-{2-fluoro-4-methyl-5-(2,2,2-trifluoroethylthio)phenyl}-3-(2,2,3,3,3-pentafluoropropoxy)pyrazole-5-carboxylate (compound No. 1-143 of the present invention)

1.0 g of ethyl 1-{2-fluoro-4-methyl-5-(2,2,2-trifluoroethylthio)phenyl}-3-hydroxypyrazole-5-carboxylate was dissolved in 20 mL of dimethylsulfoxide, and 0.47g of potassium carbonate was added, followed by stirring at room temperature for 5minutes. To this solution, 1.14 g of 2,2,3,3,3-pentafluoropropyl nonafluorobutanesulfonate was added, followed by stirring at room temperature for 12hours. Extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 1.1 g of ethyl 1-{2-fluoro-4-methyl-5-(2,2,2-trifluoroethylthio)phenyl}-3-(2,2,3,3,3-pentafluoropropoxy)pyrazole-5-carboxylate.

$^1$H-NMR (CDCL$_3$/TMS δ (ppm) value) δ: 1.25 (3H, t), 2.53 (3H, s), 3.37 (2H, q), 4.24 (2H, q), 4.70 (2H, t), 6.51 (1H, s), 7.09 (1H, d), 7.60 (1H, d)

Example 46

Preparation of 1-{2-fluoro-4-methyl-5-(2,2,2-trifluoroethylthio)phenyl}-3-(2,2,3,3,3-pentafluoropropoxy)pyrazole-5-carboxylic acid (compound No. 1-145 of the present invention)

0.95 g of ethyl 1-{2-fluoro-4-methyl-5-(2,2,2-trifluoroethylthio)phenyl}-3-(2,2,3,3,3-pentafluoropropoxy)pyrazole-5-carboxylate was dissolved in 20 mL of ethanol. To this solution, a solution having 0.42 g of potassium hydroxide dissolved in 10 mL of water was added, followed by stirring at room temperature for 30 minutes. Concentrated hydrochloric acid was added to adjust the pH to 2, the solvent was distilled off under reduced pressure, extraction with ethyl acetate was carried out, and the organic layer was dried over anhydrous sodium sulfate. Then, the solvent was distilled off under reduced pressure to obtain 0.90 g of 1-{2-fluoro-4-methyl-5-(2,2,2-trifluoroethylthio)phenyl}-3-(2,2,3,3,3-pentafluoropropoxy)pyrazole-5-carboxylic acid.

$^1$H-NMR (CDCL$_3$/TMS δ (ppm) value) δ: 2.54 (3H, s), 3.36 (2H, q), 4.70 (2H, t), 6.58 (1H, s), 7.08 (1H, d), 7.59 (1H, d)

Example 47

Preparation of 1-{2-fluoro-4-methyl-5-(2,2,2-trifluoroethylthio)phenyl}-3-(2,2,3,3,3-pentafluoropropoxy)pyrazole-5-carboxyamide (compound No. 1-139 of the present invention)

0.84 g of 1-{2-fluoro-4-methyl-5-(2,2,2-trifluoroethylthio)phenyl}-3-(2,2,3,3,3-pentafluoropropoxy)pyrazole-5-carboxylic acid was dissolved in 10 mL of dichloromethane, and 0.2 mL of oxalyl dichloride and N,N-dimethylformamide in a catalytic amount were added, followed by stirring at room temperature for 1 hour. Then, the solvent was distilled off under reduced pressure, and the resulting product was dissolved in 10 mL of tetrahydrofuran, and the solution was dropwise added to a mixed solution comprising 30 mL of a 25 mass % ammonia water and 40 mL of tetrahydrofuran at −30° C. Then, stirring was carried out for 12 hours while the temperature was slowly increased to room temperature. Then, the solvent was distilled off under reduced pressure, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:3) to obtain 0.80 g of 1-{2-fluoro-4-methyl-5-(2,2,2-trifluoroethylthio)phenyl}-3-(2,2,3,3,3-pentafluoropropoxy)pyrazole-5-carboxyamide.

$^1$H-NMR (CDCL$_3$/TMS δ (ppm) value) δ: 2.51 (3H, s), 3.38 (2H, q), 4.71 (2H, t), 5.57 (1H, br), 5.80 (1H, br), 6.25 (1H, s), 7.07 (1H, d), 7.63 (1H, d)

Example 48

Preparation of 5-cyano-1-{2-fluoro-4-methyl-5-(2,2,2-trifluoroethylthio)phenyl}-3-(2,2,3,3,3-pentafluoropropoxy)pyrazole (compound No. 1-133 of the present invention)

0.80 g of 1-{2-fluoro-4-methyl-5-(2,2,2-trifluoroethylthio)phenyl}-3-(2,2,3,3,3-pentafluoropropoxy)pyrazole-5-carboxyamide was dissolved in 20 mL of tetrahydrofuran, 0.42 g of triethylamine was added, and 0.52 g of trifluoroacetic anhydride was slowly dropwise added under cooling with ice. After stirring at room temperature for 2 hours, the solvent was distilled off under reduced pressure, and extraction with ethyl acetate was carried out. The organic layer was dried over anhydrous magnesium sulfate, the solvent was distilled off under reduced pressure, and the obtained residue was purified by column chromatography (developing solvent ethyl acetate:hexane=1:4) to obtain 0.60 g of 5-cyano-1-{2-fluoro-4-methyl-5-(2,2,2-trifluoroethylthio)phenyl}-3-(2,2,3,3,3-pentafluoropropoxy)pyrazole.

$^1$H-NMR (CDCL$_3$/TMS δ (ppm) value) δ: 2.56 (3H, s), 3.40 (2H, q), 4.74 (2H, t), 6.52 (1H, s), 7.21 (1H, d), 7.65 (1H, d)

Example 49

Preparation of 5-cyano-1-{2-fluoro-4-methyl-5-(2,2,2-trifluoroethylsulfinyl)phenyl}-3-(2,2,3,3,3-pentafluoropropoxy)pyrazole (compound No. 1-134 of the present invention)

0.40 g of 5-cyano-1-{2-fluoro-4-methyl-5-(2,2,2-trifluoroethylthio)phenyl}-3-(2,2,3,3,3-pentafluoropropoxy)pyrazole was dissolved in 10 mL of chloroform, and 200mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.40 g of 5-cyano-1-{2-fluoro-4-methyl-5-(2,2,2-trifluoroethylsulfinyl)phenyl}-3-(2,2,3,3,3-pentafluoropropoxy)pyrazole.

$^1$H-NMR (CDCL$_3$/TMS δ (ppm) value) δ: 2.49 (3H, s), 3.43-3.58 (2H, m), 4.74 (2H, t), 6.56 (1H, s), 7.27 (1H, d), 8.16 (1H, d)

Example 50

Preparation of 1-{2-fluoro-4-methyl-5-(2,2,2-trifluoroethylthio)phenyl}-5-hydroxymethyl-3-(2,2,3,3,3-pentafluoropropoxy)pyrazole (compound No. 1-201 of the present invention)

3.97 g of 1-{2-fluoro-4-methyl-5-(2,2,2-trifluoroethylthio)phenyl}-3-(2,2,3,3,3-pentafluoropropoxy)pyrazole-5-carboxylic acid was dissolved in 60 mL of dichloromethane, and 0.93 mL of oxalyl dichloride and N,N-dimethylformamide in a catalytic amount were added, followed by stirring at room temperature for 1 hour. Then, the solvent was distilled off under reduced pressure, the resulting product was dissolved in 50 mL of tetrahydrofuran, and 1.56 g of sodium borohydride was added, followed by cooling to −20° C. 20 mL of water was slowly dropwise added, and then, stirring was carried out for 12 hours while the temperature was slowly increased to room temperature. Then, the solvent was distilled off under reduced pressure, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:2) to obtain 3.01 g of 1-{2-fluoro-4-methyl-5-(2,2,2-trifluoroethylthio)phenyl}-5-hydroxymethyl-3-(2,2,3,3,3-pentafluoropropoxy)pyrazole.

$^1$H-NMR (CDCL$_3$/TMS δ (ppm) value) δ: 2.52 (3H, s), 3.39 (2H, q), 4.49 (2H, d), 4.67 (2H, t), 6.00 (1H, s), 7.12 (1H, d), 7.63 (1H, d)

Example 51

Preparation of 1-{2-fluoro-4-methyl-5-(2,2,2-trifluoroethylthio)phenyl}-5-formyl-3-(2,2,3,3,3-pentafluoropropoxy)pyrazole (compound No. 1-199 of the present invention)

1.5 g of 1-{2-fluoro-4-methyl-5-(2,2,2-trifluoroethylsulfinyl)phenyl}-5-hydroxymethyl-3-(2,2,3,3,3-pentafluoropropoxy)pyrazole was dissolved in 30 mL of chloroform and 10 mL of methanol, and 3.0 g of manganese dioxide was added, followed by stirring at room temperature for 12 hours. Then, the reaction solution as subjected to filtration, the filtrate was distilled under reduced pressure, and the obtained residue was purified by column chromatography (developing solvent ethyl acetate:hexane=1:4) to obtain 1.02 g of 1-{2-fluoro-4-methyl-5-(2,2,2-trifluoroethylthio)phenyl}-5-formyl-3-(2,2,3,3,3-pentafluoropropoxy)pyrazole.

$^1$H-NMR (CDCL$_3$/TMS δ (ppm) value) δ: 2.55 (3H, s), 3.38 (2H, q), 4.73 (2H, t), 6.56 (1H, s), 7.14 (1H, d), 7.63 (1H, d)

Example 52

Preparation of 1-{2-fluoro-4-methyl-5-(2,2,2-trifluoroethylthio)phenyl}-5-(hydroxyimino)methylene-3-(2,2,3,3,3-pentafluoropropoxy)pyrazole (compound No. 1-205 of the present invention)

0.3 g of 1-{2-fluoro-4-methyl-5-(2,2,2-trifluoroethylsulfinyl)phenyl}-5-formyl-3-(2,2,3,3,3-pentafluoropropoxy)pyrazole was dissolved in 10 mL of methanol, and 79mg of sodium acetate and 67 mg of hydroxylammonium chloride were added, followed by stirring under reflux with heating for 2 hours. Then, the solvent was distilled off under reduced pressure, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:3) to obtain 0.31 g of 1-{2-fluoro-4-methyl-5-(2,2,2-trifluoroethylthio)phenyl}-5-(hydroxyimino)methylene-3-(2,2,3,3,3-pentafluoropropoxy)pyrazole.

$^1$H-NMR (CDCL$_3$/TMS δ (ppm) value) δ: (majar) 2.54 (3H, s), 3.38 (2H, q), 4.69 (2H, t), 6.25 (1H, s), 7.13 (1H, d), 7.58 (1H, s), 7.58 (1H, d), 7.80 (1H, s)

Example 53

Preparation of 5-cyano-1-{2-fluoro-4-methyl-5-(2,2,2-trifluoroethylthio)phenyl}-3-{1,1,2-trifluoro-2-(trifluoromethoxy)ethoxy}pyrazole (compound No. 1-668 of the present invention)

1.1 g of ethyl 1-{2-fluoro-4-methyl-5-(2,2,2-trifluoroethylthio)phenyl}-3-{1,1,2-trifluoro-2-(trifluoromethoxy)ethoxy}pyrazole-5-carboxylate was dissolved in 30 mL of toluene, followed by cooling to −78° C., and 2.6 mL of a toluene solution (1.0 mol/L) of diisobutyl aluminum hydride was slowly dropwise added. After stirring for 3 hours, a saturated aqueous solution of ammonium chloride was added, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:3) to obtain 0.95 g of 5-formyl-1-{2-fluoro-4-methyl-5-(2,2,2-trifluoroethylthio)phenyl}-3-{1,1,2-trifluoro-2-(trifluoromethoxy)ethoxy}pyrazole ($^1$H-NMR (CDCL$_3$/TMS δ (ppm) value) δ: 2.56 (3H, s), 3.39 (2H, q), 6.05 (1H, dt), 6.85 (1H, s), 7.17 (1H, d), 7.66 (1H, d), 9.72 (1H, d)).

Then, 0.43 g of 5-formyl-1-{2-fluoro-4-methyl-5-(2,2,2-trifluoroethylthio)phenyl}-3-{1,1,2-trifluoro-2-(trifluoromethoxy)ethoxy}pyrazole was dissolved in 15 mL of methanol, and 110 mg of sodium acetate and 90 mg of hydroxylammonium chloride were added, followed by stirring under reflux with heating for 2 hours. Then, the solvent was distilled off under reduced pressure, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:3) to obtain 0.29g of 1-{2-fluoro-4-methyl-5-(2,2,2-trifluoroethylthio)phenyl}-5-(hydroxyimino)methylene-3-{1,1,2-trifluoro-2-(trifluoromethoxy)ethoxy}pyrazole
($^1$H-NMR (CDCL$_3$/TMS δ (ppm) value) 6: (majar) 2.55 (3H, s), 3.38 (2H, q), 6.05 (1H, dt), 6.54 (1H, s), 7.15 (1H, d), 7.61 (1H, d), 7.71 (1H, brs), 7.83 (1H, d)).

Then, 0.28 g of 1-{2-fluoro-4-methyl-5-(2,2,2-trifluoroethylthio)phenyl}-5-(hydroxyimino)methylene-3-{1,1,2-trifluoro-2-(trifluoromethoxy)ethoxy}pyrazole was dissolved in 10 mL of tetrahydrofuran, 0.12 g of triethylamine was added, and 0.13 g of trifluoroacetic anhydride was slowly dropwise added under cooling with ice. After stirring at room temperature for 2 hours, the solvent was distilled off under reduced pressure, and extraction with ethyl acetate was carried out. The organic layer was dried over anhydrous magnesium sulfate, the solvent was distilled off under reduced pressure, and the obtained residue was purified by column chromatography (developing solvent ethyl acetate:hexane=1:4) to obtain 0.28 g of 5-cyano-1-{2-fluoro-4-methyl-5-(2,2,2-trifluoroethylthio)phenyl}-3-{1,1,2-trifluoro-2-(trifluoromethoxy)ethoxy}pyrazole.
$^1$H-NMR (CDCL$_3$/TMS δ (ppm) value) δ: 2.57 (3H, s), 3.40 (2H, q), 6.05 (1H, dt), 6.79 (1H, s), 7.23 (1H, d), 7.68 (1H, d)

Example 54

Preparation of 5-cyano-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-669 of the present invention)

0.19 g of 5-cyano-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 88 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:1) to obtain 0.16 g of 5-cyano-1-{2-fluoro-4-methyl-5-(2,2,2-trifluoroethylsulfinyl)phenyl}-3-{1,1,2-trifluoro-2-(trifluoromethoxy)ethoxy}pyrazole.
$^1$H-NMR (CDCL$_3$/TMS δ (ppm) value) δ: 2.50 (3H, s), 3.43-3.57 (2H, m), 6.04 (1H, dt), 6.83 (1H, s), 7.28 (1H, d), 8.20 (1H, d)

Example 55

Preparation of 1-{2-fluoro-4-methyl-5-(2,2,2-trifluoroethylthio)phenyl}-5-fluoromethyl-3-{1,1,2-trifluoro-2-(trifluoromethoxy)ethoxy}pyrazole (compound No. 1-1579 of the present invention)

0.22 g of 1-{2-fluoro-4-methyl-5-(2,2,2-trifluoroethylthio)phenyl}-5-hydroxymethyl-3-{1,1,2-trifluoro-2-(trifluoromethoxy)ethoxy}pyrazole was dissolved in 10 mL of dichloromethane, and 85 mg of diethylaminosulfur trifluoride was dropwise added under cooling with ice, followed by stirring for 3 hours under cooling with ice. Extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 0.17 g of 1-{2-fluoro-4-methyl-5-(2,2,2-trifluoroethylthio)phenyl}-5-fluoromethyl-3-{1,1,2-trifluoro-2-(trifluoromethoxy)ethoxy}pyrazole.
$^1$H-NMR (CDCL$_3$/TMS δ (ppm) value) δ: 2.54 (3H, s), 3.38 (2H, q), 5.20 (2H, d), 6.05 (1H, dt), 6.39 (1H, s), 7.16 (1H, d), 7.63 (1H, d)

Example 56

Preparation of 1-{2-fluoro-4-methyl-5-(2,2,2-trifluoroethylsulfinyl)phenyl}-5-fluoromethyl-3-{1,1,2-trifluoro-2-(trifluoromethoxy)ethoxy}pyrazole (compound No. 1-1580 of the present invention)

0.17 g of 1-{2-fluoro-4-methyl-5-(2,2,2-trifluoroethylthio)phenyl}-5-fluoromethyl-3-{1,1,2-trifluoro-2-(trifluoromethoxy)ethoxy}pyrazole was dissolved in 10 mL of chloroform, and 78 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.12 g of 1-{2-fluoro-4-methyl-5-(2,2,2-trifluoroethylsulfinyl)phenyl}-5-fluoromethyl-3-{1,1,2-trifluoro-2-(trifluoromethoxy)ethoxy}pyrazole.
$^1$H-NMR (CDCL$_3$/TMS δ (ppm) value) δ: 2.48 (3H, s), 3.40-3.58 (2H, m), 5.24 (2H, d), 6.04 (1H, dt), 6.40 (1H, s), 7.21 (1H, d), 8.13 (1H, d)

Example 57

Preparation of 5-difluoromethyl-1-{2-fluoro-4-methyl-5-(2,2,2-trifluoroethylthio)phenyl}-3-{1,1,2-trifluoro-2-(trifluoromethoxy)ethoxy}pyrazole (compound No. 1-1531 of the present invention)

0.50 g of 5-formyl-1-{2-fluoro-4-methyl-5-(2,2,2-trifluoroethylthio)phenyl}-3-{1,1,2-trifluoro-2-(trifluoromethoxy)ethoxy}pyrazole was dissolved in 15 mL of dichloromethane, and 0.65 g of diethylaminosulfur trifluoride was dropwise added under cooling with ice, followed by stirring at room temperature for 12 hours. Extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 0.50 g of 5-difluoromethyl-1-{2-fluoro-4-methyl-5-(2,2,2-trifluoroethylthio)phenyl}-3-{1,1,2-trifluoro-2-(trifluoromethoxy)ethoxy}pyrazole.
$^1$H-NMR (CDCL$_3$/TMS δ (ppm) value) δ: 2.55 (3H, s), 3.38 (2H, q), 6.05 (1H, dt), 6.52 (1H, s), 6.56 (1H, t), 7.16 (1H, d), 7.63 (1H, d)

Example 58

Preparation of 5-difluoromethyl-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-1532 of the present invention)

0.35 g of 5-difluoromethyl-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 150 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.35 g of 5-difluoromethyl-1-{2-fluoro-4-methyl-5-(2,2,2-trifluoroethylsulfinyl)phenyl}-3-{1,1,2-trifluoro-2-(trifluoromethoxy)ethoxy}pyrazole.

$^1$H-NMR (CDCL$_3$/TMS δ (ppm) value) δ: 2.48 (3H, s), 3.38-3.59 (2H, m), 6.04 (1H, dt), 6.54 (1H, s), 6.62 (1H, t), 7.21 (1H, d), 8.14 (1H, d)

Example 59

Preparation of 1-{2-fluoro-4-methyl-5-(2,2,2-trifluoroethylthio)phenyl}-5-methoxy-3-{1,1,2-trifluoro-2-(trifluoromethoxy)ethoxy}pyrazole (compound No. 1-794 of the present invention)

1.5 g of 1-{2-fluoro-4-methyl-5-(2,2,2-trifluoroethylthio)phenyl}-3-hydroxy-5-methoxypyrazole was dissolved in 30 mL of N,N-dimethylformamide, 40 g of triethylamine was added, and stirring was carried out at 50° C. for 3 hours while trifluoromethyl trifluorovinyl ether was blown. To this solution, ethyl acetate was added, followed by washing with a saturated aqueous solution of citric acid, and then the organic layer was dried over anhydrous magnesium sulfate, the solvent was distilled off under reduced pressure, and the obtained residue was purified by column chromatography (developing solvent ethyl acetate:hexane=1:4) to obtain 1.1 g of 1-{2-fluoro-4-methyl-5-(2,2,2-trifluoroethylthio)phenyl}-5-methoxy-3-{1,1,2-trifluoro-2-(trifluoromethoxy)ethoxy}pyrazole.

$^1$H-NMR (CDCL$_3$/TMS δ (ppm) value) δ: 2.51 (3H, s), 3.36 (2H, q), 3.92 (3H, s), 5.52 (1H, s), 6.07 (1H, dt), 7.09 (1H, d), 7.59 (1H, d)

Example 60

Preparation of 1-{2-fluoro-4-methyl-5-(2,2,2-trifluoroethylsulfinyl)phenyl}-5-methoxy-3-{1,1,2-trifluoro-2-(trifluoromethoxy)ethoxy}pyrazole (compound No. 1-795 of the present invention)

0.2 g of 1-{2-fluoro-4-methyl-5-(2,2,2-trifluoroethylthio)phenyl}-5-methoxy-3-{1,1,2-trifluoro-2-(trifluoromethoxy)ethoxy}pyrazole was dissolved in 10 mL of chloroform, and 92 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.20 g of 1-{2-fluoro-4-methyl-5-(2,2,2-trifluoroethylsulfinyl)phenyl}-5-methoxy-3-{1,1,2-trifluoro-2-(trifluoromethoxy)ethoxy}pyrazole.

$^1$H-NMR (CDCL$_3$/TMS δ (ppm) value) δ: 2.45 (3H, s), 3.35-3.59 (2H, m), 3.93 (3H, s), 5.54 (1H, s), 6.05 (1H, dt), 7.14 (1H, d), 8.08 (1H, d)

Example 61

Preparation of 1-{2-fluoro-4-methyl-5-(2,2,2-trifluoroethylthio)phenyl}-5-formylamino-3-(2,2,3,3,4,4,4-heptafluorobutoxy)pyrazole (compound No. 1-1593 of the present invention)

1.18 g of 5-amino-1-{2-fluoro-4-methyl-5-(2,2,2-trifluoroethylthio)phenyl}-3-(2,2,3,3,4,4,4-heptafluorobutoxy)pyrazole was dissolved in 15 mL of formic acid, and 8mL of acetic anhydride was added under cooling with ice, followed by stirring at room temperature for 12 hours. Then, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:2) to obtain 0.92 g of 1-{2-fluoro-4-methyl-5-(2,2,2-trifluoroethylthio)phenyl}-5-formylamino-3-(2,2,3,3,4,4,4-heptafluorobutoxy)pyrazole.

$^1$H-NMR (CDCL$_3$/TMS δ (ppm) value) δ: 2.54 (3H, s), 3.40 (2H, q), 4.73 (2H, t), 6.30 (1H, s), 7.05 (1H, brs), 7.17 (1H, d), 8,43 (1H, s)

Example 62

Preparation of 1-{2-fluoro-4-methyl-5-(2,2,2-trifluoroethylsulfinyl)phenyl}-5-formylamino-3-(2,2,3,3,4,4-heptafluorobutoxy)pyrazole (compound No. 1-1594 of the present invention)

0.7 g of 1-{2-fluoro-4-methyl-5-(2,2,2-trifluoroethylthio)phenyl}-5-formylamino-3-(2,2,3,3,4,4,4-heptafluorobutoxy)pyrazole was dissolved in 20 mL of chloroform, and 360 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:1) to obtain 0.72 g of 1-{2-fluoro-4-methyl-5-(2,2,2-trifluoroethylsulfinyl)phenyl}-5-formylamino-3-(2,2,3,3,4,4,4-heptafluorobutoxy)pyrazole.

$^1$H-NMR (d-DMSO/TMS δ (ppm) value) δ: 2.47 (3H, s), 4.04-4.24 (2H, m), 4.95 (2H, t), 6.24 (1H, s), 7.58 (1H, d), 7.89 (1H, d), 8,15 (1H, s), 10.56 (1H, s)

Example 63

Preparation of 1-{2-fluoro-4-methyl-5-(2,2,2-trifluoroethylthio)phenyl}-5-methyl-3-{(4-trifluoromethoxy)benzyloxy}pyrazole (compound No. 1-1599 of the present invention)

0.7 g of 3-hydroxy 1-{2-fluoro-4-methyl-5-(2,2,2-trifluoroethylthio)phenyl}-5-methylpyrazole was dissolved in 15 mL of dimethylsulfoxide, and 0.36 g of potassium carbonate and 0.57 g of (4-trifluoromethoxy)benzyl bromide were added, followed by stirring at room temperature for 12 hours. After completion of the reaction, the reaction solution was poured into water, extraction with ethyl acetate was carried out, followed by washing with a saturated salt solution, and the organic layer was dried over anhydrous magnesium sulfate. Then, the solvent was distilled off under reduced pressure, and the obtained residue was purified by column chromatography (ethyl acetate:hexane=1:10) to obtain 0.80 g of 1-{2-fluoro-4-methyl-5-(2,2,2-trifluoroethylthio)phenyl}-5-methyl-3-{(4-trifluoromethoxy)benzyloxy}pyrazole.

$^1$H-NMR (CDCL$_3$/TMS δ (ppm) value) δ: 2.18 (3H, s), 2.52 (3H, s), 3.72 (2H, q), 5.22 (2H, s), 5.70 (1H, s), 7.10 (1H, d), 7.21 (2H, d), 7.57 (2H, d), 7.58 (1H, d)

Example 64

Preparation of 1-{2-fluoro-4-methyl-5-(2,2,2-trifluoroethylsulfinyl)phenyl}-5-methyl-3-{(4-trifluoromethoxy)benzyloxy}pyrazole (compound No. 1-1600 of the present invention)

0.5 g of 1-{2-fluoro-4-methyl-5-(2,2,2-trifluoroethylthio)phenyl}-5-methyl-3-{(4-trifluoromethoxy)benzyloxy}pyrazole was dissolved in 20 mL of chloroform, and 240mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.50 g of 1-{2-fluoro-4-methyl-5-(2,2,2-trifluoroethylsulfinyl)phenyl}-5-methyl-3-{(4-trifluoromethoxy)benzyloxy}pyrazole.

$^1$H-NMR (CDCL$_3$/TMS δ (ppm) value) δ: 2.15 (3H, s), 2.45 (3H, s), 3.50 (2H, m), 5.25 (2H, s), 5.72 (1H, s), 7.16 (1H, s), 7.26 (2H, d), 7.49 (2H, d), 8.10 (1H, d)

Example 65

Preparation of 1-{2-fluoro-4-methyl-5-(2,2,2-trifluoroethylsulfinyl)phenyl}-3-{4-(trifluoromethyl)phenoxy}pyrazole (compound No. 1-1586 of the present invention)

0.5 g of 1-{2-fluoro-4-methyl-5-(2,2,2-trifluoroethylthio)phenyl}-3-hydroxypyrazole was dissolved in 20 mL of dichloromethane, and 0.44 g of 4-trifluoromethylbenzeneboronic acid, 0.47 g of triethylamine, 0.37 g of pyridine, 0.43 g of copper(II) acetate and 0.5 g of powdery molecular sieves 4 A were added, followed by stirring at room temperature for 12 hours. To this solution, ethyl acetate was added, followed by washing with a saturated aqueous solution of citric acid, and then the organic layer was dried over anhydrous magnesium sulfate, the solvent was distilled off under reduced pressure, the obtained residue was dissolved in 10 mL of chloroform, and under cooling with ice, 80 mg of m-chloroperbenzoic acid (purity: 75%) was added. After stirring for one hour under cooling with ice, the solution was washed with an aqueous sodium thiosulfate solution and then washed with an aqueous sodium hydrogen carbonate solution, and then dried over anhydrous magnesium sulfate. Then, the solvent was distilled off under reduced pressure, the obtained residue was purified by silica gel column chromatography (developing solvent ethyl acetate:hexane=1:2) to obtain 0.15 g of 1-{2-fluoro-4-methyl-5-(2,2,2-trifluoroethylsulfinyl)phenyl}-3-{4-(trifluoromethyl)phenoxy}pyrazole.

$^1$H-NMR (CDCL$_3$/TMS δ (ppm) value) δ: 2.43 (3H, s), 3.47 (2H, m), 6.13 (1H, d), 7.17 (1H, d), 7.29 (2H, d), 7.62 (2H, d), 7.94 (1H, d), 8.43 (1H, d)

Example 66

Preparation of 4-cyano-1-{2-fluoro-4-methyl-5-(2,2,2-trifluoroethylthio)phenyl}-3-{1,1,2-trifluoro-2-(trifluoromethoxy)ethoxy}pyrazole (compound No. 1-1587 of the present invention)

1.20 g of ethyl-1-{2-fluoro-4-methyl-5-(2,2,2-trifluoroethylthio)phenyl}-3-hydroxypyrazole-4-carboxylate was dissolved in 40 mL of N,N-dimethylformamide, 25 g of triethylamine was added, and stirring was carried out at 50° C. for 3 hours while trifluoromethyl trifluorovinyl ether was blown. To this solution, ethyl acetate was added, followed by washing with a saturated aqueous solution of citric acid, and then the organic layer was dried over anhydrous magnesium sulfate, and the solvent was distilled off under reduced pressure. The obtained residue was purified by column chromatography (developing solvent ethyl acetate:hexane=1:4) to obtain 0.73 g of ethyl-1-{2-fluoro-4-methyl-5-(2,2,2-trifluoroethylthio)phenyl}-3-{1,1,2-trifluoro-2-(trifluoromethoxy)ethoxy}pyrazole-4-carboxylate ($^1$H-NMR (CDCL$_3$/TMS δ (ppm) value) δ: 1.36 (3H, t), 2.51 (3H, s), 3.41 (2H, q), 4.34 (2H, q), 6.21 (1H, dt), 7.16 (1H, d), 7.97 (1H, d), 8.38 (1H, d)).

Then, 0.73 g of ethyl-1-{2-fluoro-4-methyl-5-(2,2,2-trifluoroethylthio)phenyl}-3-{1,1,2-trifluoro-2-(trifluoromethoxy)ethoxy}pyrazole-4-carboxylate was dissolved in 20mL of ethanol. To this solution, a solution having 0.25 g of potassium hydroxide dissolved in 5 mL of water was added, followed by stirring at room temperature for 30minutes. Concentrated hydrochloric acid was added to adjust the pH to 2, the solvent was distilled off under reduced pressure, and extraction with ethyl acetate was carried out. The organic layer was dried over anhydrous sodium sulfate, and the solvent was distilled off under reduced pressure. The obtained residue was dissolved in 10 mL of dichloromethane, and 0.22 g of oxalyl dichloride and N,N-dimethylformamide in a catalytic amount were added, followed by stirring at room temperature for 1 hour. Then, the solvent was distilled off under reduced pressure, and the resulting product was dissolved in 5 mL of tetrahydrofuran, and the solution was dropwise added to a mixed solution comprising 20 mL of a 25 mass % ammonia water and 30 mL of tetrahydrofuran at −30° C. Then, stirring was carried out for 12 hours while the temperature was slowly increased to room temperature. Then, the solvent was distilled off under reduced pressure, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:3) to obtain 0.45 g of 1-{2-fluoro-4-methyl-5-(2,2,2-trifluoroethylthio)phenyl}-3-{1,1,2-trifluoro-2-(trifluoromethoxy)ethoxy}pyrazole-4-carboxyamide ($^1$H-NMR (CDCL$_3$/TMS δ (ppm) value) δ: 2.51 (3H, s), 3.40 (2H, q), 5.81 (1H, brs), 6.23 (1H, brs), 6.37 (1H, dt), 7.16 (1H, d), 7.92 (1H, d), 8.45 (1H, d)).

Then, 0.45 g of 1-{2-fluoro-4-methyl-5-(2,2,2-trifluoroethylthio)phenyl}-3-{1,1,2-trifluoro-2-(trifluoromethoxy)ethoxy}pyrazole-4-carboxyamide was dissolved in 20 mL of tetrahydrofuran, 0.23 g of triethylamine was added, and 0.28 g of trifluoroacetic anhydride was slowly dropwise added under cooling with ice. After stirring at room temperature for 2 hours, the solvent was distilled off under reduced pressure, and extraction with ethyl acetate was carried out. The organic layer was dried over anhydrous magnesium sulfate, the solvent was distilled off under reduced pressure, and the obtained residue was purified by column chromatography (developing solvent ethyl acetate:hexane=1:4) to obtain 0.30 g of 4-cyano-1-{2-fluoro-4-methyl-5-(2,2,2-trifluoroethylthio)phenyl}-3-{1,1,2-trifluoro-2-(trifluoromethoxy)ethoxy}pyrazole.

$^1$H-NMR (CDCL$_3$/TMS δ (ppm) value) δ: 2.53 (3H, s), 3.41 (2H, q), 6.15 (1H, dt), 7.19 (1H, d), 7.96 (1H, d), 8.30 (1H, d)

Example 67

Preparation of 4-cyano-1-{2-fluoro-4-methyl-5-(2,2,2-trifluoroethylsulfinyl)phenyl}-3-{1,1,2-trifluoro-2-(trifluoromethoxy)ethoxy}pyrazole (compound No. 1-1588 of the present invention)

0.2 g of 4-cyano-1-{2-fluoro-4-methyl-5-(2,2,2-trifluoroethylthio)phenyl}-3-{1,1,2-trifluoro-2-(trifluoromethoxy)ethoxy}pyrazole was dissolved in 10 mL of chloroform, and 93 mg of m-chloroperbenzoic acid (purity: 75%) was added under cooling with ice. After stirring for one hour under cooling with ice, the solution was washed with an aqueous sodium thiosulfate solution and then washed with an aqueous sodium hydrogen carbonate solution, and then dried over anhydrous magnesium sulfate. The solvent was distilled off under reduced pressure, the obtained residue was purified by silica gel column chromatography (developing solvent ethyl acetate:hexane=1:2) to obtain 0.19 g of 4-cyano-1-{2-fluoro-4-methyl-5-(2,2,2-trifluoroethylsulfinyl)phenyl}-3-{1,1,2-trifluoro-2-(trifluoromethoxy)ethoxy}pyrazole.

$^1$H-NMR (CDCL$_3$/TMS δ (ppm) value) δ: 2.47 (3H, s), 3.38-3.63 (2H, m), 6.13 (1H, dt), 7.25 (1H, d), 8.34 (1H, s), 8.44 (1H, d)

Example 68

Preparation of 5-acetylamino-1-{2-fluoro-4-methyl-5-(2,2,2-trifluoroethylthio)phenyl}-3-(1,1,2,2,3,3,4,4,5,5,5-undecafluoropentyloxy)pyrazole (compound No. 1-488 of the present invention)

To a mixed solution comprising 35 mL of trifluoroacetic acid and 103 mL of trifluoroacetic anhydride, 6.9 g of a 31 mass % hydrogen peroxide solution was added at −10° C., followed by stirring at −10° C. for 10 minutes. Then, 25 g of undecafluoropentane iodide was dropwise added at −10° C., and stirring was carried out for 12 hours while the temperature was slowly increased to room temperature. The solvent was distilled off under reduced pressure at room temperature, the obtained solid was dissolved in 70 mL of benzene and 70 mL of trifluoroacetic acid, and 9.4 g of trifluoromethanesulfonic acid was dropwise added under cooling with ice, followed by stirring at room temperature for 12 hours. Then, the solvent was distilled off under reduced pressure at room temperature to obtain crude (perfluoropentyl)phenyliodonium trifluoromethanesulfonate.

2.0 g of 5-acetylamino-1-{2-fluoro-4-methyl-5-(2,2,2-trifluoroethylthio)phenyl}-3-hydroxypyrazole was dissolved in 30 mL of dichloromethane, 2.18 g of pyridine was added, and the above prepared crude (perfluoropentyl)phenyliodonium trifluoromethanesulfonate was added at room temperature until 5-acetylamino-1-{2-fluoro-4-methyl-5-(2,2,2-trifluoroethylthio)phenyl}-3-hydroxypyrazole disappeared (disappearance was confirmed by thin layer chromatography). Then, the solvent was distilled off under reduced pressure, a saturated salt solution was added, extraction with ethyl acetate was carried out, the organic layer was dried over anhydrous sodium sulfate, the solvent was distilled off under reduced pressure, and the obtained residue was purified by column chromatography (developing solvent ethyl acetate:hexane=1:3) to obtain 0.64 g of 5-acetylamino-1-{2-fluoro-4-methyl-5-(2,2,2-trifluoroethylthio)phenyl}-3-(1,1,2,2,3,3,4,4,5,5,5-undecafluoropentyloxy)pyrazole.

$^1$H-NMR (CDCL$_3$/TMS δ (ppm) value) δ: 2.11 (3H, s), 2.55 (3H, s), 3.41 (2H, q), 6.53 (1H, s), 7.09 (1H, brs), 7.18 (1H, d), 7.63 (1H, d)

Example 69

Preparation of 5-acetylamino-1-{2-fluoro-4-methyl-5-(2,2,2-trifluoroethylsulfinyl)phenyl}-3-(1,1,2,2,3,3,4,4,5,5,5-undecafluoropentyloxy)pyrazole (compound No. 1-489 of the present invention)

0.12 g of 5-acetylamino-1-{2-fluoro-4-methyl-5-(2,2,2-trifluoroethylthio)phenyl}-3-(1,1,2,2,3,3,4,4,5,5,5-undecafluoropentyloxy)pyrazole was dissolved in 10 mL of chloroform, and 44 mg of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:hexane=1:1) to obtain 0.095 g of 5-acetylamino-1-{2-fluoro-4-methyl-5-(2,2,2-trifluoroethylsulfinyl)phenyl}-3-(1,1,2,2,3,3,4,4,5,5,5-undecafluoropentyloxy)pyrazole.

$^1$H-NMR (CDCL$_3$/TMS δ (ppm) value) δ: 2.10 (3H, s), 2.48 (3H, s), 3.42-3.60 (2H, m), 6.52 (1H, s), 7.23 (1H, d), 8.11 (1H, d)

Example 70

Preparation of 1-{2-fluoro-4-methyl-5-(2,2,2-trifluoroethylthio)phenyl}-5-methylamino-3-(1,1,2,2,3,3,4,4,5,5,5-undecafluoropentyloxy)pyrazole (compound No. 1-524 of the present invention)

0.45 g of 5-acetylamino-1-{2-fluoro-4-methyl-5-(2,2,2-trifluoroethylthio)phenyl}-3-(1,1,2,2,3,3,4,4,5,5,5-undecafluoropentyloxy)pyrazole was dissolved in 5 mL of N,N-dimethylformamide, the solution was dropwise added to a suspension having 40 mg of sodium hydride suspended in 10 mL of N,N-dimethylformamide under cooling with ice, and after completion of the dropwise addition, stirring was carried out at room temperature for 30 minutes. The reaction solution was cooled with ice again, and 0.15 g of methyl iodide was added, followed by stirring at room temperature for one hour. Then, water was injected, extraction with ethyl acetate was carried out, followed by washing with water, and the organic layer was dried over anhydrous magnesium sulfate. Then, the solvent was distilled off under reduced pressure, the obtained residue was dissolved in 10 mL of ethanol, and 10 mL of a 35 mass % hydrochloric acid aqueous solution was added, followed by stirring under reflux with heating for one hour. Then, the reaction mixture was poured into water, extraction with ethyl acetate was carried out, followed by washing with water, and the organic layer was dried over anhydrous magnesium sulfate. Then, the solvent was distilled off under reduced pressure, and the obtained residue was purified by column chromatography (developing solvent ethyl acetate:hexane=1:4) to obtain 0.39 g of 1-{2-fluoro-4-methyl-5-(2,2,2-trifluoroethylthio)phenyl}-5-methylamino-3-(1,1,2,2,3,3,4,4,5,5,5-undecafluoropentyloxy)pyrazole.

¹H-NMR (CDCL₃/TMS δ (ppm) value) δ: 2.51 (3H, s), 2.85 (3H, d), 3.39 (2H, q), 3.64 (1H, brs), 5.36 (1H, s), 7.12 (1H, d), 7.61 (1H, d)

Example 71

Preparation of 1-{2-fluoro-4-methyl-5-(2,2,2-trifluoroethylsulfinyl)phenyl}-5-methylamino-3-(1,1,2,2,3,3,4,4,5,5,5-undecafluoropentyloxy)pyrazole (compound No. 1-525 of the present invention)

0.25 g of 1-{2-fluoro-4-methyl-5-(2,2,2-trifluoroethylthio)phenyl}-5-methylamino-3-(1,1,2,2,3,3,4,4,5,5,5-undecafluoropentyloxy)pyrazole was dissolved in 10 mL of chloroform, and 95 mg of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:hexane=1:1) to obtain 0.23 g of 1-{2-fluoro-4-methyl-5-(2,2,2-trifluoroethylsulfinyl)phenyl}-5-methylamino-3-(1,1,2,2,3,3,4,4,5,5,5-undecafluoropentyloxy)pyrazole.

¹H-NMR (CDCL₃/TMS δ (ppm) value) δ: 2.45 (3H, s), 2.85 (3H, s), 3.36-3.62 (2H, m), 3.66 (1H, brs), 5.37 (1H, s), 7.18 (1H, d), 8.11 (1H, d)

Example 72

Preparation of 1-{2-fluoro-4-methyl-5-(2,2,2-trifluoroethylthio)phenyl}-5-hydroxy-3-methoxypyrazole (compound No. 1-1615 of the present invention)

1.5 g of 2-fluoro-4-methyl-5-(2,2,2-trifluoroethylthio)phenylhydrazine was dissolved in 70 mL of tetrahydrofuran, and 0.83 g of malonyl chloride was added under cooling with ice. Stirring was carried out under reflux with heating for 5 hours, and the solvent was distilled off under reduced pressure. To the obtained residue, 20 mL of dichloromethane and 2 mL of methanol were added, and 0.7 mL of a diethyl ether solution (2.0 mol/L) of trimethylsilyldiazomethane was added under cooling with ice, followed by stirring at room temperature for 5 hours. Then, the solvent was distilled off under reduced pressure, and the obtained residue was purified by column chromatography (developing solvent ethyl acetate:hexane=1:1) to obtain 0.14 g of 1-{2-fluoro-4-methyl-5-(2,2,2-trifluoroethylthio)phenyl}-5-hydroxy-3-methoxypyrazole.

¹H-NMR (CDCL₃/TMS δ (ppm) value) δ: 2.48 (3H, s), 3.35 (2H, q), 3.45 (2H, s), 3.92 (3H, s), 7.08 (1H, d), 7.64 (1H, d)

Example 73

Preparation of 1-{2-fluoro-4-methyl-5-(2,2,2-trifluoroethylthio)phenyl}-3-methoxy-5-(2,2,3,3,3-pentafluoropropoxy)pyrazole (compound No. 1-1469 of the present invention) 0.14 g of 1-{2-fluoro-4-methyl-5-(2,2,2-trifluoroethylthio)phenyl}-5-hydroxy-3-methoxypyrazole was dissolved in 100 mL of dimethylsulfoxide, and 63 mg of potassium carbonate was added, followed by stirring at room temperature for 5minutes. To this solution, 0.20 g of 2,2,3,3,3-pentafluoropropyl nonafluorobutanesulfonate was added, followed by stirring at room temperature for 12hours. Then, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:4) to obtain 0.16 g of 1-{2-fluoro-4-methyl-5-(2,2,2-trifluoroethylthio)phenyl}-3-methoxy-5-(2,2,3,3,3-pentafluoropropoxy)pyrazole.

¹H-NMR (CDCL₃/TMS δ (ppm) value) δ: 2.50 (3H, s), 3.36 (2H, q), 3.91 (3H, s), 4.44 (2H, t), 5.26 (1H, s), 7.08 (1H, d), 7.60 (1H, d)

Example 74

Preparation of 1-{2-fluoro-4-methyl-5-(2,2,2-trifluoroethylsulfinyl)phenyl}-3-methoxy-5-(2,2,3,3,3-pentafluoropropoxy)pyrazole (compound No. 1-1470 of the present invention)

0.16 g of 1-{2-fluoro-4-methyl-5-(2,2,2-trifluoroethylthio)phenyl}-3-methoxy-5-(2,2,3,3,3-pentafluoropropoxy)pyrazole was dissolved in 10 mL of chloroform, and 0.079 g of m-chloroperbenzoic acid (purity: 75%) was added under cooling with ice. After stirring for 30 minutes under cooling with ice, the solution was washed with an aqueous sodium thiosulfate solution and then washed with an aqueous potassium carbonate solution, and then dried over anhydrous magnesium sulfate. Then, the solvent was distilled off under reduced pressure, and the obtained residue was purified by column chromatography (developing solvent ethyl acetate:hexane=1:2) to obtain 0.13 g of 1-{2-fluoro-4-methyl-5-(2,2,2-trifluoroethylsulfinyl)phenyl}-3-methoxy-5-(2,2,3,3,3-pentafluoropropoxy)pyrazole.

¹H-NMR (CDCL₃/TMS δ (ppm) value) δ: 2.43 (3H, s), 3.39-3.54 (2H, m), 3.91 (3H, s), 4.46 (2H, t), 5.27 (1H, s), 7.12 (1H, d), 8.09 (1H, d)

¹H-NMR (CDCL₃/TMS δ (ppm)) values of compounds [I] of the present invention prepared in accordance with the above Examples are given below together with values in the above Examples.

TABLE 39

| Comp. No. | ¹H-NMR (CDCl₃/TMS d(ppm) value) | m.p. (° C.) or refractive indx ($n_D^{20}$) |
|---|---|---|
| 1-1 | 2.50(3H, s), 3.37(3H, s), 3.40(2H, q), 6.36(1H, d), 7.13(1H, d), 7.90(1H, t), 7.96(1H, d) | 82-83 |
| 1-2 | 2.45(3H, s), 3.39(3H, s), 3.37-3.58(2H, m), 6.40(1H, d), 7.19(1H, d), 7.96(1H, t), 8.44(1H, d) | 96-97 |
| 1-3 | 2.10(3H, s), 2.55(3H, s), 3.41(2H, q), 6.61(1H, s), 7.20(1H, d), 7.21(1H, brs), 7.61(1H, d) | Measurement impossible |

TABLE 39-continued

| Comp. No. | $^1$H-NMR (CDCl$_3$/TMS d(ppm) value) | m.p. (° C.) or refractive indx ($n_D^{20}$) |
|---|---|---|
| 1-4 | 2.08(3H, s), 2.46(3H, s), 3.43-3.54(2H, m), 6.57(1H, s), 7.23(1H, s), 7.82(1H, brs), 8.03(1H, d) | Measurement impossible |
| 1-6 | 2.07(3H, s), 2.45(3H, s), 3.43-3.53(2H, m), 5.62(2H, s), 6.16(1H, s), 7.19(1H, d), 7.46(1H, d), 8.04(1H, d) | Measurement impossible |
| 1-7 | 2.48(3H, s), 3.40(2H, q), 4.76(2H, t), 5.98(1H, d), 7.09(1H, d), 7.82(1H, t), 7.98(1H, d) | 1.4751 |
| 1-8 | 2.41(3H, s), 3.36-3.63(2H, m), 4.79(2H, t), 6.01(1H, d), 7.14(1H, d), 7.89(1H, t), 8.44(1H, d) | 100-101 |
| 1-9 | see Ex. 3 | 1.4818 |
| 1-10 | 2.46(3H, s), 3.39-3.60(2H, m), 3.86(2H, s), 5.03-5.18(1H, m), 5.50(1H, s), 7.19(1H, d), 8.13(1H, d) | 125-128 |
| 1-11 | 2.51(3H, s), 3.39(2H, q), 3.75(3H, s), 4.65(2H, t), 5.22(1H, s), 7.13(1H, d), 7.62(1H, d) | 59-61 |
| 1-12 | 2.45(3H, s), 3.37-3.57(2H, m), 3.76(2H, s), 4.65(2H, t), 5.25(1H, s), 7.17(1H, d), 8.12(1H, d) | Measurement impossible |
| 1-13 | 2.10(3H, s), 2.54(3H, s), 3.40(2H, q), 5.01-5.22(1H, m), 6.50(1H, s), 7.14(1H, brs), 7.17(1H, d), 7.62(1H, d) | Measurement impossible |
| 1-14 | 2.08(3H, s), 2.46(3H, s), 3.40-3.58(2H, m), 5.03-5.18(1H, m, 6.46(1H, s), 7.21(1H, d), 7.58(1H, brs), 8.06(1H, d) | Measurement impossible |
| 1-15 | see Ex. 13 | 1.4850 |
| 1-16 | see Ex. 14 | 57-58 |
| 1-17 | see Ex. 1 | 90-92 |
| 1-18 | see Ex. 2 | 69-72 |
| 1-19 | 2.07(3H, s), 2.51(3H, s), 2.53(1H, s), 3.40(2H, q), 4.84(2H, s), 6.18(1H, s), 7.13(1H, d), 7.19(1H, brs), 7.60(1H, d) | 138-140 |
| 1-20 | 2.06(3H, s), 2.45(3H, s), 2.55(1H, s), 3.40-3.58(2H, m), 4.84(2H, s), 6.14(1H, s), 7.17(1H, d), 7.54(1H, brs), 8.06(1H, d) | 80-82 |
| 1-21 | 2.08(3H, s), 2.52(3H, s), 3.40(2H, q), 4.70(2H, d), 6.13(1H, s), 6.17-6.23(1H, m), 6.40(1H, d), 7.08(1H, brs), 7.14(1H, d), 7.60(1H, d) | 105-106 |
| 1-22 | 2.07(3H, s), 2.45(3H, s), 3.38-3.54(2H, m), 4.70(2H, d), 6.10(1H, s), 6.14-6.23(1H, m), 6.40(1H, d), 7.18(1H, d), 7.42(1H, brs), 8.06(1H, d) | 1.5406 |
| 1-23 | 0.88(3H, t), 1.75-1.84(2H, m), 2.07(3H, s), 2.51(3H, s), 3.40(2H, q), 4.12(2H, t), 6.13(1H, s), 7.12(1H, brs), 7.13(1H, d), 7.61(1H, d) | 73-76 |
| 1-24 | 1.04(3H, t), 1.75-1.83(2H, m), 2.04(3H, s), 2.43(3H, s), 3.39-3.60(2H, m), 4.11(2H, t), 6.07(1H, s), 7.15(1H, d), 7.64(1H, brs), 8.05(1H, d) | 71-74 |
| 1-25 | 1.36(3H, s), 1.37(3H, s), 2.08(3H, s), 2.51(3H, s), 3.40(2H, q), 4.80(1H, t), 6.12(1H, s), 7.12(1H, brs), 7.13(1H, d), 7.62(1H, d) | Measurement impossible |
| 1-26 | 1.35(3H, s), 1.37(3H, s), 2.06(3H, s), 2.43(3H, s), 3.38-3.57(2H, m), 4.79(1H, t), 6.05(1H, s), 7.15(1H, d), 7.63(1H, brs), 8.03(1H, d) | 79-81 |
| 1-27 | 2.50(3H, s), 2.81(3H, d), 3.38(2H, q), 3.41(1H, brs), 4.65(2H, t), 5.11(1H, s), 7.11(1H, d), 7.59(1H, d) | 64-66 |
| 1-29 | see Ex. 7 | 69-70 |
| 1-30 | 2.46(3H, s), 3.37-3.60(2H, m), 4.69(2H, m), 6.25(1H, s), 7.22(1H, d), 8.07(1H, d) | 111-112 |
| 1-31 | 2.53(3H, s), 3.39(2H, q), 3.75(3H, s), 4.66(2H, t), 6.05(1H, s), 6.45(1H, brs), 7.15(1H, d), 7.59(1H, d) | 99-100 |
| 1-32 | 2.46(3H, s), 3.37-3.62(2H, m), 3.74(3H, s), 4.66(2H, t), 6.05(1H, s), 6.59(1H, brs), 7.19(1H, d), 8.09(1H, d) | 103-105 |

TABLE 40

| Comp. No. | $^1$H-NMR (CDCl$_3$/TMS d(ppm) value) | m.p. (° C.) or refractive indx ($n_D^{20}$) |
|---|---|---|
| 1-33 | 1.90(3H, s), 2.53(3H, s), 3.01(3H, s), 3.34(2H, q), 4.70(2H, t), 5.87(1H, s), 7.12(1H, d), 7.55(1H, d) | 1.4783 |
| 1-34 | 1.90(3H, s), 2.45(3H, s), 3.04(3H, s), 3.47(2H, q), 4.70(2H, t), 5.91(1H, s), 7.17(1H, d), 8.05(1H, d) | 1.4834 |
| 1-35 | (d6-DMSO, 150° C.) 1.91(3H, s), 2.50(3H, s), 3.76(2H, q), 4.40(2H, s), 4.87(2H, t), 6.30(1H, s), 7.32(1H, d), 7.69(1H, d) | 1.4891 |
| 1-36 | 2.00(3H, s), 2.45(3H, s), 3.49(2H, q), 4.25(2H, s), 4.71(2H, t), 6.11(1H, s), 7.20(1H, d), 8.08(1H, d) | 62-64 |
| 1-37 | 2.46(3H, s), 2.50(3H, s), 3.34(2H, q), 3.71(3H, s), 4.69(2H, t), 5.89(1H, s), 7.08(1H, d), 7.47(1H, d) | 1.4805 |
| 1-38 | 2.44(3H, s), 2.47(3H, s), 3.38-3.53(2H, m), 3.74(3H, s), 4.70(2H, t), 5.93(1H, s), 7.13(1H, d), 7.97(1H, d) | Measurement impossible |
| 1-39 | 2.49(3H, s), 3.39(2H, q), 4.83(2H, t), 7.10(1H, d), 7.84(1H, d), 7.94(1H, d) | 66-69 |
| 1-40 | 2.42(3H, s), 3.35-3.61(2H, m), 4.80(2H, t), 7.15(1H, d), 7.94(1H, d), 8.42(1H, d) | 82-83 |
| 1-41 | see Ex. 4 | 1.4837 |
| 1-42 | 2.45(3H, s), 3.39-3.59(2H, m), 3.64(2H, s), 4.70(2H, t), 7.17(1H, d), 8.08(1H, d) | 1.4862 |
| 1-43 | see Ex. 5 | |
| 1-44 | 2.49(3H, s), 3.39-3.58(2H, m), 3.91(2H, s), 4.70(2H, t), 7.18(1H, d), 8.10(1H, d) | 1.4965 |

TABLE 40-continued

| Comp. No. | $^1$H-NMR (CDCl$_3$/TMS d(ppm) value) | m.p. (° C.) or refractive indx ($n_D^{20}$) |
|---|---|---|
| 1-45 | see Ex. 6 | Measurement impossible |
| 1-46 | 2.45(3H, s), 3.39-3.59(2H, m), 4.00(2H, s), 4.69(2H, t), 7.18(1H, d), 8.09(1H, d) | Measurement impossible |
| 1-47 | 2.07(3H, s), 2.51(3H, s), 3.39(3H, q), 4.71(2H, t), 6.98(1H, brs), 7.10(1H, d), 7.59(1H, d) | 104-106 |
| 1-48 | 2.05(3H, s), 2.44(3H, s), 3.42-3.55(2H, m), 4.71(2H, t), 7.14(1H, d), 7.51(1H, brs), 8.03(1H, d) | 68-70 |
| 1-49 | 2.53(3H, s), 3.38(2H, q), 4.74(2H, t), 7.13(1H, d), 7.61(1H, d), 7.80(1H, brs) | 113-114 |
| 1-50 | 2.45(3H, s), 3.37-3.52(2H, m), 4.72(2H, t), 7.18(1H, d), 8.01(1H, d), 8.85(1H, brs) | 81-82 |
| 1-51 | 2.48(3H, s), 3.40(2H, q), 4.79(2H, t), 5.99(1H, d), 7.08(1H, d), 7.82(1H, t), 7.99(1H, d) | 1.4609 |
| 1-52 | 2.42(3H, s), 3.36-3.63(2H, m), 4.81(2H, t), 6.03(1H, d), 7.14(1H, d), 7.88(1H, t), 8.44(1H, d) | 90-91 |
| 1-53 | 2.51(3H, s), 3.39(2H, q), 3.74(2H, s), 4.69(2H, t), 5.23(1H, s), 7.13(1H, d), 7.62(1H, d) | 34-36 |
| 1-54 | 2.45(3H, s), 3.41-3.57(2H, m), 3.76(2H, s), 4.68(2H, t), 5.26(1H, s), 7.17(1H, d), 8.12(1H, d) | Measurement impossible |
| 1-55 | 2.50(3H, s), 3.39(2H, q), 3.72(2H, s), 3.92-3.99(4H, m), 4.35(2H, t), 5.18(1H, s), 7.11(1H, d), 7.63(1H, d) | 1.5094 |
| 1-57 | 2.08(3H, s), 2.53(3H, s), 3.40(2H, q), 4.71(2H, t), 6.22(1H, s), 7.07(1H, brs), 7.16(1H, d), 7.60(1H, d) | 1.4719 |
| 1-58 | 2.08(3H, s), 2.46(3H, s), 3.42-3.54(2H, m), 4.70(2H, t), 6.19(1H, s), 7.20(1H, d), 7.22(1H, brs), 8.08(1H, d) | 62-64 |
| 1-59 | 1.23-1.70(2H, m), 1.99-2.21(1H, m), 2.08(3H, s), 2.52(3H, s), 3.39(2H, q), 4.25-4.37(2H, m), 6.15(1H, s), 7.07(1H, brs), 7.14(1H, d), 7.60(1H, d) | 1.5063 |
| 1-60 | 1.26-1.71(2H, m), 2.07(3H, s), 2.11-2.17(1H, m), 2.44(3H, s), 3.38-3.53(2H, m), 4.25(2H, d), 6.10(1H, s), 7.17(1H, d), 7.42(1H, brs), 8.05(1H, d) | 74-77 |
| 1-61 | 1.99-2.08(2H, m), 2.08(3H, s), 2.22-2.42(2H, m), 2.52(3H, s), 3.44(2H, q), 4.23(2H, t), 6.14(1H, s), 7.09(1H, brs), 7.14(1H, d), 7.60(1H, d) | 91-93 |
| 1-62 | 2.02-2.07(2H, m), 2.07(3H, s), 2.23-2.41(2H, m), 2.45(3H, s), 3.39-3.54(2H, m), 4.23(2H, t), 6.10(1H, s), 7.18(1H, d), 7.43(1H, brs), 8.06(1H, d) | Measurement impossible |

TABLE 41

| Comp. No. | $^1$H-NMR (CDCl$_3$/TMS d(ppm) value) | m.p. (° C.) or refractive indx ($n_D^{20}$) |
|---|---|---|
| 1-63 | 2.08(3H, s), 2.52(3H, s), 3.40(2H, q), 3.93-3.99(4H, m), 4.38(2H, t), 6.16(1H, s), 7.07(1H, brs), 7.14(1H, d), 7.60(1H, d) | 128-130 |
| 1-64 | 2.06(3H, s), 2.44(3H, s), 3.39-3.53(2H, m), 3.92-3.99(4H, m), 4.36(2H, t), 6.09(1H, s), 7.17(1H, d), 7.56(1H, brs), 8.04(1H, d) | Measurement impossible |
| 1-65 | 0.98(3H, t), 1.34(3H, d), 1.61-1.80(2H, m), 2.07(3H, s), 2.51(3H, s), 3.40(2H, q), 4.58(1H, q), 6.11(1H, s), 7.12(1H, s), 7.18(1H, brs), 7.62(1H, d) | Measurement impossible |
| 1-66 | 0.98(3H, t), 1.34(3H, d), 1.60-1.78(2H, m), 2.05(3H, s), 2.44(3H, s), 3.42-3.55(2H, m), 4.60(1H, q), 6.08(1H, s), 7.16(1H, d), 7.47(1H, brs), 8.08(1H, d) | 60-62 |
| 1-67 | 0.13(9H, s), 2.07(3H, s), 2.51(3H, s), 3.40(2H, q), 3.86(2H, s), 6.14(1H, s), 7.12(1H, d), 7.14(1H, brs), 7.62(1H, d) | 68-70 |
| 1-68 | 0.14(9H, s), 2.07(3H, s), 2.44(3H, s), 3.38-3.55(2H, m), 3.85(2H, s), 6.10(1H, s), 7.15(1H, d), 7.48(1H, brs), 8.07(1H, d) | 87-89 |
| 1-69 | 2.48(3H, s), 3.39(2H, q), 4.88(2H, t), 7.09(1H, d), 7.85(1H, d), 7.94(1H, d) | 1.4747 |
| 1-70 | 2.42(3H, s), 3.36-3.61(2H, m), 3.84(2H, t), 7.15(1H, d), 7.94(1H, d), 8.42(1H, d) | 105-106 |
| 1-71 | 1.90(3H, s), 2.52(3H, s), 3.01(3H, s), 3.34(2H, q), 3.92-4.01(4H, m), 4.41(2H, t), 5.81(1H, s), 7.10(1H, d), 7.60(1H, d) | 1.5006 |
| 1-72 | 1.90(3H, s), 2.44(3H, s), 3.03(3H, s), 3.46(2H, q), 3.93-4.00(4H, m), 4.42(2H, t), 5.85(1H, s), 7.15(1H, d), 8.05(1H, d) | 1.4955 |
| 1-73 | 2.48(3H, s), 3.40(2H, q), 4.81(2H, t), 5.98(1H, d), 7.08(1H, d), 7.82(1H, t), 7.98(1H, d) | 32-34 |
| 1-74 | 2.42(3H, s), 3.36-3.63(2H, m), 4.82(2H, t), 6.03(1H, d), 7.14(1H, d), 7.88(1H, t), 8.45(1H, d) | 85-87 |
| 1-75 | 2.51(3H, s), 3.39(2H, q), 3.75(2H, s), 4.70(2H, t), 5.22(1H, s), 7.12(1H, d), 7.62(1H, d) | 1.4621 |
| 1-76 | 2.44(3H, s), 3.33-3.60(2H, m), 3.78(2H, s), 4.69(2H, t), 5.25(1H, s), 7.17(1H, d), 8.12(1H, d) | Measurement impossible |
| 1-77 | see Ex. 43 | |
| 1-78 | see Ex. 44 | |
| 1-79 | 1.61-1.91(8H, m), 2.08(3H, s), 2.51(3H, s), 3.40(2H, q), 4.98(1H, s), 6.12(1H, s), 7.13(1H, d), 7.14(1H, brs), 7.62(1H, d) | Measurement impossible |
| 1-80 | 1.61-1.90(8H, m), 2.07(3H, s), 2.44(3H, s), 3.41-4.54(2H, m), 4.99(1H, s), 6.08(1H, s), 7.16(1H, d), 7.47(1H, brs), 8.06(1H, d) | 90-91 |

TABLE 41-continued

| Comp. No. | $^1$H-NMR (CDCl$_3$/TMS d(ppm) value) | m.p. (° C.) or refractive indx ($n_D^{20}$) |
|---|---|---|
| 1-81 | 2.48(3H, s), 3.40(2H, q), 4.81(2H, t), 5.99(1H, d), 7.08(1H, d), 7.82(1H, t), 7.99(1H, d) | 33-34 |
| 1-82 | 2.42(3H, s), 3.36-3.63(2H, m), 4.82(2H, t), 6.03(1H, d), 7.14(1H, d), 7.88(1H, t), 8.45(1H, d) | 70-71 |
| 1-83 | 2.51(3H, s), 3.39(2H, q), 3.76(2H, s), 4.70(2H, t), 5.22(1H, s), 7.12(1H, d), 7.62(1H, d) | 1.4509 |
| 1-85 | 2.08(3H, s), 2.53(3H, s), 3.40(2H, q), 4.72(2H, t), 6.22(1H, s), 7.04(1H, brs), 7.16(1H, d), 7.60(1H, d) | 1.4545 |
| 1-86 | 2.07(3H, s), 2.46(3H, s), 3.42-3.54(2H, m), 4.72(2H, t), 6.19(1H, s), 7.20(1H, d), 7.31(1H, brs), 8.08(1H, d) | Measurement impossible |
| 1-87 | 2.28(6H, s), 2.33(3H, s), 2.50(3H, s), 3.36(2H, q), 6.44(1H, s), 7.09(1H, s), 7.52(1H, s) | 1.5286 |
| 1-89 | 2.19 (3H, s), 2.53 (3H, s), 3.38 (2H, q), 5.02-5.20 (1H, m), 6.02 (1H, s), 7.13 (1H, d), 7.59 (1H, d) | 40-41 |
| 1-90 | 2.21 (3H, s), 2.47 (3H, s), 3.38-3.62 (2H, m), 5.00-5.21 (1H, m), 6.05 (1H, s), 7.18 (1H, d), 8.08 (1H, d) | 1.4720 |
| 1-91 | see Ex. 8 | 85-87 |
| 1-92 | see Ex. 9 | 92-93 |
| 1-93 | 2.14 (3H, s), 2.53 (3H, s), 3.37 (2H, q), 4.71 (2H, t), 7.13 (1H, d), 7.54 (1H, d) | Measurement impossible |

TABLE 42

| Comp. No. | $^1$H-NMR (CDCl$_3$/TMS d(ppm) value) | m.p. (° C.) or refractive indx ($n_D^{20}$) |
|---|---|---|
| 1-94 | 2.16 (3H, s), 2.46 (3H, s), 3.42-3.58 (2H, m), 4.70 (2H, t), 7.18 (1H, d), 8.04 (1H, d) | 1.4859 |
| 1-95 | 1.02 (3H, t), 1.79 (2H, m), 2.13 (3H, s), 2.51 (3H, s), 3.37 (2H, q), 4.11 (2H, t), 5.66 (1H, s), 7.09 (1H, d), 7.58 (1H, d) | 90-91 |
| 1-96 | 1.02 (3H, t), 1.79 (2H, m), 2.14 (3H, s), 2.44 (3H, s), 3.39-3.60 (2H, m), 4.11 (2H, t), 5.69 (1H, s), 7.14 (1H, d), 8.07 (1H, d) | 105-107 |
| 1-97 | 0.98 (3H, t), 1.32 (3H, d), 1.60-1.80 (2H, m), 2.13 (3H, s), 2.51 (3H, s), 3.38 (2H, q), 4.56 (1H, m), 5.64 (1H, s), 7.09 (1H, d), 7.59 (1H, d) | 1.5159 |
| 1-98 | 0.98 (3H, t), 1.33 (3H, dd), 1.61-1.79 (2H, m), 2.14 (3H, s), 2.44 (3H, s), 3.39-3.58 (2H, m), 4.58 (1H, m), 5.67 (1H, s), 7.13 (1H, d), 8.07 (1H, d) | 90-92 |
| 1-99 | 2.14 (3H, s), 2.52 (3H, s), 3.37 (2H, q), 4.69 (2H, t), 5.74 (1H, s), 7.12 (1H, d), 7.56 (1H, d) | 62-64 |
| 1-100 | 2.16 (3H, s), 2.46 (3H, s), 3.40-3.59 (2H, m), 4.69 (2H, t), 5.77 (1H, s), 7.16 (1H, d), 8.06 (1H, d) | 74-75 |
| 1-101 | 2.14 (3H, s), 2.52 (3H, s), 3.38 (2H, q), 4.71 (2H, t), 5.74 (1H, s), 7.12 (1H, d), 7.56 (1H, d) | 44-46 |
| 1-102 | 2.16 (3H, s), 2.46 (3H, s), 3.43-3.57 (2H, m), 4.70 (2H, t), 5.77 (1H, s), 7.17 (1H, d), 8.06 (1H, d) | 1.4527 |
| 1-103 | 1.99-2.06 (2H, m), 2.13 (3H, s), 2.23-2.36 (2H, m), 2.51 (3H, s), 3.37 (2H, q), 4.22 (2H, t), 5.66 (1H, s), 7.10 (1H, d), 7.56 (1H, d) | 92-93 |
| 1-104 | 1.99-2.06 (2H, m), 2.15 (3H, s), 2.24-2.36 (2H, m), 2.45 (3H, s), 3.39-3.59 (2H, m), 4.22 (2H, t), 5.68 (1H, s), 7.15 (1H, d), 8.06 (1H, d) | 1.4975 |
| 1-105 | 2.19 (3H, s), 2.53 (3H, s), 3.38 (2H, q), 6.01 (1H, s), 6.04 (1H, dt), 7.13 (1H, d), 7.58 (1H, d) | 1.4577 |
| 1-106 | 2.21 (3H, s), 2.47 (3H, s), 3.40-3.60 (2H, m), 6.03 (1H, dt), 6.04 (1H, s), 7.18 (1H, d), 8.08 (1H, d) | 1.4623 |
| 1-107 | 2.14 (3H, s), 2.52 (3H, s), 3.37 (2H, q), 4.71 (2H, t), 5.74 (1H, s), 7.12 (1H, d), 7.56 (1H, d) | Measurement impossible |
| 1-108 | 2.16 (3H, s), 2.46 (3H, s), 3.43-3.57 (2H, m), 4.70 (2H, t), 5.76 (1H, s), 7.17 (1H, d), 8.06 (1H, d) | 1.4431 |
| 1-109 | 2.14 (3H, s), 2.52 (3H, s), 3.37 (2H, q), 5.29 (1H, s), 5.71 (1H, s), 7.11 (1H, d), 7.55-7.64 (5H, m) | 98-99 |
| 1-110 | 2.16 (3H, s), 2.45 (3H, s), 3.40-3.60 (2H, m), 5.29 (1H, s), 5.74 (1H, s), 7.16 (1H, d), 7.57 (2H, d), 7.64 (2H, d), 8.08 (1H, s) | 1.5297 |
| 1-111 | see Ex. 10 | |
| 1-112 | 2.48 (3H, s), 3.44-3.55 (2H, m), 4.71 (2H, t), 7.21 (1H, d), 8.06 (1H, d) | 1.4899 |
| 1-113 | 2.55 (3H, s), 3.37 (2H, q), 4.70 (2H, t), 7.15 (1H, d), 7.54 (1H, d) | Measurement impossible |
| 1-114 | 2.48 (3H, s), 3.41-3.58 (2H, m), 4.70 (2H, t), 7.20 (1H, d), 8.05 (1H, d) | 1.5083 |
| 1-115 | 1.15(3H, t), 2.29(2H, q), 2.53(3H, s), 3.39(2H, q), 4.67(2H, t), 6.23(1H, s), 7.05(1H, brs), 7.16(1H, d), 7.60(1H, d) | 78-80 |
| 1-116 | 1.14(3H, t), 2.30(2H, q), 2.46(3H, s), 3.40-3.58(2H, m), 4.67(2H, t), 6.20(1H, s), 7.20(1H, d), 8.08(1H, d) | 91-92 |
| 1-117 | 2.54(3H, s), 3.34(3H, s), 3.40(2H, q), 3.97(2H, t), 4.68(2H, t), 6.29(1H, s), 7.17(1H, d), 7.61(1H, d), 8.35(1H, brs) | 82-84 |

TABLE 42-continued

| Comp. No. | ¹H-NMR (CDCl₃/TMS d(ppm) value) | m.p. (° C.) or refractive indx ($n_D^{20}$) |
|---|---|---|
| 1-118 | 2.48(3H, s), 3.37-3.60(2H, m), 3.41(3H, s), 3.98(2H, d), 4.68(2H, t), 6.30(1H, s), 7.22(1H, d), 8.11(1H, d), 8.36(1H, brs) | 128-129 |
| 1-119 | 0.85(2H, d), 1.04(2H, s), 1.38(1H, s), 2.54(3H, s), 3.40(2H, q), 4.66(2H, t), 6.20(1H, s), 7.17(1H, d), 7.60(1H, d | 108-110 |
| 1-120 | 0.82(2H, q), 0.99(2H, s), 1.46(1H, s), 2.45(3H, s), 3.38-3.56(2H, m), 4.65(2H, t), 6.12(1H, s), 7.19(1H, d), 7.75(1H, brs), 8.03(1H, d) | 84-85 |
| 1-121 | 2.53(3H, s), 3.39(2H, q), 4.68(2H, t), 5.80(1H, d), 6.11(1H, q), 6.30(1H, s), 6.40(1H, d), 7.16(1H, d), 7.18(1H, brs), 7.61(1H, d) | 86-87 |

TABLE 43

| Comp. No. | ¹H-NMR (CDCl₃/TMS d(ppm) value) | m.p. (° C.) or refractive indx ($n_D^{20}$) |
|---|---|---|
| 1-122 | 2.44(3H, s), 3.38-3.57(2H, m), 4.66(2H, t), 5.77(1H, d), 6.15(1H, q), 6.23(1H, s), 6.37(1H, d), 7.19(1H, d), 7.70(1H, brs), 8.02(1H, d) | 85-86 |
| 1-123 | 2.54(3H, s), 3.40(2H, q), 4.69(2H, t), 5.98(1H, t), 6.32(1H, s), 7.19(1H, s), 7.62(1H, d), 7.91(1H, brs) | 61-63 |
| 1-124 | 2.47(3H, s), 3.38-3.61(2H, m), 4.69(2H, t), 5.97(1H, t), 6.28(1H, s), 7.22(1H, d), 8.10(1H, d) | Measurement impossible |
| 1-125 | 2.21(3H, s), 2.52(3H, s), 3.37(2H, q), 4.37(2H, q), 4.69(2H, t), 5.46(1H, s), 7.08(1H, d), 7.61(1H, d) | 1.4585 |
| 1-127 | 1.92(3H, s), 2.53(3H, s), 3.34(2H, q), 4.69(2H, t), 5.11(2H, dd), 5.66-5.76(1H, m), 5.85(1H, s), 7.11(1H, d), 7.54(1H, d) | 1.4884 |
| 1-128 | 1.93(3H, s), 2.45(3H, s), 3.47(2H, q), 4.69(2H, t), 5.12(2H, dd), 5.68-5.78(1H, m), 5.90(1H, s), 7.16(1H, d), 8.03(1H, d) | 1.4820 |
| 1-129 | 1.91(3H, s), 2.22(3H, s), 2.52(3H, s), 3.35(2H, q), 4.71(2H, t), 6.06(1H, s), 7.11(1H, d), 7.60(1H, d) | 1.4880 |
| 1-130 | 1.92(3H, s), 2.24(3H, s), 2.45(3H, s), 3.43-3.51(2H, m), 4.71(2H, t), 6.09(1H, s), 7.15(1H, d), 8.09(1H, d) | 1.4863 |
| 1-131 | 1.89(3H, t), 2.13(3H, s), 2.51(3H, s), 3.37(2H, q), 4.79(2H, dd), 5.72(1H, s), 7.09(1H, d), 7.57(1H, d) | 72-74 |
| 1-132 | 1.89(3H, t), 2.14(3H, s), 2.45(3H, s), 3.39-3.58(2H, m), 4.79(2H, s), 5.74(1H, s), 7.14(1H, d), 8.07(1H, d) | 117-120 |
| 1-133 | see Ex. 48 | 36-37 |
| 1-134 | see Ex. 49 | 1.4870 |
| 1-135 | 1.29(3H, t), 2.51(3H, s), 3.40(2H, q), 3.81(2H, d), 4.23(2H, q), 4.64(2H, t), 5.07(1H, s), 7.14(1H, d), 7.62(1H, d) | 1.4780 |
| 1-136 | 1.29(3H, t), 2.45(3H, s), 3.40-3.58(2H, m), 3.81(2H, d), 4.23(2H, q), 4.64(2H, t), 5.09(1H, s), 7.18(1H, d), 8.11(1H, d) | 1.4778 |
| 1-137 | 2.51(3H, s), 3.38(2H, q), 3.88(3H, s), 4.64(2H, t), 5.10(1H, s), 7.14(1H, d), 7.61 (1H, d) | 94-97 |
| 1-139 | see Ex. 47 | 102-104 |
| 1-140 | 2.44(3H, s), 3.42-3.54(2H, m), 4.71(2H, t), 5.53(1H, br), 5.89(1H, br), 6.27(1H, s), 7.10(1H, d), 8.10(1H, d) | 168-170 |
| 1-141 | 2.51(3H, s), 2.91(3H, d), 3.38(2H, q), 4.70(2H, t), 5.91(1H, br), 6.15(1H, s), 7.06(1H, d), 7.63(1H, d) | 93-95 |
| 1-142 | 2.43(3H, s), 2.91(3H, d), 3.40-3.55(2H, m), 4.70(2H, t), 6.09(1H, br), 6.18(1H, s), 7.10(1H, d), 8.08(1H, d) | 108-110 |
| 1-143 | see Ex. 45 | 81-84 |
| 1-144 | 1.29(3H, t), 2.45(3H, s), 3.42-3.55(2H, m), 4.26(2H, q), 4.70(2H, t), 6.53(1H, s), 7.13(1H, d), 8.07(1H, d) | 1.4806 |
| 1-145 | see Ex. 46 | 95-96 |
| 1-146 | 2.49(3H, s), 2.86(3H, s), 3.02(3H, s), 3.37(2H, q), 4.67(2H, t), 5.38(1H, s), 7.04(1H, d), 7.62(1H, d), 7.71(1H, s) | Measurement impossible |
| 1-147 | 2.42(3H, s), 2.88(3H, s), 3.03(3H, s), 3.39-3.54(2H, m), 4.67(2H, t), 5.40(1H, s), 7.08(1H, d), 7.73(1H, s), 8.15(1H, d) | Measurement impossible |
| 1-148 | 2.51(3H, s), 3.38(2H, q), 4.75(2H, t), 5.58(1H, brs), 5.79 (1H, brs), 6.25(1H, s), 7.07(1H, d), 7.65(1H, d) | 77-79 |
| 1-149 | 2.44(3H, s), 3.39-3.57(2H, m), 4.75(2H, t), 5.51(1H, brs), 5.88 (1H, brs), 6.27(1H, s), 7.10(1H, d), 8.10(1H, d) | 153-154 |
| 1-151 | 2.45(3H, s), 3.36-3.56(2H, m), 5.12(2H, dq), 5.65(1H, brs), 6.02(1H, brs), 6.58(1H, d), 7.12(1H, d), 8.10(1H, d) | 80-81 |
| 1-152 | 1.25(3H, s), 2.53(3H, s), 3.37(2H, q), 4.24(2H, q), 4.74(2H, t), 6.51(1H, s), 7.09(1H, d), 7.60(1H, d) | 62-64 |
| 1-153 | 1.29(3H, t), 2.45(3H, s), 3.40-3.57(2H, m), 4.26(2H, q), 4.93(2H, t), 6.53(1H, s), 7.13(1H, d), 8.07(1H, d) | Measurement impossible |

TABLE 44

| Comp. No. | $^1$H-NMR (CDCl$_3$/TMS d(ppm) value) | m.p. (° C.) or refractive indx ($n_D^{20}$) |
|---|---|---|
| 1-154 | 2.54 (3H, s), 3.36 (2H, q), 4.74 (2H, t), 6.58 (1H, s), 7.08 (1H, d), 7.59 (1H, d) | 96-99 |
| 1-155 | 2.56 (3H, s), 3.40 (2H, q), 5.12 (2H, dq), 6.80 (1H, s), 7.23 (1H, d), 7.69 (1H, d) | 1.4744 |
| 1-156 | 2.50 (3H, s), 3.42-3.59 (2H, m), 5.11 (2H, dq), 6.83 (1H, s), 7.28 (1H, d), 8.20 (1H, d) | 1.4817 |
| 1-157 | 2.56 (3H, s), 3.40 (2H, q), 4.77 (2H, t), 6.51 (1H, s), 7.21 (1H, d), 7.65 (1H, d) | 1.4680 |
| 1-158 | 2.49 (3H, s), 3.42-3.56 (2H, m), 4.77 (2H, t), 6.55 (1H, s), 7.26 (1H, d), 8.16 (1H, d) | 85-87 |
| 1-159 | 2.51 (3H, s), 3.38 (2H, q), 3.70 (3H, brs), 4.64 (2H, t), 5.11 (1H, s), 5.20 (2H, dd) 5.82-5.90 (1H, m), 7.12 (1H, d), 7.60 (1H, d) | 45-56 |
| 1-160 | 2.44 (3H, s), 3.41-3.57 (2H, m), 3.70 (2H, d), 4.64 (2H, t), 5.13 (1H, s), 5.21 (2H, dd) 5.83-5.90 (1H, m), 7.17 (1H, d), 8.10 (1H, d) | Measurement impossible |
| 1-161 | see Ex. 25 | 54-56 |
| 1-162 | see Ex. 26 | 1.4955 |
| 1-163 | 2.28 (1H, t), 2.51 (3H, s), 3.61 (2H, t), 3.84 (2H, s), 4.65 (2H, t), 5.30 (1H, s), 7.12 (1H, d), 7.61 (1H, d) | 1.5031 |
| 1-164 | 2.29 (1H, t), 2.45 (3H, s), 3.57-3.76 (2H, m), 3.84 (2H, s), 4.65 (2H, t), 5.33 (1H, s), 7.17 (1H, d), 8.09 (1H, d) | 1.5080 |
| 1-165 | 1.91 (3H, s), 2.23 (1H, t), 2.53 (3H, s), 3.57 (2H, t), 4.71 (2H, t), 6.06 (1H, s), 7.10 (1H, d), 7.61 (1H, d) | 1.4890 |
| 1-166 | 2.50 (3H, s), 3.36 (2H, q), 3.88 (3H, s), 4.71 (2H, t), 5.26 (1H, s), 7.08 (1H, d), 7.57 (1H, d) | Measurement impossible |
| 1-167 | 2.54 (3H, s), 3.39 (2H, q), 4.71 (2H, t), 6.10 (2H, s), 7.20 (1H, d), 7.63 (1H, d) | 77-78 |
| 1-168 | 2.48 (3H, s), 3.41-3.56 (2H, m), 4.71 (2H, t), 6.18 (2H, s), 7.25 (1H, d), 8.15 (1H, d) | 141-142 |
| 1-169 | 2.52 (3H, s), 3.39 (2H, q), 3.97 (1H, brs), 4.01 (2H, s), 4.66 (2H, t), 5.40 (1H, s), 7.14 (1H, d), 7.60 (1H, d) | |
| 1-170 | 2.45 (3H, s), 3.39-3.60 (2H, m), 4.00 (2H, s), 4.66 (2H, t), 5.43 (1H, s), 7.19 (1H, d), 8.09 (1H, d) | 106-108 |
| 1-171 | 1.92 (3H, s), 2.53 (3H, s), 3.34 (2H, q), 4.41 (1H, dd), 4.69 (1H, dd), 4.69 (2H, t), 5.96 (1H, s), 7.12 (1H, d), 7.55 (1H, d) | 1.4850 |
| 1-172 | 1.92 (3H, s), 2.53 (3H, s), 3.57 (2H, t), 4.42 (1H, dd), 4.69 (2H, t), 4.70 (1H, dd), 5.97 (1H, s), 7.12 (1H, d), 7.55 (1H, d) | Measurement impossible |
| 1-173 | 2.51 (3H, s), 3.38 (2H, q), 3.76 (2H, dd), 3.88 (1H, brs), 4.51 (1H, dd), 4.63 (2H, t), 4.73 (1H, dd), 5.16 (1H, s), 7.12 (1H, d), 7.59 (1H, d) | 1.4859 |
| 1-174 | 2.44 (3H, s), 3.36-3.58 (2H, m), 3.76 (2H, dd), 3.91 (1H, brs), 4.44-4.89 (3H, m), 4.64 (2H, t), 5.19 (1H, s), 7.17 (1H, d), 8.10 (1H, d) | Measurement impossible |
| 1-175 | 2.51 (3H, s), 3.61 (2H, t), 3.76 (2H, dd), 3.88 (1H, brs), 4.51 (1H, dd), 4.64 (2H, t), 4.74 (1H, dd), 5.16 (1H, s), 7.13 (1H, d), 7.60 (1H, d) | Measurement impossible |
| 1-176 | 2.45 (3H, s), 3.57-3.79 (2H, m), 3.76 (2H, dd), 3.93 (1H, brs), 4.53 (1H, dd), 4.64 (2H, t), 4.75 (1H, dd), 5.19 (1H, s), 7.18 (1H, d), 8.09 (1H, d) | Measurement impossible |
| 1-177 | see Ex. 35 | |
| 1-178 | see Ex. 36 | 71-73 |
| 1-179 | 2.08 (3H, s), 2.43 (3H, s), 2.43 (2H, quint), 3.05 (2H, t), 4.66 (2H, t), 6.20 (1H, s), 7.13 (1H, d), 7.13 (1H, brs), 7.38 (1H, d) | 106-108 |
| 1-180 | 2.06 (3H, s), 2.34-2.46 (1H, m), 2.42 (3H, s), 2.69-2.76 (1H, m), 2.81-2.88 (1H, m), 3.07-3.14 (1H, m), 4.66 (2H, t), 6.16 (1H, s), 7.17 (1H, d), 7.41 (1H, brs), 7.93 (1H, d) | 79-80 |
| 1-181 | 2.07 (3H, s), 2.54 (3H, s), 3.39 (2H, t), 4.65 (2H, t), 6.20 (1H, s), 7.09 (1H, brs), 7.15 (1H, d), 7.59 (1H, d) | 78-81 |

TABLE 45

| Comp. No. | $^1$H-NMR (CDCl$_3$/TMS d(ppm) value) | m.p. (° C.) or refractive indx ($n_D^{20}$) |
|---|---|---|
| 1-182 | 0.26-0.30(2H, m), 0.59-0.64(2H, m), 1.01-1.06(1H, m), 2.08(3H, s), 2.42(3H, s), 2.82(2H, d), 4.66(2H, t), 6.21(1H, s), 7.08(1H, d), 7.11(1H, brs), 7.31(1H, d) | Measurement impossible |
| 1-183 | 0.30-0.32(2H, m), 0.67-0.70(2H, m), 1.03(1H, m), 2.08(3H, s), 2.42(3H, s), 2.63-2.84(2H, m), 4.64(2H, t), 6.20(1H, s), 7.12(1H, d), 7.69(1H, brs), 7.94(1H, d) | 1.5106 |
| 1-184 | 2.08(3H, s), 2.47(3H, s), 3.55(2H, d), 4.39(1H, dd), 4.65(1H, dd), 4.66(2H, t), 6.21(1H, s), 7.11(1H, brs), 7.13(1H, d), 7.46(1H, d) | 1.5130 |
| 1-185 | 2.07(3H, s), 2.42(1H, s), 3.62(2H, d), 4.56(1H, dd), 4.65(2H, t), 4.89(1H, dd), 6.19(1H, s), 7.15(1H, d), 7.58(1H, brs), 7.92(1H, d) | Measurement impossible |
| 1-186 | see Ex. 21 | 1.4843 |
| 1-187 | see Ex. 22 | 58-60 |
| 1-188 | 1.91(3H, s), 2.53(3H, s), 3.03(3H, s), 3.35(2H, q), 5.05-5.20(1H, m), 6.15(1H, s), 7.13(1H, d), 7.58(1H, d) | 1.4803 |
| 1-189 | 2.08(3H, s), 2.53(3H, s), 3.62(2H, t), 4.70(2H, t), 6.21(1H, s), 7.09(1H, brs), 7.15(1H, d), 7.60(1H, d) | Measurement impossible |
| 1-190 | 2.06(3H, s), 2.45(3H, s), 3.57-3.74(2H, m), 4.69(2H, t), 6.16(2H, t), 7.19(1H, d), 7.50(1H, brs), 8.03(1H, d) | 68-70 |
| 1-191 | 2.08(3H, s), 2.52(3H, s), 3.39(2H, q), 4.80(2H, d), 5.48(1H, dq), 6.19(1H, s), 7.09(1H, brs), 7.16(1H, d), 7.58(1H, d) | 86-87 |
| 1-192 | 2.07(3H, s), 2.44(3H, s), 3.39-3.54(2H, m), 4.79(2H, d), 5.48(1H, dq), 6.15(1H, s), 7.19(1H, d), 7.44(1H, brs), 8.01(1H, d) | 71-73 |

TABLE 45-continued

| Comp. No. | ¹H-NMR (CDCl₃/TMS d(ppm) value) | m.p. (° C.) or refractive indx ($n_D^{20}$) |
|---|---|---|
| 1-193 | 2.50(3H, s), 3.36(2H, q), 3.88(3H, s), 4.66(2H, t), 5.26(1H, s), 7.08(1H, d), 7.57(1H, d) | |
| 1-194 | 2.43(3H, s), 3.37-3.55(2H, m), 3.88(3H, s), 4.66(2H, t), 5.28(1H, s), 7.12(1H, d), 8.05(1H, d) | Measurement impossible |
| 1-195 | 2.51(3H, s), 3.36(2H, q), 3.92(3H, s), 5.13(2H, dq), 5.52(1H, s), 7.09(1H, d), 7.60(1H, d) | 1.4630 |
| 1-196 | 2.44(3H, s), 3.37-3.57(2H, m), 3.93(3H, s), 5.12(2H, dq), 5.54(1H, s), 7.14(1H, d), 8.08(1H, d) | 1.4663 |
| 1-197 | 2.50(3H, s), 3.36(2H, q), 3.88(3H, s), 4.70(2H, t), 5.26(1H, s), 7.08(1H, d), 7.57(1H, d) | 1.4560 |
| 1-198 | 2.43(3H, s), 3.37-3.57(2H, m), 3.88(3H, s), 4.70(2H, t), 5.28(1H, s), 7.12(1H, d), 8.05(1H, d) | 1.4600 |
| 1-199 | see Ex. 51 | |
| 1-200 | 2.47(3H, s), 3.44-3.55(2H, m), 4.73(2H, t), 6.60(1H, s), 7.17(1H, d), 8.09(1H, d) | Measurement impossible |
| 1-201 | see Ex. 50 | 71-72 |
| 1-202 | 2.46(3H, s), 3.40-3.59(2H, m), 4.51(2H, s), 4.67(2H, t), 6.01(1H, s), 7.17(1H, d), 8.12(1H, d) | Measurement impossible |
| 1-203 | 2.53(3H, s), 3.38(2H, q), 4.65(2H, t), 5.22(2H, s), 5.96(1H, s), 7.14(1H, d), 7.53(1H, d), 7.88(1H, s), 7.90(1H, s) | 66-68 |
| 1-204 | 2.46(3H, s), 3.38-3.57(2H, m), 4.66(2H, t), 5.26(2H, s), 5.99(1H, s), 7.18(1H, d), 7.87(1H, d), 7.93(1H, s), 8.01(1H, d) | Measurement impossible |
| 1-205 | see Ex. 52 | 131-133 |
| 1-206 | (majar) 2.47(3H, s), 3.41-3.58(2H, m), 4.69(2H, t), 6.24(1H, s), 7.16(1H, d), 7.81(1H, brs), 7.82(1H, s), 8.10(1H, d) | 160-163 |
| 1-207 | (majar) 2.53(3H, s), 3.37(2H, q), 3.88(3H, s), 4.69(2H, t), 6.27(1H, s), 7.12(1H, d), 7.57(1H,d), 7.71(1H, d) | 48-49 |
| 1-208 | (majar) 2.46(3H, s), 3.42-3.57(2H, m), 3.86(3H, s), 4.69(2H, t), 6.27(1H, s), 7.16(1H, d), 7.72(1H, s), 8.08(1H, d) | Measurement impossible |

TABLE 46

| Comp. No. | ¹H-NMR (CDCl₃/TMS d(ppm) value) | m.p. (° C.) or refractive indx ($n_D^{20}$) |
|---|---|---|
| 1-209 | 2.07(3H, s), 2.51(3H, s), 3.38(2H, q), 4.72(2H, t), 6.91(1H, brs), 7.10(1H, d), 7.60(1H, d) | 85-87 |
| 1-210 | 2.07(3H, s), 2.45(3H, s), 3.42-3.56(2H, m), 4.72(2H, t), 7.15(1H, d), 8.07(1H, d) | 68-71 |
| 1-211 | 1.93(3H, d), 2.54(3H, s), 3.01(3H, s), 3.34(2H, q), 4.75(2H, t), 7.13(1H, d), 7.52(1H, d) | 1.4895 |
| 1-212 | 1.93(3H, d), 2.46(3H, s), 3.03(3H, d), 3.47(2H, q), 4.75(2H, t), 7.18(1H, d), 8.03(1H, d) | 83-86 |
| 1-213 | 2.30(6H, s), 2.51(3H, s), 3.35(2H, q), 4.75(2H, t), 7.10(1H, d), 7.47(1H, d) | 1.4880 |
| 1-214 | 2.52(3H, s), 2.88(3H, d), 3.37(2H, q), 4.67(2H, t), 7.13(1H, d), 7.56(1H, d) | 2.30-233 |
| 1-215 | 2.45(3H, s), 2.88(3H, s), 3.39-3.58(2H, m), 4.67(2H, t), 7.17(1H, d), 8.07(1H, d) | Measurement impossible |
| 1-216 | 2.24(2H, brs), 2.50(3H, s), 3.38(2H, q), 3.72(2H, brs), 4.69(2H, t), 7.11(1H, d), 7.59(1H, d) | 86-89 |
| 1-217 | 1.88(3H, t), 2.07(3H, s), 2.51(3H, s), 3.39(2H, q), 4.80(2H, s), 6.17(1H, s), 7.13(1H, d), 7.15(1H, brs), 7.61(1H, d) | 104-106 |
| 1-218 | 1.89(3H, s), 2.06(3H, s), 2.44(3H, s), 3.38-3.52(2H, m), 4.79(2H, s), 6.13(1H, s), 7.17(1H, d), 7.31(1H, brs), 8.07(1H, d) | 68-70 |
| 1-219 | 0.91-0.99(3H, m), 1.33(3H, d), 1.42-1.61(3H, m), 1.68-1.78(1H, m), 2.13(3H, s), 2.51(3H, s), 3.37(2H, q), 4.61-4.67(1H, m), 5.64(1H, s), 7.08(1H, d), 7.58(1H, d) | 1.5100 |
| 1-220 | 0.96(3H, t), 1.33(3H, d), 1.35-1.79(4H, m), 2.14(3H, s), 2.44(3H, s), 3.36-3.61(2H, m), 4.62-4.68(1H, m), 5.66(1H, s), 7.13(1H, d), 8.07(1H, d) | 1.5082 |
| 1-221 | 0.94(3H, t), 1.00(3H, d), 1.17-1.34(1H, m), 1.49-1.58(1H, m), 1.60-1.90(1H, m), 2.13(3H, s), 2.51(3H, s), 3.37(2H, q), 3.90-4.04(2H, m), 5.67(1H, s), 7.09(1H, d), 7.58(1H, d) | 65-67 |
| 1-222 | 0.94(3H, t), 1.00(3H, d), 1.17-1.29(1H, m), 1.49-1.63(1H, m), 1.77-1.92(1H, m), 2.14(3H, s), 2.44(3H, s), 3.36-3.61(2H, m), 3.90-4.05(2H, m), 5.68(1H, s), 7.13(1H, d), 8.08(1H, d) | Measurement impossible |
| 1-223 | 0.97(9H, s), 1.72(2H, t), 2.12(3H, s), 2.51(3H, s), 3.38(2H, q), 4.21(2H, t), 5.65(1H, s), 7.09(1H, d), 7.59(1H, d) | 1.5040 |
| 1-224 | 0.98(9H, s), 1.72(2H, t), 2.13(3H, s), 2.48(3H, s), 3.36-3.60(2H, m), 4.16-4.25(2H, m), 5.67(1H, s), 7.14(1H, d), 8.08(1H, d) | 75-77 |
| 1-225 | 0.33-0.36(2H, m), 0.57-0.63(2H, m), 1.23-1.33(1H, m), 2.14(3H, s), 2.51(3H, s), 3.37(2H, q), 4.01(2H, d), 5.68(1H, s), 7.09(1H, d), 7.57(1H, d) | 87-89 |
| 1-226 | 0.33-0.37(2H, m), 0.59-0.64(2H, m), 1.25-1.32(1H, m), 2.14(3H, s), 2.45(3H, s), 3.36-3.59(2H, m), 3.96-4.04(2H, m), 5.71(1H, s), 7.13(1H, d), 8.06(1H, d) | 116-119 |
| 1-227 | 1.83-1.99(4H, m), 2.08-2.16(2H, m), 2.12(3H, s), 2.51(3H, s), 2.71-2.81(1H, m), 3.37(2H, q), 4.13(2H, d), 5.66(1H, s), 7.09(1H, d), 7.58(1H, d) | 78-79 |

TABLE 46-continued

| Comp. No. | $^1$H-NMR (CDCl$_3$/TMS d(ppm) value) | m.p. (° C.) or refractive indx (n$_D^{20}$) |
|---|---|---|
| 1-228 | 1.83-2.00(4H, m), 2.23(2H, m), 2.14(3H, s), 2.44(3H, s), 2.71-2.81(1H, m), 3.36-3.62(2H, m), 4.14(2H, d), 5.69(1H, s), 7.14(1H, d), 8.08(1H, d) | 90-91 |
| 1-229 | 1.31-1.43(2H, m), 1.51-1.66(4H, m), 1.76-1.86(2H, m), 2.12(3H, s), 2.27-2.40(1H, m), 2.51(3H, s), 3.37(2H, q), 4.02(2H, d), 5.67(1H, s), 7.09(1H, d), 7.58(1H, d) | 63-64 |
| 1-230 | 1.33-1.43(2H, m), 1.55-1.66(4H, m), 1.81-1.85(2H, m), 2.14(3H, s), 2.31-2.41(2H, m), 2.44(3H, s), 3.36-3.61 (2H, m), 4.03(2H, d), 5.69(1H, s), 7.13(1H, d), 8.07(1H, d) | 79-82 |
| 1-231 | 1.68-1.76(1H, m), 1.87-2.08(3H, m), 2.15(3H, s), 2.51(3H, s), 3.36(2H, q), 3.82(1H, dd), 3.93(1H, dd), 4.11-4.15(1H, m), 4.24-4.30(2H, m), 5.70(1H, s), 7.09(1H, d), 7.57(1H, d) | 91-92 |
| 1-232 | 1.69-1.76(1H, m), 1.87(2H, m), 2.00-2.07(1H, m), 2.14(3H, s), 2.44(3H, s), 3.38-3.59(2H, m), 3.83(1H, dd), 3.93(1H, dd), 4.10-4.16(1H, m), 4.20-4.30(3H, m), 5.72(1H, s), 7.13(1H, d), 8.06(1H, d) | 1.5219 |
| 1-233 | 1.67-1.78(1H, m), 2.02-2.13(1H, m), 2.14(3H, s), 2.51(3H, s), 2.69-2.79(1H, m), 3.37(2H, q), 3.66-3.94(4H, m), 4.05-4.18(2H, m), 5.66(1H, s), 7.10(1H, d), 7.57(1H, d) | 69-70 |

TABLE 47

| Comp. No. | $^1$H-NMR (CDCl$_3$/TMS d(ppm) value) | m.p. (° C.) or refractive indx (n$_D^{20}$) |
|---|---|---|
| 1-234 | 1.70-1.77(1H, m), 2.07-2.14(1H, m), 2.14(3H, s), 2.45(3H, s), 2.72-2.76(1H, m), 3.38-3.57(2H, m), 3.68(1H, dd), 3.78(1H, dd), 3.85-3.94(2H, m), 4.05-4.18(2H, m), 5.68(1H, s), 7.14(1H, d), 8.07(1H, d) | 1.5262 |
| 1-235 | 1.57-1.65(2H, m), 1.73-1.93(6H, m), 2.13(3H, s), 2.51(3H, s), 3.37(2H, q), 4.93-4.99(1H, m), 7.08(1H, d), 7.58(1H, d) | 1.5340 |
| 1-236 | 1.54-1.62(2H, m), 1.77-1.91(6H, m), 2.14(3H, s), 2.44(3H, s), 3.36-3.61(2H, m), 4.95-5.01(1H, m), 5.66(1H, s), 7.13(1H, d), 8.07(1H, d) | 70-71 |
| 1-237 | 0.96(6H, t), 1.66-1.75(4H, m), 2.13(3H, s), 2.50(3H, s), 3.37(2H, q), 4.38-4.46(1H, m), 5.64(1H, s), 7.08(1H, d), 7.58(1H, d) | 1.5173 |
| 1-238 | 0.96(6H, t), 1.66-1.73(4H, m), 2.14(3H, s), 2.44(3H, s), 3.36-3.61(2H, m), 4.40-4.48(1H, m), 5.67(1H, s), 7.13(1H, d), 8.07(1H, d) | 1.5108 |
| 1-239 | 2.12(3H, s), 2.51(3H, s), 3.37(2H, q), 3.44(3H, s), 3.71-3.75(2H, m), 4.32-4.36(2H, m), 5.70(1H, s), 7.09(1H, d), 7.57(1H, d) | 76-78 |
| 1-240 | 2.14(3H, s), 2.44(3H, s), 3.37-3.58(2H, m), 3.44(3H, s), 3.71-3.75(2H, m), 4.32-4.36(2H, m), 5.73(1H, s), 7.14(1H, d), 8.06(1H, d) | 86-89 |
| 1-241 | 2.13(3H, s), 2.19(3H, s), 2.51(3H, s), 2.88(2H, t), 3.37(2H, q), 4.36(2H, t), 5.67(1H, s), 7.10(1H, d), 7.57(1H, d) | 73-74 |
| 1-243 | 2.13(3H, s), 2.52(3H, s), 2.68(3H, s), 3.05-3.28(2H, m), 3.38(2H, q), 4.59-4.65(2H, m), 5.68(1H, s), 7.10(1H, d), 7.57(1H, d) | 73-74 |
| 1-244 | 2.15(3H, s), 2.46(3H, s), 3.03(3H, s), 3.41-3.57(4H, m), 4.65(2H, t), 5.70(1H, s), 7.17(1H, d), 8.05(1H, d) | 142-144 |
| 1-245 | 1.77(3H, d), 2.09(3H, s), 2.53(3H, s), 3.41(2H, q), 5.35(1H, q), 6.21(1H, s), 7.10(1H, brs), 7.16(1H, d), 7.61(1H, d) | Measurement impossible |
| 1-246 | 1.77(3H, dd), 2.08(3H, s), 2.46(3H, s), 3.43-3.59(2H, m), 5.32-5.40(1H, m), 6.16(1H, s), 7.20(1H, d), 7.34(1H, brs), 8.07(1H, d) | 151-153 |
| 1-247 | 2.08(3H, s), 2.53(3H, s), 3.40(2H, q), 4.58(2H, t), 6.02(1H, tt), 6.20(1H, s), 7.07(1H, brs), 7.16(1H, d), 7.59(1H, d) | Measurement impossible |
| 1-248 | 2.08(3H, s), 2.45(3H, s), 3.39-3.52(2H, m), 4.58(2H, t), 6.02(1H, tt), 6.17(1H, s), 7.19(1H, d), 7.30(1H, brs), 8.00(1H, d) | 78-81 |
| 1-249 | see Ex. 19 | 72-74 |
| 1-250 | see Ex. 20 | 76-78 |
| 1-251 | 2.50(3H, s), 3.41(2H, q), 5.15(1H, dq), 6.26(1H, s), 7.12(1H, d), 7.89(1H, t), 7.98(1H, d) | |
| 1-252 | 2.44(3H, s), 3.39-3.64(2H, m), 5.13(1H, dq), 6.30(1H, s), 7.17(1H, d), 7.92(1H, d), 8.44(1H, d) | Measurement impossible |
| 1-253 | see Ex. 29 | |
| 1-254 | see Ex. 30 | |
| 1-255 | 2.49(3H, s), 3.41-3.58(2H, m), 5.18(1H, dq), 7.17(1H, d), 7.58(1H, d) | 1.4952 |
| 1-256 | 2.56(3H, s), 3.38(2H, q), 5.17(1H, dq), 7.22(1H, d), 8.09(1H, d) | 100-103 |
| 1-257 | 2.50(3H, s), 3.41(2H, q), 5.21(1H, dq), 7.13(1H, d), 7.93(1H, d), 7.94(1H, d) | 1.4833 |
| 1-258 | 2.44(3H, s), 3.39-3.62(2H, m), 5.18(1H, dq), 7.19(1H, d), 7.97(1H, d), 8.41(1H, d) | 1.4878 |
| 1-259 | 2.50(3H, s), 3.41(2H, q), 5.22(1H, dq), 7.13(1H, d), 7.93(1H, s), 7.94(1H, d) | 1.4871 |
| 1-260 | 2.44(3H, s), 3.39-3.63(2H, m), 5.19(1H, dq), 7.19(1H, d), 7.98(1H, d), 8.41(1H, d) | 1.4997 |
| 1-261 | see Ex. 41 | 1.4862 |
| 1-262 | see Ex. 42 | 1.4880 |
| 1-263 | see Ex. 39 | 86-87 |

TABLE 48

| Comp. No. | $^1$H-NMR (CDCl$_3$/TMS d(ppm) value) | m.p. (° C.) or refractive indx ($n_D^{20}$) |
|---|---|---|
| 1-264 | see Ex. 40 | |
| 1-265 | 2.56(3H, s), 3.38(2H, q), 5.18(1H, dq), 7.17(1H, d), 7.59(1H, d) | Measurement impossible |
| 1-266 | 2.49(3H, s), 3.40-3.58(2H, m), 5.16(1H, dq), 7.23(1H, d), 8.10(1H, d) | 1.4873 |
| 1-267 | see Ex. 11 | |
| 1-268 | see Ex. 12 | |
| 1-269 | 2.20(3H, s), 2.55(3H, s), 3.38(2H, q), 6.03(1H, s), 7.13(1H, d), 7.59(1H, d) | 1.4537 |
| 1-270 | 2.21(3H, s), 2.47(3H, s), 3.38-3.58(2H, m), 6.05(1H, s), 7.18(1H, d), 8.09(1H, d) | 1.4541 |
| 1-271 | 2.10(3H, s), 2.52(3H, s), 3.40(2H, q), 6.37(1H, s), 7.12(1H, brs), 7.16(1H, d), 7.53(1H, d) | Measurement impossible |
| 1-272 | 2.09(3H, s), 2.47(3H, s), 3.42-3.60(2H, m), 6.35(1H, s), 7.21(1H, d), 7.31(1H, brs), 8.03(1H, d) | 79-80 |
| 1-273 | 1.52(3H, d), 2.14(3H, s), 2.52(3H, s), 3.37(2H, q), 5.13-5.23(1H, m), 5.71(1H, s), 7.11(1H, d), 7.56(1H, d) | 1.4843 |
| 1-274 | 1.51-1.54(3H, m), 2.15(3H, s), 2.45(3H, s), 3.38-3.61(2H, m), 5.14-5.24(1H, m), 5.74(1H, s), 7.16(1H, d), 8.05(1H, d) | 101-104 |
| 1-275 | 1.53(3H, d), 2.08(3H, s), 2.52(3H, s), 3.39(2H, q), 5.19(1H, sept), 6.18(1H, s), 7.03(1H, brs), 7.15(1H, d), 7.59(1H, d) | 1.5040 |
| 1-276 | 1.52(3H, d), 2.06(3H, s), 2.44(3H, s), 3.37-3.57(2H, m), 5.19(1H, sept), 6.12(1H, s), 7.18(1H, d), 7.37(1H, brs), 8.05(1H, d) | Measurement impossible |
| 1-277 | 1.55(3H, d), 2.13(3H, s), 2.52(3H, s), 3.37(2H, q), 5.22-5.39(1H, m), 5.69(1H, s), 7.11(1H, d), 7.56(1H, d) | Measurement impossible |
| 1-278 | 1.53-1.58(3H, m), 2.15(3H, s), 2.45(3H, s), 3.37-3.61(2H, m), 5.20-5.37(1H, m), 5.72(1H, s), 7.16(1H, d), 8.05(1H, d) | Measurement impossible |
| 1-279 | 1.55(3H, d), 2.07(3H, s), 2.52(3H, s), 3.39(2H, q), 5.28-5.35(1H, m), 6.16(1H, s), 7.05(1H, brs), 7.15(1H, d), 7.58(1H, d) | |
| 1-280 | 1.55(3H, d), 2.04(3H, s), 2.44(3H, s), 3.39-3.59(2H, m), 5.26-5.34(1H, m), 6.11(1H, s), 7.18(1H, d), 7.46(1H, brd), 8.04(1H, d) | Measurement impossible |
| 1-281 | 1.54-1.58(3H, m), 2.13(3H, s), 2.52(3H, s), 3.37(2H, q), 5.27-5.44(1H, m), 5.69(1H, s), 7.11(1H, d), 7.55(1H, d) | Measurement impossible |
| 1-282 | 1.54-1.59(3H, m), 2.15(3H, s), 2.46(3H, s), 3.37-3.63(2H, m), 5.26-5.43(1H, m), 5.72(1H, s), 7.16(1H, d), 8.05(1H, d) | Measurement impossible |
| 1-283 | 1.57(3H, d), 2.07(3H, s), 2.53(3H, s), 3.40(2H, q), 5.32-5.42(1H, m), 6.16(1H, s), 7.11(1H, brs), 7.15(1H, d), 7.59(1H, d) | Measurement impossible |
| 1-284 | 1.57(3H, d), 2.07(3H, s), 2.46(3H, s), 3.41-3.61(2H, m), 5.33-5.40(1H, m), 6.13(1H, s), 7.19(1H, d), 7.34(1H, brs), 8.06(1H, d) | 82-85 |
| 1-285 | 0.06(9H, s), 1.11-1.17(2H, m), 2.12(3H, s), 2.51(3H, s), 3.37(2H, q), 4.21-4.27(2H, m), 5.65(1H, s), 7.09(1H, d), 7.59(1H, d) | 1.5092 |
| 1-286 | 0.07(9H, s), 1.11-1.17(2H, m), 2.13(3H, s), 2.44(3H, s), 3.40-3.57(2H, m), 4.21-4.28(2H, m), 5.67(1H, s), 7.13(1H, d), 8.08(1H, d) | 1.5122 |
| 1-287 | 2.51(3H, s), 2.85(3H, d), 3.38(2H, q), 3.64(1H, brs), 5.35(1H, s), 6.07(1H, dt), 7.12(1H, d), 7.60(1H, d) | Measurement impossible |
| 1-288 | 2.45(3H, s), 2.84(3H, s), 3.38-3.56(2H, m), 3.67(1H, brs), 5.36(1H, s), 6.05(1H, dt), 7.17(1H, d), 8.10(1H, d) | Measurement impossible |
| 1-289 | see Ex. 15 | |
| 1-290 | see Ex. 16 | 1.4782 |
| 1-291 | see Ex. 17 | 1.4657 |
| 1-292 | see Ex. 18 | 1.4751 |

TABLE 49

| Comp. No. | $^1$H-NMR (CDCl$_3$/TMS d(ppm) value) | m.p. (° C.) or refractive indx ($n_D^{20}$) |
|---|---|---|
| 1-293 | 0.90(6H, d), 1.26-1.36(2H, m), 1.54-1.67(1H, m), 1.72-1.82(2H, m), 2.13(3H, s), 2.51(3H, s), 3.37(2H, q), 4.13(2H, t), 5.66(1H, s), 7.09(1H, d), 7.58(1H, d) | 86-88 |
| 1-294 | 0.91(6H, d), 1.28-1.35(2H, m), 1.55-1.64(1H, m), 1.73-1.79(2H, m), 2.13(3H, s), 2.44(3H, s), 3.38-3.59(2H, m), 4.09-4.15(2H, m), 5.68(1H, s), 7.13(1H, d), 8.07(1H, d) | 1.5109 |
| 1-295 | 2.12(3H, s), 2.51(3H, s), 3.37(2H, q), 3.39(3H, s), 3.58(2H, t), 3.71(2H, t), 3.84(2H, t), 4.35(2H, t), 5.68(1H, s), 7.08(1H, dz), 7.56(1H, d) | 57-58 |
| 1-296 | 2.13(3H, s), 2.44(3H, s), 3.39(3H, s), 3.40-3.60(4H, m), 3.71(2H, t), 3.84(2H, t), 4.35(2H, t), 5.71(1H, s), 7.13(1H, d), 8.06(1H, d) | 1.5126 |
| 1-297 | 2.04(2H, tt), 2.13(3H, s), 2.51(3H, s), 3.35(3H, s), 3.28-3.42(2H, m), 3.54(2H, t), 4.24(2H, t), 5.67(1H, s), 7.09(1H, d), 7.58(1H, d) | 70-72 |
| 1-298 | 2.04(2H, tt), 2.14(3H, s), 2.44(3H, s), 3.35(3H, s), 3.37-3.60(4H, m), 4.25(2H, t), 5.69(1H, s), 7.14(1H, d), 8.07(1H, d) | 1.5180 |
| 1-299 | 0.01(9H, s), 0.55-0.62(2H, m), 1.71-1.81(2H, m), 2.12(3H, s), 2.51(3H, s), 3.37(2H, q), 4.11(2H, t), 5.66(1H, s), 7.09(1H, dz), 7.58(1H, d) | 1.5070 |
| 1-300 | 0.01(9H, s), 0.55-0.61(2H, m), 1.72-1.81(2H, m), 2.14(3H, s), 2.44(3H, s), 3.39-3.57(2H, m), 4.11(2H, t), 5.68(1H, s), 7.13(1H, d), 8.07(1H, d) | 1.5112 |

TABLE 49-continued

| Comp. No. | ¹H-NMR (CDCl₃/TMS d(ppm) value) | m.p. (° C.) or refractive indx ($n_D^{20}$) |
|---|---|---|
| 1-301 | 1.98-2.10(2H, m), 2.13(3H, s), 2.22-2.37(2H, m), 2.52(3H, s), 3.37(2H, q), 4.21(2H, t), 5.66(1H, s), 7.10(1H, d), 7.57(1H, d) | 54-56 |
| 1-302 | 2.00-2.13(2H, m), 2.15(3H, s), 2.22-2.37(2H, m), 2.45(3H, s), 3.40-3.57(2H, m), 4.21(2H, t), 5.69(1H, s), 7.15(1H, d), 8.06(1H, d) | Measurement impossible |
| 1-303 | 2.00-2.35(4H, m), 2.17(3H, s), 2.52(3H, s), 3.37(2H, q), 4.23(2H, t), 5.66(1H, s), 7.10(1H, d), 7.57(1H, d) | 107-108 |
| 1-304 | 2.01-2.16(2H, m), 2.19(3H, s), 2.21-2.30(2H, m), 2.45(3H, s), 3.38-3.60(2H, m), 4.24(2H, t), 5.69(1H, s), 7.15(1H, d), 8.06(1H, d) | 63-65 |
| 1-305 | 2.03-2.17(2H, m), 2.13(3H, s), 2.20-2.41(2H, m), 2.52(3H, s), 3.37(2H, q), 4.23(2H, t), 5.66(1H, s), 7.10(1H, d), 7.57(1H, d) | 75-78 |
| 1-306 | 2.03-2.12(2H, m), 2.15(3H, s), 2.16-2.36(2H, m), 2.45(3H, s), 3.38-3.60(2H, m), 4.24(2H, t), 5.69(1H, s), 7.15(1H, d), 8.07(1H, d) | 1.4690 |
| 1-307 | 2.02-2.14(2H, m), 2.13(3H, s), 2.20-2.42(2H, m), 2.52(3H, s), 3.37(2H, q), 4.24(2H, t), 5.67(1H, s), 7.10(1H, d), 7.57(1H, d) | 72-73 |
| 1-308 | 2.02-2.13(2H, m), 2.15(3H, s), 2.20-2.37(2H, m), 2.45(3H, s), 3.36-3.62(2H, m), 4.25(2H, t), 5.69(1H, s), 7.15(1H, d), 8.07(1H, d) | 1.4592 |
| 1-309 | 2.02-2.14(2H, m), 2.13(3H, s), 2.20-2.42(2H, m), 2.52(3H, s), 3.37(2H, q), 4.24(2H, t), 5.67(1H, s), 7.10(1H, d), 7.57(1H, d) | 64-65 |
| 1-310 | 2.02-2.13(2H, m), 2.15(3H, s), 2.20-2.41(2H, m), 2.45(3H, s), 3.35-3.62(2H, m), 4.25(2H, t), 5.69(1H, s), 7.15(1H, d), 8.07(1H, d) | 1.4415 |
| 1-311 | 2.13(3H, s), 2.52(3H, s), 2.52-2.72(2H, m), 3.37(2H, q), 4.49(2H, t), 5.67(1H, s), 7.11(1H, d), 7.57(1H, d) | 62-63 |
| 1-312 | 2.15(3H, s), 2.45(3H, s), 2.52-2.73(2H, m), 3.36-3.63(2H, m), 4.49(2H, t), 5.70(1H, s), 7.16(1H, d), 8.06(1H, d) | Measurement impossible |
| 1-313 | 2.13(3H, s), 2.52(3H, s), 2.51-2.71(2H, m), 3.37(2H, q), 4.49(2H, t), 5.67(1H, s), 7.11(1H, d), 7.57(1H, d) | 50-52 |
| 1-314 | 2.15(3H, s), 2.45(3H, s), 2.53-2.72(2H, m), 3.36-3.62(2H, m), 4.49(2H, t), 5.70(1H, s), 7.16(1H, d), 8.06(1H, d) | 70-72 |
| 1-315 | 2.13(3H, s), 2.52(3H, s), 2.51-2.73(2H, m), 3.37(2H, q), 4.49(2H, t), 5.67(1H, s), 7.11(1H, d), 7.57(1H, d) | 63-65 |
| 1-316 | 2.15(3H, s), 2.45(3H, s), 2.55-2.72(2H, m), 3.36-3.62(2H, m), 4.49(2H, t), 5.70(1H, s), 7.15(1H, d), 8.06(1H, d) | 76-78 |
| 1-317 | 2.19(3H, s), 2.53(3H, s), 3.38(2H, q), 6.01(1H, s), 6.17(1H, dt), 7.13(1H, d), 7.58(1H, d) | 1.4479 |
| 1-318 | 2.20(3H, s), 2.47(3H, s), 3.33-3.58(2H, m), 6.04(1H, m), 6.15(1H, dt), 7.18(1H, d), 8.08(1H, d) | 1.4530 |
| 1-319 | 2.13(3H, s), 2.52(3H, s), 3.37(2H, q), 4.33-4.43(4H, m), 5.68(1H, s), 7.10(1H, d), 7.56(1H, d) | 73-74 |

TABLE 50

| Comp. No. | ¹H-NMR (CDCl₃/TMS d(ppm) value) | m.p. (° C.) or refractive indx ($n_D^{20}$) |
|---|---|---|
| 1-320 | 2.15(3H, s), 2.45(3H, s), 3.40-3.56(2H, m), 4.32-4.43(4H, m), 5.71(1H, s), 7.15(1H, d), 8.06(1H, d) | 72-73 |
| 1-321 | 2.14(3H, s), 2.53(3H, s), 3.37(2H, q), 4.70(2H, t), 5.74(1H, s), 6.07(1H, tt), 7.12(1H, d), 7.56(1H, d) | 1.4501 |
| 1-322 | 2.16(3H, s), 2.46(3H, s), 3.37-3.59(2H, m), 4.70(2H, t), 5.77(1H, s), 6.08(1H, tt), 7.16(1H, d), 8.06(1H, d) | 1.4625 |
| 1-323 | 2.14(3H, s), 2.52(3H, s), 3.37(2H, q), 4.59(2H, t), 5.74(1H, s), 7.12(1H, d), 7.55(1H, d) | 41-43 |
| 1-324 | 2.16(3H, s), 2.46(3H, s), 3.39-3.59(2H, m), 4.59(2H, t), 5.78(1H, s), 7.16(1H, d), 8.05(1H, d) | 1.4415 |
| 1-325 | 2.19(3H, s), 2.53(3H, s), 3.38(2H, q), 6.00(1H, s), 6.20(1H, dt), 7.13(1H, d), 7.58(1H, d) | Measurement impossible |
| 1-326 | 2.21(3H, s), 2.47(3H, s), 3.39-3.60(2H, m), 6.02(1H, s), 6.18(1H, dt), 7.18(1H, d), 8.08(1H, d) | 1.4404 |
| 1-327 | 2.17(3H, s), 2.50(3H, s), 3.35(2H, q), 5.88(1H, s), 7.08(1H, d), 7.50(1H, d) | 1.5143 |
| 1-328 | 2.18(3H, s), 2.43(3H, s), 3.33-3.59(2H, m), 5.91(1H, s), 7.14(1H, d), 8.00(1H, d) | 1.5100 |
| 1-329 | 2.17(3H, s), 2.50(3H, s), 3.35(2H, q), 5.90(1H, s), 7.08(1H, d), 7.50(1H, d) | 63-65 |
| 1-330 | 2.18(3H, s), 2.43(3H, s), 3.35-3.58(2H, m), 5.93(1H, s), 7.14(1H, d), 8.00(1H, d) | 125-126 |
| 1-331 | (majar) 2.53(3H, s), 3.37(2H, q), 3.89(3H, s), 4.74(2H, t), 6.27(1H, s), 7.12(1H, d), 7.58(1H, d), 7.71(1H, d) | Measurement impossible |
| 1-332 | (majar) 2.47(3H, s), 3.41-3.61(2H, m), 3.86(3H, s), 4.74(2H, t), 6.27(1H, s), 7.16(1H, d), 7.73(1H, d), 8.08(1H, d) | 1.4727 |
| 1-333 | (majar) 1.22(3H, t), 2.53(3H, s), 3.37(2H, q), 4.12(2H, q), 4.74(2H, t), 6.26(1H, s), 7.11(1H, d), 7.58(1H, d), 7.73(1H, d) | 1.4638 |
| 1-334 | (majar) 1.20(3H, t), 2.46(3H, s), 3.39-3.59(2H, m), 4.09(2H, q), 3.86(3H, s), 4.74(2H, t), 6.26(1H, s), 7.15(1H, d), 7.74(1H, d), 8.08(1H, d) | 85-88 |
| 1-335 | (majar) 1.18(6H, t), 2.53(3H, s), 3.37(2H, q), 4.30(1H, quint), 4.74(2H, t), 6.24(1H, s), 7.11(1H, d), 7.58(1H, d), 7.72(1H, d) | 1.4617 |

TABLE 50-continued

| Comp. No. | $^1$H-NMR (CDCl$_3$/TMS d(ppm) value) | m.p. (° C.) or refractive indx ($n_D^{20}$) |
|---|---|---|
| 1-336 | (majar) 1.16(6H, t), 2.46(3H, s), 3.37-3.57(2H, m), 4.26(1H, quint), 4.73(2H, t), 6.24(1H, s), 7.15(1H, d), 7.73(1H, d), 8.08(1H, d) | 99-100 |
| 1-337 | (majar) 2.53(3H, s), 3.37(2H, q), 4.56(2H, d), 4.74(2H, t), 5.25(2H, dd), 5.85-5.98(1H, m), 6.26(1H, s), 7.11(1H, d), 7.57(1H, d), 7.77(1H, d) | 1.4692 |
| 1-338 | (majar) 2.46(3H, s), 3.39-3.59(2H, m), 4.53(2H, d), 4.74(2H, t), 5.20(2H, dd), 5.85-5.94(1H, m), 6.26(1H, s), 7.14(1H, d), 7.79(1H, d), 8.08(1H, d) | 75-78 |
| 1-339 | 2.56(3H, s), 3.40(2H, q), 4.79(2H, t), 6.51(1H, s), 7.21(1H, d), 7.65(1H, d) | 1.4569 |
| 1-340 | 2.49(3H, s), 3.42-3.58(2H, m), 4.79(2H, t), 6.55(1H, s), 7.26(1H, d), 8.16(1H, d) | 1.4613 |
| 1-341 | 2.55(3H, s), 3.38(2H, q), 4.79(2H, t), 6.56(1H, s), 7.14(1H, d), 7.63(1H, d), 9.69(1H, d) | 1.4620 |
| 1-342 | 2.51(3H, s), 3.38(2H, q), 4.76(2H, t), 5.72(2H, brd), 6.25(1H, s), 7.07(1H, d), 7.65 (1H, d) | 85-86 |
| 1-343 | 1.25(3H, t), 2.53(3H, s), 3.37(2H, q), 4.24(2H, q), 4.75(2H, t), 6.51(1H, s), 7.09(1H, d), 7.60(1H, d) | 45-47 |
| 1-344 | 2.50(3H, s), 2.81(3H, d), 3.37(2H, q), 3.57(1H, s), 4.70(2H, t), 5.10(1H, s), 7.11(1H, d), 7.58(1H, d) | 1.4630 |
| 1-345 | 2.51(3H, s), 2.84(3H, d), 3.38(2H, q), 3.65(1H, brs), 5.34(1H, s), 6.20(1H, dt), 7.12(1H, d), 7.60(1H, d) | Measurement impossible |
| 1-346 | 2.45(3H, s), 2.84(3H, d), 3.38-3.60(2H, m), 3.67(1H, brs), 5.36(1H, s), 6.18(1H, dt), 7.18(1H, d), 8.10(1H, d) | Measurement impossible |
| 1-347 | see Ex. 23 | 1.4419 |

TABLE 51

| Comp. No. | $^1$H-NMR (CDCl$_3$/TMS d(ppm) value) | m.p. (° C.) or refractive indx ($n_D^{20}$) |
|---|---|---|
| 1-348 | see Ex. 24 | |
| 1-349 | 2.50(3H, s), 3.37(2H, q), 3.69(2H, s), 3.70(1H, s), 4.69(2H, t), 5.11(1H, s), 5.17(1H, d), 5.24(1H, d), 5.82-5.90(1H, m), 7.12(1H, d), 7.59(1H, d) | 1.4649 |
| 1-350 | 2.44(3H, s), 3.33-3.59(2H, m), 3.69(2H, s), 3.70(1H, s), 4.69(2H, t), 5.16(1H, s), 5.22(1H, d), 5.28(1H, d), 5.83-5.93(1H, m), 7.16(1H, d), 8.10(1H, d) | 1.4718 |
| 1-351 | 2.27(1H, t), 2.50(3H, s), 3.38(2H, q), 3.84(2H, s), 3.85(1H, brs), 4.70(2H, t), 5.29(1H, s), 7.12(1H, d), 7.59(1H, d) | 1.4672 |
| 1-352 | 2.28(1H, s), 2.44(3H, s), 3.38-3.58(2H, m), 4.70(2H, t), 5.33(1H, s), 7.17(1H, d), 8.09(1H, d) | Measurement impossible |
| 1-353 | 2.30(1H, t), 2.52(3H, s), 3.39(2H, q), 3.87(3H, s), 5.53(1H, s), 6.20(1H, dt), 7.14(1H, d), 7.61(1H, d) | Measurement impossible |
| 1-354 | 2.30(1H, t), 2.46(3H, s), 3.38-3.60(2H, m), 3.88(3H, s), 5.57(1H, s), 6.18(1H, dt), 7.19(1H, d), 8.11(1H, d) | Measurement impossible |
| 1-355 | 2.27(1H, t), 2.50(3H, s), 3.38(2H, q), 3.83-3.85(3H, m), 4.70(2H, t), 5.29(1H, s), 7.12(1H, d), 7.59(1H, d) | Measurement impossible |
| 1-356 | 2.28(1H, t), 2.44(3H, s), 3.38-3.58(2H, m), 3.81-3.86(3H, m), 4.70(2H, t), 5.33(1H, s), 7.17(1H, d), 8.09(1H, d) | Measurement impossible |
| 1-357 | see Ex. 27 | 1.4524 |
| 1-358 | see Ex. 28 | |
| 1-359 | 2.51(3H, s), 3.38(2H, q), 3.77(1H, dd), 3.88(1H, brs), 4.41(1H, dd), 4.69(2H, t), 4.74(1H, dd), 5.16(1H, s), 7.13(1H, d), 7.59(1H, d) | 1.4649 |
| 1-360 | 2.44(3H, s), 3.38-3.59(2H, m), 3.77(1H, dd), 3.91(1H, brs), 4.58-4.88(2H, m), 4.69(2H, t), 5.19(1H, s), 7.18(1H, d), 8.10(1H, d) | Measurement impossible |
| 1-361 | 1.92(3H, s), 2.53(3H, s), 3.33(2H, q), 4.74(2H, t), 5.06(1H, d), 5.12(1H, d), 5.70-5.76(1H, m), 5.85(1H, s), 7.11(1H, d), 7.54(1H, d) | 1.4622 |
| 1-362 | 1.90(3H, s), 2.22(1H, t), 2.52(3H, s), 3.34(2H, q), 4.76(2H, t), 6.06(1H, s), 7.10(1H, d), 7.60(1H, d) | 1.4665 |
| 1-363 | 1.92(3H, s), 2.53(3H, s), 3.34(2H, q), 4.41(1H, dd), 4.72(1H, dd), 4.74(2H, t), 5.97(1H, s), 7.12(1H, d), 7.55(1H, d) | 1.4638 |
| 1-364 | 2.50(3H, s), 3.36(2H, q), 3.88(3H, s), 4.71(2H, t), 5.26(1H, s), 7.08(1H, d), 7.57(1H, d) | 1.4473 |
| 1-365 | 2.43(3H, s), 3.37-3.57(2H, m), 3.88(3H, s), 4.71(2H, t), 5.28(1H, s), 7.12(1H, d), 8.05(1H, d) | 1.4554 |
| 1-366 | 2.11(3H, s), 2.55(3H, s), 3.39(2H, q), 6.51(1H, s), 7.11(1H, brs), 7.18(1H, d), 7.60(1H, d) | Measurement impossible |
| 1-367 | 2.09(3H, s), 2.47(3H, s), 3.39-3.59(2H, m), 6.48(1H, s), 7.22(1H, d), 7.55(1H, brs), 8.05(1H, d) | 143-146 |
| 1-368 | 2.09(3H, s), 2.54(3H, s), 3.40(2H, q), 6.18(1H, dt), 6.49(1H, s), 7.17(1H, d), 7.19(1H, brs), 7.61(1H, d) | 1.4607 |
| 1-369 | 2.07(3H, s), 2.45(3H, s), 3.39-3.61(2H, m), 6.16(1H, dt), 6.44(1H, s), 7.20(1H, d), 7.74(1H, brs), 8.04(1H, d) | 57-60 |
| 1-370 | see Ex. 31 | 1.4518 |
| 1-371 | see Ex. 32 | 62-65 |
| 1-372 | 2.04-2.09(2H, m), 2.09(3H, s), 2.26-2.35(2H, m), 2.52(3H, s), 3.39(2H, q), 4.23(2H, t), 6.15(1H, s), 7.06(1H, brs), 7.15(1H, d), 7.60(1H, d) | Measurement impossible |

TABLE 51-continued

| Comp. No. | $^1$H-NMR (CDCl$_3$/TMS d(ppm) value) | m.p. (° C.) or refractive indx ($n_D^{20}$) |
|---|---|---|
| 1-373 | 2.00-2.10(2H, m), 2.08(3H, s), 2.23-2.35(2H, m), 2.45(3H, s), 3.40-3.60(2H, m), 4.23(2H, t), 6.12(1H, s), 7.18(1H, d), 7.30(1H, brs), 8.08(1H, d) | 79-81 |
| 1-374 | see Ex. 33 | 75-76 |
| 1-375 | see Ex. 34 | |
| 1-376 | 2.08(3H, s), 2.53(3H, s), 3.40(2H, q), 4.71(2H, t), 6.08(1H, tt), 6.22(1H, s), 7.07(1H, brs), 7.16(1H, d), 7.60(1H, d) | 1.4703 |
| 1-377 | 2.07(3H, s), 2.46(3H, s), 3.41-3.60(2H, m), 4.71(2H, t), 6.09(1H, tt), 6.17(1H, s), 7.20(1H, d), 7.44(1H, brs), 8.06(1H, d) | Measurement impossible |

TABLE 52

| Comp. No. | $^1$H-NMR (CDCl$_3$/TMS d (ppm) value) | m.p. (° C.) or refractive indx ($n_D^{20}$) |
|---|---|---|
| 1-378 | 2.45 (3H, s), 2.50 (3H, s), 3.34 (2H, q), 3.77 (2H, brs), 5.51 (1H, s), 7.09 (1H, d), 7.34 (1H, d), 7.47 (1H, d), 7.86 (1H, d) | 126-128 |
| 1-380 | 2.06 (3H, s), 2.45 (3H, s), 2.51 (3H, s), 3.37 (2H, q), 6.42 (1H, s), 7.13 (1H, d), 7.35 (1H, d), 7.48 (1H, d), 7.85 (1H, d) | Measurement impossible |
| 1-381 | 2.04 (3H, s), 2.45 (3H, s), 2.45 (3H, s), 3.38-3.55 (2H, m), 6.35 (1H, s), 7.17 (1H, d), 7.37 (1H, d), 7.84 (1H, d), 7.93 (1H, d) | 1.5552 |
| 1-382 | 2.50 (3H, s), 3.40 (2H, q), 6.28 (1H, dt), 7.13 (1H, d), 7.93 (1H, s), 7.94 (1H, d) | 93-96 |
| 1-383 | 2.45 (3H, s), 3.39-3.62 (2H, m), 6.25 (1H, dt), 7.19 (1H, d), 7.97 (1H, d), 8.41 (1H, d) | Measurement impossible |
| 1-384 | 2.56 (3H, s), 3.38 (2H, q), 6.23 (1H, dt), 7.17 (1H, d), 7.59 (1H, d) | Measurement impossible |
| 1-385 | 2.49 (3H, s), 3.41-3.58 (2H, m), 6.21 (1H, dt), 7.23 (1H, d), 8.10 (1H, d) | Measurement impossible |
| 1-386 | 2.13 (3H, s), 2.52 (3H, s), 3.37 (2H, q), 4.18 (2H, t), 4.35 (1H, tt), 4.40 (2H, t), 5.68 (1H, s), 7.10 (1H, d), 7.56 (1H, d) | Measurement impossible |
| 1-387 | 2.15 (3H, s), 2.45 (3H, s), 3.38-3.58 (2H, m), 4.35-4.51 (4H, m), 5.22 (1H, tt), 5.67 (1H, s), 7.16 (1H, d,), 8.06 (1H, d) | 94-96 |
| 1-388 | 2.13 (3H, s), 2.08-2.18 (2H, m), 2.51 (3H, s), 3.37 (2H, q), 4.21 (2H, t), 4.26 (2H, t), 5.65 (1H, s), 7.09 (1H, d), 7.57 (1H, d) | 1.4408 |
| 1-389 | 2.10-2.19 (2H, m), 2.15 (3H, s), 2.45 (3H, s), 3.38-3.60 (2H, m), 4.21 (2H, t), 4.27 (2H, t), 5.68 (1H, s), 7.14 (1H, d), 8.06 (1H, d) | 63-64 |
| 1-390 | 2.13 (3H, s), 2.03-2.20 (2H, m), 2.51 (3H, s), 3.37 (2H, q), 4.03 (2H, t), 4.18 (2H, tt), 4.26 (2H, t), 5.65 (1H, s), 7.09 (1H, d), 7.57 (1H, d) | 1.4551 |
| 1-391 | 2.09-2.19 (2H, m), 2.14 (3H, s), 2.45 (3H, s), 3.37-3.65 (2H, m), 4.01-4.12 (2H, m), 4.03-4.32 (1H, m), 4.22-4.29 (2H, m), 5.68 (1H, s), 7.14 (1H, d), 8.06 (1H, d) | 81-83 |
| 1-392 | 2.50 (3H, s), 3.41 (2H, q), 6.22 (1H, t), 7.11 (1H, d), 7.87 (1H, t), 7.98 (1H, d) | Measurement impossible |
| 1-393 | 2.44 (3H, s), 3.37-3.65 (2H, m), 6.26 (1H, t), 7.17 (1H, d), 7.90 (1H, t), 8.43 (1H, d) | 88-89 |
| 1-394 | 2.50 (3H, s), 3.42 (2H, q), 6.27 (1H, s), 7.12 (1H, d), 7.90 (1H, d), 8.00 (1H, d) | Measurement impossible |
| 1-395 | 2.44 (3H, s), 3.37-3.66 (2H, m), 6.30 (1H, s), 7.18 (1H, d), 7.93 (1H, d), 8.45 (1H, d) | 1.4649 |
| 1-397 | 2.44 (3H, s), 3.37-3.65 (2H, m), 6.31 (1H, s), 7.17 (1H, d), 7.93 (1H, t), 8.45 (1H, d) | 77-78 |
| 1-400 | 2.50 (3H, s), 3.42 (2H, q), 6.28 (1H, s), 7.12 (1H, d), 7.90 (1H, t), 8.00 (1H, d) | Measurement impossible |
| 1-401 | 2.45 (3H, s), 3.37-3.66 (2H, m), 6.31 (1H, s), 7.18 (1H, d), 7.93 (1H, t), 8.46 (1H, d) | 66-68 |
| 1-410 | 2.50 (3H, s), 3.41 (2H, q), 6.08 (1H, dt), 6.27 (1H, s), 7.12 (1H, d), 7.89 (1H, d), 7.98 (1H, d) | Measurement impossible |
| 1-411 | 2.44 (3H, s), 3.37-3.64 (2H, m), 6.06 (1H, dt), 6.30 (1H, s), 7.17 (1H, d), 7.92 (1H, d), 8.44 (1H, d) | 1.4669 |
| 1-413 | 2.48 (3H, s), 3.50 (2H, m), 6.18 (1H, dd), 6.29 (1H, s), 7.17 (1H, d), 7.92 (1H, d), 8.43 (1H, d) | 73-74 |
| 1-414 | 2.50 (3H, s), 3.41 (2H, q), 6.24 (1H, dt), 6.25 (1H, s), 7.12 (1H, d), 7.80 (1H, t), 7.98 (1H, d) | Measurement impossible |
| 1-415 | 2.44 (3H, s), 3.37-3.64 (2H, m), 6.22 (1H, dt), 6.29 (1H, s), 7.17 (1H, d), 7.92 (1H, t), 8.43 (1H, d) | 1.4400 |
| 1-443 | 2.46 (3H, s), 3.39-3.59 (2H, m), 3.84 (2H, brs), 5.51 (1H, s), 7.19 (1H, d), 8.15 (1H, d) | 85-86 |
| 1-447 | 2.46 (3H, s), 3.38-3.60 (2H, m), 3.83 (2H, brs), 5.52 (1H, s), 7.19 (1H, d), 8.15 (1H, d) | 159-161 |
| 1-458 | 2.52 (3H, s), 3.38 (2H, q), 3.81 (2H, s), 5.47 (1H, s), 6.18 (1H, dt), 7.14 (1H, d), 7.64 (1H, d) | Measurement impossible |

TABLE 53

| Comp. No. | $^1$H-NMR (CDCl$_3$/TMS d (ppm) value) | m.p. (° C.) or refractive indx ($n_D^{20}$) |
|---|---|---|
| 1-459 | 2.46 (3H, s), 3.36-3.62 (2H, m), 3.83 (2H, s), 5.49 (1H, s), 6.16 (1H, dt), 7.18 (1H, d), 8.14 (1H, d) | 118-120 |

TABLE 53-continued

| Comp. No. | $^1$H-NMR (CDCl$_3$/TMS d (ppm) value) | m.p. (° C.) or refractive indx (n$_D^{20}$) |
|---|---|---|
| 1-460 | 2.52 (3H, s), 3.38 (2H, q), 3.81 (2H, s), 5.46 (1H, s), 6.21 (1H, dt), 7.14 (1H, d), 7.63 (1H, d) | Measurement impossible |
| 1-461 | 2.45 (3H, s), 3.38-3.59 (2H, m), 3.84 (2H, s), 5.48 (1H, s), 6.19 (1H, dt), 7.18 (1H, d), 8.13 (1H, d) | 127-129 |
| 1-485 | 2.10 (3H, s), 2.48 (3H, s), 3.39-3.63 (2H, m), 6.47 (1H, s), 7.23 (1H, d), 8.09 (1H, d) | 132-134 |
| 1-486 | 2.11 (3H, s), 2.55 (3H, s), 3.41 (2H, q), 6.53 (1H, s), 7.09 (1H, brs), 7.19 (1H, d), 7.63 (1H, d) | Measurement impossible |
| 1-487 | 2.10 (3H, s), 2.48 (3H, s), 3.41-3.62 (2H, m), 6.51 (1H, s), 7.23 (1H, d), 8.12 (1H, d) | 75-76 |
| 1-488 | see Ex. 68 | |
| 1-489 | see Ex. 69 | 129-130 |
| 1-490 | 2.09 (3H, s), 2.54 (3H, s), 3.40 (2H, q), 6.51 (1H, s), 7.14 (1H, brs), 7.17 (1H, d), 7.62 (1H, d) | Measurement impossible |
| 1-491 | 2.07 (3H, s), 2.44 (3H, s), 3.38-3.60 (2H, m), 6.46 (1H, s), 7.20 (1H, d), 7.82 (1H, brs), 8.01 (1H, d) | 154-157 |
| 1-495 | 2.10 (3H, s), 2.48 (3H, s), 3.36-3.61 (2H, m), 6.51 (1H, s), 7.23 (1H, d), 8.12 (1H, d) | 141-143 |
| 1-524 | see Ex. 70 | 33-34 |
| 1-525 | see Ex. 71 | |
| 1-526 | 2.51 (3H, s), 2.85 (3H, d), 3.39 (2H, q), 3.64 (1H, brs), 5.36 (1H, s), 7.12 (1H, d), 7.62 (1H, d) | Measurement impossible |
| 1-527 | 2.45 (3H, s), 2.84 (3H, s), 3.36-3.62 (2H, m), 5.37 (1H, s), 7.17 (1H, d), 8.10 (1H, d) | 1.4398 |
| 1-546 | 2.50 (3H, s), 2.81 (3H, d), 3.37 (2H, q), 3.55 (1H, brs), 4.59 (2H, t), 5.11 (1H, s), 7.11 (1H, d), 7.58 (1H, d) | Measurement impossible |
| 1-550 | 2.50 (3H, s), 2.81 (3H, d), 3.34 (2H, q), 3.58 (1H, brs), 4.70 (2H, t), 5.10 (1H, s), 6.08 (1H, tt), 7.11 (1H, d), 7.59 (1H, d) | 1.4760 |
| 1-578 | 2.30 (1H, t), 2.52 (3H, s), 3.39 (2H, q), 3.88 (1H, brs), 5.54 (1H, s), 6.07 (1H, dt), 7.14 (1H, d), 7.62 (1H, d) | Measurement impossible |
| 1-579 | 2.30 (1H, t), 2.46 (3H, s), 3.37-3.63 (2H, m), 3.92 (1H, brs), 5.57 (1H, s), 6.05 (1H, dt), 7.19 (1H, d), 8.11 (1H, d) | Measurement impossible |
| 1-590 | 2.27 (1H, t), 2.50 (3H, s), 3.37 (2H, q), 3.84 (2H, d), 3.85 (1H, brs), 4.59 (2H, t), 5.30 (1H, s), 7.12 (1H, d), 7.59 (1H, d) | Measurement impossible |
| 1-591 | 2.28 (1H, s), 2.44 (3H, s), 3.39-3.58 (2H, m), 3.84 (1H, brs), 3.84 (2H, brs), 4.59 (2H, t), 5.33 (1H, s), 7.16 (1H, d), 8.08 (1H, d) | Measurement impossible |
| 1-668 | see Ex. 53 | |
| 1-669 | see Ex. 54 | |
| 1-670 | 2.57 (3H, s), 3.40 (2H, q), 6.17 (1H, dt), 6.79 (1H, s), 7.23 (1H, d), 7.68 (1H, d) | 1.4470 |
| 1-671 | 2.50 (3H, s), 3.42-3.57 (2H, m), 6.16 (1H, dt), 6.83 (1H, s), 7.28 (1H, d), 8.20 (1H, d) | Measurement impossible |
| 1-696 | 2.18 (3H, s), 2.53 (3H, s), 3.37 (2H, q), 5.98 (1H, s), 7.13 (1H, d), 7.56 (1H, d) | Measurement impossible |
| 1-697 | 2.19 (3H, s), 2.47 (3H, s), 3.37-3.62 (2H, m), 6.00 (1H, s), 7.18 (1H, d), 8.06 (1H, d) | 1.4473 |
| 1-702 | 2.20 (3H, s), 2.53 (3H, s), 3.38 (2H, q), 6.03 (1H, s), 7.13 (1H, d), 7.59 (1H, d) | 1.4194 |
| 1-703 | 2.21 (3H, s), 2.47 (3H, s), 3.37-3.63 (2H, m), 6.06 (1H, s), 7.18 (1H, d), 8.09 (1H, d) | 97-98 |

TABLE 54

| Comp. No. | $^1$H-NMR (CDCl$_3$/TMS d (ppm) value) | m.p. (° C.) or refractive indx (n$_D^{20}$) |
|---|---|---|
| 1-707 | 2.21 (3H, s), 2.47 (3H, s), 3.36-3.61 (2H, m), 6.06 (1H, s), 7.18 (1H, d), 8.10 (1H, d) | 91-92 |
| 1-794 | see Ex. 59 | |
| 1-795 | see Ex. 60 | 1.4582 |
| 1-872 | 2.55 (3H, s), 3.38 (2H, q), 6.26 (1H, s), 7.16 (1H, d), 7.61 (1H, d) | Measurement impossible |
| 1-873 | 2.48 (3H, s), 3.38-3.61 (2H, m), 6.29 (1H, s), 7.21 (1H, d), 8.12 (1H, d) | Measurement impossible |
| 1-875 | 2.48 (3H, s), 3.38-3.60 (2H, m), 6.29 (1H, s), 7.21 (1H, d), 8.11 (1H, d) | 84-85 |
| 1-879 | 2.48 (3H, s), 3.41-3.57 (2H, m), 6.29 (1H, s), 7.21 (1H, d), 8.12 (1H, d) | 88-91 |
| 1-888 | 2.55 (3H, s), 3.38 (2H, q), 6.03 (1H, dt), 6.24 (1H, s), 7.16 (1H, d), 7.60 (1H, d) | Measurement impossible |
| 1-889 | 2.48 (3H, s), 3.40-3.58 (2H, m), 6.02 (1H, dt), 6.27 (1H, s), 7.21 (1H, d), 8.10 (1H, d) | Measurement impossible |
| 1-890 | 2.55 (3H, s), 3.37 (2H, q), 6.16 (1H, dt), 6.23 (1H, s), 7.16 (1H, d), 7.60 (1H, d) | Measurement impossible |
| 1-891 | 2.48 (3H, s), 3.38-3.60 (2H, m), 6.15 (1H, dt), 6.26 (1H, s), 7.21 (1H, d), 8.11 (1H, d) | Measurement impossible |
| 1-892 | 2.55 (3H, s), 3.37 (2H, q), 6.19 (1H, dt), 6.22 (1H, s), 7.16 (1H, d), 7.60 (1H, d) | Measurement impossible |
| 1-893 | 2.47 (3H, s), 3.38-3.60 (2H, m), 6.18 (1H, dt), 6.25 (1H, s), 7.21 (1H, d), 8.10 (1H, d) | Measurement impossible |
| 1-1062 | 2.55 (3H, s), 3.37 (2H, q), 6.31 (1H, dt), 7.17 (1H, d), 7.58 (1H, d) | 1.4434 |
| 1-1063 | 2.49 (3H, s), 3.43-3.56 (2H, m), 6.24 (1H, dt), 7.23 (1H, d), 8.10 (1H, d) | 1.4476 |
| 1-1104 | 2.55 (3H, s), 3.37 (2H, q), 6.11 (1H, dt), 7.17 (1H, d), 7.57 (1H, d) | Measurement impossible |

TABLE 54-continued

| Comp. No. | ¹H-NMR (CDCl₃/TMS d (ppm) value) | m.p. (° C.) or refractive indx ($n_D^{20}$) |
|---|---|---|
| 1-1105 | 2.48 (3H, s), 3.39-3.60 (2H, m), 6.09 (1H, dt), 7.22 (1H, d), 8.09 (1H, d) | 88-89 |
| 1-1106 | 2.56 (3H, s), 3.49 (2H, q), 6.24 (1H, dt), 7.17 (1H, d), 7.57 (1H, d) | 1.4677 |
| 1-1107 | 2.49 (3H, s), 3.41-3.58 (2H, m), 6.22 (1H, dt), 7.22 (1H, d), 8.09 (1H, d) | 62-64 |
| 1-1108 | 2.56 (3H, s), 3.37 (2H, q), 6.27 (1H, dt), 7.17 (1H, d), 7.57 (1H, d) | 1.4583 |
| 1-1109 | 2.49 (3H, s), 3.43-3.54 (2H, m), 6.24 (1H, dt), 7.22 (1H, d), 8.09 (1H, d) | 77-78 |
| 1-1134 | 2.51 (3H, s), 3.41 (2H, q), 7.13 (1H, d), 7.95 (1H, s), 7.95 (1H, d) | Measurement impossible |
| 1-1135 | 2.45 (3H, s), 3.39-3.62 (2H, m), 7.19 (1H, d), 7.98 (1H, s), 8.43 (1H, d) | 1.4685 |
| 1-1137 | 2.45 (3H, s), 3.39-3.62 (2H, m), 7.19 (1H, d), 7.98 (1H, s), 8.43 (1H, d) | 76-78 |
| 1-1150 | 2.50 (3H, s), 3.40 (2H, q), 6.30 (1H, dt), 7.13 (1H, d), 7.92-7.94 (2H, m) | 1.4437 |
| 1-1151 | 2.44 (3H, s), 3.39-3.61 (2H, m), 6.27 (1H, dt), 7.19 (1H, d), 7.96 (1H, s), 8.40 (1H, d) | 1.4459 |
| 1-1176 | 2.51 (3H, s), 3.41 (2H, q), 7.13 (1H, d), 7.95 (1H, s), 7.96 (1H, d) | Measurement impossible |
| 1-1177 | 2.45 (3H, s), 3.37-3.64 (2H, m), 7.19 (1H, d), 7.99 (1H, d), 8.43 (1H, d) | 1.4800 |

TABLE 55

| Comp. No. | ¹H-NMR (CDCl₃/TMS d (ppm) value) | m.p. (° C.) or refractive indx ($n_D^{20}$) |
|---|---|---|
| 1-1179 | 2.45 (3H, s), 3.40-3.61 (2H, m), 7.19 (1H, d), 7.99 (1H, d), 8.42 (1H, d) | 1.4694 |
| 1-1192 | 2.49 (3H, s), 3.40 (2H, q), 6.16 (1H, dt), 7.12 (1H, d), 7.92 (1H, d), 7.93 (1H, d) | Measurement impossible |
| 1-1193 | 2.44 (3H, s), 3.36-3.64 (2H, m), 6.13 (1H, dt), 7.18 (1H, d), 7.97 (1H, d), 8.41 (1H, d) | Measurement impossible |
| 1-1194 | 2.50 (3H, s), 3.40 (2H, q), 6.29 (1H, dt), 7.13 (1H, d), 7.93 (1H, d), 7.97 (1H, s) | 1.4596 |
| 1-1195 | 2.44 (3H, s), 3.37-3.64 (2H, m), 6.25 (1H, dt), 7.19 (1H, d), 7.97 (1H, d), 8.41 (1H, d) | Measurement impossible |
| 1-1196 | 2.50 (3H, s), 3.40 (2H, q), 6.32 (1H, dt), 7.13 (1H, d), 7.92-7.94 (2H, m) | 1.4500 |
| 1-1197 | 2.44 (3H, s), 3.38-3.61 (2H, m), 6.28 (1H, dt), 7.19 (1H, d), 7.97 (1H, d), 8.40 (1H, d) | 1.4500 |
| 1-1250 | 2.13 (3H, s), 2.52 (3H, s), 3.37 (2H, q), 4.18 (2H, t), 4.33 (1H, qq), 4.41 (2H, t), 5.68 (1H, s), 7.10 (1H, d), 7.56 (1H, d) | 94-96 |
| 1-1251 | 2.15 (3H, s), 2.45 (3H, s), 3.38-3.58 (2H, m), 4.37 (2H, t), 4.47 (2H, t), 5.22 (1H, qq), 5.67 (1H, s), 7.16 (1H, d), 8.05 (1H, d) | 1.4408 |
| 1-1252 | 2.08-2.18 (5H, m), 2.51 (3H, s), 3.37 (2H, q), 4.21 (2H, t), 4.26 (2H, t), 5.65 (1H, s), 7.09 (1H, d), 7.57 (1H, d) | 63-64 |
| 1-1253 | 2.10-2.18 (5H, m), 2.45 (3H, s), 3.37-3.59 (2H, m), 4.21 (2H, t), 4.27 (2H, t), 5.68 (1H, s), 7.14 (1H, d), 8.06 (1H, d) | 1.4551 |
| 1-1254 | 2.08-2.20 (5H, m), 2.51 (3H, s), 3.37 (2H, q), 4.01-4.31 (1H, m), 4.03 (2H, t) 4.26 (2H, t), 5.65 (1H, s), 7.09 (1H, d), 7.57 (1H, d) | 81-83 |
| 1-1255 | 2.08-2.19 (5H, m), 2.45 (3H, s), 3.37-3.57 (2H, m), 4.00-4.31 (1H, m), 4.03 (2H, t), 4.25 (2H, t), 5.68 (1H, s), 7.14 (1H, d), 8.06 (1H, d) | 1.4660 |
| 1-1256 | 2.50 (3H, s), 2.81 (3H, d), 3.38 (2H, q), 3.57 (1H, brs), 4.70 (2H, t), 5.11 (1H, s), 7.11 (1H, d), 7.59 (1H, d) | 1.4559 |
| 1-1257 | 2.52 (3H, s), 3.38 (2H, q), 3.96 (2H, s), 6.32 (1H, dt), 7.15 (1H, d), 7.61 (1H, d) | Measurement impossible |
| 1-1258 | 2.08 (3H, s), 2.53 (3H, s), 3.39 (2H, q), 4.00 (2H, q), 4.13 (2H, t), 4.65 (2H, t), 6.21 (1H, s), 7.03 (1H, brs), 7.15 (1H, d), 7.60 (1H, d) | 1.4852 |
| 1-1259 | 2.06 (3H, s), 2.44 (3H, s), 3.37-3.60 (2H, m), 4.01 (2H, q), 4.13 (2H, t), 4.64 (2H, t), 6.16 (1H, s), 7.18 (1H, d), 7.43 (1H, brs), 8.04 (1H, d) | Measurement impossible |
| 1-1282 | 2.53 (3H, s), 3.39 (2H, q), 3.97 (2H, brs), 6.31 (1H, dt), 7.15 (1H, d), 7.61 (1H, d) | Measurement impossible |
| 1-1283 | 2.47 (3H, s), 3.37-3.62 (2H, m), 4.00 (2H, brs), 6.26 (1H, dt), 7.21 (1H, d), 8.12 (1H, d) | Measurement impossible |
| 1-1355 | 2.49 (3H, s), 3.40 (2H, q), 6.11 (1H, d), 6.97 (1H, t), 7.10 (1H, d), 7.88 (1H, t), 7.92 (1H, d) | 1.5188 |
| 1-1356 | 2.43 (3H, s), 3.36-3.63 (2H, m), 6.14 (1H, d), 7.10 (1H, t), 7.16 (1H, d), 7.90 (1H, t), 8.42 (1H, d) | 71-73 |
| 1-1357 | 2.47 (3H, s), 3.41 (2H, q), 3.99 (3H, s), 5.91 (1H, d), 7.06 (1H, d), 7.80 (1H, t), 8.05 (1H, d) | 1.5407 |
| 1-1358 | 2.41 (3H, s), 3.37-3.62 (2H, m), 4.00 (3H, s), 5.94 (1H, d), 7.11 (1H, d), 7.85 (1H, t), 8.50 (1H, d) | 104-105 |
| 1-1359 | 2.07 (3H, s), 2.53 (3H, s), 3.39 (2H, q), 6.30 (1H, s), 6.88 (1H, t), 7.16 (1H, d), 7.29 (1H, s), 7.59 (1H, d) | |
| 1-1360 | 2.06 (3H, s), 2.44 (3H, s), 3.38-3.56 (2H, m), 6.25 (1H, s), 6.87 (1H, t), 7.19 (1H, d), 7.89 (1H, brs), 7.98 (1H, d) | 60-62 |
| 1-1361 | 1.77 (3H, d), 2.09 (3H, s), 2.53 (3H, s), 3.41 (2H, q), 5.35 (1H, q), 6.21 (1H, s), 7.10 (1H, brs), 7.16 (1H, d), 7.61 (1H, d) | Measurement impossible |
| 1-1362 | 1.77 (3H, dd), 2.08 (3H, s), 2.46 (3H, s), 3.43-3.59 (2H, m), 5.32-5.40 (1H, m), 6.16 (1H, s), 7.20 (1H, d), 7.34 (1H, brs), 8.07 (1H, d) | 151-153 |
| 1-1363 | 2.48 (3H, s), 3.39 (2H, q), 4.68 (2H, q), 5.98 (1H, d), 7.08 (1H, d), 7.82 (1H, t), 7.98 (1H, d) | 1.5000 |

TABLE 56

| Comp. No. | $^1$H-NMR (CDCl$_3$/TMS d (ppm) value) | m.p. (° C.) or refractive indx ($n_D^{20}$) |
|---|---|---|
| 1-1364 | 2.41 (3H, s), 3.35-3.63 (2H, m), 4.70 (2H, q), 6.01 (1H, t), 7.13 (1H, d), 7.89 (1H, t), 8.45 (1H, d) | 85-86 |
| 1-1365 | 2.51 (3H, s), 3.38 (2H, q), 3.75 (2H, s), 4.57 (2H, q), 5.22 (1H, s), 7.12 (1H, d), 7.62 (1H, d) | 70-73 |
| 1-1366 | 2.44 (3H, s), 3.37-3.59 (2H, m), 3.79 (2H, s), 4.57 (2H, q), 5.25 (1H, s), 7.17 (1H, d), 8.11 (1H, d) | 45-47 |
| 1-1367 | see Ex. 37 | |
| 1-1368 | see Ex. 38 | 133-134 |
| 1-1369 | 2.08 (3H, s), 2.53 (3H, s), 3.40 (2H, q), 4.59 (2H, q), 6.22 (1H, s), 7.03 (1H, brs), 7.16 (1H, d), 7.60 (1H, d) | Measurement impossible |
| 1-1370 | 2.07 (3H, s), 2.45 (3H, s), 3.43-3.54 (2H, m), 4.59 (2H, q), 6.12 (1H, s), 7.19 (1H, d), 7.35 (1H, brs), 8.06 (1H, d) | Measurement impossible |
| 1-1371 | 2.07 (3H, s), 2.53 (3H, s), 3.40 (2H, q), 4.68 (2H, t), 6.21 (1H, s), 7.14 (1H, brs), 7.15 (1H, d), 7.59 (1H, d) | 1.5197 |
| 1-1372 | 2.06 (3H, s), 2.44 (3H, s), 3.40-3.57 (2H, m), 4.67 (2H, t), 6.15 (1H, s), 7.18 (1H, d), 7.71 (1H, brs), 8.02 (1H, d) | 1.5129 |
| 1-1373 | 2.52 (3H, s), 3.39 (2H, q), 4.49 (2H, d), 4.67 (2H, t), 6.00 (1H, s), 7.12 (1H, d), 7.63 (1H, d) | 71-72 |
| 1-1374 | 2.46 (3H, s), 3.40-3.59 (2H, m), 4.51 (2H, s), 4.67 (2H, t), 6.01 (1H, s), 7.17 (1H, d), 8.12 (1H, d) | Measurement impossible |
| 1-1375 | 2.09 (3H, s), 2.53 (3H, s), 3.41 (2H, q), 4.92 (2H, s), 6.22 (1H, s), 7.15 (1H, brs), 7.16 (1H, d), 7.61 (1H, d) | 1.5449 |
| 1-1376 | 2.07 (3H, s), 2.46 (3H, s), 3.40-3.60 (2H, m), 4.93 (2H, s), 6.18 (1H, s), 7.20 (1H, d), 7.46 (1H, brs), 8.06 (1H, d) | 1.5302 |
| 1-1377 | 2.08 (3H, s), 2.52 (3H, s), 3.40 (2H, q), 4.45 (2H, d), 4.74 (2H, d), 6.17 (1H, s), 7.11 (1H, brs), 7.15 (1H, d), 7.61 (1H, d) | 51-53 |
| 1-1378 | 2.08 (3H, s), 2.45 (3H, s), 3.39-3.53 (2H, m), 4.45 (2H, d), 4.73 (2H, d), 6.13 (1H, s), 7.18 (1H, d), 7.24 (1H, brs), 8.09 (1H, d) | 178-179 |
| 1-1379 | 2.42 (3H, s), 3.39 (2H, q), 4.72 (2H, q), 7.10 (1H, d), 7.86 (1H, d), 7.94 (1H, d) | 61-63 |
| 1-1380 | 2.42 (3H, s), 3.35-3.61 (2H, m), 4.65-4.83 (2H, m), 7.15 (1H, d), 7.94 (1H, d), 8.42 (1H, d) | 109-111 |
| 1-1381 | 2.51 (3H, s), 3.38 (2H, q), 3.62 (2H, s), 4.62 (2H, q), 7.12 (1H, d), 7.58 (1H, d) | |
| 1-1382 | 2.45 (3H, s), 3.3903.58 (2H, m), 4.63 (2H, q), 7.17 (1H, d), 9.08 (1H, d) | Measurement impossible |
| 1-1383 | 2.52 (3H, s), 3.38 (2H, q), 3.88 (2H, s), 4.62 (2H, q), 7.13 (1H, d), 7.60 (1H, d) | 78-81 |
| 1-1384 | 2.45 (3H, s), 3.41-3.56 (2H, m), 3.91 (2H, s), 4.63 (2H, q), 7.18 (1H, d), 8.10 (1H, d) | Measurement impossible |
| 1-1385 | 2.48 (3H, s), 3.40 (2H, q), 4.76 (2H, t), 5.98 (1H, d), 7.09 (1H, d), 7.82 (1H, t), 7.98 (1H, d) | 1.4751 |
| 1-1386 | 2.41 (3H, s), 3.36-3.63 (2H, m), 4.79 (2H, t), 6.01 (1H, d), 7.14 (1H, d), 7.89 (1H, t), 8.44 (1H, d) | 100-101 |
| 1-1387 | 2.10 (3H, s), 2.54 (3H, s), 3.62 (2H, t), 5.99 (1H, t), 6.50 (1H, s), 7.10 (1H, brs), 7.17 (1H, d), 7.62 (1H, d) | Measurement impossible |
| 1-1388 | 2.09 (3H, s), 2.46 (3H, s), 3.54-3.77 (2H, m), 5.98 (1H, tt), 6.46 (1H, s), 7.22 (1H, d), 7.55 (1H, brs), 8.04 (1H, d) | 95-97 |
| 1-1390 | 2.07 (3H, s), 2.45 (3H, s), 3.57-3.75 (2H, m), 4.67 (2H, t), 6.18 (1H, s), 7.19 (1H, d), 7.42 (1H, brs), 8.03 (1H, d) | 146-148 |
| 1-1392 | 1.91 (3H, s), 2.53 (3H, s), 3.03 (3H, s), 3.35 (2H, q), 6.01 (1H, tt), 6.15 (1H, s), 7.13 (1H, d), 7.58 (1H, d) | 1.4978 |

TABLE 57

| Comp. No. | $^1$H-NMR (CDCl$_3$/TMS d (ppm) value) | m.p. (° C.) or refractive indx ($n_D^{20}$) |
|---|---|---|
| 1-1394 | 1.91 (3H, s), 2.45 (3H, s), 3.04 (3H, s), 3.57 (2H, t), 6.01 (1H, tt), 6.14 (1H, s), 7.13 (1H, d), 7.59 (1H, d) | 64-66 |
| 1-1400 | 1.91 (3H, s), 2.24 (1H, s), 2.53 (3H, s), 3.36 (2H, q), 6.01 (1H, tt), 6.33 (1H, s), 7.12 (1H, d), 7.62 (1H, d) | 1.4958 |
| 1-1402 | 2.51 (3H, s), 2.84 (3H, d), 3.38 (2H, q), 3.64 (1H, brs), 5.35 (1H, s), 5.85-6.13 (1H, m), 7.12 (1H, d), 7.61 (1H, d) | 1.5000 |
| 1-1403 | 2.44 (3H, s), 2.84 (3H, d), 3.37-3.58 (2H, m), 3.62 (1H, brs), 5.37 (1H, s), 5.85-6.13 (1H, m), 7.17 (1H, d), 8.10 (1H, d) | 1.4940 |
| 1.1404 | 2.51 (3H, s), 2.84 (3H, d), 3.60 (2H, t), 3.63 (1H, brs), 5.35 (1H, s), 6.00 (1H, tt), 7.12 (1H, d), 7.61 (1H, d) | 1.5103 |
| 1-1405 | 2.45 (3H, s), 2.84 (3H, s), 3.55-3.75 (2H, m), 3.71 (1H, brs), 5.36 (1H, s), 5.99 (1H, tt), 7.17 (1H, d), 8.09 (1H, d) | 39-42 |
| 1-1406 | 2.50 (3H, s), 3.41 (2H, q), 6.10 (2H, tt), 7.13 (1H, d), 7.93 (1H, d), 7.95 (1H, d) | 1.5053 |
| 1-1407 | 2.44 (3H, s) 3.39-3.62 (2H, m), 6.10 (2H, tt), 7.19 (1H, d), 7.97 (1H, t), 8.41 (1H, d) | 1.5105 |
| 1-1408 | 2.56 (3H, s), 3.38 (2H, q), 6.06 (1H, tt), 7.17 (1H, d), 7.58 (1H, d) | 60-62 |
| 1-1409 | 2.49 (3H, s), 3.41-3.59 (2H, q), 6.06 (1H, tt), 7.22 (1H, d), 8.09 (1H, d) | 109-111 |
| 1-1411 | 2.16 (3H, s), 2.53 (3H, s) 3.37 (2H, q), 5.87 (1H, s), 6.88 (1H, t), 7.12 (1H, d), 7.57 (1H, d) | 81-83 |

TABLE 57-continued

| Comp. No. | $^1$H-NMR (CDCl$_3$/TMS d (ppm) value) | m.p. (° C.) or refractive indx (n$_D^{20}$) |
|---|---|---|
| 1-1412 | 2.18 (3H, s), 2.46 (3H, s), 3.43-5.37 (2H, q), 5.89 (1H, s), 6.89 (1H, t), 7.17 (1H, d), 8.07 (1H, d) | 86-87 |
| 1-1413 | 2.13 (3H, s), 2.51 (3H, s), 3.38 (2H, q), 3.91 (3H, s), 5.67 (1H, s), 7.10 (1H, d), 7.59 (1H, d) | 78-80 |
| 1-1414 | 2.14 (3H, s), 2.45 (3H, s), 3.40-3.59 (2H, q), 3.91 (3H, s), 5.69 (1H, s), 7.14 (1H, d), 8.08 (1H, d) | 109-110 |
| 1-1415 | 7.56 (1H, d), 7.12 (1H, d), 5.74 (1H, s), 4.58 (2H, q), 3.37 (2H, q), 2.53 (3H, s), 2.14 (3H, s) | 92-93 |
| 1-1416 | 8.05 (1H, d), 7.16 (1H, d), 5.77 (1H, s), 4.58 (2H, t), 3.40-3.59 (2H, m), 2.45 (3H, s), 2.16 (3H, s) | 126-127 |
| 1-1417 | 7.59 (1H, d), 7.13 (1H, d), 6.02 (1H, s), 5.99 (1H, t t), 3.38 (2H, q), 2.54 (3H, s), 2.20 (3H, s) | 58-60 |
| 1-1418 | 8.09 (1H, d), 7.18 (1H, d), 6.05 (1H, s), 5.99 (1H, t t), 3.40-3.60 (2H, m), 2.47 (3H, s), 2.21 (3H, s) | 1.4868 |
| 1-1419 | 7.56 (1H, d), 7.12 (1H, d), 5.75 (1H, s), 4.67 (2H, t), 3.37 (2H, q), 2.52 (3H, s), 2.15 (3H, s) | 72-74 |
| 1-1420 | 8.05 (1H, d), 7.16 (1H, d), 5.78 (1H, s), 4.67 (2H, t), 3.40-3.60 (2H, m), 2.46 (3H, s), 2.16 (3H, s) | 134-135 |
| 1-1421 | 2.30 (1H, t), 2.51 (3H, s), 3.38 (2H, q), 3.87 (2H, s), 3.87 (1H, s), 5.54 (1H, s), 5.86-6.14 (1H, m), 7.13 (1H, d), 7.62 (1H, d) | 1.5000 |
| 1-1422 | 3.87 (1H, s), 2.30 (1H, s), 2.45 (3H, s), 3.37-3.58 (2H, m), 3.87 (2H, s), 5.57 (1H, s), 5.85-6.03 (1H, m), 7.18 (1H, d), 8.11 (1H, d) | Measurement impossible |
| 1-1423 | 2.55 (3H, s), 3.38 (2H, q), 5.99 (1H, tt), 6.25 (1H, q), 7.16 (1H, d), 7.61 (1H, d) | 1.4858 |
| 1-1424 | 2.48 (3H, s), 3.40-3.59 (2H, q), 5.99 (1H, tt), 6.28 (1H, q), 7.21 (1H, d), 8.11 (1H, d) | 1.4957 |
| 1-1425 | 2.20 (3H, s), 2.53 (3H, s), 3.38 (2H, q, J = 9.5 Hz), 6.02 (1H, s), 6.36 (1H, dt, J = 4.7, 48.0 Hz), 7.13 (1H, d, J = 10.7 Hz), 7.59 (1H, d, J = 7.1 Hz) | 1.4967 |
| 1-1426 | 2.21 (3H, s), 2.47 (3H, s), 3.38-3.60 (2H, m), 6.05 (1H, s), 6.36 (1H, dt, J = 4.6, 48.0 Hz), 7.18 (1H, d, J = 100 Hz), 8.09 (1H, d, J = 7.3 Hz) | 1.5008 |
| 1-1427 | 2.09 (3H, s), 2.54 (3H, s), 3.40 (2H, q), 6.37 (1H, dt), 6.49 (1H, s), 7.17 (1H, d), 7.19 (1H, brs), 7.62 (1H, d) | Measurement impossible |
| 1-1428 | 2.08 (3H, s), 2.46 (3H, s), 3.39-3.58 (2H, m), 6.36 (1H, dt), 6.45 (1H, s), 7.20 (1H, d), 7.67 (1H, brs), 8.05 (1H, d) | Measurement impossible |

TABLE 58

| Comp. No. | $^1$H-NMR (CDCl$_3$/TMS d (ppm) value) | m.p. (° C.) or refractive indx (n$_D^{20}$) |
|---|---|---|
| 1-1429 | 1.15 (3H, t), 2.30 (2H, d), 2.53 (3H, s), 3.39 (2H, q), 4.59 (2H, q), 6.23 (1H, s), 7.03 (1H, brs), 7.16 (1h, d), 7.60 (1H, d) | 74-76 |
| 1-1430 | 1.13 (3H, t), 2.29 (2H, d), 2.45 (3H, s), 3.39-3.56 (2H, m), 4.59 (2H, q), 6.17 (1H, s), 7.19 (1H, d), 7.40 (1H, brs), 8.04 (1H, d) | 63-65 |
| 1-1431 | 2.54 (3H, s), 3.39 (2H, q), 3.97 (2H, s), 4.60 (2H, q), 6.29 (1H, s), 7.17 (1H, d), 7.61 (1H, d), 8.35 (1H, brs) | 87-88 |
| 1-1432 | 2.47 (3H, s), 3.38-3.60 (2H, m), 3.41 (3H, s), 3.98 (2H, d), 4.61 (2H, q), 6.30 (1H, s), 7.21 (1H, d), 8.11 (1H, d), 8.36 (1H, brs) | 132-134 |
| 1-1433 | 0.84 (2H, d), 1.04 (2H, s), 1.39 (1H, s), 2.53 (3H, s), 3.39 (2H, q), 4.59 (2H, q), 6.19 (1H, s), 7.16 (1H, s), 7.30 (1H, brs), 7.60 (1H, d) | 105-107 |
| 1-1434 | 0.83 (2H, d), 1.02 (2H, s), 1.42 (1H, s), 2.46 (3H, s), 3.39-3.53 (2H, m), 4.59 (2H, q), 6.16 (1H, s), 7.20 (1H, d), 7.47 (1H, brs), 8.08 (1H, d) | 83-85 |
| 1-1436 | 2.15 (3H, s), 2.53 (3H, s), 3.38 (2H, q), 4.91 (2H, s), 5.74 (1H, s), 7.12 (1H, d), 7.58 (1H, d) | 75-76 |
| 1-1437 | 2.16 (3H, s), 2.46 (3H, s), 3.44-3.58 (2H, m), 4.91 (2H, s), 5.76 (1H, s), 7.17 (1H, d), 8.05 (1H, d) | 141-143 |
| 1-1439 | 2.56 (3H, s), 3.39 (2H, q), 4.66 (2H, q), 6.51 (1H, s), 7.20 (1H, d), 7.65 (1H, d) | 59-60 |
| 1-1440 | 2.49 (3H, s), 3.44-3.56 (2H, m), 4.67 (2H, q), 6.55 (1H, s), 7.26 (1H, d), 8.16 (1H, d) | 106-107 |
| 1-1441 | 2.51 (3H, s), 3.38 (2H, q), 4.64 (2H, q), 5.68 (1H, brs), 5.83 (1H, brs), 6.24 (1H, s), 7.07 (1H, d), 7.64 (1H, d | 110-111 |
| 1-1442 | 2.43 (3H, s), 3.39-3.57 (2H, m), 4.64 (2H, q), 5.54 (1H, brs), 5.93 (1H, brs), 6.27 (1H, s), 7.10 (1H, d), 8.09 (1H, d) | 181-183 |
| 1-1443 | 2.50 (3H, s), 2.90 (3H, d), 3.38 (2H, q), 4.63 (2H, q), 5.95 (1H, brs), 6.15 (1H, s), 7.06 (1H, d), 7.63 (1H, d) | 102-103 |
| 1-1444 | 2.43 (3H, s), 2.92 (3H, d), 3.39-3.55 (2H, m), 4.63 (2H, q), 6.00 (1H, brs), 6.17 (1H, s), 7.10 (1H, d), 8.08 (1H, d) | 113-115 |
| 1-1445 | 1.25 (3H, t), 2.53 (3H, s), 3.37 (2H, q), 4.24 (3H, q), 4.62 (2H, q), 6.50 (1H, s), 7.09 (1H, d), 7.60 (1H, d) | 88-90 |
| 1-1446 | 1.29 (3H, t), 2.45 (3H, s), 3.40-3.57 (2H, m), 4.26 (3H, q), 4.63 (2H, q), 6.52 (1H, s), 7.13 (1H, d), 8.07 (1H, d) | 118-120 |
| 1-1447 | 2.54 (3H, s), 3.36 (2H, q), 4.62 (2H, q), 6.58 (1H, s), 7.08 (1H, d), 7.59 (1H, d) | 81-83 |
| 1-1449 | 2.53 (3H, s), 3.40 (2H, q), 4.13 (2H, s), 4.68 (2H, t), 6.27 (1H, s), 7.18 (1H, d), 7.62 (1H, d), 8.34 (1H, s) | 1.5024 |
| 1-1450 | 2.47 (3H, s), 3.41-3.57 (2H, m), 4.69 (2H, t), 6.27 (1H, s), 7.23 (1H, d), 8.12 (1H, d), 8.36 (1H, s) | 59-62 |

TABLE 58-continued

| Comp. No. | ¹H-NMR (CDCl₃/TMS d (ppm) value) | m.p. (° C.) or refractive indx ($n_D^{20}$) |
|---|---|---|
| 1-1451 | 2.50 (3H, s), 3.41 (2H, q), 6.09 (2H, tt), 7.13 (1H, d), 7.93 (1H, d), 7.95 (1H, d) | Measurement impossible |
| 1-1452 | 2.48 (3H, s), 3.39-3.63 (2H, m), 6.09 (2H, tt), 7.19 (1H, d), 7.97 (1H, d), 8.42 (1H, d) | Measurement impossible |
| 1-1453 | 2.53 (3H, s), 3.40 (2H, q), 4.13 (2H, s), 4.61 (2H, q), 6.27 (1H, s), 7.18 (1H, d), 7.62 (1H, d), 8.35 (1H, brs) | Measurement impossible |
| 1-1454 | 2.47 (3H, s), 3.40-3.57 (2H, m), 4.14 (2H, s), 4.62 (2H, q), 6.27 (1H, s), 7.22 (1H, d), 8.12 (1H, d), 8.36 (1H, brs) | Measurement impossible |
| 1-1455 | 2.52 (3H, s), 3.38 (2H, q), 4.60 (2H, q), 5.78 (1H, d), 6.06-6.13 (1H, m), 6.27 (1H, brs), 6.38 (1H, d), 7.14 (1H, d), 7.23 (1H, brs), 7.60 (1H, d) | 90-91 |
| 1-1456 | 2.44 (3H, s), 3.37-3.57 (2H, m), 4.59 (2H, q), 5.78 (1H, d), 6.10-6.17 (1H, m), 6.24 (1H, brs), 6.37 (1H, d), 7.18 (1H, d), 7.57 (1H, brs), 8.03 (1H, d) | 90-92 |
| 1-1457 | 2.52 (3H, s), 3.39 (2H, q), 5.73 (1H, brd), 6.37 (2H, dt), 6.54 (1H, s), 7.08 (1H, d), 7.67 (1H, d) | 96-99 |
| 1-1458 | 2.45 (3H, s), 3.36-3.59 (2H, m), 5.61 (1H, brs), 5.97 (1H, brs), 6.37 (2H, dt), 6.57 (1H, s), 7.12 (1H, d), 8.11 (1H, d) | 87-90 |
| 1-1459 | 2.57 (3H, s), 3.40 (2H, q), 6.37 (2H, dt), 6.80 (1H, s), 7.23 (1H, d), 7.69 (1H, d) | Measurement impossible |

TABLE 59

| Comp. No. | ¹H-NMR (CDCl₃/TMS d (ppm) value) | m.p. (° C.) or refractive indx ($n_D^{20}$) |
|---|---|---|
| 1-1460 | 2.50 (3H, s), 3.40-3.61 (2H, m), 6.37 (2H, dt), 6.83 (1H, s), 7.28 (1H, d), 8.21 (1H, d) | Measurement impossible |
| 1-1461 | 2.49 (3H, s), 3.36 (2H, q), 3.86 (2H, s), 3.90 (3H, s), 5.17 (1H, s), 7.06 (1H, d), 7.60 (1H, d) | 65-66 |
| 1-1462 | 2.42 (3H, s), 3.36-3.57 (2H, m), 3.87 (2H, s), 3.90 (3H, s), 5.18 (1H, s), 7.10 (1H, d), 8.08 (1H, d) | 110-113 |
| 1-1463 | 2.50 (3H, s), 3.36 (2H, q), 3.90 (3H, s), 5.37 (1H, s), 6.93 (1H, t), 7.08 (1H, brs), 7.58 (1H, d) | |
| 1-1464 | 2.44 (3H, s), 3.38-3.60 (2H, m), 3.91 (3H, s), 5.38 (1H, s), 6.95 (1H, t), 7.13 (1H, brs), 8.06 (1H, d) | Measurement impossible |
| 1-1465 | 2.51 (3H, s), 3.36 (2H, q), 3.92 (3H, s), 5.53 (1H, s), 6.38 (1H, dt), 7.09 (1H, d), 7.60 (1H, d | Measurement impossible |
| 1-1466 | 2.44 (3H, s), 3.38-3.57 (2H, m), 3.92 (3H, s), 5.54 (1H, s), 6.39 (1H, dt), 7.14 (1H, d), 8.07 (1H, d) | 1.5009 |
| 1-1467 | 2.50 (3H, s), 3.36 (2H, q), 3.88 (3H, s), 4.59 (2H, q), 5.26 (1H, s), 7.08 (1H, d), 7.57 (1H, d) | 91-92 |
| 1-1468 | 2.43 (3H, s), 3.37-3.56 (2H, m), 3.88 (3H, s), 4.59 (2H, q), 5.27 (1H, s), 7.12 (1H, d), 8.05 (1H, d) | 115-117 |
| 1-1469 | see Ex. 73 | |
| 1-1470 | see Ex. 74 | |
| 1-1476 | 2.34 (3H, s), 3.38 (2H, m), 6.21 (1H, s), 7.06 (1H, d), 7.86 (1H, d), 8.36 (1H, d) | Measurement impossible |
| 1-1505 | 2.49 (3H, s), 3.39 (2H, q), 4.85 (2H, t), 7.10 (1H, d), 7.87 (1H, d), 7.94 (1H, d) | Measurement impossible |
| 1-1506 | 2.42 (3H, s), 3.36-3.62 (2H, m), 4.86 (2H, t), 7.15 (1H, d), 7.94 (1H, d), 8.42 (1H, d) | 89-90 |
| 1-1507 | 2.52 (3H, s), 3.38 (2H, q), 3.91 (2H, brs), 4.75 (2H, t), 7.14 (1H, d), 7.60 (1H, d) | Measurement impossible |
| 1-1509 | 2.49 (3H, s), 3.39 (2H, q), 4.85 (2H, t), 7.10 (1H, d), 7.88 (1H, d), 7.94 (1H, d) | 1.4672 |
| 1-1510 | 2.42 (3H, s), 3.38-3.60 (2H, m), 4.85 (2H, t), 7.15 (1H, d), 7.95 (1H, d), 8.42 (1H, d) | 92-93 |
| 1-1511 | 2.55 (3H, s), 3.37 (2H, q), 4.76 (2H, t), 7.16 (1H, d), 7.55 (1H, d) | Measurement impossible |
| 1-1512 | 2.48 (3H, s), 3.44-3.55 (2H, m), 4.76 (2H, t), 7.21 (1H, d), 8.06 (1H, d) | 1.4656 |
| 1-1513 | 1.22 (3H, t), 2.52 (3H, s), 3.15 (2H, q), 3.38 (2H, q), 3.53 (1H, brs), 5.33 (1H, s), 6.20 (1H, dt), 7.13 (1H, d), 7.61 (1H, d) | Measurement impossible |
| 1-1514 | 1.22 (3H, t), 2.46 (3H, s), 3.15 (2H, q), 3.39-3.60 (2H, m), 5.35 (1H, s), 6.17 (1H, dt), 7.18 (1H, d), 8.11 (1H, d) | 1.4560 |
| 1-1515 | 2.53 (3H, s), 3.39 (2H, q), 3.95 (2H, brs), 6.29 (1H, dt), 7.15 (1H, d), 7.61 (1H, d) | Measurement impossible |
| 1-1516 | 2.47 (3H, s), 3.37-3.62 (2H, m), 3.99 (2H, brs), 6.26 (1H, dt), 7.21 (1H, d), 8.11 (1H, d) | Measurement impossible |
| 1-1517 | 2.30 (2H, m), 2.47 (3H, s), 3.16 (2H, t), 3.43 (2H, q), 4.47 (2H, t), 5.90 (1H, d), 7.07 (1H, d), 7.80 (1H, d), 8.01 (1H, d) | Measurement impossible |
| 1-1519 | 1.56 (3H, d), 2.47 (3H, s), 3.41 (2H, q), 5.29 (1H, m), 5.95 (1H, d), 7.08 (1H, d), 7.80 (1H, d), 7.98 (1H, d) | Measurement impossible |
| 1-1520 | 1.57 (3H, d), 2.38 (3H, s), 3.50 (2H, m), 5.38 (1H, m), 5.99 (1H, d), 7.25 (1H, d), 7.86 (1H, d), 8.43 (1H, d) | 1.4974 |
| 1-1521 | 2.08 (3H, s), 2.53 (3H, s), 3.40 (2H, q), 4.72 (2H, t), 6.22 (1H, s), 7.08 (1H, brs), 7.16 (1H, d), 7.60 (1H, d) | Measurement impossible |
| 1-1522 | 2.08 (3H, s), 2.46 (3H, s), 3.38-3.62 (2H, m), 4.72 (2H, t), 6.19 (1H, s), 7.20 (1H, d), 8.08 (1H, d) | 57-58 |

TABLE 60

| Comp. No. | ¹H-NMR (CDCl₃/TMS d (ppm) value) | m.p. (° C.) or refractive indx ($n_D^{20}$) |
|---|---|---|
| 1-1523 | 2.50 (3H, s), 2.81 (3H, s), 3.38 (3H, q), 4.71 (2H, t), 5.11 (1H, s), 7.11 (1H, d), 7.59 (1H, d) | 1.4471 |
| 1-1525 | 2.28 (1H, t), 2.51 (3H, s), 3.38 (2H, q), 3.84 (1H, brs), 4.71 (2H, t), 5.30 (1H, s), 7.12 (1H, d), 7.60 (1H, d) | Measurement impossible |
| 1-1526 | 2.29 (1H, t), 2.44 (3H, s), 3.36-3.61 (2H, m), 3.84 (1H, brs), 4.70 (2H, t), 5.34 (1H, s), 7.17 (1H, d), 8.10 (1H, d) | Measurement impossible |
| 1-1527 | 2.08 (3H, s), 2.52 (3H, s), 2.65 (2H, dt), 3.39 (2H, q), 4.45 (2H, t), 6.14 (1H, s), 7.07 (1H, brs), 7.15 (1H, d), 7.61 (1H, d) | Measurement impossible |
| 1-1528 | 2.08 (3H, s), 2.46 (3H, s), 2.68 (2H, dt), 3.38-3.62 (2H, m), 4.45 (2H, t), 6.12 (1H, s), 7.19 (1H, d), 8.08 (1H, d) | Measurement impossible |
| 1-1529 | 2.55 (3H, s), 3.38 (2H, q), 5.04-5.22 (1H, m), 6.52 (1H, s), 6.56 (1H, t), 7.16 (1H, d), 7.63 (1H, d) | Measurement impossible |
| 1-1530 | 2.48 (3H, s), 3.40-3.57 (2H, m), 5.02-5.20 (1H, m), 6.54 (1H, s), 6.62 (1H, t), 7.21 (1H, d), 8.14 (1H, d) | Measurement impossible |
| 1-1531 | see Ex. 57 | |
| 1-1532 | see Ex. 58 | 1.4482 |
| 1-1533 | 2.55 (3H, s), 3.38 (2H, q), 6.17 (1H, dt), 6.51 (1H, s), 6.56 (1H, t), 7.16 (1H, d), 7.63 (1H, d) | Measurement impossible |
| 1-1534 | 2.48 (3H, s), 3.38-3.59 (2H, m), 6.16 (1H, dt), 6.53 (1H, s), 6.62 (1H, t), 7.21 (1H, d), 8.14 (1H, d) | 1.4370 |
| 1-1535 | 1.43 (3H, t), 2.46 (3H, s), 3.37 (2H, q), 4.24 (2H, q), 5.86 (1H, d), 7.05 (1H, d), 7.76 (1H, d), 8.04 (1H, d) | 34-36 |
| 1-1536 | 1.42 (3H, t), 2.40 (3H, s), 3.49 (2H, m), 4.33 (2H, q), 5.89 (1H, d), 7.06 (1H, d), 7.84 (1H, d), 8.48 (1H, d) | 73-74 |
| 1-1538 | 1.02 (3H, t), 1.81 (2H, m), 2.40 (3H, s), 3.50 (2H, m), 4.21 (2H, t), 5.90 (1H, d), 7.10 (1H, d), 7.84 (1H, d), 8.48 (1H, d) | 105-107 |
| 1-1539 | 1.38 (6H, d), 2.44 (3H, s), 3.40 (2H, q), 4.58 (1H, m), 5.86 (1H, d), 7.03 (1H, d), 7.78 (1H, d), 8.02 (1H, d) | 1.5290 |
| 1-1540 | 1.40 (6H, d), 2.40 (3H, s), 3.49 (2H, m), 4.97 (1H, m), 5.91 (1H, d), 7.10 (1H, d), 7.85 (1H, d), 8.47 (1H, d) | 71-73 |
| 1-1541 | 2.54 (3H, s), 3.37 (2H, q), 4.69 (2H, t), 6.24 (1H, s), 6.52 (1H, t), 7.14 (1H, d), 7.60 (1H, d) | Measurement impossible |
| 1-1542 | 2.47 (3H, s), 3.41-3.56 (2H, m), 4.69 (2H, t), 6.26 (1H, s), 6.59 (1H, t) 7.19 (1H, d), 8.11 (1H, d) | 1.4610 |
| 1-1543 | 2.54 (3H, s), 3.37 (2H, q), 4.74 (2H, t), 6.24 (1H, s), 6.52 (1H, t), 7.14 (1H, d), 7.60 (1H, d) | Measurement impossible |
| 1-1544 | 2.47 (3H, s), 3.42-3.56 (2H, m), 4.74 (2H, t), 6.26 (1H, s), 6.59 (1H, t), 7.19 (1H, d), 8.11 (1H, d) | 1.4418 |
| 1-1545 | 2.50 (3H, s), 3.40 (2H, q), 5.11-5.36 (1H, m), 7.13 (1H, d), 7.93 (1H, s), 7.93 (1H, d) | Measurement impossible |
| 1-1546 | 2.44 (3H, s), 3.36-3.64 (2H, m), 5.08-5.33 (1H, m), 7.19 (1H, d), 7.96 (1H, s), 8.40 (1H, d) | 121-123 |
| 1-1547 | 2.53 (3H, s), 3.39 (2H, q), 4.00 (2H, brs), 5.14-5.38 (1H, m), 7.15 (1H, d), 7.61 (1H, d) | Measurement impossible |
| 1-1548 | 2.46 (3H, s), 3.37-3.62 (2H, m), 4.00 (2H, brs), 5.12-5.33 (1H, m), 7.66 (1H, d), 8.12 (1H, d) | Measurement impossible |
| 1-1549 | 2.54 (3H, s), 3.37 (2H, q), 6.31 (1H, dt), 7.11 (1H, d), 7.42-7.55 (3H, m), 7.66 (1H, d), 7.78 (2H, d) | 65-67 |
| 1-1550 | 2.48 (3H, s), 3.37-3.60 (2H, m), 6.28 (1H, dt), 7.16 (1H, d), 7.42-7.56 (3H, m), 7.78 (1H, d), 8.17 (1H, d) | 108-110 |
| 1-1552 | 2.48 (3H, s), 3.50-3.67 (2H, m), 4.67 (2H, t), 6.23 (1H, s), 7.20 (1H, d), 8.06 (1H, d), 8.16 (1H, d), 9.77 (1H, s) | 195-198 |
| 1-1553 | 2.49 (3H, s), 3.78 (2H, q), 6.21 (1H, d), 6.39 (1H, dd), 7.08 (1H, d), 7.88 (1H, d), 8.01 (1H, d) | 1.5090 |

TABLE 61

| Comp. No. | ¹H-NMR (CDCl₃/TMS d (ppm) value) | m.p. (° C.) or refractive indx ($n_D^{20}$) |
|---|---|---|
| 1-1554 | 2.44 (3H, s), 3.51 (2H, m), 6.30 (1H, s), 6.39 (1H, dd), 7.06 (1H, d), 7.92 (1H, d), 8.42 (1H, d) | 1.5110 |
| 1-1555 | 2.47 (3H, s), 3.40 (2H, q), 5.30 (2H, s), 5.94 (1H, s), 7.06 (1H, d), 7.24 (2H, d), 7.53 (2H, d), 7.81 (1H, d), 8.02 (1H, d) | 1.5262 |
| 1-1556 | 2.41 (3H, s), 3.48 (2H, m), 5.33 (2H, s), 5.98 (1H, d), 7.11 (1H, d), 7.25 (2H, d), 7.53 (2H, d), 7.88 (1H, d), 8.50 (1H, d) | 102-104 |
| 1-1557 | 2.49 (3H, s), 3.40 (2H, q), 6.36 (1H, d), 7.11 (1H, d), 8.01 (2H, s), 8.06 (1H, d), 8.36 (1H, d) | 1.5460 |
| 1-1558 | 2.41 (3H, s), 3.47 (2H, m), 6.42 (1H, d), 7.19 (1H, d), 8.03 (2H, m), 8.36 (1H, s), 8.50 (1H, d) | 144-145 |
| 1-1559 | 2.47 (3H, s), 3.87 (2H, q), 5.35 (2H, s), 5.95 (1H, s), 6.99 (1H, d), 7.46 (2H, d), 7.65 (2H, d), 7.82 (1H, d), 8.00 (1H, d) | 76-77 |
| 1-1560 | 2.41 (3H, s), 3.48 (2H, m), 5.37 (2H, s), 5.98 (1H, d), 7.12 (1H, d), 7.55 (2H, d), 7.66 (2H, d), 7.88 (1H, d), 8.49 (1H, d) | 145-147 |

TABLE 61-continued

| Comp. No. | $^1$H-NMR (CDCl$_3$/TMS d (ppm) value) | m.p. (° C.) or refractive indx (n$_D^{20}$) |
|---|---|---|
| 1-1561 | 2.48 (3H, s), 3.38 (2H, q), 5.41 (2H, s), 7.08 (1H, d), 7.57 (2H, d), 7.69 (2H, d), 7.86 (1H, d), 7.94 (1H, d) | 73-74 |
| 1-1562 | 2.41 (3H, s), 3.36-3.57 (2H, m), 5.42 (2H, s), 7.13 (1H, d), 7.58 (2H, d), 7.70 (2H, d), 7.94 (1H, s), 8.46 (1H, d) | 148-149 |
| 1-1563 | 2.48 (3H, s), 3.39 (2H, q), 5.37 (2H, s), 7.08 (1H, d), 7.24 (2H, d), 7.55 (2H, d), 7.86 (1H, d), 7.96 (1H, d) | 61-62 |
| 1-1564 | 2.41 (3H, s), 3.34-3.59 (2H, m), 5.38 (2H, s), 7.13 (1H, d), 7.25 (2H, d), 7.56 (2H, d), 7.93 (1H, d), 8.47 (1H, d) | 118-119 |
| 1-1565 | 2.47 (3H, s), 3.85 (2H, q), 5.37 (2H, s), 5.95 (1H, d), 7.07 (1H, d), 7.60 (2H, d), 7.65 (2H, d), 7.82 (1H, d), 8.00 (1H, d) | 55-57 |
| 1-1566 | 2.40 (3H, s), 3.47 (2H, m), 5.39 (2H, s), 5.99 (1H, d), 7.12 (1H, d), 7.59 (2H, d), 7.65 (2H, d), 7.88 (1H, d), 8.49 (1H, d) | 111-112 |
| 1.1567 | 2.46 (3H, s), 3.39 (2H, q), 5.31 (2H, s), 5.94 (1H, d), 7.08 (1H, d), 7.21 (1H, dd), 7.68 (1H, dd), 7.75 (1H, d), 7.81 (1H, dd), 8.00 (1H, d) | 1.5286 |
| 1-1568 | 2.41 (3H, s), 3.48 (2H, m), 5.34 (2H, s), 5.98 (1H, d), 7.13 (1H, d), 7.22 (1H, d), 7.68 (1H, dd), 7.75 (1H, d), 7.88 (1H, d), 8.49 (1H, d) | 120-121 |
| 1-1569 | 2.49 (3H, s), 3.39 (2H, q), 6.38 (1H, d), 7.08 (1H, d), 7.18 (1H, d), 7.96 (1H, dd), 7.99 (1H, d), 8.03 (1H, s), 8.51 (1H, s) | Measurement impossible |
| 1-1570 | 2.43 (3H, s), 3.48 (2H, m), 6.41 (1H, s), 7.16 (1H, d), 7.20 (1H, d), 7.96 (1H, dd), 8.01 (1H, t), 8.49 (1H, d), 8.50 (1H, s) | 98-100 |
| 1-1571 | 2.48 (3H, s), 3.38 (2H, q), 5.37 (1H, d), 7.18 (1H, d), 7.21 (1H, d), 7.70 (1H, m), 7.77 (1H, d), 7.85 (1H, d) | 44-46 |
| 1-1572 | 2.41 (3H, s), 3.47 (2H, m), 5.38 (1H, s), 7.14 (1H, d), 7.25 (1H, q), 7.76 (1H, d), 7.93 (1H, d), 8.46 (1H, d) | 138-140 |
| 1-1573 | 2.50 (3H, s), 3.39 (2H, q), 7.13 (1H, d), 8.01-8.05 (3H, m), 8.33 (1H, s) | 102-104 |
| 1-1574 | 2.44 (3H, s), 3.34-3.60 (2H, m), 7.18 (1H, d), 8.04 (1H, s), 8.09 (1H, d), 8.32 (1H, s), 8.49 (1H, d) | 47-49 |
| 1-1576 | 2.44 (3H, s), 3.35-3.61 (2H, m), 7.18 (1H, d), 7.24 (1H, d), 8.00 (1H, dd), 8.08 (1H, d), 8.47 (1H, s), 8.48 (1H, d) | Measurement impossible |
| 1-1577 | 2.54 (3H, s), 3.38 (2H, q), 5.04-5.20 (1H, m), 5.20 (2H, d), 6.39 (1H, s), 7.15 (1H, d), 7.64 (1H, d) | Measurement impossible |
| 1-1578 | 2.48 (3H, s), 3.38-3.61 (2H, m), 4.99-5.23 (1H, m), 5.23 (2H, d), 6.40 (1H, s), 7.21 (1H, d), 8.13 (1H, d) | Measurement impossible |
| 1-1579 | see Ex. 55 | |
| 1-1580 | see Ex. 56 | 68-70 |
| 1-1581 | 2.53 (3H, s), 3.38 (2H, q), 4.47 (2H, t), 5.16 (2H, d), 6.10 (1H, d), 7.14 (1H, d), 7.61 (1H, d) | Measurement impossible |
| 1-1582 | 2.47 (3H, s), 3.38-3.61 (2H, m), 4.74 (2H, t), 5.20 (2H, d), 6.12 (1H, d), 7.19 (1H, d), 8.11 (1H, d) | 1.4525 |

TABLE 62

| Comp. No. | $^1$H-NMR (CDCl$_3$/TMS d (ppm) value) | m.p. (° C.) or refractive indx (n$_D^{20}$) |
|---|---|---|
| 1-1583 | 2.11 (3H, s), 2.54 (3H, s), 3.36 (2H, q), 5.26 (2H, s), 5.71 (1H, s), 7.10 (1H, d), 7.54 (2H, d), 7.56 (1H, d), 7.66 (2H, d) | 114-115 |
| 1-1586 | see Ex. 65 | |
| 1-1587 | see Ex. 66 | 57-58 |
| 1-1588 | see Ex. 67 | 1.4800 |
| 1-1589 | 1.35 (3H, t), 1.50 (3H, t), 2.49 (3H, s), 3.40 (2H, q), 4.31 (2H, q), 4.44 (2H, q), 7.11 (1H, d), 8.03 (1H, d), 8.29 (1H, s) | 73-74 |
| 1-1591 | 1.36 (3H, t), 2.41 (3H, s), 4.34 (2H, q), 5.11 (1H, d), 6.22 (1H, dt), 7.10 (1H, d), 7.67 (1H, d), 8.36 (1H, d) | 72-74 |
| 1-1593 | see Ex. 61 | 54-55 |
| 1-1594 | see Ex. 62 | 198-200 |
| 1-1595 | 2.45 (3H, s), 3.40 (2H, q), 5.50 (2H, s), 5.98 (1H, d), 7.08 (1H, d), 7.25 (1H, dd), 7.40 (1H, dd), 7.76 (1H, dd), 7.86 (1H, d), 8.05 (1H, d) | 62-63 |
| 1-1596 | 2.41 (3H, s), 3.49 (2H, m), 5.46 (2H, s), 5.98 (1H, d), 7.11 (1H, d), 7.30 (1H, dd), 7.40 (1H, dd), 7.76 (1H, dd), 7.87 (1H, dd), 8.46 (1H, d) | 114-116 |
| 1-1598 | 2.43 (3H, s), 3.50 (2H, m), 6.33 (2H, m), 6.46 (1H, s), 7.16 (1H, d), 7.90 (1H, d), 8.46 (1H, d) | 58-61 |
| 1-1599 | see Ex. 63 | |
| 1-1600 | see Ex. 64 | 1.5300 |
| 1-1601 | 2.46 (3H, s), 3.40 (2H, q), 5.43 (2H, s), 5.96 (1H, d), 7.07 (1H, d), 7.37 (1H, d), 7.45 (1H, d), 7.72 (1H, t), 7.82 (1H, d), 8.01 (1H, d) | 60-62 |
| 1-1602 | 2.41 (3H, s), 3.49 (2H, m), 5.45 (2H, s), 5.99 (1H, d), 7.12 (1H, d), 7.38 (1H, d), 7.47 (1H, d), 7.73 (1H, t), 7.93 (1H, d), 8.48 (1H, d) | 103-104 |
| 1-1603 | 2.47 (3H, s), 3.41 (2H, q), 3.81 (3H, s), 5.47 (2H, s), 5.92 (1H, d), 6.92 (2H, d), 7.24 (1H, d), 7.43 (2H, d), 7.80 (1H, d), 8.05 (1H, d) | 1.5706 |
| 1-1604 | 2.41 (3H, s), 3.50 (2H, m), 3.63 (3H, s), 5.26 (2H, s), 5.95 (1H, d), 6.93 (2H, d), 7.12 (1H, d), 7.44 (2H, d), 7.85 (1H, d), 8.52 (1H, d) | 191-193 |

TABLE 62-continued

| Comp. No. | ¹H-NMR (CDCl₃/TMS d (ppm) value) | m.p. (° C.) or refractive indx ($n_D^{20}$) |
|---|---|---|
| 1-1605 | 2.48 (3H, s), 3.41 (2H, q), 5.32 (2H, s), 5.93 (1H, d), 7.07 (1H, d), 7.36 (1H, d), 7.80 (2H, m), 7.99 (1H, d), 8.52 (1H, d) | 78-80 |
| 1-1606 | 2.41 (3H, s), 3.49 (2H, m), 5.34 (2H, s), 5.97 (1H, d), 7.12 (1H, d), 7.44 (1H, d), 7.49 (1H, d), 7.82 (1H, d), 7.92 (1H, d), 8.51 (1H, s) | 102-103 |
| 1-1607 | 2.54 (3H, s), 3.40 (2H, q), 6.18 (1H, dt), 6.56 (1H, s), 7.18 (1H, d), 7.32 (1H, brs), 7.63 (1H, d), 8.26 (1H, s) | 1.4631 |
| 1-1608 | (d-DMSO, 100° C.) 2.48 (3H, s), 3.91-4.15 (2H, m), 6.39 (1H, s) 7.14 (1H, dt), 7.48 (1H, d), 7.94 (1H, d), 8.21 (1H, brs), 10.27 (1H, brs) | 150-153 |
| 1-1609 | 2.46 (3H, s), 3.40 (2H, q), 5.44 (2H, s), 6.00 (1H, d), 7.05 (1H, d), 7.23 (1H, d), 7.56 (1H, d), 7.73 (1H, t), 7.86 (1H, d), 8.01 (1H, d), 8.61 (1H, d) | 1.5585 |
| 1-1610 | 2.41 (3H, s), 3.50 (2H, m), 5.45 (2H, s), 6.03 (1H, d), 7.10 (1H, d), 7.23 (1H, d), 7.55 (1H, d), 7.74 (1H, t), 7.86 (1H, d), 8.47 (1H, d), 8.62 (1H, d) | 102-105 |
| 1-1611 | 0.60-1.1 (4H, br), 2.51 (3H, s), 3.32 (2H, q), 4.14 (1H, br), 5.06 (1H, br), 5.22 (2H, s), 5.61 (1H, s), 7.05 (1H, d), 7.25 (2H, d), 7.47 (2H, d), 7.51 (1H, d) | Measurement impossible |
| 1-1613 | 2.44 (3H, s), 2.47 (3H, s), 3.41 (2H, q), 5.26 (2H, s), 5.92 (1H, d), 7.06 (1H, d), 7.19 (2H, d), 7.39 (2H, d), 7.79 (1H, d), 8.04 (1H, d) | 1.5585 |
| 1-1614 | 2.36 (3H, s), 2.41 (3H, s), 3.49 (2H, m), 5.28 (2H, s), 5.96 (1H, d), 7.10 (1H, d), 7.18 (2H, d), 7.39 (2H, d), 7.85 (1H, d), 8.52 (1H, d) | 157-160 |
| 1-1615 | see Ex. 72 | |

INTERMEDIATE PREPARATION EXAMPLES

Intermediate Preparation Example 1

Preparation of 1-{2-fluoro-4-methyl-5-(2,2,2-trifluoroethylthio)phenyl}-3-hydroxypyrazole (compound No. 2-1 of the present invention)

12 g of 2-fluoro-4-methyl-5-(2,2,2-trifluoroethylthio)phenylhydrazine was dissolved in 200 mL of tetrahydrofuran, and 100 mL of water was added. To this solution, 16 g of potassium carbonate and 8.1 g of 3-bromopropionyl chloride were added, followed by stirring at room temperature for 5 hours. The aqueous layer was neutralized to the vicinity of pH 2 with 6N hydrochloric acid. Then, the solvent was distilled off under reduced pressure, and the residue was subjected to extraction with ethyl acetate. The organic layer was dried over anhydrous magnesium sulfate, and the solvent was distilled off under reduced pressure to obtain a solid, which was washed with hexane. Then, this solid was dissolved in 200 mL of toluene, and 100mL of water was added. Then, 3.7 g of potassium permanganate and tetra n-butyl ammonium bromide in a catalytic amount were added, followed by stirring at room temperature for 10 minutes. Then, an insoluble solid was removed by filtration, and the organic layer was dried over anhydrous magnesium sulfate. Then, the solvent was distilled off under reduced pressure, and the solid was washed with hexane to obtain 8.7 g of pale yellow crystals (melting point: 166-168° C.).

¹H-NMR (CDCL₃/TMS δ (ppm) value) δ: 2.46 (3H, s), 3.69 (2H, q), 5.89 (1H, d), 7.08 (1H, d), 7.72 (1H, d), 7.77 (1H, d), 11.88 (1H, brs)

Intermediate Preparation Example 2

Preparation of 5-amino-1-{2-fluoro-4-methyl-5-(2,2,2-trifluoroethylthio)phenyl}-3-hydroxypyrazole (compound No. 2-2 of the present invention)

27.5 g of 2-fluoro-4-methyl-5-(2,2,2-trifluoroethylthio)phenylhydrazine was dissolved in 300 mL of tetrahydrofuran, and to this solution, 14 g of cyanoacetyl chloride was added, followed by stirring at room temperature for 5 minutes. Then, the solvent was distilled off under reduced pressure, the residue was dissolved in 300 mL of 1-propanol, and 10.6 g of methanesulfonic acid was added, followed by reflux with heating for 3 hours. After cooling to room temperature, the solvent was distilled off under reduced pressure, the reaction solution was neutralized to pH=7 with sodium hydrogen carbonate, and extraction with ethyl acetate was carried out. The organic layer was dried over anhydrous magnesium sulfate, the solvent was distilled off under reduced pressure, and the obtained residue was purified by column chromatography (developing solvent ethyl acetate:hexane:acetic acid=50:50:1) to obtain 20.2 g of 5-amino-1-{2-fluoro-4-methyl-5-(2,2,2-trifluoroethylthio)phenyl}-3-hydroxypyrazole in the form of brown crystals (melting point: 110-113° C.).

¹H-NMR (CDCL₃/TMS δ (ppm) value) δ: 2.49 (3H, s), 3.49 (2H, q), 5.04 (1H, s), 7.10 (1H, d), 7.57 (1H, d)

Intermediate Preparation Example 3

Preparation of 5-acetylamino-1-{2-fluoro-4-methyl-5-(2,2,2-trifluoroethylthio)phenyl}-3-hydroxypyrazole (compound No. 2-4 of the present invention)

10.6 g of 5-amino-1-{2-fluoro-4-methyl-5-(2,2,2-trifluoroethylthio)phenyl}-3-hydroxypyrazole was dissolved in 200 mL of toluene, and to this solution, 20.0 g of acetyl chloride was added, followed by reflux with heating for 12 hours. After cooling to room temperature, the solvent was distilled off under reduced pressure, and the obtained residue was purified by column chromatography (developing solvent ethyl acetate:hexane=1:4) to obtain 9.4 g of 3-acetoxy-5-(N,N-diacetylamino)-1-{2-fluoro-4-methyl-5-(2,2,2-trifluoroethylthio)phenyl}pyrazole. Then, 9.4 g of the obtained 3-acetoxy-5-(N,N-diacetylamino)-1-{2-fluoro-4-methyl-5-(2,2,2-trifluoroethylthio)phenyl}pyrazole was dissolved in 100 mL of ethanol, and 10 mL of a 25 mass % ammonia water was added, followed by stirring at room temperature for 30 minutes. Then, the solvent was distilled off under reduced pressure, and the obtained solid was washed with diisopropyl ether to obtain 7.0 g of 5-acetylamino-1-{2-fluoro-4-methyl-5-(2,2,2-trifluoroethylthio)phenyl}-3-hydroxypyrazole in the form of white crystals (melting point: 223-225° C.).

¹H-NMR (d6-DMSO/TMS δ (ppm) value) δ: 2.01 (3H, s), 2.50 (3H, s), 3.49 (2H, q), 5.91 (1H, s), 7.10 (1H, d), 7.60 (1H, d), 9.33 (1H, brs)

Intermediate Preparation Example 4

Preparation of 1-{2-fluoro-4-methyl-5-(2,2,2-trifluoroethylthio)phenyl}-3-hydroxy-5-methylpyrazole (compound No. 2-11 of the present invention)

4.6 g of 1-(5-(2,2,2-trifluoroethylthio)-2-fluoro-4-methylphenyl)hydrazine was dissolved in 100 mL of diethyl ether, and 1.85 g of acetic anhydride was dropwise added under cooling with ice, followed by stirring at room temperature for one hour. The obtained crystals were collected by filtration and washed with a solution of hexane:diisopropyl ether=3:1 (mass ratio) to obtain 4.41 g of N'-{2-fluoro-4-methyl-5-(2,2,2-trifluoroethylthio)phenyl}acetohydrazide in the form of colorless crystals. Then, to 4.4 g of this hydrazide, 1.93 g of ethyl acetoacetate and 4.02 g of phosphorus tribromide were added, followed by stirring at 50° C. for 2 hours. Then, after stirring under cooling with ice for 10 minutes, ice was put, and the pH was adjusted to 5 with a 1N sodium hydroxide aqueous solution. Then, extraction with ethyl acetate was carried out, followed by washing with a saturated salt solution, the organic layer was dried over anhydrous sodium sulfate, the solvent was distilled off under reduced pressure, and the obtained residue was purified by column chromatography (ethyl acetate:hexane=1:3) to obtain 2.03 g of 1-{2-fluoro-4-methyl-5-(2,2,2-trifluoroethylthio)phenyl}-3-hydroxy-5-methylpyrazole in the form of colorless solid.

$^1$H-NMR (CDCL$_3$/TMS δ (ppm) value) δ: 2.14 (3H, s), 2.50 (3H, s), 3.55 (2H, q), 5.55 (1H, s), 7.09 (1H, d), 7.58 (1H, d)

Intermediate Preparation Example 5

Preparation of ethyl-1-{2-fluoro-4-methyl-5-(2,2,2-trifluoroethylthio)phenyl}-3-hydroxypyrazole-5-carboxylate (compound No. 2-12 of the present invention)

14 g of a 20 mass % sodium ethoxide ethanol solution was added to 20 mL of ethanol, and 10 g of 2-fluoro-4-methyl-5-(2,2,2-trifluoroethylthio)phenylhydrazine was rapidly added under reflux with heating. After stirring for 30 seconds, 7.8 g of diethyl maleate was dropwise added, followed by stirring under reflux with heating for 10minutes. The reaction solution was cooled to 50° C. or below, and 4.5 g of acetic acid was added. Then, the solvent was distilled off under reduced pressure, extraction with ethyl acetate was carried out, the organic layer was dried over anhydrous sodium sulfate, and the solvent was distilled off under reduced pressure. The obtained residue was dissolved in 80 mL of toluene, 0.68 g of tetra n-butyl ammonium bromide was added, and 3.5 g of a 10 mass % aqueous solution of potassium permanganate was gradually added. After completion of the reaction, ethyl acetate and 20 mL of a saturated aqueous solution of citric acid were added, and the solution was washed with an aqueous sodium thiosulfate solution and then dried over anhydrous magnesium sulfate. Then, the solvent was distilled off under reduced pressure, and the obtained residue was purified by column chromatography (developing solvent ethyl acetate:hexane=1:1) to obtain 3.80 g of ethyl 1-{2-fluoro-4-methyl-5-(2,2,2-trifluoroethylthio)phenyl}-3-hydroxypyrazole-5-carboxylate.

$^1$H-NMR (CDCL$_3$/TMS δ (ppm) value) δ: 1.26 (3H, t), 2.52 (3H, s), 3.53 (2H, q), 4.66 (2H, q), 4.25 (2H, q), 6.31 (1H, s), 7.07 (1H, d), 7.62 (1H, d)

Intermediate Preparation Example 6

Preparation of 1-{2-fluoro-4-methyl-5-(2,2,2-trifluoroethylthio)phenyl}-3-hydroxy-5-methoxypyrazole (compound No. 2-16 of the present invention)

2.0 g of N'-{2-fluoro-4-methyl-5-(2,2,2-trifluoroethylthio)phenyl}acetohydrazide was dissolved in 100 mL of tetrahydrofuran, 0.95 g of malonyl chloride was added under cooling with ice, stirring was carried out under cooling with ice for one hour, and then stirring was carried out under reflux with heating for 5 hours. Then, the solvent was distilled off under reduced pressure, and the obtained crystals were washed with isopropyl ether to obtain 1.74 g of 1-acetyl-2-{2-fluoro-4-methyl-5-(2,2,2-trifluoroethylthio)phenyl}pyrazolidine-3,5-dione.

Then, 1.50 g of 1-acetyl-2-{2-fluoro-4-methyl-5-(2,2,2-trifluoroethylthio)phenyl}pyrazolidine-3,5-dione was dissolved in 50 mL of dichloromethane, 5 mL of methanol was added, and 2.1 mL of a diethyl ether solution (2.0 mol/L) of trimethylsilyldiazomethane was added under cooling with ice, followed by stirring at room temperature for 5 hours. Then, the solvent was distilled off under reduced pressure, and the obtained residue was purified by column chromatography (developing solvent ethyl acetate:hexane=1:2) to obtain 0.69 g of 2-acetyl-1-{2-fluoro-4-methyl-5-(2,2,2-trifluoroethylthio)phenyl}-5-methoxypyrazol-3-one.

$^1$H-NMR (CDCL$_3$/TMS δ (ppm) value) δ: 2.47 (3H, s), 2.53 (3H, s), 3.32 (2H, q), 3.88 (3H, s), 4.88 (1H, s), 7.03 (1H, d), 7.51 (1H, d)

Then, 0.65 g of 2-acetyl-1-{2-fluoro-4-methyl-5-(2,2,2-trifluoroethylthio)phenyl}-5-methoxypyrazol-3-one was dissolved in 20 mL of tetrahydrofuran, and 0.2 g of potassium hydroxide was added, followed by stirring at room temperature for 2 hours. Concentrated hydrochloric acid was added to adjust pH to 3, the solvent was distilled off under reduced pressure, and extraction with ethyl acetate was carried out. The organic layer was dried over anhydrous sodium sulfate, and the solvent was distilled off under reduced pressure to obtain 0.57 g of 1-{2-fluoro-4-methyl-5-(2,2,2-trifluoroethylthio)phenyl}-3-hydroxy-5-methoxypyrazole.

$^1$H-NMR (CDCL$_3$/TMS δ (ppm) value) δ: 2.48 (3H, s), 3.46 (2H, q), 3.91 (3H, s), 5.15 (1H, s), 7.07 (1H, d), 7.53 (1H, d)

Intermediate Preparation Example 7

Preparation of ethyl-1-{2-fluoro-4-methyl-5-(2,2,2-trifluoroethylthio)phenyl}-3-hydroxypyrazole-4-carboxylate (compound No. 2-17 of the present invention)

5.0 g of 2-fluoro-4-methyl-5-(2,2,2-trifluoroethylthio)phenylhydrazine was dissolved in 50 mL of ethanol, and 5.0 g of ethyl 2-cyano-3,3-diethoxyacrylate was added, followed by stirring under reflux with heating for 6 hours. Then, the solvent was distilled off under reduced pressure, and extraction with ethyl acetate was carried out. The organic layer was dried over anhydrous magnesium sulfate, and the solvent was distilled off under reduced pressure. The obtained residue was purified by column chromatography (developing solvent ethyl acetate:hexane=1:3) to obtain 1.48g of ethyl-5-amino- 3-ethoxy-1-{2-fluoro-4-methyl-5-(2,2,2-trifluoroethylthio) phenyl}pyrazole-4-carboxylate.

¹H-NMR (CDCL₃/TMS δ (ppm) value) δ: 1.37 (3H, t), 1.44 (3H, t), 2.51 (3H, s), 3.38 (2H, q), 4.31 (2H, q), 5.29 (2H, brs), 7.14 (1H, d), 7.64 (1H, d)

Then, 1.48 g of ethyl-5-amino-3-ethoxy-1-{2-fluoro-4-methyl-5-(2,2,2-trifluoroethylthio)phenyl}pyrazole-4-carboxylate was dissolved in 50 mL of tetrahydrofuran, and 0.44 g of tert-butyl nitrite was added under cooling with ice, followed by stirring at room temperature for 12 hours. Then, the solvent was distilled off under reduced pressure, and the obtained residue was purified by column chromatography (developing solvent ethyl acetate:hexane=1:4) to obtain 1.18 g of ethyl-3-ethoxy-1-{2-fluoro-4-methyl-5-(2,2,2-trifluoroethylthio)phenyl}pyrazole-4-carboxylate.

¹H-NMR (CDCL₃/TMS δ (ppm) value) δ: 1.35 (3H, t), 1.50 (3H, t), 2.49 (3H, s), 3.40 (2H, q), 4.31 (2H, q), 4.44 (2H, q), 7.11 (1H, d), 8.03 (1H, d), 8.29 (1H, s)

Then, 1.0 g of ethyl-3-ethoxy-1-{2-fluoro-4-methyl-5-(2,2,2-trifluoroethylthio)phenyl}pyrazole-4-carboxylate was dissolved in 30 mL of dichloromethane, and 3.08 g of boron tribromide was added under cooling with ice, followed by stirring at room temperature for 12 hours. Then, 10 mL of a saturated aqueous solution of citric acid was added, extraction with ethyl acetate was carried out, the organic layer was dried over anhydrous magnesium sulfate, the solvent was distilled off under reduced pressure, and the obtained residue was purified by column chromatography (developing solvent ethyl acetate:hexane=1:1) to obtain 0.45 g of ethyl-1-{2-fluoro-4-methyl-5-(2,2,2-trifluoroethylthio)phenyl}-3-hydroxypyrazole-4-carboxylate.

¹H-NMR (CDCL₃/TMS δ (ppm) value) δ: 1.39 (3H, t), 2.49 (3H, s), 3.43 (2H, q), 4.38 (2H, q), 7.11 (1H, d), 8.08 (1H, d), 8.21 (1H, d)

Structural formulae of intermediates for compounds [I] of the present invention prepared in accordance with the above Intermediate Preparation Examples are given below together with structural formulae in the above Examples. Symbols in the Table are as defined above.

¹H-NMR data (TMS standard, δ (ppm)) values of the intermediates for the compounds [I] of the present invention prepared in accordance with the above Intermediate Preparation Examples are given below together with the values in the above Examples. CDCl₃ and d6-DMSO in brackets represent the solvent for measurement.

Compound No. 2-3 (CDCl₃), 2.50 (3H, s), 3.57 (3H, t), 3.83 (1H, brs), 4.50 (1H, s), 7.09 (1H, d), 7.62 (1H, d), Compound No. 2-5 (d6-DMSO), 2.00 (3H, s), 2.52 (3H, s), 3.47 (2H, t), 5.90 (1H, s), 7.11 (1H, d), 7.61 (1H, d), 9.29 (1H, brs), 9.95 (1H, brs), Compound No. 2-6 (d6-DMSO), 2.50 (3H, s), 3.58 (2H, q), 4.07 (2H, s), 5.93 (1H, s), 7.15 (1H, d), 7.59 (1H, d), 9.98 (1H, brs), Compound No. 2-7 (CDCl₃), 1.11 (3H, t), 2.26 (2H, q), 2.50 (3H, s), 3.48 (2H, q), 5.96 (1H, s), 7.10 (1H, d), 7.61 (1H, d), 8.64 (1H, brs), Compound No. 2-8 (d6-DMSO), 2.50 (3H, s), 3.50 (2H, q), 5.67 (1H, q), 5.99 (1H, s), 6.33 (2H, t), 7.11 (1H d), 7.60 (1H, d), 9.66 (1h, brs), 9.93 (1H, brs), Compound No. 2-9 (CDCl₃), 2.52 (3H, s), 3.40 (3H, s), 3.58 (2H, q), 3.97 (2H, s), 6.14 (1H, s), 7.15 (1H, d), 7.61 (1H, d), 8.43 (1H, brs), Compound No. 2-10 (d6-DMSO), 0.74 (2H, d), 0.88 (2H, s), 1.70 (1H, s), 2.50 (3H, s), 3.51 (2H, q), 5.88 (1H, s), 7.12 (1H, d), 7.59 (1H, d), 9.60 (1H, brs), Compound No. 2-13 (CDCl₃), 2.50 (3H, s), 3.43 (2H, q), 4.53 (1H, brs), 7.07 (1H, d), 7.80 (1H, s), 7.94 (1H, d), Compound No. 2-14 (CDCl₃), 2.50 (3H, s), 3.52 (2H, q), 4.18 (2H, brs), 7.11 (1H, d), 7.61 (1H, d), Compound No. 2-15 (CDCl₃), 2.47 (3H, s), 3.51 (2H, q), 7.09 (1H, d), 7.81 (1H, s), 7.89 (1H, s), 11.10 (1H, brs)

Now, formulation methods will be described in detail with reference to typical Formulation Examples. The types of the compounds and adjuvants, and their blend ratios are not lim-

TABLE 63

| Comp. No | R₂ | R₃ | R₄ | R₅ | R₆ | R₇ | R₈ |
|---|---|---|---|---|---|---|---|
| 2-1 | H | H | F | H | CH₃ | SCH₂CF₃ | H |
| 2-2 | H | NH₂ | F | H | CH₃ | SCH₂CF₃ | H |
| 2-3 | H | NH₂ | F | H | CH₃ | SCH₂CF₂CF₃ | H |
| 2-4 | H | NHC(O)CH₃ | F | H | CH₃ | SCH₂CF₃ | H |
| 2-5 | H | NHC(O)CH₃ | F | H | CH₃ | SCH₂CF₂CF₃ | H |
| 2-6 | H | NHC(O)CH₂Cl | F | H | CH₃ | SCH₂CF₃ | H |
| 2-7 | H | NHC(O)CH₂CH₃ | F | H | CH₃ | SCH₂CF₃ | H |
| 2-8 | H | NHC(O)CH=CH₂ | F | H | CH₃ | SCH₂CF₃ | H |
| 2-9 | H | NHC(O)CH₂OCH₃ | F | H | CH₃ | SCH₂CF₃ | H |
| 2-10 | H | NHC(O)Pr-c | F | H | CH₃ | SCH₂CF₃ | H |
| 2-11 | H | CH₃ | F | H | CH₃ | SCH₂CF₃ | H |
| 2-12 | H | C(O)OEt | F | H | CH₃ | SCH₂CF₃ | H |
| 2-13 | Cl | H | F | H | CH₃ | SCH₂CF₃ | H |
| 2-14 | Cl | NH₂ | F | H | CH₃ | SCH₂CF₃ | H |
| 2-15 | Br | H | F | H | CH₃ | SCH₂CF₃ | H |
| 2-16 | H | OCH₃ | F | H | CH₃ | SCH₂CF₃ | H |
| 2-17 | C(O)OCH₂CH₃ | H | F | H | CH₃ | SCH₂CF₃ | H |

Formulation Example 1

Emulsifiable Concentrate

| | |
|---|---|
| Compound No. 1-11 | 30 parts |
| Cyclohexanone | 20 parts |
| Polyoxyethylene alkyl aryl ether | 11 parts |
| Calcium alkylbenzenesulfonate | 4 parts |
| Methyl naphthalene | 35 parts |

The above compounds were uniformly dissolved to obtain an emulsifiable concentrate. Further, emulsifiable concentrates can be obtained in the same manner by using compounds as identified in Tables 1 to 38 instead of the compound No. 1-11.

Formulation Example 2

Wettable Powder

| | |
|---|---|
| Compound No. 1-78 | 10 parts |
| Sodium salt of naphthalenesulfonic acid formalin condensate | 0.5 part |
| Polyoxyethylene alkyl aryl ether | 0.5 part |
| Diatomaceous earth | 24 parts |
| Clay | 65 parts |

The above compounds were uniformly mixed and pulverized to obtain a wettable powder. Further, wettable powders can be obtained in the same manner by using compounds as identified in Tables 1 to 38 instead of the compound No. 1-78.

Formulation Example 3

Dust

| | |
|---|---|
| Compound No. 1-106 | 2 parts |
| Diatomaceous earth | 5 parts |
| Clay | 93 parts |

The above compounds were uniformly mixed and pulverized to obtain a dust. Further, dusts can be obtained in the same manner by using compounds as identified in Tables 1 to 38 instead of the compound No. 1-106.

Example 4

Granule

| | |
|---|---|
| Compound No. 1-110 | 5 parts |
| Sodium lauryl alcohol sulfate | 2 parts |
| Sodium lignin sulfonate | 5 parts |
| Carboxymethyl cellulose | 2 parts |
| Clay | 86 parts |

The above compounds were uniformly mixed and pulverized. To this mixture, water in an amount corresponding to 20 parts was added, followed by kneading, and the kneaded product was formed into granules of 14 to 32 mesh by an extrusion granulator, which were dried to obtain a granule. Further, granules can be obtained in the same manner by using compounds as identified in Tables 1 to 38 instead of the compound No. 1-110.

Now, the effect of the pesticide comprising the compound of the present invention as an active ingredient will be described with reference to Test Examples.

Test Example 1

Insecticidal Test on Cotton Aphid

A wettable powder prepared in accordance with Formulation Example 2 was diluted with water to a concentration of an active ingredient of 500 ppm. Cucumber seedlings which had been inoculated with larvae of cotton aphid were dipped in this solution and dried in air. The treated cucumber seedlings were placed in a thermostatic chamber at 25° C. for 3 days, and the live insects were counted for calculation of the mortality by Equation 2. The test was carried out by one series system.

Compounds which exhibit a mortality of 90% or higher in this test are indicated by compound numbers.

1-6, 1-9, 1-10, 1-11, 1-13, 1-14, 1-15, 1-16, 1-17, 1-18, 1-22, 1-25, 1-26, 1-27, 1-29, 1-30, 1-31, 1-33, 1-34, 1-35, 1-37, 1-38, 1-48, 1-53, 1-58, 1-60, 1-62, 1-89, 1-90, 1-91, 1-92, 1-93, 1-97, 1-99, 1-100, 1-101, 1-102, 1-105, 1-106, 1-108, 1-113, 1-115, 1-116, 1-118, 1-123, 1-125, 1-127, 1-129, 1-130, 1-133, 1-137, 1-157, 1-159, 1-161, 1-162, 1-171, 1-177, 1-186, 1-187, 1-192, 1-195, 1-196, 1-197, 1-207, 1-208, 1-223, 1-235, 1-237, 1-247, 1-248, 1-250, 1-252, 1-253, 1-254, 1-269, 1-270, 1-273, 1-274, 1-275, 1-276, 1-277, 1-278, 1-280, 1-281, 1-282, 1-284, 1-287, 1-288, 1-300, 1-301, 1-302, 1-308, 1-312, 1-317, 1-318, 1-321, 1-322, 1-323, 1-324, 1-325, 1-326, 1-332, 1-345, 1-346, 1-347, 1-353, 1-357, 1-364, 1-376, 1-377, 1-392, 1-393, 1-395, 1-397, 1-401, 1-410, 1-414, 1-458, 1-460, 1-550, 1-578, 1-579, 1-668, 1-670, 1-696, 1-794, 1-795, 1-873, 1-1151, 1-1194, 1-1282, 1-1365, 1-1366, 1-1368, 1-1369, 1-1370, 1-1371, 1-1372, 1-1382, 1-1392, 1-1400, 1-1402, 1-1403, 1-1417, 1-1419, 1-1421, 1-1422, 1-1423, 1-1425, 1-1432, 1-1439, 1-1513, 1-1514, 1-1519, 1-1520, 1-1523, 1-1529, 1-1531, 1-1535, 1-1541, 1-1553, 1-1577, 1-1578, 1-1579, 1-1580, 1-1582, 1-1593 and 1-1594.

On the other hand, compound Nos. V-613 and V-660 disclosed in JPA-2000-198768 exhibited a mortality of 0% in this test. Further, compound No. 1-80 disclosed in WO2007/081019 exhibited a mortality of 33% in this test.

Comparative Compounds

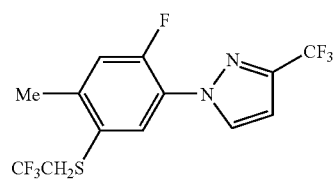

Compound No. V-613 disclosed in JP-A-2000-198768

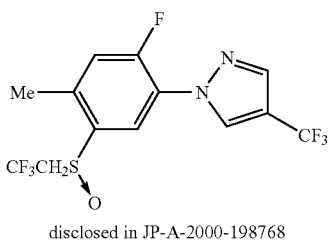

disclosed in JP-A-2000-198768

Compound No. V-660

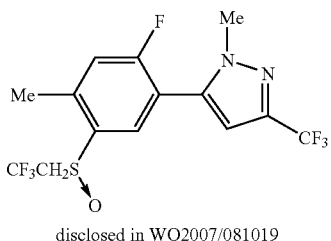

disclosed in WO2007/081019

Compound No. I-80

Test Example 2

Insecticidal Test on Cotton Aphid

A wettable powder prepared in accordance with Formulation Example 2 was diluted with water to a concentration of an active ingredient of 100 ppm. The root zone of cucumber seedlings which had been inoculated with larvae of cotton aphid was irrigated with 5 mL of the solution. The treated cucumber seedlings were placed in a thermostatic chamber at 25° C. for 3 days, and the live insects were counted for calculation of the mortality by Equation 2. The test was carried out by one series system.

Compounds which exhibit a mortality of 90% or higher in this test are indicated by compound numbers.

1-18, 1-30, 1-36, 1-1369 and 1-1371.

Test Example 3

Insecticidal Test on Diamondback Moth

A wettable powder prepared in accordance with Formulation Example 2 was diluted with water to a concentration of an active ingredient of 500 ppm. Cabbage leaves were dipped in this solution and dried in air and then put in a plastic cup having a capacity of 60 mL. 10 second-instar larvae of diamondback moth were released in the cup and the cup was lidded. Then, the cup was placed in a thermostatic chamber at 25° C. for 6 days, and dead moths were counted for calculation of the mortality by Equation 2. The test was carried out by one series system.

Compounds which exhibit a mortality of 90% or higher in this test are indicated by compound numbers.

1-9, 1-10, 1-11, 1-12, 1-13, 1-14, 1-15, 1-16, 1-17, 1-18, 1-22, 1-27, 1-29, 1-31, 1-32, 1-35, 1-36, 1-37, 1-38, 1-41, 1-42, 1-43, 1-44, 1-47, 1-48, 1-49, 1-53, 1-54, 1-55, 1-57, 1-58, 1-61, 1-62, 1-75, 1-76, 1-77, 1-78, 1-83, 1-85, 1-86, 1-89, 1-91, 1-99, 1-100, 1-101, 1-102, 1-105, 1-107, 1-108, 1-109, 1-110, 1-115, 1-116, 1-117, 1-118, 1-119, 1-120, 1-121, 1-123, 1-125, 1-127, 1-128, 1-129, 1-130, 1-133, 1-135, 1-136, 1-137, 1-142, 1-146, 1-147, 1-157, 1-158, 1-159, 1-160, 1-161, 1-162, 1-163, 1-164, 1-167, 1-170, 1-173, 1-174, 1-175, 1-176, 1-177, 1-178, 1-179, 1-181, 1-182, 1-184, 1-186, 1-187, 1-189, 1-190, 1-191, 1-192, 1-194, 1-196, 1-197, 1-198, 1-199, 1-200, 1-202, 1-205, 1-207, 1-208, 1-214, 1-215, 1-237, 1-245, 1-252, 1-261, 1-262, 1-263, 1-264, 1-268, 1-271, 1-272, 1-273, 1-275, 1-276, 1-277, 1-278, 1-280, 1-281, 1-282, 1-283, 1-284, 1-285, 1-287, 1-288, 1-291, 1-292, 1-293, 1-301, 1-302, 1-304, 1-306, 1-308, 1-310, 1-311, 1-312, 1-313, 1-314, 1-316, 1-317, 1-318, 1-321, 1-322, 1-323, 1-324, 1-325, 1-326, 1-331, 1-333, 1-334, 1-337, 1-338, 1-339, 1-340, 1-341, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-363, 1-364, 1-365, 1-366, 1-368, 1-369, 1-370, 1-371, 1-372, 1-373, 1-374, 1-375, 1-376, 1-377, 1-389, 1-395, 1-401, 1-410, 1-413, 1-414, 1-415, 1-443, 1-447, 1-458, 1-459, 1-460, 1-461, 1-485, 1-486, 1-487, 1-488, 1-489, 1-490, 1-491, 1-524, 1-525, 1-526, 1-527, 1-546, 1-550, 1-578, 1-579, 1-590, 1-591, 1-668, 1-670, 1-671, 1-707, 1-794, 1-795, 1-873, 1-879, 1-888, 1-889, 1-890, 1-891, 1-892, 1-893, 1-1063, 1-1104, 1-1107, 1-1193, 1-1195, 1-1197, 1-1253, 1-1255, 1-1256, 1-1257, 1-1258, 1-1259, 1-1282, 1-1283, 1-1361, 1-1365, 1-1366, 1-1368, 1-1369, 1-1370, 1-1371, 1-1374, 1-1382, 1-1400, 1-1402, 1-1403, 1-1404, 1-1415, 1-1418, 1-1419, 1-1421, 1-1422, 1-1426, 1-1427, 1-1428, 1-1429, 1-1430, 1-1431, 1-1432, 1-1433, 1-1434, 1-1449, 1-1450, 1-1453, 1-1455, 1-1476, 1-1507, 1-1512, 1-1513, 1-1514, 1-1515, 1-1516, 1-1519, 1-1521, 1-1522, 1-1523, 1-1525, 1-1526, 1-1527, 1-1528, 1-1531, 1-1533, 1-1543, 1-1544, 1-1547, 1-1548, 1-1549, 1-1550, 1-1552, 1-1579, 1-1581, 1-1582, 1-1593, 1-1594, 1-1599, 1-1600, 1-1607 and 1-1608.

On the other hand, compound Nos. V-660 and V-718 disclosed in JP-A-2000-198768 and compound No. 1-80 disclosed in WO2007/081019 exhibited a mortality of 0% in this test.

Comparative Compounds

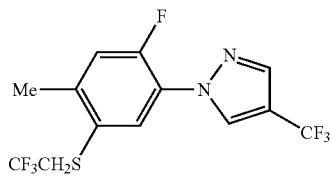

disclosed in JP-A-2000-198768

Compound No. V-660

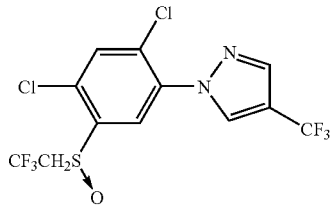

disclosed in JP-A-2000-198768

Compound No. V-718

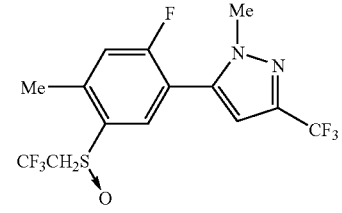

disclosed in WO2007/081019

Compound No. I-80

Test Example 4

Insecticidal Test on Cotton Bollworm

A wettable powder prepared in accordance with Formulation Example 2 was diluted with water to a concentration of an active ingredient of 500 ppm. Cabbage leaves were dipped in this solution and dried in air and then put in a plastic cup having a capacity of 60 mL. Five hatched larvae of cotton bollworm were released in the cup, and the cup was lidded and placed in a thermostatic chamber at 25° C. for 6 days, and the number of dead larvae were assessed for calculation of the mortality by Equation 2. The test was carried out by two series system.

Compounds which exhibit a mortality of 90% or higher in this test are indicated by compound numbers.

1-6, 1-9, 1-10, 1-11, 1-12, 1-13, 1-14, 1-15, 1-16, 1-17, 1-18, 1-27, 1-30, 1-32, 1-37, 1-38, 1-42, 1-48, 1-53, 1-54, 1-57, 1-58, 1-62, 1-74, 1-75, 1-76, 1-77, 1-78, 1-79, 1-83, 1-85, 1-86, 1-99, 1-100, 1-101, 1-102, 1-105, 1-106, 1-107, 1-108, 1-115, 1-116, 1-117, 1-118, 1-120, 1-121, 1-125, 1-129, 1-130, 1-159, 1-160, 1-161, 1-162, 1-163, 1-170, 1-173, 1-177, 1-178, 1-187, 1-189, 1-191, 1-192, 1-206, 1-207, 1-208, 1-214, 1-247, 1-248, 1-268, 1-269, 1-270, 1-276, 1-278, 1-280, 1-281, 1-282, 1-283, 1-284, 1-287, 1-288, 1-301, 1-302, 1-304, 1-306, 1-308, 1-310, 1-312, 1-313, 1-314, 1-316, 1-317, 1-318, 1-321, 1-322, 1-323, 1-324, 1-325, 1-326, 1-331, 1-332, 1-333, 1-334, 1-336, 1-338, 1-344, 1-345, 1-346, 1-347, 1-348, 1-349, 1-350, 1-351, 1-352, 1-353, 1-354, 1-355, 1-356, 1-357, 1-358, 1-359, 1-360, 1-361, 1-362, 1-364, 1-365, 1-366, 1-368, 1-369, 1-370, 1-371, 1-372, 1-373, 1-374, 1-375, 1-376, 1-377, 1-386, 1-387, 1-388, 1-389, 1-391, 1-400, 1-401, 1-411, 1-413, 1-443, 1-447, 1-458, 1-459, 1-460, 1-461, 1-486, 1-487, 1-488, 1-489, 1-490, 1-491, 1-495, 1-524, 1-525, 1-526, 1-527, 1-546, 1-550, 1-578, 1-579, 1-590, 1-591, 1-702, 1-703, 1-707, 1-795, 1-889, 1-891, 1-892, 1-893, 1-1193, 1-1250, 1-1251, 1-1252, 1-1253, 1-1255, 1-1256, 1-1257, 1-1259, 1-1282, 1-1283, 1-1366, 1-1368, 1-1370, 1-1372, 1-1403, 1-1417, 1-1425, 1-1426, 1-1428, 1-1430, 1-1432, 1-1449, 1-1450, 1-1507, 1-1513, 1-1514, 1-1515, 1-1516, 1-1521, 1-1522, 1-1523, 1-1525, 1-1526, 1-1527, 1-1528, 1-1552, 1-1582, 1-1593, 1-1594, 1-1599, 1-1600, 1-1607 and 1-1608.

Test Example 5

Insecticidal Test on Brown Rice Planthopper

A wettable powder prepared in accordance with Formulation Example 2 was diluted with water to a concentration of an active ingredient of 500 ppm. Rice sprouts were dipped in this solution and put in a plastic cup having a capacity of 60 mL. Ten third-instar larvae of brown rice planthopper were released in the cup, the cup was lidded and placed in a thermostatic chamber at 25° C. for 6 days, and the number of dead larvae were counted for calculation of the mortality by Equation 2. The test was carried out by one series system.

Compounds which exhibit a mortality of 90% or higher in this test are indicated by compound numbers.

1-1, 1-3, 1-4, 1-6, 1-7, 1-8, 1-9, 1-10, 1-11, 1-12, 1-13, 1-14, 1-15, 1-17, 1-18, 1-20, 1-22, 1-24, 1-25, 1-26, 1-27, 1-29, 1-30, 1-31, 1-32, 1-35, 1-36, 1-37, 1-38, 1-39, 1-40, 1-41, 1-42, 1-43, 1-44, 1-48, 1-51, 1-52, 1-53, 1-54, 1-57, 1-58, 1-60, 1-63, 1-64, 1-65, 1-66, 1-69, 1-70, 1-73, 1-74, 1-75, 1-76, 1-77, 1-78, 1-80, 1-81, 1-82, 1-89, 1-90, 1-91, 1-92, 1-93, 1-94, 1-95, 1-97, 1-99, 1-100, 1-101, 1-102, 1-103, 1-104, 1-105, 1-106, 1-107, 1-108, 1-111, 1-112, 1-113, 1-114, 1-115, 1-117, 1-118, 1-121, 1-122, 1-123, 1-127, 1-128, 1-129, 1-130, 1-131, 1-133, 1-134, 1-136, 1-137, 1-145, 1-155, 1-157, 1-159, 1-160, 1-161, 1-171, 1-173, 1-178, 1-182, 1-183, 1-185, 1-186, 1-187, 1-190, 1-192, 1-194, 1-195, 1-196, 1-197, 1-198, 1-201, 1-205, 1-207, 1-208, 1-214, 1-215, 1-218, 1-219, 1-221, 1-223, 1-227, 1-235, 1-237, 1-239, 1-240, 1-241, 1-243, 1-244, 1-245, 1-246, 1-247, 1-248, 1-249, 1-250, 1-252, 1-253, 1-254, 1-257, 1-258, 1-259, 1-260, 1-261, 1-262, 1-263, 1-264, 1-265, 1-266, 1-269, 1-270, 1-273, 1-274, 1-275, 1-276, 1-277, 1-278, 1-281, 1-282, 1-285, 1-287, 1-288, 1-289, 1-290, 1-291, 1-292, 1-297, 1-298, 1-299, 1-301, 1-311, 1-312, 1-317, 1-318, 1-321, 1-322, 1-323, 1-324, 1-325, 1-326, 1-327, 1-331, 1-332, 1-333, 1-334, 1-339, 1-340, 1-341, 1-344, 1-345, 1-346, 1-347, 1-349, 1-351, 1-353, 1-357, 1-359, 1-364, 1-365, 1-383, 1-384, 1-385, 1-392, 1-393, 1-394, 1-395, 1-397, 1-401, 1-410, 1-411, 1-413, 1-414, 1-415, 1-447, 1-458, 1-460, 1-486, 1-524, 1-525, 1-526, 1-546, 1-550, 1-578, 1-579, 1-590, 1-668, 1-669, 1-670, 1-671, 1-696, 1-697, 1-794, 1-795, 1-872, 1-873, 1-875, 1-888, 1-889, 1-890, 1-891, 1-892, 1-893, 1-1062, 1-1063, 1-1104, 1-1105, 1-1106, 1-1107, 1-1108, 1-1134, 1-1135, 1-1137, 1-1150, 1-1151, 1-1176, 1-1177, 1-1179, 1-1192, 1-1194, 1-1195, 1-1196, 1-1197, 1-1255, 1-1256, 1-1257, 1-1282, 1-1283, 1-1355, 1-1356, 1-1357, 1-1358, 1-1360, 1-1361, 1-1362, 1-1363, 1-1364, 1-1365, 1-1366, 1-1368, 1-1369, 1-1370, 1-1371, 1-1373, 1-1375, 1-1376, 1-1377, 1-1378, 1-1379, 1-1380, 1-1382, 1-1383, 1-1384, 1-1385, 1-1386, 1-1400, 1-1402, 1-1403, 1-1404, 1-1406, 1-1408, 1-1411, 1-1413, 1-1414, 1-1415, 1-1416, 1-1417, 1-1418, 1-1419, 1-1421, 1-1422, 1-1423, 1-1425, 1-1427, 1-1428, 1-1429, 1-1430, 1-1431, 1-1432, 1-1433, 1-1434, 1-1436, 1-1439, 1-1449, 1-1451, 1-1452, 1-1453, 1-1455, 1-1459, 1-1460, 1-1461, 1-1465, 1-1467, 1-1476, 1-1505, 1-1507, 1-1510, 1-1511, 1-1512, 1-1513, 1-1514, 1-1515, 1-1516, 1-1519, 1-1520, 1-1523, 1-1525, 1-1527, 1-1528, 1-1529, 1-1530, 1-1531, 1-1532, 1-1533, 1-1534, 1-1535, 1-1536, 1-1539, 1-1540, 1-1541, 1-1542, 1-1543, 1-1544, 1-1545, 1-1547, 1-1549, 1-1550, 1-1552, 1-1553, 1-1554, 1-1577, 1-1578, 1-1579, 1-1580, 1-1581, 1-1582, 1-1586, 1-1593, 1-1598, 1-1599 and 1-1600.

Test Example 6

Miticidal Test on Two-Spotted Spider Mites

A wettable powder prepared in accordance with Formulation Example 2 was diluted with water to a concentration of an active ingredient of 500 ppm. Soybean seedlings which had been inoculated with imago two-spotted spider mites were dipped in the solution and dried in air. The treated soybean seedlings were placed in a thermostatic chamber at 25° C. for 13 days, and the number of live mites were assessed for calculation of the protective value by Equation 1. The test was carried out by one series system.

Compounds which exhibit a protective value of 90 or higher in this test are indicated by compound numbers.

1-1, 1-2, 1-3, 1-4, 1-6, 1-7, 1-8, 1-9, 1-10, 1-13, 1-14, 1-15, 1-16, 1-17, 1-18, 1-20, 1-22, 1-26, 1-27, 1-29, 1-30, 1-31, 1-32, 1-33, 1-34, 1-35, 1-36, 1-37, 1-38, 1-39, 1-40, 1-42, 1-43, 1-44, 1-46, 1-47, 1-48, 1-49, 1-50, 1-51, 1-52, 1-55, 1-57, 1-58, 1-62, 1-64, 1-69, 1-70, 1-73, 1-74, 1-77, 1-78, 1-81, 1-82, 1-86, 1-89, 1-90, 1-91, 1-92, 1-93, 1-94, 1-99, 1-100, 1-101, 1-102, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-125, 1-127, 1-128, 1-129, 1-130, 1-131, 1-132, 1-133, 1-134, 1-137, 1-155, 1-156, 1-157, 1-158, 1-159, 1-160, 1-161, 1-162, 1-167, 1-168, 1-170, 1-180, 1-182, 1-183, 1-186, 1-191, 1-192, 1-194, 1-195, 1-196, 1-197, 1-198, 1-199, 1-200, 1-201, 1-202, 1-205, 1-206, 1-207, 1-208, 1-209, 1-210, 1-213, 1-214, 1-215, 1-218, 1-219, 1-221, 1-223, 1-227, 1-228, 1-229, 1-230, 1-231, 1-232, 1-233, 1-234, 1-235, 1-237, 1-239, 1-240, 1-241, 1-243, 1-244, 1-245, 1-246, 1-247, 1-248, 1-249, 1-250, 1-252, 1-253, 1-254, 1-255, 1-256, 1-257, 1-258, 1-259, 1-260, 1-261, 1-262, 1-263, 1-264, 1-265, 1-266, 1-268, 1-269, 1-270, 1-273, 1-274, 1-275, 1-276, 1-277, 1-278, 1-280, 1-281, 1-282, 1-283, 1-284, 1-285, 1-286, 1-287, 1-288, 1-289, 1-290, 1-291, 1-292, 1-293, 1-294, 1-295, 1-296, 1-297, 1-298, 1-299, 1-300, 1-301, 1-302, 1-303, 1-304, 1-305, 1-306, 1-307, 1-308, 1-310, 1-311, 1-312, 1-313, 1-314, 1-317, 1-318, 1-320, 1-321, 1-322, 1-323, 1-324, 1-326, 1-327, 1-329, 1-330, 1-331, 1-339, 1-340, 1-345, 1-346, 1-347, 1-348, 1-353, 1-354, 1-357, 1-364, 1-365, 1-368, 1-369, 1-370, 1-371, 1-373, 1-374, 1-375, 1-376, 1-377, 1-383, 1-384, 1-385, 1-386, 1-389, 1-391, 1-392, 1-393, 1-394, 1-395, 1-397, 1-400, 1-401, 1-410, 1-411, 1-413, 1-414, 1-415, 1-443, 1-458, 1-459, 1-460, 1-461, 1-485, 1-486, 1-487, 1-489, 1-524, 1-525, 1-526, 1-527, 1-550, 1-578, 1-579, 1-590, 1-668, 1-669, 1-670, 1-671, 1-696, 1-697, 1-702, 1-703, 1-794, 1-795, 1-872, 1-873, 1-875, 1-879, 1-888, 1-889, 1-890, 1-891, 1-892, 1-893, 1-1062, 1-1063, 1-1104, 1-1105, 1-1106, 1-1107, 1-1108, 1-1109, 1-1134, 1-1135, 1-1137, 1-1150, 1-1176, 1-1177, 1-1179, 1-1192, 1-1193, 1-1194, 1-1195, 1-1196, 1-1197, 1-1250, 1-1257, 1-1259, 1-1282, 1-1283, 1-1355, 1-1356, 1-1357, 1-1358, 1-1360, 1-1362, 1-1363, 1-1364, 1-1365, 1-1366, 1-1368, 1-1369, 1-1370, 1-1371, 1-1372, 1-1373, 1-1374, 1-1376, 1-1378, 1-1379, 1-1380, 1-1382, 1-1383, 1-1384, 1-1385, 1-1386, 1-1392, 1-1400, 1-1402, 1-1403, 1-1404, 1-1406, 1-1407, 1-1408, 1-1409, 1-1411, 1-1412, 1-1413, 1-1415, 1-1416, 1-1417, 1-1418, 1-1419, 1-1420, 1-1421, 1-1422, 1-1423, 1-1424, 1-1425, 1-1426, 1-1427, 1-1428, 1-1429, 1-1430, 1-1431, 1-1432, 1-1433, 1-1434, 1-1436, 1-1439, 1-1440, 1-1449, 1-1450, 1-1451, 1-1452, 1-1453, 1-1455, 1-1456, 1-1459, 1-1460, 1-1465, 1-1466, 1-1467, 1-1468, 1-1476, 1-1505, 1-1506, 1-1507, 1-1509, 1-1510, 1-1511, 1-1512, 1-1513, 1-1514, 1-1515, 1-1516, 1-1517, 1-1519, 1-1520, 1-1527, 1-1528, 1-1529, 1-1530, 1-1531, 1-1532, 1-1533, 1-1534, 1-1535, 1-1536, 1-1538, 1-1539, 1-1540, 1-1541, 1-1542, 1-1544, 1-1545, 1-1546, 1-1547, 1-1548, 1-1549, 1-1550, 1-1553, 1-1554, 1-1555, 1-1557, 1-1559, 1-1561, 1-1565, 1-1566, 1-1571, 1-1573, 1-1574, 1-1576, 1-1577, 1-1578, 1-1579, 1-1580, 1-1581, 1-1582, 1-1586, 1-1587, 1-1588, 1-1593, 1-1595, 1-1598, 1-1599, 1-1600, 1-1601, 1-1602, 1-1603, 1-1605, 1-1607, 1-1608, 1-1609, 1-1610 and 1-1613.

Test Example 7

Miticidal Test on Two-Spotted Spider Mites

A wettable powder prepared in accordance with Formulation Example 2 was diluted with water to a concentration of an active ingredient of 100 ppm. The soil (100 g) in a cup of soybean seedlings which had been inoculated with imago two-spotted spider mites was irrigated with 5 mL of the solution. The treated soybean seedlings were placed in a thermostatic chamber at 25° C. for 13 days, and the number of live mites were assessed for calculation of the protective value by Equation 1. The test was carried out by one series system.

Compounds which exhibit a protective value of 90 or higher in this test are indicated by compound numbers.

1-16, 1-32, 1-34, 1-36, 1-38, 1-48, 1-90, 1-92, 1-106, 1-116, 1-120, 1-132, 1-218, 1-1356, 1-1360, 1-1364, 1-1368, 1-1412, 1-1416, 1-1418, 1-1420, 1-1428, 1-1430, 1-1434 and 1-1440.

Test Example 8

Nematicidal Test on Root-Knot Nematode

A compound to be tested was dissolved in N,N-dimethylformamide containing 1 mass % of tween 20, and this solution was diluted with distilled water to a concentration of an active ingredient of 20 ppm. 0.5 mL of the solution was mixed with 0.5 mL of a suspension containing about 30 second-instar larvaes of southern root-knot nematodes, and the mixture was placed in a thermostatic chamber at 25° C. for 5 days. The number of dead nematodes and the number of live nematodes were assessed by a microscope for calculation of the mortality by Equation 3. The test was carried out by two series system.

Compounds which exhibit a mortality of 90% or higher in this test are indicated by compound numbers.

1-11, 1-12, 1-30, 1-42, 1-54, 1-90, 1-92, 1-106, 1-116, 1-118, 1-120, 1-124, 1-160, 1-162, 1-270, 1-348, 1-1412, 1-1414, 1-1416, 1-1418 and 1-1420.

$$\text{Protective value} = \left(1 - \frac{\text{Numbers of live female mites in treated area}}{\text{Number of live female mites in non-treated area}}\right) \times 100 \quad \text{Equation 1}$$

$$\text{Mortality (\%)} = \left(1 - \frac{\text{Number of live insects}}{\text{Number of test insects}}\right) \times 100 \quad \text{Equation 2}$$

$$\text{Mortality (\%)} = \frac{\text{Number of dead nematode in treated area}}{\text{Number of dead nematode in treated area} + \text{Number of live nematode in treated area}} \times 100 \quad \text{Equation 3}$$

INDUSTRIAL APPLICABILITY

The pesticide comprising the pyrazole derivative of the present invention or an agriculturally acceptable salt thereof exhibits an excellent pesticidal effect against a wide range of pests in agricultural and horticultural fields, can control pests which have acquired resistance, and exhibits outstanding effects against mites, pest hemipterans, pest coleoptera, nematodes and pest lepidopterans. Further, since it is excellent in infiltration, safe and labor-saving application by soil treatment is possible, and it is agriculturally and horticulturally useful.

The entire disclosures of Japanese Patent Application No. 2007-271857 filed on Oct. 18, 2007 and Japanese Patent Application No. 2007-271858 filed on Oct. 18, 2007 including specifications, claims and summaries are incorporated herein by reference in their entireties.

The invention claimed is:
1. A 3-alkoxy-1-phenyl-pyrazole derivative represented by the formula [I] or an agriculturally acceptable salt thereof:

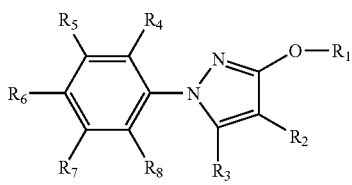

wherein $R_1$ is a $C_1$-$C_{10}$ alkyl group which may be substituted, a $C_1$-$C_{10}$ haloalkyl group, a $C_3$-$C_{10}$ cycloalkyl group which may be mono-substituted or poly-substituted by a substituent group α, a $C_3$-$C_8$ cycloalkyl $C_1$-$C_8$ alkyl group which may be mono-substituted or poly-substituted by a substituent group α, a $C_1$-$C_8$ alkoxy $C_1$-$C_8$ alkyl group which may be mono-substituted or poly-substituted by a substituent group α, a $C_1$-$C_8$ alkoxy $C_2$-$C_8$ alkenyl group which may be mono-substituted or poly-substituted by a substituent group α, a $C_1$-$C_8$ alkoxy $C_1$-$C_8$ alkoxy $C_1$-$C_8$ alkyl group which may be mono-substituted or poly-substituted by a substituent group α, a $C_2$-$C_{10}$ alkenyl group which may be mono-substituted or poly-substituted by a substituent group α, a $C_2$-$C_{10}$ alkynyl group which may be mono-substituted or poly-substituted by a substituent group α, a $C_2$-$C_{10}$ alkynyloxy $C_1$-$C_6$ alkyl group which may be mono-substituted or poly-substituted by a substituent group α, a $C_1$-$C_8$ alkylthio $C_1$-$C_8$ alkyl group which may be mono-substituted or poly-substituted by a substituent group α, a $C_1$-$C_8$ alkylsulfinyl $C_1$-$C_8$ alkyl group which may be mono-substituted or poly-substituted by a substituent group α, a $C_1$-$C_8$ alkylsulfonyl $C_1$-$C_8$ alkyl group which may be mono-substituted or poly-substituted by a substituent group α, a $C_1$-$C_{10}$ alkylsulfonyl group which may be mono-substituted or poly-substituted by a substituent group α, a benzenesulfonyl group which may be mono-substituted or poly-substituted by a substituent group α, a $C_1$-$C_{10}$ thiocyanatoalkyl group which may be mono-substituted or poly-substituted by a substituent group α, an aryl-C(=X) group which may be mono-substituted or poly-substituted by a substituent group α, a $C_1$-$C_{10}$ alkyl-C(=X) group which may be mono-substituted or poly-substituted by a substituent group α, a $C_1$-$C_8$ alkyl C(=X)$C_1$-$C_4$ alkyl group which may be mono-substituted or poly-substituted by a substituent group α, a $C_1$-$C_8$ alkoxy C(=X)$C_1$-$C_8$ alkyl group which may be mono-substituted or poly-substituted by a substituent group α, a pentafluorothio $C_1$-$C_{10}$ alkyl group, a tri($C_1$-$C_3$)alkylsilyl $C_1$-$C_8$ alkyl group which may be mono-substituted or poly-substituted by a substituent group α, a $C_3$-$C_{10}$ trialkylsilyl group which may be mono-substituted or poly-substituted by a substituent group α, an aryl group which may be mono-substituted or poly-substituted by a substituent group α, an aryl $C_1$-$C_8$ alkyl group which may be mono-substituted or poly-substituted by a substituent group α, an aryloxy $C_1$-$C_8$ alkyl group which may be mono-substituted or poly-substituted by a substituent group α, an arylthio $C_1$-$C_8$ alkyl group which may be mono-substituted or poly-substituted by a substituent group α, a heteroaryl group which may be mono-substituted or poly-substituted by a substituent group α, a heteroaryl $C_1$-$C_8$ alkyl group which may be mono-substituted or poly-substituted by a substituent group α, a heteroaryloxy $C_1$-$C_8$ alkyl group which may be mono-substituted or poly-substituted by a substituent group α, a heteroarylthio $C_1$-$C_8$ alkyl group which may be mono-substituted or poly-substituted by a substituent group α, a tetrahydrofurfuryl group, a tetrahydrofurfuryl $C_1$-$C_8$ alkyl group which may be mono-substituted or poly-substituted by a substituent group α, an $R_{1a}(R_{1b})$NC(=X) group, or an $R_{1a}(R_{1b})$NC(=X)$C_1$-$C_4$ alkyl group;

$R_2$ is a hydrogen atom, a hydroxy group, a halogen atom, a cyano group, a $H_2$NC(=X) group, a carboxy group, a $C_1$-$C_4$ alkoxy C(=X) group, a HC(=X) group, a nitro group, an amino group, an azide group, a $C_1$-$C_4$ alkyl group which may be mono-substituted or poly-substituted by a substituent group α, a $C_1$-$C_4$ alkoxy group which may be mono-substituted or poly-substituted by a substituent group α, a $C_1$-$C_4$ alkoxy $C_1$-$C_4$ alkyl group which may be mono-substituted or poly-substituted by a substituent group α, a $C_2$-$C_6$ alkenyl group which may be mono-substituted or poly-substituted by a substituent group α, a $C_2$-$C_6$ alkynyl group which may be mono-substituted or poly-substituted by a substituent group α, a $C_3$-$C_8$ cycloalkyl group which may be mono-substituted or poly-substituted by a substituent group α, or a $C_1$-$C_4$ alkyl C(=X) group which may be mono-substituted or poly-substituted by a substituent group α, $R_3$ is a hydrogen atom, a hydroxy group, a halogen atom, a cyano group, a carboxy group, a HC(=X) group, an $R_{3a}(R_{3b})$N(C=X) group, an azide group, a nitro group, a $C_1$-$C_4$ alkyl group which may be mono-substituted or poly-substituted by a substituent group α, a $C_2$-$C_4$ alkenyl group which may be mono-substituted or poly-substituted by a substituent group α*, a $C_2$-$C_4$ alkynyl group which may be mono-substituted or poly-substituted by a substituent group α, a $C_3$-$C_8$ cycloalkyl group which may be mono-substituted or poly-substituted by a substituent group α, a $C_1$-$C_8$ cycloalkyl $C_1$-$C_4$ alkyl group which may be mono-substituted or poly-substituted by a substituent group α, a $C_1$-$C_6$ alkyl C(=X) group which may be mono-substituted or poly-substituted by a substituent group α, a $C_2$-$C_8$ alkenyl C(=X) group which may be mono-substituted or poly-substituted by a substituent group α, a $C_3$-$C_8$ cycloalkyl C(=X) group which may be mono-substituted or poly-substituted by a substituent group α, a $C_1$-$C_6$ alkoxy group which may be mono-substituted or poly-substituted by a substituent group α, a $C_3$-$C_8$ cycloalkyloxy group which may be mono-substituted or poly-substituted by a substituent group α, a $C_1$-$C_6$ alkoxy $C_1$-$C_4$ alkyl group which may be mono-substituted or poly-substituted by a substituent group α, a $C_1$-$C_6$ alkoxy C(=X) group which may be mono-substituted or poly-substituted by a substituent group α, a mercapto group, a thiocyanato group, a $C_1$-$C_6$ alkylthio group which may be mono-substituted or poly-substituted by a substituent group α, a $C_1$-$C_6$ alkylsulfinyl group which may be mono-substituted or poly-substituted by a substituent group α, a $C_1$-$C_6$ alkylsulfonyl group which may be mono-substituted or poly-substituted by a substituent group α, a $C_3$-$C_8$ cycloalkylthio group which may be mono-substituted or poly-substituted by a substituent group α, a $C_3$-$C_8$ cycloalkylsulfinyl group which may be mono-substituted or poly-substituted by a substituent group α, a $C_3$-$C_8$ cycloalkylsulfonyl group which may be mono-substituted or poly-substituted by a substituent group α, a $C_1$-$C_6$ alkylsulfonyloxy group which may be mono-substituted or poly-substituted by a substituent group α, an $R_{3a}(R_{3b})$N group, an $R_{3f}(R_{3g})$C=N group, or an $R_{3h}$ON=C($R_{3i}$) group;

each of $R_4$, $R_5$, $R_6$ and $R_8$ which are independent of one another, is a hydrogen atom, an amino group, an azide group, a nitro group, a hydroxy group, a halogen atom, a carbamoyl group, a cyano group, a carboxy group, a HC(=X) group, a $C_1$-$C_4$ alkyl group which may be mono-substituted or poly-substituted by a substituent group α, a $C_1$-$C_4$ alkoxy group which may be mono-substituted or poly-substituted by a substituent group α, a formylamino group, a $C_1$-$C_6$ alkyl C(=X) group, an amino group which may be mono-substituted or poly-substituted by a substituent group α, a $C_1$-$C_6$ alkylthiocarbonylamino group which may be mono-substituted or poly-substituted by a substituent group α, a $C_2$-$C_4$ alkenyl group which may be mono-substituted or poly-substituted by a substituent group α, a $C_2$-$C_4$ alkynyl group which may be mono-substituted or poly-substituted by a substituent group α, or a $C_3$-$C_6$ cycloalkyl group which may be mono-substituted or poly-substituted by a substituent group α;

$R_7$ is a $C_2$-$C_4$ haloalkylthio group, a $C_2$-$C_4$ haloalkylsulfinyl group, a $C_2$-$C_4$ haloalkenylthio group, a $C_2$-$C_4$ haloalkenylsulfinyl group, a cyclopropylmethylthio group which may be mono-substituted or poly-substituted by a substituent group α, or a cyclopropylmethylsulfinyl group which may be mono-substituted or poly-substituted by a substituent group α, X is an oxygen atom or a sulfur atom;

each of $R_{1a}$ and $R_{1b}$ which are independent of each other, is a hydrogen atom, a $C_1$-$C_4$ alkyl group which may be mono-substituted or poly-substituted by a substituent group α, a $C_3$-$C_8$ cycloalkyl group which may be mono-substituted or poly-substituted by a substituent group α, or a $C_1$-$C_4$ alkoxy group which may be mono-substituted or poly-substituted by a substituent group α, $R_{1a}$ and $R_{1b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{1a}$ and $R_{1b}$ are bonded;

each of $R_{3a}$ and $R_{3b}$ which are independent of each other, is a hydrogen atom, a cyano group, an amino group, a hydroxy group, a formyl group, a $C_1$-$C_6$ alkyl group which may be mono-substituted or poly-substituted by a substituent group α, a $C_2$-$C_8$ alkenyl group which may be mono-substituted or poly-substituted by a substituent group α, a $C_2$-$C_8$ alkynyl group which may be mono-substituted or poly-substituted by a substituent group α, a $C_1$-$C_4$ alkoxy group which may be mono-substituted or poly-substituted by a substituent group α, a $C_3$-$C_8$ cycloalkyl group which may be mono-substituted or poly-substituted by a substituent group α, a $C_3$-$C_8$ cycloalkyl $C_1$-$C_4$ alkyl group which may be mono-substituted or poly-substituted by a substituent group α, a $C_1$-$C_8$ alkoxy $C_1$-$C_4$ alkyl group which may be mono-substituted or poly-substituted by a substituent group α, a $C_1$-$C_8$ alkylthio $C_1$-$C_4$ alkyl group which may be mono-substituted or poly-substituted by a substituent group α, a $C_1$-$C_8$ alkylsulfinyl $C_1$-$C_4$ alkyl group which may be mono-substituted or poly-substituted by a substituent group α, a $C_1$-$C_8$ alkylsulfonyl $C_1$-$C_4$ alkyl group which may be mono-substituted or poly-substituted by a substituent group α, a $C_1$-$C_8$ alkylsulfonyl group which may be mono-substituted or poly-substituted by a substituent group α, a $C_1$-$C_8$ alkylsulfinyl group which may be mono-substituted or poly-substituted by a substituent group α, a $C_1$-$C_8$ alkylthio group which may be mono-substituted or poly-substituted by a substituent group α, a $C_2$-$C_8$ alkenylsulfonyl group which may be mono-substituted or poly-substituted by a substituent group α, a $C_1$-$C_8$ alkoxy $C_1$-$C_4$ alkylsulfonyl group which may be mono-substituted or poly-substituted by a substituent group α, a $C_3$-$C_8$ cycloalkylsulfonyl group which may be mono-substituted or poly-substituted by a substituent group α, a di($C_1$-$C_6$ alkyl)aminosulfonyl group which may be mono-substituted or poly-substituted by a substituent group α, a benzenesulfonyl group which may be mono-substituted or poly-substituted by a substituent group α, a $C_1$-$C_8$ alkyl C(=X) group which may be mono-substituted or poly-substituted by a substituent group α, a $C_1$-$C_8$ alkyl C(=X)C(=X) group which may be mono-substituted or poly-substituted by a substituent group α, a $C_1$-$C_8$ alkoxy C(=X) group which may be mono-substituted or poly-substituted by a substituent group α, a $C_1$-$C_8$ alkoxy C(=X)C(=X) group which may be mono-substituted or poly-substituted by a substituent group α, a $C_2$-$C_8$ alkenyl C(=X) group which may be mono-substituted or poly-substituted by a substituent group α, a $C_2$-$C_8$ alkynyl C(=X) group which may be mono-substituted or poly-substituted by a substituent group α, a $C_3$-$C_8$ cycloalkyl C(=X) group which may be mono-substituted or poly-substituted by a substituent group α, a $C_1$-$C_8$ alkyl C(=X)$C_1$-$C_4$ alkyl group which may be mono-substituted or poly-substituted by a substituent group α, an $R_{3c}(R_{3d})$N group, an $R_{3c}(R_{3d})$NC(=X) group, or a $C_1$-$C_8$ alkylthio C(=X) group which may be mono-substituted or poly-substituted by a substituent group α, each of $R_{3c}$ and $R_{3d}$ which are independent of each other, is a hydrogen atom, a $C_1$-$C_4$ alkyl group which may be mono-substituted or poly-substituted by a substituent group α, a $C_1$-$C_4$ alkoxy group which may be mono-substituted or poly-substituted by a substituent group α, or a $C_3$-$C_8$ cycloalkyl group which may be mono-substituted or poly-substituted by a substituent group α, $R_{3c}$ and $R_{3d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3c}$ and $R_{3d}$ are bonded;

each of $R_{3f}$ and $R_{3g}$ which are independent of each other, is a hydrogen atom, a halogen atom, a $C_1$-$C_8$ alkyl group which may be mono-substituted or poly-substituted by a substituent group α, a $C_1$-$C_8$ alkoxy group which may be mono-substituted or poly-substituted by a substituent group α, a $C_3$-$C_8$ cycloalkyl group which may be mono-substituted or poly-substituted by a substituent group α, an amino group, a dimethylamino group, a $C_1$-$C_4$ alkylthio group, an imidazolyl group, an aryl group which may be mono-substituted or poly-substituted by a substituent group α, or a heteroaryl group which may be mono-substituted or poly-substituted by a substituent group α, $R_{3f}$ and $R_{3g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3f}$ and $R_{3g}$ are bonded; and each of $R_{3h}$ and $R_{3i}$ which are independent of each other, is hydrogen atom, a $C_1$-$C_4$ alkyl group which may be mono-substituted or poly-substituted by a substituent group α, a $C_2$-$C_8$ alkenyl group which may be mono-substituted or poly-substituted by a substituent group α, or a $C_2$-$C_8$ alkynyl group which may be mono-substituted or poly-substituted by a substituent group α,
wherein substituent group α is a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a $C_3$-$C_8$ cycloalkyl group, a $C_1$-$C_4$ alkylthio group, a $C_1$-$C_4$ alkylsulfinyl group, $C_1$-$C_4$ alkylsulfonyl group, or a $C_1$-$C_4$ alkylsulfonyloxy group, and
wherein substituent group α* is a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a $C_3$-$C_8$ cycloalkyl group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group.

2. The 3-alkoxy-1-phenyl-pyrazole derivative or an agriculturally acceptable salt thereof according to claim 1, wherein in the above formula [I],
$R_1$ is a $C_1$-$C_{10}$ alkyl group which may be mono-substituted or poly-substituted by a substituent group α, a $C_1$-$C_{10}$ haloalkyl group, a $C_3$-$C_{10}$ cycloalkyl group which may be mono-substituted or poly-substituted by a substituent group α, a $C_3$-$C_8$ cycloalkyl $C_1$-$C_8$ alkyl group which may be mono-substituted or poly-substituted by a substituent group α, a $C_1$-$C_8$ alkoxy $C_1$-$C_8$ alkyl group which may be mono-substituted or poly-substituted by a substituent group α, a $C_1$-$C_8$ alkoxy $C_2$-$C_8$ alkenyl group which may be mono-substituted or poly-substituted by a substituent group α, a $C_1$-$C_8$ alkoxy $C_1$-$C_8$ alkoxy $C_1$-$C_8$ alkyl group which may be mono-substituted or poly-substituted by a substituent group α, a $C_{2l}$-$C_{10}$ alkenyl group which may be mono-substituted or poly-substituted by a substituent group α, a $C_2$-$C_{10}$ alkynyl group which may be mono-substituted or poly-substituted by a substituent group α, a $C_2$-$C_{10}$ alkynyloxy $C_1$-$C_6$ alkyl group which may be mono-substituted or poly-substituted by a substituent group α, a $C_1$-$C_8$ alkylthio $C_1$-$C_8$ alkyl group which may be mono-substituted or poly-substituted by a substituent group α, a $C_1$-$C_8$ alkylsulfinyl $C_1$-$C_8$ alkyl group which may be mono-substituted or poly-substituted by a substituent group α, a $C_1$-$C_8$ alkylsulfonyl $C_1$-$C_8$ alkyl group which may be mono-substituted or poly-substituted by a substituent group α, a $C_1$-$C_{10}$ alkylsulfonyl group which may be mono-substituted or poly-substituted by a substituent group α, a benzenesulfonyl group which may be mono-substituted or poly-substituted by a substituent group α, a $C_1$-$C_{10}$ thiocyanatoalkyl group which may be mono-substituted or poly-substituted by a substituent group α, an aryl-C(=X) group which may be mono-substituted or poly-substituted by a substituent group α, a $C_1$-$C_{10}$ alkyl-C(=X) group which may be mono-substituted or poly-substituted by a substituent group α, a $C_1$-$C_8$ alkyl C(=X)$C_1$-$C_4$ alkyl group which may be mono-substituted or poly-substituted by a substituent group α, a $C_1$-$C_8$ alkoxy C(=X)$C_1$-$C_8$ alkyl group which may be mono-substituted or poly-substituted by a substituent group α, a pentafluorothio $C_1$-$C_{10}$ alkyl group, a tri($C_1$-$C_3$)alkylsilyl $C_1$-$C_8$ alkyl group which may be mono-substituted or poly-substituted by a substituent group α, a $C_3$-$C_{10}$ trialkylsilyl group which may be mono-substituted or poly-substituted by a substituent group α, an aryl group which may be mono-substituted or poly-substituted by a substituent group α, an aryl $C_1$-$C_8$ alkyl group which may be mono-substituted or poly-substituted by a substituent group α, an aryloxy $C_1$-$C_8$ alkyl group which may be mono-substituted or poly-substituted by a substituent group α, an arylthio $C_1$-$C_8$ alkyl group which may be mono-substituted or poly-substituted by a substituent group α, a heteroaryl group which may be mono-substituted or poly-substituted by a substituent group α, a heteroaryl $C_1$-$C_8$ alkyl group which may be mono-substituted or poly-substituted by a substituent group α, a heteroaryloxy $C_1$-$C_8$ alkyl group which may be mono-substituted or poly-substituted by a substituent group α, a heteroarylthio $C_1$-$C_8$ alkyl group which may be mono-substituted or poly-substituted by a substituent group α, a tetrahydrofurfuryl group, a tetrahydrofurfuryl $C_1$-$C_8$ alkyl group which may be mono-substituted or poly-substituted by a substituent group α, an $R_{1a}(R_{1b})NC(=X)$ group, or an $R_{1a}(R_{1b})NC(=X)$ $C_1$-$C_4$ alkyl group;

$R_2$ is a hydrogen atom, a hydroxy group, a halogen atom, a cyano group, a $H_2$ NC(=X) group, a carboxy group, a HC(=X) group, a nitro group, an amino group, an azide group, a $C_1$-$C_4$ alkyl group which may be mono-substituted or poly-substituted by a substituent group α, a $C_1$-$C_4$ alkoxy group which may be mono-substituted or poly-substituted by a substituent group α, a $C_1$-$C_4$ alkoxy $C_1$-$C_4$ alkyl group which may be mono-substituted or poly-substituted by a substituent group α, a $C_2$-$C_6$ alkenyl group which may be mono-substituted or poly-substituted by a substituent group α, a $C_2$-$C_6$ alkynyl group which may be mono-substituted or poly-substituted by a substituent group α, a $C_3$-$C_8$ cycloalkyl group which may be mono-substituted or poly-substituted by a substituent group α, or a $C_1$-$C_4$ alkyl C(=X) group which may be mono-substituted or poly-substituted by a substituent group α, $R_3$ is a hydrogen atom, a hydroxy group, a halogen atom, a cyano group, a carboxy group, a HC(=X) group, an $R_{3a}(R_{3b})N(C=X)$ group, an azide group, a nitro group, a $C_1$-$C_4$ alkyl group which may be mono-substituted or poly-substituted by a substituent group α, a $C_2$-$C_4$ alkenyl group which may be mono-substituted or poly-substituted by a substituent group α, a $C_2$-$C_4$ alkynyl group which may be mono-substituted or poly-substituted by a substituent group α, a $C_3$-$C_8$ cycloalkyl group which may be mono-substituted or poly-substituted by a substituent group α, a $C_1$-$C_8$ cycloalkyl $C_1$-$C_4$ alkyl group which may be mono-substituted or poly-substituted by a substituent group α, a $C_1$-$C_6$ alkyl C(=X) group which may be mono-substituted or poly-substituted by a substituent group α, a $C_2$-$C_8$ alkenyl C(=X) group which may be mono-substituted or poly-substituted by a substituent group α, a $C_3$-$C_8$ cycloalkyl C(=X) group which may be mono-substituted or poly-substituted by a substituent group α, a $C_1$-$C_6$ alkoxy group which may be mono-substituted or poly-substituted by a substituent group α, a $C_3$-$C_8$ cycloalkyloxy group which may be mono-substituted or poly-substituted by a substituent group α, a $C_1$-$C_6$ alkoxy $C_1$-$C_4$ alkyl group which may be mono-substituted or poly-substituted by a substituent group α, a $C_1$-$C_6$ alkoxy C(=X) group which may be mono-substituted or poly-substituted by a substituent group α, a mercapto group, a thiocyanato group, a $C_1$-$C_6$ alkylthio group which may be mono-substituted or poly-substituted by a substituent group α, a $C_1$-$C_6$ alkylsulfinyl group which may be mono-substituted or poly-substituted by a substituent group α, a $C_1$-$C_6$ alkylsulfonyl group which may be mono-substituted or poly-substituted by a substituent group α, a $C_3$-$C_8$ cycloalkylthio group which may be mono-substituted or poly-substituted by a substituent group α, a $C_3$-$C_8$ cycloalkylsulfinyl group which may be mono-substituted or poly-substituted by a substituent group α, a $C_3$-$C_8$ cycloalkylsulfonyl group which may be mono-substituted or poly-substituted by a substituent group α, a $C_1$-$C_6$ alkylsulfonyloxy group which may be mono-substituted or poly-substituted by a substituent group α, an $R_{3a}(R_{3b})N$ group, an $R_{3f}(R_{3g})C=N$ group, or an $R_{3h}ON=C(R_{3i})$ group;

each of $R_4$, $R_5$, $R_6$ and $R_8$ which are independent of one another, is a hydrogen atom, an amino group, an azide group, a nitro group, a hydroxy group, a halogen atom, a carbamoyl group, a cyano group, a carboxy group, a $HC(=X)$ group, a $C_1$-$C_4$ alkyl group which may be mono-substituted or poly-substituted by a substituent group α, a $C_1$-$C_4$ alkoxy group which may be mono-substituted or poly-substituted by a substituent group α, a formylamino group, a $C_1$-$C_6$ alkylcarbonylamino group which may be mono-substituted or poly-substituted by a substituent group α, a $C_1$-$C_6$ alkylthiocarbonylamino group which may be mono-substituted or poly-substituted by a substituent group α, a $C_2$-$C_4$ alkenyl group which may be mono-substituted or poly-substituted by a substituent group α, a $C_2$-$C_4$ alkynyl group which may be mono-substituted or poly-substituted by a substituent group α, or a $C_3$-$C_6$ cycloalkyl group which may be mono-substituted or poly-substituted by a substituent group α, $R_7$ is a $C_2$-$C_4$ haloalkylthio group, a $C_2$-$C_4$ haloalkylsulfinyl group, a $C_2$-$C_4$ haloalkenylthio group, a $C_2$-$C_4$ haloalkenylsulfinyl group, a cyclopropylmethylthio group which may be mono-substituted or poly-substituted by a substituent group α, or a cyclopropylmethylsulfinyl group which may be mono-substituted or poly-substituted by a substituent group α, X is an oxygen atom or a sulfur atom;

each of $R_{1a}$ and $R_{1b}$ which are independent of each other, is a hydrogen atom, a $C_1$-$C_4$ alkyl group which may be mono-substituted or poly-substituted by a substituent group α, a $C_3$-$C_8$ cycloalkyl group which may be mono-substituted or poly-substituted by a substituent group α, or a $C_1$-$C_4$ alkoxy group which may be mono-substituted or poly-substituted by a substituent group α, $R_{1a}$ and $R_{1b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{1a}$ and $R_{1b}$ are bonded;

each of $R_{3a}$ and $R_{3b}$ which are independent of each other, is a hydrogen atom, a cyano group, an amino group, a hydroxy group, a $C_1$-$C_6$ alkyl group which may be mono-substituted or poly-substituted by a substituent group α, a $C_2$-$C_8$ alkenyl group which may be mono-substituted or poly-substituted by a substituent group α, a $C_2$-$C_8$ alkynyl group which may be mono-substituted or poly-substituted by a substituent group α, a $C_1$-$C_4$ alkoxy group which may be mono-substituted or poly-substituted by a substituent group α, a $C_3$-$C_8$ cycloalkyl group which may be mono-substituted or poly-substituted by a substituent group α, a $C_3$-$C_8$ cycloalkyl $C_1$-$C_4$ alkyl group which may be mono-substituted or poly-substituted by a substituent group α, a $C_1$-$C_8$ alkoxy $C_1$-$C_4$ alkyl group which may be mono-substituted or poly-substituted by a substituent group α, a $C_1$-$C_8$ alkylthio $C_1$-$C_4$ alkyl group which may be mono-substituted or poly-substituted by a substituent group α, a $C_1$-$C_8$ alkylsulfinyl $C_1$-$C_4$ alkyl group which may be mono-substituted or poly-substituted by a substituent group α, a $C_1$-$C_8$ alkylsulfonyl $C_1$-$C_4$ alkyl group which may be mono-substituted or poly-substituted by a substituent group α, a $C_1$-$C_8$ alkylsulfonyl group which may be mono-substituted or poly-substituted by a substituent group α, a $C_1$-$C_8$ alkylsulfinyl group which may be mono-substituted or poly-substituted by a substituent group α, a $C_1$-$C_8$ alkylthio group which may be mono-substituted or poly-substituted by a substituent group α, a $C_2$-$C_8$ alkenylsulfonyl group which may be mono-substituted or poly-substituted by a substituent group α, a $C_1$-$C_8$ alkoxy $C_1$-$C_4$ alkylsulfonyl group which may be mono-substituted or poly-substituted by a substituent group α, a $C_3$-$C_8$ cycloalkylsulfonyl group which may be mono-substituted or poly-substituted by a substituent group α, a di($C_1$-$C_6$ alkyl)aminosulfonyl group which may be mono-substituted or poly-substituted by a substituent group α, a benzenesulfonyl group which may be mono-substituted or poly-substituted by a substituent group α, a $C_1$-$C_8$ alkyl $C(=X)$ group which may be mono-substituted or poly-substituted by a substituent group α, a $C_1$-$C_8$ alkyl $C(=X)C(=X)$ group which may be mono-substituted or poly-substituted by a substituent group α, a $C_1$-$C_8$ alkoxy $C(=X)$ group which may be mono-substituted or poly-substituted by a substituent group α, a $C_1$-$C_8$ alkoxy $C(=X)C(=X)$ group which may be mono-substituted or poly-substituted by a substituent group α, a $C_2$-$C_8$ alkenyl $C(=X)$ group which may be mono-substituted or poly-substituted by a substituent group α, a $C_2$-$C_8$ alkynyl $C(=X)$ group which may be mono-substituted or poly-substituted by a substituent group α, a $C_3$-$C_8$ cycloalkyl $C(=X)$ group which may be mono-substituted or poly-substituted by a substituent group α, a $C_1$-$C_8$ alkyl $C(=X)C_1$-$C_4$ alkyl group which may be mono-substituted or poly-substituted by a substituent group α, an $R_{3c}(R_{3d})N$ group, an $R_{3c}(R_{3d})NC(=X)$ group, or a $C_1$-$C_8$ alkylthio $C(=X)$ group which may be mono-substituted or poly-substituted by a substituent group α, each of $R_{3c}$ and $R_{3d}$ which are independent of each other, is a hydrogen atom, a $C_1$-$C_4$ alkyl group which may be mono-substituted or poly-substituted by a substituent group α, a $C_1$-$C_4$ alkoxy group which may be mono-substituted or poly-substituted by a substituent group α, or a $C_3$-$C_8$ cycloalkyl group which may be mono-substituted or poly-substituted by a substituent group α, $R_{3c}$ and $R_{3d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3c}$ and $R_{3d}$ are bonded;

each of $R_{3f}$ and $R_{3g}$ which are independent of each other, is a hydrogen atom, a halogen atom, a $C_1$-$C_8$ alkyl group which may be mono-substituted or poly-substituted by a substituent group α, a $C_1$-$C_8$ alkoxy group which may be mono-substituted or poly-substituted by a substituent group α, a $C_3$-$C_8$ cycloalkyl group which may be mono-substituted or poly-substituted by a substituent group α, an amino group, a dimethylamino group, a $C_1$-$C_4$ alkylthio group or an imidazolyl group;

$R_{3f}$ and $R_{3g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{3f}$ and $R_{3g}$ are bonded; and each of $R_{3h}$ and $R_{3i}$ which are independent of each other, is hydrogen atom, a $C_1$-$C_4$ alkyl group which may be mono-substituted or poly-substituted by a substituent group α, a $C_2$-$C_8$ alkenyl group which may be mono-substituted or poly-substituted by a substituent group α, or a $C_2$-$C_8$ alkynyl group which may be mono-substituted or poly-substituted by a substituent group α, wherein substituent group α is a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a difluoromethoxy group, a trifluoromethoxy group, a $C_3$-$C_8$ cycloalkyl group, a trifluoromethyl group, a trifluoromethylthio group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group.

3. A 3-alkoxy-1-phenylpyrazole derivative represented by the formula [I'] or an agriculturally acceptable salt thereof:

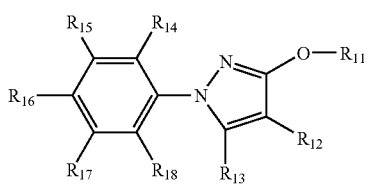

[I']

wherein $R_{11}$ is a $C_1$-$C_3$ alkyl group which may be mono-substituted or poly-substituted by a substituent group α, or a $C_1$-$C_3$ haloalkyl group, $R_{12}$ is a hydrogen atom, a hydroxy group, a halogen atom, a cyano group, a nitro group, an amino group, or a $C_1$-$C_3$ alkyl group which may be mono-substituted or poly-substituted by a substituent group α, $R_{13}$ is a hydrogen atom, a hydroxy group, a halogen atom, a cyano group, a carboxy group, a HC(=X) group, an $R_{13c}(R_{13d})$N(C=X) group, a $C_1$-$C_3$ alkyl group which may be mono-substituted or poly-substituted by a substituent group α*, a $C_2$-$C_3$ alkenyl group which may be mono-substituted or poly-substituted by a substituent group α, a $C_2$-$C_3$ alkynyl group which may be mono-substituted or poly-substituted by a substituent group α, a $C_3$-$C_8$ cycloalkyl group which may be mono-substituted or poly-substituted by a substituent group α, a $C_1$-$C_3$ alkyl C(=X) group which may be mono-substituted or poly-substituted by a substituent group α, a $C_2$-$C_3$ alkenyl C(=X) group which may be mono-substituted or poly-substituted by a substituent group α, a $C_3$-$C_8$ cycloalkyl C(=X) group which may be mono-substituted or poly-substituted by a substituent group α, a $C_1$-$C_3$ alkoxy group which may be mono-substituted or poly-substituted by a substituent group α, a $C_3$-$C_6$ cycloalkyloxy group which may be mono-substituted or poly-substituted by a substituent group α, a $C_1$-$C_3$ alkoxy $C_1$-$C_3$ alkyl group which may be mono-substituted or poly-substituted by a substituent group α, a $C_1$-$C_3$ alkoxy C(=X) group which may be mono-substituted or poly-substituted by a substituent group α, an $R_{13a}(R_{13b})$N group, or an $R_{13c}(R_{13d})$C=N group, each of $R_{14}$, $R_{15}$, $R_{16}$ and $R_{18}$ which are independent of one another, is a hydrogen atom, a hydroxy group, a halogen atom, a cyano group, a $C_1$-$C_3$ alkyl group which may be mono-substituted or poly-substituted by a substituent group α, or a $C_1$-$C_3$ alkoxy group which may be mono-substituted or poly-substituted by a substituent group α, $R_{17}$ is a $C_2$-$C_3$ haloalkylthio group or a $C_2$-$C_3$ haloalkylsulfinyl group, X is an oxygen atom or a sulfur atom, each of $R_{13a}$ and $R_{13b}$ which are independent of each other, is a hydrogen atom, a cyano group, a $C_1$-$C_3$ alkyl group which may be mono-substituted or poly-substituted by a substituent group α, a $C_2$-$C_3$ alkenyl group which may be mono-substituted or poly-substituted by a substituent group α, a $C_2$-$C_3$ alkynyl group which may be mono-substituted or poly-substituted by a substituent group α, a $C_1$-$C_3$ alkoxy group which may be mono-substituted or poly-substituted by a substituent group α, a $C_1$-$C_3$ alkoxy $C_1$-$C_3$ alkyl group which may be mono-substituted or poly-substituted by a substituent group α, a $C_1$-$C_3$ alkyl C(=X) group which may be mono-substituted or poly-substituted by a substituent group α, a $C_1$-$C_3$ alkoxy C(=X) group which may be mono-substituted or poly-substituted by a substituent group α, a $C_2$-$C_3$ alkenyl C(=X) group which may be mono-substituted or poly-substituted by a substituent group α, a $C_3$-$C_6$ cycloalkyl C(=X) group which may be mono-substituted or poly-substituted by a substituent group α, or an $R_{13c}(R_{13d})$NC(=X) group, and each of $R_{13c}$ and $R_{13d}$ which are independent of each other, is a hydrogen atom, a $C_1$-$C_4$ alkyl group which may be mono-substituted or poly-substituted by a substituent group α, or a $C_1$-$C_4$ alkoxy group which may be mono-substituted or poly-substituted by a substituent group α, wherein the substituent group α is a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a $C_3$-$C_8$ cycloalkyl group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group, and wherein substituent group α* is a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a $C_3$-$C_8$ cycloalkyl group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group.

4. A 3-alkoxy-1-phenyl-pyrazole derivative represented by the formula [I''] or an agriculturally acceptable salt thereof:

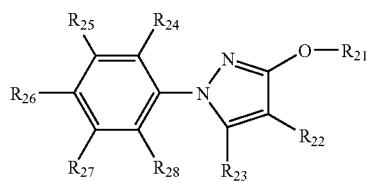

[I'']

wherein $R_{21}$ is a $C_3$-$C_{10}$ alkyl group which may be mono-substituted or poly-substituted by a substituent group α, a $C_3$-$C_{10}$ haloalkyl group, a $C_3$-$C_{10}$ cycloalkyl group, a $C_3$-$C_8$ cycloalkyl $C_1$-$C_8$ alkyl group which may be mono-substituted or poly-substituted by a substituent group α, a $C_1$-$C_8$ alkoxy $C_1$-$C_8$ alkyl group which may be mono-substituted or poly-substituted by a substituent group α, a $C_1$-$C_8$ alkoxy $C_2$-$C_8$ alkenyl group which may be mono-substituted or poly-substituted by a substituent group α, a $C_1$-$C_8$ alkoxy $C_1$-$C_8$ alkoxy $C_1$-$C_8$ alkyl group which may be mono-substituted or poly-substituted by a substituent group α, a $C_2$-$C_{10}$ alkenyl group which may be mono-substituted or poly-substituted by a substituent group α, a $C_2$-$C_{10}$ alkynyl group which may be mono-substituted or poly-substituted by a substituent group α, a $C_2$-$C_{10}$ alkynyloxy $C_1$-$C_6$ alkyl group which may be mono-substituted or poly-substituted by a substituent group α, a $C_1$-$C_8$ alkylthio $C_1$-$C_8$ alkyl group which may be mono-substituted or poly-substituted by a substituent group α, a $C_1$-$C_8$ alkylsulfinyl $C_1$-$C_8$ alkyl group which may be mono-substituted or poly-substituted by a substituent group α, a $C_1$-$C_8$ alkylsulfonyl $C_1$-$C_8$ alkyl group which may be mono-substituted or poly-substituted by a substituent group α, a $C_1$-$C_{10}$ alkylsulfonyl group which may be mono-substituted or poly-substituted by a substituent group α, a benzenesulfonyl group which may be mono-substituted or poly-substituted by a substituent group α, a $C_1$-$C_{10}$ thiocyanatoalkyl group which may be mono-substituted or poly-substituted by a substituent group α, an aryl-C($=$X) group which may be mono-substituted or poly-substituted by a substituent group α, a $C_1$-$C_{10}$ alkyl-C($=$X) group which may be mono-substituted or poly-substituted by a substituent group α, a $C_1$-$C_8$ alkyl C($=$X)$C_1$-$C_4$ alkyl group which may be mono-substituted or poly-substituted by a substituent group α, a $C_1$-$C_8$ alkoxy C($=$X)$C_1$-$C_8$ alkyl group which may be mono-substituted or poly-substituted by a substituent group α, a pentafluorothio $C_1$-$C_{10}$ alkyl group, a tri($C_1$-$C_3$)alkylsilyl $C_1$-$C_8$ alkyl group which may be mono-substituted or poly-substituted by a substituent group α, a $C_3$-$C_{10}$ trialkylsilyl group which may be mono-substituted or poly-substituted by a substituent group α, an aryl group which may be mono-substituted or poly-substituted by a substituent group α, an aryl $C_1$-$C_8$ alkyl group which may be mono-substituted or poly-substituted by a substituent group α, an aryloxy $C_1$-$C_8$ alkyl group which may be mono-substituted or poly-substituted by a substituent group α, an arylthio $C_1$-$C_8$ alkyl group which may be mono-substituted or poly-substituted by a substituent group α, a heteroaryl group which may be mono-substituted or poly-substituted by a substituent group α, a heteroaryl $C_1$-$C_8$ alkyl group which may be mono-substituted or poly-substituted by a substituent group α, a heteroaryloxy $C_1$-$C_8$ alkyl group which may be mono-substituted or poly-substituted by a substituent group α, a heteroarylthio $C_1$-$C_8$ alkyl group which may be mono-substituted or poly-substituted by a substituent group α, a tetrahydrofurfuryl group, a tetrahydrofurfuryl $C_1$-$C_8$ alkyl group which may be mono-substituted or poly-substituted by a substituent group α, an $R_{21a}(R_{21b})$NC($=$X) group, or an $R_{21a}(R_{21b})$NC($=$X)$C_1$-$C_4$ alkyl group;

$R_{22}$ is a hydrogen atom, a hydroxy group, a halogen atom, a cyano group, a $H_2$NC($=$X) group, a carboxy group, a HC($=$X) group, a nitro group, an amino group, an azide group, a $C_1$-$C_4$ alkyl group which may be mono-substituted or poly-substituted by a substituent group α, a $C_1$-$C_4$ alkoxy group which may be mono-substituted or poly-substituted by a substituent group α, a $C_1$-$C_4$ alkoxy $C_1$-$C_4$ alkyl group which may be mono-substituted or poly-substituted by a substituent group α, a $C_2$-$C_6$ alkenyl group which may be mono-substituted or poly-substituted by a substituent group α, a $C_2$-$C_6$ alkynyl group which may be mono-substituted or poly-substituted by a substituent group α, a $C_3$-$C_8$ cycloalkyl group which may be mono-substituted or poly-substituted by a substituent group α, or a $C_1$-$C_4$ alkyl C($=$X) group which may be mono-substituted or poly-substituted by a substituent group α, $R_{23}$ is a hydrogen atom, a hydroxy group, a halogen atom, a cyano group, a carboxy group, a HC($=$X) group, an $R_{23a}$ $(R_{23b})$N(C$=$X) group, an azide group, a nitro group, a $C_1$-$C_4$ alkyl group which may be mono-substituted or poly-substituted by a substituent group α*, a $C_2$-$C_4$ alkenyl group which may be mono-substituted or poly-substituted by a substituent group α, $C_2$-$C_4$ alkynyl group which may be mono-substituted or poly-substituted by a substituent group α, a $C_3$-$C_8$ cycloalkyl group which may be mono-substituted or poly-substituted by a substituent group α, a $C_1$-$C_8$ cycloalkyl $C_1$-$C_4$ alkyl group which may be mono-substituted or poly-substituted by a substituent group α, a $C_1$-$C_6$ alkyl C($=$X) group which may be mono-substituted or poly-substituted by a substituent group α, a $C_2$-$C_8$ alkenyl C($=$X) group which may be mono-substituted or poly-substituted by a substituent group α, a $C_3$-$C_8$ cycloalkyl C($=$X) group which may be mono-substituted or poly-substituted by a substituent group α, a $C_1$-$C_6$ alkoxy group which may be mono-substituted or poly-substituted by a substituent group α, a $C_3$-$C_8$ cycloalkoxy group which may be mono-substituted or poly-substituted by a substituent group α, a $C_1$-$C_6$ alkoxy $C_1$-$C_4$ alkyl group which may be mono-substituted or poly-substituted by a substituent group α, a $C_1$-$C_6$ alkoxy C($=$X) group which may be mono-substituted or poly-substituted by a substituent group α, a mercapto group, a thiocyanato group, a $C_1$-$C_6$ alkylthio group which may be mono-substituted or poly-substituted by a substituent group α, a $C_1$-$C_6$ alkylsulfinyl group which may be mono-substituted or poly-substituted by a substituent group α, a $C_1$-$C_6$ alkylsulfonyl group which may be mono-substituted or poly-substituted by a substituent group α, a $C_3$-$C_8$ cycloalkylthio group which may be mono-substituted or poly-substituted by a substituent group α, a $C_3$-$C_8$ cycloalkylsulfinyl group which may be mono-substituted or poly-substituted by a substituent group α, a $C_3$-$C_8$ cycloalkylsulfonyl group which may be mono-substituted or poly-substituted by a substituent group α, a $C_1$-$C_6$ alkylsulfonyloxy group which may be mono-substituted or poly-substituted by a substituent group α, an $R_{23a}(R_{23b})$N group, an $R_{23f}(R_{23g})$C$=$N group, or an $R_{23h}$ON$=$C($R_{23i}$) group;

each of $R_{24}$, $R_{25}$, $R_{26}$ and $R_{28}$ which are independent of one another, is a hydrogen atom, an amino group, an azide group, a nitro group, a hydroxy group, a halogen atom, a carbamoyl group, a cyano group, a carboxy group, a HC($=$X) group, a $C_1$-$C_4$ alkyl group which may be mono-substituted or poly-substituted by a substituent group α, a $C_1$-$C_4$ alkoxy group which may be mono-substituted or poly-substituted by a substituent group α, a formylamino group, a $C_1$-$C_6$ alkylcarbonylamino group which may be mono-substituted or poly-substituted by a substituent group α, a $C_1$-$C_6$ alkylthiocarbonylamino group which may be mono-substituted or poly-substituted by a substituent group α, a $C_2$-$C_4$ alkenyl group which may be mono-substituted or poly-substituted by a substituent group α, a $C_2$-$C_4$ alkynyl group which may be mono-substituted or poly-substituted by a substituent group α, or a $C_3$-$C_6$ cycloalkyl group which may be mono-substituted or poly-substituted by a substituent group α

$R_{27}$ is a $C_2$-$C_4$ haloalkylthio group, a $C_2$-$C_4$ haloalkylsulfinyl group, a $C_2$-$C_4$ haloalkenylthio group, a $C_2$-$C_4$ haloalkenylsulfinyl group, a cyclopropylmethylthio group which may be mono-substituted or poly-substituted by a substituent group α, or a cyclopropylmethylsulfinyl group which may be mono-substituted or poly-substituted by a substituent group α;

X is an oxygen atom or a sulfur atom;

each of $R_{21a}$ and $R_{21b}$ which are independent of each other, is a hydrogen atom, a $C_1$-$C_4$ alkyl group which may be mono-substituted or poly-substituted by a substituent group α, a $C_3$-$C_8$ cycloalkyl group which may be mono-substituted or poly-substituted by a substituent group α, or a $C_1$-$C_4$ alkoxy group which may be mono-substituted or poly-substituted by a substituent group α, $R_{21a}$ and $R_{21b}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{21a}$ and $R_{21b}$ are bonded;

each of $R_{23a}$ and $R_{23b}$ which are independent of each other, is a hydrogen atom, a cyano group, an amino group, a hydroxy group, a $C_1$-$C_6$ alkyl group which may be mono-substituted or poly-substituted by a substituent group α, a $C_2$-$C_8$ alkenyl group which may be mono-substituted or poly-substituted by a substituent group α, a $C_2$-$C_8$ alkynyl group which may be mono-substituted or poly-substituted by a substituent group α, a $C_1$-$C_4$ alkoxy group which may be mono-substituted or poly-substituted by a substituent group α, a $C_3$-$C_8$ cycloalkyl group which may be mono-substituted or poly-substituted by a substituent group α, a $C_3$-$C_8$ cycloalkyl $C_1$-$C_4$ alkyl group which may be mono-substituted or poly-substituted by a substituent group α, a $C_1$-$C_8$ alkoxy $C_1$-$C_4$ alkyl group which may be mono-substituted or poly-substituted by a substituent group α, a $C_1$-$C_8$ alkylthio $C_1$-$C_4$ alkyl group which may be mono-substituted or poly-substituted by a substituent group α, a $C_1$-$C_8$ alkylsulfinyl $C_1$-$C_4$ alkyl group which may be mono-substituted or poly-substituted by a substituent group α, a $C_1$-$C_8$ alkylsulfonyl $C_1$-$C_4$ alkyl group which may be mono-substituted or poly-substituted by a substituent group α, a $C_1$-$C_8$ alkylsulfonyl group which may be mono-substituted or poly-substituted by a substituent group α, a $C_1$-$C_8$ alkylsulfinyl group which may be mono-substituted or poly-substituted by a substituent group α, a $C_1$-$C_8$ alkylthio group which may be mono-substituted or poly-substituted by a substituent group α, a $C_2$-$C_8$ alkenylsulfonyl group which may be mono-substituted or poly-substituted by a substituent group α, a $C_1$-$C_8$ alkoxy $C_1$-$C_4$ alkylsulfonyl group which may be mono-substituted or poly-substituted by a substituent group α, a $C_3$-$C_8$ cycloalkylsulfonyl group which may be mono-substituted or poly-substituted by a substituent group α, a di($C_1$-$C_6$ alkyl)aminosulfonyl group which may be mono-substituted or poly-substituted by a substituent group α, a benzenesulfonyl group which may be mono-substituted or poly-substituted by a substituent group α, a $C_1$-$C_8$ alkyl C(=X) group which may be mono-substituted or poly-substituted by a substituent group α, a $C_1$-$C_8$ alkyl C(=X)C(=X) group which may be mono-substituted or poly-substituted by a substituent group α, a $C_1$-$C_8$ alkoxy C(=X) group which may be mono-substituted or poly-substituted by a substituent group α, a $C_1$-$C_8$ alkoxy C(=X)C(=X) group which may be mono-substituted or poly-substituted by a substituent group α, a $C_2$-$C_8$ alkenyl C(=X) group which may be mono-substituted or poly-substituted by a substituent group α, a $C_2$-$C_8$ alkynyl C(=X) group which may be mono-substituted or poly-substituted by a substituent group α, a $C_3$-$C_8$ cycloalkyl C(=X) group which may be mono-substituted or poly-substituted by a substituent group α, a $C_1$-$C_8$ alkyl C(=X)$C_1$-$C_4$ alkyl group which may be mono-substituted or poly-substituted by a substituent group α, an $R_{23c}(R_{23d})$N group, an $R_{23c}(R_{23d})$NC(=X) group which may be mono-substituted or poly-substituted by a substituent group α, or a $C_1$-$C_8$ alkylthio C(=X) group;

each of $R_{23c}$ and $R_{23d}$ which are independent of each other, is a hydrogen atom, a $C_1$-$C_4$ alkyl group which may be mono-substituted or poly-substituted by a substituent group α, a $C_1$-$C_4$ alkoxy group which may be mono-substituted or poly-substituted by a substituent group α, or a $C_3$-$C_8$ cycloalkyl group which may be mono-substituted or poly-substituted by a substituent group α, $R_{23c}$ and $R_{23d}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{23c}$ and $R_{23d}$ are bonded;

each of $R_{23f}$ and $R_{23g}$ which are independent of each other, is a hydrogen atom, a halogen atom, a $C_1$-$C_8$ alkyl group which may be mono-substituted or poly-substituted by a substituent group α, a $C_1$-$C_8$ alkoxy group which may be mono-substituted or poly-substituted by a substituent group α, a $C_3$-$C_8$ cycloalkyl group which may be mono-substituted or poly-substituted by a substituent group α, an amino group, a dimethylamino group, a $C_1$-$C_4$ alkylthio group, or an imidazolyl group;

$R_{23f}$ and $R_{23g}$ may form a 3- to 6-membered ring together with the nitrogen atom to which they are bonded, and in such a case, in this ring, at least one structure selected from the group consisting of an oxygen atom, a sulfur atom, a carbonyl group and an N-methylamino group may be present in addition to the nitrogen atom to which $R_{23f}$ and $R_{23g}$ are bonded; and each of $R_{23h}$ and $R_{23i}$ which are independent of each other, is hydrogen atom, a $C_1$-$C_4$ alkyl group which may be mono-substituted or poly-substituted by a substituent group α, a $C_2$-$C_8$ alkenyl group which may be mono-substituted or poly-substituted by a substituent group α, or a $C_2$-$C_8$ alkynyl group which may be mono-substituted or poly-substituted by a substituent group α, wherein substituent group α is a halogen atom, a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a difluoromethoxy group, a trifluoromethoxy group, a $C_3$-$C_8$ cycloalkyl group, a trifluoromethyl group, a trifluoromethylthio group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group, and wherein substituent group α* is a cyano group, a hydroxy group, a nitro group, an amino group, a carboxy group, a formyl group, a $C_1$-$C_4$ alkyl group, a $C_1$-$C_4$ alkoxy group, a $C_1$-$C_4$ alkoxycarbonyl group, a $C_3$-$C_8$ cycloalkyl group, a $C_1$-$C_4$ alkylthio group, a $C_1$-$C_4$ alkylsulfinyl group, a $C_1$-$C_4$ alkylsulfonyl group, or a $C_1$-$C_4$ alkylsulfonyloxy group.

5. A pesticide comprising as an active ingredient the 3-alkoxy-1-phenylpyrazole derivative or an agriculturally acceptable salt thereof as defined in claim 1.

6. An agricultural or horticultural insecticide comprising as an active ingredient the 3-alkoxy-1-phenylpyrazole derivative or an agriculturally acceptable salt thereof as defined in claim 1.

7. A miticide comprising as an active ingredient the 3-alkoxy-1-phenylpyrazole derivative or an agriculturally acceptable salt thereof as defined in claim 1.

8. A nematicide comprising as an active ingredient the 3-alkoxy-1-phenylpyrazole derivative or an agriculturally acceptable salt thereof as defined in claim 1.

9. A method for controlling a pest, which comprises applying an effective amount of the 3-alkoxy-1-phenylpyrazole derivative or an agriculturally acceptable salt thereof as defined in claim 1.

10. A pesticide comprising as an active ingredient the 3-alkoxy-1-phenylpyrazole derivative or an agriculturally acceptable salt thereof as defined in claim 3.

11. An agricultural or horticultural insecticide comprising as an active ingredient the 3-alkoxy-1-phenylpyrazole derivative or an agriculturally acceptable salt thereof as defined in claim 3.

12. A miticide comprising as an active ingredient the 3-alkoxy-1-phenylpyrazole derivative or an agriculturally acceptable salt thereof as defined in claim 3.

13. A nematicide comprising as an active ingredient the 3-alkoxy-1-phenylpyrazole derivative or an agriculturally acceptable salt thereof as defined in claim 3.

14. A method for controlling a pest, which comprises applying an effective amount of the 3-alkoxy-1-phenylpyrazole derivative or an agriculturally acceptable salt thereof as defined in claim 3.

15. A pesticide comprising as an active ingredient the 3-alkoxy-1-phenylpyrazole derivative or an agriculturally acceptable salt thereof as defined in claim 4.

16. An agricultural or horticultural insecticide comprising as an active ingredient the 3-alkoxy-1-phenylpyrazole derivative or an agriculturally acceptable salt thereof as defined in claim 4.

17. A miticide comprising as an active ingredient the 3-alkoxy-1-phenylpyrazole derivative or an agriculturally acceptable salt thereof as defined in claim 4.

18. A nematicide comprising as an active ingredient the 3-alkoxy-1-phenylpyrazole derivative or an agriculturally acceptable salt thereof as defined in claim 4.

19. A method for controlling a pest, which comprises applying an effective amount of the 3-alkoxy-1-phenylpyrazole derivative or an agriculturally acceptable salt thereof as defined in claim 4.

20. The 3-alkoxy-1-phenylpyrazole derivative according to claim 1, wherein $R_1$ is at least one selected from the group consisting of $CH_2SCF_3$, $CF_2CHFCF_3$, $CH_2C_2F_5$, $CF_2CHFCF_3$, $CF_2CHFOCF_3$, $CH_2CH=CHCl$, $CH(CH_3)_2$, $CH_2C_3F_7$, $CH_2CH_2CH_2CF_3$, $CH(CH_3)CH_2CH_3$, $CH_2C_5F_{11}$, $CH_2CH_2C(CH_3)_3$, Hex-c, $CH(CH_2CH_3)_2$, $CH_2CH_2CH_2SI(CH_3)_3$, $CH_2CH_2CH_2CF(CF_3)_2$, $CH_2CH_2CH_2C_4F_9$, $CH_2CH_2CH_4F_9$, $CH_2CH_2C_4F_9$, $CF_2CHFOC_2F_5$, $CH_2CF_2CF_2CHF_2$, $CH_2CF_2OCF_2CF_2OCF_3$, $CF_2CHFOC_3F_7$, $CF_2(CF_2)_8CF_3$, $CF(CF_3)_2$, $CF_2CHFOCF_3$, $CF_2CF_2CF_3$, $CF_2CHFOCF(CF_3)_2$, $CF_2CHFOC_2F_5$, $CF_2CHFOC_2F_5$, $CH_2CF_3$, $CH_2CF_3$, and $CH_2CF_2Cl$; $R_2$ is at least one of H, F, Cl, and Br; $R_3$ is at least one of $NHC(O)CH_3$, $NH_2$, $NHC(O)CF_3$, $NHC(O)OCH_3$, $N(C(O)CH_3)CH_2CN$, $N(C(O)CH)C(O)OCH_3$, $CH_3$, $NHC(O)CH_2CH_3$, $NHC(O)CH_2OCH_3$, $NHC(O)CHF_2$, $N=C(CH_3)OCH_2CF_3$, $N(C(O)CH_3)CH_2CH=CH_2$, $N(C(O)CH_3)CH_2C\equiv CH$, $NHCH_2C(O)OH$, $CN$, $NHCH_2CH=CH_2$, $NHCH_2C\equiv CH$, $NHCH_3$, $OCH_3$, $CH=NOCH_3$, $Cl$, $CH=NOCH_3$, $NHCH_3$, $OCH_3$, H, and Br; $R_4$ is F; $R_5$ is H; $R_6$ is $CH_3$; $R_7$ is at least one of $SCH_2CH_3$ and $S(O)CH_2CF_3$; and $R_8$ is H.

21. The 3-alkoxy-1-phenylpyrazole derivative of claim 1, wherein $R_3$ is not a hydrogen atom.

22. The 3-alkoxy-1-phenylpyrazole derivative of claim 3, wherein $R_{13}$ is not a hydrogen atom.

23. The 3-alkoxy-1-phenylpyrazole derivative of claim 4, wherein $R_{23}$ is not a hydrogen atom.

* * * * *